US006528484B1

(12) United States Patent
Ensign et al.

(10) Patent No.: US 6,528,484 B1
(45) Date of Patent: Mar. 4, 2003

(54) INSECTICIDAL PROTEIN TOXINS FROM PHOTORHABDUS

(75) Inventors: Jerald C. Ensign, Madison, WI (US); David J. Bowen, Oregon, WI (US); James Petell, Zionsville, IN (US); Raymond Fatig, Zionsville, IN (US); Sue Schoonover, Brownsburg, IN (US); Richard H. ffrench-Constant, Madison, WI (US); Thomas A. Rocheleau, Madison, WI (US); Michael B. Blackburn, Madison, WI (US); Timothy D. Hey, Zionsville, IN (US); Donald J. Merlo, Carmel, IN (US); Gregory L. Orr, Indianapolis, IN (US); Jean L. Roberts, Arcadia, IN (US); James A. Strickland, Lebanon, IN (US); Lining Guo, Brownsburg, IN (US); Todd A. Ciche, Madison, WI (US); Kitisri Sukhapinda, Zionsville, IN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 08/851,567

(22) Filed: May 5, 1997

Related U.S. Application Data

(63) Continuation-in-part of application No. 08/743,699, filed on Nov. 6, 1996, now abandoned, which is a continuation-in-part of application No. 08/705,484, filed on Aug. 29, 1996, now abandoned, which is a continuation-in-part of application No. 08/608,423, filed on Feb. 8, 1996, now abandoned, which is a continuation-in-part of application No. 08/395,947, filed on Feb. 28, 1995, now abandoned, which is a continuation-in-part of application No. 08/063,615, filed on May 18, 1993, now abandoned

(60) Provisional application No. 60/007,255, filed on Nov. 6, 1995.

(51) Int. Cl.$^7$ ..................... A01N 37/18; C07K 14/195; C12P 21/02
(52) U.S. Cl. ......................................... 514/12; 530/350
(58) Field of Search .................................. 530/350, 825; 514/12, 2; 424/94.1, 93.4; 435/69.1

(56) References Cited

U.S. PATENT DOCUMENTS

| | | | | |
|---|---|---|---|---|
| 4,394,443 | A | | 7/1983 | Weissman et al. ............. 435/6 |
| 4,672,130 | A | | 6/1987 | Rhodes et al. ............... 548/453 |
| 5,039,523 | A | | 8/1991 | Payne et al. ........... 424/93.461 |
| 5,254,799 | A | | 10/1993 | DeGreve et al. ............ 800/302 |
| 5,308,760 | A | | 5/1994 | Brown et al. .............. 435/69.1 |
| 5,460,963 | A | | 10/1995 | Botterman et al. ......... 800/279 |
| 6,048,838 | A | * | 4/2000 | Ensign et al. .................. 514/2 |
| 6,174,860 | B1 | * | 1/2001 | Kramer et al. ................ 514/12 |

FOREIGN PATENT DOCUMENTS

WO WO 92/16637 10/1992
WO WO 95/00647 1/1995

OTHER PUBLICATIONS

Masai et al. Drosophila retinal degeneration A gene encodes an eye-specific diacylglycerol kinase with cysteine-rich zinc-finger motifs and ankyrin repeats. Proc. Natl. Acad. Sci. U. S. A. 90(23), 11157–11161, Dec. 1993.*

Hoey et al. Molecular cloning and functional analysis of Drosophila TAF110 reveal properties expected of coactivators. Cell 72(2), 247–260, Jan. 29, 1993.*

Ugaki et al. The complete nucleotide sequence of cucumber green mottle mosaic virus (SH strain) genomic RNA. J. Gen. Virol. 72(7), 1487–1495. 1991.*

Aebersold, et al., "Internal Amino Acid Sequence Analysis of Proteins Separated by One–or Two–Dimensional Gel Electrophoresis After in Situ Protease Digestion on Nitrocellulose," *Proc. Natl. Acad. Sci. USA*, 84:6970–6974 (1987).

Balcerzak, M., "Comparative Studies on Parasitism Caused by Entomogenous nematodes, *Steinernema feltiae* and *Heterorhabaditis bacteriophora*. I. The Roles of the Nematode–Bacterial Complex, and of the Associated Bacteria Alone, in Pathogenesis," *Acta Parasitologica Polonica*, 36:175–181 (1991).

Bowen, D.J., et al., "Extracellular Insecticidal Factor Produced by *Xenorhabdus luminescens*," Abstract from the *89th Annual Meeting of the American Society for Microbiology (ASM)*, (1989).

Ensign, J.C., "Insecticidal Toxin Protein from *Xenorhabdus luminescens*: Potential Use for Control of Insects," *Knowledge Express*, Computer Database Abstract of USDA Research Report (1992).

Ensign, J.C., et al., "Crystalline Inclusion Proteins and an Insecticidal Toxin of *Xenorhabdus luminescens* strain NC–19," Abstract, p. 218, from *Vth International Colloquium on Invertebrate Pathology and Microbial Control (ICIPMC)*, (Aug. 1990).

Flyg, C., et al., "Insect Pathogenic Properties of *Serratia marcescens*: Phage–resistant Mutants with a Decreased Resistance to Cecropia Immunity and a Decreased Virulence to Drosophila," *J. Gen. Microb.*, 120:173–181 (1980).

Flyg, C., and K. G. Xanthopoulos, "Insect Pathogenic Properties of *Serratia marcescens*. Passive and Active Resistance to Insect Immunity Studied with Protease–deficient and Phage–resistant Mutants," *J. Gen. Microb.*, 129:453–464 (1983).

(List continued on next page.)

Primary Examiner—Gabrielle Bugaisky
(74) Attorney, Agent, or Firm—Andrea T. Borucki; Donald R. Stuart

(57) ABSTRACT

Proteins from the genus Photorhabdus are toxic to insects upon exposure. *Photorhabdus luminescens* (formerly *Xenorhabdus luminescens*) have been found in mammalian clinical samples and as a bacterial symbiont of entomopathogenic nematodes of genus Heterorhabditis. These protein toxins can be applied to, or genetically engineered into, insect larvae food and plants for insect control.

2 Claims, 9 Drawing Sheets

OTHER PUBLICATIONS

Hammock, et al., *Nature,* 344:458–461 (1990).

Huxham, I.M., and A. M. Lackie, "A Simple Visual Method for Assessing the Activation and Inhibition of Phenoloxidase Production by Insect Haemocytes in vitro," *J. Imm. Methods.,* 94:271–277 (1986).

Jarosz, et al., "Involvement of Larvicidal Toxins in Pathogenesis of Insect Parasitism with the Rhabditoid Nematodes, *Steinernema feltiae* and *Heterorhabditis bacteriophora,*" *Entomophaga,* 36:361–368 (1991).

Jarosz, et al., "Entomocidal Metabolite/s/ in Larvae of the Greater Wax Moth Parasitized by Insect–Pathogenic Nematodes," p. 231 in *Fundamental and Applied Aspects of Invertebrate Pathology* (R. A. Samson, J. M. Viak, and D. Peters, eds.), Fourth International Colloquium on Invertebrate Pathology, Wageningen, The Netherlands (1986).

Johnson, et al., "Expression of Proteinase Inhibitors I and II in Transgenic Tobacco Plants: Effects on Natural Defense Against *Manduca sexta* Larvae," *Proc. Natl. Acad. Sci. USA,* 86:9871–9875 (1989).

Johnson, et al., "Expression of Proteinase Inhibitor Genes from Potato and Tomato in Transgenic Plants Enhances Defense Against an Insect Predator," in *The Molecular and Cellular Biology of the Potato* (M. E. Vayda and W. D. Park, eds.) Chapter 8, pp. 97–102 (1991).

Kaska, I., et al., "Exocellular Proteases of *Serratia marcescens* and Their Toxicity to Larvae of *Galleria mellonella,*" *Follia Microbiol.,* 21:465–473 (1976).

Lysenko, "Non–sporeforming Bacteria Pathogenic to Insects: Incidence and Mechanisms," *Ann. Rev. Microbiol.,* 39:673–695 (1985).

Lysenko, O., and M. Kucera, "The Mechanism of Pathogenicity of *Pseudomonas aeruginosa,*" pp. 295–299.

Morihara, K., "Comparative Specificity of Microbial Proteinases," pp. 179–243.

Potrykus, "Gene Transfer to Plants: Assessment of Published Approaches and Results," *Ann. Rev. Plant. Physiol. Plant Mol. Biol.,* 42:205–225 (1991).

Ratcliffe, N.A., et al., "Prophenoloxidase Activation: Non-self Recognition and Cell Cooperation in Insect Immunity," *Science,* 226:557–559 (1984).

Richardson, et al., "Identification of an Anthraquinone Pigment and a Hydroxystilbene Antibiotic from *Xenorhabdus luminescens,*" *App. Env. Microb.,* 54:1602–1605 (1988).

Schmidt, et al., "Characterization of an Extracellular Protease from the Insect Pathogen *Xenorhabdus luminescens,*" *App. Env. Microb.,* 54:2793–2797 (1988).

SIGMA Cell Culture Reagents, *Catalogue/Price List,* p. 85 (1991).

Soderhall and V. J. Smith, "Prophenoloxidase Activating System: The Biochemistry of its Activation and Role in Arthropod Cellular Immunity, with Special Reference to Crustaceans," Chapter 15, pp. 208–215.

Yoshida, H., and M. Ashida, "Microbial Activation of Two Serine Enzymes and Prophenoloxidase in the Plasma Fraction of Hemolymph of the Silkworm, *Bombyx Mori,*" *Insect Biochem.,* 16:539–545 (1986).

Yoshida, H., et al., "$\beta$–1,3–Glucan Receptor and Peptidoglycan Receptor are Present as Separate Entities within Insect Prophenoloxidase Activating System," *Biochem. Biophys. Res. Comm.,* 141:1177–1184 (1986).

Clarke, D. J., and Barbara C. A. Dowds, "Virulence Mechanisms of *Photorhabdus* sp Strain K122 toward Wax Moth Larvae," *J. Invertebrate Pathology,* 66:149–155 (1995).

Gerritsen, et al., "Variation in pathogenicity of recombinations of Heterorhabditis and *Xenorhabdus luminescens* strains," Fundam. Appl. Nematol, 16(4):367–373 (1993).

Wilson, et al., "Laboratory Tests of the Potential of Entomopathogenic Nematodes for the Control of Field Slugs (*Deroceras reticulatum*)," *Journal of Invertebrate Pathology,* 64:182–187 (1994).

Vaeck, et al., "Transgenic Plants Protected from Insect Attack," *Nature,* 328:33–37 (Jul. 1987).

\* cited by examiner

```
1    ATG CAG GAT TGT CTA GAA GTA TCG ATT ACA ACG CTG TCA CTT CCC AAA GGT GGC GGT
     TAC GTC CTA ACA GAT CTT CAT AGC TAA TGT TGC GAC AGT GAA GGG TTT CCA CCG CCA
1►   Met Gln Asp Cys Pro Glu Val Ser Ile Thr Thr Leu Ser Leu Pro Lys Gly Gly Gly
                        ──────►
                         P2Psh

58   GCT ATC AAT GGC ATG GGA GAA GCA CTG AAT GCT GCC CCT GAT GGA ATG GCC TCC
     CGA TAG TTA CCG TAC CCT CTT CGT GAC TTA CGA CGG GGA CTA CCT TAC CGG AGG
20►  Ala Ile Asn Gly Met Gly Glu Ala Leu Asn Ala Ala Pro Asp Gly Met Ala Ser

115  CTA TCT CTG CCA TTA CCC CTT TCG ACC GGC AGA GGG ACG GCT CCT GGA TTA TCG CTG
     GAT AGA GAC GGT AAT GGG GAA AGC TGG CCG TCT CCC TGC CGA GGA CCT AAT AGC GAC
39►  Leu Ser Leu Pro Leu Pro Leu Ser Thr Gly Arg Gly Thr Ala Pro Gly Leu Ser Leu

172  ATT TAC AGC AAC AGT GCA GGT CCA CGT GTA AAT GGG CCT TTC AAG CCG ATC TGG CAA TGC GGT GTT
     TAA ATG TCG TTG TCA CGT CCA GGT GCA CAT TTA CCC GGA AAG TTC GGC TAG CCG ACG CCA CAA
58►  Ile Tyr Ser Asn Ser Ala Gly Pro Arg Val Asn Gly Pro Phe Gly Ile Trp Gln Cys Gly Val

229  ATG TCC ATT AGC CGA CGC CGA ACC CAA CAT GGC CTT CAA GAA GTT CCG TGA CGA CGT
     TAC AGG TAA TCG GCT GCG GCT TGG GTT GTA CCG GAA GTT CTT CAA GGC ACT GCT GCA
77►  Met Ser Ile Ser Arg Arg Arg Thr Gln His Gly Leu Gln Glu Val Pro ••• Arg Arg

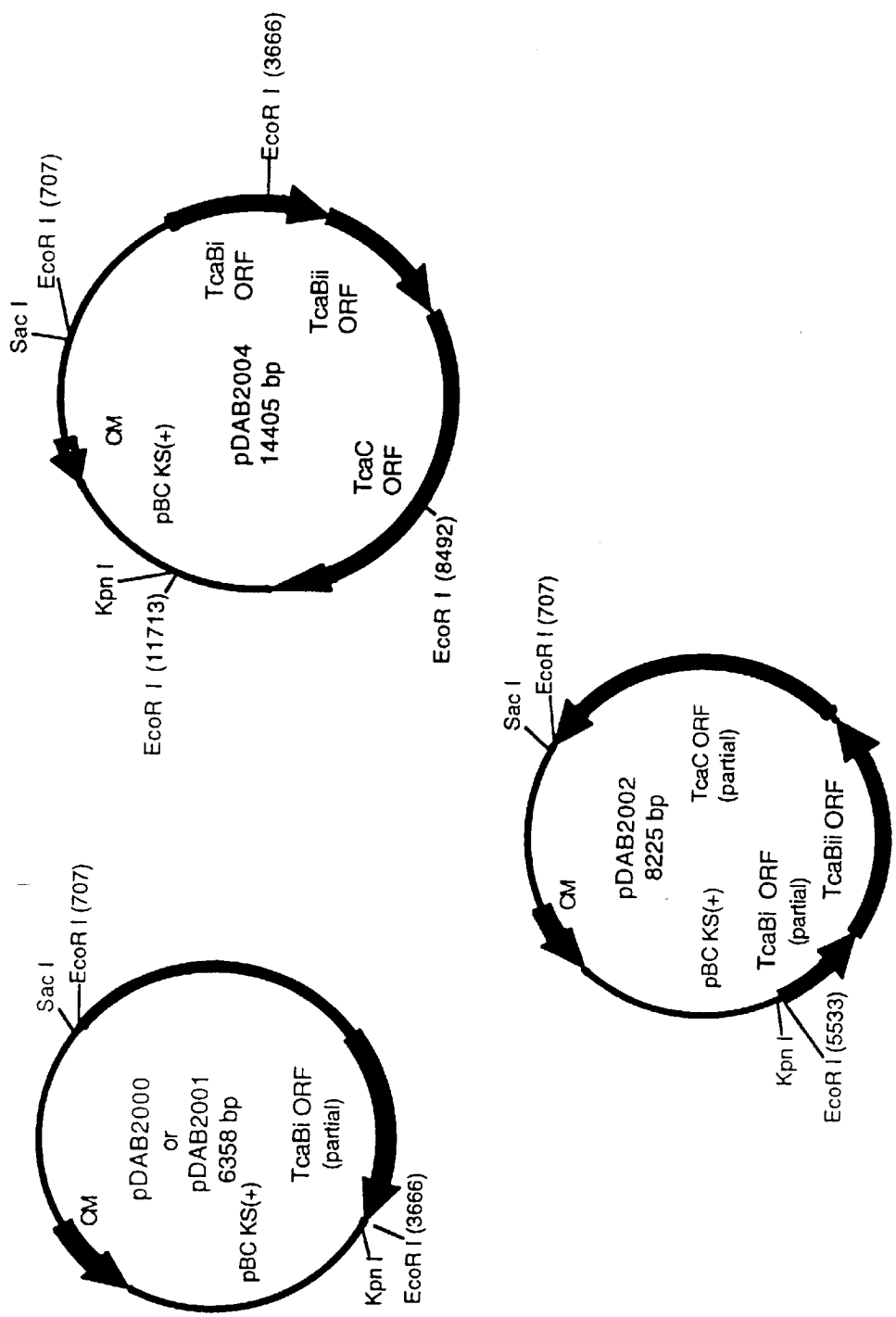
FIG. 2 Plasmids used in sequencing the *tca* locus. CM = Chloramphenicol resistance gene. ORF = Open Reading Frame

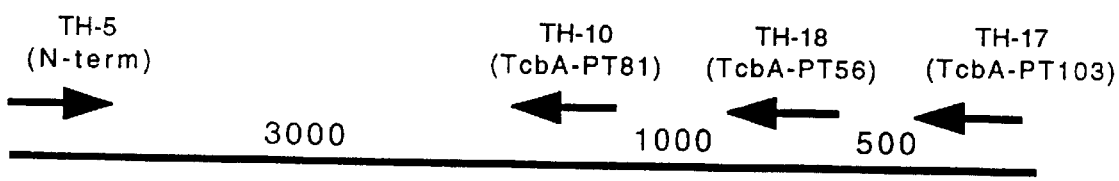
FIG. 3 Physical Map of DNA fragments of *tcb* locus. Estimated distance between fragments given in nucleotides.

```
           1740        1750        1760        1770        1780
TcbA   SSAQALKNDS  EPMDFSGANA  LYFWELFYYT  PMMMAHRLLQ  EQNFDAANHW
                       n
                      |450        460         470         480
TcaBi  _____gS  nPvDFSGpyg  iYlWEiFfhi  PflvtvRmqt  EQryedAdtW>
       ^^          ^^^^^^^^v^  ^^^^^^^^--  ^-^^^v^^vv  ^^-^^-^^v^

1790        1800        1810        1820        1830
TcbA   FRYVWSPSGY  IVDGKIAIYH  WNVRPLEEDT  SWNAQQLDST  DPDAVAQDDP
            rdangql           |           |           |
        490         510         520         530
TcaBi  ykYifrsaGY  ImDGskprY-  WNVmPLqlDT  aWdttQpatT  DPDviAmaDP>
       ^^^^--^^^^  ^^^^-v^v^|  ^^^-^^^v^^  ^^^^v^v-^^  ^^^-^^v-^^

1840        1850        1860        1870        1880
TcbA   MHYKVATFMA  TLDLLMARGD  AAYRQLERDT  LAEAKMWYTQ  ALNLLGDEPQ
        |           |           |           |           |
       540         550         560         570         580
TcaBi  MHYKlAiFlh  TLDLLiARGD  sAYRQLERDT  LvEAKMyYiQ  AqqLLGprPd>
       ^^^^^^-^^v  ^^^^^^^^^^  ^^^^^^^^^^  ^-^^^^-^-^  ^v^^^^vv^^

1890        1900        1910        1920        1930
TcbA   VMLSTTWANP  TLGNAASKTT  QQVRQQVLTQ  LRLNSRVKTP  LLGTANSLTA
        |
       600
TcaBi  ihttnTWpNP  TLsk>
       ^vv^-^^^^^  ^^^^

1940        1950        1960        1970        1980
TcbA   LFLPQENSKL  KGYWRTLAQR  MFNLRHNLSI  DGQPLSLPLY  AKPADPKALL
        |           |           |           |           |
        20          30          40          50          60
TcaBii _FLPpyNdvL  lGYWdkLelR  lyNLRHNLSl  DGQPLnLPLY  AtPvDPKtLq>
       ^^^-v^-v^   v^^^v-^-v^  ^^^^^^^^^^  ^^^^^^^^^^  ^-^-^^^^^v 1990        2000        2010        2020        2030
TcbA   SAAVSASQGG  ADLPKAPLTI  HRFPQMLEGA  RGLVNQLIQF  GSSLLGYSER
        |          |gw         |           |           |
        70          80          90          100         110
TcaBii rqqaggdgtG  sspaggqgsv  qRyPllvErA  RsaVsllLtQF GnSLqttlEh>
       ----^^-v-^  ^-v^v^-v^^  ^^^^v^^^v^  ^^v^^v-^^   ^^^^v-vv^^

2040        2050        2060        2070        2080
TcbA   QDAEAMSQLL  QTQASELILT  SIRMQDNQLA  ELDSEKTALQ  VSLAGVQQRF
        |           |           |           |           |
       120         130         140         150         160
TcaBii QDnEkMtiLL  QTQqeailkh  qhdiQqNnLk  gLqhslTALQ  aSrdGdtlRq>
       ^^-^v^^v^^  ^^^---^^vv  vvv^^^^^^v  -^^v-v^^^^  -^v-^vvv^v
```

FIG. 4A

```
              2090       2100       2110       2120       2130
TcbA    DSYSQLYEEN INAGEQRALA LRSESAIESQ GAQISRMAGA GVDMAPNIFG
                                                        a
          170  |     180  |     190|      200 |      210  |
TcaBii  khYSdLingg lsAaEiagLt LRStamI-tn Gvatglliag GinavPNvFG>
        -v^^^^v^-- ^^^^^vv^^^ ^^^-^v^ ^^ ^---^v^v^^ ^^^v-^^^^^

2140       2150       2160       2170       2180
TcbA    LADGGMHYGA IAYAIADGIE LSASAKMVDA EKVAQSEIYR RRRQEWKIQR
          220  |     230  |     240  |     250  |     260  |
TcaBii  LAnGGsewGA pligsgqatq vgAgiqdqsA gisevtagYq RRqeEWalQR>
        ^^^^^v^-^^ vvv^v^^^-^ ^^^^^v^vv-^ -vv-v^-v^^ ^^^^^^v^^^

2190       2200       2210       2220       2230
TcbA    DNAQAEINQL NAQLESLSIR REAAEMQKEY LKTQQAQAQA QLTFLRSKFS
          270  |     280  |     290  |     300  |     310  |
TcaBii  DiAdnEItQL dAQiqSLqeq itmAqkQitl seTeQAnAQA iydlqttrFt>
        ^v^^-^^-^^ ^^^^^^^vv^ v-v^^-^v-v v-^^^^^^^^ vv-^vv^^^^

2240       2250       2260       2270       2280
TcbA    NQALYSWLRG RLSGIYFQFY DLAVSRCLMA EQSYQWEAND NSISFVKPGA
                                                 l
          320  |     330  |     340  |        |     360  |
TcaBii  gQALYnWmaG RLSalYyQmY DstlpiCLqp kaalvqEgek eSdSlfqvpv>
        -^^^^^^^v^ ^^^^^^^^-^ ^v^^^v^^v^ --^vvv^^^- ^^v^^v^vv- 2290       2300       2310       2320       2330
TcbA    WQGTYAGLLC GEALIQNLAQ MEEAYLKWES RALEVERTVS LAVVYDSLEG
          370  |     380  |     390  |     400  |     410  |
TcaBii  WndlwqGLLa GEgLsseLqk ldaiwLargg igLEaiRTVS Ldtlfgt--G>
        ^^^v--^^^v ^^^^vv^^-^ ^^-v-^v^-^ v^^^-v^^^^ ^--^^^^  ^

2340       2350       2360       2370       2380
TcbA    NDRFNLAEQI PALLDKGEGT AGTKKNGLSL ANAILSASVK LSDLKLGTDY
                     420  |     430  |     440  |     450  |
TcaBii  ----tLsEnI nkvLn-GEtv spsggvtLaL tgdIfqAtld LSqLgLdnsY>
        -^^^^^     vv^^^ ^^-- ^v^vvv-^^^ ^--^^v^^^- ^^^^v^^-^^

2390       2400       2410       2420       2430
TcbA    PDSIVGSNKV RRIKQISVSL PALVGPYQDV QAMLSYGGST QLPKGCSALA
                                                 i
          460  |     470  |     480  |     490  ||    500  |
TcaBii  -n--lGneKk RRIKrIaVtL PtLlGPYQDl eAtLvmGaea aLshGvndgg>
        ^     ^^^^v ^^^^^^^^^^ ^^^^^^^^^^ ^^^v^vv^^-^ -^^-^v^-v^

2440       2450       2460       2470
TcbA    VSHGTNDSGQ FQLDFNDGKY LPFEGIALDD QGTLNLQFPN
          510  |     520  |     530  |
TcaBii  rfvtdfndsr F-LpF-eGrd attgtleLn>
        vvv--v^-^^ ^ ^v^ ^^^v v-v--^-^^|
```

FIG. 4B

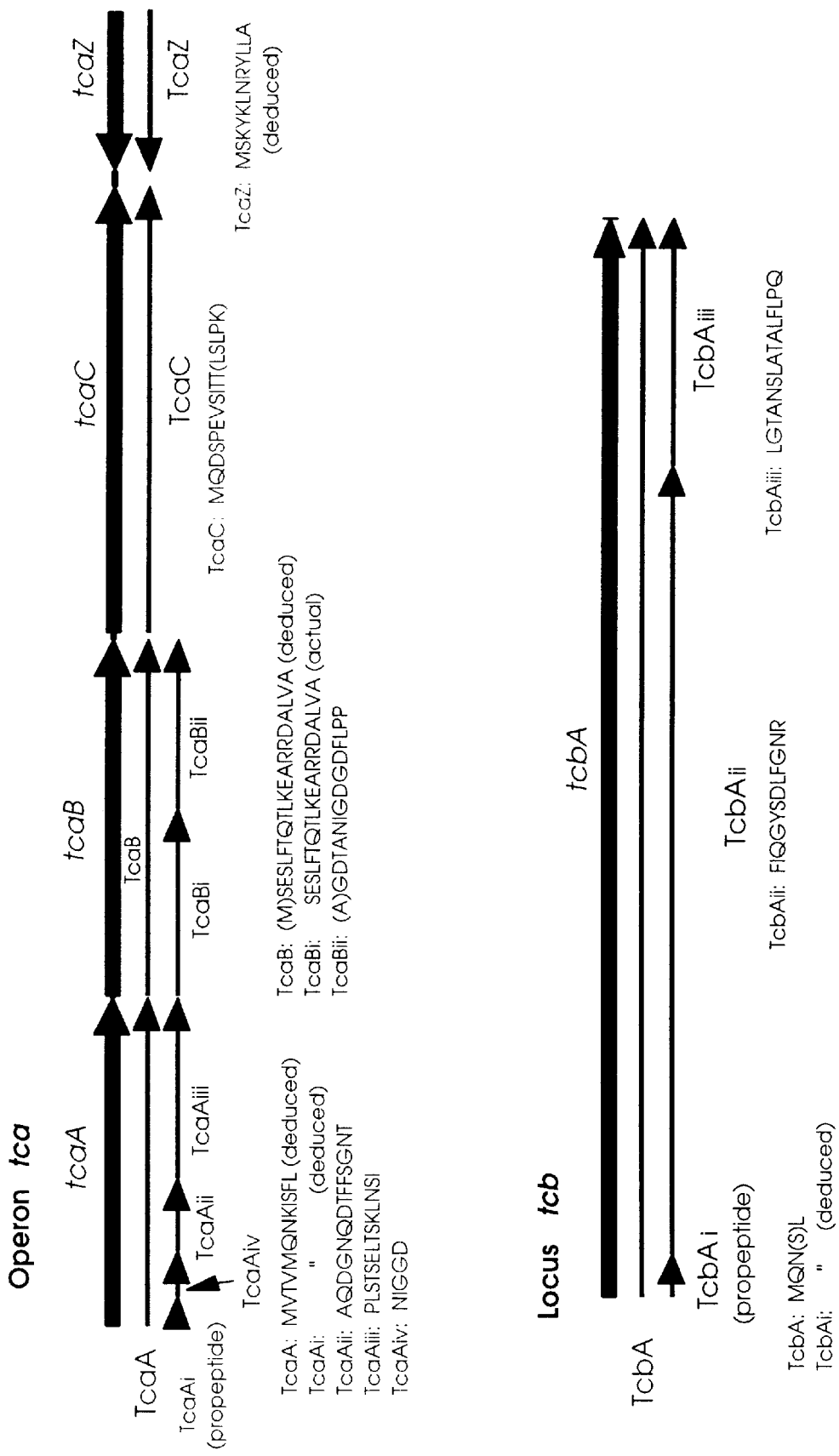
FIG.6A loci *tca* and *tcb*, primary gene products, and derived peptides

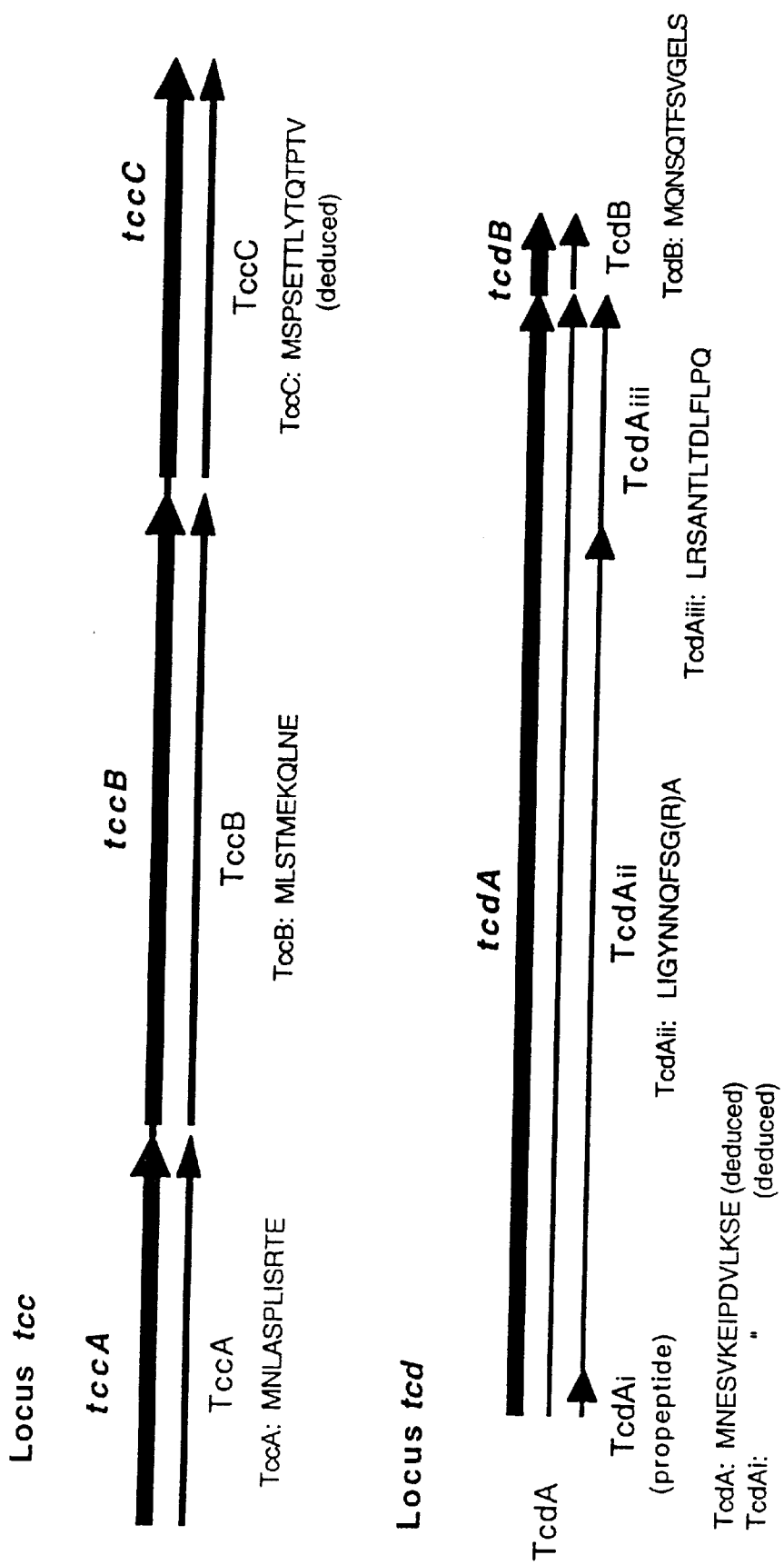
FIG. 6B Loci *tcc* and *tcd*, primary gene products, and derived peptides.

INSECTICIDAL PROTEIN TOXINS FROM PHOTORHABDUS

CROSS-REFERENCE TO RELATED APPLICATION

This patent application is a continuation-in-part of U.S. patent application Ser. No. 08/743,699 filed on Nov. 6, 1996 abandoned, which is a continuation-in-part of U.S. patent application Ser. No. 08/705,484 filed on Aug. 29, 1996 abandoned, which is a continuation-in-part of U.S. patent application Ser. No. 08/608,423 filed Feb. 28, 1996 abandoned, which is a continuation-in-part of U.S. patent application Ser. No. 08/395,947 filed Feb. 28, 1995 abandoned, which was a continuation-in-part of U.S. patent application Ser. No. 08/063,615 filed May 18, 1993 abandoned. This application is also a continuation-in-part of provisional U.S. patent application Serial No. 60/007,255 filed Nov. 6, 1995.

This invention was made with United States government support awarded by the following agencies:

NIH, Grant Nos: NS29623; AI28781; AI35026

NSF, Grant Nos: INT-9513285

USDA HATCH Funds 2867; 3543; 5206; 3443

USDA, AGRICREE Nos: 94-37313-0675; 96-34363-2831

The United States has certain rights in this invention.

FIELD OF THE INVENTION

The present invention relates to toxins isolated from bacteria and the use of said toxins as insecticides.

BACKGROUND OF THE INVENTION

Many insects are widely regarded as pests to homeowners, to picnickers, to gardeners, and to farmers and others whose investments in agricultural products are often destroyed or diminished as a result of insect damage to field crops. Particularly in areas where the growing season is short, significant insect damage can mean the loss of all profits to growers and a dramatic decrease in crop yield. Scarce supply of particular agricultural products invariably results in higher costs to food processors and, then, to the ultimate consumers of food plants and products derived from those plants.

Preventing insect damage to crops and flowers and eliminating the nuisance of insect pests have typically relied on strong organic pesticides and insecticides with broad toxicities. These synthetic products have come under attack by the general population as being too harsh on the environment and on those exposed to such agents. Similarly in non-agricultural settings, homeowners would be satisfied to have insects avoid their homes or outdoor meals without needing to kill the insects.

The extensive use of chemical insecticides has raised environmental and health concerns for farmers, companies that produce the insecticides, government agencies, public interest groups, and the public in general. The development of less intrusive pest management strategies has been spurred along both by societal concern for the environment and by the development of biological tools which exploit mechanisms of insect management. Biological control agents present a promising alternative to chemical insecticides.

Organisms at every evolutionary development level have devised means to enhance their own success and survival. The use of biological molecules as tools of defense and aggression is known throughout the animal and plant kingdoms. In addition, the relatively new tools of the genetic engineer allow modifications to biological insecticides to accomplish particular solutions to particular problems.

One such agent, *Bacillus thuringiensis* (Bt), is an effective insecticidal agent, and is widely commercially used as such. In fact, the insecticidal agent of the Bt bacterium is a protein which has such limited toxicity, it can be used on human food crops on the day of harvest. To non-targeted organisms, the Bt toxin is a digestible non-toxic protein.

Another known class of biological insect control agents are certain genera of nematodes known to be vectors of transmission for insect-killing bacterial symbionts. Nematodes containing insecticidal bacteria invade insect larvae. The bacteria then kill the larvae. The nematodes reproduce in the larval cadaver. The nematode progeny then eat the cadaver from within. The bacteria-containing nematode progeny thus produced can then invade additional larvae.

In the past, insecticidal nematodes in the Steinernema and Heterorhabditis genera were used as insect control agents. Apparently, each genus of nematode hosts a particular species of bacterium. In nematodes of the Heterorhabditis genus, the symbiotic bacterium is *Photorhabdus luminescens*.

Although these nematodes are effective insect control agents, it is presently difficult, expensive, and inefficient to produce, maintain, and distribute nematodes for insect control.

It has been known in the art that one may isolate an insecticidal toxin from *Photorhabdus luminescens* that has activity only when injected into Lepidopteran and Coleopteran insect larvae. This has made it impossible to effectively exploit the insecticidal properties of the nematode or its bacterial symbiont. What would be useful would be a more practical, less labor-intensive wide-area delivery method of an insecticidal toxin which would retain its biological properties after delivery. It would be quite desirous to discover toxins with oral activity produced by the genus Photorhabdus. The isolation and use of these toxins are desirous due to efficacious reasons. Until applicants' discoveries, these toxins had not been isolated or characterized.

SUMMARY OF THE INVENTION

The native toxins are protein complexes that are produced and secreted by growing bacteria cells of the genus Photorhabdus, of interest are the proteins produced by the species Photorhabdus luminescens. The protein complexes, with a molecular size of approximately 1,000 kDa, can be separated by SDS-PAGE gel analysis into numerous component proteins. The toxins contain no hemolysin, lipase, type C phospholipase, or nuclease activities. The toxins exhibit significant toxicity upon exposure administration to a number of insects.

The present invention provides an easily administered insecticidal protein as well as the expression of toxin in a heterologous system.

The present invention also provides a method for delivering insecticidal toxins that are functional active and effective against many orders of insects.

Objects, advantages, and features of the present invention will become apparent from the following specification.

BRIEF DESCRIPTION OF THE DRAWINGS

FIG. 1 is an illustration of a match of cloned DNA isolates used as a part of sequence genes for the toxin of the present invention.

FIG. 2 is a map of three plasmids used in the sequencing process.

FIG. 3 is a map illustrating the inter-relationship of several partial DNA fragments.

FIG. 4 is an illustration of a homology analysis between the protein sequences of TcbA$_{ii}$ and TcaB$_{ii}$ proteins.

Figure 5:
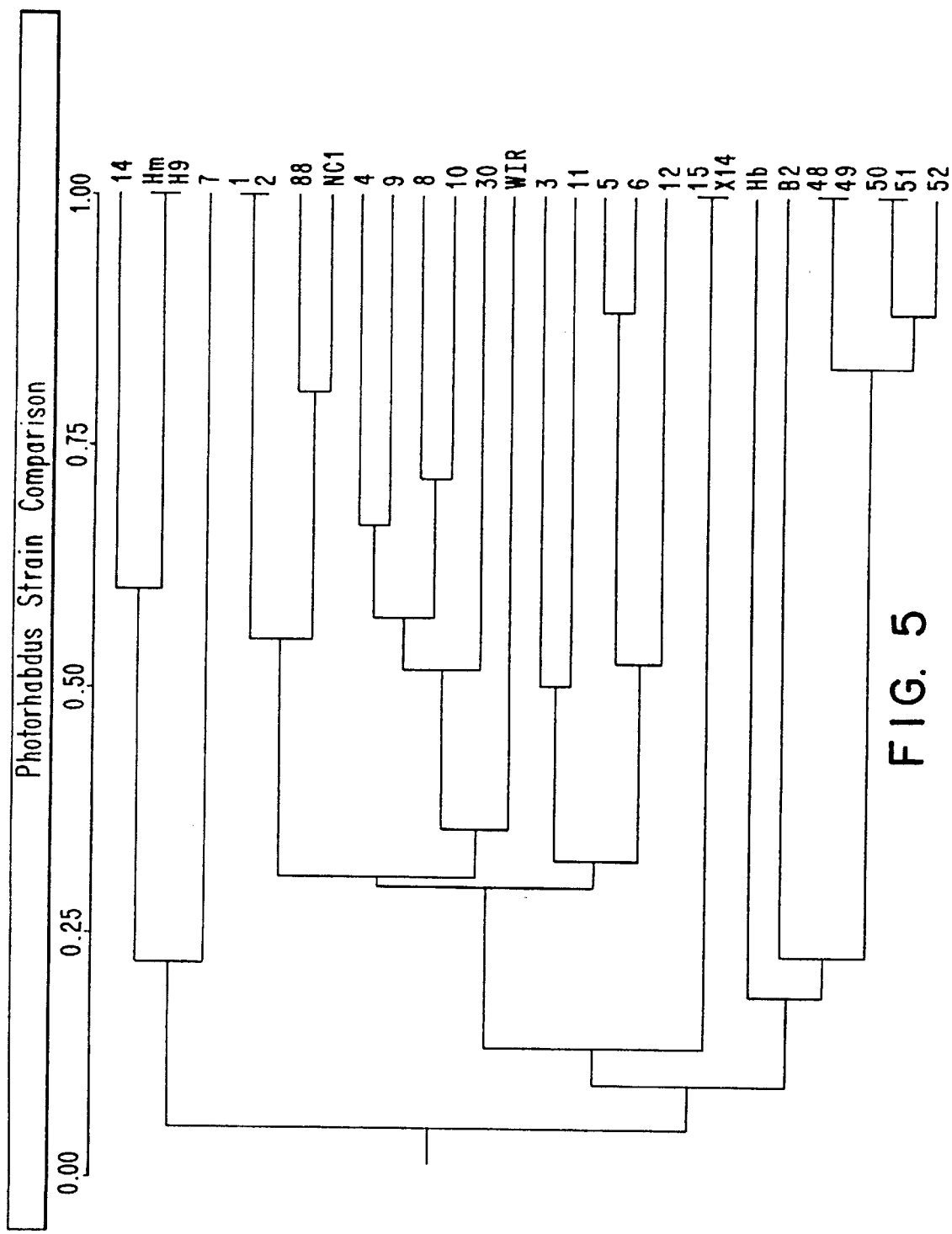

FIG. 5 is a phenogram of Photorhabdus strains. Relationship of Photorhabdus Strains was defined by rep-PCR. The upper axis of FIG. 5 measures the percentage similarity of strains based on scoring of rep-PCR products (i.e., 0.0 [no similarity] to 1.0 [100% similarity]). At the right axis, the numbers and letters indicate the various strains tested; 14=W-14, Hm=Hm, H9=H9, 7=WX-7, 1=WX-1, 2=WX-2, 88=HP88, NC-1=NC-1, 4=WX-4, 9=WX-9, 8=WX-8, 10=WX-10, WIR=WIR, 3=WX-3, 11=WX-11, 5=WX-5, 6=WX-6, 12=WX-12, x14=WX-14, 15=WX-15, Hb=Hb, B2=B2, 48 through 52=ATCC 43948 through ATCC 43952. Vertical lines separating horizontal lines indicate the degree of relatedness (as read from the extrapolated intersection of the vertical line with the upper axis) between strains or groups of strains at the base of the horizontal lines (e.g., strain W-14 is approximately 60% similar to strains H9 and Hm).

FIG. 6A is an illustration of the genomic maps of the W-14 Strain.

FIG. 6B is an illustration of the tca and tcb loci and primary gene products.

Figure 7:
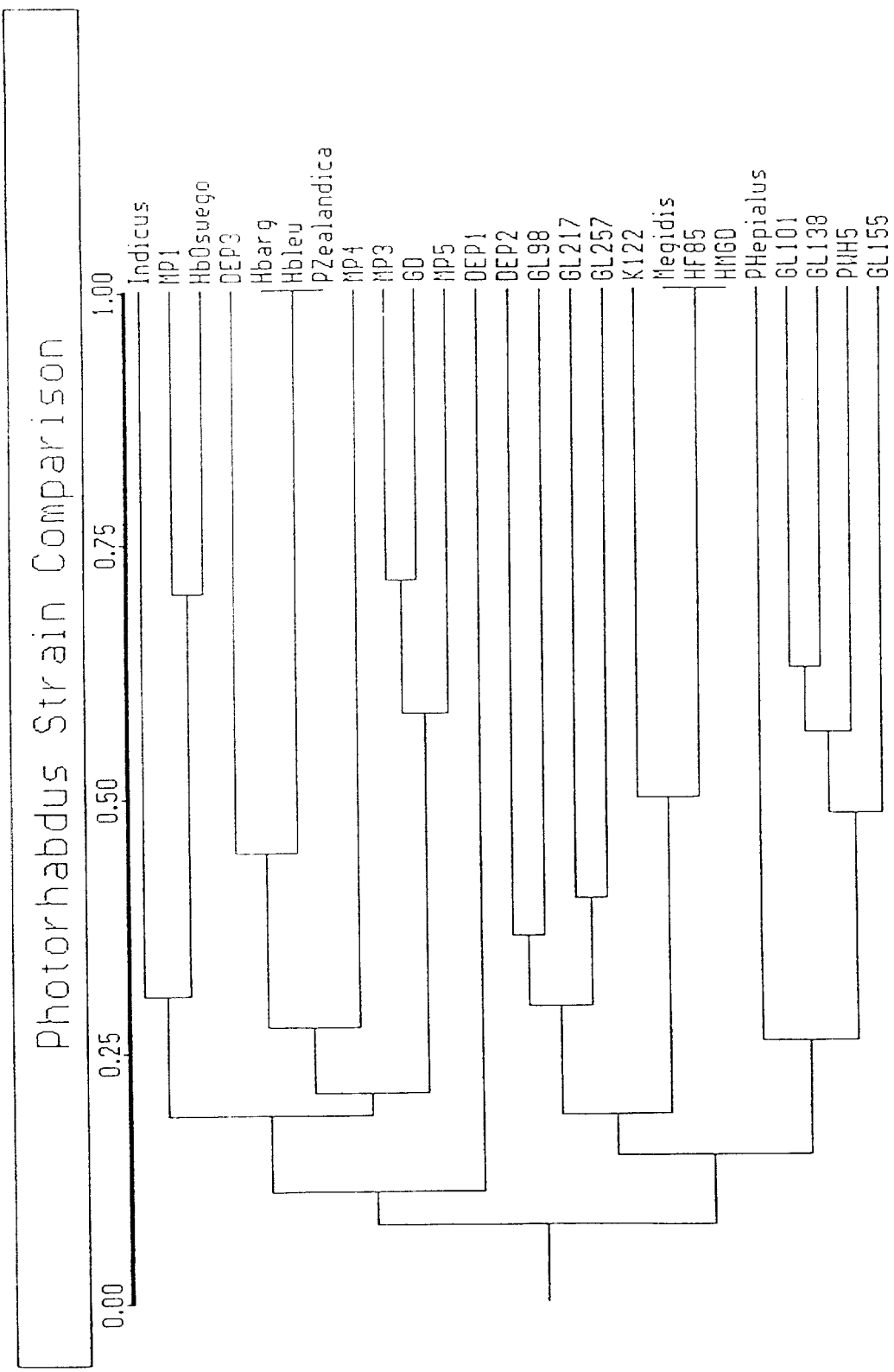

FIG. 7 is a phenogram of Photorhabdus strains as defined by rep-PCR. The upper axis of FIG. 7 measures the percentage similarity of strains based on scoring of rep-PCR products (i.e., 0.0 [no similarity] to 1.0 [100% similarity]). At the right axis, the numbers and letters indicate the various strains tested. Vertical lines separating horizontal lines indicate the degree of relatedness (as read from the extrapolated intersection of the vertical line with the upper axis) between strains or groups of strains at the base of the horizontal lines (e.g., strain Indicus is approximately 30% similar to strains MP1 and HB Oswego). Note that the Photorhabdus strains on the phenogram are as follows: 14=W-14; Hm=Hm; H9=H9; 7=WX-7; 1=WX-1; 2=WX-2; 88=HP88; NC1= NC-1; 4=WX-4; 9=WX-9; 8=WX-8; 10=WX-10; 30=W30; WIR=WIR; 3-WX-3; 11=WX-11; 5=WX-5; 6=WX-6; 12=WX-12; 15=WX-15; X14=WX-14; Hb=Hb; B2=B2; 48=ATCC 43948; 49=ATCC 43949; 50=ATCC 43950; 51=ATCC 43951; 52=ATCC 43952.

DETAILED DESCRIPTION OF THE INVENTION

The present inventions are directed to the discovery of a unique class of insecticidal protein toxins from the genus Photorhabdus that have oral toxicity against insects. A unique feature of Photorhabdus is its bioluminescence. Photorhabdus may be isolated from a variety of sources. One such source is nematodes, more particularly nematodes of the genus Heterorhabditis. Another such source is from human clinical samples from wounds, see Farmer et al. 1989 J. Clin. Microbiol. 27 pp. 1594–1600. These saprohytic strains are deposited in the American Type Culture Collection (Rockville, Md.) ATCC #s 43948, 43949, 43950, 43951, and 43952, and are incorporated herein by reference. It is possible that other sources could harbor Photorhabdus bacteria that produce insecticidal toxins. Such sources in the environment could be either terrestrial or aquatic based.

The genus Photorhabdus is taxonomically defined as a member of the Family Enterobacteriaceae, although it has certain traits atypical of this family. For example, strains of this genus are nitrate reduction negative, yellow and red pigment producing and bioluminescent. This latter trait is otherwise unknown within the Enterobacteriaceae. Photorhabdus has only recently been described as a genus separate from the Xenorhabdus (Boemare et al., 1993 Int. J. Syst. Bacteriol. 43, 249–255). This differentiation is based on DNA-DNA hybridization studies, phenotypic differences (e.g., presence (Photorhabdus) or absence (Xenorhabdus) of catalase and bioluminescence) and the Family of the nematode host (Xenorhabdus; Steinernematidae, Photorhabdus; Heterorhabditidae). Comparative, cellular fatty-acid analyses (Janse et al. 1990, Lett. Appl. Microbiol 10, 131–135; Suzuki et al. 1990, J. Gen. Appl. Microbiol., 36, 393–401) support the separation of Photorhabdus from Xenorhabdus.

In order to establish that the strain collection disclosed herein was comprised of Photorhabdus strains, the strains were characterized based on recognized traits which define Photorhabdus and differentiate it from other Enterobacteriaceae and Xenorhabdus species. (Farmer, 1984 Bergey's Manual of Systemic Bacteriology Vol. 1 pp.510–511; Akhurst and Boemare 1988, J. Gen. Microbiol. 134 pp. 1835–1845; Boemare et al. 1993 Int. J. Syst. Bacteriol. 43 pp. 249–255, which are incorporated herein by reference). The traits studied were the following: gram stain negative rods, organism size, colony pigmentation, inclusion bodies, presence of catalase, ability to reduce nitrate, bioluminescence, dye uptake, gelatin hydrolysis, growth on selective media, growth temperature, survival under anerobic conditions and motility. Fatty acid analysis was used to confirm that the strains herein all belong to the single genus Photorhabdus.

Currently, the bacterial genus Photorhabdus is comprised of a single defined species, *Photorhabdus luminescens* (ATCC Type strain #29999, Poinar et al., 1977, Nematologica 23, 97–102). A variety of related strains have been described in the literature (e.g., Akhurst et al. 1988 J. Gen. Microbiol., 134, 1835–1845; Boemare et al. 1993 Int. J. Syst. Bacteriol. 43 pp. 249–255; Putz et al. 1990, Appl. Environ. Microbiol., 56, 181–186). Numerous Photorhabdus strains have been characterized herein. Because there is currently only one species (*luminescens*) defined within the genus Photorhabdus, the *luminescens* species traits were used to characterize the strains herein. As can be seen in FIG. 5, these strains are quite diverse. It is not unforeseen that in the future there may be other Photorhabdus species that will have some of the attributes of the *luminescens* species as well as some different characteristics that are presently not defined as a trait of *Photorhabdus luminescens*. However, the scope of the invention herein is to any Photorhabdus species or strains which produce proteins that have functional activity as insect control agents, regardless of other traits and characteristics.

Furthermore, as is demonstrated herein, the bacteria of the genus Photorhabdus produce proteins that have functional activity as defined herein. Of particular interest are proteins produced by the species *Photorhabdus luminescens*. The inventions herein should in no way be limited to the strains which are disclosed herein. These strains illustrate for the first time that proteins produced by diverse isolates of Photorhabdus are toxic upon exposure to insects. Thus, included within the inventions described herein are the strains specified herein and any mutants thereof, as well as any strains or species of the genus Photorhabdus that have the functional activity described herein.

There are several terms that are used herein that have a particular meaning and are as follows:

By "functional activity" it is meant herein that the protein toxin(s) function as insect control agents in that the proteins are orally active, or have a toxic effect, or are able to disrupt or deter feeding, which may or may not cause death of the insect. When an insect comes into contact with an effective amount of toxin delivered via transgenic plant expression, formulated protein compositions(s), sprayable protein composition(s), a bait matrix or other delivery system, the results are typically death of the insect, or the insects do not feed upon the source which makes the toxins available to the insects.

By the use of the term "genetic material" herein, it is meant to include all genes, nucleic acid, DNA and RNA.

By "homolog" it is meant an amino acid sequence that is identified as possessing homology to a reference W-14 toxin polypeptide amino acid sequence.

By "homology" it is meant an amino acid sequence that has a similarity index of at least 33% and/or an identity index of at least 26% to a reference W-14 toxin polypeptide amino acid sequence, as scored by the GAP algorithm using the B10sum 62 protein scoring matrix (Wisconsin Package Version 9.0, Genetics Computer Group (GCG), Madison, Wis.).

By "identity" is meant an amino acid sequence that contains an identical residue at a given position, following alignment with a reference W-14 toxin polypeptide amino acid sequence by the GAP algorithm.

The protein toxins discussed herein are typically referred to as "insecticides". By insecticides it is meant herein that the protein toxins have a "functional activity" as further defined herein and are used as insect control agents.

By the use of the term "oligonucleotides" it is meant a macromolecule consisting of a short chain of nucleotides of either RNA or DNA. Such length could be at least one nucleotide, but typically are in the range of about 10 to about 12 nucleotides. The determination of the length of the oligonucleotide is well within the skill of an artisan and should not be a limitation herein. Therefore, oligonucleotides may be less than 10 or greater than 12.

By the use of the term "Photorhabdus toxin" it is meant any protein produced by a Photorhabdus microorganism strain which has functional activity against insects, where the Photorhabdustoxin could be formulated as a sprayable composition, expressed by a transgenic plant, formulated as a bait matrix, delivered via baculovirus, or delivered by any other applicable host or delivery system.

By the use of the term "toxic" or "toxicity" as used herein it is meant that the toxins produced by Photorhabdus have "functional activity" as defined herein.

By "truncated peptide" it is meant herein to include any peptide that is fragment(s) of the peptides observed to have functional activity.

By "substantial sequence homology" is meant either: a DNA fragment having a nucleotide sequence sufficiently similar to another DNA fragment to produce a protein having similar biochemical properties; or a polypeptide having an amino acid sequence sufficiently similar to another polypeptide to exhibit similar biochemical properties.

Fermentation broths from selected strains reported in Table 20 were used to determine the following: breadth of insecticidal toxin production by the Photorhabdus genus, the insecticidal spectrum of these toxins, and to provide source material to purify the toxin complexes. The strains characterized herein have been shown to have oral toxicity against a variety of insect orders. Such insect orders include but are not limited to Coleoptera, Homoptera, Lepidoptera, Diptera, Acarina, Hymenoptera and Dictyoptera.

As with other bacterial toxins, the rate of mutation of the bacteria in a population causes many related toxins slightly different in sequence to exist. Toxins of interest here are those which produce protein complexes toxic to a variety of insects upon exposure, as described herein. Preferably, the toxins are active against Lepidoptera, Coleoptera, Homopotera, Diptera, Hymenoptera, Dictyoptera and Acarina. The inventions herein are intended to capture the protein toxins homologous to protein toxins produced by the strains herein and any derivative strains thereof, as well as any protein toxins produced by Photorhabdus. These homologous proteins may differ in sequence, but do not differ in function from those toxins described herein. Homologous toxins are meant to include protein complexes of between 300 kDa to 2,000 kDa and are comprised of at least two (2) subunits, where a subunit is a peptide which may or may not be the same as the other subunit. Various protein subunits have been identified and are taught in the Examples herein. Typically, the protein subunits are between about 18 kDa to about 230 kDa; between about 160 kDa to about 230 kDa; 100 kDa to 160 kDa; about 80 kDa to about 100 kDa; and about 50 kDa to about 80 kDa.

As discussed above, some Photorhabdus strains can be isolated from nematodes. Some nematodes, elongated cylindrical parasitic worms of the phylum Nematoda, have evolved an ability to exploit insect larvae as a favored growth environment. The insect larvae provide a source of food for growing nematodes and an environment in which to reproduce. One dramatic effect that follows invasion of larvae by certain nematodes is larval death. Larval death results from the presence of, in certain nematodes, bacteria that produce an insecticidal toxin which arrests larval growth and inhibits feeding activity.

Interestingly, it appears that each genus of insect parasitic nematode hosts a particular species of bacterium, uniquely adapted for symbiotic growth with that nematode. In the interim since this research was initiated, the name of the bacterial genus Xenorhabdus was reclassified into the Xenorhabdus and the Photorhabdus. Bacteria of the genus Photorhabdus are characterized as being symbionts of Heterorhabditus nematodes while Xenorhabdus species are symbionts of the Steinernema species. This change in nomenclature is reflected in this specification, but in no way should a change in nomenclature alter the scope of the inventions described herein.

The peptides and genes that are disclosed herein are named according to the guidelines recently published in the Journal of Bacteriology "Instructions to Authors" p. i–xii (January 1996), which is incorporated herein by reference. The following peptides and genes were isolated from Photorhabdus strain W-14.

TABLE 1

Peptide/Gene Nomenclature
Toxin Complex

| 1<br>Peptide<br>Name | 2<br>Peptide<br>Sequence ID No.* | 3<br>Gene<br>Name | 4<br>Gene<br>Sequence ID No.* |
|---|---|---|---|
| tca genomic region | | | |
| TcaA | 34[c] | tcaA | 33 |
| TcaA$_i$ | pro-peptide | tcaA | — |
| TcaA$_{ii}$ | [15][a], 34[c] | tcaA | — |
| TcaA$_{iii}$ | [4][a], 35[c] | tcaA | — |
| TcaA$_{iv}$ | [62][a] | tcaA | — |
| TcaB | [3][a], (19, 20)[b], 26[c] | tcaB | 25 |
| TcaB$_i$ | [3][a], (19, 20)[b], 28[c] | tcaB | 27 |
| TcaB$_{ii}$ | [5][a], 30[c] | tcaB | 29 |
| TcaC | [2][a], 32[c] | tcaC | 31 |
| tcb genomic region | | | |
| TcbA | 12[c], [16][a], (21, 22, 23, 24)[b] | tcbA | 11 |
| TcbA$_i$ | pro-peptide | tcbA | — |
| TcbA$_{ii}$ | [1][a], (21, 22, 23, 24)[b], 53[c] | tcbA | 52 |
| TcbA$_{iii}$ | [40][a], 55[c] | tcbA | 54 |
| tcc genomic region | | | |
| TccA | [8][a], 57[c] | tccA | 56 |
| TccB | [7][a], 59[c] | tccB | 58 |
| TccC | 61[c] | tccC | 60 |
| tcd genomic region | | | |
| TcdA | (17, 18, 37, 38, 39, 42, 43)[b], 47[c] | tcdA | (36)[d], 46 |
| TcdA$_i$ | pro-peptide | tcdA | — |
| TcdA$_{ii}$ | [13][a], (17, 18, 37, 38, 39)[b], 49[c] | tcdA | 48 |
| TcdA$_{iii}$ | [41][a], (42, 43)[b], 51[c] | tcdA | 50 |
| TcdB | [14][a] | tcdB | — |

[a]Sequence ID No.'s in brackets are peptide N-termini;
[b]Numbers in parentheses are N-termini of internal peptide tryptic fragments
[c]deduced from gene sequence
[d]internal gene fragment The sequences listed above are grouped by genomic region. More specifically, the *Photorhabdus luminesence* bacteria (W-14) has at least four distinct genomic regions-tca, tcb, tcc and tcd. As can be seen in Table 1, peptide products are produced from these distinct genomic regions. Furthermore, as illustrated in the Examples, specifically Examples 15 and 21, individual gene products produced from three genomic regions are associated with insect activity. There is also considerable homology between these four genomic regions.

As is further illustrated in the Examples, the tcbA gene was expressed in *E. coli* as two possible biological active protein fragments (TcbA and TcbAii/iii). The tcda gene was also expressed in *E. coli*. As illustrated in Example 16, when the native unprocessed TcbA toxin was treated with the endogeneous metalloproteases or insect gut contents containing proteases, the TcbA protein toxin was processed into smaller subunits that were less than the size of the native peptides and Southern Corn Rootworm activity increased. The smaller toxin peptides remained associated as part of a toxin complex. It may be desirable in some situations to increase activation of the toxin(s) by proteolytic processing or using truncated peptides. Thus, it may be more desirable to use truncated peptide(s) in some applications, i.e., commercial transgenic plant applications.

In addition to the W-14 strain, there are other species within the Photorhabdus genus that have functional activity which is differential (specifically see Tables 20 and 36). Even though there is differential activity, the amino acid sequences in some cases have substantial sequence homology. Moreover, the molecular probes indicate that some genes contained in the strains are homologous to the genes contained in the W-14 strain. In fact all of the strains illustrated herein have one or more homologs of W-14 toxin genes. The antibody data in Example 26 and the N-terminal sequence data in Example 25 further support the conclusion that there is homology and identity (based on amino acid sequence) between the protein toxin(s) produced by these strains. At the molecular level, the W-14 gene probes indicated that the homologs or the W-14 genes themselves (Tables 37, 38, and 39) are dispersed throughout the Photorhabdus genus. Further, it is possible that new toxin genes exist in other strains which are not homologous to W-14, but maintain overall protein attributes (see specifically Examples 14 and 25).

Even though there is homology or identity between toxin genes produced by the Photorhabdus strains, the strains themselves are quite diverse. Using polymerase chain reaction technology further discussed in Example 22, most of the strains illustrated herein are quite distinguishable. For example as can be seen in FIGS. 5, the percentage relative similarity of some of the strains, such as HP8B and NC-1, was about 0.8, which indicates that the strains are similar, while HP88 and Hb was about 0.1, which indicates substantial diversity. Therefore, even though the insect toxin genes or gene products that the strains produce are the same or similar, the strains themselves are diverse.

In view of the data further disclosed in the Examples and discussions herein, it is clear that a new and unique family of insecticidal protein toxin(s) has been discovered. It has been further illustrated herein that these toxin(s) widely exist within bacterial strains of the Photorhabdus genus. It may also be the case that these toxin genes widely exist within the family Enterobacteracaea. Antibodies prepared as described in Example 21 or gene probes prepared as described in Example 25 may be used to further screen for bacterial strains within the family Enterobacteracaea that produce the homologous toxin(s) that have functional activity. It may also be the case that specific primer sets exist that could facilitate the identification of new genes within the Photorhabdus genus or family Enterobacteracaea.

As stated above, the antibodies may be used to rapidly screen bacteria of the genus Photorhabdus or the family Enterbacteracaea for homologous toxin products as illustrated in Example 26. Those skilled in the art are quite familiar with the use of antibodies as an analysis or screening tool (see U.S. Pat. No. 5,430,137, which is incorporated herein by reference). Moreover, it is generally accepted in the literature that antibodies are elicited against 6 to 20 amino acid residue segments that tend to occupy exposed surface of polypeptides (Current Protocols in Immunology, Coligan et al, National Institutes of Health, John Wiley & Sons, Inc.). Usually the amino acid consist of contiguous amino acid residues, however, in certain cases they may be formed by non-contiguous amino acids that are constrained by specific conformation. The amino acid segments recognized by antibodies are highly specific and commonly referred to epitopes. The amino acid fragment can be generated by chemical and/or enzymatic cleavage of the native protein, by automated, solid-phase peptide synthesis, or by production from genetic engineering organisms. Polypeptide fragments can be isolated by a variety and/or combination of HPLC and FPLC chromatographic methods known in the art. Selection of polypeptide fragment can be aided by the use of algorithms, for example Kyte and Doolittle, 1982, Journal of Molecular Biology 157: 105–132 and Chou and Fasman, 1974, Biochemistry 13: 222–245, that predict those sequences most likely to exposed on the surface of the protein. For preparation of immunogen containing the polypeptide fragment of interest, in general, polypeptides are covalently coupled using chemical reactions to carrier proteins such as keyhole limpet hemocyanin via free amino (lysine), sulfhydyl (cysteine), phenolic (tyrosine) or carboxylic (aspartate or glutamate) groups. Immunogen with an adjuvant is injected in animals, such as mice or rabbits, or chickens to elicit an immune response against the immunogen. Analysis of antibody titer in antisera of inject animals against polypeptide fragment can be determined by a variety of immunological methods such as ELISA and Western blot. Alternatively, monoclonal antibodies can be prepared using spleen cells of the injected animal for fusion with tumor cells to produce immortalized hybridomas cells producing a single antibody species. Hybridomas cells are screened using immunological methods to select lines that produce a specific antibody to the polypeptide fragment of interest. Purification of antibodies from different sources can be performed by a variety of antigen affinity or antibody affinity columns or other chromatographic HPLC or FPLC methods.

The toxins described herein are quite unique in that the toxins have functional activity, which is key to developing an insect management strategy. In developing an insect management strategy, it is possible to delay or circumvent the protein degradation process by injecting a protein directly into an organism, avoiding its digestive tract. In such cases, the protein administered to the organism will retain its function until it is denatured, non-specifically degraded, or eliminated by the immune system in higher organisms. Injection into insects of an insecticidal toxin has potential application only in the laboratory, and then only on large insects which are easily injected. The observation that the insecticidal protein toxins herein described exhibits their toxic activity after oral ingestion or contact with the toxins permits the development of an insect management plan based solely on the ability to incorporate the protein toxins into the insect diet. Such a plan could result in the production of insect baits.

The Photorhabdus toxins may be administered to insects in a purified form. The toxins may also be delivered in amounts from about 1 to about 100 mg/liter of broth. This may vary upon formulation condition, conditions of the inoculum source, techniques for isolation of the toxin, and the like. The toxins may be administered as an exudate secretion or cellular protein originally expressed in a heterologous prokaryotic or eukaryotic host. Bacteria are typically the hosts in which proteins are expressed. Eukaryotic hosts could include but are not limited to plants, insects and yeast. Alternatively, the toxins may be produced in bacteria or transgenic plants in the field or in the insect by a baculovirus vector. Typically the toxins will be introduced to the insect by incorporating one or more of the toxins into the insects' feed.

Complete lethality to feeding insects is useful but is not required to achieve useful toxicity. If the insects avoid the toxin or cease feeding, that avoidance will be useful in some applications, even if the effects are sublethal. For example, if insect resistant transgenic crop plants are desired, a reluctance of insects to feed on the plants is as useful as lethal toxicity to the insects since the ultimate objective is protection of the plants rather than killing the insect.

There are many other ways in which toxins can be incorporated into an insect's diet. As an example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, the protein could be genetically engineered directly into an insect food source. For instance, the major food source of many insect larvae is plant material.

By incorporating genetic material that encodes the insecticidal properties of the Photorhabdus toxins into the genome of a plant eaten by a particular insect pest, the adult or larvae would die after consuming the food plant. Numerous members of the monocotyledonous and dictyledenous genera have been transformed. Transgenic agronmonic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. No. 4,945,050 to Cornell and U.S. Pat. No. 5,141,131 to DowElanco). Plants may be transformed using Agrobacterium technology, see U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to MaxPlanck, European Patent Applications 604662 and 627752 to Japan Tobacco, European Patent Applications 0267159, and 0292435 and U.S. Pat. No. 5,231,019 all to Ciba Geigy, U.S. Pat. Nos. 5,463,174 and 4,762,785 both to Calgene, and U.S. Pat. Nos. 5,004,863 and 5,159,135 both to Agracetus. Other transformation technology includes whiskers technology, see U.S. Pat. Nos. 5,302,523 and 5,464,765 both to Zeneca. Electroporation technology has also been used to transform plants, see WO 87/06614 to Boyce Thompson Institute, U.S. Pat. Nos. 5,472,869 and 5,384,253 both to Dekalb, WO9209696 and WO9321335 both to PGS. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques within the skill of an artisan.

Another variable is the choice of a selectable marker. The preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which code for resistance or tolerance to glyphosate; hygromycin; methotrexate; phosphinothricin (bialophos); imidazolinones, sulfonylureas and triazolopyrimidine herbicides, such as chlorosulfuron; bromoxynil, dalapon and the like.

In addition to a selectable marker, it may be desirous to use a reporter gene. In some instances a reporter gene may be used without a selectable marker. Reporter genes are genes which are typically not present or expressed in the recipient organism or tissue. The reporter gene typically encodes for a protein which provides for some phenotypic change or enzymatic property. Examples of such genes are provided in K. Weising et al. Ann. Rev. Genetics, 22, 421 (1988), which is incorporated herein by reference. A preferred reporter gene is the glucuronidase (GUS) gene.

Regardless of transformation technique, the gene is preferably incorporated into a gene transfer vector adapted to express the Photorhabdus toxins in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the cauliflower mosaic virus (35S and 19S), reengineered 35S, known as 35T (see PCT/US96/16582, WO 97/13402 published Apr. 17, 1997, which is incorporated herein by reference) and the like may be used.

Plant promoters include, but are not limited to ribulose-1,6-bisphosphate (RUBP) carboxylase small subunit (ssu), beta-conglycinin promoter, phaseolin promoter, ADH promoter, heat-shock promoters and tissue specific promoters. Promoters may also contain certain enhancer sequence elements that may improve the transcription efficiency. Typical enhancers include but are not limited to Adh-intron 1 and Adh-intron 6. Constitutive promoters may be used. Constitutive promoters direct continuous gene expression in all cells types and at all times (e.g., actin, ubiquitin, CaMV 35S). Tissue specific promoters are responsible for gene expression in specific cell or tissue types, such as the leaves or seeds (e.g., zein, oleosin, napin, ACP) and these promoters may also be used. Promoters may also be are active during a certain stage of the plants' development as well as active in plant tissues and organs. Examples of such promoters include but are not limited to pollen-specific, embryo specific, corn silk specific, cotton fiber specific, root specific, seed endosperm specific promoters and the like.

Under certain circumstances it may be desirable to use an inducible promoter. An inducible promoter is responsible for expression of genes in response to a specific signal, such as: physical stimulus (heat shock genes); light (RUBP carboxylase); hormone (Em); metabolites; and stress. Other desirable transcription and translation elements that function in plants may be used. Numerous plant-specific gene transfer vectors are known to the art.

In addition, it is known that to obtain high expression of bacterial genes in plants it is preferred to reengineer the bacterial genes so that they are more efficiently expressed in the cytoplasm of plants. Maize is one such plant where it is preferred to reengineer the bacterial gene(s) prior to transformation to increase the expression level of the toxin in the plant. One reason for the reengineering is the very low G+C content of the native bacterial gene(s) (and consequent skewing towards high A+T content). This results in the generation of sequences mimicking or duplicating plant gene control sequences that are known to be highly A+T rich. The presence of some A+T-rich sequences within the DNA of the gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of reengineered bacterial gene(s), more preferably referred to as plant optimized gene(s), is to generate a DNA sequence having a higher G+C content, and preferably one close to that of plant genes coding for metabolic enzymes. Another goal in the design of the plant optimized gene(s) is to generate a DNA sequence that not only has a higher G+C content, but by modifying the sequence changes, should be made so as to not hinder translation.

An example of a plant that has a high G+C content is maize. The table below illustrates how high the G+C content is in maize. As in maize, it is thought that G+C content in other plants is also high.

TABLE 2

Compilation of G + C Contents of Protein Coding Regions of Maize Genes

| Protein Class[a] | Range % G + C | Mean % G + C[b] |
|---|---|---|
| Metabolic Enzymes (40) | 44.4–75.3 | 59.0 (8.0) |
| Storage Proteins | | |
| Group I (23) | 46.0–51.9 | 48.1 (1.3) |
| Group II (13) | 60.4–74.3 | 67.5 (3.2) |
| Group I + II (36) | 46.0–74.3 | 55.1 (9.6)[c] |
| Structural Proteins (18) | 48.6–70.5 | 63.6 (6.7) |
| Regulatory Proteins (5) | 57.2–68.9 | 62.0 (4.9) |
| Uncharacterized Proteins (9) | 41.5–70.3 | 64.3 (7.2) |
| All Proteins (108) | 44.4–75.3 | 60.8 (5.2) |

[a]Number of genes in class given in parentheses.
[b]Standard deviations given in parentheses.
[c]Combined groups mean ignored in calculation of overall mean.

For the data in Table 2, coding regions of the genes were extracted from GenBank (Release 71) entries, and base compositions were calculated using the MacVector™ program (IBI, New Haven, Conn.). Intron sequences were ignored in the calculations. Group I and II storage protein gene sequences were distinguished by their marked difference in base composition.

Due to the plasticity afforded by the redundancy of the genetic code (i.e., some amino acids are specified by more than one codon), evolution of the genomes of different organisms or classes or organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a gene's mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by the synthesis of low levels of the encoded protein.

In order to reengineer the bacterial gene(s), the codon bias of the plant is determined. The codon bias is the statistical codon distribution that the plant uses for coding its proteins. After determining the bias, the percent frequency of the codons in the gene(s) of interest is determined. The primary codons preferred by the plant should be determined as well as the second and third choice of preferred codons. The amino acid sequence of the protein of interest is reverse translated so that the resulting nucleic acid sequence codes for the same protein as the native bacterial gene, but the resulting nucleic acid sequence corresponds to the first preferred codons of the desired plant. The new sequence is analyzed for restriction enzyme sites that might have been created by the modification. The identified sites are further modified by replacing the codons with second or third choice preferred codons. Other sites in the sequence which could affect the transcription or translation of the gene of interest are the exon:intron 5' or 3' junctions, poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice. It is preferred that the plant optimized gene(s) contains about 63% of first choice codons, between about 22% to about 37% second choice codons, and between 15% and 0% third choice codons, wherein the total percentage is 100%. Most preferred the plant optimized gene(s) contain about 63% of first choice codons, at least about 22% second choice codons, about 7.5% third choice codons, and about 7.5% fourth choice codons, wherein the total percentage is 100%. The method described above enables one skilled in the art to modify gene(s) that are foreign to a particular plant so that the genes are optimally expressed in plants. The method is further illustrated in application PCT/US96/16582, WO 97/13402 published Apr. 17, 1997.

Thus, in order to design plant optimized gene(s) the amino acid sequence of the toxins are reverse translated into a DNA sequence, utilizing a nonredundant genetic code established from a codon bias table compiled for the gene DNA sequence for the particular plant being transformed. The resulting DNA sequence, which is completely homogeneous in codon usage, is further modified to establish a DNA sequence that, besides having a higher degree of codon diversity, also contains strategically placed restriction enzyme recognition sites, desirable base composition, and a lack of sequences that might interfere with transcription of the gene, or translation of the product mRNA.

It is theorized that bacterial genes may be more easily expressed in plants if the bacterial genes are expressed in the plastids. Thus, it may be possible to express bacterial genes in plants, without optimizing the genes for plant expression, and obtain high express of the protein. See U.S. Pat. Nos. 4,762,785; 5,451,513 and 5,545,817, which are incorporated herein by reference.

One of the issues regarding commercial exploiting transgenic plants is resistance management. This is of particular concern with *Bacillus thuringiensis* toxins. There are numerous companies commerically exploiting *Bacillus thuringiensis* and there has been much concern about Bt toxins becoming resistant. One strataegy for insect resistant management would be to combine the toxins produced by Photorhabdus with toxins such as Bt, vegetative insect proteins (Ciba Geigy) or other toxins. The combinations could be formulated for a sprayable application or could be molecular combinations. Plants could be transformed with Photorhabdus genes that produce insect toxins and other insect toxin genes such as Bt as with other insect toxin genes such as Bt.

European Patent Application 0400246A1 describes transformation of 2 Bt in a plant, which could be any 2 genes. Another way to produce a transgenic plant that contains more than one insect resistant gene would be to produce two plants, with each plant containing an insect resistant gene. These plants would be backcrossed using traditional plant breeding techniques to produce a plant containing more than one insect resistant gene.

In addition to producing a transformed plant containing plant optimized gene(s), there are other delivery systems where it may be desirable to reengineer the bacterial gene(s). Along the same lines, a genetically engineered, easily isolated protein toxin fusing together both a molecule attractive to insects as a food source and the insecticidal activity of the toxin may be engineered and expressed in bacteria or in eukaryotic cells using standard, well-known techniques. After purification in the laboratory such a toxic agent with "built-in" bait could be packaged inside standard insect trap housings.

Another delivery scheme is the incorporation of the genetic material of toxins into a baculovirus vector. Baculoviruses infect particular insect hosts, including those desirably targeted with the Photorhabdus toxins. Infectious baculovirus harboring an expression construct for the Photorhabdus toxins could be introduced into areas of insect infestation to thereby intoxicate or poison infected insects.

Transfer of the insecticidal properties requires nucleic acid sequences encoding the coding the amino acid sequences for the Photorhabdus toxins integrated into a protein expression vector appropriate to the host in which the vector will reside. One way to obtain a nucleic acid sequence encoding a protein with insecticidal properties is to isolate the native genetic material which produces the toxins from Photorhabdus, using information deduced from the toxin's amino acid sequence, large portions of which are set forth below. As described below, methods of purifying the proteins responsible for toxin activity are also disclosed.

Using N-terminal amino acid sequence data, such as set forth below, one can construct oligonucleotides complementary to all, or a section of, the DNA bases that encode the first amino acids of the toxin. These oligonucleotides can be radiolabeled and used as molecular probes to isolate the genetic material from a genomic genetic library built from genetic material isolated from strains of Photorhabdus. The genetic library can be cloned in plasmid, cosmid, phage or phagemid vectors. The library could be transformed into *Escherichia coli* and screened for toxin production by the transformed cells using antibodies raised against the toxin or direct assays for insect toxicity.

This approach requires the production of a battery of oligonucleotides, since the degenerate genetic code allows an amino acid to be encoded in the DNA by any of several three-nucleotide combinations. For example, the amino acid arginine can be encoded by nucleic acid triplets CGA, CGC, CGG, CGT, AGA, and AGG. Since one cannot predict which triplet is used at those positions in the toxin gene, one must prepare oligonucleotides with each potential triplet represented. More than one DNA molecule corresponding to a protein subunit may be necessary to construct a sufficient number of oligonucleotide probes to recover all of the protein subunits necessary to achieve oral toxicity.

From the amino acid sequence of the purified protein, genetic materials responsible for the production of toxins can readily be isolated and cloned, in whole or in part, into an expression vector using any of several techniques well-known to one skilled in the art of molecular biology. A typical expression vector is a DNA plasmid, though other transfer means including, but not limited to, cosmids, phagemids and phage are also envisioned. In addition to features required or desired for plasmid replication, such as an origin of replication and antibiotic resistance or other form of a selectable marker such as the bar gene of *Streptomyces hygroscopicus* or *viridochromogenes*, protein expression vectors normally additionally require an expression cassette which incorporates the cis-acting sequences necessary for transcription and translation of the gene of interest. The cis-acting sequences required for expression in prokaryotes differ from those required in eukaryotes and plants.

A eukaryotic expression cassette requires a transcriptional promoter upstream (5') to the gene of interest, a transcriptional termination region such as a poly-A addition site, and a ribosome binding site upstream of the gene of interest's first codon. In bacterial cells, a useful transcriptional promoter that could be included in the vector is the T7 RNA Polymerase-binding promoter. Promoters, as previously described herein, are known to efficiently promote transcription of mRNA. Also upstream from the gene of interest the vector may include a nucleotide sequence encoding a signal sequence known to direct a covalently linked protein to a particular compartment of the host cells such as the cell surface.

Insect viruses, or baculoviruses, are known to infect and adversely affect certain insects. The affect of the viruses on insects is slow, and viruses do not stop the feeding of insects. Thus viruses are not viewed as being useful as insect pest control agents. Combining the Photorhabdus toxins genes into a baculovirus vector could provide an efficient way of transmitting the toxins while increasing the lethality of the virus. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

As is described above, it might become necessary to modify the sequence encoding the protein when expressing it in a non-native host, since the codon preferences of other hosts may differ from that of Photorhabdus. In such a case, translation may be quite inefficient in a new host unless compensating modifications to the coding sequence are made. Additionally, modifications to the amino acid sequence might be desirable to avoid inhibitory cross-reactivity with proteins of the new host, or to refine the insecticidal properties of the protein in the new host. A genetically modified toxin gene might encode a toxin exhibiting, for example, enhanced or reduced toxicity, altered insect resistance development, altered stability, or modified target species specificity.

In addition to the Photorhabdus genes encoding the toxins, the scope of the present invention is intended to include related nucleic acid sequences which encode amino acid biopolymers homologous to the toxin proteins and which retain the toxic effect of the Photorhabdus proteins in insect species after oral ingestion.

For instance, the toxins used in the present invention seem to first inhibit larval feeding before death ensues. By manipulating the nucleic acid sequence of Photorhabdus toxins or its controlling sequences, genetic engineers placing the toxin gene into plants could modulate its potency or its mode of action to, for example, keep the eating-inhibitory activity while eliminating the absolute toxicity to the larvae. This change could permit the transformed plant to survive until harvest without having the unnecessarily dramatic effect on the ecosystem of wiping out all target insects. All such modifications of the gene encoding the toxin, or of the protein encoded by the gene, are envisioned to fall within the scope of the present invention.

Other envisioned modifications of the nucleic acid include the addition of targeting sequences to direct the toxin to particular parts of the insect larvae for improving its efficiency.

Strains W-14, ATCC 55397, 43948, 43949, 43950, 43951, 43952 have been deposited in the American Type Culture Collection, 12301 Parklawn Drive, Rockville, Md. 20852 USA. Amino acid and nucleotide sequence data for the W-14 native toxin (ATCC 55397) is presented below. Isolation of the genomic DNA for the toxins from the bacterial hosts is also exemplified herein. The other strains identified herein have been deposited with the United States Department of Agriculture, 1815 North University Drive, Peoria, Ill. 61604. The deposits were made under the Budapest Treaty. The deposited strains and the corresponding deposit numbers are indicated in the following table:

| strain name | deposit number |
| --- | --- |
| W-14 | ATCC 55397 |
| WX1 | NRRL B-21710 |
| WX2 | NRRL B-21711 |
| WX3 | NRRL B-21712 |
| WX4 | NRRL B-21713 |
| WX5 | NRRL B-21714 |
| WX6 | NRRL B-21715 |
| WX7 | NRRL B-21716 |
| WX8 | NRRL B-21717 |
| WX9 | NRRL B-21718 |
| WX10 | NRRL B-21719 |
| WX11 | NRRL B-21720 |
| WX12 | NRRL B-21721 |
| WX14 | NRRL B-21722 |
| WX15 | NRRL B-21723 |
| H9 | NRRL B-21727 |
| Hb | NRRL B-21726 |
| Hm | NRRL B-21725 |
| HP88 | NRRL B-21724 |
| NC-1 | NRRL B-21728 |
| W30 | NRRL B-21729 |
| WIR | NRRL B-21730 |
| B2 | NRRL B-21731 |
| ATCC 43948 | ATCC 55878 |
| ATCC 43949 | ATCC 55879 |
| ATCC 43950 | ATCC 55880 |
| ATCC 43951 | ATCC 55881 |
| ATCC 43952 | ATCC 55882 |
| DEP1 | NRRL B-21707 |
| DEP2 | NRRL B-21708 |
| DEP3 | NRRL B-21709 |
| *P. zealandrica* | NRRL B-21683 |
| *P. hepialus* | NRRL B-21684 |
| HB-Arg | NRRL B-21685 |
| HB Oswego | NRRL B-21686 |

-continued

| strain name | deposit number |
| --- | --- |
| Hb Lewiston | NRRL B-21687 |
| K-122 | NRRL B-21688 |
| HMGD | NRRL B-21689 |
| Indicus | NRRL B-21690 |
| GD | NRRL B-21691 |
| PWH-5 | NRRL B-21692 |
| Megidis | NRRL B-21693 |
| HF-85 | NRRL B-21694 |
| A. Cows | NRRL B-21695 |
| MP1 | NRRL B-21696 |
| MP2 | NRRL B-21697 |
| MP3 | NRRL B-21698 |
| MP4 | NRRL B-21699 |
| MP5 | NRRL B-21700 |
| GL98 | NRRL B-21701 |
| G1101 | NRRL B-21702 |
| GL138 | NRRL B-21703 |
| GL155 | NRRL B-21704 |
| GL217 | NRRL B-21705 |
| GL257 | NRRL B-21706 |

Standard and molecular biology techniques were followed and taught in the specification herein. Additional information may be found in Sambrook, J., Fritsch, E. F., and Maniatis, T. (1989), *Molecular Cloning, A Laboratory Manual*, Cold Spring Harbor Press; *Current Protocol in Molecular Biology*, ed. F. M. Ausubel et al., (1997), which are both incorporated herein by reference.

The following abbreviations are used throughout the Examples: Tris=tris (hydroxymethyl)amino methane; SDS=sodium dodecyl sulfate; EDTA=ethylenediaminetetraacetic acid, IPTG=isopropylthio-B-galactoside, X-gal=5-bromo-4-chloro-3-indoyl-β-D-galactoside, CTAB=cetyltrimethylammonium bromide; kbp=kilobase pairs; DATP, dCTP, dGTP, dTTP, 1=2'-deoxynucleoside 5'-triphosphates of adenine, cytosine, guanine, thymine, and inosine, respectively; ATP=adenosine 5'triphosphate.

EXAMPLE 1

Purification of Toxin from *Photorhabdus luminescens* and Demonstration of Toxicity After Oral Delivery of Purified Toxin The insecticidal protein toxin of the present invention was purified from *Photorhabdus luminescens* strain W-14, ATCC Accession Number 55397. Stock cultures of *Photorhabdus luminescens* were maintained on petri dishes containing 2% Proteose Peptone No. 3 (i.e., PP3, Difco Laboratories, Detroit Mich.) in 1.5% agar, incubated at 25° C. and transferred weekly. Colonies of the primary form of the bacteria were inoculated into 200 ml of PP3 broth supplemented with 0.5% polyoxyethylene sorbitan mono-stearate (TWEEN-60, Sigma Chemical Company, St. Louis, Mo.) in a one liter flask. The broth cultures were grown for 72 hours at 30° C. on a rotary shaker. The toxin proteins can be recovered from cultures grown in the presence or absence of TWEEN surfactant; however, the absence of Tween can affect the form of the bacteria grown and the profile of-proteins produced by the bacteria. In the absence of TWEEN surfactant, a variant shift occurs insofar as the molecular weight of at least one identified toxin subunit shifts from about 200 kDa to about 185 kDa.

The 72 hour cultures were centrifuged at 10,000×g for 30 minutes to remove cells and debris. The supernatant fraction that contained the insecticidal activity was decanted and brought to 50 mM $K_2HPO_4$ by adding an appropriate volume of 1.0 M $K_2HPO_4$. The pH was adjusted to 8.6 by adding potassium hydroxide. This supernatant fraction was then mixed with DEAE-SEPHACEL resin (Pharmacia LKB Biotechnology) which had been equilibrated with 50 mM $K_2HPO_4$. The toxic activity was adsorbed to the DEAE resin. This mixture was then poured into a 2.6×40 cm column and washed with 50 mM $K_2HPO_4$ at room temperature at a flow rate of 30 ml/hr until the effluent reached a steady baseline UV absorbance at 280 nm. The column was then washed with 150 mM KCl until the effluent again reached a steady 280 nm baseline. Finally the column was washed with 300 mM KCl and fractions were collected.

Fractions containing the toxin were pooled and filter sterilized using a 0.2 micron pore membrane filter. The toxin was then concentrated and equilibrated to 100 mM $KPO_4$, pH 6.9, using an ultrafiltration membrane with a molecular weight cutoff of 100 kDa at 4° C. (Centriprep 100, Amicon Division-W.R. Grace and Company). A 3 ml sample of the toxin concentrate was applied to the top of a 2.6×95 cm SEPHACRYL resin S-400 HR gel filtration column (Pharmacia LKB Biotechnology). The eluent buffer was 100 mM $KPO_4$, pH 6.9, which was run at a flow rate of 17 ml/hr, at 4° C. The effluent was monitored at 280 nm.

Fractions were collected and tested for toxic activity. Toxicity of chromatographic fractions was examined in a biological assay using *Manduca sexta* larvae. Fractions were either applied directly onto the insect diet (Gypsy moth wheat germ diet, ICN Biochemicals Division—ICN Biomedicals, Inc.) or administered by intrahemocelic injection of a 5 μl sample through the first proleg of 4th or 5th instar larva using a 30 gauge needle. The weight of each larva within a treatment group was recorded at 24 hour intervals. Toxicity was presumed if the insect ceased feeding and died within several days of consuming treated insect diet or if death occurred within 24 hours after injection of a fraction.

The toxic fractions were pooled and concentrated using the Centriprep-100 and were then analyzed by HPLC using a 7.5 mm×60 cm TSK-GEL G-4000 SW gel permeation column with 100 mM potassium phosphate, pH 6.9 eluent buffer running at 0.4 ml/min. This analysis revealed the toxin protein to be contained within a single sharp peak that eluted from the column with a retention time of approximately 33.6 minutes. This retention time corresponded to an estimated molecular weight of 1,000 kDa. Peak fractions were collected for further purification while fractions not containing this protein were discarded. The peak eluted from the HPLC absorbs UV light at 218 and 280 nm but did not absorb at 405 nm. Absorbance at 405 nm was shown to be an attribute of xenorhabdin antibiotic compounds.

Electrophoresis of the pooled peak fractions in a non-denaturing agarose gel (Metaphor Agarose, FMC BioProducts) showed that two protein complexes are present in the peak. The peak material, buffered in 50 mM Tris-HCl, pH 7.0, was separated on a 1.5% agarose stacking gel buffered with 100 mM Tris-HCl at pH 7.0 and 1.9% agarose resolving gel buffered with 200 mM Tris-borate at pH 8.3 under standard buffer conditions (anode buffer 1M Tris-HCl, pH 8.3; cathode buffer 0.025 M Tris, 0.192 M glycine). The gels were run at 13 mA constant current at 15° C. until the phenol red tracking dye reached the end of the gel. Two protein bands were visualized in the agarose gels using Coomassie brilliant blue staining.

The slower migrating band was referred to as "protein band 1" and faster migrating band was referred to as "protein band 2." The two protein bands were present in approximately equal amounts. The Coomassie stained agarose gels were used as a guide to precisely excise the two protein bands from unstained portions of the gels. The excised pieces containing the protein bands were macerated and a small amount of sterile water was added. As a control, a portion of the gel that contained no protein was also excised and treated in the same manner as the gel pieces containing the protein. Protein was recovered from the gel pieces by electroelution into 100 mM Tris-borate pH 8.3, at 100 volts (constant voltage) for two hours. Alternatively, protein was passively eluted from the gel pieces by adding an equal volume of 50 mM Tris-HCl, pH 7.0, to the gel pieces, then incubating at 30° C. for 16 hours. This allowed the protein to diffuse from the gel into the buffer, which was then collected.

Results of insect toxicity tests using HPLC-purified toxin (33.6 min. peak) and agarose gel purified toxin demonstrated toxicity of the extracts. Injection of 1.5 μg of the HPLC purified protein kills within 24 hours. Both protein bands 1 and 2, recovered from agarose gels by passive elution or electroelution, were lethal upon injection. The protein concentration estimated for these samples was less than 50 ng/larva. A comparison of the weight gain and the mortality between the groups of larvae injected with protein bands 1 or 2 indicate that protein band 1 was more toxic by injection delivery.

When HPLC-purified toxin was applied to larval diet at a concentration of 7.5 μg/larva, it caused a halt in larval weight gain (24 larvae tested). The larvae begin to feed, but after consuming only a very small portion of the toxin treated diet they began to show pathological symptoms induced by the toxin and the larvae cease feeding. The insect frass became discolored and most larva showed signs of diarrhea. Significant insect mortality resulted when several 5 μg toxin doses were applied to the diet over a 7–10 day period.

Agarose-separated protein band 1 significantly inhibited larval weight gain at a dose of 200 ng/larva. Larvae fed similar concentrations of protein band 2 were not inhibited and gained weight at the same rate as the control larvae. Twelve larvae_were fed eluted protein and 45 larvae were fed protein-containing agarose pieces. These two sets of data indicate that protein band 1 was orally toxic to *Manduca sexta*. In this experiment it appeared that protein band 2 was not toxic to *Manduca sexta*.

Further analysis of protein bands 1 and 2 by SDS-PAGE under denaturing conditions showed that each band was composed of several smaller protein subunits. Proteins were visualized by Coomassie brilliant blue staining followed by silver staining to achieve maximum sensitivity.

The protein subunits in the two bands were very similar. Protein band 1 contains 8 protein subunits of 25.1, 56.2, 60.8, 65.6, 166, 171, 184 and 208 kDa. Protein band 2 had an identical profile except that the 25.1, 60.8, and 65.6 kDa proteins were not present. The 56.2, 60.8, 65.6, and 184 kDa proteins were present in the complex of protein band 1 at approximately equal concentrations and represent 80% or more of the total protein content of that complex.

The native HPLC-purified toxin was further characterized as follows. The toxin was heat labile in that after being heated to 60° C. for 15 minutes it lost its ability to kill or to inhibit weight gain when injected or fed to *Manduca sexta* larvae. Assays were designed to detect lipase, type C phospholipase, nuclease or red blood cell hemolysis activities and were performed with purified toxin. None of these activities were present. Antibiotic zone inhibition assays were also done and the purified toxin failed to inhibit growth of Gram-negative or -positive bacteria, yeast or filamentous fungi, indicating that the toxic is not a xenorhabdin antibiotic.

The native HPLC-purified toxin was tested for ability to kill insects other than *Manduca sexta*. Table 3 lasts insects killed by the HPLC-purified *Photorhabdus luminescens* toxin in this study.

TABLE 3

Insects Killed by *Photorhabdus luminescens* Toxin

| Common Name | Order | Genus and species | Route of Delivery |
| --- | --- | --- | --- |
| Tobacco horn worm | Lepidoptera | *Manduca sexta* | Oral and injected |
| Mealworm | Coleoptera | *Tenebrio molitor* | Oral |
| Pharaoh ant | Hymenoptera | *Monomorium pharoanis* | Oral |
| German cockroach | Dictyoptera | *Blattella germanica* | Oral and injected |
| Mosquito | Diptera | *Aedes aegypti* | Oral |

Further Characterization of the High Molecular Weight Toxin Complex

In yet further analysis, the toxin protein complex was subjected to further characterization from W-14 growth medium. The culture conditions and initial purification steps through the S-400 HR column were identical to those described above. After isolation of the high molecular weight toxin complex from the S-400 HR column fractions, the toxic fractions were equilibrated with 10 mM Tris-HCl, pH 8.6, and concentrated in the centriplus 100 (Amicon) concentrators. The protein toxin complex was then applied to a weak anion exchange (WAX) column, Vydac 301VPH575 (Hesparia, Calif.), at a flow rate of 0.5 ml/min. The proteins were eluted with a linear potassium chloride gradient, 0–250 mM KCl, in 10 mM Tris-HCl pH 8.6 for 50 min. Eight protein peaks were detected by absorbance at 280 nm.

Bioassays using neonate southern corn rootworm (*Diabrotica undecimpunctata howardi*, SCR) larvae and tobacco horn worm (*Manduca sexta*, THW) were performed on all fractions eluted from the HPLC column. THW were grown on Gypsy Moth wheat germ diet (ICN) at 25° C. with a 16 hr light 8 hr dark cycle. SCR were grown on Southern Corn Rootworm Larval Insecta-Diet (BioServ) at 25° C. with a 16 hr light/8 hr dark cycle.

The highest mortality for SCR and THW larvae was observed for peak 6, which eluted with ca. 112 mM to 132mM KCl. SDS-PAGE analysis of peak 6 showed predominant peptides of 170 kDa, 66 kDa, 63 kDa, 59.5 kDa and 31 kDa. Western blot analysis was performed on peak 6 protein fraction with a mixture of polyclonal antibodies made against TcaA$_{ii}$-syn, TcaA$_{iii}$-syn, TcaB$_{ii}$-syn, TcaC-syn, and TcbA$_{ii}$-syn peptides (described in Example 21) and C5F2, a monoclonal antibody against the TcbA$_{iii}$ peptide. Peak 6 contained immuno-reactive bands of 170 kDa, 90 kDa, 66 kDa, 59.5 kDa and 31 kDa. These are very close to the predicted sizes for the TcaC (166 kDa), TcaA$_{ii}$+TcaA$_{iii}$ (92 kDa), TcaA$_{iii}$ (66 kDa), TcaB$_{ii}$ (60 kDa) and TcaA$_{ii}$ (25 kDa), respectively. Peak 6 which was further analyzed by native agarose gel electrophoresis, as described herein, migrated as a single band with similar mobility to that of band 1.

The protein concentration of the purified peak 6 toxin protein was determined using the BCA reagents (Pierce). Dilutions of the protein were made in 10 mM Tris, pH 8.6 and applied to the diet bioassays. After 240 hours all neonate larvae on diet bioassays that received 450 ng or greater of the peak 6 protein fraction were dead. The group of larvae that received 90 ng of the same fraction had 40% mortality. After 240 hrs the survivors that received 90 ng and 20 ng of peak 6 protein fraction were ca. 10% and 70%, respectively, of the control weight.

EXAMPLE 2

Insecticide Utility

The *Photorhabdus luminescens* utility and toxicity were further characterized. *Photorhabdus luminescens* (strain W-14) culture broth was produced as follows. The production medium was 2% Bacto Proteose Peptone® Number 3 (PP3, Difco Laboratories, Detroit, Mich.) in Milli-Q® deionized water. Seed culture flasks consisted of 175 ml medium placed in a 500 ml tribaffled flask with a Delong neck, covered with a Kaput and autoclaved for 20 minutes, T=250° F. Production flasks consisted of 500 mls in a 2.8 liter 500 ml tribaffled flask with a Delong neck, covered by a Shin-etsu silicon foam closure. These were autoclaved for 45 minutes, T=250° F. The seed culture was incubated at 28° C. at 150 rpm in a gyrotory shaking incubator with a 2 inch throw. After 16 hours of growth, 1% of the seed culture was placed in the production flask which was allowed to grow for 24 hours before harvest. Production of the toxin appears to be during log phase growth. The microbial broth was transferred to a 1 L centrifuge bottle and the cellular biomass was pelleted (30 minutes at 2500 RPM at 4° C., [R.C.F.= about 1600] HG-4L Rotor RC3 Sorval centrifuge, Dupont, Wilmington, Del.). The primary broth was chilled at 4° C. for 8–16 hours and recentrifuged at least 2 hours (conditions above) to further clarify the broth by removal of a putative mucopolysaccharide which precipitated upon standing. (An alternative processing method combined both steps and involved the use of a 16 hour clarification centrifugation, same conditions as above.) This broth was then stored at 4° C. prior to bioassay or filtration.

Photorhabdus culture broth and protein toxin(s) purified from this broth showed activity (mortality and/or growth inhibition, reduced adult emergence) against a number of insects. More specifically, the activity is seen against corn rootworm (larvae and adult), Colorado potato beetle, and turf grubs, which are members of the insect order Coleoptera. Other members of the Coleoptera include wireworms, pollen beetles, flea beetles, seed beetles and weevils. Activity has also been observed against aster leafhopper, which is a member of the order, Homoptera. Other members of the Homoptera include planthoppers, pear pyslla, apple sucker, scale insects, whiteflies, and spittle bugs, as well as numerous host specific aphid species. The broth and purified fractions are also active against beet armyworm, cabbage looper, black cutworm, tobacco budworm, European corn borer, corn earworm, and codling moth, which are members of the order Lepidoptera. Other typical members of this order are clothes moth, Indian mealmoth, leaf rollers, cabbage worm, cotton bollworm, bagworm, Eastern tent caterpillar, sod webworm, and fall armyworm. Activity is also seen against fruitfly and mosquito larvae, which are members of the order Diptera. Other members of the order Diptera are pea midge, carrot fly, cabbage root fly, turnip root fly, onion fly, crane fly, house fly, and various mosquito species. Activity is seen against carpenter ant and Argentine ant, which are members of the order that also includes fire ants, oderous house ants, and little black ants.

The broth/fraction is useful for reducing populations of insects and were used in a method of inhibiting an insect population. The method may comprise applying to a locus of the insect an effective insect inactivating amount of the active described. Results are reported in Table 4.

Activity against corn rootworm larvae was tested as follows. Photorhabdus culture broth (filter sterilized, cell-free) or purified HPLC fractions were applied directly to the surface (about 1.5 cm$^2$) of 0.25 ml of artificial diet in 30 μl aliquots following dilution in control medium or 10 mM sodium phosphate buffer, pH 7.0, respectively. The diet plates were allowed to air-dry in a sterile flow-hood and the wells were infested with single, neonate *Diabrotica undecimpunctata howardi* (Southern corn rootworm, SCR) hatched from sterilized eggs, with second instar SCR grown on artificial diet or with second instar *Diabrotica virgifera virgifera* (Western corn rootworm, WCR) reared on corn seedlings grown in Metromix®. Second instar larvae were weighed prior to addition to the diet. The plates were sealed, placed in a humidified growth chamber and maintained at 27° C. for the appropriate period (4 days for neonate and adult SCR, 2–5 days for WCR larvae, 7–14 days for second instar SCR). Mortality and weight determinations were scored as indicated. Generally, 16 insects per treatment were used in all studies. Control mortalities were as follows: neonate larvae, <5%, adult beetles, 5%.

Activity against Colorado potato beetle was tested as follows. Photorhabdus culture broth or control medium was applied to the surface (about 2.0 cm$^2$) of 1.5 ml of standard artificial diet held in the wells of a 24-well tissue culture plate. Each well received 50 μl of treatment and was allowed to air dry. Individual second instar Colorado potato beetle (*Leptinotarsa decemlineata*, CPB) larvae were then placed onto the diet and mortality was scored after 4 days. Ten larvae per treatment were used in all studies. Control mortality was 3.3%.

Activity against Japanese beetle grubs and beetles was tested as follows. Turf grubs (*Popillia japonica*, 2–3rd instar) were collected from infested lawns and maintained in the laboratory in soil/peat mixture with carrot slices added as additional diet. Turf beetles were pheromone-trapped locally and maintained in the laboratory in plastic containers with maple leaves as food. Following application of undiluted Photorhabdus culture broth or control medium to corn rootworm artificial diet (30 μl/1.54 cm$^2$, beetles) or carrot slices (larvae), both stages were placed singly in a diet well and observed for any mortality and feeding. In both cases there was a clear reduction in the amount of feeding (and feces production) observed.

Activity against mosquito larvae was tested as follows. The assay was conducted in a 96-well microtiter plate. Each well contained 200 μl of aqueous solution (Photorhabdus culture broth, control medium or H$_2$O) and approximately 20, 1-day old larvae (*Aedes aegypti*). There were 6 wells per treatment. The results were read at 2 hours after infestation and did not change over the three day observation period. No control mortality was seen.

Activity against fruitflies was tested as follows. Purchased *Drosophila melanogaster* medium was prepared using 50% dry medium and a 50% liquid of either water, control medium or Photorhabdus culture broth. This was accomplished by placing 8.0 ml of dry medium in each of 3 rearing vials per treatment and adding 8.0 ml of the appropriate liquid. Ten late instar *Drosophila melanogaster* maggots were then added to each vial. The vials were held on a laboratory bench, at room temperature, under fluorescent ceiling lights. Pupal or adult counts were made after 3, 7 and 10 days of exposure. Incorporation of Photorhabdus culture broth into the diet media for fruitfly maggots caused a slight (17%) but significant reduction in day-10 adult emergence as compared to water and control medium (3% reduction).

Activity against aster leafhopper was tested as follows. The ingestion assay for aster leafhopper (*Macrosteles severini*) is designed to allow ingestion of the active without other external contact. The reservoir for the active/"food" solution is made by making 2 holes in the center of the bottom portion of a 35×10 mm Petri dish. A 2 inch Parafilm M® square is placed across the top of the dish and secured with an "O" ring. A 1 oz. plastic cup is then infested with approximately 7 leafhoppers and the reservoir is placed on top of the cup, Parafilm down. The test solution is then added to the reservoir through the holes. In tests using undiluted Photorhabdus culture broth, the broth and control medium were dialyzed against water to reduce control mortality. Mortality is reported at day 2 where 26.5% control mortality was seen. In the tests using purified fractions (200 mg protein/ml) a final concentration of 5% sucrose was used in all treatments to improve survivability of the aster leafhoppers. The assay was held in an incubator at 28° C., 70% RH with a 16/8 photoperiod. The assay was graded for mortality at 72 hours. Control mortality was 5.5%.

Activity against Argentine ants was tested as follows. A 1.5 ml aliquot of 100% Photorhabdus culture broth, control medium or water was pipetted into 2.0 ml clear glass vials. The vials were plugged with a piece of cotton dental wick that was moistened with the appropriate treatment. Each vial was placed into a separate 60×16mm Petri dish with 8 to 12 adult Argentine ants (*Linepithema humile*). There were three replicates per treatment. Bioassay plates were held on a laboratory bench, at room temperature under fluorescent ceiling lights. Mortality readings were made after 5 days of exposure. Control mortality was 24%.

Activity against carpenter ant was tested as follows. Black carpenter ant workers (*Camponotus pennsylvanicus*) were collected from trees on DowElanco property in Indianapolis, Ind. Tests with Photorhabdus culture broth were performed as follows. Each plastic bioassay container (7⅛"×3") held fifteen workers, a paper harborage and 10 ml of broth or control media in a plastic shot glass. A cotton wick delivered the treatment to the ants through a hole in the shot glass lid. All treatments contained 5% sucrose. Bioassays were held in the dark at room temperature and graded at 19 days. Control mortality was 9%. Assays delivering purified fractions utilized artificial ant diet mixed with the treatment (purified fraction or control solution) at a rate of 0.2 ml treatment/2.0 g diet in a plastic test tube. The final protein concentration of the purified fraction was less than 10 $\mu$g/g diet. Ten ants per treatment, a water source, harborage and the treated diet were placed in sealed plastic containers and maintained in the dark at 27° C. in a humidified incubator. Mortality was scored at day 10. No control mortality was seen.

Activity against various lepidopteran larvae was tested as follows. Photorhabdus culture broth or purified fractions were applied directly to the surface (about 1.5 cm$^2$) of 0.25 ml of standard artificial diet in 30 $\mu$l aliquots following dilution in control medium or 10 mM sodium phosphate buffer, pH 7.0, respectively. The diet plates were allowed to air-dry in a sterile flow-hood and the wells were infested with single, neonate larva. European corn borer (*Ostrinia nubilalis*) and corn earworm (*Helicoverpa zea*) eggs were supplied from commercial sources and hatched in-house, whereas beet armyworm (*Spodoptera exigua*), cabbage looper (*Trichoplusia ni*), tobacco budworm (*Heliothis virescens*), codling moth (*Laspeyresia pomonella*) and black cutworm (*Agrotis ipsilon*) larvae were supplied internally. Following infestation with larvae, the diet plates were sealed, placed in a humidified growth chamber and maintained in the dark at 27° C. for the appropriate period. Mortality and weight determinations were scored at days 5–7 for Photorhabdus culture broth and days 4–7 for the purified fraction. Generally, 16 insects per treatment were used in all studies. Control mortality ranged from 4–12.5% for control medium and was less than 10% for phosphate buffer.

TABLE 4

Effect of *Photohabdus luminescens* (Strain W-14) Culture Broth and Purified Toxin Fraction on Mortality and Growth Inhibition of Different Insect Orders/Species

| Insect Order/Species | Broth | | Purified Fraction | |
|---|---|---|---|---|
| | % Mort. | % G. I. | % Mort. | % G. I. |
| COLEOPTERA | | | | |
| Corn Rootworm | | | | |
| Southern/neonate larva | 100 | na | 100 | na |
| Southern/2$^{nd}$ instar | na | 38.5 | nt | nt |
| Southern/adult | 45 | nt | nt | nt |
| Western/2$^{nd}$ instar | na | 35 | nt | nt |
| Colorado Potato Beetle 2$^{nd}$ instar | 93 | nt | nt | nt |
| Turf Grub | na | a.f. | nt | nt |
| 3$^{rd}$ instar adult | na | a.f. | nt | nt |
| DIPTERA | | | | |
| Fruit Fly (adult emergence) | 17 | nt | nt | nt |
| Mosquito larvae | 100 | na | nt | nt |
| HOMOPTERA | | | | |
| Aster Leafhopper | 96.5 | na | 100 | na |
| HYMENOPTERA | | | | |
| Argentine Ant | 75 | na | nt | na |
| Carpenter Ant | 71 | na | 100 | na |
| LEPIDOPTERA | | | | |
| Beet Armyworm | 12.5 | 36 | 18.75 | 41.4 |
| Black Cutworm | nt | nt | 0 | 71.2 |
| Cabbage Looper | nt | nt | 21.9 | 66.8 |
| Codling Moth | nt | nt | 6.25 | 45.9 |
| Corn Earworm | 56.3 | 94.2 | 97.9 | na |
| European Corn Borer | 96.7 | 98.4 | 100 | na |
| Tobacco Budworm | 13.5 | 52.5 | 19.4 | 85.6 |

Mort. = mortality, G. I. = growth inhibition, na = not applicable, nt = not tested, a.f. = anti-feedant

EXAMPLE 3

Insecticide Utility upon Soil Application

*Photorhabdus luminescens* (strain W-14) culture broth was shown to be active against corn rootworm when applied directly to soil or a soil-mix (Metromix®). Activity against neonate SCR and WCR in Metromix® was tested as follows (Table 5). The test was run using corn seedlings (United Agriseeds brand CL614) that were germinated in the light on moist filter paper for 6 days. After roots were approximately 3–6 cm long, a single kernel/seedling was planted in a 591 ml clear plastic cup with 50 gm of dry Metromix®. Twenty neonate SCR or WCR were then placed directly on the roots of the seedling and covered with Metromix®. Upon infestation, the seedlings were then drenched with 50 ml total volume of a diluted broth solution. After drenching, the cups were sealed and left at room temperature in the light for 7 days. Afterwards, the seedlings were washed to remove all Metromix® and the roots were excised and weighed. Activity was rated as the percentage of corn root remaining relative to the control plants and as leaf damage induced by feeding. Leaf damage was scored visually and rated as either −, +, ++, or +++, with − representing no damage and +++ representing severe damage.

Activity against neonate SCR in soil was tested as follows (Table 6). The test was run using corn seedlings (United Agriseeds brand CL614) that were germinated in the light on moist filter paper for 6 days. After the roots were approximately 3–6 cm long, a single kernel/seedling was planted in a 591 ml clear plastic cup with 150 gm of soil from a field in Lebanon, Ind. planted the previous year with corn. This soil had not been previously treated with insecticides. Twenty neonate SCR were then placed directly on the roots of the seedling and covered with soil. After infestation, the seedlings were drenched with 50 ml total volume of a diluted broth solution. After drenching, the unsealed cups were incubated in a high relative humidity chamber (80%) at 78° F. Afterwards, the seedlings were washed to remove all soil and the roots were excised and weighed. Activity was rated as the percentage of corn root remaining relative to the control plants and as leaf damage induced by feeding. Leaf damage was scored visually and rated as either −, +, ++, or +++, with − representing no damage and +++ representing severe damage.

TABLE 5

Effect of *Photorhabdus luminescens* (Strain W-14) Culture Broth on Rootworm Larvae after Post-Infestation Drenching (Metromix ® )

| Treatment | Larvae | Leaf Damage | Root Weight (g) | % |
|---|---|---|---|---|
| Southern Corn Rootworm | | | | |
| Water | − | − | 0.4916 ± 0.023 | 100 |
| Medium (2.0% v/v) | − | − | 0.4415 ± 0.029 | 100 |
| Broth (6.25% v/v) | − | − | 0.4641 ± 0.081 | 100 |
| Water | + | +++ | 0.1410 ± 0.006 | 28.7 |
| Media (2.0% v/v) | + | +++ | 0.1345 ± 0.028 | 30.4 |
| Broth (1.56% v/v) | + | − | 0.4830 ± 0.031 | 104 |
| Western Corn Rootworm | | | | |
| Water | − | − | 0.4446 ± 0.019 | 100 |
| Broth (2.0% v/v) | − | − | 0.4069 ± 0.026 | 100 |
| Water | + | − | 0.2202 ± 0.015 | 49 |
| Broth (2.0% v/v) | + | − | 0.3879 ± 0.013 | 95 |

TABLE 6

Effect of *Photorhabdus luminescens* (Strain W-14) Culture Broth on Southern Corn Rootworm Larvae after Post-Infestation Drenching (Soil)

| Treatment | Larvae | Leaf Damage | Root Weight (g) | % |
|---|---|---|---|---|
| Water | − | − | 0.2148 ± 0.014 | 100 |
| Broth (50% v/v) | − | − | 0.2260 ± 0.016 | 103 |
| Water | + | +++ | 0.0916 ± 0.009 | 43 |
| Broth (50% v/v) | + | − | 0.2428 ± 0.032 | 113 |

Activity of *Photorhabdus luminescens* (strain W-14) culture broth against second instar turf grubs in Metromix® was observed in tests conducted as follows (Table 7). Approximately 50 gm of dry Metromix® was added to a 591 ml clear plastic cup. The Metromix® was then drenched with 50 ml total volume of a 50% (v/v) diluted Photorhabdus broth solution. The dilution of crude broth was made with water, with 50% broth being prepared by adding 25 ml of crude broth to 25 ml of water for 50 ml total volume. A 1% (w/v) solution of proteose peptone #3 (PP3), which is a 50% dilution of the normal media concentration, was used as a broth control. After drenching, five second instar turf grubs were placed on the top of the moistened Metromix®. Healthy turf grub larvae burrowed rapidly into the Metromix®. Those larvae that did not burrow within 1 h were removed and replaced with fresh larvae. The cups were sealed and placed in a 28° C. incubator, in the dark. After seven days, larvae were removed from the Metromix® and scored for mortality. Activity was rated the percentage of mortality relative to control.

TABLE 7

Effect of *Photorhabdus luminescens* (Strain W-14) Culture Broth on Turf Grub after Pre-Infestation Drenching (Metromix ® )

| Treatment | Mortality* | Mortality % |
|---|---|---|
| Water | 7/15 | 47 |
| Control medium (1.0% w/v) | 12/19 | 63 |
| Broth (50% v/v) | 17/20 | 85 |

*expressed as a ratio of dead/living larvae

EXAMPLE 4

Insecticide Utility upon Leaf Application

Activity of Photorhabdus broth against European corn borer was seen when the broth was applied directly to the surface of maize leaves (Table 8). In these assays Photorhabdus broth was diluted 100-fold with culture medium and applied manually to the surface of excised maize leaves at a rate of about 6.0 $\mu l/cm^2$ of leaf surface. The leaves were air dried and cut into equal sized strips approximately 2×2 inches. The leaves were rolled, secured with paper clips and placed in 1 oz plastic shot glasses with 0.25 inch of 2% agar on the bottom surface to provide moisture. Twelve neonate European corn borers were then placed onto the rolled leaf and the cup was sealed. After incubation for 5 days at 27° C. in the dark, the samples were scored for feeding damage and recovered larvae.

TABLE 8

Effect of *Photorhabdus luminescens* (Strain W-14) Culture Broth on European Corn Borer Larvae Following Pre-Infestation Application to Excised Maize Leaves

| Treatment | Leaf Damage | Larvae Recovered | Weight (mg) |
|---|---|---|---|
| Water | Extensive | 55/120 | 0.42 mg |
| Control Medium | Extensive | 40/120 | 0.50 mg |
| Broth (1.0% v/v) | Trace | 3/120 | 0.15 mg |

Activity of the culture broth against neonate tobacco budworm (*Heliothis virescens*) was demonstrated using a leaf dip methodology. Fresh cotton leaves were excised from the plant and leaf disks were cut with an 18.5 mm corkborer. The disks were individually emersed in control medium (PP3) or *Photorhabdus luminescens* (strain W-14) culture broth which had been concentrated approximately 10-fold using an Amicon (Beverly, Mass.), Proflux M12 tangential filtration system with a 10 kDa filter. Excess liquid was removed and a straightened paper clip was placed through the center of the disk. The paper clip was then wedged into a plastic, 1.0 oz shot glass containing approximately 2.0 ml of 1% Agar. This served to suspend the leaf disk above the agar. Following drying of the leaf disk, a single neonate tobacco budworm larva was placed on the disk and the cup was capped. The cups were then sealed in a plastic bag and placed in a darkened, 27° C. incubator for 5 days. At this time the remaining larvae and leaf material were weighed to establish a measure of leaf damage (Table 9).

TABLE 9

Effect of *Photorhabdus luminescens* (Strain W-14) Culture Broth on Tobacco Budworm Neonates in a Cotton-Leaf Dip Assay

| Treatment | Final Weights (mg) Leaf Disk | Larvae |
|---|---|---|
| Control leaves | 55.7 ± 1.3 | na* |
| Control Medium | 34.0 ± 2.9 | 4.3 ± 0.91 |
| Photorhabdus broth | 54.3 ± 1.4 | 0.0** |

*- not applicable, **- no live larvae found

EXAMPLE 5

Part A

Characterization of Toxin Peptide Components

In a subsequent analysis, the toxin protein subunits of the bands isolated as in Example 1 were resolved on a 7% SDS polyacrylamide electrophoresis gel with a ratio of 30:0.8 (acrylamide:BIS-acrylamide). This gel matrix facilitates better resolution of the larger proteins. The gel system used to estimate the Band 1 and Band 2 subunit molecular weights in Example 1 was an 18% gel with a ratio of 38:0.18 (acrylamide:BIS-acrylamide), which allowed for a broader range of size separation, but less resolution of higher molecular weight components.

In this analysis, 10, rather than 8, protein bands were resolved. Table 10 reports the calculated molecular weights of the 10 resolved bands, and directly compares the molecular weights estimated under these conditions to those of the prior example. It is not surprising that additional bands were detected under the different separation conditions used in this example. Variations between the prior and new estimates of molecular weight are also to be expected given the differences in analytical conditions. In the analysis of this example, it is thought that the higher molecular weight estimates are more accurate than in Example 1, as a result of improved resolution. However, these are estimates based on SDS PAGE analysis, which are typically not analytically precise and result in estimates of peptides and which may have been further altered due to post- and co-translational modifications.

Amino acid sequences were determined for the N-terminal portions of five of the 10 resolved peptides. Table 10+correlates the molecular weight of the proteins and the identified sequences. In SEQ ID NO:2, certain analyses suggest that the proline at residue 5 may be an asparagine (asn). In SEQ ID NO:3, certain analyses suggest that the amino acid residues at positions 13 and 14 are both arginine (arg). In SEQ ID NO:4, certain analyses suggest that the amino acid residue at position 6 may be either alanine (ala) or serine (ser). In SEQ ID NO:5, certain analyses suggest that the amino acid residue at position 3 may be aspartic acid (asp).

TABLE 10

| ESTIMATE | NEW ESTIMATE* | SEQ. LISTING |
|---|---|---|
| 208 | 200.2 kDa | SEQ ID NO: 1 |
| 184 | 175.0 kDa | SEQ ID NO: 2 |
| 65.6 | 68.1 kDa | SEQ ID NO: 3 |
| 60.8 | 65.1 kDa | SEQ ID NO: 4 |
| 56.2 | 58.3 kDa | SEQ ID NO: 5 |
| 25.1 | 23.2 kDa | SEQ ID NO: 15 |

*New estimates are based on SDS PAGE and are not based on gene sequences. SDS PAGE is not analytically precise.

EXAMPLE 5

Part B

Characterization of Toxin Peptide Components

New N-terminal sequence, SEQ ID NO:15, Ala Gln Asp Gly Asn Gln Asp Thr Phe Phe Ser Gly Asn Thr, was obtained by further N-terminal sequencing of peptides isolated from Native HPLC-purified toxin as described in Example 5, Part A, above. This peptide comes from the tcaA gene. The peptide labeled $TcaA_{ii}$, starts at position 254 and goes to position 491, where the $TcaA_{iii}$ peptide starts, SEQ ID NO:4. The estimated size of the peptide based on the gene sequence is 25,240 Da.

EXAMPLE 6

Characterization of Toxin Peptide Components

In yet another analysis, the toxin protein complex was re-isolated from the *Photorhabdus luminescens* growth medium (after culture without TWEEN surfactant) by performing a 10%–80% ammonium sulfate precipitation followed by an ion exchange chromatography step (Mono Q) and two molecular sizing chromatography steps. These conditions were like those used in Example 1. During the first molecular sizing step, a second biologically active peak was found at about 100±10 kDa. Based upon protein measurements, this fraction was 20–50 fold less active than the larger, or primary, active peak of about 860±100 kDa (native). During this isolation experiment, a smaller active peak of about 325±50 kDa that retained a considerable portion of the starting biological activity was also resolved. It is thought that the 325 kDa peak is related to or derived from the 860 kDa peak.

A 56 kDa protein was resolved in this analysis. The N-terminal sequence of this protein is presented in SEQ ID NO:6. It is noteworthy that this protein shares significant identity and conservation with SEQ ID NO:5 at the N-terminus, suggesting that the two may be encoded by separate members of a gene family and that the proteins produced by each gene are sufficiently similar to both be operable in the insecticidal toxin complex.

A second, prominent 185 kDa protein was consistently present in amounts comparable to that of protein 3 from Table 10, and may be the same protein or protein fragment. The N-terminal sequence of this 185 kDa protein is shown at SEQ ID NO:7.

Additional N-terminal amino acid sequence data were also obtained from isolated proteins. None of the determined N-terminal sequences appear identical to a protein identified in Table 10. Other proteins were present in isolated preparation. One such protein has an estimated molecular weight of 108 kDa and an N-terminal sequence as shown in SEQ ID NO:8. A second such protein has an estimated molecular weight of 80 kDa and an N-terminal sequence as shown in SEQ ID NO:9.

When the protein material in the approximately 325 kDa active peak was analyzed by size, bands of approximately 51, 31, 28, and 22 kDa were observed. As in all cases in which a molecular weight was determined by analysis of electrophoretic mobility, these molecular weights were subject to error effects introduced by buffer ionic strength differences, electrophoresis power differences, and the like. One of ordinary skill would understand that definitive molecular weight values cannot be determined using these standard methods and that each was subject to variation. It was hypothesized that proteins of these sizes are degradation products of the larger protein species (of approximately 200 kDa size) that were observed in the larger primary toxin complex.

Finally, several preparations included a protein having the N-terminal sequence shown in SEQ ID NO:10. This sequence was strongly homologous to known chaperonin proteins, accessory proteins known to function in the assembly of large protein complexes. Although the applicants could not ascribe such an assembly function to the protein identified in SEQ ID NO:10, it was consistent with the existence of the described toxin protein complex that such a chaperonin protein could be involved in its assembly. Moreover, although such proteins have not directly been suggested to have toxic activity, this protein may be important to determining the overall structural nature of the protein toxin, and thus, may contribute to the toxic activity or durability of the complex in vivo after oral delivery.

Subsequent analysis of the stability of the protein toxin complex to proteinase K was undertaken. It was determined that after 24 hour incubation of the complex in the presence of a 10-fold molar excess of proteinase K, activity was virtually eliminated (mortality on oral application dropped to about 5%). These data confirm the proteinaceous nature of the toxin.

The toxic activity was also retained by a dialysis membrane, again confirming the large size of the native toxin complex.

EXAMPLE 7

Isolation, Characterization and Partial Amino Acid Sequencing of Photorhabdus Toxins Isolation and N-Terminal Amino Acid Sequencing In a set of experiments conducted in parallel to Examples 5 and 6, ammonium sulfate precipitation of Photorhabdus proteins was performed by adjusting Photorhabdus broth, typically 2–3 liters, to a final concentration of either 10% or 20% by the slow addition of ammonium sulfate crystals. After stirring for 1 hour at 4° C., the material was centrifuged at 12,000×g for 30 minutes. The supernatant was adjusted to 80% ammonium sulfate, stirred at 4° C. for 1 hour, and centrifuged at 12,000×g for 60 minutes. The pellet was resuspended in one-tenth the volume of 10 mM $Na_2.PO_4$, pH 7.0 and dialyzed against the same phosphate buffer overnight at 4° C. The dialyzed material was centrifuged at 12,000×g for 1 hour prior to ion exchange chromatography.

A.HR 16/50 Q Sepharose (Pharmacia) anion exchange column was equilibrated with 10 mM $Na_2.PO_4$, pH 7.0. Centrifuged, dialyzed ammonium sulfate pellet was applied to the Q Sepharose column at a rate of 1.5 ml/min and washed extensively at 3.0 ml/min with equilibration buffer until the optical density (O.D. 280) reached less than 0.100. Next, either a 60 minute NaCl gradient ranging from 0 to 0.5 M at 3 ml/min, or a series of step elutions using 0.1 M, 0.4 M and finally 1.0 NaCl for 60 minutes each was applied to the column. Fractions were pooled and concentrated using a Centriprep 100. Alternatively, proteins could be eluted by a single 0.4 M NaCl wash without prior elution with 0.1 M NaCl.

Two milliliter aliquots of concentrated Q Sepharose samples were loaded at 0.5 ml/min onto a HR 16/50 Superose 12 (Pharmacia) gel filtration column equilibrated with 10 mM $Na_2.PO_4$, pH 7.0. The column was washed with the same buffer for 240 min at 0.5 ml/min and 2 min samples were collected. The void volume material was collected and concentrated using a centriprep 100. Two milliliter aliquots of concentrated Superose 12 samples were loaded at 0.5 ml/min onto a HR 16/50 Sepharose 4B-CL (Pharmacia) gel filtration column equilibrated with 10 mM $Na_2.PO_4$, pH 7.0. The column was washed with the same buffer for 240 min at 0.5 ml/min and 2 min samples were collected.

The excluded protein peak was subjected to a second fractionation by application to a gel filtration column that used a Sepharose CL-4B resin, which separates proteins ranging from about 30 kDa to 1000 kDa. This fraction was resolved into two peaks; a minor peak at the void volume (>1000 kDa) and a major peak which eluted at an apparent molecular weight of about 860 kDa. Over a one week period subsequent samples subjected to gel filtration showed the gradual appearance of a third peak (approximately 325 kDa) that seemed to arise from the major peak, perhaps by limited proteolysis. Bioassays performed on the three peaks showed that the void peak had no activity, while the 860 kDa toxin complex fraction was highly active, and the 325 kDa peak was less active, although quite potent. SDS PAGE analysis of Sepharose CL-4B toxin complex peaks from different fermentation productions revealed two distinct peptide patterns, denoted "P" and "S". The two patterns had marked differences in the molecular weights and concentrations of peptide components in their fractions. The "S" pattern, produced most frequently, had 4 high molecular weight peptides (>150 kDa) while the "P" pattern had 3 high molecular weight peptides. In addition, the "S" peptide fraction was found to have 2–3 fold more activity against European Corn Borer. This shift may be related to variations in protein expression due to age of inoculum and/or other factors based on growth parameters of aged cultures.

Milligram quantities of peak toxin complex fractions determined to be "P" or "S" peptide patterns were subjected to preparative SDS PAGE, and transblotted with TRIS-glycine (Seprabuff™ to PVDF membranes (ProBlott™, Applied Biosystems) for 3–4 hours. Blots were sent for amino acid analysis and N-terminal amino acid sequencing at Harvard MicroChem and Cambridge ProChem, respectively. Three peptides in the "S" pattern had unique N-terminal amino acid sequences compared to the sequences identified in the previous example. A 201 kDa ($TcdA_{ii}$) peptide set forth as SEQ ID NO:13 below shared between 33% amino acid identity and 50% similarity (similarity and identity were calculated by hand) with SEQ ID NO:1 ($TcbA_{ii}$)(in Table 10 vertical lines denote amino acid identities and colons indicate conservative amino acid substitutions). A second peptide of 197 kDa, SEQ ID NO:14 (TcdB), had 42% identity and 58% similarity with SEQ ID NO:2 (TcaC) (similarity and identity were calculated by hand). Yet a third peptide of 205 kDa was denoted $TcdA_{ii}$. In addition, a limited N-terminal amino acid sequence, SEQ ID NO:16 (TcbA), of a peptide of at least 235 kDa was identical with the amino acid sequence, SEQ ID NO:12, deduced from a cloned gene (tcbA), SEQ ID NO:11, containing a deduced amino acid sequence corresponding to SEQ ID NO:1 (TcbA$_{ii}$). This indicates that the larger 235+ kDa peptide was proteolytically processed to the 201 kDa peptide, (TcbA$_{ii}$), (SEQ ID NO:1) during fermentation, possibly resulting in activation of the molecule. In yet another sequence, the sequence originally reported as SEQ ID NO:5 (TcaB$_{ii}$) reported in Example 5 above, was found to contain an aspartic acid residue (Asp) at the third position rather than glycine (Gly) and two additional amino acids Gly and Asp at the eighth and ninth positions, respectively. In yet two other sequences, SEQ ID NO:2 (TcaC) and SEQ ID NO:3 (TcaB$_i$), additional amino acid sequence was obtained. Densitometric quantitation was performed using a sample that was identical to the "S" preparation sent for N-terminal analysis. This analysis showed that the 201 kDa and 197 kDa peptides represent 7.0% and 7.2%, respectively, of the total Coomassie brillant blue stained protein in the "S" pattern and are present in amounts similar to the other abundant peptides. It was speculated that these peptides may represent protein homologs, analogous to the situation found with other bacterial toxins, such as various CryI Bt toxins. These proteins vary from 40–90% similarity at their N-terminal amino acid sequence, which encompasses the toxic fragment.

Internal Amino Acid Sequencing

To facilitate cloning of toxin peptide genes, internal amino acid sequences of selected peptides were obtained as followed. Milligram quantities of peak 2A fractions determined to be "P" or "S" peptide patterns were subjected to preparative SDS PAGE, and transblotted with TRIS-glycine (Seprabuff™ to PVDF membranes (ProBlott™, Applied Biosystems) for 3–4 hours. Blots were sent for amino acid analysis and N-terminal amino acid sequencing at Harvard MicroChem and Cambridge ProChem, respectively. Three peptides, referred to as TcbA$_{ii}$(containing SEQ ID NO:1), TcdA$_{ii}$, and TcaB$_i$ (containing SEQ ID NO:3) were subjected to trypsin digestion by Harvard MicroChem followed by HPLC chromatography to separate individual peptides. N-terminal amino acid analysis was performed on selected tryptic peptide fragments. Two internal peptides were sequenced for the peptide TcdA$_{ii}$ (205 kDa peptide) referred to as TcdA$_{ii}$-PT111 (SEQ ID NO:17) and TcdA$_{ii}$-PT79 (SEQ ID NO:18). Two internal peptides were sequenced for the peptide TcaB$_i$ (68 kDa peptide) referred to as TcaB$_i$-PT158 (SEQ ID NO:19) and TcaB$_i$-PT108 (SEQ ID NO:20). Four internal peptides were sequenced for the peptide TcbA$_{ii}$ (201 kDa peptide) referred to as TcbA$_{ii}$-PT103 (SEQ ID NO:21), TcbA$_{ii}$-PTS6 (SEQ ID NO:22), TcbA$_{ii}$-PT81(a) (SEQ ID NO:23), and TcbA$_{ii}$-PT81(b) (SEQ ID NO:24).

TABLE 11

N-Terminal Amino Acid Sequences
(similarity and identity were calculated by hand)

```
201 kDa (33% identity & 50% similarity to
SEQ ID NO.1)
  L I G Y N N O F S G * A  SEQ ID NO:13
  : | |       | :     |
  F I Q G Y S D L F G N - A  SEQ ID NO:1

197 kDa (42% identity & 58% similarity to
SEQ ID NO.2)
  M Q N S Q T F S V G E L  SEQ ID NO.14
  | | : |       | : :  |
  M Q D S P E V S I T T L  SEQ ID NO.2
```

EXAMPLE 8

Construction of a Cosmid Library of *Photorhabdus luminescens* W-14 Genomic DNA and its Screening to Isolate Genes Encoding Peptides Comprising the Toxic Protein Preparation As a prerequisite for the production of Photorhabdus insect toxic proteins in heterologous hosts, and for other uses, it is necessary to isolate and characterize the genes that encode those peptides. This objective was pursued in parallel. One approach, described later, was based on the use of monoclonal and polyclonal antibodies raised against the purified toxin which were then used to isolate clones from an expression library. The other approach, described in this example, is based on the use of the N-terminal and internal amino acid sequence data to design degenerate oligonucleotides for use in PCR amplication. Either method can be used to identify DNA clones that contain the peptide-encoding genes so as to permit the isolation of the respective genes, and the determination of their DNA base sequence.

Genomic DNA Isolation

*Photorhabdus luminescens* strain W-14 (ATCC accession number 55397) was grown on 2% proteose peptone #3 agar (Difco Laboratories, Detroit, Mich.) and insecticidal toxin competence was maintained by repeated bioassay after passage, using the method described in Example 1 above. A 50 ml shake culture was produced in a 175 ml baffled flask in 2% proteose peptone #3 medium, grown at 28° C. and 150 rpm for approximately 24 hours. 15 ml of this culture was pelleted and frozen in its medium at −20° C. until it was thawed for DNA isolation. The thawed culture was centrifuged, (700×g, 30 min) and the floating orange mucopolysaccharide material was removed. The remaining cell material was centrifuged (25,000×g, 15 min) to pellet the bacterial cells, and the medium was removed and discarded.

Genomic DNA was isolated by an adaptation of the CTAB method described in section 2.4.1 of Current Protocols in Molecular Biology (Ausubel et al. eds, John Wiley & Sons, 1994) [modified to include a salt shock and with all volumes increased 10-fold]. The pelleted bacterial cells were resuspended in TE buffer (10 mM Tris-HCl, 1 mM EDTA, pH 8.0) to a final volume of 10 ml, then 12 ml of 5 M NaCl was added; this mixture was centrifuged 20 min at 15,000×g. The pellet was resuspended in 5.7 ml TE and 300 ml of 10% SDS and 60 ml of 20 mg/ml proteinase K (Gibco BRL Products, Grand Island, N.Y.; in sterile distilled water) were added to the suspension. This mixture was incubated at 37° C. for 1 hr; then approximately 10 mg lysozyme (Worthington Biochemical Corp., Freehold, N.J.) was added. After an additional 45 min, 1 ml of 5 M NaCl and 800 ml of CTAB/NaCl solution (10% w/v CTAB, 0.7 M NaCl) were added. This preparation was incubated 10 min at 65° C., then gently agitated and further incubated and agitated for approximately 20 min to assist clearing of the cellular material. An equal volume of chloroform/isoamyl alcohol solution (24:1, v/v) was added, mixed gently and centrifuged. After two extractions with an equal volume of PCI (phenol/chloroform/isoamyl alcohol; 50:49:1, v/v/v; equilibrated with 1 M Tris-HCl, pH 8.0; Intermountain Scientific Corporation, Kaysville, Utah), the DNA was precipitated with 0.6 volume of isopropanol. The DNA precipitate was gently removed with a glass rod, washed twice with 70% ethanol, dried, and dissolved in 2 ml STE (10 mM Tris-HCl pH 8.0, 10 mM NaCl, 1 mM EDTA). This preparation contained 2.5 mg/ml DNA, as determined by optical density at 260 nm (i.e., OD$_{260}$)

The molecular size range of the isolated genomic DNA was evaluated for suitability for library construction. CHEF gel analysis was performed in 1.5% agarose (Seakem® LE, FMC BioProducts, Rockland, Me.) gels with 0.5×TBE buffer (44.5 mM Tris-HCl pH 8.0, 44.5 mM $H_3BO_3$, 1 mM EDTA) on a BioRad CHEF-DR II apparatus with a Pulsewave 760 Switcher (Bio-Rad Laboratories, Inc., Richmond, Calif.). The running parameters were: initial A time, 3 sec; final A time, 12 sec; 200 volts; running temperature, 4–18° C.; run time, 16.5 hr. Ethidium bromide staining and examination of the gel under ultraviolet light indicated the DNA ranged from 30–250 kbp in size.

Construction of Library

A partial Sau3A 1 digest was made of this Photorhabdus genomic DNA preparation. The method was based on section 3.1.3 of Ausubel (supra.). Adaptions included running smaller scale reactions under various conditions until nearly optimal results were achieved. Several scaled-up large reactions with varied conditions were run, the results analyzed on CHEF gels, and only the best large scale preparation was carried forward. In the optimal case, 200 μg of Photorhabdus genomic DNA was incubated with 1.5 units of Sau3A 1 (New England Biolabs, "NEB", Beverly, Mass.) for 15 min at 37° C. in 2 ml total volume of 1×NEB 4 buffer (supplied as 10× by the manufacturer). The reaction was stopped by adding 2 ml of PCI and centrifuging at 8000×g for 10 min. To the supernatant were added 200 μl of 5 M NaCl plus 6 ml of ice-cold ethanol. This preparation was chilled for 30 min at −20° C., then centrifuged at 12,000×g for 15 min. The supernatant was removed and the precipitate was dried in a vacuum oven at 40° C., then resuspended in 400 μl STE. Spectrophotometric assay indicated about 40% recovery of the input DNA. The digested DNA was size fractionated on a sucrose gradient according to section 5.3.2 of CPMB (op. cit.). A 10% to 40% (w/v) linear sucrose gradient was prepared with a gradient maker in Ultra-Clear™ tubes (Beckman Instruments, Inc., Palo Alto, Calif.) and the DNA sample was layered on top. After centrifugation, (26,000 rpm, 17 hr, Beckman SW41 rotor, 20° C.), fractions (about 750 μl) were drawn from the top of the gradient and analyzed by CHEF gel electrophoresis (as described earlier). Fractions containing Sau3A 1 fragments in the size range 20–40 kbp were selected and DNA was precipitated by a modification (amounts of all solutions increased approximately 6.3-fold) of the method in section 5.3.3 of Ausubel (supra.). After overnight precipitation, the DNA was collected by centrifugation (17,000×g, 15 min), dried, redissolved in TE, pooled into a final volume of 80 μl, and reprecipitated with the addition of 8 μl 3 M sodium acetate and 220 μl ethanol. The pellet collected by centrifugation as above was resuspended in 12 μl TE. Concentration of the DNA was determined by Hoechst 33258 dye (Polysciences, Inc., Warrington, Pa.) fluorometry in a Hoefer TKO100 fluorimeter (Hoefer Scientific Instruments, San Francisco, Calif.). Approximately 2.5 μg of the size-fractionated DNA was recovered.

Thirty μg of cosmid pWE15 DNA (Stratagene, La Jolla, Calif.) was digested to completion with 100 units of restriction enzyme BamH 1 (NEB) in the manufacturer's buffer (final volume of 200 μl, 37° C., 1 hr). The reaction was extracted with 100 μl of PCI and DNA was precipitated from the aqueous phase by addition of 20 μl 3M sodium acetate and 550 μl −20° C. absolute ethanol. After 20 min at −70° C., the DNA was collected by centrifugation (17,000×g, 15 min), dried under vacuum, and dissolved in 180 μl of 10 mM Tris-HCl, pH 8.0. To this were added 20 μl of 10×CIP buffer (100 mM Tris-HCl, pH 8.3; 10 mM $ZnCl_2$; 10 mM $MgCl_2$), and 1 μl (0.25 units) of 1:4 diluted calf intestinal alkaline phosphatase (Boehringer Mannheim Corporation, Indianapolis, Ind.). After 30 min at 37° C., the following additions were made: 2 μl 0.5 M EDTA, pH 8.0; 10 μl 10% SDS; 0.5 μl of 20 mg/ml proteinase K (as above), followed by incubation at 55° C. for 30 min. Following sequential extractions with 100 μl of PCI and 100 μl phenol (Intermountain Scientific Corporation, equilibrated with 1 M Tris-HCl, pH 8.0), the dephosphorylated DNA was precipitated by addition of 72 μl of 7.5 M ammonium acetate and 550 μl −20° C. ethanol, incubation on ice for 30 min, and centrifugation as above. The pelleted DNA was washed once with 500 μl −20° C. 70% ethanol, dried under vacuum, and dissolved in 20 μl of TE buffer.

Ligation of the size-fractionated Sau3A 1 fragments to the BamH 1-digested and phosphatased pWE15 vector was accomplished using T4 ligase (NEB) by a modification (i.e., use of premixed 10×ligation buffer supplied by the manufacturer) of the protocol in section 3.33 of Ausubel. Ligation was carried out overnight in a total volume of 20 μl at 15° C., followed by storage at −20° C.

Four μl of the cosmid DNA ligation reaction, containing about 1 μl of DNA, was packaged into bacteriophage lambda using a commercial packaging extract (Gigapack® III Gold Packaging Extract, Stratagene), following the manufacturer's directions. The packaged preparation was stored at 4° C. until use. The packaged cosmid preparation was used to infect Escherichia coli XL1 Blue MR cells (Stratagene) according to the Gigapack® III Gold protocols ("Titering the Cosmid Library"), as follows. XL1 Blue MR cells were grown in LB medium (g/L: Bacto-tryptone, 10; Bacto-yeast extract, 5; Bacto-agar, 15; NaCl, 5; [Difco Laboratories, Detroit, Mich.] containing 0.2% (w/v) maltose plus 10 mM $MgSO_4$, at 37° C. After 5 hr growth, cells were pelleted at 700×g (15 min) and resuspended in 6 ml of 10 mM $MgSO_4$. The culture density was adjusted with 10 mM $MgSO_4$ to $OD_{600}$=0.5. The packaged cosmid library was diluted 1:10 or 1:20 with sterile SM medium (0.1 M NaCl, 10 mM $MgSO_4$, 50 mM Tris-HCl pH 7.5, 0.01% w/v gelatin), and 25 μl of the diluted preparation was mixed with 25 μl of the diluted XL1 Blue MR cells. The mixture was incubated at 25° C. for 30 min (without shaking), then 200 μl of LB broth was added, and incubation was continued for approximately 1 hr with occasional gentle shaking. Aliquots (20–40 μl) of this culture were spread on LB agar plates containing 100 mg/l ampicillin (i.e., LB-$Amp_{100}$) and incubated overnight at 37° C. To store the library without amplification, single colonies were picked and inoculated into individual wells of sterile 96-well microwell plates; each well containing 75 μl of Terrific Broth (TB media: 12 g/l Bacto-tryptone, 24 g/l Bacto-yeast extract, 0.4% v/v glycerol, 17 mM $KH_2PO_4$, 72 mM $K_2HPO_4$) plus 100 mg/l ampicillin (i.e., TB-$Amp_{100}$) and incubated (without shaking) overnight at 37° C. After replicating the 96-well plate into a copy plate, 75 μl/well of filter-sterilized TB:glycerol (1:1, v/v; with, or without, 100 mg/l ampicillin) was added to the plate, it was shaken briefly at 100 rpm, 37° C., and then closed with Parafilm® (American National Can, Greenwich, Conn.) and placed in a −70° C. freezer for storage. Copy plates were grown and processed identically to the master plates. A total of 40 such master plates (and their copies) were prepared.

Screening of the Library with Radiolabeled DNA Probes

To prepare colony filters for probing with radioactively labeled probes, ten 96-well plates of the library were thawed at 25° C. (bench top at room temperature). A replica plating tool with 96 prongs was used to inoculate a fresh 96-well copy plate containing 75 μl/well of TB-Amp$_{100}$. The copy plate was grown overnight (stationary) at 37° C., then shaken about 30 min at 100 rpm at 37° C. A total of 800 colonies was represented in these copy plates, due to non-growth of some isolates. The replica tool was used to inoculate duplicate impressions of the 96-well arrays onto Based on the N-terminal amino acid sequence determined for the purified TcaC peptide fraction [disclosed herein as SEQ ID NO:2], a pool of degenerate oligonucleotides (pool S4Psh) was synthesized by standard β-cyanoethyl chemistry on an Applied BioSystem ABI394 DNA/RNA Synthesizer (Perkin Elmer, Foster City, Calif.). The oligonucleotides were deprotected 8 hours at 55° C., dissolved in water, quantitated by spectrophotometric measurement, and diluted for use. This pool corresponds to the determined N-terminal amino acid sequence of the TcaC peptide. The determined amino acid sequence and the corresponding degenerate DNA sequence are given below, where A, C, G, and T are the standard DNA bases, and I represents inosine:

| Amino Acid | Met | Gln | Asp | Ser | Pro | Glu | Val |
|---|---|---|---|---|---|---|---|
| S4Psh | 5' ATG | CA(A/G) | GA(T/C) | (T/A)(C/G)(T/A) | CCI | GA(A/G) | GT 3' |

Magna NT (MSI, Westboro, Mass.) nylon membranes (0.45 micron, 220×250 mm) which had been placed on solid LB-Amp$_{100}$ (100 ml/dish) in Bio-assay plastic dishes (Nunc, 243×243×18 mm; Curtin Mathison Scientific, Inc., Wood Another set of degenerate oligonucleotides was synthesized (pool P2.3.5R), representing the complement of the coding strand for determined amino acid sequence of the SEQ ID NO:17:

| Amino Acid | Ala | Phe | Asn | Ile | Asp | Asp | Val |
|---|---|---|---|---|---|---|---|
| Codons | 5' GCN | TT(T/C) | AA(T/C) | AT(A/T/C) | GA(T/C) | GA(T/C) | GT 3' |
| P2.3.5R | 3' CG(A/C/G/T) | AA(A/G) | TT(A/G) | TA(T/A/G) | CT(A/G) | CT(A/G) | CA 5' |

Dale, Ill.). The colonies were grown on the membranes at 37° C. for about 3 hr.

A positive control colony (a bacterial clone containing a GZ4 sequence insert, see below) was grown on a separate Magna NT membrane (Nunc, 0.45 micron, 82 mm circle) on LB medium supplemented with 35 mg/l chloramphenicol (i.e., LB-Cam$_{35}$), and processed alongside the library colony membranes. Bacterial colonies on the membranes were lysed, and the DNA was denatured and neutralized according to a protocol taken from the Genius™ System User's Guide version 2.0 (Boehringer Mannheim, Indianapolis, Ind.). Membranes were placed colony side up on filter paper soaked with 0.5 N NaOH plus 1.5 M NaCl for 15 min to denature, and neutralized on filter paper soaked with 1 M Tris-HCl pH 8.0, 1.5 M NaCl for 15 min. After UV-crosslinking using a Stratagene UV Stratalinker set on auto crosslink, the membranes were stored dry at 25° C. until use. Membranes were trimmed into strips containing the duplicate impressions of a single 96-well plate, then washed extensively by the method of section 6.4.1 in CPMB (op. cit.): 3 hr at 25° C. in 3×SSC, 0.1% (w/v) SDS, followed by 1 hr at 65° C. in the same solution, then rinsed in 2×SSC in preparation for the hybridization step (20×SSC=3 M NaCl, 0.3 M sodium citrate, pH 7.0).

Amplification of a Specific Genomic Fragment of a TcaC Gene

These oligonucleotides were used as primers in Polymerase Chain Reactions (PCR®, Roche Molecular Systems, Branchburg, N.J.) to amplify a specific DNA fragment from genomic DNA prepared from Photorhabdus strain W-14 (see above). A typical reaction (50 μl) contained 125 pmol of each primer pool P2Psh and P2.3.5R, 253 ng of genomic template DNA, 10 nmol each of dATP, dCTP, dGTP, and dTTP, 1×GeneAmp® PCR buffer, and 2.5 units of AmpliTaq® DNA polymerase (both from Roche Molecular Systems; 10×GeneAmp buffer is 100 mM Tris-HCl pH 8.3, 500 mM KCl, 0.01% w/v gelatin). Amplifications were performed in a Perkin Elmer Cetus DNA Thermal Cycler (Perkin Elmer, Foster City, Calif., using 35 cycles of 94° C. (1.0 min), 55° C. (2.0 min), 72° C. (3.0 min), followed by an extension period of 7.0 min at 72° C. Amplification products were analyzed by electrophoresis through 2% w/v NuSieve® 3:1 agarose (FMC BioProducts) in TEA buffer (40 mM Tris-acetate, 2 mM EDTA, pH 8.0). A specific product of estimated size 250 bp was observed amongst numerous other amplification products by ethidium bromide (0.5 μg/ml) staining of the gel and examination under ultraviolet light.

The region of the gel containing an approximately 250 bp product was excised, and a small plug (0.5 mm dia.) was removed and used to supply template for PCR amplification (40 cycles). The reaction (50 μl) contained the same components as above, minus genomic template DNA. Following amplification, the ends of the fragments were made blunt and were phosphorylated by incubation at 25° C. for 20 min with 1 unit of T4 DNA polymerase (NEB), 1 nmol ATP, and 2.15 units of T4 kinase (Pharmacia Biotech Inc., Piscataway, N.J.).

DNA fragments were separated from residual primers by electrophoresis through 1% w/v GTG® agarose (FMC) in TEA. A gel slice containing fragments of apparent size 250 bp was excised, and the DNA was extracted using a Qiaex kit (Qiagen Inc., Chatsworth, Calif.).

The extracted DNA fragments were ligated to plasmid vector pBC KS(+) (Stratagene) that had been digested to completion with restriction enzyme Sma 1 and extracted in a manner similar to that described for pWE15 DNA above. A typical ligation reaction (16.3 $\mu$l) contained 100 ng of digested pBC KS(+) DNA, 70 ng of 250 bp fragment DNA, 1 nmol $[Co(NH_3)_6]Cl_3$, and 3.9 Weiss units of T4 DNA ligase (Collaborative Biomedical Products, Bedford, Mass.), in 1×ligation buffer (50 mM Tris-HCl, pH 7.4; 10 mM $MgCl_2$; 10 M dithiothreitol; 1 mM spermidine, 1 mM ATP, 100 mg/ml bovine serum albumin). Following overnight incubation at 14° C., the ligated products were transformed into frozen, competent *Escherichia coli* DH5α cells (Gibco BRL) according to the suppliers' recommendations, and plated on LB-$Cam_{35}$ plates, containing IPTG (119 $\mu$g/ml) and X-gal (50 $\mu$g/ml). Independent white colonies were picked, and plasmid DNA was prepared by a modified alkaline-lysis/PEG precipitation method (PRISM™ Ready Reaction DyeDeoxy™ Terminator Cycle Sequencing Kit Protocols; ABI/Perkin Elmer). The nucleotide sequence of both strands of the insert DNA was determined, using T7 primers [pBC KS(+) bases 601–623: TAAAACGACGGCCAGTGAGCGCG) and LacZ primers [pBC KS(+) bases 792–816: ATGACCATGATTACGCCAAGCGCGC) and protocols supplied with the PRISM™ sequencing kit (ABI/Perkin Elmer) Nonincorporated dye-terminator dideoxyribonucleotides were removed by passage through Centri-Sep 100 columns (Princeton Separations, Inc., Adelphia, N.J.) according to the manufacturer's instructions. The DNA sequence was obtained by analysis of the samples on an ABI Model 373A DNA Sequencer (ABI/Perkin Elmer). The DNA sequences of two isolates, GZ4 and HB14, were found to be as illustrated in FIG. 1.

This sequence illustrates the following features: 1) bases 1–20 represent one of the 64 possible sequences of the S4Psh degenerate oligonucleotides, ii) the sequence of amino acids 1–3 and 6–12 correspond exactly to that determined for the N-terminus of TcaC (disclosed as SEQ ID NO:2), iii) the fourth amino acid encoded is a cysteine residue rather than serine. This difference is encoded within the degeneracy for the serine codons (see above), iv) the fifth amino acid encoded is proline, corresponding to the TcaC N-terminal sequence given as SEQ ID NO:2, v) bases 257–276 encode one of the 192 possible sequences designed into the degenerate pool, vi) the TGA termination codon introduced at bases 268–270 is the result of complementarity to the degeneracy built into the oligonucleotide pool at the corresponding position, and does not indicate a shortened reading frame for the corresponding gene.

Labeling of a TcaC Peptide Gene-specific Probe

DNA fragments corresponding to the above 276 bases were amplified (35 cycles) by PCR® in a 100 $\mu$l reaction volume, using 100 pmol each of P2Psh and P2.3.5R primers, 10 ng of plasmids GZ4 or HB14 as templates, 20 nmol each of DATP, dCTP, dGTP, and dTTP, 5 units of AmpliTAq® DNA polymerase, and 1× concentration of GeneAmp® buffer, under the same temperature regimes as described above. The amplification products were extracted from a 1% GTG® agarose gel by Qiaex kit and quantitated by fluorometry.

The extracted amplification products from plasmid HB14 template (approximately 400 ng) were split into five aliquots and labeled with $^{32}$P-dCTP using the High Prime Labeling Mix (Boehringer Mannheim) according to the manufacturer's instructions. Nonincorporated radioisotope was removed by passage through NucTrap® Probe Purification Columns (Stratagene), according to the supplier's instructions. The specific activity of the labeled DNA product was determined by scintillation counting to be $3.11 \times 10^8$ dpm/$\mu$g. This labeled DNA was used to probe membranes prepared from 800 members of the genomic library.

Screening with a TcaC-peptide Gene Specific Probe

The radiolabeled HB14 probe was boiled approximately 10 min, then added to "minimal hyb" solution. [Note: The "minimal hyb" method is taken from a CERES protocol; "Restriction Fragment Length Polymorphism Laboratory Manual version 4.0", sections 4–40 and 4–47; CERES/NPI, Salt Lake City, Utah. NPI is now defunct, with its successors operating as Linkage Genetics]. "Minimal hyb" solution contains 10% w/v PEG (polyethylene glycol, M.W. approx. 8000), 7% w/v SDS; 0.6×SSC, 10 mM sodium phosphate buffer (from a 1M stock containing 95 g/l $NaH_2PO_4.1H_2O$ and 84.5 g/l $Na_2HPO_4.7H_2O$), 5 mM EDTA, and 100 mg/ml denatured salmon sperm DNA. Membranes were blotted dry briefly then, without prehybridization, 5 strips of membrane were placed in each of 2 plastic boxes containing 75 ml of "minimal hyb" and 2.6 ng/ml of radiolabeled HB14 probe. These were incubated overnight with slow shaking (50 rpm) at 60° C. The filters were washed three times for approximately 10 min each at 25° C. in "minimal hyb wash solution" (0.25×SSC, 0.2% SDS), followed by two 30-min washes with slow shaking at 60° C. in the same solution. The filters were placed on paper covered with Saran Wrap® (Dow Brands, Indianapolis, Ind.) in a light-tight autoradiographic cassette and exposed to X-Omat X-ray film (Kodak, Rochester, N.Y.) with two DuPont Cronex Lightning-Plus C1 enhancers (Sigma Chemical Co., St. Louis, Mo.), for 4 hr at $-70°$ C. Upon development (standard photographic procedures), significant signals were evident in both replicates amongst a high background of weaker, more irregular signals. The filters were again washed for about 4 hr at 68° C. in "minimal hyb wash solution" and then placed again in the cassettes and film was exposed overnight at $-70°$ C. Twelve possible positives were identified due to strong signals on both of the duplicate 96-well colony impressions. No signal was seen with negative control membranes (colonies of XL1 Blue MR cells containing pWE15), and a very strong signal was seen with positive control membranes (DH5α cells containing the GZ4 isolate of the PCR product) that had been processed concurrently with the experimental samples.

The twelve putative hybridization-positive colonies were retrieved from the frozen 96-well library plates and grown overnight at 37° C. on solid LB-$Amp_{100}$ medium. They were then patched (3/plate, plus three negative controls: XL1 Blue MR cells containing the pWE15 vector) onto solid LB-$Amp_{100}$. Two sets of membranes (Magna NT nylon, 0.45 micron) were prepared for hybridization. The first set was prepared by placing a filter directly onto the colonies on a patch plate, then removing it with adherent bacterial cells, and processing as below. Filters of the second set were placed on plates containing LB-$Amp_{100}$ medium, then inoculated by transferring cells from the patch plates onto the filters. After overnight growth at 37° C., the filters were removed from the plates and processed.

Bacterial cells on the filters were lysed and DNA denatured by placing each filter colony-side-up on a pool (1.0 ml) of 0.5 N NaOH in a plastic plate for 3 min. The filters were blotted dry on a paper towel, then the process was repeated with fresh 0.5 N NaOH. After blotting dry, the filters were neutralized by placing each on a 1.0 ml pool of 1 M Tris-HCl, pH 7.5 for 3 min, blotted dry, and reneutralised with fresh buffer. This was followed by two similar soakings (5 min each) on pools of 0.5 M Tris-HCl pH 7.5 plus 1.5 M NaCl. After blotting dry, the DNA was UV crosslinked to the filter (as above), and the filters were washed (25° C., 100 rpm) in about 100 ml of 3×SSC plus 0.1%(w/v) SDS (4 times, 30 min each with fresh solution for each wash). They were then placed in a minimal volume of prehybridization solution [6×SSC plus 1% w/v each of Ficoll 400 (Pharmacia), polyvinylpyrrolidone (av. M.W. 360,000; Sigma) and bovine serum albumin Fraction V; (Sigma)] for 2 hr at 65° C., 50 rpm. The prehybridization solution was removed, and replaced with the HB14 $^{32}$P-labeled probe that had been saved from the previous hybridization of the library membranes and which had been denatured at 95° C. for 5 min. Hybridization was performed at 60° C. for 16 hr with shaking at 50 rpm.

Following removal of the labeled probe solution, the membranes were washed 3 times at 25° C. (50 rpm, 15 min) in 3×SSC (about 150 ml each wash). They were then washed for 3 hr at 68° C. (50 rpm) in 0.25×SSC plus 0.2% SDS (minimal hyb wash solution), and exposed to X-ray film as described above for 1.5 hr at 25° C. (no enhancer screens). This exposure revealed very strong hybridization signals to cosmid isolates 22G12, 25A10, 26A5, and 26B10, and a very weak signal with cosmid isolate 8B10. No signal was seen with the negative control (pWE15) colonies, and a very strong signal was seen with positive control membranes (DH5a cells containing the GZ4 isolate of the PCR product) that had been processed concurrently with the experimental samples.

Amplification of a Specific Genomic Fragment of a TcaB Gene

Based on the N-terminal amino acid sequence determined for the purified TcaB$_i$ peptide fraction (disclosed here as SEQ ID NO:3) a pool of degenerate oligonucleotides (pool P8F) was synthesized as described for peptide TcaC. The determined amino acid sequence and the corresponding degenerate DNA sequence are given below, where A, C, G, and T are the standard DNA bases, and I represents inosine:

nmol each of DATP, dCTP, dGTP, and dTTP, in 1×GeneAmp® PCR buffer, and (top layer) 230 ng of genomic template DNA, 8 nmol each of DATP, dCTP, dGTP, and dTTP, and 2.5 units of AmpliTaq® DNA polymerase, in 1×GeneAmp® PCR buffer. Amplifications were performed by 35 cycles as described for the TcaC peptide. Amplification products were analyzed by electrophoresis through 0.7% w/v SeaKem® LE agarose (FMC) in TEA buffer. A specific product of estimated size 1600 bp was observed.

Four such reactions were pooled, and the amplified DNA was extracted from a 1.0% SeaKem® LE gel by Qiaex kit as described for the TcaC peptide. The extracted DNA was used directly as the template for sequence determination (PRISM™ Sequencing Kit) using the P8F and P8.108.3R primer pools. Each reaction contained about 100 ng template DNA and 25 pmol of one primer pool, and was processed according to standard protocols as described for the TcaC peptide. An analysis of the sequence derived from extension of the P8F primers revealed the short DNA sequence (and encoded amino acid sequence):

| GAT | GCA | TTG | NTT | GCT |
|-----|-----|-----|-----|-----|
| Asp | Ala | Leu | (Val) | Ala | which corresponds to a portion of the N-terminal peptide sequence disclosed as SEQ ID NO:3 (TcaB$_i$).

Labeling of a TcaB$_i$-peptide Gene-specific Probe

Approximately 50 ng of gel-purified TcaB$_i$ DNA fragment was labeled with $^{32}$P-dCTP as described above, and nonincorporated radioisotopes were removed by passage through a NICK Column® (Pharmacia). The specific activity of the labelled DNA was determined to be 6×10$^9$ dpm/μg. This labeled DNA was used to probe colony membranes prepared from members of the genomic library that had hybridized to the TcaC-peptide specific probe.

The membranes containing the 12 colonies identified in the TcaC-probe library screen (see above) were stripped of

| Amino Acid | Leu | Phe | Thr | Gln | Thr | Leu | Lys | Glu | Ala | Arg |
|---|---|---|---|---|---|---|---|---|---|---|
| P8F | 5' (C/T)TI | TTT | ACI | CA(A/G) | ACI | (C/T)TI | AAA | GAA | GCI | (A/C)G 3' |

Another set of degenerate oligonucleotides was synthesized (pool P8.108.3R), representing the complement of the coding strand for the determined amino acid sequence of the TcaB$_i$-PT108 internal peptide (disclosed herein as SEQ ID NO:20):

radioactive TcaC-specific label by boiling twice for approximately 30 min each time in 1 liter of 0.1×SSC plus 0.1% SDS. Removal of radiolabel was checked with a 6 hr film exposure. The stripped membranes were then incubated with the TcaB$_i$ peptide-specific probe prepared above. The

| Amino Acid | Met | Tyr | Tyr | Ile | Gln | Ala | Gln | Gln |
|---|---|---|---|---|---|---|---|---|
| Codons | ATG | TA(T/C) | TA(T/C) | AT(T/C/A) | CA(A/G) | GC(A/C/G/T) | CA(A/G | CA(A/G) |
| P8.108.3R | 3' TAC | AT(A/G) | AT(A/G) | TA(A/G/T) | GT(T/C) | CGI | GT(T/C) | GT 5' |

These oligonucleotides were used as primers for PCR® using HotStart 50 Tubes™ (Molecular Bio-Products, Inc., San Diego, Calif.) to amplify a specific DNA fragment from genomic DNA prepared from Photorhabdus strain W-14 (see above). A typical reaction (50 μl) contained (bottom layer) 25 pmol of each primer pool P8F and PB.108.3R, with 2 labeled DNA was denatured by boiling for 10 min, and then added to the filters that had been incubated for 1 hr in 100 ml of "minimal hyb" solution at 60° C. After overnight hybridization at this temperature, the probe solution was removed, and the filters were washed as follows (all in 0.3×SSC plus 0.1% SDS): once for 5 min at 25° C., once for 1 hr at 60° C. in fresh solution, and once for 1 hr at 63° C. in fresh solution. After 1.5 hr exposure to X-ray film by standard procedures, 4 strongly-hybridizing colonies were observed. These were, as with the TcaC-specific probe, isolates 22G12, 25A10, 26A5, and 26B10.

The same TcaB$_i$ probe solution was diluted with an equal volume (about 100 ml) of "minimal hyb" solution, and then used to screen the membranes containing the 800 members of the genomic library. After hybridization, washing, and exposure to X-ray film as described above, only the four cosmid clones 22G12, 25A10, 26A5, and 26B10, were found to hybridize strongly to this probe.

Isolation of Subclones Containing Genes Encoding TcaC and YcaB$_i$ Peptides, and Determination of DNA Base Sequence Thereof Three hybridization-positive cosmids in strain XL1 Blue MR were grown with shaking overnight (200 rpm) at 30° C. in 100 ml TB-Amp$_{100}$. After harvesting the cells by centrifugation, cosmid DNA was prepared using a commercially available kit (BIGprep™, 5 Prime 3 Prime, Inc., Boulder, Colo.), following the manufacturer's protocols. Only one cosmid, 26A5, was successfully isolated by this procedure. When digested with restriction enzyme EcoR 1 (NEB) and analyzed by gel electrophoresis, fragments of approximate sizes 14, 10, 8 (vector), 5, 3.3, 2.9, and 1.5 kbp were detected. A second attempt to isolate cosmid DNA from the same three strains (8 ml cultures; TB-Amp$_{100}$, 30° C.) utilized a boiling miniprep method (Evans G. and G. Wahl., 1987, "Cosmid vectors for genomic walking and rapid restriction mapping." in *Guide to Molecular Cloning Techniques, Meth. Enzymology*, Vol. 152, S. Berger and A. Kimmel, eds., pgs. 604–610). Only one cosmid, 25A10, was successfully isolated by this method. When digested with restriction enzyme EcoR I (NEB) and analyzed by gel electrophoresis, this cosmid showed a fragmentation pattern identical to that previously seen with cosmid 26A5.

A 0.15 μg sample of 26A5 cosmid DNA was used to transform 50 ml of *E. coli* DH5α cells (Gibco BRL), by the supplier's protocols. A single colony isolate of that strain was inoculated into 4 ml of TB-Amp$_{100}$, and grown for 8 hr at 37° C. Chloramphenicol was added to a final concentration of 225 μg/ml, incubation was continued for another 24 hr, then cells were harvested by centrifugation and frozen at −20° C. Isolation of the 26A5 cosmid DNA was by a standard alkaline lysis miniprep (Maniatis et al., op. cit., p. 382), modified by increasing all volumes by 50% and with stirring or gentle mixing, rather than vortexing, at every step. After washing the DNA pellet in 70% ethanol, it was dissolved in TE containing 25 μg/ml ribonuclease A (Boehringer Mannheim).

Identification of EcoR I Fragments Hybridizing to GZ4-derived and TcaB$_i$-Probes Approximately 0.4 μg of cosmid 25A10 (from XL1 Blue MR cells) and about 0.5 μg of cosmid 26A5 (from chloramphenicol-amplified DH5α cells) were each digested with about 15 units of EcoR I(NEB) for 85 min, frozen overnight, then heated at 65° C. for five min, and electrophoresed in a 0.7% agarose gel (Seakem® LE, 1×TEA, 80 volts, 90 min). The DNA was stained with ethidium bromide as described above, and photographed under ultraviolet light. The EcoR I digest of cosmid 25A10 was a complete digestion, but the sample of cosmid 26A5 was only partially digested under these conditions. The agarose gel containing the DNA fragments was subjected to depurination, denaturation and neutralization, followed by Southern blotting onto a Magna NT nylon membrane, using a high salt (20×SSC) protocol, all as described in section 2.9 of Ausubel et al. (CPMB, op. cit.). The transferred DNA was then UV-crosslinked to the nylon membrane as before.

An TcaC-peptide specific DNA fragment corresponding to the insert of plasmid isolate GZ4 was amplified by PCR® in a 100 ml reaction volume as described previously above. The amplification products from three such reactions were pooled and were extracted from a 1% GTR® agarose gel by Qiaex kit, as described above, and quantitated by fluorometry. The gel-purified DNA (100 ng) was labeled with $^{32}$P-dCTP using the High Prime Labeling Mix (Boehringer Mannheim) as described above, to a specific activity of 6.34×10$^8$ dpm/μg.

The $^{32}$P-labeled GZ4 probe was boiled 10 min, then added to "minimal hyb" buffer (at 1 ng/ml), and the Southern blot membrane containing the digested cosmid DNA fragments was added, and incubated for 4 hr at 60° C. with gentle shaking at 50 rpm. The membrane was then washed 3 times at 25° C. for about 5 min each (minimal hyb wash solution), followed by two washes for 30 min each at 60° C. The blot was exposed to film (with enhancer screens) for about 30 min at −70° C. The GZ4 probe hybridized strongly to the 5.0 kbp (apparent size) EcoR I fragment of both these two cosmids, 26A5 and 25A10.

The membrane was stripped of radioactivity by boiling for about 30 min in 0.1×SSC plus 0.1% SDS, and absence of radiolabel was checked by exposure to film. It was then hybridized at 60° C. for 3.5 hours with the (denatured) TcaB$_i$ probe in "minimal hyb" buffer previously used for screening the colony membranes (above), washed as described previously, and exposed to film for 40 min at −70° C. with two enhancer screens. With both cosmids, the TcaB$_i$ probe hybridized lightly with the about 5.0 kbp EcoR 1 fragment, and strongly with a fragment of approximately 2.9 kbp.

The sample of cosmid 26A5 DNA previously described, (from DH5α cells) was used as the source of DNA from which to subclone the bands of interest. This DNA (2.5 μg) was digested with about 3 units of EcoR I (NEB) in a total volume of 30 μl for 1.5 hr, to give a partial digest, as confirmed by gel electrophoresis. Ten μg of pBC KS (+) DNA (Stratagene) were digested for 1.5 hr with 20 units of EcoR I in a total volume of 20 μl, leading to total digestion as confirmed by electrophoresis. Both EcoR I-cut DNA preparations were diluted to 50 μl with water, to each an equal volume of PCI was added, the suspension was gently mixed, spun in a microcentrifuge and the aqueous supernatant was collected. DNA was precipitated by 150 μl ethanol, and the mixture was placed at −20° C. overnight. Following centrifugation and drying, the EcoR I -digested pBC KS (+) was dissolved in 100 μl TE; the partially digested 26A5 was dissolved in 20 μl TE. DNA recovery was checked by fluorometry.

In separate reactions, approximately 60 ng of EcoR I-digested pBC KS(+) DNA was ligated with approximately 180 ng or 270 ng of partially digested cosmid 26A5 DNA. Ligations were carried out in a volume of 20 μl at 15° C. for 5 hr, using T4 ligase and buffer from New England BioLabs. The ligation mixture, diluted to 100 μl with sterile TE, was used to transform frozen, competent DH5α cells (Gibco BRL) according to the supplier's instructions. Varying amounts (25–200 μl) of the transformed cells were plated on freshly prepared solid LB-Cam$_{35}$ medium with 1 mM IPTG and 50 mg/l X-gal. Plates were incubated at 37° C. about 20 hr, then chilled in the dark for approximately 3 hr to intensify color for insert selection. White colonies were picked onto patch plates of the same composition and incubated overnight at 37° C.

Two colony lifts of each of the selected patch plates were prepared as follows. After picking white colonies to fresh plates, round Magna NT nylon membranes were pressed onto the patch plates, the membrane was lifted off, and subjected to denaturation, neutralization and UV crosslinking as described above for the library colony membranes. The crosslinked colony lifts were vigorously washed, including gently wiping off the excess cell debris with a tissue. One set was hybridized with the GZ4(TcaC) probe solution described earlier, and the other set was hybridized with the TcaB$_i$ probe solution described earlier, according to the 'minimal hyb' protocol, followed by washing and film exposure as described for the library colony membranes.

Colonies showing hybridization signals either only with the GZ4 probe, with both GZ4 and TcaB$_i$ probes, or only with the TcaB$_i$ probe, were selected for further work and cells were streaked for single colony isolation onto LB-Cam$_{35}$ media with IPTG and X-gal as before. Approximately 35 single colonies, from 16 different isolates, were picked into liquid LB-Cam$_{35}$ media and grown overnight at 37° C.; the cells were collected by centrifugation and plasmid DNA was isolated by a standard alkaline lysis miniprep according to Maniatis et al. (op. cit. p. 368). DNA pellets were dissolved in TE+25 µg/ml ribonuclease A and DNA concentration was determined by fluorometry. The EcoR I digestion pattern was analyzed by gel electrophoresis. The following isolates were picked as useful. Isolate A17.2 contains religated pBC KS(+) only and was used for a (negative) control. Isolates D38.3 and C44.1 each contain only the 2.9 kbp, TcaB$_i$-hybridizing EcoR I fragment inserted into pBC KS(+). These plasmids, named pDAB2000 and pDAB2001, respectively, are illustrated in FIG. 2.

Isolate A35.3 contains only the approximately 5 kbp, GZ4)-hybridizing EcoR 1 fragment, inserted into pBC KS(+). This plasmid was named pDAB2002 (also FIG. 2). These isolates provided templates for DNA sequencing.

Plasmids pDAB2000 and pDAB2001 were prepared using the BIGprep™ kit as before. Cultures (30 ml) were grown overnight in TB-Cam$_{35}$ to an OD$_{600}$ of 2, then plasmid was isolated according to the manufacturer's directions. DNA pellets were redissolved in 100 µl TE each, and sample integrity was checked by EcoR I digestion and gel electrophoretic analysis.

Sequencing reactions were run in duplicate, with one replicate using as template pDAB2000 DNA, and the other replicate using as template pDAB2001 DNA. The reactions were carried out using the dideoxy dye terminator cycle sequencing method, as described above for the sequencing of the GZ4/HB14 DNAs. Initial sequencing runs utilized as primers the LacZ and T7 primers described above, plus primers based on the determined sequence of the TcaB$_i$ PCR amplification product (TH1= ATTGCAGACTGCCAATCGCTTCGG, TH12= GAGAGTATCCAGACCGCGGATGATCTG).

After alignment and editing of each sequencing output, each was truncated to between 250 to 350 bases, depending on the integrity of the chromatographic data as interpreted by the Perkin Elmer Applied Biosystems Division SeqEd 675 software. Subsequent sequencing "steps" were made by selecting appropriate sequence for new primers. With a few exceptions, primers (synthesized as described above) were 24 bases in length with a 50% G+C composition. Sequencing by this method was carried out on both strands of the approximately 2.9 kbp EcoR I fragment.

To further serve as template for DNA sequencing, plasmid DNA from isolate pDAB2002 was prepared by BIGprep™ kit. Sequencing reactions were performed and analyzed as described above. Initially, a T3 primer (pBS SK (+) bases 774–796: CGCGCAATTAACCCTCACTAAAG) and a T7 primer (pBS KS (+) bases 621–643: GCGCGTAATACGACTCACTATAG) were used to prime the sequencing reactions from the flanking vector sequences, reading into the insert DNA. Another set of primers, (GZ4F: GTATCGATTACAACGCTGTCACTTCCC; TH13: GGGAAGTGACAGCGTTGTAATCGATAC; TH14: ATGTTGGGTGCGTCGGCTAATGGACATAAC; and LW1-204: GGGAAGTGACAGCGTTGTAATCGATAC) was made to prime from internal sequences, which were determined previously by degenerate oligonucleotide-mediated sequencing of subcloned TcaC-peptide PCR products. From the data generated during the initial rounds of sequencing, new sets of primers were designed and used to walk the entire length of the about 5 kbp fragment. A total of 55 oligo primers was used, enabling the identification of 4832 total bp of contiguous sequence.

When the DNA sequence of the EcoR I fragment insert of pDAB2002 is combined with part of the determined sequence of the pDAB2000/pDAB2001 isolates, a total contiguous sequence of 6005 bp was generated (disclosed herein as SEQ ID NO:25). When long open reading frames were translated into the corresponding amino acids, the sequence clearly shows the TcaB$_i$ N-terminal peptide (disclosed as SEQ ID NO:3), encoded by bases 68–124, immediately following a methionine residue (start of translation). Upstream lies a potential ribosome binding site (bases 51–58), and downstream, at bases 215–277 is encoded the TcaB$_i$-PT158 internal peptide (disclosed herein as SEQ ID NO:19). Further downstream, in the same reading frame, at bases 1787–1822, exists a sequence encoding the TcaB$_i$-PT108 internal peptide (disclosed herein as SEQ ID NO:20). Also in the same reading frame, at bases 1946–1972, is encoded the TcaB$_{ii}$ N-terminal peptide (disclosed herein as SEQ ID NO:5), and the reading frame continues uninterrupted to a translation termination codon at nucleotides 3632–3634.

The lack of an in-frame stop codon between the end of the sequence encoding TcaB$_i$-PT108 and the start of the TcaB$_{ii}$ encoding region, and the lack of a discernible ribosome binding site immediately upstream of the TcaB$_{ii}$ coding region, indicate that peptides TcaB$_{ii}$ and TcaB$_i$ are encoded by a single open reading frame of 3567 bp beginning at base pair 65 in SEQ ID NO:25), and are most likely derived from a single primary gene product TcaB of 1189 amino acids (131,586 Daltons; disclosed herein as SEQ ID NO:26) by post-translational cleavage. If the amino acid immediately preceding the TcaB$_{ii}$ N-terminal peptide represents the C-terminal amino acid of peptide TcaB$_i$, then the predicted mass of TcaB$_{ii}$ (627 amino acids) is 70,814 Daltons (disclosed herein as SEQ ID NO:28), somewhat higher than the size observed by SDS-PAGE (68 kDa). This peptide would be encoded by a contiguous stretch of 1881 base pairs (disclosed herein as SEQ ID NO:27). It is thought that the native C-terminus of TcaB$_i$ lies somewhat closer to the C-terminus of TcaB$_i$-PT108. The molecular mass of PT108 [3.438 kDa; determined during N-terminal amino acid sequence analysis of this peptide] predicts a size of 30 amino acids. Using the size of this peptide to designate the C-terminus of the TcaB$_i$ coding region [Glu at position 604 of SEQ ID NO:28], the derived size of TcaB$_i$ is determined to be 604 amino acids or 68,463 Daltons, more in agreement with experimental observations.

Translation of the TcaB$_{ii}$ peptide coding region of 1686 base pairs (disclosed herein as SEQ ID NO:29) yields a protein of 562 amino acids (disclosed herein as SEQ ID NO:30) with predicted mass of 60,789 Daltons, which corresponds well with the observed 61 kDa.

A potential ribosome binding site (bases 3682–3687) is found 48 bp downstream of the stop codon for the tcaB open reading frame. At bases 3694–3726 is found a sequence encoding the N-terminus of peptide TcaC, (disclosed as SEQ ID NO.2). The open reading frame initiated by this N-terminal peptide continues uninterrupted to base 6005 (2361 base pairs, disclosed herein as the first 2361 base pairs of SEQ ID NO.31). A gene (tcaC) encoding the entire TcaC peptide, (apparent size about 165 kDa; about 1500 amino acids), would comprise about 4500 bp.

Another isolate containing cloned EcoR I fragments of cosmid 26A5, E20.6, was also identified by its homology to the previously mentioned GZ4 and TcaB$_i$ probes. Agarose gel analysis of EcoR I digests of the DNA of the plasmid harbored by this strain (pDAB2004, FIG. 2), revealed insert fragments of estimated sizes 2.9, 5, and 3.3 kbp. DNA sequence analysis initiated from primers designed from the sequence of plasmid pDAB2002 revealed that the 3.3 kbp EcoR I fragment of pDAB2004 lies adjacent to the 5 kbp EcoR I fragment represented in pDAB2002. The 2361 base pair open reading frame discovered in pDAB2002 continues uninterrupted for another 2094 bases in pDAB2004 [disclosed herein as base pairs 2362 to 4458 of SEQ ID NO:31]. DNA sequence analysis using the parent cosmid 26A5 DNA as template confirmed the continuity of the open reading frame. Altogether, the open reading frame (tcaC SEQ ID NO:31) comprises 4455 base pairs, and encodes a protein (TcaC) of 1485 amino acids [disclosed herein as SEQ ID NO:32]. The calculated molecular size of 166,214 Daltons is consistent with the estimated size of the TcaC peptide (165 kDa), and the derived amino acid sequence matches exactly that disclosed for the TcaC N-terminal sequence [SEQ ID NO:2].

The lack of an amino acid sequence corresponding to SEQ ID NO:17; used to design the degenerate oligonucleotide primer pool in the discovered sequence indicates that the generation of the PCR® products found in isolates GZ4 and HB14, which were used as probes in the initial library screen, were fortuitously generated by reverse-strand priming by one of the primers in the degenerate pool. Further, the derived protein sequence does not include the internal fragment disclosed herein as SEQ ID NO:18. These sequences reveal that plasmid pDAB2004 contains the complete coding region for the TcaC peptide.

Further analysis of SEQ ID NO:25 reveals the end of an open reading frame (bases 1–43), which encodes the final 13 amino acids of the TcaA$_{iii}$ peptide, disclosed herein as SEQ ID NO:35. Only 24 bases separate the end of the TcaA$_{iii}$ coding region and the start of the TcaB$_i$ coding region. Included within the 24 bases are sequences that may serve as a ribosome binding site. Although possible, it is not likely that a Photorhabdus gene promoter is encoded within this short region. We propose that genomic region tca, which includes three long open reading frames [tcaA (SEQ ID NO:33), tcaB (SEQ ID NO:25, bases 65–36334), and tcaC (SEQ ID NO:31),which is separated from the end of tcaB by only 59 bases] is regulated as an operon, with transcription initiating upstream of the start of the tcaA gene (SEQ ID NO:33), and resulting in a polycistronic messenger RNA.

EXAMPLE 9

Screening of the Photorhabdus Genomic Library for Genes Encoding the TcbA$_{ii}$ Peptide This example describes a method used to identify DNA clones that contain the TcbA$_{ii}$ peptide-encoding genes, the isolation of the gene, and the determination of its partial DNA base sequence.

Primers and PCR Reactions

The TcbA$_{ii}$ polypeptide of the insect active preparation is about 206 kDa. The amino acid sequence of the N-terminus of this peptide is disclosed as SEQ ID NO:1. Four pools of degenerate oligonucleotide primers ("Forward primers": TH-4, TH-5, TH-6, and TH-7) were synthesized to encode a portion of this amino acid sequence, as described in Example 8, and are shown below.

TABLE 12

| Amino Acid | Phe | Ile | Gln | Gly | Tyr | Ser | Asp | Leu | Phe |
|---|---|---|---|---|---|---|---|---|---|
| TH-4 | 5'-TT(T/C) | ATI | CA(A/G) | GGI | TA(T/C) | TCI | GA(T/C) | CTI | TT-3' |
| TH-5 | 5'-TT(T/C) | ATI | CA(A/G) | GGI | TA(T/C) | AG(T/C) | GA(T/C) | CTI | TT-3' |
| TH-6 | 5'-TT(T/C) | ATI | CA(A/G) | GGI | TA(T/C) | TCI | GA(T/C) | TA(A/G) | TT-3' |
| TH-7 | 5'-TT(T/C) | ATI | CA(A/G) | GGI | TA(T/C) | AG(T/C) | GA(T/C) | TT(A/G) | TT-3' |

In addition, a primary ("a") and a secondary ("b") sequence of an internal peptide preparation ($TcbA_{ii}$-PT81) have been determined and are disclosed herein as SEQ ID NO:23 and SEQ ID NO:24, respectively. Four pools of degenerate oligonucleotides ("Reverse Primers": TH-8, TH-9, TH-10 and TH-11) were similarly designed and synthesized to encode the reverse complement of sequences that encode,a portion of the peptide of SEQ ID NO:23, as shown below.

TABLE 13

| Amino Acid | Thr | Tyr | Leu | Thr | Ser | Phe | Glu | Gln | Val | Ala | Asn |
|---|---|---|---|---|---|---|---|---|---|---|---|
| TH-8 | 3'-TGI | AT(A/G) | GAI | TGI | AGI | AA(A/G) | CT(T/C) | GT(T/C) | CAI | CGI | TT(G/A)-5' |
| TH-9 | 3'-TGI | AT(A/G) | TT(A/G) | TGI | AGI | AA(A/G) | CT(T/C) | GT(T/C) | CAI | CGI | TT(G/A)-5' |
| TH-10 | 3'-TGI | AT(A/G) | GAI | TGI | TC(G/A) | AA(A/G) | CT(T/C) | GT(T/C) | CAI | CGI | TT(G/A)-5' |
| TH-11 | 3'-TGI | AT(A/G) | TT(A/G) | TGI | TC(G/A) | AA(A/G) | CT(T/C) | GT(T/C) | CAI | CGI | TT(G/A)-5' |

Sets of these primers were used in PCR® reactions to amplify $TcbA_{ii}$-encoding gene fragments from the genomic *Photorhabdus luminescens* W-14 DNA prepared in Example 6. All PCR® reactions were run with the "Hot Start"

technique using AmpliWax™ gems and other Perkin Elmer reagents and protocols. Typically, a mixture (total volume 11 μl) of MgCl₂, dNTP's, 10×GeneAmp® PCR Buffer II, and the primers were added to tubes containing a single wax bead. [10×GeneAmp® PCR Buffer II is composed of 100 mM Tris-HCl, pH 8.3; and 500 mM KCl.] The tubes were heated to 80° C. for 2 minutes and allowed to cool. To the top of the wax seals, a solution containing 10×GeneAmp PCR Buffer II, DNA template, and AmpliTaq® DNA polymerase were added. Following melting of the wax seal and mixing of components by thermal cycling, final reaction conditions (volume of 50 μl) were: 10 mM Tris-HCl, pH 8.3; 50 mM KCl; 2.5 mM MgCl₂; 200 μM each in dATP, dCTP, dGTP, dTTP; 1.25 mM in a single Forward primer pool; 1.25 μM in a single Reverse primer pool, 1.25 units of Ampli-Taq® DNA polymerase, and 170 ng of template DNA.

The reactions were placed in a thermocycler (as in Example 8) and run with the following program:

cation products from primer pairs TH-7 plus TH-8, TH-9, TH-10, or TH-11.

To obtain sufficient PCR amplification product for cloning and DNA sequence determination, 10 separate PCR reactions were set up using the primers TH-5+TH-10, and were run using the above conditions with a 55° C. annealing temperature. All reactions were pooled and the 2.9 kbp product was purified by Qiaex extraction from an agarose gel as described above.

Additional sequences determined for TcbA$_{ii}$ internal peptides are disclosed herein as SEQ ID NO:21 and SEQ ID NO:22. As before, degenerate oligonucleotides (Reverse primers TH-17 and TH-18) were made corresponding to the reverse complement of sequences that encode a portion of the amino acid sequence of these peptides.

TABLE 15

From SEQ ID NO: 21

| Amino Acid | Met | Glu | Thr | Gln | Asn | Ile | Gln | Glu | Pro |
|---|---|---|---|---|---|---|---|---|---|
| TH-17 | 3'-TAC | CTT/C | TGI | GTT/C | TTA/G | TAI | GTT/C | GTT/C | GG-5' |

TABLE 16

From SEQ ID NO: 22

| Amino Acid | Asn | Pro | Ile | Asn | Ile | Asn | Thr | Gly | Ile | Asp |
|---|---|---|---|---|---|---|---|---|---|---|
| TH-18 | 3'-TT(A/G) | GGI | TAI | TT(A/G) | TAI | TT(A?G) | TGI | CCI | TAI | CT(A/G)-5' |

TABLE 14

| Temperature | Time | Cycle Repetition |
|---|---|---|
| 94° C. | 2 minutes | 1X |
| 94° C. | 15 seconds | |
| 55–65° C. | 30 seconds | 30X |
| 72° C. | 1 minute | |
| 72° C. | 7 minutes | 1X |
| 15° C. | Constant | |

A series of amplifications was run at three different annealing temperatures (55°, 60°, 65° C.) using the degenerate primer pools. Reactions with annealing at 65° C. had no amplification products visible following agarose gel electrophoresis. Reactions having a 60° C. annealing regime and containing primers TH-5+TH-10 produced an amplification product that had a mobility corresponding to 2.9 kbp. A lesser amount of the 2.9 kbp product was produced under these conditions with primers TH-7+TH-10. When reactions were annealed at 55° C.,these primer pairs produced more of the 2.9 kbp product, and this product was also produced by primer pairs TH-5+TH-8 and TH-5+TH-11. Additional very faint 2.9 kbp bands were seen in lanes containing amplifi- Degenerate oligonucleotides TH-18 and TH-17 were used in an amplification experiment with *Photorhabdus luminescens* W-14 DNA as template and primers TH-4, TH-5, TH-6, or TH-7 as the 5'-(Forward) primers. These reactions amplified products of approximately 4 kbp and 4.5 kbp, respectively. These DNAs were transferred from agarose gels to nylon membranes and hybridized with a ³²P-labeled probe (as described above) prepared from the 2.9 kbp product amplified by the TH-5+TH10 primer pair. Both the 4 kbp and the 4.5 kbp amplification products hybridized strongly to the 2.9 kbp probe. These results were used to construct a map ordering the TcbA$_{ii}$ internal peptide sequences as shown in FIG. 3. Approximate distances between the primers are shown in nucleotides in FIG. 3.

DNA Sequence of the 2.9 kbp TcbA$_{ii}$-encoding Fragment

Approximately 200 ng of the purified 2.9 kbp fragment (prepared above) was precipitated with ethanol and dissolved in 17 ml of water. One-half of this was used as sequencing template with 25 pmol of the TH-5 pool as primers, the other half was used as template for TH-10 priming. Sequencing reactions were as given in Example 8. No reliable sequence was produced using the TH-10 primer pool; however, reactions with TH-5 primer pool produced the sequence disclosed below:.

```
  1 AATCGTGTTG ATCCCTATGC CGNGCCGGGT TCGGTGGAAT CGATGTCCTC ACCGGGGGTT
 61 TATTNGAGGG ANTNGTCCCG TGAGGCCAAA AANTGGAATG AAAGAAGTTC AATTTNTTAC
```

-continued

```
121 CTAGATAAAC GTCGCCCGGN TTTAGAAAGN TTANTGNTCA GCCAGAAAAT TTTGGTTGAG

181 GAAATTCCAC CGNTGGTTCT CTCTATTGAT TNGGGCCTGG CCGGGTTCGA ANNAAAACNA

241 GGAAATNCAC AAGTTGAGGT GATGGNTTTG TNGCNANCTT NTCGTTTAGG TGGGGAGAAA

301 CCTTNTCANC ACGNTTNTGA AACTGTCCGG GAAATCGTCC ATGANCGTGA NCCAGGNTTN

361 CGCCATTGG
```

Based on this sequence, a sequencing primer (TH-21, 5'-CCGGGCGACGTTTATCTAGG-3') was designed to reverse complement bases 120–139, and initiate polymerization towards the 5' end (i.e., TH-5 end) of the gel-purified 2.9 kbp TcbA$_{ii}$-encoding PCR fragment. The determined sequence is shown below, and is compared to the biochemically determined N-terminal peptide sequence of TcbA$_{ii}$ SEQ ID NO:1.

$TcbA_{ii}$ 2.9 kbp PCR Fragment Sequence Confirmation

[Underlined amino acids=encoded by degenerate oligonucleotides]

```
SEQ ID NO:1 F   I   O   G   Y   S   D   L   F   G   -   -   A
                    |   |   |   |   |   |   |   |   |   |   |
2.9 kbp seq GC ATG CAG GGG TAT AGT GAC CTG TTT GGT AAT CGT GCT
                M   Q   G   Y   S   D   L   F   G   N   R   A >
```

From the homology of the derived amino acid sequence to the biochemically determined one, it is clear that the 2.9 kbp PCR fragment represents the TcbA coding region. This 2.9 kbp fragment was then used as a hybridization probe to screen the Photorhabdus W-14 genomic library prepared in Example 8 for cosmids containing the $TcbA_{ii}$-encoding gene.

Screening the Photorhabdus Cosmid Library

The 2.9 kb gel-purified PCR fragment was labeled with $^{32}P$ using the Boehringer Mannheim High Prime labeling kit as described in Example 8. Filters containing remnants of approximately 800 colonies from the cosmid library were screened as described previously (Example 8), and positive clones were streaked for isolated colonies and rescreened. Three clones (8A11, 25G8, and 26D1) gave positive results through several screening and characterization steps. No hybridization of the $TcbA_{ii}$-specific probe was ever observed with any of the four cosmids identified in Example 8, and which contain the tcaB and tcaC genes. DNA from cosmids 8A11, 25G8, and 26D1 was digested with restriction enzymes Bgl II, EcoR I or Hind III (either alone or in combination with one another), and the fragments were separated on an agarose gel and transferred to a nylon membrane as described in Example 8. The membrane was hybridized with $^{32}P$-labeled probe prepared from the 4.5 kbp fragment (generated by amplification of Photorhabdus genomic DNA with primers TH-5+TH-17). The patterns generated from cosmid DNAs 8A11 and 26D1 were identical to those generated with similarly-cut genomic DNA on the same membrane. It is concluded that cosmids 8A11 and 26D1 are accurate representations of the genomic $TcbA_{ii}$ encoding locus. However, cosmid 25G8 has a single Bgl II fragment which is slightly larger than the genomic DNA. This may result from positioning of the insert within the vector.

DNA Sequence of the tcbA-encoding Gene

The membrane hybridization analysis of cosmid 26D1 revealed that the 4.5 kbp probe hybridized to a single large EcoR I fragment (greater than 9 kbp). This fragment was gel purified and ligated into the EcoR I site of pBC KS (+) as described in Example 8, to generate plasmid pBC-S1/R1. The partial DNA sequence of the insert DNA of this plasmid was determined by "primer walking" from the flanking vector sequence, using procedures described in Example 8. Further sequence was generated by extension from new oligonucleotides designed from the previously determined sequence. When compared to the determined DNA sequence for the tcbA gene identified by other methods (disclosed herein as SEQ ID NO:11 as described in Example 12 below), complete homology was found to nucleotides 1–272, 319–826, 2578–3036, and 3068–3540 (total bases=1712). It was concluded that both approaches can be used to identify DNA fragments encoding the $TcbA_{ii}$ peptide.

Analysis of the Derived Amino Acid Sequence of the tcbA Gene

The sequence of the DNA fragment identified as SEQ ID NO:11 encodes a protein whose derived amino acid sequence is disclosed herein as SEQ ID NO:12. Several features verify the identity of the gene as that encoding the $TcbA_{ii}$ protein. The $TcbA_{ii}$ N-terminal peptide (SEQ ID NO:1; Phe Ile Gln Gly Tyr Ser Asp Leu Phe Gly Asn Arg Ala) is encoded as amino acids 88–100. The $TcbA_{ii}$ internal peptide $TcbA_{ii}$-PT81(a) (SEQ ID NO:23) is encoded as amino acids 1065–1077, and $TcbA_{ii}$-PT81(b) (SEQ ID NO:24) is encoded as amino acids 1571–1592. Further, the internal peptide $TcbA_{ii}$-PT56 (SEQ ID NO:22) is encoded as amino acids 1474–1488, and the internal peptide $TcbA_{ii}$-PT103 (SEQ ID NO:21) is encoded as amino acids 1614–1639. It is obvious that this gene is an authentic clone encoding the $TcbA_{ii}$ peptide as isolated from insecticidal protein preparations of *Photorhabdus luminescens* strain W-14.

The protein isolated as peptide $TcbA_{ii}$ is derived from cleavage of a longer peptide. Evidence for this is provided by the fact that the nucleotides encoding the $TcbA_{ii}$ N-terminal peptide SEQ ID NO:1are preceded by 261 bases (encoding 87 N-terminal-proximal amino acids) of a longer open reading frame (SEQ ID NO:11). This reading frame begins with nucleotides that encode the amino acid sequence Met Gln Asn Ser Leu, which corresponds to the N-terminal sequence of the large peptide TcbA, and is disclosed herein as SEQ ID NO:16. It is thought that TcbA is the precursor protein for $TcbA_{ii}$.

Relationship of tcbA, tcaB and tcaC Genes

The tcaB and tcaC genes are closely linked and may be transcribed as a single mRNA (Example 8). The tcbA gene is borne on cosmids that apparently do not overlap the ones harboring the tcaB and tcaC cluster, since the respective genomic library screens identified different cosmids. However, comparison of the amino sequences encoded by the tcaB and tcaC genes with the tcbA gene reveals a substantial degree of homology. The amino acid conservation (Protein Alignment Mode of MacVector™ Sequence Analysis Software, scoring matrix pam250, hash value=2; Oxford Molecular Group, Campbell, Calif.) is shown in FIG. 4. On the score line of each panel in FIG. 4, up carats (^) indicate homology or conservative amino acid changes, and down carats (v) indicate nonhomology.

This analysis shows that the amino acid sequence of the TcbA peptide from residues 1739 to 1894 is highly homologous to amino acids 441 to 603 of the TcaB$_i$ peptide (162 of the total 627 amino acids of TcaB; SEQ ID NO:28). In addition, the sequence of TcbA amino acids 1932 to 2459 is highly homologous to amino acids 12 to 531 of peptide TcaB$_{ii}$ (520 of the total 562 amino acids; SEQ ID NO:30). Considering that the TcbA peptide (SEQ ID NO:12) comprises 2505 amino acids, a total of 684 amino acids (27%) at the C-proximal end of it is homologous to the TcaB$_i$ or TcaB$_{ii}$ peptides, and the homologies are arranged colinear to the arrangement of the putative TcaB preprotein (SEQ ID NO:26). A sizeable gap in the TcbA homology coincides with the junction between the TcaB$_i$ and TcaB$_{ii}$ portions of the TcaB preprotein. Clearly the TcbA and TcaB gene products are evolutionarily related, and it is proposed that they share some common function(s) in Photorhabdus.

EXAMPLE 10

Characterization of Zinc-metalloproteases in Photorhabdus Broth: Protease Inhibition, Classification, and Purification Protease Inhibition and Classification Assays: Protease assays were performed using FITC-casein dissolved in water as substrate (0.08% final assay concentration). Proteolysis reactions were performed at 25° C. for 1 h in the appropriate buffer with 25 μl of Photorhabdus broth (150 μl total reaction volume). Samples were also assayed in the presence and absence of dithiothreitol. After incubation, an equal volume of 12% trichloroacetic acid was added to precipitate undigested protein. Following precipitation for 0.5 h and subsequent centrifugation, 100 μl of the supernatant was placed into a 96-well microtiter plate and the pH of the solution was adjusted by addition of an equal volume of 4N NaOH. Proteolysis was then quantitated using a Fluoroskan II fluorometric plate reader at excitation and emission wavelengths of 485 and 538 nm, respectively. Protease activity was tested over a range from pH 5.0–10.0 in 0.5 units increments. The following buffers were used at 50 mM final concentration: sodium acetate (pH 5.0–6.5); Tris-HCL (pH 7.0–8.0); and bis-Tris propane (pH 8.5–10.0). To identify the class of protease(s) observed, crude broth was treated with a variety of protease inhibitors (0.5 μg/μl final concentration) and then examined for protease activity at pH 8.0 using the substrate described above. The protease inhibitors used included E-64 (L-trans-expoxysaccinylleucylamido[4-,-guanidino]-butane), 3,4 dichloroisocoumarin, Leupeptin, pepstatin, amastatin, ethylenediaminetetraacetic acid (EDTA) and 1,10 phenanthroline.

Protease assays performed over a pH range revealed that indeed protease(s) were present which exhibited maximal activity at about pH 8.0 (Table 17). Addition of DTT did not have any effect on protease activity. Crude broth was then treated with a variety of protease inhibitors (Table 18). Treatment of crude broth with the inhibitors described above revealed that 1,10 phenanthroline caused complete inhibition of all protease activity when added at a final concentration of 50 μg, with the IC$_{50}$=5 μg in 100 μl of a 2 mg/ml crude broth solution. These data indicate that the most abundant protease(s) found in the Photorhabdus broth are from the zinc-metalloprotease class of enzymes.

TABLE 17

Effect of pH on the Protease Activity Found in a Day 1 Production of *Photorhabdus luminescens* (Strain W-14)

| pH | Flu. Units[a] | Percent Activity[b] |
|---|---|---|
| 5.0 | 3013 ± 78 | 17 |
| 5.5 | 7994 ± 448 | 45 |
| 6.0 | 12965 ± 483 | 74 |
| 6.5 | 14390 ± 1291 | 82 |
| 7.0 | 14386 ± 1287 | 82 |
| 7.5 | 14135 ± 198 | 80 |
| 8.0 | 17582 ± 831 | 100 |
| 8.5 | 16183 ± 953 | 92 |
| 9.0 | 16795 ± 760 | 96 |
| 9.5 | 16279 ± 1022 | 93 |
| 10.0 | 15225 ± 210 | 87 |

[a]Flu. Units = Fluorescence Units (Maximum = about 28,000; background = about 2200).
[b]Percent activity relative to the maximum at pH 8.0

TABLE 18

Effect of Different Protease Inhibitors on the Protease Activity at pH 8 Found in a Day 1 Production of *Photorhabdus luminescens* (Strain W-14)

| Inhibitor | Corrected Flu. Units[a] | Percent Inhibition[b] |
|---|---|---|
| Control | 13053 | 0 |
| E-64 | 14259 | 0 |
| 1,10 Phenanthroline[c] | 15 | 99 |
| 3,4 Dichloroisocoumarin[d] | 7956 | 39 |
| Leupeptin | 13074 | 0 |
| Pepstatin[c] | 13441 | 0 |
| Amastatin | 12474 | 4 |
| DMSO Control | 12005 | 8 |
| Methanol Control | 12125 | 7 |

[a]Corrected Flu. Units = Fluorescence Units - background (2200 flu. units).
[b]Percent Inhibition relative to protease activity at pH 8.0.
[c]Inhibitors were dissolved in methanol.
[d]Inhibitors were dissolved in DMSO.

The isolation of a zinc-metalloprotease was performed by applying dialyzed 10–80% ammonium sulfate pellet to a Q Sepharose column equilibrated at 50 mM Na$_2$PO$_4$, pH 7.0 as described in Example 5 for Photorhabdus toxin. After extensive washing, a 0 to 0.5 M NaCl gradient was used to elute toxin protein. The majority of biological activity and protein was eluted from 0.15–0.45 M NaCl. However, it was observed that the majority of proteolytic activity was present in the 0.25–0.35 M NaCl fraction with some activity in the 0.15–0.25 M NaCl fraction. SDS PAGE analysis of the 0.25–0.35 M NaCl fraction showed a major peptide band of approximately 60 kDa. The 0.15–0.25 M NaCl fraction contained a similar 60 kDa band but at lower relative protein concentration. Subsequent gel filtration of this fraction using a Superose 12 HR 16/50 column resulted in a major peak migrating at 57.5 kDa that contained a predominant (>90% of total stained protein) 58.5 kDa band by SDS PAGE analysis. Additional analysis of this fraction using various protease inhibitors as described above determined that the protease was a zinc-metalloprotease. Nearly all of the protease activity present in Photorhabdus broth at day 1 of fermentation corresponded to the about 58 kDa zinc-metalloprotease.

In yet a second isolation of zinc-metalloprotease(s), W-14 Photorhabdus broth grown for three days was taken and protease activity was visualized using sodium dodecyl sulfate-polyacrylamide gel electrophoresis (SDS-PAGE) laced with gelatin as described in Schmidt, T. M., Bleakley, B. and Nealson, K. M. 1988. SDS running gels (5.5×8 cm) were made with 12.5% polyacrylamide (40% stock solution of acrylamide/bis-acrylamide; Sigma Chemical Co., St. Louis, Mo.) into which 0.1% gelatin final concentration (Biorad EIA grade reagent; Richmond Calif.) was incorporated upon dissolving in water. SDS-stacking gels (1.0×8 cm) were made with 5% polyacrylamide, also laced with 0.1% gelatin. Typically, 2.5 µg of protein to be tested was diluted in 0.03 ml of SDS-PAGE loading buffer without dithiothreitol (DTT) and loaded onto the gel. Proteins were electrophoresed in SDS running buffer (Laemmli, U.K. 1970. Nature 227, 680) at 0° C. and at 8 mA. After electrophoresis was complete, the gel was washed for 2 h in 2.5% (v/v) Triton X-100. Gels were then incubated for 1 h at 37° C. in 0.1 M glycine (pH 8.0). After incubation, gels were fixed and stained overnight with 0.1% amido black in methanol-acetic acid- water (30:10:60, vol./vol./vol.; Sigma Chemical Co.). Protease activity was visualized as light areas against a dark, amido black stained background due to proteolysis and subsequent diffusion of incorporated gelatin. At least three distinct bands produced by proteolytic activity at 58-, 41-, and 38 kDa were observed.

Activity assays of the different proteases in W-14 day three culture broth were performed using FITC-casein dissolved in water as substrate (0.02% final assay concentration). Proteolysis experiments were performed at 37° C. for 0–0.5 h in 0.1M Tris-HCl (pH 8.0) with different protein fractions in a total volume of 0.15 ml. Reactions were terminated by addition of an equal volume of 12% trichloroacetic acid (TCA) dissolved in water. After incubation at room temperature for 0.25 h, samples were centrifuged at 10,000×9 for 0.25 h and 0.10 ml aliquots were removed and placed into 96-well microtiter plates. The solution was then neutralized by the addition of an equal volume of 2 N sodium hydroxide, followed by quantitation using a Fluoroskan II fluorometric plate reader with excitation and emission wavelengths of 485 and 538 nm, respectively. Activity measurements were performed using FITC-Casein with different protease concentrations at 37° C. for 0–10 min. A unit of activity was arbitrarily defined as the amount of enzyme needed to produce 1000 fluorescent units/min and specific activity was defined as units/mg of protease.

Inhibition studies were performed using two zinc-metalloprotease inhibitors; 1,10 phenanthroline and N-(a-rhamnopyranosyloxyhydroxyphosphinyl)-Leu-Trp (phosphoramidon) with stock solutions of the inhibitors dissolved in 100% ethanol and water, respectively. Stock concentrations were typically 10 mg/ml and 5 mg/ml for 1,10 phenanthroline and phosphoramidon, respectively, with final concentrations of inhibitor at 0.5–1.0 mg/ml per reaction. Treatment of three day W-14 crude broth with 1,10 phenanthroline, an inhibitor of all zinc metalloproteases, resulted in complete elimination of all protease activity while treatment with phosphoramidon, an inhibitor of thermolysin-like proteases (Weaver, L. H., Kester, W. R., and Matthews, B. W. 1977. J. Mol. Biol. 114, 119–132), resulted in about 56% reduction of protease activity. The residual proteolytic activity could not be further reduced with additional phosphoramidon.

The proteases of three day W-14 Photorhabdus broth were purified as follows: 4.0 liters of broth were concentrated using an Amicon spiral ultra filtration cartridge Type S1Y100 attached to an Amicon M-12 filtration device. The flow-through material having native proteins less than 100 kDa in size (3.8 L) was concentrated to 0.375 L using an Amicon spiral ultra filtration cartridge Type S1Y10 attached to an Amicon M-12 filtration device. The retentate material contained proteins ranging in size from 10–100 kDa. This material was loaded onto a Pharmacia HR16/10 column which had been packed with PerSeptive Biosystem (Framington, Mass.) Poros® 50 HQ strong anion exchange packing that had been equilibrated in 10 mM sodium phosphate buffer (pH 7.0). Proteins were loaded on the column at a flow rate of 5 ml/min, followed by washing unbound protein with buffer until A280=0.00. Afterwards, proteins were eluted using a NaCl gradient of 0–1.0 M NaCl in 40 min at a flow rate of 7.5 ml/min. Fractions were assayed for protease activity, supra., and active fractions were pooled. Proteolytically active fractions were diluted with 50% (v/v) 10 mM sodium phosphate buffer (pH 7.0) and loaded onto a Pharmacia HR 10/10 Mono Q column equilibrated in 10 mM sodium phosphate. After washing the column with buffer until $A_{280}$=0.00, proteins were eluted using a NaCl gradient of 0–0.5 M NaCl for 1 h at a flow rate of 2.0 ml/min. Fractions were assayed for protease activity. Those fractions having the greatest amount of phosphoramidon-sensitive protease activity, the phosphoramidon sensitive activity being due to the 41/38 kDa protease, infra., were pooled. These fractions were found to elute at a range of 0.15–0.25 M NaCl. Fractions containing a predominance of phosphoramidon-insensitive protease activity, the 58 kDa protease, were also pooled. These fractions were found to elute at a range of 0.25–0.35 M NaCl. The phosphoramidon-sensitive protease fractions were then concentrated to a final volume of 0.75 ml using a Millipore Ultrafree®-15 centrifugal filter device Biomax-5K NMWL membrane. This material was applied at a flow rate of 0.5 ml/min to a Pharmacia HR 10/30 column that had been packed with Pharmacia Sephadex G-50 equilibrated in 10 mM sodium phosphate buffer (pH 7.0)/0.1 M NaCl. Fractions having the maximal phosphoramidon-sensitive protease activity were then pooled and centrifuged over a Millipore Ultrafree®-15 centrifugal filter device Biomax-50K NMWL membrane. Proteolytic activity analysis, supra., indicated this material to have only phosphoramidon-sensitive protease activity. Pooling of the phosphoramidon-insensitive protease, the 58 kDa protein, was followed by concentrating in a Millipore Ultrafree®-15 centrifugal filter device Biomax-50K NMWL membrane and further separation on a Pharmacia Superdex-75 column. Fractions containing the protease were pooled.

Analysis of purified 58—and 41/38 kDa purified proteases revealed that, while both types of protease were completely inhibited with 1,10 phenanthroline, only the 41/38 kDa protease was inhibited with phosphoramidon. Further analysis of crude broth indicated that protease activity of day 1 W-14 broth has 23% of the total protease activity due to the 41/38 kDa protease, increasing to 44% in day three W-14 broth.

Standard SDS-PAGE analysis for examining protein purity and obtaining amino terminal sequence was performed using 4–20% gradient MiniPlus SepraGels purchased from Integrated Separation Systems (Natick, Mass.). Proteins to be amino-terminal sequenced were blotted onto PVDF membrane following purification, infra., (ProBlott™ Membranes; Applied Biosystems, Foster City, Calif.), visualized with 0.1% amido black, excised, and sent to Cambridge Prochem; Cambridge, Mass., for sequencing.

Deduced amino terminal sequence of the 58-(SEQ ID NO:45) and 41/38 kDa (SEQ ID NO:44) proteases from three day old W-14 broth were DV-GSEKANEKLK (SEQ ID NO: 45) and DSGDDDKVTNTDIHR (SEQ ID NO:44), respectively.

Sequencing of the 41/38 kDa protease revealed several amino termini, each one having an additional amino acid removed by proteolysis. Examination of the primary, secondary, tertiary and quarternary sequences for the 38 and 41 kDa polypeptides allowed for deduction of the sequence shown above and revealed that these two proteases are homologous.

EXAMPLE 11

Part A

Screening of Photorhabdus Genomic Library Via Use of Antibodies for Genes Encoding TcbA Peptide In parallel to the sequencing described above, suitable probing and sequencing was done based on the TcbA$_{ii}$ peptide (SEQ ID No:1). This sequencing was performed by preparing bacterial culture broths and purifying the toxin as described in Examples 1 and 2 above.

Genomic DNA was isolated from the *Photorhabdus luminescens* strain W-14 grown in Grace's insect tissue culture medium. The bacteria were grown in 5 ml of culture medium in a 250 ml Erlenmeyer flask at 28° C. and 250 rpm for approximately 24 hours. Bacterial cells from 100 ml of culture medium were pelleted at 5000×g for 10 minutes. The supernatant was discarded, and the cell pellets then were used for the genomic DNA isolation.

The genomic DNA was isolated using a modification of the CTAB method described in Section 2.4.3 of Ausubel (supra.). The section entitled "Large Scale CsCl prep of bacterial genomic DNA" was followed through step 6. At this point, an additional chloroform/isoamyl alcohol (24:1) extraction was performed followed by a phenol/chloroform/isoamyl (25:24:1) extraction step and a final chloroform/isoamyl/alcohol (24:1) extraction. The DNA was precipitated by the addition of a 0.6 volume of isopropanol. The precipitated DNA was hooked and wound around the end of a bent glass rod, dipped briefly into 70% ethanol as a final wash, and dissolved in 3 ml of TE buffer.

The DNA concentration, estimated by optical density at 280/260 nm, was approximately 2 mg/ml.

Using this genomic DNA, a library was prepared. Approximately 50 μg of genomic DNA was partly digested with Sau3 A1. Then NaCl density gradient centrifugation was used to size fractionate the partially digested DNA fragments. Fractions containing DNA fragments with an average size of 12 kb, or larger, as determined by agarose gel electrophoresis, were ligated into the plasmid BluScript, Stratagene, La Jolla, Calif., and transformed into an *E. coli* DH5α or DHB10 strain.

Separately, purified aliquots of the protein were sent to the biotechnology hybridoma center at the University of Wisconsin, Madison for production of monoclonal antibodies to the proteins. The material that was sent was the HPLC purified fraction containing native bands 1 and 2 which had been denatured at 65° C., and 20 μg of which was injected into each of four mice. Stable monoclonal antibody-producing hybridoma cell lines were recovered after spleen cells from unimmunized mouse were fused with a stable myeloma cell line. Monoclonal antibodies were recovered from the hybridomas.

Separately, polyclonal antibodies were created by taking native agarose gel purified band 1 (see Example 1) protein which was then used to immunize a New Zealand white rabbit. The protein was prepared by excising the band from the native agarose gels, briefly heating the gel pieces to 65° C. to melt the agarose, and immediately emulsifying with adjuvant. Freund's complete adjuvant was used for the primary immunizations and Freund's incomplete was used for 3 additional injections at monthly intervals. For each injection, approximately 0.2 ml of emulsified band 1, containing 50 to 100 micrograms of protein, was delivered by multiple subcontaneous injections into the back of the rabbit. Serum was obtained 10 days after the final injection and additional bleeds were performed at weekly intervals for 3 weeks. The serum complement was inactivated by heating to 56° C. for 15 minutes and then stored at −20° C.

The monoclonal and polyclonal antibodies were then used to screen the genomic library for the expression of antigens which could be detected by the epitope. Positive clones were detected on nitrocellulose filter colony lifts. An immunoblot analysis of the positive clones was undertaken.

An analysis of the clones as defined by both immunoblot and Southern analysis resulted in the tentative identification of four genomic regions.

In the first region was a gene encoding the peptide designated here as $TcbA_{ii}$. Full DNA sequence of this gene (tcbA) was obtained. It is set forth as SEQ ID NO:11. Confirmation that the sequence encodes the internal sequence of SEQ ID NO:1 is demonstrated by the presence of SEQ ID NO:1 at amino acid number 88 from the deduced amino acid sequence created by the open reading frame of SEQ ID NO:11. This can be confirmed by referring to SEQ ID NO:12, which is the deduced amino acid sequence created by SEQ ID NO:11.

The second region of toxin peptides contains the segments referred to above as $TcaB_i$, $TcaB_{ii}$ and TcaC. Following the screening of the library with the polyclonal antisera, this second region of toxin genes was identified by several clones which produced different size proteins, all of which cross-reacted with the polyclonal antibody on an immunoblot and were also found to share DNA homology on a Southern Blot. Sequence comparison revealed that they belonged to the gene complex designated TcaBand TcaC above.

Two other regions of antibody toxin clones were also isolated in the polyclonal screen. These regions produced proteins that cross-react with a polyclonal antibody and also shared DNA homology with the regions as determined by Southern blotting. Thus, it appears that the *Photorhabdus luminescens* extracellular protein genes represent a family of genes which are evolutionarily related.

To further pursue the concept that there might be evolutionarily related variations in the toxin peptides contained within this organism, two approaches have been undertaken to examine other strains of *Photorhabdus luminescens* for the presence of related proteins. This was done both by PCR amplification of genomic DNA and by immunoblot analysis using the polyclonal and monoclonal antibodies.

The results indicate that related proteins are produced by Photorhabdus. luminescens strains WX-2, WX-3, WX-4, WX-5, WX-6, WX-7, WX-8, WX-11, WX-12, WX-15 and W-14.

EXAMPLE 11

Part B

Sequence and Analysis of tcc Toxin Clones

Further DNA sequencing was performed on plasmids isolated from *E. coli* clones described in Example 11, Part A.

The nucleotide sequence from the third region of *E. coli* clones was shown to be three closely linked open reading frames at this genomic locus. This locus was designated tcc with the three open reading frames designated tccA SEQ ID NO:56, tccB SEQ ID NO:58 and tccC SEQ ID NO:60. The close linkage between these open reading frames is revealed by examination of SEQ ID NO:56, in which 93 bp separate the stop codon of tccA from the start codon of tccb (bases 2992–2994 of SEQ ID NO:56), and by examination of SEQ ID NO:58, in which 131 bases separate the stop codon of tccB and the tccC (bases 4930–4932 of SEQ ID NO:58). The physical map is presented in FIG. 6B.

The deduced amino acid sequence from the tccA open reading frame indicates that the gene encodes a protein of 10S,459 Da. This protein was designated TccA (SEQ ID NO:57). The first 12 amino acids of this protein match the N-terminal sequence obtained from a 108 kDa protein, SEQ ID NO:8, previously identified as part of the toxin complex.

The deduced amino acid sequence from the tccB open reading frame indicates that this gene encodes a protein of 175,716 Da. This protein was designated TccB (SEQ ID NO:59). The first 11 amino acids of this protein match the N-terminal sequence obtained from a protein with estimated molecular weight of 185 kDa, SEQ ID NO:7. Similarity analysis revealed that the TccB protein is related to the proteins identified as TcbA SEQ ID NO:12; 37% similarity and 28% identity, TcdA SEQ ID NO:47; 35% similarity and 28%identity, and TcaB SEQ ID NO:26; 32% similarity and 26% identity (using the GAP algorithm Wisconsin Package Version 9.0, Genetics Computer Group (GCG) Madison Wis.).

The deduced amino acid sequence of tccC indicated that this open reading frame encodes a protein of 111,694 Da and the protein product was designated TccC (SEQ ID NO:61).

EXAMPLE 12

Characterization of Photorhabdus Strains

In order to establish that the collection described herein was comprised of Photorhabdus strains, the strains herein were assessed in terms of recognized microbiological traits that are characteristic of Photorhabdus and which differentiate it from other Enterobacteriaceae and Xenorhabdus spp. (Farmer, J. J. 1984. Bergey's Manual of Systemic Bacteriology, Vol 1. pp. 510–511. (ed. Kreig N. R. and Holt, J. G.). Williams & Wilkins, Baltimore; Akhurst and Boemare, 1988, Boemare et al., 1993). These characteristic traits are as follows: Gram's stain negative rods, organism size of 0.5–2 μm in width and 2–10 μm in length, red/yellow colony pigmentation, presence of crystalline inclusion bodies, presence of catalase, inability to reduce nitrate, presence of bioluminescence, ability to take up dye from growth media, positive for protease production, growth-temperature range below 37° C., survival under anaerobic conditions and positively motile. (Table 20). Reference *Escherichia coli*, Xenorhabdus and Photorhabdus strains were included in all tests for comparison. The overall results are consistent with all strains being part of the family Enterobacteriaceae and the genus Photorhabdus.

A luminometer was used to establish the bioluminescence of each strain and provide a quantitative and relative measurement of light production. For measurement of relative light emitting units, the broths from each strain (cells and media) were measured at three time intervals after inoculation in liquid culture (6, 12, and 24 hr) and compared to background luminosity (uninoculated media and water). Prior to measuring light emission from the various broths, cell density was established by measuring light absorbance (560 nM) in a Gilford Systems (Oberlin, Ohio) spectrophotometer using a sipper cell. Appropriate dilutions were then made (to normalize optical density to 1.0 unit) before measuring luminosity. Aliquots of the diluted broths were then placed into cuvettes (300 μl each) and read in a Bio-Orbit 1251 Luminometer (Bio-Orbit Oy, Twiku, Finland). The integration period for each sample was 45 seconds. The samples were continuously mixed (spun in baffled cuvettes) while being read to provide oxygen availability. A positive test was determined as being ≧5-fold background luminescence (about 5–10 units). In addition, colony luminosity was detected with photographic film overlays and visually, after adaptation in a darkroom. The Gram's staining characteristics of each strain were established with a commercial Gram's stain kit (BBL, Cockeysville, Md.) used in conjunction with Gram's stain control slides (Fisher Scientific, Pittsburgh, Pa.). Microscopic evaluation was then performed using a Zeiss microscope (Carl Zeiss, Germany) 100×oil immersion objective lens (with 10×ocular and 2×body magnification). Microscopic examination of individual strains for organism size, cellular description and inclusion bodies (the latter after logarithmic growth) was performed using wet mount slides (10×ocular, 2×body and 40×objective magnification) with oil immersion and phase contrast microscopy with a micrometer (Akhurst, R. J. and Boemare, N. E. 1990. *Entomopathogenic Nematodes in Biological Control* (ed. Gaugler, R. and Kaya, H.). pp. 75–90. CRC Press, Boca Raton, USA.; Baghdiguian S., Boyer-Giglio M. H., Thaler, J. O., Bonnot G., Boemare N. 1993. Biol. Cell 79, 177–185.). Colony pigmentation was observed after inoculation on Bacto nutrient agar, (Difco Laboratories, Detroit, Mich.) prepared as per label instructions. Incubation occurred at 28° C. and descriptions were produced after 5–7 days. To test for the presence of the enzyme catalase, a colony of the test organism was removed on a small plug from a nutrient agar plate and placed into the bottom of a glass test tube. One ml of a household hydrogen peroxide solution was gently added down the side of the tube. A positive reaction was recorded when bubbles of gas (presumptive oxygen) appeared immediately or within 5 seconds. Controls of uninoculated nutrient agar and hydrogen peroxide solution were also examined. To test for nitrate reduction, each culture was inoculated into 10 ml of Bacto Nitrate Broth (Difco Laboratories, Detroit, Mich.). After 24 hours incubation at 28° C., nitrite production was tested by the addition of two drops of sulfanilic acid reagent and two drops of alpha-naphthylamine reagent (see Difco Manual, 10th edition, Difco Laboratories, Detroit, Mich., 1984). The generation of a distinct pink or red color indicates the formation of nitrite from nitrate. The ability of each strain to uptake dye from growth media was tested with Bacto MacConkey agar containing the dye neutral red; Bacto Tergitol-7 agar containing the dye bromothymol blue and Bacto EMB Agar containing the dye eosin-Y (agars from Difco Laboratories, Detroit, Mich., all prepared according to label instructions). After inoculation on these media, dye uptake was recorded after incubation at 28° C. for 5 days. Growth on these latter media is characteristic for members of the family Enterobacteriaceae. Motility of each strain was tested using a solution of Bacto Motility Test Medium (Difco Laboratories, Detroit, Mich.) prepared as per label instructions. A butt-stab inoculation was performed with each strain and motility was judged macroscopically by a diffuse zone of growth spreading from the line of inoculum.

In many cases, motility was also observed microscopically from liquid culture under wet mount slides. Biochemical nutrient evaluation for each strain was performed using BBL Enterotube II (Benton, Dickinson, Germany). Product instructions were followed with the exception that incubation was carried out at 28° C. for 5 days. Results were consistent with previously cited reports for Photorhabdus. The production of protease was tested by observing hydrolysis of gelatin using Bacto gelatin (Difco Laboratories, Detroit, Mich.) plates made as per label instructions. Cultures were inoculated and the plates were incubated at 28° C. for 5 days. To assess growth at different temperatures, agar plates [2% proteose peptone #3 with two percent Bacto-Agar (Difco, Detroit, Mich.) in deionized water] were streaked from a common source of inoculum. Plates were sealed with Nesco® film and incubated at 20, 28 and 37° C. for up to three weeks. Plates showing no growth at 37° C. showed no cell viability after transfer to a 28° C. incubator for one week. Oxygen requirements for Photorhabdus strains were tested in the following manner. A butt-stab inoculation into fluid thioglycolate broth medium (Difco, Detroit, Mich.) was made. The tubes were incubated at room temperature for one week and cultures were then examined for type and extent of growth. The indicator resazurin demonstrates the level of medium oxidation or the aerobiosis zone (Difco Manual, 10th edition, Difco Laboratories, Detroit, Mich.). Growth zone results obtained for the Photorhabdus strains tested were consistent with those of a facultative anaerobic microorganism.

Cellular fatty acid analysis is a recognized tool for bacterial characterization at the genus and species level (Tornabene, T. G. 1985. *Lipid Analysis and the Relationship to Chemotaxonomy in Methods in Microbiology*, Vol. 18, 209–234.; Goodfellow, M. and O'Donnell, A. G. 1993. *Roots of Bacterial Systematics in Handbook of New Bacterial Systematics* (ed. Goodfellow, M. & O'Donnell, A. G.) pp. 3–54. London: Academic Press Ltd.), these references are incorporated herein by reference, and were used to confirm that our collection was related at the genus level. Cultures were shipped to an external, contract laboratory for fatty acid methyl ester analysis (FAME) using a Microbial ID (MIDI, Newark, Del., USA) Microbial Identification System (MIS). The MIS system consists of a Hewlett Packard HP5890A gas chromatograph with a 25 mm×0.2 mm 5% methylphenyl silicone fused silica capillary column. Hydrogen is used as the carrier gas and a flame-ionization detector functions in conjunction with an automatic sampler, integrator and computer. The computer compares the sample fatty acid methyl esters to a microbial fatty acid library and against a calibration mix of known fatty acids. As selected by the contract laboratory, strains were grown for 24 hours at 28° C. on trypticase soy agar prior to analysis. Extraction of samples was performed by the contract lab as per standard FAME methodology. There was no direct identification of the strains to any luminescent bacterial group other than Photorhabdus. When the cluster analysis was performed, which compares the fatty acid profiles of a group of isolates, the strain fatty acid profiles were related at the genus level.

TABLE 19

Taxonomic Traits of Photorhabdus Strains
Traits Assessed*

| Strain | A | B | C | D | E | F | G | H | I | J | K | L | M | N | O | P | Q |
|---|---|---|---|---|---|---|---|---|---|---|---|---|---|---|---|---|---|
| W-14 | −† | + | + | rd S | + | − | + | + | + | O | + | + | + | + | + | + | − |
| WX-1 | − | + | + | rd S | + | − | + | + | + | O | + | + | + | + | + | + | − |
| WX-2 | − | + | + | rd S | + | − | + | + | + | O | + | + | + | + | + | + | − |
| WX-3 | − | + | + | rd S | + | − | + | + | + | YT | + | + | + | + | + | + | − |
| WX-4 | − | + | + | rd S | + | − | + | + | + | YT | + | + | + | + | + | + | − |
| WX-5 | − | + | + | rd S | + | − | + | + | + | LO | + | + | + | + | + | + | − |
| WX-6 | − | + | + | rd S | + | − | + | + | + | LY | + | + | + | + | + | + | − |
| WX-7 | − | + | + | rd S | + | − | + | + | + | R | + | + | + | + | + | + | − |
| WX-8 | − | + | + | rd S | + | − | + | + | + | O | + | + | + | + | + | + | − |
| WX-9 | − | + | + | rd S | + | − | + | + | + | YT | + | + | + | + | + | + | − |
| WX-10 | − | + | + | rd S | + | − | + | + | + | Ro | + | + | + | + | + | + | − |
| WX-11 | − | + | + | rd S | + | − | + | + | + | Ro | + | + | + | + | + | + | − |
| WX-12 | − | + | + | rd S | + | − | + | + | + | O | + | + | + | + | + | + | − |
| WX-14 | − | + | + | rd S | + | − | + | + | + | LR | + | + | + | + | + | + | − |
| WX-15 | − | + | + | rd S | + | − | + | + | + | LR | + | + | + | + | + | + | − |
| H9 | − | + | + | rd S | + | − | + | + | + | LY | + | + | + | + | + | + | − |
| Hb | − | + | + | rd S | + | − | + | + | + | YT | + | + | + | + | + | + | − |
| Hm | − | + | + | rd S | + | − | + | + | + | TY | + | + | + | + | + | + | − |
| HP88 | − | + | + | rd S | + | − | + | + | + | LY | + | + | + | + | + | + | − |
| NC-1 | − | + | + | rd S | + | − | + | + | + | O | + | + | + | + | + | + | − |
| W30 | − | + | + | rd S | + | − | + | + | + | YT | + | + | + | + | + | + | − |
| WIR | − | + | + | rd S | + | − | + | + | + | RO | + | + | + | + | + | + | − |
| B2 | − | + | + | rd S | + | − | + | + | + | R | + | + | + | + | + | + | − |
| 43948 | − | + | + | rd S | + | − | + | + | + | O | + | + | + | + | + | + | − |
| 43949 | − | + | + | rd S | + | − | + | + | + | O | + | + | + | + | + | + | − |
| 43950 | − | + | + | rd S | + | − | + | + | + | O | + | + | + | + | + | + | − |
| 43951 | − | + | + | rd S | + | − | + | + | + | O | + | + | + | + | + | + | − |
| 43952 | − | + | + | rd S | + | − | + | + | + | O | + | + | + | + | + | + | − |

*- A = Gram's stain, B = Crystaline inclusion bodies, C = Bioluminescence, D = Cell form, E = Motility, F = Nitrate reduction, G = Presence of catalase, H = Gelatin hydrolysis, I = Dye uptake, J = Pigmentation, K = Growth on EMB agar, L = Growth on MacConkey agar, M = Growth on Tergitol-7 agar, N = Facultative anaerobe, O = Growth at 20° C., P = Growth at 28° C., Q = Growth at 37° C., †: + = positive for trait, − = negative for trait, rd = rod, S = sized within Genus descriptors, RO = red-orange, LR = light red, R = red, O = orange, Y = yellow, T = tan, LY = light yellow, YT = yellow tan, and LO = light orange.

The evolutionary diversity of the Photorhabdus strains in our collection was measured by analysis of PCR (Polymerase Chain Reaction) mediated genomic fingerprinting using genomic DNA from each strain. This technique is based on families of repetitive DNA sequences present throughout the genome of diverse bacterial species (reviewed by Versalovic, J., Schneider, M., Del. Bruijn, F. J. and Lupski, J. R. 1994. Methods Mol. Cell. Biol., 5, 25–40.). Three of these, repetitive extragenic palindromic sequence (REP), enterobacterial repetitive intergenic consensus (ERIC) and the BOX element are thought to play an important role in the organization of the bacterial genome. Genomic organization is believed to be shaped by selection and the differential dispersion of these elements within the genome of closely related bacterial strains can be used to discriminate these strains (e.g., Louws, F. J., Fulbright, D. W., Stephens, C. T. and D E Bruijn, F. J. 1994. Appl. Environ. Micro. 60, 2286–2295). Rep-PCR utilizes oligonucleotide primers complementary to these repetitive sequences to amplify the variably sized DNA fragments lying between them. The resulting products are separated by electrophoresis to establish the DNA "fingerprint" for each strain.

To isolate genomic DNA from our strains, cell pellets were resuspended in TE buffer (10 mM Tris-HCl, 1 mM EDTA, pH 8.0) to a final volume of 10 ml and 12 ml of 5 M NaCl was then added. This mixture was centrifuged 20 min. at 15,000×g. The resulting pellet was resuspended in 5.7 ml of TE and 300 $\mu$l of 10% SDS and 60 $\mu$l 20 mg/ml proteinase K (Gibco BRL Products, Grand Island, N.Y.) were added. This mixture was incubated at 37° C. for 1 hr, approximately 10 mg of lysozyme was then added and the mixture was incubated for an additional 45 min. One milliliter of 5M NaCl and 800 $\mu$l of CTAB/NaCl solution (10% w/v CTAB, 0.7 M NaCl) were then added and the mixture was incubated 10 min. at 65° C., gently agitated, then incubated and agitated for an additional 20 min. to aid in clearing of the cellular material. An equal volume of chloroform/isoamyl alcohol solution (24:1, v/v) was added, mixed gently then centrifuged. Two extractions were then performed with an equal volume of phenol/chloroform/isoamyl alcohol (50:49:1). Genomic DNA was precipitated with 0.6 volume of isopropanol. Precipitated DNA was removed with a glass rod, washed twice with 70% ethanol, dried and dissolved in 2 ml of STE (10 mM Tris-HCl pH8.0, 10 mM NaCl, 1 mM EDTA). The DNA was then quantitated by optical density at 260 nm. To perform rep-PCR analysis of Photorhabdus genomic DNA the following primers were used, REP1R-I; 5'-IIIICGICGICATCIGGC-3' and REP2-I; 5'-ICGICTTATCIGGCCTAC-3'. PCR was performed using the following 25 $\mu$l reaction: 7.75 $\mu$l H$_2$O, 2.5 $\mu$l 10×LA buffer (PanVera Corp., Madison, Wis.), 16 $\mu$l dNTP mix (2.5 mM each), 1 $\mu$l of each primer at 50 pM/$\mu$l, 1 $\mu$l DMSO, 1.5 $\mu$l genomic DNA (concentrations ranged from 0.075–0.480 $\mu$g/$\mu$l) and 0.25 $\mu$l TaKaRa EX Taq (PanVera Corp., Madison, Wis.). The PCR amplification was performed in a Perkin Elmer DNA Thermal Cycler (Norwalk, Conn.) using the following conditions: 95° C./7 min. then 35 cycles of; 94° C./1 min., 44° C./1 min., 65° C./8 min., followed by 15 min. at 65° C. After cycling, the 25 $\mu$l reaction was added to 5 $\mu$l of 6×gel loading buffer (0.25% bromophenol blue, 40% w/v sucrose in H$_2$O). A 15×20 cm 1%-agarose gel was then run in TBE buffer (0.09 M Tris-borate, 0.002 M EDTA) using 8 $\mu$l of each reaction. The gel was run for approximately 16 hours at 45 v. Gels were then stained in 20 $\mu$g/ml ethidium bromide for 1 hour and destained in TBE buffer for approximately 3 hours. Polaroid® photographs of the gels were then taken under UV illumination.

The presence or absence of bands at specific sizes for each strain was scored from the photographs and entered as a similarity matrix in the numerical taxonomy software program, NTSYS-pc (Exeter Software, Setauket, N.Y.). Controls of E. coli strain HB101 and Xanthomonas oryzae pv. oryzae assayed at the same time produced PCR "fingerprints" corresponding to published reports (Versalovic, J., Koeuth, T. and Lupski, J. R. 1991. Nucleic Acids Res. 19, 6823–6831; Vera Cruz, C. M., Halda-Alija, L., Louws, F., Skinner, D. Z., George, M. L., Nelson, R. J., Del. Bruijn, F. J., Rice, C. and Leach, J. E. 1995. Int. Rice Res. Notes, 20, 23–24.; Vera Cruz, C. M., Ardales, E. Y., Skinner, D. Z., Talag, J., Nelson, R. J., Louws, F. J., Leung, H., Mew, T. W. and Leach, J. E. 1996. Phytopathology (in press, respectively). The data from Photorhabdus strains were then analyzed with a series of programs within NTSYS-pc; SIMQUAL (Similarity for Qualitative data) to generate a matrix of similarity coefficients (using the Jaccard coefficient) and SAHN (Sequential, Agglomerative, Heirarchical and Nested) clustering [using the UPGMA (Unweighted Pair-Group Method with Arithmetic Averages) method] which groups related strains and can be expressed as a phenogram (FIG. 5). The COPH (cophenetic values) and MXCOMP (matrix comparison) programs were used to generate a cophenetic value matrix and compare the correlation between this and the original matrix upon which the clustering was based. A resulting normalized Mantel statistic (r) was generated which is a measure of the goodness of fit for a cluster analysis (r=0.8–0.9 represents a very good fit). In our case r=0.919. Therefore, our collection is comprised of a diverse group of easily distinguishable strains representative of the Photorhabdus genus.

EXAMPLE 13

Insecticidal Utility of Toxin(s) Produced by Various Photorhabdus Strains

Initial "seed" cultures of the various Photorhabdus strains were produced by inoculating 175 ml of 2% Proteose Peptone #3 (PP3) (Difco Laboratories, Detroit, Mich.) liquid media with a primary variant subclone in a 500 ml tribaffled flask with a Delong neck, covered with a Kaput. Inoculum for each seed culture was derived from oil-overlay agar slant cultures or plate cultures. After inoculation, these flasks were incubated for 16 hrs at 28° C. on a rotary shaker at 150 rpm. These seed cultures were then used as uniform inoculum sources for a given fermentation of each strain. Additionally, overlaying the post-log seed culture with sterile mineral oil, adding a sterile magnetic stir bar for future resuspension and storing the culture in the dark, at room temperature provided long-term preservation of inoculum in a toxin-competent state. The production broths were inoculated by adding 1% of the actively growing seed culture to fresh 2% PP3 media (e.g., 1.75 ml per 175 ml fresh media). Production of broths occurred in either 500 ml tribaffled flasks (see above), or 2800 ml baffled, convex bottom flasks (500 ml volume) covered by a silicon foam closure. Production flasks were incubated for 24–48 hrs under the above mentioned conditions. Following incubation, the broths were dispensed into sterile 1 L polyethylene bottles, spun at 2600×g for 1 hr at 10° C. and decanted from the cell and debris pellet. The liquid broth was then vacuum filtered through Whatman GF/D (2.7 $\mu$M retention) and GF/B (1.0 $\mu$M retention) glass filters to remove debris. Further broth clarification was achieved with a tangential flow microfiltration device (Pall Filtron, Northborough, Mass.) using a 0.5 M open-channel filter. When necessary, additional clarification could be obtained by chilling the broth (to 4° C.) and centrifuging for several hours at 2600×g. Following these procedures, the broth was filter sterilized using a 0.2 µM nitrocellulose membrane filter. Sterile broths were then used directly for biological assay, biochemical analysis or concentrated (up to 15-fold) using a 10,000 MW cut-off, M12 ultra-filtration device (Amicon, Beverly Mass.) or centrifugal concentrators (Millipore, Bedford, Mass. and Pall Filtron, Northborough, Mass.) with a 10,000 MW pore size. In the case of centrifugal concentrators, the broth was spun at 2000×g for approximately 2 hr. The 10,000 MW permeate was added to the corresponding retentate to achieve the desired concentration of components greater than 10,000 MW. Heat inactivation of processed broth samples was acheived by heating the samples at 100° C. in a sand-filled heat block for 10 minutes.

The broth(s) and toxin complex(es) from different Photorhabdus strains are useful for reducing populations of insects and were used in a method of inhibiting an insect population which comprises applying to a locus of the insect an effective insect inactivating amount of the active described. A demonstration of the breadth of insecticidal activity observed from broths of a selected group of Photorhabdus strains fermented as described above is shown in Table 20. It is possible that additional insecticidal activities could be detected with these strains through increased concentration of the broth or by employing different fermentation methods. Consistent with the activity being associated with a protein, the insecticidal activity of all strains tested was heat labile (see above).

Culture broth(s) from diverse Photorhabdus strains show differential insecticidal activity (mortality and/or growth inhibition, reduced adult emergence) against a number of insects. More specifically, the activity is seen against corn rootworm larvae and boll weevil larvae which are members of the insect order Coleoptera. Other members of the Coleoptera include wireworms, pollen beetles, flea beetles, seed beetles and Colorado potato beetle. Activity is also observed against aster leafhopper and corn plant hopper, which are members of the order Homoptera. Other members of the Homoptera include planthoppers, pear psylla, apple sucker, scale insects, whiteflies, spittle bugs as well as numerous host specific aphid species. The broths and purified toxin complex(es) are also active against tobacco budworm, tobacco hornworm and European corn borer which are members of the order Lepidoptera. Other typical members of this order are beet armyworm, cabbage looper, black cutworm, corn earworm, codling moth, clothes moth, Indian mealmoth, leaf rollers, cabbage worm, cotton bollworm, bagworm, Eastern tent caterpillar, sod webworm and fall armyworm. Activity is also seen against fruitfly and mosquito larvae which are members of the order Diptera. Other members of the order Diptera are, pea midge, carrot fly, cabbage root fly, turnip root fly, onion fly, crane fly and house fly and various mosquito species. Activity with broth (s) and toxin complex(es) is also seen against two-spotted spider mite which is a member of the order Acarina which includes strawberry spider mites, broad mites, citrus red mite, European red mite, pear rust mite and tomato russet mite.

Activity against corn rootworm larvae was tested as follows. Photorhabdus culture broth(s) (0–15 fold concentrated, filter sterilized), 2% Proteose Peptone #3, purified toxin complex(es), 10 mM sodium phosphate buffer , pH 7.0 were applied directly to the surface (about 1.5 cm$^2$) of artificial diet (Rose, R. I. and McCabe, J. M. (1973). J. Econ. Entomol. 66, (398–400) in 40 µl aliquots. Toxin complex was diluted in 10 mM sodium phosphate buffer, pH 7.0. The diet plates were allowed to air-dry in a sterile flow-hood and the wells were infested with single, neonate *Diabrotica undecimpunctata howardi* (Southern corn rootworm, SCR) hatched from surface sterilized eggs. The plates were sealed, placed in a humidified growth chamber and maintained at 27° C. for the appropriate period (3–5 days). Mortality and larval weight determinations were then scored. Generally, 16 insects per treatment were used in all studies. Control mortality was generally less than 5%.

Activity against boll weevil (*Anthomonas grandis*) was tested as follows. Concentrated (1–10 fold) Photorhabdus broths, control medium (2% Proteose Peptone #3), purified toxin complex(es) [0.23 mg/ml] or 10 mM sodium phosphate buffer, pH 7.0 were applied in 60 µl aliquots to the surface of 0.35 g of artificial diet (Stoneville Yellow lepidopteran diet) and allowed to dry. A single, 12–24 hr boll weevil larva was placed on the diet, and the wells were sealed and held at 25° C., 50% RH for 5 days. Mortality and larval weights were then assessed. Control mortality ranged between 0–13%.

Activity against mosquito larvae was tested as follows. The assay was conducted in a 96-well microtiter plate. Each well contained 200 µl of aqueous solution (10-fold concentrated Photorhabdus culture broth(s), control medium (2% Proteose Peptone #3), 10 mM sodium phosphate buffer, toxin complex(es) @ 0.23 mg/ml or $H_2O$) and approximately 20, 1-day old larvae (*Aedes aegypti*). There were 6 wells per treatment. The results were read at 3–4 days after infestation. Control mortality was between 0–20%.

Activity against fruitflies was tested as follows. Purchased *Drosophila melanogaster* medium was prepared using 50% dry medium and a 50% liquid of either water, control medium (2% Proteose Peptone #3), 10-fold concentrated Photorhabdus culture broth(s), purified toxin complex(es) [0.23 mg/ml] or 10 mM sodium phosphate buffer , pH 7.0. This was accomplished by placing 4.0 ml of dry medium in each of 3 rearing vials per treatment and adding 4.0 ml of the appropriate liquid. Ten late instar *Drosophila melanogaster* maggots were then added to each 25 ml vial. The vials were held on a laboratory bench, at room temperature, under fluorescent ceiling lights. Pupal or adult counts were made after 15 days of exposure. Adult emergence as compared to water and control medium (0–16% reduction).

Activity against aster leafhopper adults (*Macrosteles severini*) and corn planthopper nymphs (*Peregrinus maidis*) was tested with an ingestion assay designed to allow ingestion of the active without other external contact. The reservoir for the active/"food" solution is made by making 2 holes in the center of the bottom portion of a 35×10 mm Petri dish. A 2 inch Parafilm M® square is placed across the top of the dish and secured with an "O" ring. A 1 oz. plastic cup is then infested with approximately 7 hoppers and the reservoir is placed on top of the cup, Parafilm down. The test solution is then added to the reservoir through the holes. In tests using 10-fold concentrated Photorhabdus culture broth (s), the broth and control medium (2% Proteose Peptone #3) were dialyzed against 10 mM sodium phosphate buffer, pH 7.0 and sucrose (to 5%) was added to the resulting solution to reduce control mortality. Purified toxin complex(es) [0.23 mg/ml] or 10 mM sodium phosphate buffer, pH 7.0 was also tested. Mortality is reported at day 3. The assay was held in an incubator at 28° C., 70% RH with a 16/8 photoperiod. The assays were graded for mortality at 72 hours. Control mortality was less than 6%.

Activity against lepidopteran larvae was tested as follows. Concentrated (10-fold) Photorhabdus culture broth(s), control medium (2% Proteose Peptone #3), purified toxin complex(es) [0.23 mg/ml] or 10 mM sodium phosphate buffer, pH 7.0 were applied directly to the surface (about 1.5 cm$^2$) of standard artificial lepidopteran diet (Stoneville Yellow diet) in 40 μl aliquots. The diet plates were allowed to air-dry in a sterile flow-hood and each well was infested with a single, neonate larva. European corn borer (*Ostrinia nubilalis*) and tobacco hornworm (*Manduca sexta*) eggs were obtained from commercial sources and hatched in-house, whereas tobacco budworm (*Heliothis virescens*) larvae were supplied internally. Following infestation with larvae, the diet plates were sealed, placed in a humidified growth chamber and maintained in the dark at 27° C. for the appropriate period. Mortality and weight determinations were scored at day 5. Generally, 16 insects per treatment were used in all studies. Control mortality generally ranged from about 4 to about 12.5% for control medium and was less than 10% for phosphate buffer.

Activity against two-spotted spider mite (*Tetranychus urticae*) was determined as follows. Young squash plants were trimmed to a single cotyledon and sprayed to run-off with 10-fold concentrated broth(s), control medium (2% Proteose Peptone #3), purified toxin complex(es), 10 mM sodium phosphate buffer, pH 7.0. After drying, the plants were infested with a mixed population of spider mites and held at lab temperature and humidity for 72 hr. Live mites were then counted to determine levels of control.

TABLE 20

Observed Insecticidal Spectrum of Broths from Different Photorhabdus Strains

| Photorhabdus Strain | Sensitive* Insect Species |
|---|---|
| WX-1 | 3**, 4, 5, 6, 7, 8 |
| WX-2 | 2, 4 |
| WX-3 | 1, 4 |
| WX-4 | 1, 4 |
| WX-5 | 4 |
| WX-6 | 4 |
| WX-7 | 3, 4, 5, 6, 7, 8 |
| WX-8 | 1, 2, 4 |
| WX-9 | 1, 2, 4 |
| WX-10 | 4 |
| WX-11 | 1, 2, 4 |
| WX-12 | 2, 4, 5, 6, 7, 8 |
| WX-14 | 1, 2, 4 |
| WX-15 | 1, 2, 4 |
| W30 | 3, 4, 5, 8 |
| NC-1 | 1, 2, 3, 4, 5, 6, 7, 8, 9 |
| WIR | 2, 3, 5, 6, 7, 8 |
| HP88 | 1, 3, 4, 5, 7, 8 |
| Hb | 3, 4, 5, 7, 8 |
| Hm | 1, 2, 3, 4, 5, 7, 8 |
| H9 | 1, 2, 3, 4, 5, 6, 7, 8 |
| W-14 | 1, 2, 3, 4, 5, 6, 7, 8, 10 |
| ATCC 43948 | 4 |
| ATCC 43949 | 4 |
| ATCC 43950 | 4 |
| ATCC 43951 | 4 |
| ATCC 43952 | 4 |

*= ≧25% mortality and/or growth inhibition vs. control
**= 1; Tobacco budworm, 2; European corn borer, 3; Tobacco hornworm, 4; Southern corn rootworm, 5; Boll weevil, 6; Mosquito, 7; Fruit fly, 8; Aster Leafhopper, 9; Corn planthopper, 10; Two-spotted spider mite.

EXAMPLE 14

Non W-14 Photorhabdus Strains: Purification, Characterization and Activity Spectrum Purification The protocol, as follows, is similar to that developed for the purification of W-14 and was established based on purifying those fractions having the most activity against Southern corn root worm (SCR), as determined in bioassays (see Example 13). Typically, 4–20 L of broth that had been filtered, as described in Example 13, were received and concentrated using an Amicon spiral ultra filtration cartridge Type S1Y100 attached to an Amicon M-12 filtration device. The retentate contained native proteins consisting of molecular sizes greater than 100 kDa, whereas the flow through material contained native proteins less than 100 kDa in size. The majority of the activity against-SCR was contained in the 100 kDa retentate. The retentate was then continually diafiltered with 10 mM sodium phosphate (pH= 7.0) until the filtrate reached an $A_{280}<0.100$. Unless otherwise stated, all procedures from this point were performed in buffer as defined by 10 mM sodium phosphate (pH 7.0). The retentate was then concentrated to a final volume of approximately 0.20 L and filtered using a 0.45 mm Nalgene™ Filterware sterile filtration unit. The filtered material was loaded at 7.5 ml/min onto a Pharmacia HR16/10 column which had been packed with PerSeptive Biosystem Poros® 50 HQ strong anion exchange matrix equilibrated in buffer using a PerSeptive Biosystem Sprint® HPLC system. After loading, the column was washed with buffer until an $A_{280}<0.100$ was achieved. Proteins were then eluted from the column at 2.5 ml/min using buffer with 0.4 M NaCl for 20 min for a total volume of 50 ml. The column was then washed using buffer with 1.0 M NaCl at the same flow rate for an additional 20 min (final volume=50 ml). Proteins eluted with 0.4 M and 1.0 M NaCl were placed in separate dialysis bags (Spectra/Por® Membrane MWCO: 2,000) and allowed to dialyze overnight at 4° C. in 12 L buffer. The majority of the activity against SCR was contained in the 0.4 M fraction. The 0.4 M fraction was further purified by application of 20 ml to a Pharmacia XK 26/100 column that had been prepacked with Sepharose CL4B (Pharmacia) using a flow rate of 0.75 ml/min. Fractions were pooled based on $A_{280}$ peak profile and concentrated to a final volume of 0.75 ml using a Millipore Ultrafree®-15 centrifugal filter device Biomax-50K NMWL membrane. Protein concentrations were determined using a Biorad Protein Assay Kit with bovine gamma globulin as a standard.

Characterization

The native molecular weight of the SCR toxin complex was determined using a Pharmacia HR 16/50 that had been prepacked with Sepharose CL4B in buffer. The column was then calibrated using proteins of known molecular size thereby allowing for calculation of the toxin approximate native molecular size. As shown in Table 21, the molecular size of the toxin complex ranged from 777 kDa with strain Hb to 1,900 kDa with strain WX-14. The yield of toxin complex also varied, from strain WX-12 producing 0.8 mg/L to strain Hb, which produced 7.0 mg/L.

Proteins found in the toxin complex were examined for individual polypeptide size using SDS-PAGE analysis. Typically, 20 mg protein of the toxin complex from each strain was loaded onto a 2–15% polyacrylamide gel (Integrated Separation Systems) and electrophoresed at 20 mA in Biorad SDS-PAGE buffer. After completion of electrophoresis, the gels were stained overnight in Biorad Coomassie blue R-250 (0.2% in methanol: acetic acid: water; 40:10:40 v/v/v). Subsequently, gels were destained in methanol:acetic acid: water; 40:10:40 (v/v/v). The gels were then rinsed with water for 15 min and scanned using a Molecular Dynamics Personal Laser Densitometer®. Lanes were quantitated and molecular sizes were calculated as compared to Biorad high molecular weight standards, which ranged from 200–45 kDa.

Sizes of the individual polypeptides comprising the SCR toxin complex from each strain are listed in Table 22. The sizes of the individual polypeptides ranged from 230 kDa with strain WX-1 to a size of 16 kDa, as seen with strain WX-7. Every strain, with the exception of strain Hb, had polypeptides comprising the toxin complex that were in the 160–230 kDa range, the 100–160 kDa range, and the 50–80 kDa range. These data indicate that the toxin complex may vary in peptide composition and components from strain to strain, however, in all cases the toxin attributes appears to consist of a large, oligomeric protein complex.

Furthermore, the toxin complex from strains Hm and W-14 also exhibited activity against two-spotted spider mite. In addition, the toxin complex from W-14 exhibited activity against mosquito larvae. These data indicate that the toxin complex, while having similarities in activities between certain orders of insects, can also exhibit differential activities against other orders of insects.

TABLE 22

The Approximate Sizes (in kDa) of Peptides in a Purified Toxin Complex From Non W-14 Photorhabdus

| H9 | Hb | Hm | HP 88 | NC-1 | WIR | WX-1 | WX-2 | WX-7 | WX-12 | WX-14 | W-14 |
|---|---|---|---|---|---|---|---|---|---|---|---|
| 180 | 150 | 170 | 170 | 180 | 170 | 230 | 200 | 200 | 180 | 210 | 190 |
| 170 | 140 | 140 | 160 | 170 | 160 | 190 | 170 | 180 | 160 | 180 | 180 |
| 160 | 139 | 100 | 140 | 140 | 120 | 170 | 150 | 110 | 140 | 160 | 170 |
| 140 | 130 | 81 | 130 | 110 | 110 | 160 | 120 | 87 | 139 | 120 | 160 |
| 120 | 120 | 72 | 129 | 44 | 89 | 110 | 110 | 75 | 130 | 110 | 150 |
| 98 | 100 | 68 | 110 | 16 | 79 | 98 | 82 | 43 | 110 | 100 | 130 |
| 87 | 98 | 49 | 100 |  | 74 | 76 | 64 | 33 | 92 | 95 | 120 |
| 84 | 88 | 46 | 86 |  | 62 | 58 | 37 | 28 | 87 | 80 | 110 |
| 79 | 81 | 30 | 81 |  | 51 | 53 | 30 | 26 | 80 | 69 | 93 |
| 72 | 75 | 22 | 77 |  | 40 | 41 |  | 23 | 73 | 49 | 90 |
| 68 | 69 | 20 | 73 |  | 39 | 35 |  | 22 | 59 | 41 | 77 |
| 60 | 60 | 19 | 60 |  | 37 | 31 |  | 21 | 56 | 33 | 69 |
| 57 | 57 |  | 58 |  | 33 | 28 |  | 19 | 51 |  | 65 |
| 52 | 54 |  | 45 |  | 30 | 24 |  | 18 | 37 |  | 63 |
| 46 | 49 |  | 39 |  | 28 | 22 |  | 16 | 33 |  | 60 |
| 40 | 44 |  | 35 |  | 27 |  |  |  | 32 |  | 51 |
| 37 | 39 |  |  |  | 25 |  |  |  | 26 |  | 46 |
|  | 37 |  |  |  | 23 |  |  |  |  |  | 40 |
|  | 35 |  |  |  |  |  |  |  |  |  | 39 |
|  |  |  |  |  |  |  |  |  |  |  | 29 |

TABLE 21

Characterization of a Toxin Complex from Non W-14 Photorhabdus Strains

| Strain | Approx. Native Molecular Wt.[a] | Yield Active Fraction (mg/L)[b] |
|---|---|---|
| H9 | 972,000 | 1.8 |
| Hb | 777,000 | 7.0 |
| Hm | 1,400,000 | 1.1 |
| HP88 | 813,000 | 2.5 |
| NCl | 1,092,000 | 3.3 |
| WIR | 979,000 | 1.0 |
| WX-1 | 973,000 | 0.8 |
| WX-2 | 951,000 | 2.2 |
| WX-7 | 1,000,000 | 1.5 |
| WX-12 | 898,000 | 0.4 |
| WX-14 | 1,900,000 | 1.9 |
| W-14 | 860,000 | 7.5 |

[a]Native molecular weight determined using a Pharmacia HR 16/50 column packed with Sepharose CL4B
[b]Amount of toxin complex recovered from culture broth.

Activity Spectrum

As shown in Table 23, the toxin complexes purified from strains Hm and H9 were tested for activity against a variety of insects, with the toxin complex from strain W-14 for comparison. The assays were performed as described in Example 13. The toxin complex from all three strains exhibited activity against tobacco bud worm, European corn borer, Southern corn root worm, and aster leafhopper.

TABLE 23

Observed Insecticidal Spectrum of a Purified Toxin Complex from Photorhabdus Strains

| Photorhabdus Strain | Sensitive* Insect Species |
|---|---|
| Hm Toxin Complex | 1**, 2, 3, 5, 6, 7, 8 |
| H9 Toxin Complex | 1, 2, 3, 6, 7, 8 |
| W-14 Toxin Complex | 1, 2, 3, 4, 5, 6, 7, 8 |

*= >25% mortality or growth inhibition
*= >25% mortality or growth inhibition
**= 1, Tobacco bud worm; 2, European corn borer; 3, Southern corn root worm; 4, Mosquito; 5, Two-spotted spider mite; 6, Aster Leafhopper; 7, Fruit Fly; 8, Boll Weevil

EXAMPLE 15

Sub-Fractionation of Photorhabdus Protein Toxin Complex

The Photorhabdus protein toxin complex was isolated as described in Example 14. Next, about 10 mg toxin was applied to a MonoQ 5/5 column equilibrated with 20 mM Tris-HCl, pH 7.0 at a flow rate of 1 ml/min. The column was washed with 20 mM Tris-HCl, pH 7.0 until the optical density at 280 nm returned to baseline absorbance. The proteins bound to the column were eluted with a linear gradient of 0 to 1.0 M NaCl in 20 mM Tris-HCl, pH 7.0 at 1 ml/min for 30 min. One ml fractions were collected and subjected to Southern corn rootworm (SCR) bioassay (see Example 13). Peaks of activity were determined by a series of dilutions of each fraction in SCR bioassays. Two activity peaks against SCR were observed and were named A (eluted at about 0.2–0.3 M NaCl) and B (eluted at 0.3–0.4 M NaCl).

Activity peaks A and B were pooled separately and both peaks were further purified using a 3-step procedure described below.

Solid (NH$_4$)2SO$_4$ was added to the above protein fraction to a final concentration of 1.7 M. Proteins were then applied to a phenyl-Superose 5/5 column equilibrated with 1.7 M (NH$_4$)$_2$SO$_4$ in 50 mM potassium phosphate buffer, pH 7 at 1 ml/min. Proteins bound to the column were eluted with a linear gradient of 1.7 M (NH$_4$)2SO$_4$, 0% ethylene glycol, 50 mM potassium phosphate, pH 7.0 to 25% ethylene glycol, 25 mM potassium phosphate, pH 7.0 (no (NH$_4$)$_2$SO$_4$) at 0.5 ml/min. Fractions were dialyzed overnight against 10 mM sodium phosphate buffer, pH 7.0. Activities in each fraction against SCR were determined by bioassay.

The fractions with the highest activity were pooled and applied to a MonoQ 5/5 column which was equilibrated with 20 mM Tris-HCl, pH 7.0 at 1 ml/min. The proteins bound to the column were eluted at 1 ml/min by a linear gradient of 0 to 1M NaCl in 20 mM Tris-HCl, pH 7.0.

For the final step of purification, the most active fractions above (determined by SCR bioassay) were pooled and subjected to a second phenyl-Superose 5/5/column. Solid (NH$_4$)$_2$SO$_4$ was added to a final concentration of 1.7 M. The solution was then loaded onto the column equilibrated with 1.7 M (NH$_4$)$_2$SO$_4$ in 50 mM potassium phosphate buffer, pH 7 at 1 ml/min. Proteins bound to the column were eluted with a linear gradient of 1.7 M (NH$_4$)$_2$SO$_4$, 50 mM potassium phosphate, pH 7.0 to 10 mM potassium phosphate, pH 7.0 at 0.5 ml/min. Fractions were dialyzed overnight against 10 mM sodium phosphate buffer, pH 7.0. Activities in each fraction against SCR were determined by bioassay.

The final purified protein by the above 3-step procedure from peak A was named toxin A and the final purified protein from peak B was named toxin B.

Characterization and Amino Acid Sequencing of Toxin A and Toxin B

In SDS-PAGE, both toxin A and toxin B contained two major (>90% of total Commassie stained protein) peptides: 192 kDa (named A1 and B1, respectively) and 58 kDa (named A2 and B2, respectively). Both toxin A and toxin B revealed only one major band in native PAGE, indicating A1 and A2 were subunits of one protein complex, and B1 and B2 were subunits of one protein complex. Further, the native molecular weight of both toxin A and toxin B were determined to be 860 kDa by gel filtration chromatography. The relative molar concentrations of A1 to A2 was judged to be a 1 to 1 equivalence as determined by densiometric analysis of SDS-PAGE gels. Similarly, B1 and B2 peptides were present at the same molar concentration.

Toxin A and toxin B were electrophoresed in 10% SDS-PAGE and transblotted to PVDF membranes. Blots were sent for amino acid analysis and N-terminal amino acid sequencing at Harvard MicroChem and Cambridge ProChem, respectively. The N-terminal amino sequence of B1 was determined to be identical to SEQ ID NO:1, the TcbA$_{ii}$ region of the tcbA gene (SEQ ID NO:12, position 87 to 99). A unique N-terminal sequence was obtained for peptide B2 (SEQ ID NO:40). The N-terminal amino acid sequence of peptide B2 was identical to the TcbA$_{iii}$ region of the derived amino acid sequence for the tcbA gene (SEQ ID NO:12, position 1935 to 1945). Therefore, the B toxin contained predominantly two peptides, TcbA$_{ii}$ and TcbA$_{iii}$, that were observed to be derived from the same gene product, TcbA.

The N-terminal sequence of A2 (SEQ ID NO:41) was unique in comparison to the TcbA$_{iii}$ peptide and other peptides. The A2 peptide was denoted TcdA$_{iii}$ (see Example 17). SEQ ID NO:6 was determined to be a mixture of amino acid sequences SEQ ID NO:40 and 41.

Peptides A1 and A2 were further subjected to internal amino acid sequencing. For internal amino acid sequencing, 10 μg of toxin A was electrophoresized in 10% SDS-PAGE and transblotted to PVDF membrane. After the blot was stained with amido black, peptides A1 and A2, denoted TcdA$_{ii}$ and TcdA$_{iii}$, respectively, were excised from the blot and sent to Harvard MicroChem and Cambridge ProChem. Peptides were subjected to trypsin digestion followed by HPLC chromatography to separate individual peptides. N-terminal amino acid analysis was performed on selected tryptic peptide fragments. Two internal amino acid sequences of peptide A1 (TcdA$_{ii}$-PK71, SEQ ID NO:38 and TcdA$_{ii}$-PK44, SEQ ID NO:39) were found to have significant homologies with deduced amino acid sequences of the TcbA$_{ii}$ region of the tcbA gene (SEQ ID NO:12). Similarly, the N-terminal sequence (SEQ ID NO:41) and two internal sequences of peptides A2 (TcdA$_{iii}$-PK57, SEQ ID NO:42 and TcdA$_{iii}$-PK20, SEQ ID NO:43) also showed significant homology with deduced amino acid sequences of TcbA$_{iii}$ region of the tcbA gene (SEQ ID NO:12).

In summary of above results, the toxin complex has at least two active protein toxin complexes against SCR; toxin A and toxin B. Toxin A and toxin B are similar in their native and subunits molecular weight, however, their peptide compositions are different. Toxin A contained peptides TcdA$_{ii}$ and TcdA$_{iii}$ as the major peptides and the toxin B contains TcbA$_{ii}$ and TcbA$_{iii}$ as the major peptides.

Purification and Characterization of Toxin C, Tca Peptides

The Photorhabdus protein toxin complex was isolated as described above. Next, about 50 mg toxin was applied to a MonoQ 10/10 column equilibrated with 20 mM Tris-HCl, pH 7.0 at a flow rate of 2 ml/min. The column was washed with 20 mM Tris-HCl, pH7.0 until the optical density at 280 nm returned to baseline level. The proteins bound to the column were eluted with a linear gradient of 0 to 1M NaCl in 20 mM Tris-HCl, pH 7.0 at 2 ml/min for 60 min. 2 ml fractions were collected and subjected to Western analysis using pAb TcaB$_{ii}$-syn antibody (see Example 21) as the primary antibody. Fractions reacted with pAb TcaB$_{ii}$-syn antibody were combined and solid (NH$_4$)$_2$SO$_4$ was added to a final concentration of 1.7 M. Proteins were then applied to a phenyl-Superose 10/10 column equilibrated with 1.7 M (NH$_4$)$_2$SO$_4$ in 50 mM potassium phosphate buffer, pH 7 at 1 ml/min. Proteins bound to the column were eluted with a linear gradient of 1.7 M (NH$_4$)$_2$SO$_4$, 50 mM potassium phosphate, pH 7.0 to 10 mM potassium phosphate, pH 7.0 at 1 ml/min for 120 min. 2 ml Fractions were collected, dialyzed overnight against 10 mM sodium phosphate buffer, pH 7.0, and analyzed by Western blots using pAb TcaB$_{ii}$-syn antibody as the primary antibody.

Fractions cross-reacted with the antibody were pooled and applied to a MonoQ 5/5 column which was equilibrated with 20 mM Tris-HCl, pH 7.0 at 1 ml/min. The proteins bound to the column were eluted at 1 ml/min by a linear gradient of 0 to 1M NaCl in 20 mM Tris-HCl, pH 7.0 for 30 min.

Fractions above reacted with pAb TcaB$_{ii}$-syn antibody were pooled and subjected to a phenyl-Superose 5/5/ column. Solid (NH$_4$)$_2$SO$_4$ added to a final concentration of 1.7 M. The solution was then applied onto the column equilibrated with 1.7 M (NH$_4$)$_2$SO$_4$ in 50 mM potassium phosphate buffer, pH 7 at 1 ml/min. Proteins bound to the column were then eluted with a linear gradient of 1.7 M (NH$_4$)$_2$SO$_4$, 50 mM potassium phosphate, pH 7.0 to 10 mM potassium phosphate, pH 7.0 at 0.5 ml/min for 60 min. Fractions were dialyzed overnight against 10 mM sodium phosphate buffer, pH 7.0.

For the final purification step, fractions reacted with pAb TcaB$_{ii}$-syn antibody above determined by Western analysis were combined and applied to a Mono Q 5/5 column equilibrated with 20 mM Tris-HCl, pH 7.0 at 1 ml/min. The proteins bound to the column were eluted at 1 ml/min by a linear gradient of 0 to 1M NaCl in 20 mM Tris-HCl, pH 7.0 for 30 min.

The final purified protein fraction contained 6 major peptides examined by SDS-PAGE: 165 kDa, 90 kDa, 64 kDa, 62 kDa, 58 kDa, and 22 kDa. The LD50 of the insecticidal activities of this purified fraction were determined to be 100 ng and 500 ng against SCR and ECB, respectively.

The above peptides were blotted to PVDF membranes and blots were sent for amino acids analysis and 5 amino acid long N-terminal sequencing at Harvard MicroChem and Cambridge ProChem, respectively. The N-terminal amino acid sequence of the 165 kDa peptide was determined to be identical to peptide TcaC (SEQ ID 2, position 1 to 5). The N-terminal amino acid sequence of the 90 kDa peptide was determined to be TcaA$_{ii}$ region of the derived amino acid sequence for the tcaA gene (SEQ ID NO 33, position 254 to 258). The N-terminal amino acid sequence of 64 kDa peptide was determined to be identical to peptide TcaB$_i$ (SEQ ID 3, position 1 to 5). The N-terminal amino acid sequence of the 62 kDa peptide was determined to be TcaA$_{ii}$ region of the derived amino acid sequence for the tcaA gene (SEQ ID NO 33, position 489 to 493). The N-terminal amino acid sequence of 58 kDa peptide was determined to be identical to peptide TcaB$_{ii}$ (SEQ ID 5, position 1 to 5). The N-terminal amino acid sequence of the 22 kDa peptide (SEQ ID NO 62) was determined to be TcaA$_i$ region, denoted TcaA$_{iv}$, of the derived amino acid sequence for the tcaA gene (SEQ ID NO 34, position 98 to 102). It is noted that all tcaA, tcaB, and tcaC genes reside in the same tca operon (FIG. 6A).

Five µg of purified Tca fraction, purified toxin A, and purified toxin B were analyzed by western blot using the following antibodies individually as primary antibody: pAb TcaBii-syn antibody, mAb CF52 antibody, pAb TcdAii-syn antibody, and pAb Tcd$_{iii}$-syn antibody (Example 21). With pAb TcaB$_{ii}$-syn antibody only the purified Tca peptides fraction reacted, but not toxin A or toxin B. With mAb CF52 antibody, only toxin B reacted but not Tca peptides fraction or toxin A. With either pAb TcdAii-syn antibody or pAb Tcdiii-syn antibody only toxin A reacted, but not Tca peptides fraction or toxin B. This indicated that the insecticidal activity observed in the purified Tca peptides fraction is independent of toxin A and toxin B. The purified Tca peptide fraction is a third unique protein toxin, denoted toxin C.

EXAMPLE 16

Cleavage and Activation of TcbA Peptide

In the toxin B complex, peptide $TcbA_{ii}$ and $TcbA_{iii}$ originate from the single gene product TcbA (Example 15). The processing of TcbA peptide to $TcbA_{ii}$ and $TcbA_{iii}$ is presumably by the action of Photorhabdus protease(s), and most likely, the metalloproteases described in Example 10. In some cases, it was noted that when Photorhabdus W-14 broth was processed, TcbA peptide was present in toxin B complex as a major component, in addition to peptides $TcbA_{ii}$ and $TcbA_{iii}$. Identical procedures, described for the purification of toxin B complex (Example 15), were used to enrich peptide TcbA from toxin complex fraction of W-14 broth. The final purified material was analyzed in a 4–20% gradient SDS-PAGE and major peptides were quantified by densitometry. It was determined that TcbA, $TcbA_{ii}$ and $TcbA_{iii}$ comprised 58%, 36%, and 6%, respectively, of total protein. The identities of these peptides were confirmed by their respective molecular sizes in SDS-PAGE and Western blot analysis using monospecific antibodies. The native molecular weight of this fraction was determined to be 860 kDa.

The cleavage of TcbA was evaluated by treating the above purified material with purified 38 kDa and 58 kDa W-14 Photorhabdus metalloproteases (Example 10), and trypsin as a control enzyme (Sigma, MO.). The standard reaction consisted 17.5 μg the above purified fraction, 1.5 unit protease, and 0.1 M Tris buffer, pH 8.0 in a total volume of 100 μl. For the control reaction, protease was omitted. The reaction mixtures were incubated at 37° C. for 90 min. At the end of the reaction, 20 μl was taken and boiled with SDS-PAGE sample buffer immediately for electrophoresis analysis in a 4–20% gradient SDS-PAGE. It was determined from SDS-PAGE that in both 38 kDa and 58 kDa protease treatments, the amount of peptides $TcbA_{ii}$ and $TcbA_{iii}$ increased about 3-fold while the amount of TcbA peptide decreased proportionally (Table 24). The relative reduction and augmentation of selected peptides was confirmed by Western blot analyses. Furthermore, gel filtration of the cleaved material revealed that the native molecular size of the complex remained the same. Upon trypsin treatment, peptides TcbA and $TcbA_{ii}$ were nonspecifically digested into small peptides. This indicated that 38 kDa and 58 kDa Photorhabdus proteases can specifically process peptide TcbA into peptides $TcbA_{ii}$ and $TcbA_{iii}$. Protease treated and untreated control of the remaining 80 μl reaction mixture were serial diluted with 10 mM sodium phosphate buffer, pH 7.0 and analyzed by SCR bioassay. By comparing activity in several dilution, it was determined that the 38 kDa protease treatment increased SCR insecticidal activity approximately 3 to 4 fold. The growth inhibition of remaining insects in the protease treatment was also more severe than control (Table 24).

TABLE 24

Conversion and Activation of Peptide TcbA into Peptides $TcbA_{ii}$ and $TcbA_{iii}$ by Protease Treatment

| | Control | 38 kDa protease treatment |
|---|---|---|
| TcbA (% of total protein) | 58 | 18 |
| $TcbA_{ii}$ (% of total protein) | 36 | 64 |
| $TcbA_{iii}$ (% of total protein) | 6 | 18 |
| LD50 (μg protein) | 2.1 | 0.52 |
| SCR Weight (mg/insect) * | 0.2 | 0.1 |

* an indication of growth inhibition by measuring the average weight of live insect after 5 days on diet in the assay.

Activation and Procession of Toxin B by SCR Gut Proteases

In yet a second demonstration of proteolytic activation, it was examined whether W-14 toxins are processed by insects. Toxin B purified from Photorhabdus W-14 broth (see Example 15) was comprised of predominantly intact TcbA peptides as judged by SDS-PAGE and Western blot analysis using monoclonal antibody. The LD50 of this fraction against SCR was determined to be around 700 ng.

SCR larva were grown on coleopteran diet until they reached the fourth instar stage (about 100–125 mg total weight each insect). SCR gut content was collected as follows: the guts were removed using dissecting scissors and forceps. After removing the excess fatty material that coats the gut lining, about 40 guts were homogenized in a microcentrifuge tube containing 100 μl sterile water. The tube was then centrifuged at 14,000 rpm for 10 minutes and the pellet discarded. The supernatant was stored at a −70° C. freezer until use.

The processing of toxin B by insect gut was evaluated by treating the above purified toxin B with the SCR gut content collected. The reaction consisted 40 μg toxin B (1 mg/ml), 50 μl SCR gut content, and 0.1M Tris buffer, pH 8.0 in a total volume of 100 μl. For the control reaction, SCR gut content was omitted. The reaction mixtures were incubated at 37° C. for overnight. At the end of reaction, 10 μl was withdraw and boiled with equal volume 2×SDS-PAGE sample buffer for SDS-PAGE analysis. The remaining 90 μl reaction mixture was serial diluted with 10 mM sodium phosphate buffer, pH 7.0 and analyzed by SCR bioassay. SDS-PAGE analysis indicated in SCR gut content treatment, peptide TcbA was digested completely into smaller peptides. Analysis of the undenatured toxin fraction showed that the native size, about 860 kDa, remained the same even though larger peptides were fragmented. In SCR bioassays, it was found that the LDSO of SCR gut treated toxin B to be about 70 ng; representing a 10-fold increase. In a separate experiment, protease K treatment completely eliminated toxin activity.

EXAMPLE 17

Screening of the Library for a Gene Encoding the TcdA$_{ii}$ Peptide

The cloning and characterization of a gene encoding the TcdA$_{ii}$ peptide, described as SEQ ID NO:17 (internal peptide TcdA$_{ii}$-PT111 N-terminal sequence) and SEQ ID NO:18 (internal peptide TcdA$_{ii}$-PT79 N-terminal sequence) was completed. Two pools of degenerate oligonucleotides, designed to encode the amino acid sequences of SEQ ID NO:17 (Table 25) and SEQ ID NO:18 (Table 26), and the reverse complements of those sequences, were synthesized as described in Example 8. The DNA sequence of the oligonucleotides is given below:

Polymerase Chain Reactions (PCR) were performed essentially as described in Example 8, using as forward primers P2.3.6.CB or P2.3.5, and as reverse primers P2.79.R.1 or P2.79R.CB, in all forward/reverse combinations, using Photorhabdus W-14 genomic DNA as template. In another set of reactions, primers P2.79.2 or P2.79.3 were used as forward primers, and P2.3.5R, P2.3.5RI, and P2.3R.CB were used as reverse primers in all forward/reverse combinations. Only in the reactions containing P2.3.6.CB as the forward primers combined with P2.79.R.1 or P2.79R.CB as the reverse primers was a non-artifactual amplified product seen, of estimated size (mobility on agarose gels) of 2500 base pairs. The order of the primers used to obtain this amplification product indicates that the peptide fragment TcdA$_{ii}$-PT111 lies amino-proximal to the peptide fragment TcdA$_{ii}$-PT79.

The 2500 bp PCR products were ligated to the plasmid vector pCR™II (Invitrogen, San Diego, Calif.) according to the supplier's instructions, and the DNA sequences across the ends of the insert fragments of two isolates (HS24 and HS27) were determined using the supplier's recommended primers and the sequencing methods described previously. The sequence of both isolates was the same. New primers were synthesized based on the determined sequence, and used to prime additional sequencing reactions to obtain a total of 2557 bases of the insert [SEQ ID NO:36]. Translation of the partial peptide encoded by SEQ ID No: 36 yields the 845 amino acid sequence disclosed as SEQ ID NO:37. Protein homology analysis of this portion of the TcdA$_{ii}$ peptide fragment reveals substantial amino acid homology ((68% similarity,and 53% identity using the Wisconsin Package Version 8.0, Genetics Computer Group (GCG), Madison, Wis.) to residues 542 to 1390 of protein TcbA [SEQ ID NO:12] or (60% similarity, and 54% identity using the Wisconsin Package Version 9.0, Genetics Computer Group (GCG), Madison, Wis. to residues 567 to 1389)). It is therefore apparent that the gene represented in part by SEQ ID NO:36 produces a protein of similar, but not identical, amino acid sequence as the TcbA protein, and which likely has similar, but not identical biological activity as the TcbA protein.

TABLE 25

Degenerate Oligonucleotide for SEQ ID NO: 17

| P2-PT111<br>Amino Acid | 1<br>Ala | 2<br>Phe | 3<br>Asn | 4<br>Ile | 5<br>Asp | 6<br>Asp | 7<br>Val | 8<br>Ser |
|---|---|---|---|---|---|---|---|---|
| Codons | 5' GCN | TT(T/C) | AA(T/C) | AT(T/C/A) | GA(T/C) | GA(T/C) | GTN 3' | |
| P2.3.6.CB | 5' GC(A/C/G/T) | TT(T/C) | AAT | ATT | GAT | GAT | GT 3' | |
| P2.3.5 | 5' GC(A/C/G/T) | TT(T/C) | AA(T/C) | AT(T/C/A) | GA(T/C) | GA(T/C) | GT 3' | |
| P2.3.5R | 5' AC | (G/A)TC | (G/A)TC | (T/G/A)AT | (G/A)TT | (G/A)AA | (A/C/G/T)GC 3' | |
| P2.3.5RI | 5' ACI | TCI | TCI | ATI | TTI | AAI | GC 3' | |
| P2.3R.CB | 5' CAG | (A/G)CT | (A/C)AC | ATC | ATC | AAT | ATT | AAA 3' |

TABLE 26

Degenerate Oligonucleotide for SEQ ID NO: 18

| P2-PT79<br>Amino Acid | 1<br>Phe | 2<br>Ile | 3<br>Val | 4<br>Tyr | 5<br>Thr | 6<br>Ser | 7<br>Leu | 8<br>Gly | 9<br>Val | 10<br>Asn | 11<br>Pro | 12<br>Asn | 13<br>Asn |
|---|---|---|---|---|---|---|---|---|---|---|---|---|---|
| Codons* | 5' TTY | ATH | GTN | TAY | ACN | 6 | 6 | GGN | GTN | AAY | CCN | AAY | AAY 3' |
| P2.79.2 | 5' TTY | ATY | GTK | TAT | ACY | TCI | YTR | GGY | GTK | AAT | CCR | AAT | AAT 3' |
| P2.79.3 | 5' TTT | ATT | GTK | TAT | ACY | AGY | YTR | GGY | GTK | AAT | CCR | AAT | AAT 3' |
| P2.79.R.1 | 5' ATT | ATT | YGG | ATT | MAC | RCC | YAR | RCT | RGT | ATA | MAC | AAT | AAA 3' |
| P2.79R.CB | 5' ATT | ATT | YGG | ATT | MAC | ACC | CAG | RCT | GGT | ATA | MAC | AAT | AAA 3' |

*According to IUPAC-IUB codes for nucleotides, Y = C or T, H = A, C or T, N = A, C, G or T, K = G or T, R = A or G, and M = A or C In yet another instance, a gene encoding the peptides TcdA$_{ii}$-PK44 and the TcdA$_{iii}$ 58 kDa N-terminal peptide, described as SEQ ID NO:39 (internal peptide TcdA$_{ii}$-PK44 sequence), and SEQ ID NO:41 (TcdA$_{iii}$ 58 kDa N-terminal peptide sequence) was isolated. Two pools of degenerate oligonucleotides, designed to encode the amino acid sequences described as SEQ ID NO:39 (Table 28) and SEQ ID NO:41 (Table 27), and the reverse complements of those sequences, were synthesized as described in Example 8, and their DNA sequences.

TABLE 27

Degenerate Oligonucleotide for SEQ ID NO: 41

| Codon # | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Amino Acid | Leu | Arg | Ser | Ala | Asn | Thr | Leu | Thr | Asp | Leu | Phe | Leu | Pro | Gln |
| A2.1 | 5' YTR | CGY | AGY | GCI | AAT | ACY | YTR | ACY | GAT | YTR | TTT | YTR | CCR | CA 3' |
| A2.2 |  |  |  | GCI | AAT | ACI | YTR | ACI | GAY | YTR | TTY | YTR | CCI | CA 3' |
| A2.3.R |  | 5' TG | YGG | YAR | AAA | YAR | RTC | RGT | YAR | RGT | RIT | IGC | RCT | RCG 3' |
| A2.4.R |  |  |  | 5' TG | IGG | CAG | AAA | CAG | RTC | IGT | CAG | IGT | ATT | IGC 3' |

TABLE 28

Degenerate Oligonucleotide for SEQ ID NO: 39

| Amino Acid # | (8) | (9) | (10) | (11) | (12) | (13) | (14) | (15) | (16) |
|---|---|---|---|---|---|---|---|---|---|
| Codon # | 1 | 2 | 3 | 4 | 5 | 6 | 7 | 8 | 9 |
| Amino Acid | Gly | Pro | Val | Glu | Ile | Asn | Thr | Ala | Ile |
| A1.44.1 | 5' GGY | CCR | GTK | GAA | ATT | AAT | ACC | GCI | AT 3' |
| A1.44.1R | 5' ATI | GCG | GTA | TTA | ATT | TCM | ACY | GGR | CC 3' |
| A1.44.2 | 5' GGI | CCI | GTI | GAR | ATY | AAY | ACI | GCI | AT 3' |
| A1.44.2R | 5' ATI | GCI | GTR | TTR | ATY | TCI | ACI | GGI | CC 3' |

Polymerase Chain Reactions (PCR) were performed essentially as described in Example 8, using as forward primers A1.44.1 or A1.44.2, and reverse primers A2.3R or A2.4R, in all forward/reverse combinations, using Photorhabdus W-14 genomic DNA as template. In another set of reactions, primers A2.1 or A2.2 were used as forward primers, and A1.44.1R, and A1.44.2R were used as reverse primers in all forward/reverse combinations. Only in the reactions containing A1.44.1 or A1.44.2 as the forward primers combined with A2.3R as the reverse primer was a non-artifactual amplified product seen, of estimated size (mobility on agarose gels) of 1400 base pairs. The order of the primers used to obtain this amplification product indicates that the peptide fragment TcdA$_{ii}$-PK44 lies amino-proximal to the 58 kDa peptide fragment of TcdA$_{iii}$.

The 1400 bp PCR products were ligated to the plasmid vector pCR™II according to the supplier's instructions. The DNA sequences across the ends of the insert fragments of four isolates were determined using primers similar in sequence to the supplier's recommended primers and using sequencing methods described previously. The nucleic acid sequence of all isolates differed as expected in the regions corresponding to the degenerate primer sequences, but the amino acid sequences deduced from these data were the same as the actual amino acid sequences for the peptides determined previously, (SEQ ID NOS:41 and 39).

Screening of the W-14 genomic cosmid library as described in Example 8 with a radiolabeled probe comprised of the DNA prepared above (SEQ ID NO:36) identified five hybridizing cosmid isolates, namely 17D9, 20B10, 21D2, 27B10, and 26D1. These cosmids were distinct from those previously identified with probes corresponding to the genes described as SEQ ID NO:11 or SEQ ID NO:25. Restriction enzyme analysis and DNA blot hybridizations identified three EcoR I fragments, of approximate sizes 3.7, 3.7, and 1.1 kbp, that span the region comprising the DNA of SEQ ID NO:36. Screening of the W-14 genomic cosmid library using as probe the radiolabeled 1.4 kbp DNA fragment prepared in this example identified the same five cosmids (17D9, 20B10, 21D2, 27B10, and 26D1). DNA blot hybridization to EcoR I-digested cosmid DNAs also showed hybridization to the same subset of EcoR I fragments as seen with the 2.5 kbp TcdA$_{ii}$ gene probe, indicating that both fragments are encoded on the genomic DNA.

DNA sequence determination of the cloned EcoR I fragments revealed an uninterrupted reading frame of 7551 base pairs (SEQ ID NO:46), encoding a 282.9 kDa protein of 2516 amino acids (SEQ ID NO:47). Analysis of the amino acid sequence of this protein revealed all expected internal fragments of peptides TcdA$_{ii}$ (SEQ ID NOS:17, 18, 37, 38 and 39) and the TcdA$_{iii}$ peptide N-terminus (SEQ ID NO:41) and all TcdA$_{iii}$ internal peptides (SEQ ID NOS:42 and 43). The peptides isolated and identified as TcdA$_{ii}$ and TcdA$_{iii}$ are each products of the open reading frame, denoted tcda, disclosed as SEQ ID NO:46. Further, SEQ ID NO:47 shows, starting at position 89, the sequence disclosed as SEQ ID NO:13, which is the N-terminal sequence of a peptide of size approximately 201 kDa, indicating that the initial protein produced from SEQ ID NO: 46 is processed in a manner similar to that previously disclosed for SEQ ID NO:12. In addition, the protein is further cleaved to generate a product of size 209.2 kDa, encoded by SEQ ID NO:48 and disclosed as SEQ ID NO:49 (TcdA$_{ii}$ peptide), and a product of size 63.6 kDa, encoded by SEQ ID NO:50 and disclosed as SEQ ID NO:51 (TcdA$_{iii}$ peptide). Thus, it is thought that the insecticidal activity identified as toxin A (Example 15) derived from the products of SEQ ID NO:46, as exemplified by the full-length protein of 282.9 kDa disclosed as SEQ ID NO:47, is processed to produce the peptides disclosed as SEQ ID NOS:49 and 51. It is thought that the insecticidal activity identified as toxin B (Example 15) derives from the products of SEQ ID NO:11, as exemplified by the 280.6 kDa protein disclosed as SEQ ID NO:12. This protein is proteolytically processed to yield the 207.6 kDa peptide disclosed as SEQ ID NO:53, which is encoded by SEQ ID NO:52, and the 62.9 kDa peptide having N-terminal sequence disclosed as SEQ ID NO:40, and further disclosed as SEQ ID NO:55, which is encoded by SEQ ID NO:54.

Amino acid sequence comparisons between the proteins disclosed as SEQ ID NO:12 and SEQ ID NO:47 reveal that they have 69% similarity and 54% identity using the Wisconsin Package Version 8.0, Genetics Computer Group (GCG), Madison, Wis. or 60% similarity and 54% identity using version 9.0 of the program. This high degree of evolutionary relationship is not uniform throughout the entire amino acid sequence of these peptides, but is higher towards the carboxy-terminal end of the proteins, since the peptides disclosed as SEQ ID NO:51 (derived from SEQ ID NO:47) and SEQ ID NO:55 (derived from SEQ ID NO:12) have 76% similarity and 64% identity using the Wisconsin Package Version 8.0, Genetics Computer Group (GCG), Madison, Wis. or 71% similarity and 64% identity using version 9.0 of the program.

EXAMPLE 18

Control of European Cornborer-Induced Leaf Damage on Maize Plants by Spray Application of Photorhabdus (Strain W-14) Broth The ability of Photorhabdus toxin(s) to reduce plant damage caused by insect larvae was demonstrated by measuring leaf damage caused by European corn borer (*Ostrinia nubilalis*) infested onto maize plants treated with Photorhabdus broth. Fermentation broth from Photorhabdus strain W-14 was produced and concentrated approximately 10-fold using ultrafiltration (10,000 MW pore-size) as described in Example 13. The resulting concentrated broth was then filter sterilized using 0.2 micron nitrocellulose membrane filters. A similarly prepared sample of uninoculated 2% proteose peptone #3 was used for control purposes. Maize plants (an inbred line) were grown from seed to vegetative stage 7 or 8 in pots containing a soilless mixture in a greenhouse (27° C. day; 22° C. night, about 50%RH, 14 hr day-length, watered/fertilized as needed). The test plants were arranged in a randomized complete block design (3 reps/treatment, 6 plants/treatment) in a greenhouse with temperature about 22° C. day; 18° C. night, no artificial light and with partial shading, about 50%RH and watered/fertilized as needed. Treatments (uninoculated media and concentrated Photorhabdus broth) were applied with a syringe sprayer, 2.0 mls applied from directly (about 6 inches) over the whorl and 2.0 additional mls applied in a circular motion from approximately one foot above the whorl. In addition, one group of plants received no treatment. After the treatments had dried (approximately 30 minutes), twelve neonate European corn borer larvae (eggs obtained from commercial sources and hatched in-house) were applied directly to the whorl. After one week, the plants were scored for damage to the leaves using a modified Guthrie Scale (Koziel, M. G., Beland, G. L., Bowman, C., Carozzi, N. B., Crenshaw, R., Crossland, L., Dawson, J., Desai, N., Hill, M., Kadwell, S., Launis, K., Lewis, K., Maddox, D., McPherson, K., Meghji, M. Z., Merlin, E., Rhodes, R., Warren, G. W., Wright, M. and Evola, S. V. 1993).

Bio/Technology, 11, 194–195.) and the scores were compared statistically [T-test (LSD) p<0.05 and Tukey's Studentized Range (HSD) Test p<0.1]. The results are shown in Table 29. For reference, a score of 1 represents no damage, a score of 2 represents fine "window pane" damage on the unfurled leaf with no pinhole penetration and a score of 5 represents leaf penetration with elongated lesions and/or mid rib feeding evident on more than three leaves (lesions <1 inch). These data indicate that broth or other protein containing fractions may confer protection against specific insect pests when delivered in a sprayable formulation or when the gene or derivative thereof, encoding the protein or part thereof, is delivered via a transgenic plant or microbe.

TABLE 29

Effect of Photorhabdus Culture Broth on European Corn Borer-Induced Leaf Damage on Maize

| Treatment | Average Guthrie Score |
| --- | --- |
| No Treatment | 5.02[a] |
| Uninoculated medium | 5.15[a] |
| Photorhabdus Broth | 2.24[b] |

Means with different letters are statistically different ($p < 0.05$ or $< 0.1$).

EXAMPLE 19

Genetic Engineering of Genes for Expression in *E. coli*

Summary of Constructions

A series of plasmids were constructed to express the tcbA gene of Photorhabdus W-14 in *Escherichia coli*. A list of the plasmids is shown in Table 30. A brief description of each construction follows as well as a summary of the *E. coli* expression data obtained.

TABLE 30

Expression Plasmids for the tcbA Gene

| Plasmid | Gene | Vector/Selection | Compartment |
| --- | --- | --- | --- |
| pDAB2025 | tcbA | pBC/Chl | Intracellular |
| pDAB2026 | tcbA | pAcGP67B/Amp | Baculovirus, secreted |
| pDAB2027 | tcbA | pET27b/Kan | Periplasm |
| pDAB2028 | tcbA | pET15-tcbA | Intracellular |

Abbreviations:
Kan = kanamycin, Chl = chloramphenicol, Amp = ampicillin

Construction of pDAB2025

In Example 9, a large EcoR I fragment which hybridizes to the TcbA$_{ii}$ probe is described. This fragment was subcloned into pBC (Stratagene, La Jolla Calif.) to create pDAB2025. Sequence analysis indicates that the fragment is 8816 base pairs. The fragment encodes the tcbA gene with the initiating ATG at position 571 and the terminating TAA at position 8086. The fragment therefore carries 570 base pairs of Photorhabdus DNA upstream of the ATG and 730 base pairs downstream of the TAA.

Construction of Plasmid pDAB2026

The tcbA gene was PCR amplified from plasmid pDAB202S using the following primers; 5' primer (SlAc51) 5' TTT AAA CCA TGG GAA ACT CAT TAT CAA GCA CTA TC 3' and 3' primer (SlAc31) 5' TTT AAA GCG GCC GCT TAA CGG ATG GTA TAA CGA ATA TG 3'. PCR was performed using a TaKaRa LA PCR kit from PanVera (Madison, Wis.) in the following reaction: 57.5 microliters water, 10 microliters 10×LA buffer, 16 microliters dNTPs (2.5 mM each stock solution), 20 microliters each primer at 10 pmoles/microliters, 300 ng of the plasmid pDAB2025 containing the W-14 tcbA gene and one microliter of TaKaRa LA Taq polymerase. The cycling conditions were 98° C./20 sec, 68° C./5 min, 72° C./10 min for 30 cycles. A PCR product of the expected about 7526 bp was isolated in a 0.8% agarose gel in TBE (100 mM Tris, 90 mM boric acid, 1 mM EDTA) buffer and purified using a Qiaex II kit from Qiagen (Chatsworth, Calif.). The purified tcbA gene was digested with Nco I and Not I and ligated into the baculovirus transfer vector pAcGP67B (PharMingen (San Diego, Calif.)) and transformed into DH5α E. coli. The resulting recombinant is called pDAB2026. The tcbA gene was then cut from pDAB2026 and transferred to pET27b to create plasmid pDAB2027. A missense mutation in the tcbA gene was repaired in pDAB2027.

The repaired tcbA gene contains two changes from the sequence shown in Sequence ID NO:11; an A>G at 212 changing an asparagine 71 to serine 71 and a G>A at 229 changing an alanine 77 to threonine 77. These changes are both upstream of the proposed $TcbA_{ii}$N-terminus.

Construction of pDAB2028

The tcbA coding region of pDAB2027 was transferred to vector pET15b. This was accomplished using shotgun ligations, the DNAs were cut with restriction enzymes Nco I and Xho I. The resulting recombinant is called pDAB2028.

Expression of TcbA in *E. coli* from Plasmid pDAB2028

Expression of tcbA in *E. coli* was obtained by modification of the methods previously described by Studier et al. (Studier, F. W., Rosenberg, A., Dunn, J., and Dubendorff, J., (1990) Use of T7 RNA polymerase to direct expression of cloned genes. Methods Enzymol., 185: 60–89.). Competent *E. coli* cells strain BL21(DE3) were transformed with plasmid pDAB2028 and plated on LB agar containing 100 μg/mL ampicillin and 40 mM glucose. The transformed cells were plated to a density of several hundred isolated colonies/plate. Following overnight incubation at 37° C. the cells were scraped from the plates and suspended in LB broth containing 100 μg/mL ampicillin. Typical culture volumes were from 200–500 mL. At time zero, culture densities (OD600) were from 0.05–0.15 depending on the experiment. Cultures were shaken at one of three temperatures (22° C., 30° C. or 37° C.) until a density of 0.15–0.5 was obtained at which time they were induced with 1 mM isopropylthio-β-galactoside (IPTG). Cultures were incubated at the designated temperature for 4–5 hours and then were transferred to 4° C. until processing (12–72 hours).

Purification and Characterization of TcbA Expressed in *E.coli* from Plasmid pDAB2028

*E. coli* cultures expressing TcbA peptides were processed as follows. Cells were harvested by centrifugation at 17,000×G and the media was decanted and saved in a separate container.

The media was concentrated about 8× using the M12 (Amicon, Beverly Mass.) filtration system and a 100 kD molecular mass cut-off filter. The concentrated media was loaded onto an anion exchange column and the bound proteins were eluted with 1.0 M NaCl. The 1.0 M NaCl elution peak was found to cause mortality against Southern corn rootworm (SCR) larvae Table 30). The 1.0 M NaCl fraction was dialyzed against 10 mM sodium phosphate buffer pH 7.0, concentrated, and subjected to gel filtration on Sepharose CL-4B (Pharmacia, Piscataway, N.J.). The region of the CL-4B elution profile corresponding to calculated molecular weight (about 900 kDa) as the native W-14 toxin complex was collected, concentrated and bioassayed against larvae. The collected 900 kDa fraction was found to have insecticidal activity (see Table 31 below), with symptomology similar to that caused by native W-14 toxin complex. This fraction was subjected to Proteinase K and heat treatment, the activity in both cases was either eliminated or reduced, providing evidence that the activity is proteinaceous in nature. In addition, the active fraction tested immunologically positive for the TcbA and $TcbA_{iii}$ peptides in immunoblot analysis when tested with an anti-$TcbA_{iii}$ monoclonal antibody (Table 31).

TABLE 31

Results of Immunoblot and SCR Bioassays

| Fraction | SCR Activity % Mortality | SCR Activity % Growth Inhibit. | Immunoblot Peptides Detected | Native Size [CL-4B Estimated Size] |
|---|---|---|---|---|
| TcbA Media 1.0 M Ion Exchange | +++ | +++ | TcbA | |
| TcbA Media CL-4B | +++ | +++ | TcbA, $TcbA_{iii}$ | about 900 kDa |
| TcbA Media CL-4B + Proteinase K | ++ | +++ | NT | |
| TcbA Media CL-4B + heat treatment | – | – | NT | |
| TcbA Cell Sup CL-4B | – | +++ | NT | about 900 kD |

PK = Proteinase K treatment 2 hours; Heat treatment = 100° C. for 10 minutes; ND = None Detected; NT = Not Tested. Scoring system for mortality and growth inhibition as compared to control samples; 5–24% = "+", 25–49% = "++", 50–100% = "+++".

The cell pellet was resuspended in 10 mM sodium phosphate buffer, pH=7.0, and lysed by passage through a Bio-Neb™ cell nebulizer (Glas-Col Inc., Terra Haute, Ind.). The pellets were treated with DNase to remove DNA and centrifuged at 17,000×g to separate the cell pellet from the cell supernatant. The supernatant fraction was decanted and filtered through a 0.2 micron filter to remove large particles and subjected to anion exchange chromatography. Bound proteins were eluted with 1.0 M NaCl, dialyzed and concentrated using Biomax™ (Millipore Corp, Bedford, Mass.) concentrators with a molecular mass cut-off of 50,000 Daltons. The concentrated fraction was subjected to gel filtration chromatography using Sepharose CL-4B beaded matrix. Bioassay data for material prepared in this way is shown in Table 30 and is denoted as "TcbA Cell Sup".

In yet another method to handle large amounts of material, the cell pellets were re-suspended in 10 mM sodium phosphate buffer, pH=7.0 and thoroughly homogenized by using a Kontes Glass Company (Vineland, N.J.) 40 ml tissue grinder. The cellular debris was pelleted by centrifugation at 25,000×g and the cell supernatant was decanted, passed through a 0.2 micron filter and subjected to anion exchange chromatography using a Pharmacia 10/10 column packed with Poros HQ 50 beads. The bound proteins were eluted by performing a NaCl gradient of 0.0 to 1.0 M. Fractions containing the TcbA protein were combined and concentrated using a 50 kDa concentrator and subjected to gel filtration chromatography using Pharmacia CL-4B beaded matrix. The fractions containing TcbA oligomer, molecular mass of approximately 900 kDa, were collected and subjected to anion exchange chromatography using a Pharmacia Mono Q 10/10 column equilibrated with 20 mM Tris buffer pH=7.3. A gradient of 0.0 to 1.0 M NaCl was used to elute recombinant TcbA protein. Recombinant TcbA eluted from the column at a salt concentration of approximately 0.3–0.4 M NaCl, the same molarity at which native TcbA oligomer is eluted from the Mono Q 10/10 column. The recombinant TcbA fraction was found to cause SCR mortality in bioassay experiments similar to those in Table 31.

A second set of expression constructions were prepared and tested for expression of the TcbA protein toxin.

Construction of pDAB2030: An Expression Plasmid for the tcbA Coding Region

The plasmid pDAB2028 (see herein) contains the tcbA coding region in the commercial vector pET15 (Novagen, Madison, Wis.), encodes an ampicillin selection marker. The plasmid pDAB2030 was created to express the tcbA coding region from a plasmid which encodes a kanamycin selection marker. This was done by cutting pET27 (Novagen, Madison, Wis.) a kanamycin selection plasmid, and pDAB2028 with Xba I and Xho I. This releases the entire multiple cloning site, including the tcbA coding region from plasmid pDAB2028. The two cut plasmids, were mixed and ligated. Recombinant plasmids were selected on kanamycin and those containing the pDAB2028 fragment were identified by restriction analysis. The new recombinant plasmid is called pDAB2030.

Construction of Plasmid pDAB2031: Correction of Mutations in tcbA$_i$

The two mutations in the N-terminus of the tcbA coding region as described in Example 19 (Sequence ID NO:11; A>G at 212 changing an asparagine 71 to serine 71; G>A at 229 changing an alanine 77 to threonine 77) were corrected as follows: A PCR product was generated using the primers TH50 (5' ACC GTC TTC TTT ACG ATC AGT G 3') and S1Ac51 (5' TTT AAA CCA TGG GAA ACT CAT TAT CAA GCA CTA TC 3') and pDAB2025 as template to generate a 1778 bp product. This PCR product was cloned into plasmid pCR2.1 (Invitrogen, San Diego, Calif.) and a clone was isolated and sequenced. The clone was digested with Nco I and Pin AI and a 1670 bp fragment was purified from a 1% agarose gel. A plasmid containing the mutated tcbA coding region (pDAB2030) was digested with Nco I and Not I and purified away from the 1670 bp fragment in a 0.8% agarose with Qiaex II (Qiagen, Chatsworth, Calif.). The corrected Nco I/Pin AI fragment was then ligated into pDAB2030. The ligated DNA was transformed into DH5α E. coli. A clone was isolated, sequenced and found to be correct. This plasmid, containing the corrected tcbA coding region, is called pDAB2031.

Construction of pDAB2033 and pDAB2034: Expression Plasmids for tcbA

The expression plasmids pDAB2025 and pDAB2027–2031 all rely on the Bacteriophage T7 expression system. An additional vector system was used for bacterial expression of the tcbA gene and its derivatives. The expression vector Trc99a (Pharmacia Biotech, Piscataway, N.J.) contains a strong trc promoter upstream of a multiple cloning site with a 5' Nco I site which is compatible with the tcbA coding region from pDAB2030 and 2031. However, the plasmid does not have a compatible 3' site. Therefore, the Hind III site of Trc99a was cut and made blunt by treatment with T4 DNA polymerase (Boehringer Mannheim, Indianapolis, Ind.). The vector plasmid was then cut by Nco I followed by treatment with alkaline phosphatase. The plasmids pDAB2030 and pDAB2031 were each cut with Xho I (cuts at the 3' end of the tcbA coding region) followed by treatment with T4 DNA polymerase to blunt the ends. The plasmids were then cut with Nco I, the DNAs were extracted with phenol, ethanol precipitated and resuspended in buffer. The Trc99a and pDAB2030 and pDAB2031 plasmids were mixed separately, ligated and transformed into DH5α cells and plated on LB media containing ampicillin and 50 mM glucose. Recombinant plasmids were identified by restriction digestion. The new plasmids are called pDAB2033 (contains the tcbA coding sequence with the two mutations in tcbA$_i$) and pDAB2034 (contains the corrected version of tcbA from pDAB2031).

Construction of Plasmid pDAB2032: An Expression Plasmid for tcbA$_{ii}$A$_{iii}$ A plasmid encoding the TcbA$_{ii}$A$_{iii}$ portion of TcbA was created in a similar way as plasmid pDAB2031. A PCR product was generated using TH42 (5' TAG GTC TCC ATG GCT TTT ATA CAA GGT TAT AGT GAT CTG 3') and TH50 (5' ACC GTC TTC TTT ACG ATC AGT G 3') primers and plasmid pDAB2025 as template. This yielded a product of 1521 bp having an initiation codon at the beginning of the coding sequence of tcbA$_{ii}$. This PCR product was isolated in a 1% agarose gel and purified. The purified product was cloned into pCR2.1 as above and a correct clone was identified by DNA sequence analysis. This clone was digested with Nco I and Pin AI, a 1414 bp fragment was isolated in a 1% agarose gel and ligated into the Nco I and Pin AI sites of plasmid pDAB2030 and transformed into DHα E. coli. This new plasmid, designed to express TcbA$_{ii}$-A$_{iii}$ in E. coli, is called pDAB2032.

Expression of tcbA and tcbA$_{ii}$A$_{iii}$ from Plasmids pDAB2030, pDAB2031 and pDAB2032

Expression of tcbA in E. coli from plasmids pDAB2030, pDAB2031 and pDAB2032 was as described herein, except expression of tcbA$_{ii}$A$_{iii}$ was done in E. coli strain HMS174 (DE3)(Novagen, Madison, Wis.).

Expression of tcbA from Plasmid pDAB2033

The plasmid pDAB2033 was transformed into BL21 cells (Novagen, Madison, Wis.) and plated on LB containing 100 micrograms/mL ampicillin and 50 mM glucose. The plates were spread such that several hundred well separated colonies were present on each plate following incubation at either 30° C. or 37° C. overnight. The colonies were scraped from the plates and suspended in LB containing 100 micrograms/mL ampicillin, but no glucose. Typical culture volume was 250 mL in a single 1 L baffle bottom flask. The cultures were induced when the culture reached a density of 0.3–0.6 OD600 nm. Most often this density was achieved immediately after suspension of the cells from the plates and did not require a growth period in liquid media. Two induction methods were used. Method 1: cells were induced with 1 mM IPTG at 37° C. The cultures were shaken at 200 rpm on a platform shaker for 5 hours and harvested. Method 2: The cultures were induced with 25 micromolar IPTG at 30° C. and shaken at 200 rpm for 15 hours at either 20° C. or 30° C. The cultures were stored at 4° C. until used for purification.

Purification of TcbA from E. coli

Purification, bioassay and immunoblot analysis of TcbA and TcbA$_{ii}$A$_{iii}$ was as described herein. Results of several representative *E. coli* expression experiments are shown in Table 32. All materials shown in Table 32 were purified from the media fraction of the cultures. The predicted native molecular weight is approximately 900 kD as described herein. The purity of the samples, the amount of TcbA relative to contaminating proteins, varied with each preparation.

Protein mass analysis data are shown in Table 33. The data obtained from MALDI-TOF was compared to that hypothesized from gene sequence information and as previously determined by SDS-PAGE.

TABLE 32

Bioassay Activity and Immunoblot Analysis of TcbA and Derivatives Produced in *E. coli* and Purified from the Culture Media

| Plasmid | Coding Region | *E. coli* Strain | Southern Corn Rootworm Bioassay Activity | | Peptides Detected by Immunoblot | Micrograms Protein Applied to Diet |
|---|---|---|---|---|---|---|
| | | | % Growth Inhibit. | % Mortal. | | |
| pDAB2030 | tcbA | BL21 (DE3) | – | +++ | TcbA + TcbA$_{iii}$ | 1–8 |
| pDAB2031 | tcbA | BL21 (DE3) | – | +++ | TcbA + TcbA$_{iii}$ | 1–10 |
| pDAB2033 | tcbA | BL21 | – | +++ | TcbA + TcbA$_{iii}$ | 1–2 |
| pDAB2032 | tcbA$_{ii}$A$_{iii}$ | HMS174 (DE3) | +++ | + | TcbA$_{ii}$A$_{iii}$ + TcbA$_{iii}$ | 13–27 |

Scoring system for mortality and growth inhibition on Southern Corn Rootworm as compared to control samples; 5–24% = "+", 25–49% = "++", 50–100% = "+++".

EXAMPLE 20

Characterization of Toxin Peptides with Matrix-Assisted Laser Desorption Ionization Time-of-Flight Mass Spectroscopy Toxins isolated from W-14 broth were purified as described in Example 15. In some cases, the TcaB protein toxin was pretreated with proteases (Example 16) that had been isolated from W-14 broth as previously described (Example 15). Protein molecular mass was determined using matrix-assisted laser desorption ionization time-of-flight mass spectroscopy, hereinafter MALDI-TOF, on a VOYAGER BIOSPECTROMETRY workstation with DELAYED EXTRACTION technology (PerSeptive Biosystems, Framingham, Mass.). Typically, the protein of interest (100–500 pmoles in 5 μl) was mixed with 1 μl of acetonitrile and dialyzed for 0.5 to 1 h on a Millipore VS filter having a pore size of 0.025 μM (Millipore Corp. Bedford, Mass.). Dialysis was performed by floating the filter on water(shinny side up) followed by adding protein-acetonitrile mixture as a droplet to the surface of the filter. After dialysis, the dialyzed protein removed using a pipette and was then mixed with a matrix consisting of sinapinic acid and trifluoroacetic acid according to manufacturers instructions. The protein and matrix were allowed to co-crystallize on a about 3 cm$^2$ gold-plated sample plate (PerSeptive Corp.). Excitation of the crystals and subsequent mass analysis was performed using the following conditions: laser setting of 3050; pressure of 4.55e-07; low mass gate of 1500.0; negative ions off; accelerating voltage of 25,000; grid voltage of 90.0%; guide wire voltage of 0.010%; linear mode; and a pulse delay time of 350 ns.

TABLE 33

Molecular Analysis of Peptides by MALDI-TOF, SDS-PAGE and Predicted Determination Based on Gene Sequence

| Peptide | Predicted (Gene) | SDS PAGE | MALDI-TOF |
|---|---|---|---|
| TcbA | 280,634 Da | 240,000 Da | 281,040 Da |
| TcbA$_{i/ii}$ | 217,710 Da | not resolved | 216,812 Da |
| TcbA$_{ii}$ | 207,698 Da | 201,000 Da | 206,473 Da |
| TcbA$_{iii}$ | 62,943 Da | 58,000 Da | 63,520 Da |
| TcdA$_{ii}$ | 209,218 Da | 188,000 Da | 208,186 Da |
| TcdA$_{iii}$ | 63,520 Da | 56,000 Da | 63,544 Da |
| TcbA$_{ii}$ | Protease Generated | 201,000 Da | 216,614 Da^ |
| | | | 215,123 Da^ |
| | | | 210,391 Da^ |
| | | | 208,680 Da^ |
| TcbA$_{iii}$ | Protease Generated | 56,000 Da | 64,111 Da |

^Data normalized TcbA, multiple fragments observed at TcbAi/ii

EXAMPLE 21

Production of Peptide Specific Polyclonal Antibodies

Nine peptide components of the W-14 toxin complex, namely, TcaA, TcaA$_{iii}$, TcaB$_i$, TcaB$_{ii}$, TcaC, TcbA$_{ii}$, TcbA$_{iii}$, TcdA$_{ii}$, and TcdA$_{iii}$ were selected as targets against which antibodies were produced. Comprehensive DNA and deduced amino acid sequence data for these peptides indicated that the sequence homology between some of these peptides was substantial. If a whole peptide was used as the immunogen to induce antibody production, the resulting antibodies might bind to multiple peptides in the toxin preparation. To avoid this problem antibodies were generated that would bind specifically to a unique region of each peptide of interest. The unique region (subpeptide) of each target peptide was selected based on the analyses described below.

Each entire peptide sequence was analyzed using MacVector™ Protein Analysis Tool (IBI Sequence Analysis Software, International Biotechnologies, Inc:, P.O. Box 9558, New Haven, Conn. 06535) to determine its antigenicity index. This program was designed to locate possible externally-located amino acid sequences, i.e., regions that might be antigenic sites. This method combined information from hydrophilicity, surface probability, and backbone flexibility predictions along with the secondary structure predictions in order to produce a composite prediction of the surface contour of a protein. The scores for each of the analyses were normalized to a value between −1.0 and +1.0 (MacVector™ Manual). The antigenicity index value was obtained for the entire sequence of the target peptide. From each peptide, an area covering 19 or more amino acids that showed a high antigenicity index from the original sequence was re-analyzed to determine the antigenicity index of the subpeptide without the flanking residues. This re-analysis was necessary because the antigenicity index of a peptide could be influenced by the flanking amino acid residues. If the isolated subpeptide sequence did not maintain a high antigenicity index, a new region was chosen and the analysis was repeated.

Each selected subpeptide sequence was aligned and compared to all seven target peptide sequences using MacVector™ alignment program. If a selected subpeptide sequence showed identity (greater than 20%) to another target peptide, a new 19 or more amino acid region was isolated and re-analyzed. Unique subpeptide sequences covering 19 or more amino acid showing high antigenicity index were selected from all target peptides.

The sequences of seven subpeptides were sent to Genemed Biotechnology Inc. The last amino acid residue on each subpeptide was deleted because it showed no apparent effect on the antigenicity index. A cysteine residue was added to the N-terminal of each subpeptide sequence, except $TcaB_i$-syn which contains an internal cysteine residue. The present of a cysteine residue facilitates conjugation of a carrier protein (KLH). The final peptide products corresponding to the appropriate toxin peptides and SEQ ID NO.s are shown in Table 34.

TABLE 34

Amino Acid Sequences for Synthetic Peptides

| SEQ ID NO. | Pepide | Amino Acid Sequence |
|---|---|---|
| 63 | $TcaA_{ii}$-syn | NH2-(C)LRGNSPTNPDKDGIFAQVA |
| 64 | $TcaA_{iii}$-syn | NH2-(C)YTPDQTPSFYETAFRSADG |
| 65 | $TcaB_i$-syn | NH2-(C)HGQSYNDNNYCNFTLSINT |
| 66 | $TcaB_{iii}$-syn | NH2-(C)VDPKTLQRQQAGGDGTGSS |
| 67 | TcaC-syn | NH2-(C)YKAPQRQEDGDSNAVTYDK |
| 68 | $TcbA_{ii}$-syn | NH2-(C)YNENPSSEDKKWYFSSKDD |
| 69 | $TcbA_{iii}$-syn | NH2-(C)FDSYSQLYEENINAGEQRA |
| 70 | $TcdA_{ii}$-syn | NH2-(C)NPNNSSNKLMFYPVYQYSGNT |
| 71 | $TcdA_{iii}$-syn | NH2-(C)VSQGSGSAGSGNNNLAFGAG |

Each conjugated synthetic peptide was injected into two rabbits according to Genemed accelerated program. The pre- and post-immune sera were available for testing after one month.

The preliminary test of both pre- and post-immune sera from each rabbit was performed by Genemed Biotechnologies Inc. Genemed reported that by using both ELISA and Western blot techniques, they detected the reaction of post-immune sera to the respective synthetic peptides. Subsequently, the sera were tested with the whole target peptides, by Western blot analysis. Two batches of partially purified Photorhabdus strain W-14 toxin complex was used as the antigen. The two samples had shown activity against the Southern corn rootworm. Their peptide patterns on an SDS-PAGE gel were slightly different.

Pre-cast SDS-polyacrylamide gels with 4–20% gradient (Integrated Separation Systems, Natick, Mass. 01760) were used. Between 1 to 8 μg of protein was applied to each gel well. Electrophoresis was performed and the protein was electroblotted onto Hybond-ECL™ nitrocellulose membrane (Amersham International). The membrane was blocked with 10% milk, in TBST (25 mM Tris HCl pH 7.4, 136 mM NaCl, 2.7 mM KCl, 0.1% TWEEN 20 surfactant) for one hour at room temperature. Each rabbit serum was diluted in 10% milk/TBST to 1:500. Other dilutions between 1:50 to 1:1000 were also used. The serum was added to the membrane and placed on a platform rocker for at least one hour. The membrane was washed thoroughly with the blocking solution or TBST. A 1:2000 dilution of secondary antibodies (goat anti-mouse IgG conjugated to horse radish peroxidase; BioRad Laboratories) in 10% milk/TBST was applied to the membrane placed on a platform rocker for one hour. The membrane was subsequently washed with excess amount of TBST. The detection of the protein was performed by using an ECL (Enhanced Chemiluminescence) detection kit (Amersham International).

Western blot analyses were performed to identify binding specificity of each anti-synthetic peptide antibodies. All synthetic polyclonal antibodies showed specificity toward to processed and, when applicable, unprocessed target peptides from protein fractions derived from Photorhabdus culture broth. Various antibodies were shown to recognize either unprocessed or processed recombinant proteins derived from heterologous expression systems such as bacteria or insect cells, using baculovirus expression constructs. In one case, the anti-$TcbA_{iii}$-syn antibody showed some cross-reactivity to anti-$TcdA_{iii}$ peptide. In a second case, the anti-TcaC-syn antibody, recognized an unidentified 190 kDa peptide in W-14 toxin complex fractions.

EXAMPLE 22

Characterization of Photorhabdus Strains

In order to establish that the collection described herein was comprised of Photorhabdus strains, the strains herein were assessed in terms of recognized microbiological traits that are characteristic of the bacterial genus Photorhabdus and which differentiate it from other Enterobacteriaceae and Xenorhabdus spp. (Farmer, J. J. 1984. Bergey's Manual of Systemic Bacteriology, Vol 1. pp. 510–511. (ed. Kreig N. R. and Holt, J. G.). Williams & Wilkins, Baltimore.; Akhurst and Boemare, 1988, J. Gen. Microbiol. 134, 1835–1845; Forst and Nealson, 1996. Microbiol. Rev. 60, 21–43). These characteristic traits are as follows: Gram stain negative rods, organism size of 0.3–2 μm in width and 2–10 μm in length [with occasional filaments (15–50 μm) and spheroplasts], yellow to orange/red colony pigmentation on nutrient agar, presence of crystalline inclusion bodies, presence of catalase, inability to reduce nitrate, presence of bioluminescence, ability to take up dye from growth media, positive for protease production, growth at temperatures below 37° C., survival under anaerobic conditions and positively motile. (Table 33). Test methods were checked using reference *Escherichia coli*, Xenorhabdus and Photorhabdus strains. The overall results are consistent with all strains being part of the family Enterobacteriaceae and the genus Photorhabdus. Note that DEP1, DEP2, and DEP3 refer to Photorhabdus strains obtained from the American Type Culture Collection, 12301 Parklawn Drive, Rockville, Md. 20852 USA (#29304, 29999 and 51583, respectively).

A luminometer was used to establish the bioluminescence associated with these Photorhabdus strains. To measure the presence or absence of relative light emitting units, the broths from each strain (cells and media) were measured at three time intervals after inoculation in liquid culture (24, 48, 72 hr) and compared to background luminosity (uninoculated media). Several Xenorhabdus strains were tested as negative controls for luminosity. Prior to measuring light emission from the various broths, cell density was established by measuring light absorbance (560 nM) in a Gilford Systems (Oberlin, Ohio) spectrophotometer using a sipper cell. The resulting light emitting units could then be normalized to density of cells. Aliquots of the broths were placed into 96-well microtiter plates (100 µl each) and read in a Packard Lumicount™ luminometer (Packard Instrument Co., Meriden, Conn.). The measurement period for each sample was 0.1 to 1.0 second. The samples were agitated in the luminometer for 10 sec prior to taking readings. A positive test was determined as being about 5-fold background luminescence (about 1–15 relative light units). In addition, degree of colony luminosity was confirmed with photographic film overlays and by eye, after visual adaptation in a darkroom. The Gram's staining characteristics of each strain were established with a commercial Gram's stain kit (BBL, Cockeysville, Md.) used in conjunction with Gram's stain control slides (Fisher Scientific, Pittsburgh, Pa.). Microscopic evaluation was then performed using a Zeiss microscope (Carl Zeiss, Germany) 100×oil immersion objective lens (with 10×ocular and 2×body magnification). Microscopic examination of individual strains for organism size, cellular description and inclusion bodies (the latter two observations after logarithmic growth) was performed using wet mount slides (10×ocular, 2×body and 40×objective magnification) and phase contrast microscopy with a micrometer (Akhurst, R. J. and Boemare, N. E. 1990. *Entomopathogenic Nematodes in Biological Control* (ed. Gaugler, R. and Kaya, H.). pp. 75–90. CRC Press, Boca Raton, USA.; Baghdiguian S., Boyer-Giglio M. H., Thaler, J. O., Bonnot G., Boemare N. 1993. Biol. Cell 79, 177–185.). Colony pigmentation was observed after inoculation on Bacto nutrient agar, (Difco Laboratories, Detroit, Mich.) prepared as per label instructions. Incubation occurred at 28° C. and descriptions were produced after 5 days. To test for the presence of the enzyme catalase, a colony of the test organism was removed on a small plug from a nutrient agar plate and placed into the bottom of a glass test tube. One ml of a household hydrogen peroxide solution was gently added down the side of the tube. A positive reaction was recorded when bubbles of gas (presumptive oxygen) appeared immediately or within 5 seconds. Controls of uninoculated nutrient agar and hydrogen peroxide solution were also examined. To test for nitrate reduction, each culture was inoculated into 10 ml of Bacto Nitrate Broth (Difco Laboratories, Detroit, Mich.). After 24 hours incubation with gentle agitation at 28° C., nitrite production was tested by the addition of two drops of sulfanilic acid reagent and two drops of alpha-naphthylamine reagent (see Difco Manual, 10th edition, Difco Laboratories, Detroit, Mich., 1984). The generation of a distinct pink or red color indicates the formation of nitrite from nitrate whereas the lack of color formation indicates that the strain is nitrate reduction negative. In the latter case, finely powdered zinc was added to further confirm the presence of unreduced nitrate; established by the formation of nitrite and the resultant red color. The ability of each strain to uptake dye from growth media was tested with Bacto MacConkey agar containing the dye neutral red; Bacto Tergitol-7 agar containing the dye bromothymol blue and Bacto EMB Agar containing the dye eosin-Y (formulated agars from Difco Laboratories, Detroit, Mich., all prepared according to label instructions). After inoculation on these media, dye uptake was recorded after incubation at 28° C. for 5 days. Growth on these latter media is characteristic for members of the family Enterobacteriaceae. Motility of each strain was tested using a solution of Bacto Motility Test Medium (Difco Laboratories, Detroit, Mich.) prepared as per label instructions. A butt-stab inoculation was performed with each strain and motility was judged macroscopically by a diffuse zone of growth spreading from the line of inoculum. The production of protease was tested by observing hydrolysis of gelatin using Bacto gelatin (Difco Laboratories, Detroit, Mich.) made as per label instructions. Cultures were inoculated and the tubes or plates were incubated at 28° C. for 5 days. Gelatin hydrolysis was then checked at room temperature, i.e. less than 22° C. To assess growth at different temperatures, agar plates [2% proteose peptone #3 with two percent Bacto-Agar (Difco, Detroit, Mich.) in deionized water] were streaked from a common source of inoculum. Plates were incubated at 20, 28 and 37° C. for up to three weeks. The incubator temperature levels were checked with an electronic thermocouple and meter to insure valid temperature settings. Oxygen requirements for Photorhabdus strains were tested in the following manner. A butt-stab inoculation into fluid thioglycolate broth medium (Difco, Detroit, Mich.) was made. The tubes were incubated at room temperature for one week and cultures were then examined for type and extent of growth. The indicator resazurin demonstrates the presence of medium oxygenation or the aerobiosis zone (Difco Manual, 10th edition, Difco Laboratories, Detroit, Mich.). Growth zone results obtained for the Photorhabdus strains tested were consistent with those of a facultative anaerobic microorganism. In the case of unclear. results, the final agar concentration of fluid thioglycolate broth medium was raised to 0.75% and the growth characteristics rechecked.

TABLE 35

Taxonomic Traits of Photorhabdus Strains

| Strain | A* | B | C | D | E | F | G | H | I | J$ | K | L | M | N | O | P | Q |
|---|---|---|---|---|---|---|---|---|---|---|---|---|---|---|---|---|---|
| P. zealandica | −† | + | + | rd S | + | − | + | + | + | PO | + | + | + | + | + | + | − |
| P. hepialus | − | + | + | rd S | + | − | + | + | + | Y | + | + | + | + | + | + | − |
| HB-Arg | − | + | + | rd S | + | − | + | + | + | W | + | + | + | + | + | + | − |
| HB Oswego | − | + | + | rd S | + | − | + | + | + | W | + | + | + | + | + | + | − |
| HB Lewiston | − | + | + | rd S | + | − | + | + | + | T | + | + | + | + | + | + | − |
| K-122 | − | + | + | rd S | + | − | + | + | + | Y | + | + | + | + | + | + | − |
| HMGD | − | + | + | rd S | + | − | + | + | + | Rd | + | + | + | + | + | + | − |
| Indicus | − | + | + | rd S | + | − | + | + | + | W | + | + | + | + | + | + | − |

TABLE 35-continued

Taxonomic Traits of Photorhabdus Strains

| Strain | A* | B | C | D | E | F | G | H | I | J$ | K | L | M | N | O | P | Q |
|---|---|---|---|---|---|---|---|---|---|---|---|---|---|---|---|---|---|
| GD | − | + | + | rd S | + | − | + | + | + | YT | + | + | + | + | + | + | − |
| PWH-5 | − | + | + | rd S | + | − | + | + | + | Y | + | + | + | + | + | + | − |
| Megidis | − | + | + | rd S | + | − | + | + | + | R | + | + | + | + | + | + | − |
| HF-85 | − | + | + | rd S | + | − | + | + | + | R | + | + | + | + | + | + | − |
| A. Cows | − | + | + | rd S | + | − | + | + | + | PR | + | + | + | + | + | + | − |
| MP1 | − | + | + | rd S | + | − | + | + | + | T | + | + | + | + | + | + | − |
| MP2 | − | + | + | rd S | + | − | + | + | + | T | + | + | + | + | + | + | − |
| MP3 | − | + | + | rd S | + | − | + | + | + | R | + | + | + | + | + | + | − |
| MP4 | − | + | + | rd S | + | − | + | + | + | Y | + | + | + | + | + | + | − |
| MP5 | − | + | + | rd S | + | − | + | + | + | PR | + | + | + | + | + | + | − |
| GL98 | − | + | + | rd S | + | − | + | + | + | W | + | + | + | + | + | + | − |
| GL101 | − | + | + | rd S | + | − | + | + | + | W | + | + | + | + | + | + | − |
| GL138 | − | + | + | rd S | + | − | + | + | + | W | + | + | + | + | + | + | − |
| GL155 | − | + | + | rd S | + | − | + | + | + | W | + | + | + | + | + | + | − |
| GL217 | − | + | + | rd S | + | − | + | + | + | Y | + | + | + | + | + | + | − |
| GL257 | − | + | + | rd S | + | − | + | + | + | O | + | + | + | + | + | + | − |
| DEP1 | − | + | + | rd S | + | − | + | + | + | W | + | + | + | + | + | + | − |
| DEP2 | − | + | + | rd S | + | − | + | + | + | PR | + | + | + | + | + | + | − |
| DEP3 | − | + | + | rd S | + | − | + | + | + | CR | + | + | + | + | + | + | − |

*A = Gram's stain, B = Crystaline inclusion bodies, C = Bioluminescence, D = Cell form, E = Motility, F = Nitrate reduction, G = Presence of catalase, H = Gelatin hydrolysis, I = Dye uptake, J = Pigmentation on Nutrient Agar (some color shifts after Day 5), K = Growth on EMB agar, L = Growth on Mac-Conkey agar, M = Growth on Tergitol-7 agar, N = Facultative anaerobe, O = Growth at 20° C., P = Growth at 28° C., Q = Growth at 37° C.
†+ = positive for trait, − = negative for trait, rd = rod, S = sized within Genus descriptors.
$W = white, CR = cream, Y = yellow, YT = yellow tan, T = tan PO = pale orange, O = orange, PR = pale red, R = red.

The evolutionary diversity of the Photorhabdus strains in our collection was measured by analysis of PCR (Polymerase Chain Reaction) mediated genomic fingerprinting using genomic DNA from each strain. This technique is based on families of repetitive DNA sequences present throughout the genome of diverse bacterial species (reviewed by Versalovic, J., Schneider, M., D E. Bruijn, F. J. and Lupski, J. R. 1994. Methods Mol. Cell. Biol., 5, 25–40). Three of these, repetitive extragenic palindromic sequence (REP), enterobacterial repetitive intergenic consensus (ERIC) and the BOX element are thought to play an important role in the organization of the bacterial genome. Genomic organization is believed to be shaped by selection and the differential dispersion of these elements within the genome of closely related bacterial strains can be used to discriminate these strains (e.g., Louws, F. J., Fulbright, D. W., Stephens, C. T. and D E Bruijn, F. J. 1994. Appl. Environ. Micro. 60, 2286–2295). Rep-PCR utilizes oligonucleotide primers complementary to these repetitive sequences to amplify the variably sized DNA fragments lying between them. The resulting products are separated by electrophoresis to establish the DNA "fingerprint" for each strain.

To isolate genomic DNA from our strains, cell pellets were resuspended in TE buffer (10 mM Tris-HCl, 1 mM EDTA, pH 8.0) to a final volume of 10 ml and 12 ml of 5 M NaCl was then added. This mixture was centrifuged 20 min. at 15,000×g. The resulting pellet was resuspended in 5.7 ml of TE and 300 μl of 10% SDS and 60 μl 20 mg/ml proteinase K (Gibco BRL Products, Grand Island, N.Y.) were added. This mixture was incubated at 37° C. for 1 hr, approximately 10 mg of lysozyme was then added and the mixture was incubated for an additional 45 min. One milliliter of 5M NaCl and 800 μl of CTAB/NaCl solution (10% w/v CTAB, 0.7 M NaCl) were then added and the mixture was incubated 10 min. at 65° C., gently agitated, then incubated and agitated for an additional 20 min. to aid in clearing of the cellular material. An equal volume of chloroform/isoamyl alcohol solution (24:1, v/v) was added, mixed gently then centrifuged. Two extractions were then performed with an equal volume of phenol/chloroform/isoamyl alcohol (50:49:1). Genomic DNA was precipitated with 0.6 volume of isopropanol. Precipitated DNA was removed with a glass rod, washed twice with 70% ethanol, dried and dissolved in 2 ml of STE (10 mM Tris-HCl pH8.0, 10 mM NaCl, 1 mM EDTA). The DNA was then quantitated by optical density at 260 nm. To perform rep-PCR analysis of Photorhabdus genomic DNA the following primers were used, REP1R-I; 5'-IIIICGICGICATCIGGC-3' and REP2-I; 5'-ICGICTTATCIGGCCTAC-3'. PCR was performed using the following 25 μl reaction: 7.75 μl $H_2O$, 2.5 μl 10×LA buffer (PanVera Corp., Madison, Wis.), 16 μl dNTP mix (2.5 mM each), 1 μl of each primer at 50 pM/μl, 1 μl DMSO, 1.5 μl genomic DNA (concentrations ranged from 0.075–0.480 μg/μl) and 0.25 μl TaKaRa EX Taq (PanVera Corp., Madison, Wis.). The PCR amplification was performed in a Perkin Elmer DNA Thermal Cycler (Norwalk, Conn.) using the following conditions: 95° C./7 min. then 35 cycles of; 94° C./1 min.,44° C./1 min., 65° C./8 min., followed by 15 min. at 65° C. After cycling, the 25 μl reaction was added to 5 μl of 6×gel loading buffer (0.25% bromophenol blue, 40% w/v sucrose in $H_2O$). A 15×20 cm 1%-agarose gel was then run in TBE buffer (0.09 M Tris-borate, 0.002 M EDTA) using 8 μl of each reaction. The gel was run for approximately 16 hours at 45 v. Gels were then stained in 20 μg/ml ethidium bromide for 1 hour and destained in TBE buffer for approximately 3 hours. Polaroid® photographs of the gels were then taken under UV illumination.

The presence or absence of bands at specific sizes for each strain was scored from the photographs and entered as a similarity matrix in the numerical taxonomy software program, NTSYS-pc (Exeter Software, Setauket, N.Y.). Controls of E. coli strain HB101 and Xanthomonas oryzae pv. oryzae assayed under the same conditions produced PCR fingerprints corresponding to published reports (Versalovic, J., Koeuth, T. and Lupski, J. R. 1991. Nucleic Acids Res. 19, 6823–6831; Vera Cruz, C. M., Halda-Alija, L., Louws, F., Skinner, D. Z., George, M. L., Nelson, R. J., D E. Bruijn, F. J., Rice, C. and Leach, J. E. 1995. Int. Rice Res. Notes, 20, 23–24.; Vera Cruz, C. M., Ardales, E. Y., Skinner, D. Z., Talag, J., Nelson, R. J., Louws, F. J., Leung, H., Mew, T. W. and Leach, J. E. 1996. Phytopathology 86, 1352–1359). The data from Photorhabdus strains were then analyzed with a series of programs within NTSYS-pc; SIMQUAL (Similarity for Qualitative data) to generate a matrix of similarity coefficients (using the Jaccard coefficient) and SAHN (Sequential, Agglomerative, Heirarchical and Nested) clustering [using the UPGMA (Unweighted Pair-Group Method with Arithmetic Averages) method] which groups related strains and can be expressed as a phenogram (FIG. 7). The COPH (cophenetic values) and MXCOMP (matrix comparison) programs were used to generate a cophenetic value matrix and compare the correlation between this and the original matrix upon which the clustering was based. A resulting normalized Mantel statistic (r) was generated which is a measure of the goodness of fit for a cluster analysis (r=0.8–0.9 represents a very good fit). In our case r=0.924. Therefore, the collection is comprised of a diverse group of easily distinguishable strains representative of the Photorhabdus genus.

EXAMPLE 23

Insecticidal Utility of Toxin(s) Produced by Various Photorhabdus Strains

Initial "storage" cultures of the various Photorhabdus strains were produced by inoculating 175 ml of 2% Proteose Peptone #3 (PP3) (Difco Laboratories, Detroit, Mich.) liquid medium with a primary variant colony in a 500 ml tribaffled flask with a Delong neck, covered with a Kaput closure. After inoculation, the flask was incubated for between 24–72 hrs at 28° C. on a rotary shaker at 150 rpm, until stationary phase was reached. The culture was transferred to a sterile bottle containing a sterile magnetic stir bar and the culture was overlayered with sterile mineral oil, to limit exposure to air. The storage culture was kept in the dark, at room temperature. These cultures were then used as inoculum sources for the fermentation of each strain.

"Seed" flasks or cultures were produced by either inoculating 2 mls of an oil overlayered storage culture or by transferring a primary variant colony into 175 ml sterile medium in a 500 ml tribaffled flask covered with a Kaput closure. (The use of other inoculum sources is also possible.) Typically, following 16 hours incubation at 28° C. on a rotary shaker at 150 rpm, the seed culture was transferred into production flasks. Production flasks were usually inoculated by adding about 1% of the actively growing seed culture to sterile 2% PP3 medium (e.g. 2.0 ml per 175 ml sterile medium). Production of broths occurred in 500 ml tribaffled flasks covered with a Kaput. Production flasks were agitated at 28° C. on a rotary shaker at 150 rpm. Production fermentations were terminated after 24–72 hrs although successful fermentation is not confined to this time duration. Following appropriate incubation, the broths were dispensed into sterile 1.0 L polyethylene bottles, spun at 2600×g for 1 hr at 10° C. and decanted from the cell and debris pellet. Further broth clarification was achieved with a tangential flow microfiltration device (Pall Filtron, Northborough, Mass.) using a 0.5 $\mu$M open-channel polyether sulfone (PES) membrane filter. The resulting broths were then concentrated (up to 10-fold) using a 10,000 or 100,000 MW cut-off membrane, M12 ultra-filtration device (Amicon, Beverly Mass.) or centrifugal concentrators (Millipore, Bedford, Mass. and Pall Filtron, Northborough, Mass.) with a 10,000 or 100,000 MW pore size. In the case of centrifugal concentrators, the broth was spun at 2000×g for approximately 2 hr. The membrane permeate was added to the corresponding retentate to achieve the desired concentration of components greater than the pore size used. Following these procedures, the broth was used for biochemical analysis or filter sterilized using a 0.2 $\mu$M cellulose nitrate membrane filter for biological assessment. Heat inactivation of processed broth samples was achieved by heating the samples at 100° C. in a sand-filled heat block for 10 minutes.

The broth(s) and toxin complex(es) from different Photorhabdus strains are useful for reducing populations of insects and were used in a method of inhibiting an insect population which comprises applying to a locus of the insect an effective insect inactivating amount of the active described. A demonstration of the breadth of insecticidal activity observed from broths of a selected group of Photorhabdus strains fermented as described above is shown in Table 36. It is possible that improved or additional insecticidal activities could be detected with these strains through increased concentration of the broth or by employing different fermentation methods. Consistent with the activity being associated with a protein, the insecticidal activity of all strains tested was heat labile.

Culture broth(s) from diverse Photorhabdus strains show differential insecticidal activity (mortality and/or growth inhibition) against a number of insects. More specifically, the activity is seen against corn rootworm which is a member of the insect order Coleoptera. Other members of the Coleoptera include boll weevils, wireworms, pollen beetles, flea beetles, seed beetles and Colorado potato beetle. The broths and purified toxin complex(es) are also active against tobacco budworm, tobacco hornworm and European corn borer which are members of the order Lepidoptera. Other typical members of this order are beet armyworm, cabbage looper, black cutworm, corn earworm, codling moth, clothes moth, Indian mealmoth, leaf rollers, cabbage worm, cotton bollworm, bagworm, Eastern tent caterpillar, sod webworm and fall armyworm. Activity is also observed against German cockroach which is a member of the order Dictyoptera (or Blattodea). Other members of this order are oriental cockroach and American cockroach.

Activity against corn rootworm larvae was tested as follows. Photorhabdus culture broth(s) (10 fold concentrated, filter sterilized), 2% Proteose Peptone #3 (10 fold concentrated), purified toxin complex(es), 10 mM sodium phosphate buffer, pH 7.0 were applied directly to the surface (about 1.5 cm$^2$) of artificial diet (Rose, R. I. and McCabe, J. M. 1973. J. Econ. Entomol. 66, 398–400) in 40 $\mu$l aliquots. Toxin complex was diluted in 10 mM sodium phosphate buffer, pH 7.0. The diet plates were allowed to air-dry in a sterile flow-hood and the wells were infested with single, neonate Diabrotica undecimpunctata howardi (Southern corn rootworm, SCR) hatched from surface sterilized eggs. The plates were sealed, placed in a humidified growth chamber and maintained at 27° C. for the appropriate period (3–5 days). Mortality and larval weight determinations were then scored. Generally, 16 insects per treatment were used in all studies. Control mortality was generally less than 5%.

Activity against lepidopteran larvae was tested as follows. Concentrated (10-fold) Photorhabdus culture broth(s), control medium (2% Proteose Peptone #3), purified toxin complex(es), 10 mM sodium phosphate buffer, pH 7.0 were applied directly to the surface (about 1.5 cm$^2$) of standard artificial lepidopteran diet (Stoneville Yellow diet) in 40 µl aliquots. The diet plates were allowed to air-dry in a sterile flow-hood and each well was infested with a single, neonate larva. European corn borer (*Ostrinia nubilalis*) and tobacco hornworm (*Manduca sexta*) eggs were obtained from commercial sources and hatched in-house, whereas tobacco budworm (*Heliothis virescens*) larvae were supplied internally. Following infestation with larvae, the diet plates were sealed, placed in a humidified growth chamber and maintained in the dark at 27° C. for the appropriate period. Mortality and weight determinations were scored at day 5. Generally, 16 insects per treatment were used in all studies. Control mortality generally ranged from about 0 to about 12.5% for control medium and was less than 10% for phosphate buffer.

Activity against cockroach was tested as follows. Concentrated (10-fold) Photorhabdus culture broth(s) and control medium (2% Proteose Peptone #3) were applied directly to the surface (about 1.5 cm$^2$) of standard artificial lepidopteran diet (Stoneville Yellow diet) in 40 µl aliquots. The diet plates were allowed to air-dry in a sterile flow-hood and each well was infested with a single, $CO_2$ anesthetized first instar German cockroach (*Blatella germanica*). Following infestation, the diet plates were sealed, placed in a humidified growth chamber and maintained in the dark at 27° C. for the appropriate period. Mortality and weight determinations were scored at day 5. Control mortality less than 10%.

TABLE 36

Observed Insecticidal Spectrum of Broths from Different Photorhabdus Strains

| Photorhabdus Strain | Sensitive* Insect Species |
|---|---|
| P. zealandica | 1**, 2, 4 |
| P. hepialus | 1, 2, 4 |
| HB-Arg | 1, 2, 4 |
| HB Oswego | 1, 2, 4 |
| HB Lewiston | 1, 2, 4 |
| K-122 | 1, 4 |
| HMGD | 1, 4 |
| Indicus | 1, 2, 4 |
| GD | 2, 4 |
| PWH-5 | 1, 2, 4 |
| Megidis | 1, 2, 4 |
| HF-85 | 1, 2, 4 |
| A. Cows | 1, 4 |
| MP1 | 1, 2, 4 |
| MP2 | 1, 2, 4 |
| MP3 | 4 |
| MP4 | 1, 4 |
| MP5 | 4 |
| GL98 | 1, 4 |
| GL101 | 1, 4, 5 |
| GL138 | 1, 2, 4 |
| GL155 | 1, 4 |
| GL217 | 1, 2, 4 |
| GL257 | 1, 4 |
| DEP1 | 1, 4 |
| DEP2 | 1, 2, 3, 4 |
| DEP3 | 4 |

*= $^3$25% mortality and/or growth inhibition vs. control
**= 1; Tobacco budworm, 2; European corn borer, 3; Tobacco hornworm, 4; Southern corn rootworm, 5; German cockroach.

EXAMPLE 24

Southern Analysis of Non-W-14 Photorhabdus Strains Using W-14 Gene Probes

Photorhabdus strains were grown on 2% proteose peptone #3 agar (Difco Laboratories, Detroit, Mich.) and insecticidal toxin competence was maintained by repeated bioassay after passage. A 50 ml shake culture was produced in 175 ml baffled flasks in 2% proteose peptone #3 medium, grown at 28° and 150 rpm for approximately 24 hours. Fifteen ml of this culture were centrifuged (700×g, 30 min) and frozen in its medium at −20° until it was thawed (slowly in ice water) for DNA isolation. The thawed W-14 culture was centrifuged (900×g, 15 min 4°), and the floating orange mucopolysaccharide material was removed. The remaining cell material was centrifuged (25,000×g, 4°) to pellet the bacterial cells, and the medium was removed and discarded.

Total DNA was isolated by an adaptation of the CTAB method described in section 2.4.1 of Ausubel et al. (1994). The modifications included a high salt shock, and all volumes were increased ten-fold over the "miniprep" recommended volumes. All centrifugations were at 4° C. unless otherwise specified. The pelleted bacterial cells were resuspended in TE buffer (10 mM Tris-HCl, 1 mM EDTA, pH 8) to a final volume of 10 ml, then 12 ml 5 M NaCl were added; this mixture was centrifuged 20 min at 15,000×g. The pellet was resuspended in 5.7 ml TE, and 300 µl of 10% SDS and 60 µl of 20 mg/ml proteinase K (in sterile distilled water, Gibco BRL Products, Grand Island, N.Y.) were added to the suspension. The mixture was incubated at 37° C. for 1 hr; then approximately 10 mg lysozyme (Worthington Biochemical Corp., Freehold, N.J.) were added. After an additional 45 min incubation, 1 ml of 5 M NaCl and 800 Al of CTAB/NaCl solution (10% w/v CTAB, 0.7 M NaCl) were added. This preparation was incubated 10 min at 65° C., then gently agitated and further incubated and agitated for approximately 20 min to assist clearing of the cellular material. An equal volume of chloroform/isoamyl alcohol solution (24:1, v:v) was added, mixed very gently, and the phases separated by centrifugation at 12,000×g for 15 min. The upper (aqueous) phase was gently removed with a wide-bore pipette and extracted twice as above with an equal volume of PCI (phenol/choloroform/isoamyl alcohol; 50:49:1, v:v:v; equilibrated with 1M Tris-HCl, pH 8.0; Intermountain Scientific Corporation, Kaysville, Utah). The DNA precipitated with 0.6 volume of isopropanol was gently removed on a glass rod, washed twice with 70% ethanol, dried, and dissolved in 2 ml STE (10 mM Tris-HCl, 10 mM NaCl, 1 mM EDTA, pH 8). This preparation contained 2.5 mg/ml DNA, as determined by optical density at 260 nm.

Identification of Bgl II/Hind III Fragments Hybridizing to tc-gene Specific Probes Approximately 10 µg of genomic DNA was digested to completion with about 30 units each of Bgl II and Hind III (NEB) for 180 min, frozen overnight, then heated at 65° C. for five min, and electrophoresed in a 0.8% agarose gel (Seakem® LE, 1×TEA, 80 volts, 90 min). The DNA was stained with ethidium bromide (50 µg/ml) as described earlier, and photographed under ultraviolet light. The DNA fragments in the agarose gel were subjected to depurination (5 min in 0.2 M HCl), denaturation (15 min in 0.5 M NaOH, 1.5 M NaCl), and neutralization (15 min in 0.5 M Tris HCl pH 8.0, 1.5 M NaCl), with 3 rinses of distilled water between each step. The DNA was transferred by Southern blotting from the gel onto a NYTRAN nylon membrane (Amersham, Arlington Heights, Ill.) using a high salt (20×SSC) protocol, as described in section 2.9 of Ausubel et al. (CPMB, op. cit.). The transferred DNA was then UV-crosslinked to the nylon membrane using a Stratagene UV Stratalinker set on auto crosslink. The membranes were stored dry at 25° C. until use.

Hybidization was performed using the ECL™direct (Amersham, Arlington Heights, Ill.) labeling and detection system following protocols provided by the manufacturer. In brief, probes were prepared by covalently linking the denatured DNA to the enzyme horseradish peroxidase. Once labeled the probe was used under hybridization conditions which maintain the enzymatic activity. Unhybridized probe was removed by two gentle washes 20 minutes each at 42° C. in 0.5×SSC, 0.4% SDS, and 6M Urea. This was followed by two washes 5 minutes each at room temperature in 2×SSC. As directed by the manufacturer, ECL™ reagents were used to detect the hybridizing DNA bands. There are several factors which influence the ability to detect gene relatedness between various Photorhabdus strains and strain W-14. First, high stringency conditions have not been employed in these hybridizations. It is known in the art that varying the stringency of hybridization and wash conditions will influence the pattern and intensity of hybridizing bands. Second, Southern blots' blot to blot variation will influence the mobility of hybridizing bands and molecular weight estamates. Therefore, W-14 was included as a standard on all Southern blots.

Gene specific probes derived from the W-14 toxin genes were used in these hybridizations. The following lists the specific coordinates within each gene sequence to which the probe corresponds. A probe specific for tcaB$_i$/B$_{ii}$: 1174 to 3642 of Sequence ID #25, a probe specific for tcaC: 3637 to 6005 of Sequence ID #25, a probe specific for tcbA: 2097 to 4964 of Sequence ID #11, and a probe specific for tcda: 1660 to 4191 of sequence ID #46. The following tables summarize Southern Blot analyses of Photorhabdus strains. In the event that hybridization of probes occurred, the hybridized fragment(s) were noted as either identical or different from the pattern observed for the W-14 strain.

TABLE 37

Southern Analysis of Photorhabdus Strains

| Strains | tcdA | tcbA | tcaC | tcaB$_{i/ii}$ |
|---|---|---|---|---|
| WX-1 | D | D | D | D |
| WX-2 | D | D | – | D |
| WX-3 | D | D | D | D |
| WX-4 | D | D | ND | D |
| WX-5 | D | D | D | D |
| WX-6 | D | D | D | D |
| WX-7 | D | D | ND | D |
| WX-8 | D | D | D | D |
| WX-9 | ND | D | D | D |
| WX-10 | ND | D | D | D |
| WX-11 | ND | D | D | D |
| WX-12 | D | D | D | D |
| WX-14 | D | D | D | D |
| WX-15 | D | D | D | D |
| HP88 | D | – | D | D |
| Hm | D | – | D | D |
| Hb | D | – | D | – |
| H9 | D | – | I | D |
| B2 | D | – | D | – |
| NC-1 | D | – | D | D |
| WIR | D | – | D | D |
| W30 | D | D | D | D |
| W-14 | I | I | I | I |

ND = Not determined; – = no detectable hybridization product; I = Identical fragment pattern; D = Different fragment pattern.

TABLE 38

Southern Analysis of Photorhabdus Strains

| Strains | tcdA | tcbA | tcaC | tcaB$_{i/ii}$ |
|---|---|---|---|---|
| K-122 | 3.3, 2.8 | D | – | ND |
| PWH-5 | + | D | D | – |
| Indicus | D | D | 3.0 | I |
| Megidis | D | D | D | – |
| GD | D | D | D | – |
| HF-85 | D | D | D | – |
| MP 3 | D | – | D | – |
| MP 1 | D | + | D | – |
| A. Cows | D | + | D | – |
| HB-Arg | D | ND | D | – |
| HMGD | D | D | D | – |
| HB Lewiston | D | D | D | – |
| HB Oswego | D | D | D | – |
| W-14 | I | I | I | I |

ND = Not determined; – = no detectable hybridization product; I = Identical fragment pattern; D = Different fragment pattern.
+ = Hybridization fragment pattern not determined.

TABLE 39

Southern Analysis of Photorhabdus Strains

| Strains | tcdA | tcbA | tcaC | tcaB$_{i/ii}$ |
|---|---|---|---|---|
| GL98 | + | + | D | |
| GL101 | – | + | D | |
| GL138 | – | + | D | |
| GL155 | – | – | – | |
| GL217 | + | – | D | |
| GL257 | + | + | D | |
| MP4 | – | + | – | |
| MP5 | – | – | – | |
| P. hepialus | + | – | D | |
| P. zealandia | + | – | 11.0 | |
| DEP1 | | | | |
| DEP2 | | | | |
| DEP3 | | | | |
| W-14 | 3.8, 2.8 | 2.8 | 2.8 | |

ND = Not determined; – = no detectable hybridization product; I = Identical fragment pattern; D = Different fragment pattern.
+ = Hybridization fragment pattern not determined.

From these analyses it is apparent that homologs of W-14 genes are dispersed throughout these diverse Photorhabdus strains, as evidenced by differences in gene fragment sizes between W-14 and the other strains.

EXAMPLE 25

N-Terminal Amino Acid Sequences of Toxin Complex Peptides from Different Photorhabdus Strains The relationship of peptides isolated from different Photorhabdus strains, as described in Example 14, were subjected to N-terminal amino acid sequencing. The N-terminal amino acid sequences of toxin peptides in several strains were compared to W-14 toxin peptides. In Table 40, a comparison of toxin peptides compared to date showed that identical or homologous (at least 40% similarity to W14 gene/peptides) toxin peptides were present in all of the strains. For example, the N-terminal amino acid sequence of TcaC, SEQ ID NO: 2, was found to be identical to that for 160 kDa peptide in HP88 but also homologs were present in strains WIR, H9, Hb, WX-1, and Hm. Some W-14 peptides or homologs have not been observed in other strains; however, not all peptides have been sequenced for toxin complexes from other strains due to N-terminal blockage or low abundance. In addition, many other N-terminal amino acid sequences (SEQ ID NOS: 82 to 88) have been obtained for toxin complex peptides from other strains that have no similarity to peptides from W-14 and in some case were identical to each other. For example, an identical amino acid sequence, SEQ ID NO: 82, was obtained for 64 kDa peptide present in both HP88 and Hb strains and a homologous sequence for a 70 kDa peptide in NC-1 strain (SEQ ID NO: 83).

TABLE 40

A Comparison of Amino Terminal Sequence Homology Between Proteins Isolated From Non-W-14 Strains

| W-14 Peptide | W-14 Gene | W-14 SEQ ID | SEQ ID NO: | Strain | Identical | Homology |
|---|---|---|---|---|---|---|
| TcaAii | tcaA | 15 | | | | |
| TcaAiii | tcaA | 4 | | | | |
| TcaBi | tcaB | 3 | 76 | H9 | — | 74 kDa |
| | | | 76 | Hm | — | 71 kDa |
| TcaBii | tcaB | 5 | | H9 | 61 kDa | — |
| | | | | Hm | 61 kDa | — |
| TcaC | tcaA | 2 | 72 | Hb | — | 160 kDa |
| | | | | HP88 | 160 kDa | — |
| | | | 73 | WIR | — | 170 kDa |
| | | | 74 | H9 | — | 180 kDa |
| | | | 75 | Hm | — | 170 kDa |
| | | | 80 | WX-1 | — | 170 kDa |
| TcbAii | tcbA | 1 | | | | |
| TcbAiii | tcbA | 40 | | | | |
| TccA | tccA | 8 | 77 | Hb | — | 81 kDa |
| TccB | tccB | 7 | | WX-1 | 170 kDa | — |
| | | | | WX-2 | 180 kDa | — |
| | | | | WX-14 | 180 kDa | — |
| | | | | WIR | 170 kDa | — |
| | | | 78 | H9 | — | 170 kDa |
| | | | | NC-1 | 140 kDa | — |
| | | | 79 | Hm | — | 190 kDa |
| TcdAii | tcdA | | | | | |
| TcdAiii | tcdA | 41 | | Hb | 57 kDa | — |
| | | | 81 | H9 | — | 69 kDa |
| ? | ? | 9 | | Hb | 86 kDa | — |
| | | | | HP88 | 86 kDa | — |

Homology refers to amino acid sequences that were at least 40% similarity to W14 gene/peptides. Similar residues were identified as being a member in one of the following five groups: (P, A, G, S, T); (Q, N, E, B, D, Z); (H, K, R); (L, I, V, M); and (F, Y, W).

EXAMPLE 26

Immunological Analysis of Photorhabdus Strains

Culture broths of Photorhabdus strains were concentrated 10 to 15 times using Centriprep-10 ultrafiltration device (amicon, Inc. Beverly, Mass. 01915). The concentration of the protein ranges from 0.3 to 3.0 mg per ml. Ten to 20 μg of total protein was loaded in each well of a precast 4–20% polyacrylamide gel (Integrated Separation Systems, Natick, Mass. 01760). Gel electrophoresis was performed for 1.25 hours using a constant current set at 25 ma per gel. The gel was electro-blotted on to Hybond-ECL™ nitrocellulose membrane (Amersham Corporation, Arlington Hts, Ill. 60005) using a semi-dry electro-blotter (Pharmacia Biotech Inc., Piscataway , N.J. 08854). A constant current was applied at 0.75 ma per cm for 2.5 hours. The membrane was blocked with 10% milk in TBST (25 mM Tris HCl pH 7.4, 136 mM NaCl, 2.7 mM KCl, 0.1% Tween 20) for one hour at room temperature. Each primary antibody was diluted in 10% milk/TBST to 1:500. Other dilution between 1:50 to 1:1000 was also used. The membrane was incubated in primary antibody for at least one hour. Then it was washed thoroughly with the blocking solution or TBST. A 1:2000 dilution of secondary antibodies (goat anti-mouse IgG or goat anti rabbit TgG conjugated to horseradish peroxidase; BioRad Laboratories, Hercules, Calif. 94547) in 10% milk/TBST was applied to the membrane which was placed on a platform rocker for one hour. The membrane was subsequently washed with excess amount of TBST. The detection of the protein was performed by using an ECL (Enhanced Chemiluminescence) detection kit (Amersham International).

A panel of peptide specific-antibodies generated against W-14 peptides were used to characterize the protein composition of broths from nine non-W-14 Photorhabdus strains using Western blot analysis. In addition, one monoclonal antibody (MAb-C5F2) which recognizes $TcbA_{iii}$ protein in W-14-derived toxin complex was used. The results (Table 39) showed cross recognition of the antibodies to some of the proteins in these broths. In some cases, the proteins that were recognized by the antibodies were the same size as the W-14 target peptides. In other cases, the proteins that were recognized by the antibodies were smaller than the W-14 target peptides. This data indicate that some of the non-W-14 Photorhabdus strains may produce similar proteins to the W-14 strain. The difference could be due to deletion or protein processing or degradation process. Some of the strains did not contain protein(s) that could be recognized by some antibodies, however, it is possible that the concentration is significantly lower than those observed for W-14 peptides. When compared for various toxin peptide homologs these results showed peptide diversity among the Photorhabdus strains.

TABLE 41

Cross Recognition by Monoclonal Antibodies or Polyclonal Antibodies Generated Against W-14 Peptides to Protein(s) in Broths of Selected Non-W-14 Photorhabdus

| Photorhabdus Strain | MAb C5F2 | PAb TcdAii-syn | PAb TcdAiii-syn | TcaC-syn | PAb-TcaBii-syn | PAb TcbAiii-syn | PAb TcaBi-syn | PAb TcaAii-syn | PAb TcaAiii-syn |
|---|---|---|---|---|---|---|---|---|---|
| MP1 | − | + | + | + | − | + | + | + | + |
| MP2 | + | + | + | + | − | + | + | + | + |
| MP3 | − | + | + | + | − | NT | + | + | − |
| A. Cows | − | + | + | + | − | NT | + | + | + |
| Hb-osw | − | − | NT | + | + | NT | + | + | + |
| H-Arg | − | + | + | + | − | NT | + | + | + |
| Hb-leu | − | + | + | + | − | NT | + | + | + |
| Indicus | + | + | + | + | + | NT | + | + | + |
| HF85 | − | + | + | + | − | + | + | + | + |

TABLE 41-continued Cross Recognition by Monoclonal Antibodies or Polyclonal Antibodies
Generated Against W–14 Peptides to Protein(s) in Broths of Selected Non-W–14 Photorhabdus

| Photo-rhabdus Strain | MAb C5F2 | PAb TcdAii-syn | PAb TcdAiii-syn | TcaC-syn | PAb-TcaBii-syn | PAb TcbAiii-syn | PAb TcaBi-syn | PAb TcaAii-syn | PAb TcaAiii-syn |
|---|---|---|---|---|---|---|---|---|---|
| W-14 | + | + | + | + | + | + | + | + | + |

+: Positive reaction; –: Negative reaction; NT: Not Tested

Additional non-W-14 Photorhabdus strains were characterized by Western blot analysis using the culture broth and/or partial purified protein fractions as antigen. The panel of antibodies include MAb-C5F2, MAb-DE1 (recognizing TcdA$_{ii}$), Pab-DE2 (recognizing TcaB), Pab-TcbA$_{ii}$-syn, Pab-TcaC-syn, Pab TcaB$_{ii}$-syn, Pab-TcbA$_{iii}$-syn, Pab-TcaB$_{i}$-syn. These antibodies showed cross-reactivity with proteins in the broth and in the partial purified fractions of non-W-14 strains.

The data indicate that antibodies could be used to identify proteins in the broth as well as in the partially purified protein fractions.

The first primer set was used to modify the 5' end of the gene, to insert a unique Nco I site at the initiator codon using the forward primer A0F1 (5' GAT CGA TCG ATC CAT GGC CAA CGA GTC TGT AAA AGA GAT ACC TGA TG TAT TAA AAA GCC AGT GTG 3') and to add unique Bgl II, Sal I and Not I sites to facilitate insertion of the remainder of the gene using the reverse primer A0R1 (5' GAT CGA TCG TAC GCG GCC GCT CGA TCG ATC GTC GAC CCA TTG ATT TGA GAT CTG GGC GGC GGG TAT CCA GAT AAT AAA CGG AGT CAC 3').

Another PCR reaction was designed to modify the 3' end of the gene by adding an additional stop codon and convenient restriction sites for cloning. The forward primer A0F2

TABLE 42

Cross Recognition by Monoclonal Antibodies or Plyclonal Antibodies
Generated Against W-14 Peptides to Protein(s) in Broths and/or
Partial Purified Protein Fractions of Selected Non-W14 Photorhabdus

| Photo-rhabdus Strain | Monoclonal Antibodies | | | Polyclonal Antibodies | | | | |
|---|---|---|---|---|---|---|---|---|
| | Mab C5F2 | Mab-DE1 | PAb-DE2 | TcbA$_{ii}$-syn | TcaC-syn | TcaB$_{ii}$-syn | TcbA$_{iii}$-syn | TcaB$_{i}$-syn |
| WX-1 | + | + | + | + | + | + | + | + |
| WX-2 | + | + | + | + | + | + | NT | + |
| WX-3 | + | NT | + | NT | NT | NT | NT | NT |
| WX-5 | + | NT | + | NT | NT | NT | NT | NT |
| WX-6 | + | NT | NT | NT | NT | NT | NT | NT |
| WX-7 | + | + | + | + | + | + | NT | + |
| WX-8 | + | NT | NT | NT | NT | NT | NT | NT |
| WX-9 | + | NT | NT | NT | NT | NT | NT | NT |
| WX-10 | + | NT | NT | NT | NT | NT | NT | NT |
| WX-12 | + | + | + | + | + | + | + | + |
| WX-14 | + | + | + | + | NT | + | NT | + |
| WX-15 | + | NT | NT | NT | NT | NT | NT | NT |
| W30 | + | + | + | NT | NT | NT | NT | NT |
| Hb | – | NT | + | NT | + | NT | – | + |
| H9 | – | – | + | NT | + | + | NT | NT |
| Hm | – | NT | + | + | + | + | NT | ++ |
| HP88 | – | NT | + | – | + | – | – | + |
| NC-1 | + | – | + | + | + | + | NT | + |
| WIR | – | NT | + | + | + | + | + | + |
| W-14 | + | + | + | + | + | + | + | + |

–: Negative reaction; +: Positive reaction; NT: Not tested

EXAMPLE 27

Bacterial Expression of the tcdA Coding Region
Engineering of the tcdA Gene for Bacterial Expression The 5' and 3' ends of the tcdA coding region (SEQ ID NO:46) were modified to add useful cloning sites for inserting the segment into heterologous expression vectors. The ends were modified using unique primers in Polymerase Chain Reactions (PCR), performed essentially as described in Example 8. Primer sets, as described below, were used in conjunction with cosmid 21D2.4 as template, to created products with the appropriately modified ends.

(5' ACT GGC TGC GTG GTC GAC TGG CGG CGA TTT ACT 3') was used to amplify across a unique Sal I site in the gene, later used to clone the modified 3' end. The reverse primer A0R2 (5' CGA TGC ATG CTG CGG CCG CAG GCC TTC CTC GAG TCA TTA TTT AAT GGT GTA GCG AAT ATG CAA AAT 3') was used to insert a second stop codon (TGA) and cloning sites Xho I, Stu I and Not I. Bacterial expression vector pET27b (Novagen, Madison, Wis.), was modified to delete the Bgl II site at position 446, according to standard molecular biology techniques.

The 497 bp PCR product from the first amplification reaction (A0F1+A0R1), to modify the 5' end of the gene, was ligated to the modified pET27b vector according to the supplier's instructions. The DNA sequences of the amplified portion of three isolates were determined using the supplier's recommended primers and the sequencing methods described previously. The sequence of all isolates was the same.

One isolate was then used as a cloning vector to insert the middle portion of the tcdA gene on a 6341 bp Bgl II to Sal I fragment. The resulting clone was called MC4 and contained all but the 3' most portion of the tcdA coding sequence. Finally, to complete the full-length coding region, the 832 bp PCR product from the second PCR amplification (AOF2+AOR2), to modify the 3' end of the gene, was ligated to isolate MC4 on a Sal I to Not I fragment, according to standard molecular biology techniques. The tcda coding region was sequenced and found to be complete, the resulting plasmid is called pDAB2035.

Construction of Plasmids pDAB2036, pDAB2037 and pDAB2038 for Bacterial Expression of tcdA The tcdA coding region was cut from plasmid pDAB2035 with restriction enzymes Nco I and Xho I and gel purified. The fragment was ligated into the Nco I and Xho I sites of the expression vector pET15 to create plasmid pDAB2036. Additionally, pDAB2035 was cut with Nco I and Not I to release the tcdA coding region which was ligated into the Nco I and Not I sites of the expression vector pET28b to create plasmid pDAB2037. Finally, plasmid pDAB2035 was cut with Nco I and Stu I to release the tcdA coding region. This fragment was ligated into the expression vector Trc99a which was cut with Hind III followed by treatment with T4 DNA polymerase to blunt the ends. The vector was then cut with Nco I and ligated with the Nco I/Stu I cut tcdA fragment. The resulting plasmid is called pDAB2038.

Expression of tcdA from Plasmid pDAB2038

Plasmid pDAB2038 was transformed into BL21 cells and expressed as described above for plasmid pDAB2033 in Example 19.

Purification of tcdA from *E. coli*

The expression culture was centrifuged at 10,300 g for 30 min and the supernatant was collected. It was diluted with two volumes of $H_2O$ and applied at a flow rate of 7.5 ml/min to a poros 50 HQ (Perspective Systems, Mass.) column (1.6 cm×10 cm) which was pre-equilibrated with 10 mM sodium phosphate buffer, pH 7.0 (Buffer A). The column was washed with Buffer A until the optical density at 280 nm returned to baseline level. The proteins bound to the column were then eluted with 1M NaCl in Buffer A.

The fraction was loaded in 20 ml aliquots onto a gel filtration column, Sepharose CL-4B (2.6×100 cm), which was equilibrated with Buffer A. The protein was eluted in Buffer A at a flow rate of 0.75 mL/min. Fractions with a retention time between 260 minutes and 460 minutes were pooled and applied at 1 mL/min to a Mono Q 5/5 column which was equilibrated with 20 mM Tris-HCl, pH 7.0 (Buffer B). The column was washed with Buffer B until the optical density at 280 nm returned to baseline level. The proteins bound to the column were eluted with a linear gradient of 0 to 1 M NaCl in Buffer B at 1 mL/min for 30 min. One milliliter fractions were collected, serial diluted, and subjected to SCR bioassay. Fractions eluted out between 0.1 and 0.3 M NaCl were found to have the highest insecticidal activity. Western analysis of the active fractions using pAb $TcdA_{ii}$-syn antibody and pAb $Tcd_{iii}$-syn antibody indicated the presence of peptides $TcdA_{ii}$ and $TcdA_{iii}$.

SEQUENCE LISTING

```
(1) GENERAL INFORMATION:

(iii) NUMBER OF SEQUENCES:  88

(2) INFORMATION FOR SEQ ID NO:1:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: protein (v) FRAGMENT TYPE: N-terminal (xi) SEQUENCE DESCRIPTION: SEQ ID NO:1:

Phe Ile Gln Gly Tyr Ser Asp Leu Phe Gly Asn
1               5                   10

(2) INFORMATION FOR SEQ ID NO:2:

(i) SEQUENCE CHARACTERISTICS:
          (A) LENGTH: 12 amino acids
          (B) TYPE: amino acid
          (C) STRANDEDNESS:
          (D) TOPOLOGY: linear (ii) MOLECULE TYPE: protein (v) FRAGMENT TYPE: N-terminal
```

(xi) SEQUENCE DESCRIPTION: SEQ ID NO:2:

Met Gln Asp Ser Pro Glu Val Ser Ile Thr Thr Trp
1               5                   10

(2) INFORMATION FOR SEQ ID NO:3:

(i) SEQUENCE CHARACTERISTICS:
            (A) LENGTH: 19 amino acids
            (B) TYPE: amino acid
            (C) STRANDEDNESS:
            (D) TOPOLOGY: linear (ii) MOLECULE TYPE: protein (v) FRAGMENT TYPE: N-terminal (xi) SEQUENCE DESCRIPTION: SEQ ID NO:3:

Ser Glu Ser Leu Phe Thr Gln Thr Leu Lys Glu Ala Arg Arg Asp Ala
1               5                   10                  15

Leu Val Ala (2) INFORMATION FOR SEQ ID NO:4:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: protein (v) FRAGMENT TYPE: N-terminal (xi) SEQUENCE DESCRIPTION: SEQ ID NO:4:

Ala Ser Pro Leu Ser Thr Ser Glu Leu Thr Ser Lys Leu Asn
1               5                   10

(2) INFORMATION FOR SEQ ID NO:5:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: protein (v) FRAGMENT TYPE: N-terminal (xi) SEQUENCE DESCRIPTION: SEQ ID NO:5:

Ala Gly Asp Thr Ala Asn Ile Gly Asp
1               5

(2) INFORMATION FOR SEQ ID NO:6:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (v) FRAGMENT TYPE: N-terminal (xi) SEQUENCE DESCRIPTION: SEQ ID NO:6:

Leu Gly Gly Ala Ala Thr Leu Leu Asp Leu Leu Leu Pro Gln Ile
1               5                   10                  15

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO:7:

```
Met Leu Ser Thr Met Glu Lys Gln Leu Asn Glu
1               5                   10
```

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO:8:

```
Met Asn Leu Ala Ser Pro Leu Ile Ser
1               5
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO:9:

```
Met Ile Asn Leu Asp Ile Asn Glu Gln Asn Lys Ile Met Val Val Ser
1               5                   10                  15
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO:10:

```
Ala Ala Lys Asp Val Lys Phe Gly Ser Asp Ala Arg Val Lys Met Leu
1               5                   10                  15
Arg Gly Val Asn
                20
```

(2) INFORMATION FOR SEQ ID NO:11:

-continued

```
    (i) SEQUENCE CHARACTERISTICS:
        (A) LENGTH: 7515 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..7515

(xi) SEQUENCE DESCRIPTION: SEQ ID NO:11:

ATG CAA AAC TCA TTA TCA AGC ACT ATC GAT ACT ATT TGT CAG AAA CTG        48
Met Gln Asn Ser Leu Ser Ser Thr Ile Asp Thr Ile Cys Gln Lys Leu
1               5                   10                  15

CAA TTA ACT TGT CCG GCG GAA ATT GCT TTG TAT CCC TTT GAT ACT TTC        96
Gln Leu Thr Cys Pro Ala Glu Ile Ala Leu Tyr Pro Phe Asp Thr Phe
                20                  25                  30

CGG GAA AAA ACT CGG GGA ATG GTT AAT TGG GGG GAA GCA AAA CGG ATT       144
Arg Glu Lys Thr Arg Gly Met Val Asn Trp Gly Glu Ala Lys Arg Ile
            35                  40                  45

TAT GAA ATT GCA CAA GCG GAA CAG GAT AGA AAC CTA CTT CAT GAA AAA       192
Tyr Glu Ile Ala Gln Ala Glu Gln Asp Arg Asn Leu Leu His Glu Lys
        50                  55                  60

CGT ATT TTT GCC TAT GCT AAT CCG CTG CTG AAA AAC GCT GTT CGG TTG       240
Arg Ile Phe Ala Tyr Ala Asn Pro Leu Leu Lys Asn Ala Val Arg Leu
65                  70                  75                  80

GGT ACC CGG CAA ATG TTG GGT TTT ATA CAA GGT TAT AGT GAT CTG TTT       288
Gly Thr Arg Gln Met Leu Gly Phe Ile Gln Gly Tyr Ser Asp Leu Phe
                85                  90                  95

GGT AAT CGT GCT GAT AAC TAT GCC GCG CCG GGC TCG GTT GCA TCG ATG       336
Gly Asn Arg Ala Asp Asn Tyr Ala Ala Pro Gly Ser Val Ala Ser Met
                100                 105                 110

TTC TCA CCG GCG GCT TAT TTG ACG GAA TTG TAC CGT GAA GCC AAA AAC       384
Phe Ser Pro Ala Ala Tyr Leu Thr Glu Leu Tyr Arg Glu Ala Lys Asn
            115                 120                 125

TTG CAT GAC AGC AGC TCA ATT TAT TAC CTA GAT AAA CGT CGC CCG GAT       432
Leu His Asp Ser Ser Ser Ile Tyr Tyr Leu Asp Lys Arg Arg Pro Asp
        130                 135                 140

TTA GCA AGC TTA ATG CTC AGC CAG AAA AAT ATG GAT GAG GAA ATT TCA       480
Leu Ala Ser Leu Met Leu Ser Gln Lys Asn Met Asp Glu Glu Ile Ser
145                 150                 155                 160

ACG CTG GCT CTC TCT AAT GAA TTG TGC CTT GCC GGG ATC GAA ACA AAA       528
Thr Leu Ala Leu Ser Asn Glu Leu Cys Leu Ala Gly Ile Glu Thr Lys
                165                 170                 175

ACA GGA AAA TCA CAA GAT GAA GTG ATG GAT ATG TTG TCA ACT TAT CGT       576
Thr Gly Lys Ser Gln Asp Glu Val Met Asp Met Leu Ser Thr Tyr Arg
                180                 185                 190

TTA AGT GGA GAG ACA CCT TAT CAT CAC GCT TAT GAA ACT GTT CGT GAA       624
Leu Ser Gly Glu Thr Pro Tyr His His Ala Tyr Glu Thr Val Arg Glu
            195                 200                 205

ATC GTT CAT GAA CGT GAT CCA GGA TTT CGT CAT TTG TCA CAG GCA CCC       672
Ile Val His Glu Arg Asp Pro Gly Phe Arg His Leu Ser Gln Ala Pro
        210                 215                 220

ATT GTT GCT GCT AAG CTC GAT CCT GTG ACT TTG TTG GGT ATT AGC TCC       720
Ile Val Ala Ala Lys Leu Asp Pro Val Thr Leu Leu Gly Ile Ser Ser
225                 230                 235                 240

CAT ATT TCG CCA GAA CTG TAT AAC TTG CTG ATT GAG GAG ATC CCG GAA       768
His Ile Ser Pro Glu Leu Tyr Asn Leu Leu Ile Glu Glu Ile Pro Glu
                245                 250                 255

AAA GAT GAA GCC GCG CTT GAT ACG CTT TAT AAA ACA AAC TTT GGC GAT       816
Lys Asp Glu Ala Ala Leu Asp Thr Leu Tyr Lys Thr Asn Phe Gly Asp
```

-continued

```
                    Lys Asp Glu Ala Ala Leu Asp Thr Leu Tyr Lys Thr Asn Phe Gly Asp
                                    260                 265                 270

ATT ACT ACT GCT CAG TTA ATG TCC CCA AGT TAT CTG GCC CGG TAT TAT              864
Ile Thr Thr Ala Gln Leu Met Ser Pro Ser Tyr Leu Ala Arg Tyr Tyr
            275                 280                 285

GGC GTC TCA CCG GAA GAT ATT GCC TAC GTG ACG ACT TCA TTA TCA CAT              912
Gly Val Ser Pro Glu Asp Ile Ala Tyr Val Thr Thr Ser Leu Ser His
    290                 295                 300

GTT GGA TAT AGC AGT GAT ATT CTG GTT ATT CCG TTG GTC GAT GGT GTG              960
Val Gly Tyr Ser Ser Asp Ile Leu Val Ile Pro Leu Val Asp Gly Val
305                 310                 315                 320

GGT AAG ATG GAA GTA GTT CGT GTT ACC CGA ACA CCA TCG GAT AAT TAT             1008
Gly Lys Met Glu Val Val Arg Val Thr Arg Thr Pro Ser Asp Asn Tyr
                325                 330                 335

ACC AGT CAG ACG AAT TAT ATT GAG CTG TAT CCA CAG GGT GGC GAC AAT             1056
Thr Ser Gln Thr Asn Tyr Ile Glu Leu Tyr Pro Gln Gly Gly Asp Asn
            340                 345                 350

TAT TTG ATC AAA TAC AAT CTA AGC AAT AGT TTT GGT TTG GAT GAT TTT             1104
Tyr Leu Ile Lys Tyr Asn Leu Ser Asn Ser Phe Gly Leu Asp Asp Phe
    355                 360                 365

TAT CTG CAA TAT AAA GAT GGT TCC GCT GAT TGG ACT GAG ATT GCC CAT             1152
Tyr Leu Gln Tyr Lys Asp Gly Ser Ala Asp Trp Thr Glu Ile Ala His
370                 375                 380

AAT CCC TAT CCT GAT ATG GTC ATA AAT CAA AAG TAT GAA TCA CAG GCG             1200
Asn Pro Tyr Pro Asp Met Val Ile Asn Gln Lys Tyr Glu Ser Gln Ala
385                 390                 395                 400

ACA ATC AAA CGT AGT GAC TCT GAC AAT ATA CTC AGT ATA GGG TTA CAA             1248
Thr Ile Lys Arg Ser Asp Ser Asp Asn Ile Leu Ser Ile Gly Leu Gln
                405                 410                 415

AGA TGG CAT AGC GGT AGT TAT AAT TTT GCC GCC GCC AAT TTT AAA ATT             1296
Arg Trp His Ser Gly Ser Tyr Asn Phe Ala Ala Ala Asn Phe Lys Ile
            420                 425                 430

GAC CAA TAC TCC CCG AAA GCT TTC CTG CTT AAA ATG AAT AAG GCT ATT             1344
Asp Gln Tyr Ser Pro Lys Ala Phe Leu Leu Lys Met Asn Lys Ala Ile
    435                 440                 445

CGG TTG CTC AAA GCT ACC GGC CTC TCT TTT GCT ACG TTG GAG CGT ATT             1392
Arg Leu Leu Lys Ala Thr Gly Leu Ser Phe Ala Thr Leu Glu Arg Ile
450                 455                 460

GTT GAT AGT GTT AAT AGC ACC AAA TCC ATC ACG GTT GAG GTA TTA AAC             1440
Val Asp Ser Val Asn Ser Thr Lys Ser Ile Thr Val Glu Val Leu Asn
465                 470                 475                 480

AAG GTT TAT CGG GTA AAA TTC TAT ATT GAT CGT TAT GGC ATC AGT GAA             1488
Lys Val Tyr Arg Val Lys Phe Tyr Ile Asp Arg Tyr Gly Ile Ser Glu
                485                 490                 495

GAG ACA GCC GCT ATT TTG GCT AAT ATT AAT ATC TCT CAG CAA GCT GTT             1536
Glu Thr Ala Ala Ile Leu Ala Asn Ile Asn Ile Ser Gln Gln Ala Val
            500                 505                 510

GGC AAT CAG CTT AGC CAG TTT GAG CAA CTA TTT AAT CAC CCG CCG CTC             1584
Gly Asn Gln Leu Ser Gln Phe Glu Gln Leu Phe Asn His Pro Pro Leu
    515                 520                 525

AAT GGT ATT CGC TAT GAA ATC AGT GAG GAC AAC TCC AAA CAT CTT CCT             1632
Asn Gly Ile Arg Tyr Glu Ile Ser Glu Asp Asn Ser Lys His Leu Pro
530                 535                 540

AAT CCT GAT CTG AAC CTT AAA CCA GAC AGT ACC GGT GAT GAT CAA CGC             1680
Asn Pro Asp Leu Asn Leu Lys Pro Asp Ser Thr Gly Asp Asp Gln Arg
545                 550                 555                 560

AAG GCG GTT TTA AAA CGC GCG TTT CAG GTT AAC GCC AGT GAG TTG TAT             1728
Lys Ala Val Leu Lys Arg Ala Phe Gln Val Asn Ala Ser Glu Leu Tyr
                565                 570                 575
```

```
CAG ATG TTA TTG ATC ACT GAT CGT AAA GAA GAC GGT GTT ATC AAA AAT      1776
Gln Met Leu Leu Ile Thr Asp Arg Lys Glu Asp Gly Val Ile Lys Asn
            580                 585                 590

AAC TTA GAG AAT TTG TCT GAT CTG TAT TTG GTT AGT TTG CTG GCC CAG      1824
Asn Leu Glu Asn Leu Ser Asp Leu Tyr Leu Val Ser Leu Leu Ala Gln
        595                 600                 605

ATT CAT AAC CTG ACT ATT GCT GAA TTG AAC ATT TTG TTG GTG ATT TGT      1872
Ile His Asn Leu Thr Ile Ala Glu Leu Asn Ile Leu Leu Val Ile Cys
        610                 615                 620

GGC TAT GGC GAC ACC AAC ATT TAT CAG ATT ACC GAC GAT AAT TTA GCC      1920
Gly Tyr Gly Asp Thr Asn Ile Tyr Gln Ile Thr Asp Asp Asn Leu Ala
625                 630                 635                 640

AAA ATA GTG GAA ACA TTG TTG TGG ATC ACT CAA TGG TTG AAG ACC CAA      1968
Lys Ile Val Glu Thr Leu Leu Trp Ile Thr Gln Trp Leu Lys Thr Gln
        645                 650                 655

AAA TGG ACA GTT ACC GAC CTG TTT CTG ATG ACC ACG GCC ACT TAC AGC      2016
Lys Trp Thr Val Thr Asp Leu Phe Leu Met Thr Thr Ala Thr Tyr Ser
        660                 665                 670

ACC ACT TTA ACG CCA GAA ATT AGC AAT CTG ACG GCT ACG TTG TCT TCA      2064
Thr Thr Leu Thr Pro Glu Ile Ser Asn Leu Thr Ala Thr Leu Ser Ser
        675                 680                 685

ACT TTG CAT GGC AAA GAG AGT CTG ATT GGG GAA GAT CTG AAA AGA GCA      2112
Thr Leu His Gly Lys Glu Ser Leu Ile Gly Glu Asp Leu Lys Arg Ala
        690                 695                 700

ATG GCG CCT TGC TTC ACT TCG GCT TTG CAT TTG ACT TCT CAA GAA GTT      2160
Met Ala Pro Cys Phe Thr Ser Ala Leu His Leu Thr Ser Gln Glu Val
705                 710                 715                 720

GCG TAT GAC CTG CTG TTG TGG ATA GAC CAG ATT CAA CCG GCA CAA ATA      2208
Ala Tyr Asp Leu Leu Leu Trp Ile Asp Gln Ile Gln Pro Ala Gln Ile
        725                 730                 735

ACT GTT GAT GGG TTT TGG GAA GAA GTG CAA ACA ACA CCA ACC AGC TTG      2256
Thr Val Asp Gly Phe Trp Glu Glu Val Gln Thr Thr Pro Thr Ser Leu
        740                 745                 750

AAG GTG ATT ACC TTT GCT CAG GTG CTG GCA CAA TTG AGC CTG ATC TAT      2304
Lys Val Ile Thr Phe Ala Gln Val Leu Ala Gln Leu Ser Leu Ile Tyr
        755                 760                 765

CGT CGT ATT GGG TTA AGT GAA ACG GAA CTG TCA CTG ATC GTG ACT CAA      2352
Arg Arg Ile Gly Leu Ser Glu Thr Glu Leu Ser Leu Ile Val Thr Gln
        770                 775                 780

TCT TCT CTG CTA GTG GCA GGC AAA AGC ATA CTG GAT CAC GGT CTG TTA      2400
Ser Ser Leu Leu Val Ala Gly Lys Ser Ile Leu Asp His Gly Leu Leu
785                 790                 795                 800

ACC CTG ATG GCC TTG GAA GGT TTT CAT ACC TGG GTT AAT GGC TTG GGG      2448
Thr Leu Met Ala Leu Glu Gly Phe His Thr Trp Val Asn Gly Leu Gly
            805                 810                 815

CAA CAT GCC TCC TTG ATA TTG GCG GCG TTG AAA GAC GGA GCC TTG ACA      2496
Gln His Ala Ser Leu Ile Leu Ala Ala Leu Lys Asp Gly Ala Leu Thr
            820                 825                 830

GTT ACC GAT GTA GCA CAA GCT ATG AAT AAG GAG GAA TCT CTC CTA CAA      2544
Val Thr Asp Val Ala Gln Ala Met Asn Lys Glu Glu Ser Leu Leu Gln
        835                 840                 845

ATG GCA GCT AAT CAG GTG GAG AAG GAT CTA ACA AAA CTG ACC AGT TGG      2592
Met Ala Ala Asn Gln Val Glu Lys Asp Leu Thr Lys Leu Thr Ser Trp
850                 855                 860

ACA CAG ATT GAC GCT ATT CTG CAA TGG TTA CAG ATG TCT TCG GCC TTG      2640
Thr Gln Ile Asp Ala Ile Leu Gln Trp Leu Gln Met Ser Ser Ala Leu
865                 870                 875                 880

GCG GTT TCT CCA CTG GAT CTG GCA GGG ATG ATG GCC CTG AAA TAT GGG      2688
Ala Val Ser Pro Leu Asp Leu Ala Gly Met Met Ala Leu Lys Tyr Gly
            885                 890                 895
```

-continued

| | |
|---|---|
| ATA GAT CAT AAC TAT GCT GCC TGG CAA GCT GCG GCG GCT GCG CTG ATG<br>Ile Asp His Asn Tyr Ala Ala Trp Gln Ala Ala Ala Ala Ala Leu Met<br>900      905      910 | 2736 |
| GCT GAT CAT GCT AAT CAG GCA CAG AAA AAA CTG GAT GAG ACG TTC AGT<br>Ala Asp His Ala Asn Gln Ala Gln Lys Lys Leu Asp Glu Thr Phe Ser<br>915      920      925 | 2784 |
| AAG GCA TTA TGT AAC TAT TAT ATT AAT GCT GTT GTC GAT AGT GCT GCT<br>Lys Ala Leu Cys Asn Tyr Tyr Ile Asn Ala Val Val Asp Ser Ala Ala<br>930      935      940 | 2832 |
| GGA GTA CGT GAT CGT AAC GGT TTA TAT ACC TAT TTG CTG ATT GAT AAT<br>Gly Val Arg Asp Arg Asn Gly Leu Tyr Thr Tyr Leu Leu Ile Asp Asn<br>945      950      955      960 | 2880 |
| CAG GTT TCT GCC GAT GTG ATC ACT TCA CGT ATT GCA GAA GCT ATC GCC<br>Gln Val Ser Ala Asp Val Ile Thr Ser Arg Ile Ala Glu Ala Ile Ala<br>965      970      975 | 2928 |
| GGT ATT CAA CTG TAC GTT AAC CGG GCT TTA AAC CGA GAT GAA GGT CAG<br>Gly Ile Gln Leu Tyr Val Asn Arg Ala Leu Asn Arg Asp Glu Gly Gln<br>980      985      990 | 2976 |
| CTT GCA TCG GAC GTT AGT ACC CGT CAG TTC TTC ACT GAC TGG GAA CGT<br>Leu Ala Ser Asp Val Ser Thr Arg Gln Phe Phe Thr Asp Trp Glu Arg<br>995      1000      1005 | 3024 |
| TAC AAT AAA CGT TAC AGT ACT TGG GCT GGT GTC TCT GAA CTG GTC TAT<br>Tyr Asn Lys Arg Tyr Ser Thr Trp Ala Gly Val Ser Glu Leu Val Tyr<br>1010      1015      1020 | 3072 |
| TAT CCA GAA AAC TAT GTT GAT CCC ACT CAG CGC ATT GGG CAA ACC AAA<br>Tyr Pro Glu Asn Tyr Val Asp Pro Thr Gln Arg Ile Gly Gln Thr Lys<br>1025      1030      1035      1040 | 3120 |
| ATG ATG GAT GCG CTG TTG CAA TCC ATC AAC CAG AGC CAG CTA AAT GCG<br>Met Met Asp Ala Leu Leu Gln Ser Ile Asn Gln Ser Gln Leu Asn Ala<br>1045      1050      1055 | 3168 |
| GAT ACG GTG GAA GAT GCT TTC AAA ACT TAT TTG ACC AGC TTT GAG CAG<br>Asp Thr Val Glu Asp Ala Phe Lys Thr Tyr Leu Thr Ser Phe Glu Gln<br>1060      1065      1070 | 3216 |
| GTA GCA AAT CTG AAA GTA ATT AGT GCT TAC CAC GAT AAT GTG AAT GTG<br>Val Ala Asn Leu Lys Val Ile Ser Ala Tyr His Asp Asn Val Asn Val<br>1075      1080      1085 | 3264 |
| GAT CAA GGA TTA ACT TAT TTT ATC GGT ATC GAC CAA GCA GCT CCG GGT<br>Asp Gln Gly Leu Thr Tyr Phe Ile Gly Ile Asp Gln Ala Ala Pro Gly<br>1090      1095      1100 | 3312 |
| ACG TAT TAC TGG CGT AGT GTT GAT CAC AGC AAA TGT GAA AAT GGC AAG<br>Thr Tyr Tyr Trp Arg Ser Val Asp His Ser Lys Cys Glu Asn Gly Lys<br>1105      1110      1115      1120 | 3360 |
| TTT GCC GCT AAT GCT TGG GGT GAG TGG AAT AAA ATT ACC TGT GCT GTC<br>Phe Ala Ala Asn Ala Trp Gly Glu Trp Asn Lys Ile Thr Cys Ala Val<br>1125      1130      1135 | 3408 |
| AAT CCT TGG AAA AAT ATC ATC CGT CCG GTT GTT TAT ATG TCC CGC TTA<br>Asn Pro Trp Lys Asn Ile Ile Arg Pro Val Val Tyr Met Ser Arg Leu<br>1140      1145      1150 | 3456 |
| TAT CTG CTA TGG CTG GAG CAG CAA TCA AAG AAA AGT GAT GAT GGT AAA<br>Tyr Leu Leu Trp Leu Glu Gln Gln Ser Lys Lys Ser Asp Asp Gly Lys<br>1155      1160      1165 | 3504 |
| ACC ACG ATT TAT CAA TAT AAC TTA AAA CTG GCT CAT ATT CGT TAC GAC<br>Thr Thr Ile Tyr Gln Tyr Asn Leu Lys Leu Ala His Ile Arg Tyr Asp<br>1170      1175      1180 | 3552 |
| GGT AGT TGG AAT ACA CCA TTT ACT TTT GAT GTG ACA GAA AAG GTA AAA<br>Gly Ser Trp Asn Thr Pro Phe Thr Phe Asp Val Thr Glu Lys Val Lys<br>1185      1190      1195      1200 | 3600 |
| AAT TAC ACG TCG AGT ACT GAT GCT GCT GAA TCT TTA GGG TTG TAT TGT<br>Asn Tyr Thr Ser Ser Thr Asp Ala Ala Glu Ser Leu Gly Leu Tyr Cys | 3648 |

|     |     |
| --- | --- |
| ```
                    1205                1210                1215
ACT GGT TAT CAA GGG GAA GAC ACT CTA TTA GTT ATG TTC TAT TCG ATG
Thr Gly Tyr Gln Gly Glu Asp Thr Leu Leu Val Met Phe Tyr Ser Met
            1220                1225                1230

CAG AGT AGT TAT AGC TCC TAT ACC GAT AAT AAT GCG CCG GTC ACT GGG
Gln Ser Ser Tyr Ser Ser Tyr Thr Asp Asn Asn Ala Pro Val Thr Gly
            1235                1240                1245

CTA TAT ATT TTC GCT GAT ATG TCA TCA GAC AAT ATG ACG AAT GCA CAA
Leu Tyr Ile Phe Ala Asp Met Ser Ser Asp Asn Met Thr Asn Ala Gln
            1250                1255                1260

GCA ACT AAC TAT TGG AAT AAC AGT TAT CCG CAA TTT GAT ACT GTG ATG
Ala Thr Asn Tyr Trp Asn Asn Ser Tyr Pro Gln Phe Asp Thr Val Met
1265                1270                1275                1280

GCA GAT CCG GAT AGC GAC AAT AAA AAA GTC ATA ACC AGA AGA GTT AAT
Ala Asp Pro Asp Ser Asp Asn Lys Lys Val Ile Thr Arg Arg Val Asn
            1285                1290                1295

AAC CGT TAT GCG GAG GAT TAT GAA ATT CCT TCC TCT GTG ACA AGT AAC
Asn Arg Tyr Ala Glu Asp Tyr Glu Ile Pro Ser Ser Val Thr Ser Asn
            1300                1305                1310

AGT AAT TAT TCT TGG GGT GAT CAC AGT TTA ACC ATG CTT TAT GGT GGT
Ser Asn Tyr Ser Trp Gly Asp His Ser Leu Thr Met Leu Tyr Gly Gly
            1315                1320                1325

AGT GTT CCT AAT ATT ACT TTT GAA TCG GCG GCA GAA GAT TTA AGG CTA
Ser Val Pro Asn Ile Thr Phe Glu Ser Ala Ala Glu Asp Leu Arg Leu
            1330                1335                1340

TCT ACC AAT ATG GCA TTG AGT ATT ATT CAT AAT GGA TAT GCG GGA ACC
Ser Thr Asn Met Ala Leu Ser Ile Ile His Asn Gly Tyr Ala Gly Thr
1345                1350                1355                1360

CGC CGT ATA CAA TGT AAT CTT ATG AAA CAA TAC GCT TCA TTA GGT GAT
Arg Arg Ile Gln Cys Asn Leu Met Lys Gln Tyr Ala Ser Leu Gly Asp
            1365                1370                1375

AAA TTT ATA ATT TAT GAT TCA TCA TTT GAT GAT GCA AAC CGT TTT AAT
Lys Phe Ile Ile Tyr Asp Ser Ser Phe Asp Asp Ala Asn Arg Phe Asn
            1380                1385                1390

CTG GTG CCA TTG TTT AAA TTC GGA AAA GAC GAG AAC TCA GAT GAT AGT
Leu Val Pro Leu Phe Lys Phe Gly Lys Asp Glu Asn Ser Asp Asp Ser
            1395                1400                1405

ATT TGT ATA TAT AAT GAA AAC CCT TCC TCT GAA GAT AAG AAG TGG TAT
Ile Cys Ile Tyr Asn Glu Asn Pro Ser Ser Glu Asp Lys Lys Trp Tyr
            1410                1415                1420

TTT TCT TCG AAA GAT GAC AAT AAA ACA GCG GAT TAT AAT GGT GGA ACT
Phe Ser Ser Lys Asp Asp Asn Lys Thr Ala Asp Tyr Asn Gly Gly Thr
1425                1430                1435                1440

CAA TGT ATA GAT GCT GGA ACC AGT AAC AAA GAT TTT TAT TAT AAT CTC
Gln Cys Ile Asp Ala Gly Thr Ser Asn Lys Asp Phe Tyr Tyr Asn Leu
            1445                1450                1455

CAG GAG ATT GAA GTA ATT AGT GTT ACT GGT GGG TAT TGG TCG AGT TAT
Gln Glu Ile Glu Val Ile Ser Val Thr Gly Gly Tyr Trp Ser Ser Tyr
            1460                1465                1470

AAA ATA TCC AAC CCG ATT AAT ATC AAT ACG GGC ATT GAT AGT GCT AAA
Lys Ile Ser Asn Pro Ile Asn Ile Asn Thr Gly Ile Asp Ser Ala Lys
            1475                1480                1485

GTA AAA GTC ACC GTA AAA GCG GGT GGT GAC GAT CAA ATC TTT ACT GCT
Val Lys Val Thr Val Lys Ala Gly Gly Asp Asp Gln Ile Phe Thr Ala
            1490                1495                1500

GAT AAT AGT ACC TAT GTT CCT CAG CAA CCG GCA CCC AGT TTT GAG GAG
Asp Asn Ser Thr Tyr Val Pro Gln Gln Pro Ala Pro Ser Phe Glu Glu
1505                1510                1515                1520

ATG ATT TAT CAG TTC AAT AAC CTG ACA ATA GAT TGT AAG AAT TTA AAT
``` | 3696<br><br>3744<br><br>3792<br><br>3840<br><br>3888<br><br>3936<br><br>3984<br><br>4032<br><br>4080<br><br>4128<br><br>4176<br><br>4224<br><br>4272<br><br>4320<br><br>4368<br><br>4416<br><br>4464<br><br>4512<br><br>4560<br><br>4608 |

-continued

```
                 Met Ile Tyr Gln Phe Asn Asn Leu Thr Ile Asp Cys Lys Asn Leu Asn
                             1525                1530                1535

TTC ATC GAC AAT CAG GCA CAT ATT GAG ATT GAT TTC ACC GCT ACG GCA              4656
Phe Ile Asp Asn Gln Ala His Ile Glu Ile Asp Phe Thr Ala Thr Ala
            1540                1545                1550

CAA GAT GGC CGA TTC TTG GGT GCA GAA ACT TTT ATT ATC CCG GTA ACT              4704
Gln Asp Gly Arg Phe Leu Gly Ala Glu Thr Phe Ile Ile Pro Val Thr
            1555                1560                1565

AAA AAA GTT CTC GGT ACT GAG AAC GTG ATT GCG TTA TAT AGC GAA AAT              4752
Lys Lys Val Leu Gly Thr Glu Asn Val Ile Ala Leu Tyr Ser Glu Asn
        1570                1575                1580

AAC GGT GTT CAA TAT ATG CAA ATT GGC GCA TAT CGT ACC CGT TTG AAT              4800
Asn Gly Val Gln Tyr Met Gln Ile Gly Ala Tyr Arg Thr Arg Leu Asn
1585                1590                1595                1600

ACG TTA TTC GCT CAA CAG TTG GTT AGC CGT GCT AAT CGT GGC ATT GAT              4848
Thr Leu Phe Ala Gln Gln Leu Val Ser Arg Ala Asn Arg Gly Ile Asp
            1605                1610                1615

GCA GTG CTC AGT ATG GAA ACT CAG AAT ATT CAG GAA CCG CAA TTA GGA              4896
Ala Val Leu Ser Met Glu Thr Gln Asn Ile Gln Glu Pro Gln Leu Gly
            1620                1625                1630

GCG GGC ACA TAT GTG CAG CTT GTG TTG GAT AAA TAT GAT GAG TCT ATT              4944
Ala Gly Thr Tyr Val Gln Leu Val Leu Asp Lys Tyr Asp Glu Ser Ile
            1635                1640                1645

CAT GGC ACT AAT AAA AGC TTT GCT ATT GAA TAT GTT GAT ATA TTT AAA              4992
His Gly Thr Asn Lys Ser Phe Ala Ile Glu Tyr Val Asp Ile Phe Lys
            1650                1655                1660

GAG AAC GAT AGT TTT GTG ATT TAT CAA GGA GAA CTT AGC GAA ACA AGT              5040
Glu Asn Asp Ser Phe Val Ile Tyr Gln Gly Glu Leu Ser Glu Thr Ser
1665                1670                1675                1680

CAA ACT GTT GTG AAA GTT TTC TTA TCC TAT TTT ATA GAG GCG ACT GGA              5088
Gln Thr Val Val Lys Val Phe Leu Ser Tyr Phe Ile Glu Ala Thr Gly
            1685                1690                1695

AAT AAG AAC CAC TTA TGG GTA CGT GCT AAA TAC CAA AAG GAA ACG ACT              5136
Asn Lys Asn His Leu Trp Val Arg Ala Lys Tyr Gln Lys Glu Thr Thr
            1700                1705                1710

GAT AAG ATC TTG TTC GAC CGT ACT GAT GAG AAA GAT CCG CAC GGT TGG              5184
Asp Lys Ile Leu Phe Asp Arg Thr Asp Glu Lys Asp Pro His Gly Trp
            1715                1720                1725

TTT CTC AGC GAC GAT CAC AAG ACC TTT AGT GGT CTC TCT TCC GCA CAG              5232
Phe Leu Ser Asp Asp His Lys Thr Phe Ser Gly Leu Ser Ser Ala Gln
            1730                1735                1740

GCA TTA AAG AAC GAC AGT GAA CCG ATG GAT TTC TCT GGC GCC AAT GCT              5280
Ala Leu Lys Asn Asp Ser Glu Pro Met Asp Phe Ser Gly Ala Asn Ala
1745                1750                1755                1760

CTC TAT TTC TGG GAA CTG TTC TAT TAC ACG CCG ATG ATG ATG GCT CAT              5328
Leu Tyr Phe Trp Glu Leu Phe Tyr Tyr Thr Pro Met Met Met Ala His
            1765                1770                1775

CGT TTG TTG CAG GAA CAG AAT TTT GAT GCG GCG AAC CAT TGG TTC CGT              5376
Arg Leu Leu Gln Glu Gln Asn Phe Asp Ala Ala Asn His Trp Phe Arg
            1780                1785                1790

TAT GTC TGG AGT CCA TCC GGT TAT ATC GTT GAT GGT AAA ATT GCT ATC              5424
Tyr Val Trp Ser Pro Ser Gly Tyr Ile Val Asp Gly Lys Ile Ala Ile
            1795                1800                1805

TAC CAC TGG AAC GTG CGA CCG CTG GAA GAA GAC ACC AGT TGG AAT GCA              5472
Tyr His Trp Asn Val Arg Pro Leu Glu Glu Asp Thr Ser Trp Asn Ala
            1810                1815                1820

CAA CAA CTG GAC TCC ACC GAT CCA GAT GCT GTA GCC CAA GAT GAT CCG              5520
Gln Gln Leu Asp Ser Thr Asp Pro Asp Ala Val Ala Gln Asp Asp Pro
1825                1830                1835                1840
```

-continued

```
ATG CAC TAC AAG GTG GCT ACC TTT ATG GCG ACG TTG GAT CTC CTA ATG       5568
Met His Tyr Lys Val Ala Thr Phe Met Ala Thr Leu Asp Leu Leu Met
            1845                1850                1855

GCC CGT GGT GAT GCT GCT TAC CGC CAG TTA GAG CGT GAT ACG TTG GCT       5616
Ala Arg Gly Asp Ala Ala Tyr Arg Gln Leu Glu Arg Asp Thr Leu Ala
        1860                1865                1870

GAA GCT AAA ATG TGG TAT ACA CAG GCG CTT AAT CTG TTG GGT GAT GAG       5664
Glu Ala Lys Met Trp Tyr Thr Gln Ala Leu Asn Leu Leu Gly Asp Glu
            1875                1880                1885

CCA CAA GTG ATG CTG AGT ACG ACT TGG GCT AAT CCA ACA TTG GGT AAT       5712
Pro Gln Val Met Leu Ser Thr Thr Trp Ala Asn Pro Thr Leu Gly Asn
            1890                1895                1900

GCT GCT TCA AAA ACC ACA CAG CAG GTT CGT CAG CAA GTG CTT ACC CAG       5760
Ala Ala Ser Lys Thr Thr Gln Gln Val Arg Gln Gln Val Leu Thr Gln
1905                1910                1915                1920

TTG CGT CTC AAT AGC AGG GTA AAA ACC CCG TTG CTA GGA ACA GCC AAT       5808
Leu Arg Leu Asn Ser Arg Val Lys Thr Pro Leu Leu Gly Thr Ala Asn
            1925                1930                1935

TCC CTG ACC GCT TTA TTC CTG CCG CAG GAA AAT AGC AAG CTC AAA GGC       5856
Ser Leu Thr Ala Leu Phe Leu Pro Gln Glu Asn Ser Lys Leu Lys Gly
            1940                1945                1950

TAC TGG CGG ACA CTG GCG CAG CGT ATG TTT AAT TTA CGT CAT AAT CTG       5904
Tyr Trp Arg Thr Leu Ala Gln Arg Met Phe Asn Leu Arg His Asn Leu
            1955                1960                1965

TCG ATT GAC GGC CAG CCG CTC TCC TTG CCG CTG TAT GCT AAA CCG GCT       5952
Ser Ile Asp Gly Gln Pro Leu Ser Leu Pro Leu Tyr Ala Lys Pro Ala
            1970                1975                1980

GAT CCA AAA GCT TTA CTG AGT GCG GCG GTT TCA GCT TCT CAA GGG GGA       6000
Asp Pro Lys Ala Leu Leu Ser Ala Ala Val Ser Ala Ser Gln Gly Gly
1985                1990                1995                2000

GCC GAC TTG CCG AAG GCG CCG CTG ACT ATT CAC CGC TTC CCT CAA ATG       6048
Ala Asp Leu Pro Lys Ala Pro Leu Thr Ile His Arg Phe Pro Gln Met
            2005                2010                2015

CTA GAA GGG GCA CGG GGC TTG GTT AAC CAG CTT ATA CAG TTC GGT AGT       6096
Leu Glu Gly Ala Arg Gly Leu Val Asn Gln Leu Ile Gln Phe Gly Ser
            2020                2025                2030

TCA CTA TTG GGG TAC AGT GAG CGT CAG GAT GCG GAA GCT ATG AGT CAA       6144
Ser Leu Leu Gly Tyr Ser Glu Arg Gln Asp Ala Glu Ala Met Ser Gln
            2035                2040                2045

CTA CTG CAA ACC CAA GCC AGC GAG TTA ATA CTG ACC AGT ATT CGT ATG       6192
Leu Leu Gln Thr Gln Ala Ser Glu Leu Ile Leu Thr Ser Ile Arg Met
            2050                2055                2060

CAG GAT AAC CAA TTG GCA GAG CTG GAT TCG GAA AAA ACC GCC TTG CAA       6240
Gln Asp Asn Gln Leu Ala Glu Leu Asp Ser Glu Lys Thr Ala Leu Gln
2065                2070                2075                2080

GTC TCT TTA GCT GGA GTG CAA CAA CGG TTT GAC AGC TAT AGC CAA CTG       6288
Val Ser Leu Ala Gly Val Gln Gln Arg Phe Asp Ser Tyr Ser Gln Leu
            2085                2090                2095

TAT GAG GAG AAC ATC AAC GCA GGT GAG CAG CGA GCG CTG GCG TTA CGC       6336
Tyr Glu Glu Asn Ile Asn Ala Gly Glu Gln Arg Ala Leu Ala Leu Arg
            2100                2105                2110

TCA GAA TCT GCT ATT GAG TCT CAG GGA GCG CAG ATT TCC CGT ATG GCA       6384
Ser Glu Ser Ala Ile Glu Ser Gln Gly Ala Gln Ile Ser Arg Met Ala
            2115                2120                2125

GGC GCG GGT GTT GAT ATG GCA CCA AAT ATC TTC GGC CTG GCT GAT GGC       6432
Gly Ala Gly Val Asp Met Ala Pro Asn Ile Phe Gly Leu Ala Asp Gly
            2130                2135                2140

GGC ATG CAT TAT GGT GCT ATT GCC TAT GCC ATC GCT GAC GGT ATT GAG       6480
Gly Met His Tyr Gly Ala Ile Ala Tyr Ala Ile Ala Asp Gly Ile Glu
2145                2150                2155                2160
```

```
TTG AGT GCT TCT GCC AAG ATG GTT GAT GCG GAG AAA GTT GCT CAG TCG    6528
Leu Ser Ala Ser Ala Lys Met Val Asp Ala Glu Lys Val Ala Gln Ser
                2165                2170                2175

GAA ATA TAT CGC CGT CGC CGT CAA GAA TGG AAA ATT CAG CGT GAC AAC    6576
Glu Ile Tyr Arg Arg Arg Gln Glu Trp Lys Ile Gln Arg Asp Asn
            2180                2185                2190

GCA CAA GCG GAG ATT AAC CAG TTA AAC GCG CAA CTG GAA TCA CTG TCT    6624
Ala Gln Ala Glu Ile Asn Gln Leu Asn Ala Gln Leu Glu Ser Leu Ser
                2195                2200                2205

ATT CGC CGT GAA GCC GCT GAA ATG CAA AAA GAG TAC CTG AAA ACC CAG    6672
Ile Arg Arg Glu Ala Ala Glu Met Gln Lys Glu Tyr Leu Lys Thr Gln
            2210                2215                2220

CAA GCT CAG GCG CAG GCA CAA CTT ACT TTC TTA AGA AGC AAA TTC AGT    6720
Gln Ala Gln Ala Gln Ala Gln Leu Thr Phe Leu Arg Ser Lys Phe Ser
2225                2230                2235                2240

AAT CAA GCG TTA TAT AGT TGG TTA CGA GGG CGT TTG TCA GGT ATT TAT    6768
Asn Gln Ala Leu Tyr Ser Trp Leu Arg Gly Arg Leu Ser Gly Ile Tyr
                2245                2250                2255

TTC CAG TTC TAT GAC TTG GCC GTA TCA CGT TGC CTG ATG GCA GAG CAA    6816
Phe Gln Phe Tyr Asp Leu Ala Val Ser Arg Cys Leu Met Ala Glu Gln
                2260                2265                2270

TCC TAT CAA TGG GAA GCT AAT GAT AAT TCC ATT AGC TTT GTC AAA CCG    6864
Ser Tyr Gln Trp Glu Ala Asn Asp Asn Ser Ile Ser Phe Val Lys Pro
            2275                2280                2285

GGT GCA TGG CAA GGA ACT TAC GCC GGC TTA TTG TGT GGA GAA GCT TTG    6912
Gly Ala Trp Gln Gly Thr Tyr Ala Gly Leu Leu Cys Gly Glu Ala Leu
            2290                2295                2300

ATA CAA AAT CTG GCA CAA ATG GAA GAG GCA TAT CTG AAA TGG GAA TCT    6960
Ile Gln Asn Leu Ala Gln Met Glu Glu Ala Tyr Leu Lys Trp Glu Ser
2305                2310                2315                2320

CGC GCT TTG GAA GTA GAA CGC ACG GTT TCA TTG GCA GTG GTT TAT GAT    7008
Arg Ala Leu Glu Val Glu Arg Thr Val Ser Leu Ala Val Val Tyr Asp
                2325                2330                2335

TCA CTG GAA GGT AAT GAT CGT TTT AAT TTA GCG GAA CAA ATA CCT GCA    7056
Ser Leu Glu Gly Asn Asp Arg Phe Asn Leu Ala Glu Gln Ile Pro Ala
                2340                2345                2350

TTA TTG GAT AAG GGG GAG GGA ACA GCA GGA ACT AAA GAA AAT GGG TTA    7104
Leu Leu Asp Lys Gly Glu Gly Thr Ala Gly Thr Lys Glu Asn Gly Leu
                2355                2360                2365

TCA TTG GCT AAT GCT ATC CTG TCA GCT TCG GTC AAA TTG TCC GAC TTG    7152
Ser Leu Ala Asn Ala Ile Leu Ser Ala Ser Val Lys Leu Ser Asp Leu
            2370                2375                2380

AAA CTG GGA ACG GAT TAT CCA GAC AGT ATC GTT GGT AGC AAC AAG GTT    7200
Lys Leu Gly Thr Asp Tyr Pro Asp Ser Ile Val Gly Ser Asn Lys Val
2385                2390                2395                2400

CGT CGT ATT AAG CAA ATC AGT GTT TCG CTA CCT GCA TTG GTT GGG CCT    7248
Arg Arg Ile Lys Gln Ile Ser Val Ser Leu Pro Ala Leu Val Gly Pro
                2405                2410                2415

TAT CAG GAT GTT CAG GCT ATG CTC AGC TAT GGT GGC AGT ACT CAA TTG    7296
Tyr Gln Asp Val Gln Ala Met Leu Ser Tyr Gly Gly Ser Thr Gln Leu
                2420                2425                2430

CCG AAA GGT TGT TCA GCG TTG GCT GTG TCT CAT GGT ACC AAT GAT AGT    7344
Pro Lys Gly Cys Ser Ala Leu Ala Val Ser His Gly Thr Asn Asp Ser
            2435                2440                2445

GGT CAG TTC CAG TTG GAT TTC AAT GAC GGC AAA TAC CTG CCA TTT GAA    7392
Gly Gln Phe Gln Leu Asp Phe Asn Asp Gly Lys Tyr Leu Pro Phe Glu
            2450                2455                2460

GGT ATT GCT CTT GAT GAT CAG GGT ACA CTG AAT CTT CAA TTT CCG AAT    7440
Gly Ile Ala Leu Asp Asp Gln Gly Thr Leu Asn Leu Gln Phe Pro Asn
```

|  |  |  | 2465 |  |  | 2470 |  |  |  | 2475 |  |  | 2480 |  |  |
|---|---|---|---|---|---|---|---|---|---|---|---|---|---|---|---|
| GCT | ACC | GAC | AAG | CAG | AAA | GCA | ATA | TTG | CAA | ACT | ATG | AGC | GAT | ATT | ATT | 7488
| Ala | Thr | Asp | Lys | Gln | Lys | Ala | Ile | Leu | Gln | Thr | Met | Ser | Asp | Ile | Ile |
|  |  |  | 2485 |  |  |  |  | 2490 |  |  |  | 2495 |  |  |  |

```
TTG CAT ATT CGT TAT ACC ATC CGT TAA                                         7515
Leu His Ile Arg Tyr Thr Ile Arg
            2500
```

(2) INFORMATION FOR SEQ ID NO:12:

(i) SEQUENCE CHARACTERISTICS:
        (A) LENGTH: 2504 amino acids
        (B) TYPE: amino acid
        (D) TOPOLOGY: linear (ii) MOLECULE TYPE: protein (xi) SEQUENCE DESCRIPTION: SEQ ID NO:12:

```
Met Gln Asn Ser Leu Ser Ser Thr Ile Asp Thr Ile Cys Gln Lys Leu
1               5                  10                  15

Gln Leu Thr Cys Pro Ala Glu Ile Ala Leu Tyr Pro Phe Asp Thr Phe
            20                  25                  30

Arg Glu Lys Thr Arg Gly Met Val Asn Trp Gly Glu Ala Lys Arg Ile
        35                  40                  45

Tyr Glu Ile Ala Gln Ala Glu Gln Asp Arg Asn Leu Leu His Glu Lys
50                  55                  60

Arg Ile Phe Ala Tyr Ala Asn Pro Leu Leu Lys Asn Ala Val Arg Leu
65                  70                  75                  80

Gly Thr Arg Gln Met Leu Gly Phe Ile Gln Gly Tyr Ser Asp Leu Phe
                85                  90                  95

Gly Asn Arg Ala Asp Asn Tyr Ala Ala Pro Gly Ser Val Ala Ser Met
            100                 105                 110

Phe Ser Pro Ala Ala Tyr Leu Thr Glu Leu Tyr Arg Glu Ala Lys Asn
        115                 120                 125

Leu His Asp Ser Ser Ser Ile Tyr Tyr Leu Asp Lys Arg Arg Pro Asp
130                 135                 140

Leu Ala Ser Leu Met Leu Ser Gln Lys Asn Met Asp Glu Glu Ile Ser
145                 150                 155                 160

Thr Leu Ala Leu Ser Asn Glu Leu Cys Leu Ala Gly Ile Glu Thr Lys
                165                 170                 175

Thr Gly Lys Ser Gln Asp Glu Val Met Asp Met Leu Ser Thr Tyr Arg
            180                 185                 190

Leu Ser Gly Glu Thr Pro Tyr His His Ala Tyr Glu Thr Val Arg Glu
        195                 200                 205

Ile Val His Glu Arg Asp Pro Gly Phe Arg His Leu Ser Gln Ala Pro
210                 215                 220

Ile Val Ala Ala Lys Leu Asp Pro Val Thr Leu Leu Gly Ile Ser Ser
225                 230                 235                 240

His Ile Ser Pro Glu Leu Tyr Asn Leu Leu Ile Glu Glu Ile Pro Glu
                245                 250                 255

Lys Asp Glu Ala Ala Leu Asp Thr Leu Tyr Lys Thr Asn Phe Gly Asp
            260                 265                 270

Ile Thr Thr Ala Gln Leu Met Ser Pro Ser Tyr Leu Ala Arg Tyr Tyr
        275                 280                 285

Gly Val Ser Pro Glu Asp Ile Ala Tyr Val Thr Thr Ser Leu Ser His
290                 295                 300
```

-continued

```
Val Gly Tyr Ser Ser Asp Ile Leu Val Ile Pro Leu Val Asp Gly Val
305                 310                 315                 320

Gly Lys Met Glu Val Arg Val Thr Arg Thr Pro Ser Asp Asn Tyr
            325                 330                 335

Thr Ser Gln Thr Asn Tyr Ile Glu Leu Tyr Pro Gln Gly Gly Asp Asn
            340                 345                 350

Tyr Leu Ile Lys Tyr Asn Leu Ser Asn Ser Phe Gly Leu Asp Asp Phe
            355                 360                 365

Tyr Leu Gln Tyr Lys Asp Gly Ser Ala Asp Trp Thr Glu Ile Ala His
370                 375                 380

Asn Pro Tyr Pro Asp Met Val Ile Asn Gln Lys Tyr Glu Ser Gln Ala
385                 390                 395                 400

Thr Ile Lys Arg Ser Asp Ser Asp Asn Ile Leu Ser Ile Gly Leu Gln
            405                 410                 415

Arg Trp His Ser Gly Ser Tyr Asn Phe Ala Ala Ala Asn Phe Lys Ile
            420                 425                 430

Asp Gln Tyr Ser Pro Lys Ala Phe Leu Leu Lys Met Asn Lys Ala Ile
            435                 440                 445

Arg Leu Leu Lys Ala Thr Gly Leu Ser Phe Ala Thr Leu Glu Arg Ile
450                 455                 460

Val Asp Ser Val Asn Ser Thr Lys Ser Ile Thr Val Glu Val Leu Asn
465                 470                 475                 480

Lys Val Tyr Arg Val Lys Phe Tyr Ile Asp Arg Tyr Gly Ile Ser Glu
            485                 490                 495

Glu Thr Ala Ala Ile Leu Ala Asn Ile Asn Ile Ser Gln Gln Ala Val
            500                 505                 510

Gly Asn Gln Leu Ser Gln Phe Glu Gln Leu Phe Asn His Pro Pro Leu
            515                 520                 525

Asn Gly Ile Arg Tyr Glu Ile Ser Glu Asp Asn Ser Lys His Leu Pro
            530                 535                 540

Asn Pro Asp Leu Asn Leu Lys Pro Asp Ser Thr Gly Asp Asp Gln Arg
545                 550                 555                 560

Lys Ala Val Leu Lys Arg Ala Phe Gln Val Asn Ala Ser Glu Leu Tyr
            565                 570                 575

Gln Met Leu Leu Ile Thr Asp Arg Lys Glu Asp Gly Val Ile Lys Asn
            580                 585                 590

Asn Leu Glu Asn Leu Ser Asp Leu Tyr Leu Val Ser Leu Leu Ala Gln
            595                 600                 605

Ile His Asn Leu Thr Ile Ala Glu Leu Asn Ile Leu Leu Val Ile Cys
            610                 615                 620

Gly Tyr Gly Asp Thr Asn Ile Tyr Gln Ile Thr Asp Asp Asn Leu Ala
625                 630                 635                 640

Lys Ile Val Glu Thr Leu Leu Trp Ile Thr Gln Trp Leu Lys Thr Gln
            645                 650                 655

Lys Trp Thr Val Thr Asp Leu Phe Leu Met Thr Thr Ala Thr Tyr Ser
            660                 665                 670

Thr Thr Leu Thr Pro Glu Ile Ser Asn Leu Thr Ala Thr Leu Ser Ser
            675                 680                 685

Thr Leu His Gly Lys Glu Ser Leu Ile Gly Glu Asp Leu Lys Arg Ala
            690                 695                 700

Met Ala Pro Cys Phe Thr Ser Ala Leu His Leu Thr Ser Gln Glu Val
705                 710                 715                 720

Ala Tyr Asp Leu Leu Leu Trp Ile Asp Gln Ile Gln Pro Ala Gln Ile
```

-continued

```
                725                 730                 735
Thr Val Asp Gly Phe Trp Glu Glu Val Gln Thr Thr Pro Thr Ser Leu
            740                 745                 750
Lys Val Ile Thr Phe Ala Gln Val Leu Ala Gln Leu Ser Leu Ile Tyr
            755                 760                 765
Arg Arg Ile Gly Leu Ser Glu Thr Glu Leu Ser Leu Ile Val Thr Gln
            770                 775                 780
Ser Ser Leu Leu Val Ala Gly Lys Ser Ile Leu Asp His Gly Leu Leu
785                 790                 795                 800
Thr Leu Met Ala Leu Glu Gly Phe His Thr Trp Val Asn Gly Leu Gly
            805                 810                 815
Gln His Ala Ser Leu Ile Leu Ala Ala Leu Lys Asp Gly Ala Leu Thr
            820                 825                 830
Val Thr Asp Val Ala Gln Ala Met Asn Lys Glu Glu Ser Leu Leu Gln
            835                 840                 845
Met Ala Ala Asn Gln Val Glu Lys Asp Leu Thr Lys Leu Thr Ser Trp
850                 855                 860
Thr Gln Ile Asp Ala Ile Leu Gln Trp Leu Gln Met Ser Ser Ala Leu
865                 870                 875                 880
Ala Val Ser Pro Leu Asp Leu Ala Gly Met Met Ala Leu Lys Tyr Gly
            885                 890                 895
Ile Asp His Asn Tyr Ala Ala Trp Gln Ala Ala Ala Ala Leu Met
            900                 905                 910
Ala Asp His Ala Asn Gln Ala Gln Lys Lys Leu Asp Glu Thr Phe Ser
            915                 920                 925
Lys Ala Leu Cys Asn Tyr Tyr Ile Asn Ala Val Asp Ser Ala Ala
            930                 935                 940
Gly Val Arg Asp Arg Asn Gly Leu Tyr Thr Tyr Leu Leu Ile Asp Asn
945                 950                 955                 960
Gln Val Ser Ala Asp Val Ile Thr Ser Arg Ile Ala Glu Ala Ile Ala
            965                 970                 975
Gly Ile Gln Leu Tyr Val Asn Arg Ala Leu Asn Arg Asp Glu Gly Gln
            980                 985                 990
Leu Ala Ser Asp Val Ser Thr Arg Gln Phe Phe Thr Asp Trp Glu Arg
            995                 1000                1005
Tyr Asn Lys Arg Tyr Ser Thr Trp Ala Gly Val Ser Glu Leu Val Tyr
            1010                1015                1020
Tyr Pro Glu Asn Tyr Val Asp Pro Thr Gln Arg Ile Gly Gln Thr Lys
1025                1030                1035                1040
Met Met Asp Ala Leu Leu Gln Ser Ile Asn Gln Ser Gln Leu Asn Ala
                    1045                1050                1055
Asp Thr Val Glu Asp Ala Phe Lys Thr Tyr Leu Thr Ser Phe Glu Gln
                    1060                1065                1070
Val Ala Asn Leu Lys Val Ile Ser Ala Tyr His Asp Asn Val Asn Val
                    1075                1080                1085
Asp Gln Gly Leu Thr Tyr Phe Ile Gly Ile Asp Gln Ala Ala Pro Gly
                    1090                1095                1100
Thr Tyr Tyr Trp Arg Ser Val Asp His Ser Lys Cys Glu Asn Gly Lys
1105                1110                1115                1120
Phe Ala Ala Asn Ala Trp Gly Glu Trp Asn Lys Ile Thr Cys Ala Val
                    1125                1130                1135
Asn Pro Trp Lys Asn Ile Ile Arg Pro Val Val Tyr Met Ser Arg Leu
                    1140                1145                1150
```

-continued

```
Tyr Leu Leu Trp Leu Glu Gln Gln Ser Lys Lys Ser Asp Asp Gly Lys
        1155                1160                1165
Thr Thr Ile Tyr Gln Tyr Asn Leu Lys Leu Ala His Ile Arg Tyr Asp
    1170                1175                1180
Gly Ser Trp Asn Thr Pro Phe Thr Phe Asp Val Thr Glu Lys Val Lys
1185                1190                1195                1200
Asn Tyr Thr Ser Ser Thr Asp Ala Ala Glu Ser Leu Gly Leu Tyr Cys
            1205                1210                1215
Thr Gly Tyr Gln Gly Glu Asp Thr Leu Leu Val Met Phe Tyr Ser Met
        1220                1225                1230
Gln Ser Ser Tyr Ser Ser Tyr Thr Asp Asn Ala Pro Val Thr Gly
        1235                1240                1245
Leu Tyr Ile Phe Ala Asp Met Ser Ser Asp Asn Met Thr Asn Ala Gln
    1250                1255                1260
Ala Thr Asn Tyr Trp Asn Asn Ser Tyr Pro Gln Phe Asp Thr Val Met
1265                1270                1275                1280
Ala Asp Pro Asp Ser Asp Asn Lys Lys Val Ile Thr Arg Arg Val Asn
            1285                1290                1295
Asn Arg Tyr Ala Glu Asp Tyr Glu Ile Pro Ser Ser Val Thr Ser Asn
        1300                1305                1310
Ser Asn Tyr Ser Trp Gly Asp His Ser Leu Thr Met Leu Tyr Gly Gly
        1315                1320                1325
Ser Val Pro Asn Ile Thr Phe Ser Ala Ala Glu Asp Leu Arg Leu
        1330                1335                1340
Ser Thr Asn Met Ala Leu Ser Ile Ile His Asn Gly Tyr Ala Gly Thr
1345                1350                1355                1360
Arg Arg Ile Gln Cys Asn Leu Met Lys Gln Tyr Ala Ser Leu Gly Asp
            1365                1370                1375
Lys Phe Ile Ile Tyr Asp Ser Ser Phe Asp Asp Ala Asn Arg Phe Asn
            1380                1385                1390
Leu Val Pro Leu Phe Lys Phe Gly Lys Asp Glu Asn Ser Asp Asp Ser
            1395                1400                1405
Ile Cys Ile Tyr Asn Glu Asn Pro Ser Ser Glu Asp Lys Lys Trp Tyr
    1410                1415                1420
Phe Ser Ser Lys Asp Asp Asn Lys Thr Ala Asp Tyr Asn Gly Gly Thr
1425                1430                1435                1440
Gln Cys Ile Asp Ala Gly Thr Ser Asn Lys Asp Phe Tyr Tyr Asn Leu
            1445                1450                1455
Gln Glu Ile Glu Val Ile Ser Val Thr Gly Gly Tyr Trp Ser Ser Tyr
        1460                1465                1470
Lys Ile Ser Asn Pro Ile Asn Ile Asn Thr Gly Ile Asp Ser Ala Lys
        1475                1480                1485
Val Lys Val Thr Val Lys Ala Gly Gly Asp Asp Gln Ile Phe Thr Ala
        1490                1495                1500
Asp Asn Ser Thr Tyr Val Pro Gln Gln Pro Ala Pro Ser Phe Glu Glu
1505                1510                1515                1520
Met Ile Tyr Gln Phe Asn Asn Leu Thr Ile Asp Cys Lys Asn Leu Asn
            1525                1530                1535
Phe Ile Asp Asn Gln Ala His Ile Glu Ile Asp Phe Thr Ala Thr Ala
            1540                1545                1550
Gln Asp Gly Arg Phe Leu Gly Ala Glu Thr Phe Ile Ile Pro Val Thr
        1555                1560                1565
```

-continued

Lys Lys Val Leu Gly Thr Glu Asn Val Ile Ala Leu Tyr Ser Glu Asn
    1570            1575            1580

Asn Gly Val Gln Tyr Met Gln Ile Gly Ala Tyr Arg Thr Arg Leu Asn
1585            1590            1595            1600

Thr Leu Phe Ala Gln Gln Leu Val Ser Arg Ala Asn Arg Gly Ile Asp
            1605            1610            1615

Ala Val Leu Ser Met Glu Thr Gln Asn Ile Gln Glu Pro Gln Leu Gly
        1620            1625            1630

Ala Gly Thr Tyr Val Gln Leu Val Leu Asp Lys Tyr Asp Glu Ser Ile
    1635            1640            1645

His Gly Thr Asn Lys Ser Phe Ala Ile Glu Tyr Val Asp Ile Phe Lys
    1650            1655            1660

Glu Asn Asp Ser Phe Val Ile Tyr Gln Gly Glu Leu Ser Glu Thr Ser
1665            1670            1675            1680

Gln Thr Val Val Lys Val Phe Leu Ser Tyr Phe Ile Glu Ala Thr Gly
            1685            1690            1695

Asn Lys Asn His Leu Trp Val Arg Ala Lys Tyr Gln Lys Glu Thr Thr
        1700            1705            1710

Asp Lys Ile Leu Phe Asp Arg Thr Asp Glu Lys Asp Pro His Gly Trp
    1715            1720            1725

Phe Leu Ser Asp His Lys Thr Phe Ser Gly Leu Ser Ser Ala Gln
    1730            1735            1740

Ala Leu Lys Asn Asp Ser Glu Pro Met Asp Phe Ser Gly Ala Asn Ala
1745            1750            1755            1760

Leu Tyr Phe Trp Glu Leu Phe Tyr Tyr Thr Pro Met Met Ala His
            1765            1770            1775

Arg Leu Leu Gln Glu Gln Asn Phe Asp Ala Ala Asn His Trp Phe Arg
        1780            1785            1790

Tyr Val Trp Ser Pro Ser Gly Tyr Ile Val Asp Gly Lys Ile Ala Ile
    1795            1800            1805

Tyr His Trp Asn Val Arg Pro Leu Glu Glu Asp Thr Ser Trp Asn Ala
    1810            1815            1820

Gln Gln Leu Asp Ser Thr Asp Pro Asp Ala Val Ala Gln Asp Pro
1825            1830            1835            1840

Met His Tyr Lys Val Ala Thr Phe Met Ala Thr Leu Asp Leu Met
            1845            1850            1855

Ala Arg Gly Asp Ala Ala Tyr Arg Gln Leu Glu Arg Asp Thr Leu Ala
        1860            1865            1870

Glu Ala Lys Met Trp Tyr Thr Gln Ala Leu Asn Leu Leu Gly Asp Glu
    1875            1880            1885

Pro Gln Val Met Leu Ser Thr Thr Trp Ala Asn Pro Thr Leu Gly Asn
    1890            1895            1900

Ala Ala Ser Lys Thr Thr Gln Gln Val Arg Gln Gln Val Leu Thr Gln
1905            1910            1915            1920

Leu Arg Leu Asn Ser Arg Val Lys Pro Leu Leu Gly Thr Ala Asn
            1925            1930            1935

Ser Leu Thr Ala Leu Phe Leu Pro Gln Glu Asn Ser Lys Leu Lys Gly
        1940            1945            1950

Tyr Trp Arg Thr Leu Ala Gln Arg Met Phe Asn Leu Arg His Asn Leu
    1955            1960            1965

Ser Ile Asp Gly Gln Pro Leu Ser Leu Pro Leu Tyr Ala Lys Pro Ala
    1970            1975            1980

Asp Pro Lys Ala Leu Leu Ser Ala Ala Val Ser Ala Ser Gln Gly Gly

-continued

Ala Asp Leu Pro Lys Ala Pro Leu Thr Ile His Arg Phe Pro Gln Met
1985           1990           1995           2000
         2005           2010           2015

Leu Glu Gly Ala Arg Gly Leu Val Asn Gln Leu Ile Gln Phe Gly Ser
         2020           2025           2030

Ser Leu Leu Gly Tyr Ser Glu Arg Gln Asp Ala Glu Ala Met Ser Gln
         2035           2040           2045

Leu Leu Gln Thr Gln Ala Ser Glu Leu Ile Leu Thr Ser Ile Arg Met
         2050           2055           2060

Gln Asp Asn Gln Leu Ala Glu Leu Asp Ser Glu Lys Thr Ala Leu Gln
2065           2070           2075           2080

Val Ser Leu Ala Gly Val Gln Gln Arg Phe Asp Ser Tyr Ser Gln Leu
         2085           2090           2095

Tyr Glu Glu Asn Ile Asn Ala Gly Glu Gln Arg Ala Leu Ala Leu Arg
         2100           2105           2110

Ser Glu Ser Ala Ile Glu Ser Gln Gly Ala Gln Ile Ser Arg Met Ala
         2115           2120           2125

Gly Ala Gly Val Asp Met Ala Pro Asn Ile Phe Gly Leu Ala Asp Gly
         2130           2135           2140

Gly Met His Tyr Gly Ala Ile Ala Tyr Ala Ile Ala Asp Gly Ile Glu
2145           2150           2155           2160

Leu Ser Ala Ser Ala Lys Met Val Asp Ala Glu Lys Val Ala Gln Ser
         2165           2170           2175

Glu Ile Tyr Arg Arg Arg Gln Glu Trp Lys Ile Gln Arg Asp Asn
         2180           2185           2190

Ala Gln Ala Glu Ile Asn Gln Leu Asn Ala Gln Leu Glu Ser Leu Ser
         2195           2200           2205

Ile Arg Arg Glu Ala Ala Glu Met Gln Lys Glu Tyr Leu Lys Thr Gln
         2210           2215           2220

Gln Ala Gln Ala Gln Ala Gln Leu Thr Phe Leu Arg Ser Lys Phe Ser
2225           2230           2235           2240

Asn Gln Ala Leu Tyr Ser Trp Leu Arg Gly Arg Leu Ser Gly Ile Tyr
         2245           2250           2255

Phe Gln Phe Tyr Asp Leu Ala Val Ser Arg Cys Leu Met Ala Glu Gln
         2260           2265           2270

Ser Tyr Gln Trp Glu Ala Asn Asp Asn Ser Ile Ser Phe Val Lys Pro
         2275           2280           2285

Gly Ala Trp Gln Gly Thr Tyr Ala Gly Leu Leu Cys Gly Glu Ala Leu
         2290           2295           2300

Ile Gln Asn Leu Ala Gln Met Glu Glu Ala Tyr Leu Lys Trp Glu Ser
2305           2310           2315           2320

Arg Ala Leu Glu Val Glu Arg Thr Val Ser Leu Ala Val Val Tyr Asp
         2325           2330           2335

Ser Leu Glu Gly Asn Asp Arg Phe Asn Leu Ala Glu Gln Ile Pro Ala
         2340           2345           2350

Leu Leu Asp Lys Gly Glu Gly Thr Ala Gly Thr Lys Glu Asn Gly Leu
         2355           2360           2365

Ser Leu Ala Asn Ala Ile Leu Ser Ala Ser Val Lys Leu Ser Asp Leu
         2370           2375           2380

Lys Leu Gly Thr Asp Tyr Pro Asp Ser Ile Val Gly Ser Asn Lys Val
2385           2390           2395           2400

Arg Arg Ile Lys Gln Ile Ser Val Ser Leu Pro Ala Leu Val Gly Pro
         2405           2410           2415

-continued

```
Tyr Gln Asp Val Gln Ala Met Leu Ser Tyr Gly Gly Ser Thr Gln Leu
            2420            2425            2430

Pro Lys Gly Cys Ser Ala Leu Ala Val Ser His Gly Thr Asn Asp Ser
            2435            2440            2445

Gly Gln Phe Gln Leu Asp Phe Asn Asp Gly Lys Tyr Leu Pro Phe Glu
            2450            2455            2460

Gly Ile Ala Leu Asp Asp Gln Gly Thr Leu Asn Leu Gln Phe Pro Asn
2465            2470            2475            2480

Ala Thr Asp Lys Gln Lys Ala Ile Leu Gln Thr Met Ser Asp Ile Ile
            2485            2490            2495

Leu His Ile Arg Tyr Thr Ile Arg
            2500
```

(2) INFORMATION FOR SEQ ID NO:13:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Leu Ile Gly Tyr Asn Asn Gln Phe Ser Gly Xaa Ala
1               5                   10
```

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Met Gln Asn Ser Gln Thr Phe Ser Val Gly Glu Leu
1               5                   10
```

(2) INFORMATION FOR SEQ ID NO:15:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Ala Gln Asp Gly Asn Gln Asp Thr Phe Phe Ser Gly Asn Thr
1               5                   10
```

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Met Gln Asn Ser Leu
1               5
```

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Ala Phe Asn Ile Asp Asp Val Ser Leu Phe
1               5                   10
```

(2) INFORMATION FOR SEQ ID NO:18:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Phe Ile Val Tyr Thr Ser Leu Gly Val Asn Pro Asn Ser Ser Asn
1               5                   10                  15
```

(2) INFORMATION FOR SEQ ID NO:19:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Ile Ser Asp Leu Val Thr Thr Ser Pro Leu Ser Glu Ala Ile Gly Ser
1               5                   10                  15
Leu Gln Leu Phe Ile
            20
```

(2) INFORMATION FOR SEQ ID NO:20:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Met Tyr Tyr Ile Gln Ala Gln Gln Leu Leu Gly Pro
1               5                   10
```

(2) INFORMATION FOR SEQ ID NO:21:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Gly Ile Asp Ala Val Leu Ser Met Glu Thr Gln Asn Ile Gln Glu Pro
1               5                   10                  15

Gln Leu Gly Ala Gly Thr Tyr Val Gln Leu
            20                  25

(2) INFORMATION FOR SEQ ID NO:22:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

Ile Ser Asn Pro Ile Asn Ile Asn Thr Gly Ile Asp Ser Ala Lys
1               5                   10                  15

(2) INFORMATION FOR SEQ ID NO:23:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

Thr Tyr Leu Thr Ser Phe Glu Gln Val Ala Asn Leu Lys
1               5                   10

(2) INFORMATION FOR SEQ ID NO:24:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

Val Leu Gly Thr Glu Asn Val Ile Ala Leu Tyr Ser Glu Asn Asn Gly
1               5                   10                  15

Val Gln Tyr Met Gln Ile
            20

(2) INFORMATION FOR SEQ ID NO:25:

(i) SEQUENCE CHARACTERISTICS:
            (A) LENGTH: 6055 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 66..3635

(xi) SEQUENCE DESCRIPTION: SEQ ID NO:25:

```
AGTAGCCCAA AACTTAAGTG CCGCAATCAG CAATCGTCAG TAACCGGATA AAGAAGGAAT    60

TGATT ATG TCT GAA TCT TTA TTT ACA CAA ACG TTG AAA GAA GCG CGC       107
      Met Ser Glu Ser Leu Phe Thr Gln Thr Leu Lys Glu Ala Arg
        1               5                      10

CGT GAT GCA TTG GTT GCT CAT TAT ATT GCT ACT CAG GTG CCC GCA GAT     155
Arg Asp Ala Leu Val Ala His Tyr Ile Ala Thr Gln Val Pro Ala Asp
 15                  20                  25                  30

TTA AAA GAG AGT ATC CAG ACC GCG GAT GAT CTG TAC GAA TAT CTG TTG     203
Leu Lys Glu Ser Ile Gln Thr Ala Asp Asp Leu Tyr Glu Tyr Leu Leu
                 35                  40                  45

CTG GAT ACC AAA ATT AGC GAT CTG GTT ACT ACT TCA CCG CTG TCC GAA     251
Leu Asp Thr Lys Ile Ser Asp Leu Val Thr Thr Ser Pro Leu Ser Glu
                 50                  55                  60

GCG ATT GGC AGT CTG CAA TTG TTT ATT CAT CGT GCG ATA GAG GGC TAT     299
Ala Ile Gly Ser Leu Gln Leu Phe Ile His Arg Ala Ile Glu Gly Tyr
             65                  70                  75

GAC GGC ACG CTG GCA GAC TCA GCA AAA CCC TAT TTT GCC GAT GAA CAG     347
Asp Gly Thr Leu Ala Asp Ser Ala Lys Pro Tyr Phe Ala Asp Glu Gln
 80                  85                  90

TTT TTA TAT AAC TGG GAT AGT TTT AAC CAC CGT TAT AGC ACT TGG GCT     395
Phe Leu Tyr Asn Trp Asp Ser Phe Asn His Arg Tyr Ser Thr Trp Ala
 95                 100                 105                 110

GGC AAG GAA CGG TTG AAA TTC TAT GCC GGG GAT TAT ATT GAT CCA ACA     443
Gly Lys Glu Arg Leu Lys Phe Tyr Ala Gly Asp Tyr Ile Asp Pro Thr
                115                 120                 125

TTG CGA TTG AAT AAG ACC GAG ATA TTT ACC GCA TTT GAA CAA GGT ATT     491
Leu Arg Leu Asn Lys Thr Glu Ile Phe Thr Ala Phe Glu Gln Gly Ile
                130                 135                 140

TCT CAA GGG AAA TTA AAA AGT GAA TTA GTC GAA TCT AAA TTA CGT GAT     539
Ser Gln Gly Lys Leu Lys Ser Glu Leu Val Glu Ser Lys Leu Arg Asp
            145                 150                 155

TAT CTA ATT AGT TAT GAC ACT TTA GCC ACC CTT GAT TAT ATT ACT GCC     587
Tyr Leu Ile Ser Tyr Asp Thr Leu Ala Thr Leu Asp Tyr Ile Thr Ala
    160                 165                 170

TGC CAA GGC AAA GAT AAT AAA ACC ATC TTC TTT ATT GGC CGT ACA CAG     635
Cys Gln Gly Lys Asp Asn Lys Thr Ile Phe Phe Ile Gly Arg Thr Gln
175                 180                 185                 190

AAT GCA CCC TAT GCA TTT TAT TGG CGA AAA TTA ACT TTA GTC ACT GAT     683
Asn Ala Pro Tyr Ala Phe Tyr Trp Arg Lys Leu Thr Leu Val Thr Asp
                195                 200                 205

GGC GGT AAG TTG AAA CCA GAT CAA TGG TCA GAG TGG CGA GCA ATT AAT     731
Gly Gly Lys Leu Lys Pro Asp Gln Trp Ser Glu Trp Arg Ala Ile Asn
                210                 215                 220

GCC GGG ATT AGT GAG GCA TAT TCA GGG CAT GTC GAG CCT TTC TGG GAA     779
Ala Gly Ile Ser Glu Ala Tyr Ser Gly His Val Glu Pro Phe Trp Glu
            225                 230                 235

AAT AAC AAG CTG CAC ATC CGT TGG TTT ACT ATC TCG AAA GAA GAT AAA     827
Asn Asn Lys Leu His Ile Arg Trp Phe Thr Ile Ser Lys Glu Asp Lys
            240                 245                 250

ATA GAT TTT GTT TAT AAA AAC ATC TGG GTG ATG AGT AGC GAT TAT AGC     875
Ile Asp Phe Val Tyr Lys Asn Ile Trp Val Met Ser Ser Asp Tyr Ser
255                 260                 265                 270

TGG GCA TCA AAG AAA AAA ATC TTG GAA CTT TCT TTT ACT GAC TAC AAT     923
Trp Ala Ser Lys Lys Lys Ile Leu Glu Leu Ser Phe Thr Asp Tyr Asn
                275                 280                 285

AGA GTT GGA GCA ACA GGA TCA TCA AGC CCG ACT GAA GTA GCT TCA CAA     971
Arg Val Gly Ala Thr Gly Ser Ser Ser Pro Thr Glu Val Ala Ser Gln
                290                 295                 300

TAT GGT TCT GAT GCT CAG ATG AAT ATT TCT GAT GAT GGG ACT GTA CTT   1019
```

```
                                                            -continued

Tyr Gly Ser Asp Ala Gln Met Asn Ile Ser Asp Asp Gly Thr Val Leu
        305                 310                 315

ATT TTT CAG AAT GCC GGC GGA GCT ACT CCC AGT ACT GGA GTG ACG TTA    1067
Ile Phe Gln Asn Ala Gly Gly Ala Thr Pro Ser Thr Gly Val Thr Leu
    320                 325                 330

TGT TAT GAC TCT GGC AAC GTG ATT AAG AAC CTA TCT AGT ACA GGA AGT    1115
Cys Tyr Asp Ser Gly Asn Val Ile Lys Asn Leu Ser Ser Thr Gly Ser
335                 340                 345                 350

GCA AAT TTA TCG TCA AAG GAT TAT GCC ACA ACT AAA TTA CGC ATG TGT    1163
Ala Asn Leu Ser Ser Lys Asp Tyr Ala Thr Thr Lys Leu Arg Met Cys
                355                 360                 365

CAT GGA CAA AGT TAC AAT GAT AAT AAC TAC TGC AAT TTT ACA CTC TCT    1211
His Gly Gln Ser Tyr Asn Asp Asn Asn Tyr Cys Asn Phe Thr Leu Ser
        370                 375                 380

ATT AAT ACA ATA GAA TTC ACC TCC TAC GGC ACA TTC TCA TCA GAT GGA    1259
Ile Asn Thr Ile Glu Phe Thr Ser Tyr Gly Thr Phe Ser Ser Asp Gly
    385                 390                 395

AAA CAA TTT ACA CCA CCT TCT GGT TCT GCC ATT GAT TTA CAC CTC CCT    1307
Lys Gln Phe Thr Pro Pro Ser Gly Ser Ala Ile Asp Leu His Leu Pro
400                 405                 410

AAT TAT GTA GAT CTC AAC GCG CTA TTA GAT ATT AGC CTC GAT TCA CTA    1355
Asn Tyr Val Asp Leu Asn Ala Leu Leu Asp Ile Ser Leu Asp Ser Leu
415                 420                 425                 430

CTT AAT TAT GAC GTT CAG GGG CAG TTT GGC GGA TCT AAT CCG GTT GAT    1403
Leu Asn Tyr Asp Val Gln Gly Gln Phe Gly Gly Ser Asn Pro Val Asp
                435                 440                 445

AAT TTC AGT GGT CCC TAT GGT ATT TAT CTA TGG GAA ATC TTC TTC CAT    1451
Asn Phe Ser Gly Pro Tyr Gly Ile Tyr Leu Trp Glu Ile Phe Phe His
        450                 455                 460

ATT CCG TTC CTT GTT ACG GTC CGT ATG CAA ACC GAA CAA CGT TAC GAA    1499
Ile Pro Phe Leu Val Thr Val Arg Met Gln Thr Glu Gln Arg Tyr Glu
    465                 470                 475

GAC GCG GAC ACT TGG TAC AAA TAT ATT TTC CGC AGC GCC GGT TAT CGC    1547
Asp Ala Asp Thr Trp Tyr Lys Tyr Ile Phe Arg Ser Ala Gly Tyr Arg
        480                 485                 490

GAT GCT AAT GGC CAG CTC ATT ATG GAT GGC AGT AAA CCA CGT TAT TGG    1595
Asp Ala Asn Gly Gln Leu Ile Met Asp Gly Ser Lys Pro Arg Tyr Trp
495                 500                 505                 510

AAT GTG ATG CCA TTG CAA CTG GAT ACC GCA TGG GAT ACC ACA CAG CCC    1643
Asn Val Met Pro Leu Gln Leu Asp Thr Ala Trp Asp Thr Thr Gln Pro
                515                 520                 525

GCC ACC ACT GAT CCA GAT GTG ATC GCT ATG GCG GAC CCG ATG CAT TAC    1691
Ala Thr Thr Asp Pro Asp Val Ile Ala Met Ala Asp Pro Met His Tyr
        530                 535                 540

AAG CTG GCG ATA TTC CTG CAT ACC CTT GAT CTA TTG ATT GCC CGA GGC    1739
Lys Leu Ala Ile Phe Leu His Thr Leu Asp Leu Leu Ile Ala Arg Gly
            545                 550                 555

GAC AGC GCT TAC CGT CAA CTT GAA CGC GAT ACT CTA GTC GAA GCC AAA    1787
Asp Ser Ala Tyr Arg Gln Leu Glu Arg Asp Thr Leu Val Glu Ala Lys
        560                 565                 570

ATG TAC TAC ATT CAG GCA CAA CAG CTA CTG GGA CCG CGC CCT GAT ATC    1835
Met Tyr Tyr Ile Gln Ala Gln Gln Leu Leu Gly Pro Arg Pro Asp Ile
575                 580                 585                 590

CAT ACC ACC AAT ACT TGG CCA AAT CCC ACC TTG AGT AAA GAA GCT GGC    1883
His Thr Thr Asn Thr Trp Pro Asn Pro Thr Leu Ser Lys Glu Ala Gly
                595                 600                 605

GCT ATT GCC ACA CCG ACA TTC CTC AGT TCA CCG GAG GTG ATG ACG TTC    1931
Ala Ile Ala Thr Pro Thr Phe Leu Ser Ser Pro Glu Val Met Thr Phe
        610                 615                 620
```

```
GCT GCC TGG CTA AGC GCA GGC GAT ACC GCA AAT ATT GGC GAC GGT GAT        1979
Ala Ala Trp Leu Ser Ala Gly Asp Thr Ala Asn Ile Gly Asp Gly Asp
            625                 630                 635

TTC TTG CCA CCG TAC AAC GAT GTA CTA CTC GGT TAC TGG GAT AAA CTT        2027
Phe Leu Pro Pro Tyr Asn Asp Val Leu Leu Gly Tyr Trp Asp Lys Leu
        640                 645                 650

GAG TTA CGC CTA TAC AAC CTG CGC CAC AAT CTG AGT CTG GAT GGT CAA        2075
Glu Leu Arg Leu Tyr Asn Leu Arg His Asn Leu Ser Leu Asp Gly Gln
655                 660                 665                 670

CCG CTA AAT CTG CCA CTG TAT GCC ACG CCG GTA GAC CCG AAA ACC CTG        2123
Pro Leu Asn Leu Pro Leu Tyr Ala Thr Pro Val Asp Pro Lys Thr Leu
                675                 680                 685

CAA CGC CAG CAA GCC GGA GGG GAC GGT ACA GGC AGT AGT CCG GCT GGT        2171
Gln Arg Gln Gln Ala Gly Gly Asp Gly Thr Gly Ser Ser Pro Ala Gly
            690                 695                 700

GGT CAA GGC AGT GTT CAG GGC TGG CGC TAT CCG TTA TTG GTA GAA CGC        2219
Gly Gln Gly Ser Val Gln Gly Trp Arg Tyr Pro Leu Leu Val Glu Arg
        705                 710                 715

GCC CGC TCT GCC GTG AGT TTG TTG ACT CAG TTC GGC AAC AGC TTA CAA        2267
Ala Arg Ser Ala Val Ser Leu Leu Thr Gln Phe Gly Asn Ser Leu Gln
720                 725                 730

ACA ACG TTA GAA CAT CAG GAT AAT GAA AAA ATG ACG ATA CTG TTG CAG        2315
Thr Thr Leu Glu His Gln Asp Asn Glu Lys Met Thr Ile Leu Leu Gln
735                 740                 745                 750

ACT CAA CAG GAA GCC ATC CTG AAA CAT CAG CAC GAT ATA CAA CAA AAT        2363
Thr Gln Gln Glu Ala Ile Leu Lys His Gln His Asp Ile Gln Gln Asn
                755                 760                 765

AAT CTA AAA GGA TTA CAA CAC AGC CTG ACC GCA TTA CAG GCT AGC CGT        2411
Asn Leu Lys Gly Leu Gln His Ser Leu Thr Ala Leu Gln Ala Ser Arg
            770                 775                 780

GAT GGC GAC ACA TTG CGG CAA AAA CAT TAC AGC GAC CTG ATT AAC GGT        2459
Asp Gly Asp Thr Leu Arg Gln Lys His Tyr Ser Asp Leu Ile Asn Gly
        785                 790                 795

GGT CTA TCT GCG GCA GAA ATC GCC GGT CTG ACA CTA CGC AGC ACC GCC        2507
Gly Leu Ser Ala Ala Glu Ile Ala Gly Leu Thr Leu Arg Ser Thr Ala
800                 805                 810

ATG ATT ACC AAT GGC GTT GCA ACG GGA TTG CTG ATT GCC GGC GGA ATC        2555
Met Ile Thr Asn Gly Val Ala Thr Gly Leu Leu Ile Ala Gly Gly Ile
815                 820                 825                 830

GCC AAC GCG GTA CCT AAC GTC TTC GGG CTG GCT AAC GGT GGA TCG GAA        2603
Ala Asn Ala Val Pro Asn Val Phe Gly Leu Ala Asn Gly Gly Ser Glu
                835                 840                 845

TGG GGA GCG CCA TTA ATT GGC TCC GGG CAA GCA ACC CAA GTT GGC GCC        2651
Trp Gly Ala Pro Leu Ile Gly Ser Gly Gln Ala Thr Gln Val Gly Ala
            850                 855                 860

GGC ATC CAG GAT CAG AGC GCG GGC ATT TCA GAA GTG ACA GCA GGC TAT        2699
Gly Ile Gln Asp Gln Ser Ala Gly Ile Ser Glu Val Thr Ala Gly Tyr
        865                 870                 875

CAG CGT CGT CAG GAA GAA TGG GCA TTG CAA CGG GAT ATT GCT GAT AAC        2747
Gln Arg Arg Gln Glu Glu Trp Ala Leu Gln Arg Asp Ile Ala Asp Asn
880                 885                 890

GAA ATA ACC CAA CTG GAT GCC CAG ATA CAA AGC CTG CAA GAG CAA ATC        2795
Glu Ile Thr Gln Leu Asp Ala Gln Ile Gln Ser Leu Gln Glu Gln Ile
895                 900                 905                 910

ACG ATG GCA CAA AAA CAG ATC ACG CTC TCT GAA ACC GAA CAA GCG AAT        2843
Thr Met Ala Gln Lys Gln Ile Thr Leu Ser Glu Thr Glu Gln Ala Asn
                915                 920                 925

GCC CAA GCG ATT TAT GAC CTG CAA ACC ACT CGT TTT ACC GGG CAG GCA        2891
Ala Gln Ala Ile Tyr Asp Leu Gln Thr Thr Arg Phe Thr Gly Gln Ala
            930                 935                 940
```

```
CTG TAT AAC TGG ATG GCC GGT CGT CTC TCC GCG CTC TAT TAC CAA ATG      2939
Leu Tyr Asn Trp Met Ala Gly Arg Leu Ser Ala Leu Tyr Tyr Gln Met
            945                 950                 955

TAT GAT TCC ACT CTG CCA ATC TGT CTC CAG CCA AAA GCC GCA TTA GTA      2987
Tyr Asp Ser Thr Leu Pro Ile Cys Leu Gln Pro Lys Ala Ala Leu Val
        960                 965                 970

CAG GAA TTA GGC GAG AAA GAG AGC GAC AGT CTT TTC CAG GTT CCG GTG      3035
Gln Glu Leu Gly Glu Lys Glu Ser Asp Ser Leu Phe Gln Val Pro Val
975                 980                 985                 990

TGG AAT GAT CTG TGG CAA GGG CTG TTA GCA GGA GAA GGT TTA AGT TCA      3083
Trp Asn Asp Leu Trp Gln Gly Leu Leu Ala Gly Glu Gly Leu Ser Ser
            995                 1000                1005

GAG CTA CAG AAA CTG GAT GCC ATC TGG CTT GCA CGT GGT GGT ATT GGG      3131
Glu Leu Gln Lys Leu Asp Ala Ile Trp Leu Ala Arg Gly Gly Ile Gly
        1010                1015                1020

CTA GAA GCC ATC CGC ACC GTG TCG CTG GAT ACC CTG TTT GGC ACA GGG      3179
Leu Glu Ala Ile Arg Thr Val Ser Leu Asp Thr Leu Phe Gly Thr Gly
        1025                1030                1035

ACG TTA AGT GAA AAT ATC AAT AAA GTG CTT AAC GGG GAA ACG GTA TCT      3227
Thr Leu Ser Glu Asn Ile Asn Lys Val Leu Asn Gly Glu Thr Val Ser
        1040                1045                1050

CCA TCC GGT GGC GTC ACT CTG GCG CTG ACA GGG GAT ATC TTC CAA GCA      3275
Pro Ser Gly Gly Val Thr Leu Ala Leu Thr Gly Asp Ile Phe Gln Ala
1055                1060                1065                1070

ACA CTG GAT TTG AGT CAG CTA GGT TTG GAT AAC TCT TAC AAC TTG GGT      3323
Thr Leu Asp Leu Ser Gln Leu Gly Leu Asp Asn Ser Tyr Asn Leu Gly
            1075                1080                1085

AAC GAG AAG AAA CGT CGT ATT AAA CGT ATC GCC GTC ACC CTG CCA ACA      3371
Asn Glu Lys Lys Arg Arg Ile Lys Arg Ile Ala Val Thr Leu Pro Thr
            1090                1095                1100

CTT CTG GGG CCA TAT CAA GAT CTT GAA GCC ACA CTG GTA ATG GGT GCG      3419
Leu Leu Gly Pro Tyr Gln Asp Leu Glu Ala Thr Leu Val Met Gly Ala
            1105                1110                1115

GAA ATC GCC GCC TTA TCA CAC GGT GTG AAT GAC GGA GGC CGG TTT GTT      3467
Glu Ile Ala Ala Leu Ser His Gly Val Asn Asp Gly Gly Arg Phe Val
        1120                1125                1130

ACC GAC TTT AAC GAC AGC CGT TTT CTG CCT TTT GAA GGT CGA GAT GCA      3515
Thr Asp Phe Asn Asp Ser Arg Phe Leu Pro Phe Glu Gly Arg Asp Ala
1135                1140                1145                1150

ACA ACC GGC ACA CTG GAG CTC AAT ATT TTC CAT GCG GGT AAA GAG GGA      3563
Thr Thr Gly Thr Leu Glu Leu Asn Ile Phe His Ala Gly Lys Glu Gly
                1155                1160                1165

ACG CAA CAC GAG TTG GTC GCG AAT CTG AGT GAC ATC ATT GTG CAT CTG      3611
Thr Gln His Glu Leu Val Ala Asn Leu Ser Asp Ile Ile Val His Leu
        1170                1175                1180

AAT TAC ATC ATT CGA GAC GCG TAA ATTTCTTTTC TTTGTCGATT ACAGGTCCCT     3665
Asn Tyr Ile Ile Arg Asp Ala  *
        1185                1190

ATCAGGGGCC TGTTATTAAG GAGTACTTTA TGCAGGATTC ACCAGAAGTA TCGATTACAA    3725

CGCTGTCACT TCCCAAAGGT GGCGGTGCTA TCAATGGCAT GGGAGAAGCA CTGAATGCTG    3785

CCGGCCCTGA TGGAATGGCC TCCCTATCTC TGCCATTACC CCTTTCGACC GGCAGAGGGA    3845

CGGCTCCTGG ATTATCGCTG ATTTACAGCA ACAGTGCAGG TAATGGGCCT TTCGGCATCG    3905

GCTGGCAATG CGGTGTTATG TCCATTAGCC GACGCACCCA ACATGGCATT CCACAATACG    3965

GTAATGACGA CACGTTCCTA TCCCCACAAG GCGAGGTCAT GAATATCGCC CTGAATGACC    4025

AAGGGCAACC TGATATCCGT CAAGACGTTA AAACGCTGCA AGGCGTTACC TTGCCAATTT    4085
```

```
CCTATACCGT GACCCGCTAT CAAGCCCGCC AGATCCTGGA TTTCAGTAAA ATCGAATACT    4145

GGCAACCTGC CTCCGGTCAA GAAGGACGCG CTTTCTGGCT GATATCGACA CCGGACGGGC    4205

ATCTACACAT CTTAGGGAAA ACCGCGCAGG CTTGTCTGGC AAATCCGCAA AATGACCAAC    4265

AAATCGCCCA GTGGTTGCTG AAGAAACTG TGACGCCAGC CGGTGAACAT GTCAGCTATC     4325

AATATCGAGC CGAAGATGAA GCCCATTGTG ACGACAATGA AAAACCGCT CATCCCAATG     4385

TTACCGCACA GCGCTATCTG GTACAGGTGA ACTACAGGCA ACATCAAACC ACAAGCCAGC    4445

CTGTTCGTAC TGGATAACGC ACCTCCCGCA CCGGAAGAGT GGCTGTTTCA TCTGGTCTTT    4505

GACCACGGTG AGCGCGTACC TCACTTCATA CCGTGCCAAC ATGGGATGCA GGTACAGCGC    4565

AATGGTCTGT ACGCCCGGAT ATCTTCTCTC GCTATGAATA TGGTTTTGAA GTGCGTACTC    4625

GCCGCTTATG TCAACAAGTG CTGATGTTTC ACCGCACCGC GCTCATGGCC GGAGAAGCCA    4685

GTACCAATGA CGCCCCGGAA CTGGTTGGAC GCTTAATACT GGAATATGAC AAAAACGCCA    4745

GCGTCACCAC GTTGATTACC ATCCGTCAAT TAAGCCATGA ATCGACGGG AGGCCAGTCA     4805

CCCAGCCACC ACTAGAACTA GCCTGGCAAC GGTTTGATCT GGAGAAAATC CCGACATGGC    4865

AACGCTTTGA CGCACTAGAT AATTTTAACT CGCAGCAACG TTATCAACTG GTTGATCTGC    4925

GGGGAGAAGG GTTGCCAGGT ATGCTGTATC AAGATCGAGG CGCTTGGTGG TATAAAGCTC    4985

CGCAACGTCA GGAAGACGGA GACAGCAATG CCGTCACTTA CGACAAAATC GCCCCACTGC    5045

CTACCCTACC CAATTTGCAG GATAATGCCT CATTGATGGA TATCAACGGA GACGGCCAAC    5105

TGGATTGGGT TGTTACCGCC TCCGGTATTC GCGGATACCA TAGTCAGCAA CCCGATGGAA    5165

AGTGGACGCA CTTTACGCCA ATCAATGCCT TGCCCGTGGA ATATTTTCAT CCAAGCATCC    5225

AGTTCGCTGA CCTTACCGGG GCAGGCTTAT CTGATTTAGT GTTGATCGGG CCGAAAAGCG    5285

TGCGTCTATA TGCCAACCAG CGAAACGGCT GGCGTAAAGG AGAAGATGTC CCCCAATCCA    5345

CAGGTATCAC CCTGCCTGTC ACAGGGACCG ATGCCCGCAA ACTGGTGGCT TTCAGTGATA    5405

TGCTCGGTTC CGGTCAACAA CATCTGGTGG AAATCAAGGG TAATCGCGTC ACCTGTTGGC    5465

CGAATCTAGG GCATGGCCGT TTCGGTCAAC CACTAACTCT GTCAGGATTT AGCCAGCCCG    5525

AAAATAGCTT CAATCCCGAA CGGCTGTTTC TGGCGGATAT CGACGGCTCC GGCACCACCG    5585

ACCTTATCTA TGCGCAATCC GGCTCTTTGC TCATTTATCT CAACCAAAGT GGTAATCAGT    5645

TTGATGCCCC GTTGACATTA GCGTTGCCAG AAGGCGTACA ATTTGACAAC ACTTGCCAAC    5705

TTCAAGTCGC CGATATTCAG GGATTAGGGA TAGCCAGCTT GATTCTGACT GTGCCACATA    5765

TCGCGCCACA TCACTGGCGT TGTGACCTGT CACTGACCAA ACCCTGGTTG TTGAATGTAA    5825

TGAACAATAA CCGGGGCGCA CATCACACGC TACATTATCG TAGTTCCGCG CAATTCTGGT    5885

TGGATGAAAA ATTACAGCTC ACCAAAGCAG GCAAATCTCC GGCTTGTTAT CTGCCGTTTC    5945

CAATGCATTT GCTATGGTAT ACCGAAATTC AGGATGAAAT CAGCGGCAAC CGGCTCACCA    6005

GTGAAGTCAA CTACAGCCAC GGCGTCTGGG ATGGTAAAGA GCGGGAATTC               6055
```

(2) INFORMATION FOR SEQ ID NO:26:

(i) SEQUENCE CHARACTERISTICS:
        (A) LENGTH: 1189 amino acids
        (B) TYPE: amino acid
        (D) TOPOLOGY: linear (ii) MOLECULE TYPE: protein (xi) SEQUENCE DESCRIPTION: SEQ ID NO:26:

Met Ser Glu Ser Leu Phe Thr Gln Thr Leu Lys Glu Ala Arg Arg Asp

-continued

```
1               5                    10                   15
Ala Leu Val Ala His Tyr Ile Ala Thr Gln Val Pro Ala Asp Leu Lys
                20                  25                  30
Glu Ser Ile Gln Thr Ala Asp Asp Leu Tyr Glu Tyr Leu Leu Leu Asp
            35                  40                  45
Thr Lys Ile Ser Asp Leu Val Thr Thr Ser Pro Leu Ser Glu Ala Ile
50                  55                  60
Gly Ser Leu Gln Leu Phe Ile His Arg Ala Ile Glu Gly Tyr Asp Gly
65                      70                  75                  80
Thr Leu Ala Asp Ser Ala Lys Pro Tyr Phe Ala Asp Glu Gln Phe Leu
                85                  90                  95
Tyr Asn Trp Asp Ser Phe Asn His Arg Tyr Ser Thr Trp Ala Gly Lys
            100                 105                 110
Glu Arg Leu Lys Phe Tyr Ala Gly Asp Tyr Ile Asp Pro Thr Leu Arg
            115                 120                 125
Leu Asn Lys Thr Glu Ile Phe Thr Ala Phe Glu Gln Gly Ile Ser Gln
130                 135                 140
Gly Lys Leu Lys Ser Glu Leu Val Glu Ser Lys Leu Arg Asp Tyr Leu
145                 150                 155                 160
Ile Ser Tyr Asp Thr Leu Ala Thr Leu Asp Tyr Ile Thr Ala Cys Gln
                165                 170                 175
Gly Lys Asp Asn Lys Thr Ile Phe Phe Ile Gly Arg Thr Gln Asn Ala
            180                 185                 190
Pro Tyr Ala Phe Tyr Trp Arg Lys Leu Thr Leu Val Thr Asp Gly Gly
        195                 200                 205
Lys Leu Lys Pro Asp Gln Trp Ser Glu Trp Arg Ala Ile Asn Ala Gly
        210                 215                 220
Ile Ser Glu Ala Tyr Ser Gly His Val Glu Pro Phe Trp Glu Asn Asn
225                 230                 235                 240
Lys Leu His Ile Arg Trp Phe Thr Ile Ser Lys Glu Asp Lys Ile Asp
                245                 250                 255
Phe Val Tyr Lys Asn Ile Trp Val Met Ser Ser Asp Tyr Ser Trp Ala
            260                 265                 270
Ser Lys Lys Lys Ile Leu Glu Leu Ser Phe Thr Asp Tyr Asn Arg Val
            275                 280                 285
Gly Ala Thr Gly Ser Ser Pro Thr Glu Val Ala Ser Gln Tyr Gly
290                 295                 300
Ser Asp Ala Gln Met Asn Ile Ser Asp Asp Gly Thr Val Leu Ile Phe
305                 310                 315                 320
Gln Asn Ala Gly Gly Ala Thr Pro Ser Thr Gly Val Thr Leu Cys Tyr
                325                 330                 335
Asp Ser Gly Asn Val Ile Lys Asn Leu Ser Ser Thr Gly Ser Ala Asn
            340                 345                 350
Leu Ser Ser Lys Asp Tyr Ala Thr Thr Lys Leu Arg Met Cys His Gly
            355                 360                 365
Gln Ser Tyr Asn Asp Asn Tyr Cys Asn Phe Thr Leu Ser Ile Asn
        370                 375                 380
Thr Ile Glu Phe Thr Ser Tyr Gly Thr Phe Ser Ser Asp Gly Lys Gln
385                 390                 395                 400
Phe Thr Pro Pro Ser Gly Ser Ala Ile Asp Leu His Leu Pro Asn Tyr
                405                 410                 415
Val Asp Leu Asn Ala Leu Leu Asp Ile Ser Leu Asp Ser Leu Leu Asn
            420                 425                 430
```

```
Tyr Asp Val Gln Gly Gln Phe Gly Gly Ser Asn Pro Val Asp Asn Phe
        435                 440                 445

Ser Gly Pro Tyr Gly Ile Tyr Leu Trp Glu Ile Phe Phe His Ile Pro
450                 455                 460

Phe Leu Val Thr Val Arg Met Gln Thr Glu Gln Arg Tyr Glu Asp Ala
465                 470                 475                 480

Asp Thr Trp Tyr Lys Tyr Ile Phe Arg Ser Ala Gly Tyr Arg Asp Ala
                485                 490                 495

Asn Gly Gln Leu Ile Met Asp Gly Ser Lys Pro Arg Tyr Trp Asn Val
            500                 505                 510

Met Pro Leu Gln Leu Asp Thr Ala Trp Asp Thr Thr Gln Pro Ala Thr
        515                 520                 525

Thr Asp Pro Asp Val Ile Ala Met Ala Asp Pro Met His Tyr Lys Leu
    530                 535                 540

Ala Ile Phe Leu His Thr Leu Asp Leu Leu Ile Ala Arg Gly Asp Ser
545                 550                 555                 560

Ala Tyr Arg Gln Leu Glu Arg Asp Thr Leu Val Glu Ala Lys Met Tyr
                565                 570                 575

Tyr Ile Gln Ala Gln Gln Leu Leu Gly Pro Arg Pro Asp Ile His Thr
            580                 585                 590

Thr Asn Thr Trp Pro Asn Pro Thr Leu Ser Lys Glu Ala Gly Ala Ile
        595                 600                 605

Ala Thr Pro Thr Phe Leu Ser Ser Pro Glu Val Met Thr Phe Ala Ala
    610                 615                 620

Trp Leu Ser Ala Gly Asp Thr Ala Asn Ile Gly Asp Gly Asp Phe Leu
625                 630                 635                 640

Pro Pro Tyr Asn Asp Val Leu Leu Gly Tyr Trp Asp Lys Leu Glu Leu
                645                 650                 655

Arg Leu Tyr Asn Leu Arg His Asn Leu Ser Leu Asp Gly Gln Pro Leu
            660                 665                 670

Asn Leu Pro Leu Tyr Ala Thr Pro Val Asp Pro Lys Thr Leu Gln Arg
        675                 680                 685

Gln Gln Ala Gly Gly Asp Gly Thr Gly Ser Ser Pro Ala Gly Gly Gln
    690                 695                 700

Gly Ser Val Gln Gly Trp Arg Tyr Pro Leu Leu Val Glu Arg Ala Arg
705                 710                 715                 720

Ser Ala Val Ser Leu Leu Thr Gln Phe Gly Asn Ser Leu Gln Thr Thr
                725                 730                 735

Leu Glu His Gln Asp Asn Glu Lys Met Thr Ile Leu Leu Gln Thr Gln
            740                 745                 750

Gln Glu Ala Ile Leu Lys His Gln His Asp Ile Gln Gln Asn Asn Leu
        755                 760                 765

Lys Gly Leu Gln His Ser Leu Thr Ala Leu Gln Ala Ser Arg Asp Gly
    770                 775                 780

Asp Thr Leu Arg Gln Lys His Tyr Ser Asp Leu Ile Asn Gly Gly Leu
785                 790                 795                 800

Ser Ala Ala Glu Ile Ala Gly Leu Thr Leu Arg Ser Thr Ala Met Ile
                805                 810                 815

Thr Asn Gly Val Ala Thr Gly Leu Leu Ile Ala Gly Ile Ala Asn
            820                 825                 830

Ala Val Pro Asn Val Phe Gly Leu Ala Asn Gly Gly Ser Glu Trp Gly
        835                 840                 845
```

```
Ala Pro Leu Ile Gly Ser Gly Gln Ala Thr Gln Val Gly Ala Gly Ile
    850                 855                 860

Gln Asp Gln Ser Ala Gly Ile Ser Glu Val Thr Ala Gly Tyr Gln Arg
865                 870                 875                 880

Arg Gln Glu Glu Trp Ala Leu Gln Arg Asp Ile Ala Asp Asn Glu Ile
                885                 890                 895

Thr Gln Leu Asp Ala Gln Ile Gln Ser Leu Gln Glu Gln Ile Thr Met
            900                 905                 910

Ala Gln Lys Gln Ile Thr Leu Ser Glu Thr Glu Gln Ala Asn Ala Gln
        915                 920                 925

Ala Ile Tyr Asp Leu Gln Thr Thr Arg Phe Thr Gly Gln Ala Leu Tyr
    930                 935                 940

Asn Trp Met Ala Gly Arg Leu Ser Ala Leu Tyr Tyr Gln Met Tyr Asp
945                 950                 955                 960

Ser Thr Leu Pro Ile Cys Leu Gln Pro Lys Ala Ala Leu Val Gln Glu
                965                 970                 975

Leu Gly Glu Lys Glu Ser Asp Ser Leu Phe Gln Val Pro Val Trp Asn
            980                 985                 990

Asp Leu Trp Gln Gly Leu Leu Ala Gly Glu Gly Leu Ser Ser Glu Leu
        995                 1000                1005

Gln Lys Leu Asp Ala Ile Trp Leu Ala Arg Gly Ile Gly Leu Glu
    1010                1015                1020

Ala Ile Arg Thr Val Ser Leu Asp Thr Leu Phe Gly Thr Gly Thr Leu
1025                1030                1035                1040

Ser Glu Asn Ile Asn Lys Val Leu Asn Gly Glu Thr Val Ser Pro Ser
                1045                1050                1055

Gly Gly Val Thr Leu Ala Leu Thr Gly Asp Ile Phe Gln Ala Thr Leu
            1060                1065                1070

Asp Leu Ser Gln Leu Gly Leu Asp Asn Ser Tyr Asn Leu Gly Asn Glu
        1075                1080                1085

Lys Lys Arg Arg Ile Lys Arg Ile Ala Val Thr Leu Pro Thr Leu Leu
    1090                1095                1100

Gly Pro Tyr Gln Asp Leu Glu Ala Thr Leu Val Met Gly Ala Glu Ile
1105                1110                1115                1120

Ala Ala Leu Ser His Gly Val Asn Asp Gly Gly Arg Phe Val Thr Asp
                1125                1130                1135

Phe Asn Asp Ser Arg Phe Leu Pro Phe Glu Gly Arg Asp Ala Thr Thr
            1140                1145                1150

Gly Thr Leu Glu Leu Asn Ile Phe His Ala Gly Lys Glu Gly Thr Gln
        1155                1160                1165

His Glu Leu Val Ala Asn Leu Ser Asp Ile Ile Val His Leu Asn Tyr
    1170                1175                1180

Ile Ile Arg Asp Ala
1185

(2) INFORMATION FOR SEQ ID NO:27:

(i) SEQUENCE CHARACTERISTICS:
        (A) LENGTH: 1881 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
```

(B) LOCATION: 1..1881

(xi) SEQUENCE DESCRIPTION: SEQ ID NO:27:

| | | | | | | | | | | | | | | | | |
|---|---|---|---|---|---|---|---|---|---|---|---|---|---|---|---|---|
| ATG | TCT | GAA | TCT | TTA | TTT | ACA | CAA | ACG | TTG | AAA | GAA | GCG | CGC | CGT | GAT | 48 |
| Met | Ser | Glu | Ser | Leu | Phe | Thr | Gln | Thr | Leu | Lys | Glu | Ala | Arg | Arg | Asp | |
| 1 | | | | 5 | | | | | 10 | | | | | 15 | | |
| GCA | TTG | GTT | GCT | CAT | TAT | ATT | GCT | ACT | CAG | GTG | CCC | GCA | GAT | TTA | AAA | 96 |
| Ala | Leu | Val | Ala | His | Tyr | Ile | Ala | Thr | Gln | Val | Pro | Ala | Asp | Leu | Lys | |
| | | | 20 | | | | | 25 | | | | | 30 | | | |
| GAG | AGT | ATC | CAG | ACC | GCG | GAT | GAT | CTG | TAC | GAA | TAT | CTG | TTG | CTG | GAT | 144 |
| Glu | Ser | Ile | Gln | Thr | Ala | Asp | Asp | Leu | Tyr | Glu | Tyr | Leu | Leu | Leu | Asp | |
| | | 35 | | | | | 40 | | | | | 45 | | | | |
| ACC | AAA | ATT | AGC | GAT | CTG | GTT | ACT | ACT | TCA | CCG | CTG | TCC | GAA | GCG | ATT | 192 |
| Thr | Lys | Ile | Ser | Asp | Leu | Val | Thr | Thr | Ser | Pro | Leu | Ser | Glu | Ala | Ile | |
| | 50 | | | | | 55 | | | | | 60 | | | | | |
| GGC | AGT | CTG | CAA | TTG | TTT | ATT | CAT | CGT | GCG | ATA | GAG | GGC | TAT | GAC | GGC | 240 |
| Gly | Ser | Leu | Gln | Leu | Phe | Ile | His | Arg | Ala | Ile | Glu | Gly | Tyr | Asp | Gly | |
| 65 | | | | | 70 | | | | | 75 | | | | | 80 | |
| ACG | CTG | GCA | GAC | TCA | GCA | AAA | CCC | TAT | TTT | GCC | GAT | GAA | CAG | TTT | TTA | 288 |
| Thr | Leu | Ala | Asp | Ser | Ala | Lys | Pro | Tyr | Phe | Ala | Asp | Glu | Gln | Phe | Leu | |
| | | | | 85 | | | | | 90 | | | | | 95 | | |
| TAT | AAC | TGG | GAT | AGT | TTT | AAC | CAC | CGT | TAT | AGC | ACT | TGG | GCT | GGC | AAG | 336 |
| Tyr | Asn | Trp | Asp | Ser | Phe | Asn | His | Arg | Tyr | Ser | Thr | Trp | Ala | Gly | Lys | |
| | | | 100 | | | | | 105 | | | | | 110 | | | |
| GAA | CGG | TTG | AAA | TTC | TAT | GCC | GGG | GAT | TAT | ATT | GAT | CCA | ACA | TTG | CGA | 384 |
| Glu | Arg | Leu | Lys | Phe | Tyr | Ala | Gly | Asp | Tyr | Ile | Asp | Pro | Thr | Leu | Arg | |
| | | 115 | | | | | 120 | | | | | 125 | | | | |
| TTG | AAT | AAG | ACC | GAG | ATA | TTT | ACC | GCA | TTT | GAA | CAA | GGT | ATT | TCT | CAA | 432 |
| Leu | Asn | Lys | Thr | Glu | Ile | Phe | Thr | Ala | Phe | Glu | Gln | Gly | Ile | Ser | Gln | |
| | 130 | | | | | 135 | | | | | 140 | | | | | |
| GGG | AAA | TTA | AAA | AGT | GAA | TTA | GTC | GAA | TCT | AAA | TTA | CGT | GAT | TAT | CTA | 480 |
| Gly | Lys | Leu | Lys | Ser | Glu | Leu | Val | Glu | Ser | Lys | Leu | Arg | Asp | Tyr | Leu | |
| 145 | | | | | 150 | | | | | 155 | | | | | 160 | |
| ATT | AGT | TAT | GAC | ACT | TTA | GCC | ACC | CTT | GAT | TAT | ATT | ACT | GCC | TGC | CAA | 528 |
| Ile | Ser | Tyr | Asp | Thr | Leu | Ala | Thr | Leu | Asp | Tyr | Ile | Thr | Ala | Cys | Gln | |
| | | | | 165 | | | | | 170 | | | | | 175 | | |
| GGC | AAA | GAT | AAT | AAA | ACC | ATC | TTC | TTT | ATT | GGC | CGT | ACA | CAG | AAT | GCA | 576 |
| Gly | Lys | Asp | Asn | Lys | Thr | Ile | Phe | Phe | Ile | Gly | Arg | Thr | Gln | Asn | Ala | |
| | | | 180 | | | | | 185 | | | | | 190 | | | |
| CCC | TAT | GCA | TTT | TAT | TGG | CGA | AAA | TTA | ACT | TTA | GTC | ACT | GAT | GGC | GGT | 624 |
| Pro | Tyr | Ala | Phe | Tyr | Trp | Arg | Lys | Leu | Thr | Leu | Val | Thr | Asp | Gly | Gly | |
| | | 195 | | | | | 200 | | | | | 205 | | | | |
| AAG | TTG | AAA | CCA | GAT | CAA | TGG | TCA | GAG | TGG | CGA | GCA | ATT | AAT | GCC | GGG | 672 |
| Lys | Leu | Lys | Pro | Asp | Gln | Trp | Ser | Glu | Trp | Arg | Ala | Ile | Asn | Ala | Gly | |
| | 210 | | | | | 215 | | | | | 220 | | | | | |
| ATT | AGT | GAG | GCA | TAT | TCA | GGG | CAT | GTC | GAG | CCT | TTC | TGG | GAA | AAT | AAC | 720 |
| Ile | Ser | Glu | Ala | Tyr | Ser | Gly | His | Val | Glu | Pro | Phe | Trp | Glu | Asn | Asn | |
| 225 | | | | | 230 | | | | | 235 | | | | | 240 | |
| AAG | CTG | CAC | ATC | CGT | TGG | TTT | ACT | ATC | TCG | AAA | GAA | GAT | AAA | ATA | GAT | 768 |
| Lys | Leu | His | Ile | Arg | Trp | Phe | Thr | Ile | Ser | Lys | Glu | Asp | Lys | Ile | Asp | |
| | | | | 245 | | | | | 250 | | | | | 255 | | |
| TTT | GTT | TAT | AAA | AAC | ATC | TGG | GTG | ATG | AGT | AGC | GAT | TAT | AGC | TGG | GCA | 816 |
| Phe | Val | Tyr | Lys | Asn | Ile | Trp | Val | Met | Ser | Ser | Asp | Tyr | Ser | Trp | Ala | |
| | | | 260 | | | | | 265 | | | | | 270 | | | |
| TCA | AAG | AAA | AAA | ATC | TTG | GAA | CTT | TCT | TTT | ACT | GAC | TAC | AAT | AGA | GTT | 864 |
| Ser | Lys | Lys | Lys | Ile | Leu | Glu | Leu | Ser | Phe | Thr | Asp | Tyr | Asn | Arg | Val | |
| | | 275 | | | | | 280 | | | | | 285 | | | | |
| GGA | GCA | ACA | GGA | TCA | TCA | AGC | CCG | ACT | GAA | GTA | GCT | TCA | CAA | TAT | GGT | 912 |
| Gly | Ala | Thr | Gly | Ser | Ser | Ser | Pro | Thr | Glu | Val | Ala | Ser | Gln | Tyr | Gly | |
| | 290 | | | | | 295 | | | | | 300 | | | | | |

```
TCT GAT GCT CAG ATG AAT ATT TCT GAT GAT GGG ACT GTA CTT ATT TTT      960
Ser Asp Ala Gln Met Asn Ile Ser Asp Asp Gly Thr Val Leu Ile Phe
305                 310                 315                 320

CAG AAT GCC GGC GGA GCT ACT CCC AGT ACT GGA GTG ACG TTA TGT TAT     1008
Gln Asn Ala Gly Gly Ala Thr Pro Ser Thr Gly Val Thr Leu Cys Tyr
                325                 330                 335

GAC TCT GGC AAC GTG ATT AAG AAC CTA TCT AGT ACA GGA AGT GCA AAT     1056
Asp Ser Gly Asn Val Ile Lys Asn Leu Ser Ser Thr Gly Ser Ala Asn
            340                 345                 350

TTA TCG TCA AAG GAT TAT GCC ACA ACT AAA TTA CGC ATG TGT CAT GGA     1104
Leu Ser Ser Lys Asp Tyr Ala Thr Thr Lys Leu Arg Met Cys His Gly
        355                 360                 365

CAA AGT TAC AAT GAT AAT AAC TAC TGC AAT TTT ACA CTC TCT ATT AAT     1152
Gln Ser Tyr Asn Asp Asn Asn Tyr Cys Asn Phe Thr Leu Ser Ile Asn
370                 375                 380

ACA ATA GAA TTC ACC TCC TAC GGC ACA TTC TCA TCA GAT GGA AAA CAA     1200
Thr Ile Glu Phe Thr Ser Tyr Gly Thr Phe Ser Ser Asp Gly Lys Gln
385                 390                 395                 400

TTT ACA CCA CCT TCT GGT TCT GCC ATT GAT TTA CAC CTC CCT AAT TAT     1248
Phe Thr Pro Pro Ser Gly Ser Ala Ile Asp Leu His Leu Pro Asn Tyr
                405                 410                 415

GTA GAT CTC AAC GCG CTA TTA GAT ATT AGC CTC GAT TCA CTA CTT AAT     1296
Val Asp Leu Asn Ala Leu Leu Asp Ile Ser Leu Asp Ser Leu Leu Asn
            420                 425                 430

TAT GAC GTT CAG GGG CAG TTT GGC GGA TCT AAT CCG GTT GAT AAT TTC     1344
Tyr Asp Val Gln Gly Gln Phe Gly Gly Ser Asn Pro Val Asp Asn Phe
        435                 440                 445

AGT GGT CCC TAT GGT ATT TAT CTA TGG GAA ATC TTC TTC CAT ATT CCG     1392
Ser Gly Pro Tyr Gly Ile Tyr Leu Trp Glu Ile Phe Phe His Ile Pro
450                 455                 460

TTC CTT GTT ACG GTC CGT ATG CAA ACC GAA CAA CGT TAC GAA GAC GCG     1440
Phe Leu Val Thr Val Arg Met Gln Thr Glu Gln Arg Tyr Glu Asp Ala
465                 470                 475                 480

GAC ACT TGG TAC AAA TAT ATT TTC CGC AGC GCC GGT TAT CGC GAT GCT     1488
Asp Thr Trp Tyr Lys Tyr Ile Phe Arg Ser Ala Gly Tyr Arg Asp Ala
                485                 490                 495

AAT GGC CAG CTC ATT ATG GAT GGC AGT AAA CCA CGT TAT TGG AAT GTG     1536
Asn Gly Gln Leu Ile Met Asp Gly Ser Lys Pro Arg Tyr Trp Asn Val
            500                 505                 510

ATG CCA TTG CAA CTG GAT ACC GCA TGG GAT ACC ACA CAG CCC GCC ACC     1584
Met Pro Leu Gln Leu Asp Thr Ala Trp Asp Thr Thr Gln Pro Ala Thr
        515                 520                 525

ACT GAT CCA GAT GTG ATC GCT ATG GCG GAC CCG ATG CAT TAC AAG CTG     1632
Thr Asp Pro Asp Val Ile Ala Met Ala Asp Pro Met His Tyr Lys Leu
530                 535                 540

GCG ATA TTC CTG CAT ACC CTT GAT CTA TTG ATT GCC CGA GGC GAC AGC     1680
Ala Ile Phe Leu His Thr Leu Asp Leu Leu Ile Ala Arg Gly Asp Ser
545                 550                 555                 560

GCT TAC CGT CAA CTT GAA CGC GAT ACT CTA GTC GAA GCC AAA ATG TAC     1728
Ala Tyr Arg Gln Leu Glu Arg Asp Thr Leu Val Glu Ala Lys Met Tyr
                565                 570                 575

TAC ATT CAG GCA CAA CAG CTA CTG GGA CCG CGC CCT GAT ATC CAT ACC     1776
Tyr Ile Gln Ala Gln Gln Leu Leu Gly Pro Arg Pro Asp Ile His Thr
            580                 585                 590

ACC AAT ACT TGG CCA AAT CCC ACC TTG AGT AAA GAA GCT GGC GCT ATT     1824
Thr Asn Thr Trp Pro Asn Pro Thr Leu Ser Lys Glu Ala Gly Ala Ile
        595                 600                 605

GCC ACA CCG ACA TTC CTC AGT TCA CCG GAG GTG ATG ACG TTC GCT GCC     1872
Ala Thr Pro Thr Phe Leu Ser Ser Pro Glu Val Met Thr Phe Ala Ala
```

```
                610              615              620
TGG CTA AGC                                                                1881
Trp Leu Ser
625
```

(2) INFORMATION FOR SEQ ID NO:28:

(i) SEQUENCE CHARACTERISTICS:
        (A) LENGTH: 627 amino acids
        (B) TYPE: amino acid
        (D) TOPOLOGY: linear (ii) MOLECULE TYPE: protein (xi) SEQUENCE DESCRIPTION: SEQ ID NO:28:

```
Met Ser Glu Ser Leu Phe Thr Gln Thr Leu Lys Glu Ala Arg Arg Asp
1               5                  10                  15

Ala Leu Val Ala His Tyr Ile Ala Thr Gln Val Pro Ala Asp Leu Lys
            20                  25                  30

Glu Ser Ile Gln Thr Ala Asp Asp Leu Tyr Glu Tyr Leu Leu Leu Asp
        35                  40                  45

Thr Lys Ile Ser Asp Leu Val Thr Thr Ser Pro Leu Ser Glu Ala Ile
50                  55                  60

Gly Ser Leu Gln Leu Phe Ile His Arg Ala Ile Glu Gly Tyr Asp Gly
65                  70                  75                  80

Thr Leu Ala Asp Ser Ala Lys Pro Tyr Phe Ala Asp Glu Gln Phe Leu
                85                  90                  95

Tyr Asn Trp Asp Ser Phe Asn His Arg Tyr Ser Thr Trp Ala Gly Lys
            100                 105                 110

Glu Arg Leu Lys Phe Tyr Ala Gly Asp Tyr Ile Asp Pro Thr Leu Arg
        115                 120                 125

Leu Asn Lys Thr Glu Ile Phe Thr Ala Phe Glu Gln Gly Ile Ser Gln
    130                 135                 140

Gly Lys Leu Lys Ser Glu Leu Val Glu Ser Lys Leu Arg Asp Tyr Leu
145                 150                 155                 160

Ile Ser Tyr Asp Thr Leu Ala Thr Leu Asp Tyr Ile Thr Ala Cys Gln
                165                 170                 175

Gly Lys Asp Asn Lys Thr Ile Phe Phe Ile Gly Arg Thr Gln Asn Ala
            180                 185                 190

Pro Tyr Ala Phe Tyr Trp Arg Lys Leu Thr Leu Val Thr Asp Gly Gly
        195                 200                 205

Lys Leu Lys Pro Asp Gln Trp Ser Glu Trp Arg Ala Ile Asn Ala Gly
    210                 215                 220

Ile Ser Glu Ala Tyr Ser Gly His Val Glu Pro Phe Trp Glu Asn Asn
225                 230                 235                 240

Lys Leu His Ile Arg Trp Phe Thr Ile Ser Lys Glu Asp Lys Ile Asp
                245                 250                 255

Phe Val Tyr Lys Asn Ile Trp Val Met Ser Ser Asp Tyr Ser Trp Ala
            260                 265                 270

Ser Lys Lys Lys Ile Leu Glu Leu Ser Phe Thr Asp Tyr Asn Arg Val
        275                 280                 285

Gly Ala Thr Gly Ser Ser Pro Thr Glu Val Ala Ser Gln Tyr Gly
    290                 295                 300

Ser Asp Ala Gln Met Asn Ile Ser Asp Asp Gly Thr Val Leu Ile Phe
305                 310                 315                 320

Gln Asn Ala Gly Gly Ala Thr Pro Ser Thr Gly Val Thr Leu Cys Tyr
```

-continued

```
                        325                 330                 335
Asp Ser Gly Asn Val Ile Lys Asn Leu Ser Ser Thr Gly Ser Ala Asn
            340                 345                 350
Leu Ser Ser Lys Asp Tyr Ala Thr Thr Lys Leu Arg Met Cys His Gly
        355                 360                 365
Gln Ser Tyr Asn Asp Asn Asn Tyr Cys Asn Phe Thr Leu Ser Ile Asn
    370                 375                 380
Thr Ile Glu Phe Thr Ser Tyr Gly Thr Phe Ser Ser Asp Gly Lys Gln
385                 390                 395                 400
Phe Thr Pro Pro Ser Gly Ser Ala Ile Asp Leu His Leu Pro Asn Tyr
                405                 410                 415
Val Asp Leu Asn Ala Leu Leu Asp Ile Ser Leu Asp Ser Leu Leu Asn
            420                 425                 430
Tyr Asp Val Gln Gly Gln Phe Gly Gly Ser Asn Pro Val Asp Asn Phe
        435                 440                 445
Ser Gly Pro Tyr Gly Ile Tyr Leu Trp Glu Ile Phe His Ile Pro
    450                 455                 460
Phe Leu Val Thr Val Arg Met Gln Thr Glu Gln Arg Tyr Glu Asp Ala
465                 470                 475                 480
Asp Thr Trp Tyr Lys Tyr Ile Phe Arg Ser Ala Gly Tyr Arg Asp Ala
                485                 490                 495
Asn Gly Gln Leu Ile Met Asp Gly Ser Lys Pro Arg Tyr Trp Asn Val
            500                 505                 510
Met Pro Leu Gln Leu Asp Thr Ala Trp Asp Thr Thr Gln Pro Ala Thr
        515                 520                 525
Thr Asp Pro Asp Val Ile Ala Met Ala Asp Pro Met His Tyr Lys Leu
    530                 535                 540
Ala Ile Phe Leu His Thr Leu Asp Leu Leu Ile Ala Arg Gly Asp Ser
545                 550                 555                 560
Ala Tyr Arg Gln Leu Glu Arg Asp Thr Leu Val Glu Ala Lys Met Tyr
                565                 570                 575
Tyr Ile Gln Ala Gln Gln Leu Leu Gly Pro Arg Pro Asp Ile His Thr
            580                 585                 590
Thr Asn Thr Trp Pro Asn Pro Thr Leu Ser Lys Glu Ala Gly Ala Ile
        595                 600                 605
Ala Thr Pro Thr Phe Leu Ser Ser Pro Glu Val Met Thr Phe Ala Ala
    610                 615                 620
Trp Leu Ser
625
```

(2) INFORMATION FOR SEQ ID NO:29:

(i) SEQUENCE CHARACTERISTICS:
        (A) LENGTH: 1689 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1689

(xi) SEQUENCE DESCRIPTION: SEQ ID NO:29:

```
GCA GGC GAT ACC GCA AAT ATT GGC GAC GGT GAT TTC TTG CCA CCG TAC    48
Ala Gly Asp Thr Ala Asn Ile Gly Asp Gly Asp Phe Leu Pro Pro Tyr
1               5                   10                  15
```

```
AAC GAT GTA CTA CTC GGT TAC TGG GAT AAA CTT GAG TTA CGC CTA TAC      96
Asn Asp Val Leu Leu Gly Tyr Trp Asp Lys Leu Glu Leu Arg Leu Tyr
            20                  25                  30

AAC CTG CGC CAC AAT CTG AGT CTG GAT GGT CAA CCG CTA AAT CTG CCA     144
Asn Leu Arg His Asn Leu Ser Leu Asp Gly Gln Pro Leu Asn Leu Pro
        35                  40                  45

CTG TAT GCC ACG CCG GTA GAC CCG AAA ACC CTG CAA CGC CAG CAA GCC     192
Leu Tyr Ala Thr Pro Val Asp Pro Lys Thr Leu Gln Arg Gln Gln Ala
    50                  55                  60

GGA GGG GAC GGT ACA GGC AGT AGT CCG GCT GGT GGT CAA GGC AGT GTT     240
Gly Gly Asp Gly Thr Gly Ser Ser Pro Ala Gly Gly Gln Gly Ser Val
65                  70                  75                  80

CAG GGC TGG CGC TAT CCG TTA TTG GTA GAA CGC GCC CGC TCT GCC GTG     288
Gln Gly Trp Arg Tyr Pro Leu Leu Val Glu Arg Ala Arg Ser Ala Val
                85                  90                  95

AGT TTG TTG ACT CAG TTC GGC AAC AGC TTA CAA ACA ACG TTA GAA CAT     336
Ser Leu Leu Thr Gln Phe Gly Asn Ser Leu Gln Thr Thr Leu Glu His
            100                 105                 110

CAG GAT AAT GAA AAA ATG ACG ATA CTG TTG CAG ACT CAA CAG GAA GCC     384
Gln Asp Asn Glu Lys Met Thr Ile Leu Leu Gln Thr Gln Gln Glu Ala
        115                 120                 125

ATC CTG AAA CAT CAG CAC GAT ATA CAA CAA AAT AAT CTA AAA GGA TTA     432
Ile Leu Lys His Gln His Asp Ile Gln Gln Asn Asn Leu Lys Gly Leu
    130                 135                 140

CAA CAC AGC CTG ACC GCA TTA CAG GCT AGC CGT GAT GGC GAC ACA TTG     480
Gln His Ser Leu Thr Ala Leu Gln Ala Ser Arg Asp Gly Asp Thr Leu
145                 150                 155                 160

CGG CAA AAA CAT TAC AGC GAC CTG ATT AAC GGT GGT CTA TCT GCG GCA     528
Arg Gln Lys His Tyr Ser Asp Leu Ile Asn Gly Gly Leu Ser Ala Ala
                165                 170                 175

GAA ATC GCC GGT CTG ACA CTA CGC AGC ACC GCC ATG ATT ACC AAT GGC     576
Glu Ile Ala Gly Leu Thr Leu Arg Ser Thr Ala Met Ile Thr Asn Gly
            180                 185                 190

GTT GCA ACG GGA TTG CTG ATT GCC GGC GGA ATC GCC AAC GCG GTA CCT     624
Val Ala Thr Gly Leu Leu Ile Ala Gly Gly Ile Ala Asn Ala Val Pro
        195                 200                 205

AAC GTC TTC GGG CTG GCT AAC GGT GGA TCG GAA TGG GGA GCG CCA TTA     672
Asn Val Phe Gly Leu Ala Asn Gly Gly Ser Glu Trp Gly Ala Pro Leu
    210                 215                 220

ATT GGC TCC GGG CAA GCA ACC CAA GTT GGC GCC GGC ATC CAG GAT CAG     720
Ile Gly Ser Gly Gln Ala Thr Gln Val Gly Ala Gly Ile Gln Asp Gln
225                 230                 235                 240

AGC GCG GGC ATT TCA GAA GTG ACA GCA GGC TAT CAG CGT CGT CAG GAA     768
Ser Ala Gly Ile Ser Glu Val Thr Ala Gly Tyr Gln Arg Arg Gln Glu
                245                 250                 255

GAA TGG GCA TTG CAA CGG GAT ATT GCT GAT AAC GAA ATA ACC CAA CTG     816
Glu Trp Ala Leu Gln Arg Asp Ile Ala Asp Asn Glu Ile Thr Gln Leu
            260                 265                 270

GAT GCC CAG ATA CAA AGC CTG CAA GAG CAA ATC ACG ATG GCA CAA AAA     864
Asp Ala Gln Ile Gln Ser Leu Gln Glu Gln Ile Thr Met Ala Gln Lys
        275                 280                 285

CAG ATC ACG CTC TCT GAA ACC GAA CAA GCG AAT GCC CAA GCG ATT TAT     912
Gln Ile Thr Leu Ser Glu Thr Glu Gln Ala Asn Ala Gln Ala Ile Tyr
    290                 295                 300

GAC CTG CAA ACC ACT CGT TTT ACC GGG CAG GCA CTG TAT AAC TGG ATG     960
Asp Leu Gln Thr Thr Arg Phe Thr Gly Gln Ala Leu Tyr Asn Trp Met
305                 310                 315                 320

GCC GGT CGT CTC TCC GCG CTC TAT TAC CAA ATG TAT GAT TCC ACT CTG    1008
Ala Gly Arg Leu Ser Ala Leu Tyr Tyr Gln Met Tyr Asp Ser Thr Leu
```

```
                        325                 330                 335
CCA ATC TGT CTC CAG CCA AAA GCC GCA TTA GTA CAG GAA TTA GGC GAG        1056
Pro Ile Cys Leu Gln Pro Lys Ala Ala Leu Val Gln Glu Leu Gly Glu
            340                 345                 350

AAA GAG AGC GAC AGT CTT TTC CAG GTT CCG GTG TGG AAT GAT CTG TGG        1104
Lys Glu Ser Asp Ser Leu Phe Gln Val Pro Val Trp Asn Asp Leu Trp
            355                 360                 365

CAA GGG CTG TTA GCA GGA GAA GGT TTA AGT TCA GAG CTA CAG AAA CTG        1152
Gln Gly Leu Leu Ala Gly Glu Gly Leu Ser Ser Glu Leu Gln Lys Leu
            370                 375                 380

GAT GCC ATC TGG CTT GCA CGT GGT GGT ATT GGG CTA GAA GCC ATC CGC        1200
Asp Ala Ile Trp Leu Ala Arg Gly Gly Ile Gly Leu Glu Ala Ile Arg
385                 390                 395                 400

ACC GTG TCG CTG GAT ACC CTG TTT GGC ACA GGG ACG TTA AGT GAA AAT        1248
Thr Val Ser Leu Asp Thr Leu Phe Gly Thr Gly Thr Leu Ser Glu Asn
            405                 410                 415

ATC AAT AAA GTG CTT AAC GGG GAA ACG GTA TCT CCA TCC GGT GGC GTC        1296
Ile Asn Lys Val Leu Asn Gly Glu Thr Val Ser Pro Ser Gly Gly Val
            420                 425                 430

ACT CTG GCG CTG ACA GGG GAT ATC TTC CAA GCA ACA CTG GAT TTG AGT        1344
Thr Leu Ala Leu Thr Gly Asp Ile Phe Gln Ala Thr Leu Asp Leu Ser
            435                 440                 445

CAG CTA GGT TTG GAT AAC TCT TAC AAC TTG GGT AAC GAG AAG AAA CGT        1392
Gln Leu Gly Leu Asp Asn Ser Tyr Asn Leu Gly Asn Glu Lys Lys Arg
            450                 455                 460

CGT ATT AAA CGT ATC GCC GTC ACC CTG CCA ACA CTT CTG GGG CCA TAT        1440
Arg Ile Lys Arg Ile Ala Val Thr Leu Pro Thr Leu Leu Gly Pro Tyr
465                 470                 475                 480

CAA GAT CTT GAA GCC ACA CTG GTA ATG GGT GCG GAA ATC GCC GCC TTA        1488
Gln Asp Leu Glu Ala Thr Leu Val Met Gly Ala Glu Ile Ala Ala Leu
            485                 490                 495

TCA CAC GGT GTG AAT GAC GGA GGC CGG TTT GTT ACC GAC TTT AAC GAC        1536
Ser His Gly Val Asn Asp Gly Gly Arg Phe Val Thr Asp Phe Asn Asp
            500                 505                 510

AGC CGT TTT CTG CCT TTT GAA GGT CGA GAT GCA ACA ACC GGC ACA CTG        1584
Ser Arg Phe Leu Pro Phe Glu Gly Arg Asp Ala Thr Thr Gly Thr Leu
            515                 520                 525

GAG CTC AAT ATT TTC CAT GCG GGT AAA GAG GGA ACG CAA CAC GAG TTG        1632
Glu Leu Asn Ile Phe His Ala Gly Lys Glu Gly Thr Gln His Glu Leu
            530                 535                 540

GTC GCG AAT CTG AGT GAC ATC ATT GTG CAT CTG AAT TAC ATC ATT CGA        1680
Val Ala Asn Leu Ser Asp Ile Ile Val His Leu Asn Tyr Ile Ile Arg
545                 550                 555                 560

GAC GCG TAA                                                            1689
Asp Ala
```

(2) INFORMATION FOR SEQ ID NO:30:

(i) SEQUENCE CHARACTERISTICS:
        (A) LENGTH: 562 amino acids
        (B) TYPE: amino acid
        (D) TOPOLOGY: linear (ii) MOLECULE TYPE: protein (xi) SEQUENCE DESCRIPTION: SEQ ID NO:30:

```
Ala Gly Asp Thr Ala Asn Ile Gly Asp Gly Asp Phe Leu Pro Pro Tyr
1               5                   10                  15

Asn Asp Val Leu Leu Gly Tyr Trp Asp Lys Leu Glu Leu Arg Leu Tyr
            20                  25                  30
```

```
Asn Leu Arg His Asn Leu Ser Leu Asp Gly Gln Pro Leu Asn Leu Pro
         35                  40                  45
Leu Tyr Ala Thr Pro Val Asp Pro Lys Thr Leu Gln Arg Gln Gln Ala
 50                  55                  60
Gly Gly Asp Gly Thr Gly Ser Ser Pro Ala Gly Gly Gln Gly Ser Val
 65                  70                  75                  80
Gln Gly Trp Arg Tyr Pro Leu Leu Val Glu Arg Ala Arg Ser Ala Val
                 85                  90                  95
Ser Leu Leu Thr Gln Phe Gly Asn Ser Leu Gln Thr Thr Leu Glu His
            100                 105                 110
Gln Asp Asn Glu Lys Met Thr Ile Leu Leu Gln Thr Gln Gln Glu Ala
            115                 120                 125
Ile Leu Lys His Gln His Asp Ile Gln Gln Asn Asn Leu Lys Gly Leu
            130                 135                 140
Gln His Ser Leu Thr Ala Leu Gln Ala Ser Arg Asp Gly Asp Thr Leu
145                 150                 155                 160
Arg Gln Lys His Tyr Ser Asp Leu Ile Asn Gly Gly Leu Ser Ala Ala
                165                 170                 175
Glu Ile Ala Gly Leu Thr Leu Arg Ser Thr Ala Met Ile Thr Asn Gly
            180                 185                 190
Val Ala Thr Gly Leu Leu Ile Ala Gly Gly Ile Ala Asn Ala Val Pro
            195                 200                 205
Asn Val Phe Gly Leu Ala Asn Gly Gly Ser Glu Trp Gly Ala Pro Leu
            210                 215                 220
Ile Gly Ser Gly Gln Ala Thr Gln Val Gly Ala Gly Ile Gln Asp Gln
225                 230                 235                 240
Ser Ala Gly Ile Ser Glu Val Thr Ala Gly Tyr Gln Arg Arg Gln Glu
                245                 250                 255
Glu Trp Ala Leu Gln Arg Asp Ile Ala Asp Asn Glu Ile Thr Gln Leu
            260                 265                 270
Asp Ala Gln Ile Gln Ser Leu Gln Glu Gln Ile Thr Met Ala Gln Lys
            275                 280                 285
Gln Ile Thr Leu Ser Glu Thr Glu Gln Ala Asn Ala Gln Ala Ile Tyr
            290                 295                 300
Asp Leu Gln Thr Thr Arg Phe Thr Gly Gln Ala Leu Tyr Asn Trp Met
305                 310                 315                 320
Ala Gly Arg Leu Ser Ala Leu Tyr Tyr Gln Met Tyr Asp Ser Thr Leu
                325                 330                 335
Pro Ile Cys Leu Gln Pro Lys Ala Ala Leu Val Gln Glu Leu Gly Glu
            340                 345                 350
Lys Glu Ser Asp Ser Leu Phe Gln Val Pro Val Trp Asn Asp Leu Trp
            355                 360                 365
Gln Gly Leu Leu Ala Gly Glu Gly Leu Ser Ser Glu Leu Gln Lys Leu
            370                 375                 380
Asp Ala Ile Trp Leu Ala Arg Gly Gly Ile Gly Leu Glu Ala Ile Arg
385                 390                 395                 400
Thr Val Ser Leu Asp Thr Leu Phe Gly Thr Gly Thr Leu Ser Glu Asn
                405                 410                 415
Ile Asn Lys Val Leu Asn Gly Glu Thr Val Ser Pro Ser Gly Gly Val
            420                 425                 430
Thr Leu Ala Leu Thr Gly Asp Ile Phe Gln Ala Thr Leu Asp Leu Ser
            435                 440                 445
Gln Leu Gly Leu Asp Asn Ser Tyr Asn Leu Gly Asn Glu Lys Lys Arg
```

```
                  450                 455                 460
Arg Ile Lys Arg Ile Ala Val Thr Leu Pro Thr Leu Leu Gly Pro Tyr
465                 470                 475                 480

Gln Asp Leu Glu Ala Thr Leu Val Met Gly Ala Glu Ile Ala Ala Leu
                    485                 490                 495

Ser His Gly Val Asn Asp Gly Gly Arg Phe Val Thr Asp Phe Asn Asp
                500                 505                 510

Ser Arg Phe Leu Pro Phe Glu Gly Arg Asp Ala Thr Thr Gly Thr Leu
            515                 520                 525

Glu Leu Asn Ile Phe His Ala Gly Lys Glu Gly Thr Gln His Glu Leu
    530                 535                 540

Val Ala Asn Leu Ser Asp Ile Ile Val His Leu Asn Tyr Ile Ile Arg
545                 550                 555                 560

Asp Ala
```

(2) INFORMATION FOR SEQ ID NO:31:

(i) SEQUENCE CHARACTERISTICS:
        (A) LENGTH: 4458 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..4458

(xi) SEQUENCE DESCRIPTION: SEQ ID NO:31:

```
ATG CAG GAT TCA CCA GAA GTA TCG ATT ACA ACG CTG TCA CTT CCC AAA       48
Met Gln Asp Ser Pro Glu Val Ser Ile Thr Thr Leu Ser Leu Pro Lys
1               5                  10                  15

GGT GGC GGT GCT ATC AAT GGC ATG GGA GAA GCA CTG AAT GCT GCC GGC       96
Gly Gly Gly Ala Ile Asn Gly Met Gly Glu Ala Leu Asn Ala Ala Gly
                20                  25                  30

CCT GAT GGA ATG GCC TCC CTA TCT CTG CCA TTA CCC CTT TCG ACC GGC      144
Pro Asp Gly Met Ala Ser Leu Ser Leu Pro Leu Pro Leu Ser Thr Gly
            35                  40                  45

AGA GGG ACG GCT CCT GGA TTA TCG CTG ATT TAC AGC AAC AGT GCA GGT      192
Arg Gly Thr Ala Pro Gly Leu Ser Leu Ile Tyr Ser Asn Ser Ala Gly
        50                  55                  60

AAT GGG CCT TTC GGC ATC GGC TGG CAA TGC GGT GTT ATG TCC ATT AGC      240
Asn Gly Pro Phe Gly Ile Gly Trp Gln Cys Gly Val Met Ser Ile Ser
65                  70                  75                  80

CGA CGC ACC CAA CAT GGC ATT CCA CAA TAC GGT AAT GAC GAC ACG TTC      288
Arg Arg Thr Gln His Gly Ile Pro Gln Tyr Gly Asn Asp Asp Thr Phe
                85                  90                  95

CTA TCC CCA CAA GGC GAG GTC ATG AAT ATC GCC CTG AAT GAC CAA GGG      336
Leu Ser Pro Gln Gly Glu Val Met Asn Ile Ala Leu Asn Asp Gln Gly
            100                 105                 110

CAA CCT GAT ATC CGT CAA GAC GTT AAA ACG CTG CAA GGC GTT ACC TTG      384
Gln Pro Asp Ile Arg Gln Asp Val Lys Thr Leu Gln Gly Val Thr Leu
        115                 120                 125

CCA ATT TCC TAT ACC GTG ACC CGC TAT CAA GCC CGC CAG ATC CTG GAT      432
Pro Ile Ser Tyr Thr Val Thr Arg Tyr Gln Ala Arg Gln Ile Leu Asp
    130                 135                 140

TTC AGT AAA ATC GAA TAC TGG CAA CCT GCC TCC GGT CAA GAA GGA CGC      480
Phe Ser Lys Ile Glu Tyr Trp Gln Pro Ala Ser Gly Gln Glu Gly Arg
145                 150                 155                 160
```

```
GCT TTC TGG CTG ATA TCG ACA CCG GAC GGG CAT CTA CAC ATC TTA GGG        528
Ala Phe Trp Leu Ile Ser Thr Pro Asp Gly His Leu His Ile Leu Gly
                165                 170                 175

AAA ACC GCG CAG GCT TGT CTG GCA AAT CCG CAA AAT GAC CAA CAA ATC        576
Lys Thr Ala Gln Ala Cys Leu Ala Asn Pro Gln Asn Asp Gln Gln Ile
                180                 185                 190

GCC CAG TGG TTG CTG GAA GAA ACT GTG ACG CCA GCC GGT GAA CAT GTC        624
Ala Gln Trp Leu Leu Glu Glu Thr Val Thr Pro Ala Gly Glu His Val
                195                 200                 205

AGC TAT CAA TAT CGA GCC GAA GAT GAA GCC CAT TGT GAC GAC AAT GAA        672
Ser Tyr Gln Tyr Arg Ala Glu Asp Glu Ala His Cys Asp Asp Asn Glu
            210                 215                 220

AAA ACC GCT CAT CCC AAT GTT ACC GCA CAG CGC TAT CTG GTA CAG GTG        720
Lys Thr Ala His Pro Asn Val Thr Ala Gln Arg Tyr Leu Val Gln Val
225                 230                 235                 240

AAC TAC GGC AAC ATC AAA CCA CAA GCC AGC CTG TTC GTA CTG GAT AAC        768
Asn Tyr Gly Asn Ile Lys Pro Gln Ala Ser Leu Phe Val Leu Asp Asn
                245                 250                 255

GCA CCT CCC GCA CCG GAA GAG TGG CTG TTT CAT CTG GTC TTT GAC CAC        816
Ala Pro Pro Ala Pro Glu Glu Trp Leu Phe His Leu Val Phe Asp His
                260                 265                 270

GGT GAG CGC GAT ACC TCA CTT CAT ACC GTG CCA ACA TGG GAT GCA GGT        864
Gly Glu Arg Asp Thr Ser Leu His Thr Val Pro Thr Trp Asp Ala Gly
                275                 280                 285

ACA GCG CAA TGG TCT GTA CGC CCG GAT ATC TTC TCT CGC TAT GAA TAT        912
Thr Ala Gln Trp Ser Val Arg Pro Asp Ile Phe Ser Arg Tyr Glu Tyr
            290                 295                 300

GGT TTT GAA GTG CGT ACT CGC CGC TTA TGT CAA CAA GTG CTG ATG TTT        960
Gly Phe Glu Val Arg Thr Arg Arg Leu Cys Gln Gln Val Leu Met Phe
305                 310                 315                 320

CAC CGC ACC GCG CTC ATG GCC GGA GAA GCC AGT ACC AAT GAC GCC CCG       1008
His Arg Thr Ala Leu Met Ala Gly Glu Ala Ser Thr Asn Asp Ala Pro
                325                 330                 335

GAA CTG GTT GGA CGC TTA ATA CTG GAA TAT GAC AAA AAC GCC AGC GTC       1056
Glu Leu Val Gly Arg Leu Ile Leu Glu Tyr Asp Lys Asn Ala Ser Val
                340                 345                 350

ACC ACG TTG ATT ACC ATC CGT CAA TTA AGC CAT GAA TCG GAC GGG AGG       1104
Thr Thr Leu Ile Thr Ile Arg Gln Leu Ser His Glu Ser Asp Gly Arg
                355                 360                 365

CCA GTC ACC CAG CCA CCA CTA GAA CTA GCC TGG CAA CGG TTT GAT CTG       1152
Pro Val Thr Gln Pro Pro Leu Glu Leu Ala Trp Gln Arg Phe Asp Leu
            370                 375                 380

GAG AAA ATC CCG ACA TGG CAA CGC TTT GAC GCA CTA GAT AAT TTT AAC       1200
Glu Lys Ile Pro Thr Trp Gln Arg Phe Asp Ala Leu Asp Asn Phe Asn
385                 390                 395                 400

TCG CAG CAA CGT TAT CAA CTG GTT GAT CTG CGG GGA GAA GGG TTG CCA       1248
Ser Gln Gln Arg Tyr Gln Leu Val Asp Leu Arg Gly Glu Gly Leu Pro
                405                 410                 415

GGT ATG CTG TAT CAA GAT CGA GGC GCT TGG TGG TAT AAA GCT CCG CAA       1296
Gly Met Leu Tyr Gln Asp Arg Gly Ala Trp Trp Tyr Lys Ala Pro Gln
                420                 425                 430

CGT CAG GAA GAC GGA GAC AGC AAT GCC GTC ACT TAC GAC AAA ATC GCC       1344
Arg Gln Glu Asp Gly Asp Ser Asn Ala Val Thr Tyr Asp Lys Ile Ala
            435                 440                 445

CCA CTG CCT ACC CTA CCC AAT TTG CAG GAT AAT GCC TCA TTG ATG GAT       1392
Pro Leu Pro Thr Leu Pro Asn Leu Gln Asp Asn Ala Ser Leu Met Asp
450                 455                 460

ATC AAC GGA GAC GGC CAA CTG GAT TGG GTT GTT ACC GCC TCC GGT ATT       1440
Ile Asn Gly Asp Gly Gln Leu Asp Trp Val Val Thr Ala Ser Gly Ile
465                 470                 475                 480
```

```
CGC GGA TAC CAT AGT CAG CAA CCC GAT GGA AAG TGG ACG CAC TTT ACG       1488
Arg Gly Tyr His Ser Gln Gln Pro Asp Gly Lys Trp Thr His Phe Thr
                485                 490                 495

CCA ATC AAT GCC TTG CCC GTG GAA TAT TTT CAT CCA AGC ATC CAG TTC       1536
Pro Ile Asn Ala Leu Pro Val Glu Tyr Phe His Pro Ser Ile Gln Phe
            500                 505                 510

GCT GAC CTT ACC GGG GCA GGC TTA TCT GAT TTA GTG TTG ATC GGG CCG       1584
Ala Asp Leu Thr Gly Ala Gly Leu Ser Asp Leu Val Leu Ile Gly Pro
            515                 520                 525

AAA AGC GTG CGT CTA TAT GCC AAC CAG CGA AAC GGC TGG CGT AAA GGA       1632
Lys Ser Val Arg Leu Tyr Ala Asn Gln Arg Asn Gly Trp Arg Lys Gly
        530                 535                 540

GAA GAT GTC CCC CAA TCC ACA GGT ATC ACC CTG CCT GTC ACA GGG ACC       1680
Glu Asp Val Pro Gln Ser Thr Gly Ile Thr Leu Pro Val Thr Gly Thr
545                 550                 555                 560

GAT GCC CGC AAA CTG GTG GCT TTC AGT GAT ATG CTC GGT TCC GGT CAA       1728
Asp Ala Arg Lys Leu Val Ala Phe Ser Asp Met Leu Gly Ser Gly Gln
                565                 570                 575

CAA CAT CTG GTG GAA ATC AAG GGT AAT CGC GTC ACC TGT TGG CCG AAT       1776
Gln His Leu Val Glu Ile Lys Gly Asn Arg Val Thr Cys Trp Pro Asn
            580                 585                 590

CTA GGG CAT GGC CGT TTC GGT CAA CCA CTA ACT CTG TCA GGA TTT AGC       1824
Leu Gly His Gly Arg Phe Gly Gln Pro Leu Thr Leu Ser Gly Phe Ser
            595                 600                 605

CAG CCC GAA AAT AGC TTC AAT CCC GAA CGG CTG TTT CTG GCG GAT ATC       1872
Gln Pro Glu Asn Ser Phe Asn Pro Glu Arg Leu Phe Leu Ala Asp Ile
        610                 615                 620

GAC GGC TCC GGC ACC ACC GAC CTT ATC TAT GCG CAA TCC GGC TCT TTG       1920
Asp Gly Ser Gly Thr Thr Asp Leu Ile Tyr Ala Gln Ser Gly Ser Leu
625                 630                 635                 640

CTC ATT TAT CTC AAC CAA AGT GGT AAT CAG TTT GAT GCC CCG TTG ACA       1968
Leu Ile Tyr Leu Asn Gln Ser Gly Asn Gln Phe Asp Ala Pro Leu Thr
                645                 650                 655

TTA GCG TTG CCA GAA GGC GTA CAA TTT GAC AAC ACT TGC CAA CTT CAA       2016
Leu Ala Leu Pro Glu Gly Val Gln Phe Asp Asn Thr Cys Gln Leu Gln
            660                 665                 670

GTC GCC GAT ATT CAG GGA TTA GGG ATA GCC AGC TTG ATT CTG ACT GTG       2064
Val Ala Asp Ile Gln Gly Leu Gly Ile Ala Ser Leu Ile Leu Thr Val
            675                 680                 685

CCA CAT ATC GCG CCA CAT CAC TGG CGT TGT GAC CTG TCA CTG ACC AAA       2112
Pro His Ile Ala Pro His His Trp Arg Cys Asp Leu Ser Leu Thr Lys
        690                 695                 700

CCC TGG TTG TTG AAT GTA ATG AAC AAT AAC CGG GGC GCA CAT CAC ACG       2160
Pro Trp Leu Leu Asn Val Met Asn Asn Asn Arg Gly Ala His His Thr
705                 710                 715                 720

CTA CAT TAT CGT AGT TCC GCG CAA TTC TGG TTG GAT GAA AAA TTA CAG       2208
Leu His Tyr Arg Ser Ser Ala Gln Phe Trp Leu Asp Glu Lys Leu Gln
                725                 730                 735

CTC ACC AAA GCA GGC AAA TCT CCG GCT TGT TAT CTG CCG TTT CCA ATG       2256
Leu Thr Lys Ala Gly Lys Ser Pro Ala Cys Tyr Leu Pro Phe Pro Met
            740                 745                 750

CAT TTG CTA TGG TAT ACC GAA ATT CAG GAT GAA ATC AGC GGC AAC CGG       2304
His Leu Leu Trp Tyr Thr Glu Ile Gln Asp Glu Ile Ser Gly Asn Arg
            755                 760                 765

CTC ACC AGT GAA GTC AAC TAC AGC CAC GGC GTC TGG GAT GGT AAA GAG       2352
Leu Thr Ser Glu Val Asn Tyr Ser His Gly Val Trp Asp Gly Lys Glu
        770                 775                 780

CGG GAA TTC AGA GGA TTT GGC TGC ATC AAA CAG ACA GAT ACC ACA ACG       2400
Arg Glu Phe Arg Gly Phe Gly Cys Ile Lys Gln Thr Asp Thr Thr Thr
```

```
                785                     790                     795                     800
TTT TCT CAC GGC ACC GCC CCC GAA CAG GCG GCA CCG TCG CTG AGT ATT                          2448
Phe Ser His Gly Thr Ala Pro Glu Gln Ala Ala Pro Ser Leu Ser Ile
                    805                     810                     815

AGC TGG TTT GCC ACC GGC ATG GAT GAA GTA GAC AGC CAA TTA GCT ACG                          2496
Ser Trp Phe Ala Thr Gly Met Asp Glu Val Asp Ser Gln Leu Ala Thr
                    820                     825                     830

GAA TAT TGG CAG GCA GAC ACG CAA GCT TAT AGC GGA TTT GAA ACC CGT                          2544
Glu Tyr Trp Gln Ala Asp Thr Gln Ala Tyr Ser Gly Phe Glu Thr Arg
                835                     840                     845

TAT ACC GTC TGG GAT CAC ACC AAC CAG ACA GAC CAA GCA TTT ACC CCC                          2592
Tyr Thr Val Trp Asp His Thr Asn Gln Thr Asp Gln Ala Phe Thr Pro
            850                     855                     860

AAT GAG ACA CAA CGT AAC TGG CTG ACG CGA GCG CTT AAA GGC CAA CTG                          2640
Asn Glu Thr Gln Arg Asn Trp Leu Thr Arg Ala Leu Lys Gly Gln Leu
865                     870                     875                     880

CTA CGC ACT GAG CTC TAC GGT CTG GAC GGA ACA GAT AAG CAA ACA GTG                          2688
Leu Arg Thr Glu Leu Tyr Gly Leu Asp Gly Thr Asp Lys Gln Thr Val
                    885                     890                     895

CCT TAT ACC GTC AGT GAA TCG CGC TAT CAG GTA CGC TCT ATT CCC GTA                          2736
Pro Tyr Thr Val Ser Glu Ser Arg Tyr Gln Val Arg Ser Ile Pro Val
                900                     905                     910

AAT AAA GAA ACT GAA TTA TCT GCC TGG GTG ACT GCT ATT GAA AAT CGC                          2784
Asn Lys Glu Thr Glu Leu Ser Ala Trp Val Thr Ala Ile Glu Asn Arg
            915                     920                     925

AGC TAC CAC TAT GAA CGT ATC ATC ACT GAC CCA CAG TTC AGC CAG AGT                          2832
Ser Tyr His Tyr Glu Arg Ile Ile Thr Asp Pro Gln Phe Ser Gln Ser
    930                     935                     940

ATC AAG TTG CAA CAC GAT ATC TTT GGT CAA TCA CTG CAA AGT GTC GAT                          2880
Ile Lys Leu Gln His Asp Ile Phe Gly Gln Ser Leu Gln Ser Val Asp
945                     950                     955                     960

ATT GCC TGG CCG CGC CGC GAA AAA CCA GCA GTG AAT CCC TAC CCG CCT                          2928
Ile Ala Trp Pro Arg Arg Glu Lys Pro Ala Val Asn Pro Tyr Pro Pro
                    965                     970                     975

ACC CTG CCG GAA ACG CTA TTT GAC AGC AGC TAT GAT GAT CAA CAA CAA                          2976
Thr Leu Pro Glu Thr Leu Phe Asp Ser Ser Tyr Asp Asp Gln Gln Gln
                980                     985                     990

CTA TTA CGT CTG GTG AGA CAA AAA AAT AGC TGG CAT CAC CTG ACT GAT                          3024
Leu Leu Arg Leu Val Arg Gln Lys Asn Ser Trp His His Leu Thr Asp
            995                     1000                    1005

GGG GAA AAC TGG CGA TTA GGT TTA CCG AAT GCA CAA CGC CGT GAT GTT                          3072
Gly Glu Asn Trp Arg Leu Gly Leu Pro Asn Ala Gln Arg Arg Asp Val
    1010                    1015                    1020

TAT ACT TAT GAC CGG AGC AAA ATT CCA ACC GAA GGG ATT TCC CTT GAA                          3120
Tyr Thr Tyr Asp Arg Ser Lys Ile Pro Thr Glu Gly Ile Ser Leu Glu
1025                    1030                    1035                    1040

ATC TTG CTG AAA GAT GAT GGC CTG CTA GCA GAT GAA AAA GCG GCC GTT                          3168
Ile Leu Leu Lys Asp Asp Gly Leu Leu Ala Asp Glu Lys Ala Ala Val
                    1045                    1050                    1055

TAT CTG GGA CAA CAA CAG ACG TTT TAC ACC GCC GGT CAA GCG GAA GTC                          3216
Tyr Leu Gly Gln Gln Gln Thr Phe Tyr Thr Ala Gly Gln Ala Glu Val
                1060                    1065                    1070

ACT CTA GAA AAA CCC ACG TTA CAA GCA CTG GTC GCG TTC CAA GAA ACC                          3264
Thr Leu Glu Lys Pro Thr Leu Gln Ala Leu Val Ala Phe Gln Glu Thr
            1075                    1080                    1085

GCC ATG ATG GAC GAT ACC TCA TTA CAG GCG TAT GAA GGC GTG ATT GAA                          3312
Ala Met Met Asp Asp Thr Ser Leu Gln Ala Tyr Glu Gly Val Ile Glu
    1090                    1095                    1100

GAG CAA GAG TTG AAT ACC GCG CTG ACA CAG GCC GGT TAT CAG CAA GTC                          3360
```

```
                                    -continued

Glu Gln Glu Leu Asn Thr Ala Leu Thr Gln Ala Gly Tyr Gln Gln Val
1105                1110                1115                1120

GCG CGG TTG TTT AAT ACC AGA TCA GAA AGC CCG GTA TGG GCG GCA CGG      3408
Ala Arg Leu Phe Asn Thr Arg Ser Glu Ser Pro Val Trp Ala Ala Arg
                1125                1130                1135

CAA GGT TAT ACC GAT TAC GGT GAC GCC GCA CAG TTC TGG CGG CCT CAG      3456
Gln Gly Tyr Thr Asp Tyr Gly Asp Ala Ala Gln Phe Trp Arg Pro Gln
                1140                1145                1150

GCT CAG CGT AAC TCG TTG CTG ACA GGG AAA ACC ACA CTG ACC TGG GAT      3504
Ala Gln Arg Asn Ser Leu Leu Thr Gly Lys Thr Thr Leu Thr Trp Asp
                1155                1160                1165

ACC CAT CAT TGT GTA ATA ATA CAG ACT CAA GAT GCC GCT GGA TTA ACG      3552
Thr His His Cys Val Ile Ile Gln Thr Gln Asp Ala Ala Gly Leu Thr
            1170                1175                1180

ACG CAA GCC CAT TAC GAT TAT CGT TTC CTT ACA CCG GTA CAA CTG ACA      3600
Thr Gln Ala His Tyr Asp Tyr Arg Phe Leu Thr Pro Val Gln Leu Thr
1185                1190                1195                1200

GAT ATT AAT GAT AAT CAA CAT ATT GTG ACT CTG GAC GCG CTA GGT CGC      3648
Asp Ile Asn Asp Asn Gln His Ile Val Thr Leu Asp Ala Leu Gly Arg
                1205                1210                1215

GTA ACC ACC AGC CGG TTC TGG GGC ACA GAG GCA GGA CAA GCC GCA GGC      3696
Val Thr Thr Ser Arg Phe Trp Gly Thr Glu Ala Gly Gln Ala Ala Gly
                1220                1225                1230

TAT TCC AAC CAG CCC TTC ACA CCA CCG GAC TCC GTA GAT AAA GCG CTG      3744
Tyr Ser Asn Gln Pro Phe Thr Pro Pro Asp Ser Val Asp Lys Ala Leu
                1235                1240                1245

GCA TTA ACC GGC GCA CTC CCT GTT GCC CAA TGT TTA GTC TAT GCC GTT      3792
Ala Leu Thr Gly Ala Leu Pro Val Ala Gln Cys Leu Val Tyr Ala Val
            1250                1255                1260

GAT AGC TGG ATG CCG TCG TTA TCT TTG TCT CAG CTT TCT CAG TCA CAA      3840
Asp Ser Trp Met Pro Ser Leu Ser Leu Ser Gln Leu Ser Gln Ser Gln
1265                1270                1275                1280

GAA GAG GCA GAA GCG CTA TGG GCG CAA CTG CGT GCC GCT CAT ATG ATT      3888
Glu Glu Ala Glu Ala Leu Trp Ala Gln Leu Arg Ala Ala His Met Ile
                1285                1290                1295

ACC GAA GAT GGG AAA GTG TGT GCG TTA AGC GGG AAA CGA GGA ACA AGC      3936
Thr Glu Asp Gly Lys Val Cys Ala Leu Ser Gly Lys Arg Gly Thr Ser
                1300                1305                1310

CAT CAG AAC CTG ACG ATT CAA CTT ATT TCG CTA TTG GCA AGT ATT CCC      3984
His Gln Asn Leu Thr Ile Gln Leu Ile Ser Leu Leu Ala Ser Ile Pro
            1315                1320                1325

CGT TTA CCG CCA CAT GTA CTG GGG ATC ACC ACT GAT CGC TAT GAT AGC      4032
Arg Leu Pro Pro His Val Leu Gly Ile Thr Thr Asp Arg Tyr Asp Ser
            1330                1335                1340

GAT CCG CAA CAG CAG CAC CAA CAG ACG GTG AGC TTT AGT GAC GGT TTT      4080
Asp Pro Gln Gln Gln His Gln Gln Thr Val Ser Phe Ser Asp Gly Phe
1345                1350                1355                1360

GGC CGG TTA CTC CAG AGT TCA GCT CGT CAT GAG TCA GGT GAT GCC TGG      4128
Gly Arg Leu Leu Gln Ser Ser Ala Arg His Glu Ser Gly Asp Ala Trp
                1365                1370                1375

CAA CGT AAA GAG GAT GGC GGG CTG GTC GTG GAT GCA AAT GGC GTT CTG      4176
Gln Arg Lys Glu Asp Gly Gly Leu Val Val Asp Ala Asn Gly Val Leu
                1380                1385                1390

GTC AGT GCC CCT ACA GAC ACC CGA TGG GCC GTT TCC GGT CGC ACA GAA      4224
Val Ser Ala Pro Thr Asp Thr Arg Trp Ala Val Ser Gly Arg Thr Glu
                1395                1400                1405

TAT GAC GAC AAA GGC CAA CCT GTG CGT ACT TAT CAA CCC TAT TTT CTA      4272
Tyr Asp Asp Lys Gly Gln Pro Val Arg Thr Tyr Gln Pro Tyr Phe Leu
1410                1415                1420
```

```
AAT GAC TGG CGT TAC GTT AGT GAT GAC AGC GCA CGA GAT GAC CTG TTT       4320
Asn Asp Trp Arg Tyr Val Ser Asp Asp Ser Ala Arg Asp Asp Leu Phe
1425                1430                1435                1440

GCC GAT ACC CAC CTT TAT GAT CCA TTG GGA CGG GAA TAC AAA GTC ATC       4368
Ala Asp Thr His Leu Tyr Asp Pro Leu Gly Arg Glu Tyr Lys Val Ile
                1445                1450                1455

ACT GCT AAG AAA TAT TTG CGA GAA AAG CTG TAC ACC CCG TGG TTT ATT       4416
Thr Ala Lys Lys Tyr Leu Arg Glu Lys Leu Tyr Thr Pro Trp Phe Ile
            1460                1465                1470

GTC AGT GAG GAT GAA AAC GAT ACA GCA TCA AGA ACC CCA TAG               4458
Val Ser Glu Asp Glu Asn Asp Thr Ala Ser Arg Thr Pro
        1475                1480                1485
```

(2) INFORMATION FOR SEQ ID NO:32:

(i) SEQUENCE CHARACTERISTICS:
        (A) LENGTH: 1485 amino acids
        (B) TYPE: amino acid
        (D) TOPOLOGY: linear (ii) MOLECULE TYPE: protein (xi) SEQUENCE DESCRIPTION: SEQ ID NO:32:

```
Met Gln Asp Ser Pro Glu Val Ser Ile Thr Thr Leu Ser Leu Pro Lys
1               5                   10                  15

Gly Gly Gly Ala Ile Asn Gly Met Gly Glu Ala Leu Asn Ala Ala Gly
                20                  25                  30

Pro Asp Gly Met Ala Ser Leu Ser Leu Pro Leu Pro Leu Ser Thr Gly
            35                  40                  45

Arg Gly Thr Ala Pro Gly Leu Ser Leu Ile Tyr Ser Asn Ser Ala Gly
        50                  55                  60

Asn Gly Pro Phe Gly Ile Gly Trp Gln Cys Gly Val Met Ser Ile Ser
65                  70                  75                  80

Arg Arg Thr Gln His Gly Ile Pro Gln Tyr Gly Asn Asp Thr Phe
                85                  90                  95

Leu Ser Pro Gln Gly Glu Val Met Asn Ile Ala Leu Asn Asp Gln Gly
                100                 105                 110

Gln Pro Asp Ile Arg Gln Asp Val Lys Thr Leu Gln Gly Val Thr Leu
            115                 120                 125

Pro Ile Ser Tyr Thr Val Thr Arg Tyr Gln Ala Arg Gln Ile Leu Asp
        130                 135                 140

Phe Ser Lys Ile Glu Tyr Trp Gln Pro Ala Ser Gly Gln Glu Gly Arg
145                 150                 155                 160

Ala Phe Trp Leu Ile Ser Thr Pro Asp Gly His Leu His Ile Leu Gly
                165                 170                 175

Lys Thr Ala Gln Ala Cys Leu Ala Asn Pro Gln Asn Asp Gln Gln Ile
            180                 185                 190

Ala Gln Trp Leu Leu Glu Glu Thr Val Thr Pro Ala Gly Glu His Val
        195                 200                 205

Ser Tyr Gln Tyr Arg Ala Glu Asp Glu Ala His Cys Asp Asp Asn Glu
    210                 215                 220

Lys Thr Ala His Pro Asn Val Thr Ala Gln Arg Tyr Leu Val Gln Val
225                 230                 235                 240

Asn Tyr Gly Asn Ile Lys Pro Gln Ala Ser Leu Phe Val Leu Asp Asn
                245                 250                 255

Ala Pro Pro Ala Pro Glu Glu Trp Leu Phe His Leu Val Phe Asp His
            260                 265                 270
```

-continued

```
Gly Glu Arg Asp Thr Ser Leu His Thr Val Pro Thr Trp Asp Ala Gly
        275                 280                 285
Thr Ala Gln Trp Ser Val Arg Pro Asp Ile Phe Ser Arg Tyr Glu Tyr
    290                 295                 300
Gly Phe Glu Val Arg Thr Arg Arg Leu Cys Gln Gln Val Leu Met Phe
305                 310                 315                 320
His Arg Thr Ala Leu Met Ala Gly Glu Ala Ser Thr Asn Asp Ala Pro
                325                 330                 335
Glu Leu Val Gly Arg Leu Ile Leu Glu Tyr Asp Lys Asn Ala Ser Val
            340                 345                 350
Thr Thr Leu Ile Thr Ile Arg Gln Leu Ser His Glu Ser Asp Gly Arg
        355                 360                 365
Pro Val Thr Gln Pro Pro Leu Glu Leu Ala Trp Gln Arg Phe Asp Leu
    370                 375                 380
Glu Lys Ile Pro Thr Trp Gln Arg Phe Asp Ala Leu Asp Asn Phe Asn
385                 390                 395                 400
Ser Gln Gln Arg Tyr Gln Leu Val Asp Leu Arg Gly Glu Gly Leu Pro
                405                 410                 415
Gly Met Leu Tyr Gln Asp Arg Gly Ala Trp Trp Tyr Lys Ala Pro Gln
            420                 425                 430
Arg Gln Glu Asp Gly Asp Ser Asn Ala Val Thr Tyr Asp Lys Ile Ala
        435                 440                 445
Pro Leu Pro Thr Leu Pro Asn Leu Gln Asp Asn Ala Ser Leu Met Asp
    450                 455                 460
Ile Asn Gly Asp Gly Gln Leu Asp Trp Val Val Thr Ala Ser Gly Ile
465                 470                 475                 480
Arg Gly Tyr His Ser Gln Gln Pro Asp Gly Lys Trp Thr His Phe Thr
                485                 490                 495
Pro Ile Asn Ala Leu Pro Val Glu Tyr Phe His Pro Ser Ile Gln Phe
            500                 505                 510
Ala Asp Leu Thr Gly Ala Gly Leu Ser Asp Leu Val Leu Ile Gly Pro
        515                 520                 525
Lys Ser Val Arg Leu Tyr Ala Asn Gln Arg Asn Gly Trp Arg Lys Gly
    530                 535                 540
Glu Asp Val Pro Gln Ser Thr Gly Ile Thr Leu Pro Val Thr Gly Thr
545                 550                 555                 560
Asp Ala Arg Lys Leu Val Ala Phe Ser Asp Met Leu Gly Ser Gly Gln
                565                 570                 575
Gln His Leu Val Glu Ile Lys Gly Asn Arg Val Thr Cys Trp Pro Asn
            580                 585                 590
Leu Gly His Gly Arg Phe Gly Gln Pro Leu Thr Leu Ser Gly Phe Ser
        595                 600                 605
Gln Pro Glu Asn Ser Phe Asn Pro Glu Arg Leu Phe Leu Ala Asp Ile
    610                 615                 620
Asp Gly Ser Gly Thr Thr Asp Leu Ile Tyr Ala Gln Ser Gly Ser Leu
625                 630                 635                 640
Leu Ile Tyr Leu Asn Gln Ser Gly Asn Gln Phe Asp Ala Pro Leu Thr
                645                 650                 655
Leu Ala Leu Pro Glu Gly Val Gln Phe Asp Asn Thr Cys Gln Leu Gln
            660                 665                 670
Val Ala Asp Ile Gln Gly Leu Gly Ile Ala Ser Leu Ile Leu Thr Val
        675                 680                 685
Pro His Ile Ala Pro His His Trp Arg Cys Asp Leu Ser Leu Thr Lys
```

-continued

```
            690                 695                 700
Pro Trp Leu Leu Asn Val Met Asn Asn Asn Arg Gly Ala His His Thr
705                 710                 715                 720
Leu His Tyr Arg Ser Ser Ala Gln Phe Trp Leu Asp Glu Lys Leu Gln
                725                 730                 735
Leu Thr Lys Ala Gly Lys Ser Pro Ala Cys Tyr Leu Pro Phe Pro Met
                740                 745                 750
His Leu Leu Trp Tyr Thr Glu Ile Gln Asp Glu Ile Ser Gly Asn Arg
                755                 760                 765
Leu Thr Ser Glu Val Asn Tyr Ser His Gly Val Trp Asp Gly Lys Glu
            770                 775                 780
Arg Glu Phe Arg Gly Phe Gly Cys Ile Lys Gln Thr Asp Thr Thr Thr
785                 790                 795                 800
Phe Ser His Gly Thr Ala Pro Glu Gln Ala Ala Pro Ser Leu Ser Ile
                805                 810                 815
Ser Trp Phe Ala Thr Gly Met Asp Glu Val Asp Ser Gln Leu Ala Thr
                820                 825                 830
Glu Tyr Trp Gln Ala Asp Thr Gln Ala Tyr Ser Gly Phe Glu Thr Arg
                835                 840                 845
Tyr Thr Val Trp Asp His Thr Asn Gln Thr Asp Gln Ala Phe Thr Pro
850                 855                 860
Asn Glu Thr Gln Arg Asn Trp Leu Thr Arg Ala Leu Lys Gly Gln Leu
865                 870                 875                 880
Leu Arg Thr Glu Leu Tyr Gly Leu Asp Gly Thr Asp Lys Gln Thr Val
                885                 890                 895
Pro Tyr Thr Val Ser Glu Ser Arg Tyr Gln Val Arg Ser Ile Pro Val
                900                 905                 910
Asn Lys Glu Thr Glu Leu Ser Ala Trp Val Thr Ala Ile Glu Asn Arg
                915                 920                 925
Ser Tyr His Tyr Glu Arg Ile Ile Thr Asp Pro Gln Phe Ser Gln Ser
                930                 935                 940
Ile Lys Leu Gln His Asp Ile Phe Gly Gln Ser Leu Gln Ser Val Asp
945                 950                 955                 960
Ile Ala Trp Pro Arg Arg Glu Lys Pro Ala Val Asn Pro Tyr Pro Pro
                965                 970                 975
Thr Leu Pro Glu Thr Leu Phe Asp Ser Ser Tyr Asp Asp Gln Gln Gln
                980                 985                 990
Leu Leu Arg Leu Val Arg Gln Lys Asn Ser Trp His His Leu Thr Asp
                995                 1000                1005
Gly Glu Asn Trp Arg Leu Gly Leu Pro Asn Ala Gln Arg Arg Asp Val
            1010                1015                1020
Tyr Thr Tyr Asp Arg Ser Lys Ile Pro Thr Glu Gly Ile Ser Leu Glu
1025                1030                1035                1040
Ile Leu Leu Lys Asp Asp Gly Leu Leu Ala Asp Glu Lys Ala Ala Val
                1045                1050                1055
Tyr Leu Gly Gln Gln Thr Phe Tyr Thr Ala Gly Gln Ala Glu Val
                1060                1065                1070
Thr Leu Glu Lys Pro Thr Leu Gln Ala Leu Val Ala Phe Gln Glu Thr
                1075                1080                1085
Ala Met Met Asp Asp Thr Ser Leu Gln Ala Tyr Glu Gly Val Ile Glu
                1090                1095                1100
Glu Gln Glu Leu Asn Thr Ala Leu Thr Gln Ala Gly Tyr Gln Gln Val
1105                1110                1115                1120
```

-continued

```
Ala Arg Leu Phe Asn Thr Arg Ser Glu Ser Pro Val Trp Ala Ala Arg
              1125                1130                1135
Gln Gly Tyr Thr Asp Tyr Gly Asp Ala Ala Gln Phe Trp Arg Pro Gln
          1140                1145                1150
Ala Gln Arg Asn Ser Leu Leu Thr Gly Lys Thr Thr Leu Thr Trp Asp
      1155                1160                1165
Thr His His Cys Val Ile Ile Gln Thr Gln Asp Ala Ala Gly Leu Thr
  1170                1175                1180
Thr Gln Ala His Tyr Asp Tyr Arg Phe Leu Thr Pro Val Gln Leu Thr
1185                1190                1195                1200
Asp Ile Asn Asp Asn Gln His Ile Val Thr Leu Asp Ala Leu Gly Arg
              1205                1210                1215
Val Thr Thr Ser Arg Phe Trp Gly Thr Glu Ala Gly Gln Ala Ala Gly
          1220                1225                1230
Tyr Ser Asn Gln Pro Phe Thr Pro Pro Asp Ser Val Asp Lys Ala Leu
      1235                1240                1245
Ala Leu Thr Gly Ala Leu Pro Val Ala Gln Cys Leu Val Tyr Ala Val
  1250                1255                1260
Asp Ser Trp Met Pro Ser Leu Ser Leu Ser Gln Leu Ser Gln Ser Gln
1265                1270                1275                1280
Glu Glu Ala Glu Ala Leu Trp Ala Gln Leu Arg Ala Ala His Met Ile
              1285                1290                1295
Thr Glu Asp Gly Lys Val Cys Ala Leu Ser Gly Lys Arg Gly Thr Ser
          1300                1305                1310
His Gln Asn Leu Thr Ile Gln Leu Ile Ser Leu Leu Ala Ser Ile Pro
      1315                1320                1325
Arg Leu Pro Pro His Val Leu Gly Ile Thr Thr Asp Arg Tyr Asp Ser
  1330                1335                1340
Asp Pro Gln Gln Gln His Gln Gln Thr Val Ser Phe Ser Asp Gly Phe
1345                1350                1355                1360
Gly Arg Leu Leu Gln Ser Ser Ala Arg His Glu Ser Gly Asp Ala Trp
              1365                1370                1375
Gln Arg Lys Glu Asp Gly Gly Leu Val Val Asp Ala Asn Gly Val Leu
          1380                1385                1390
Val Ser Ala Pro Thr Asp Thr Arg Trp Ala Val Ser Gly Arg Thr Glu
      1395                1400                1405
Tyr Asp Asp Lys Gly Gln Pro Val Arg Thr Tyr Gln Pro Tyr Phe Leu
  1410                1415                1420
Asn Asp Trp Arg Tyr Val Ser Asp Ser Ala Arg Asp Asp Leu Phe
1425                1430                1435                1440
Ala Asp Thr His Leu Tyr Asp Pro Leu Gly Arg Glu Tyr Lys Val Ile
              1445                1450                1455
Thr Ala Lys Lys Tyr Leu Arg Glu Lys Leu Tyr Thr Pro Trp Phe Ile
          1460                1465                1470
Val Ser Glu Asp Glu Asn Asp Thr Ala Ser Arg Thr Pro
      1475                1480                1485
```

(2) INFORMATION FOR SEQ ID NO:33:

(i) SEQUENCE CHARACTERISTICS:
        (A) LENGTH: 3288 base pairs
        (B) TYPE: nucleic acid
        (C) STRANDEDNESS: double
        (D) TOPOLOGY: linear -continued (ii) MOLECULE TYPE: DNA (genomic)

(xi) SEQUENCE DESCRIPTION: SEQ ID NO:33:

```
ATG GTG ACT GTT ATG CAA AAT AAA ATA TCA TTT TTA TCA GGT ACA TCC        48
Met Val Thr Val Met Gln Asn Lys Ile Ser Phe Leu Ser Gly Thr Ser
1               5                   10                  15

GAA CAG CCC CTG CTT GAC GCC GGT TAT CAA AAC GTA TTT GAT ATC GCA        96
Glu Gln Pro Leu Leu Asp Ala Gly Tyr Gln Asn Val Phe Asp Ile Ala
            20                  25                  30

TCA ATC AGC CGG GCT ACT TTC GTT CAA TCC GTT CCC ACC CTG CCC GTT       144
Ser Ile Ser Arg Ala Thr Phe Val Gln Ser Val Pro Thr Leu Pro Val
        35                  40                  45

AAA GAG GCT CAT ACC GTC TAT CGT CAG GCG CGG CAA CGT GCG GAA AAT       192
Lys Glu Ala His Thr Val Tyr Arg Gln Ala Arg Gln Arg Ala Glu Asn
    50                  55                  60

CTG AAA TCC CTC TAC CGA GCC TGG CAA TTG CGT CAG GAG CCG GTT ATT       240
Leu Lys Ser Leu Tyr Arg Ala Trp Gln Leu Arg Gln Glu Pro Val Ile
65                  70                  75                  80

AAA GGG CTG GCT AAA CTT AAC CTA CAA TCC AAC GTT TCT GTG CTT CAA       288
Lys Gly Leu Ala Lys Leu Asn Leu Gln Ser Asn Val Ser Val Leu Gln
                85                  90                  95

GAT GCT TTG GTA GAG AAT ATT GGC GGT GAT GGG GAT TTC AGC GAT TTA       336
Asp Ala Leu Val Glu Asn Ile Gly Gly Asp Gly Asp Phe Ser Asp Leu
            100                 105                 110

ATG AAC CGT GCC AGT CAA TAT GCT GAC GCT GCC TCT ATT CAA TCC CTA       384
Met Asn Arg Ala Ser Gln Tyr Ala Asp Ala Ala Ser Ile Gln Ser Leu
        115                 120                 125

TTT TCA CCG GGC CGT TAT GCT TCC GCA CTC TAC AGA GTT GCT AAA GAT       432
Phe Ser Pro Gly Arg Tyr Ala Ser Ala Leu Tyr Arg Val Ala Lys Asp
    130                 135                 140

CTG CAT AAA TCA GAT TCC AGT TTG CAT ATT GAT AAT CGC CGC GCT GAT       480
Leu His Lys Ser Asp Ser Ser Leu His Ile Asp Asn Arg Arg Ala Asp
145                 150                 155                 160

CTG AAG GAT CTG ATA TTA AGC GAA ACG ACG ATG AAT AAA GAG GTC ACT       528
Leu Lys Asp Leu Ile Leu Ser Glu Thr Thr Met Asn Lys Glu Val Thr
                165                 170                 175

TCC CTT GAT ATC TTG TTG GAT GTG CTA CAA AAA GGC GGT AAA GAT ATT       576
Ser Leu Asp Ile Leu Leu Asp Val Leu Gln Lys Gly Gly Lys Asp Ile
            180                 185                 190

ACT GAG CTG TCC GGC GCA TTC TTC CCA ATG ACG TTA CCT TAT GAC GAT       624
Thr Glu Leu Ser Gly Ala Phe Phe Pro Met Thr Leu Pro Tyr Asp Asp
        195                 200                 205

CAT CTG TCG CAA ATC GAT TCC GCT TTA TCG GCA CAA GCC AGA ACG CTG       672
His Leu Ser Gln Ile Asp Ser Ala Leu Ser Ala Gln Ala Arg Thr Leu
    210                 215                 220

AAC GGT GTG TGG AAT ACT TTG ACA GAT ACC ACG GCA CAA GCG GTT TCA       720
Asn Gly Val Trp Asn Thr Leu Thr Asp Thr Thr Ala Gln Ala Val Ser
225                 230                 235                 240

GAA CAA ACC AGT AAT ACG AAT ACA CGC AAA CTG TTC GCT GCC CAA GAT       768
Glu Gln Thr Ser Asn Thr Asn Thr Arg Lys Leu Phe Ala Ala Gln Asp
                245                 250                 255

GGT AAT CAA GAT ACA TTT TTT TCC GGA AAC ACT TTT TAT TTC AAA GCG       816
Gly Asn Gln Asp Thr Phe Phe Ser Gly Asn Thr Phe Tyr Phe Lys Ala
            260                 265                 270

GTG GGA TTC AGC GGG CAA CCT ATG GTT TAC CTG TCA CAG TAC ACC AGC       864
Val Gly Phe Ser Gly Gln Pro Met Val Tyr Leu Ser Gln Tyr Thr Ser
        275                 280                 285

GGG AAC GGC ATT GTC GGC GCA CAA TTG ATT GCA GGT AAT CCA GAC CAA       912
Gly Asn Gly Ile Val Gly Ala Gln Leu Ile Ala Gly Asn Pro Asp Gln
    290                 295                 300
```

```
GCC GCC GCC GCA ATA GTC GCA CCG TTG AAA CTC ACT TGG TCA ATG GCA      960
Ala Ala Ala Ala Ile Val Ala Pro Leu Lys Leu Thr Trp Ser Met Ala
305                 310                 315                 320

AAA CAG TGT TAC TAC CTC GTC GCT CCC GAT GGT ACA ACG ATG GGA GAC     1008
Lys Gln Cys Tyr Tyr Leu Val Ala Pro Asp Gly Thr Thr Met Gly Asp
                325                 330                 335

GGT AAT GTT CTG ACC GGC TGT TTC TTA AGA GGC AAC AGC CCA ACT AAC     1056
Gly Asn Val Leu Thr Gly Cys Phe Leu Arg Gly Asn Ser Pro Thr Asn
            340                 345                 350

CCG GAT AAA GAC GGT ATT TTT GCT CAG GTA GCC AAC AAA TCA GGC AGT     1104
Pro Asp Lys Asp Gly Ile Phe Ala Gln Val Ala Asn Lys Ser Gly Ser
        355                 360                 365

ACT CAG CCT TTG CCA AGC TTC CAT CTG CCG GTC ACA CTG GAA CAC AGC     1152
Thr Gln Pro Leu Pro Ser Phe His Leu Pro Val Thr Leu Glu His Ser
370                 375                 380

GAG AAT AAA GAT CAG TAC TAT CTG AAA ACA GAG CAG GGT TAT ATC ACG     1200
Glu Asn Lys Asp Gln Tyr Tyr Leu Lys Thr Glu Gln Gly Tyr Ile Thr
385                 390                 395                 400

GTA GAT AGT TCC GGA CAG TCA AAT TGG AAA AAC GCG CTG GTT ATC AAT     1248
Val Asp Ser Ser Gly Gln Ser Asn Trp Lys Asn Ala Leu Val Ile Asn
                405                 410                 415

GGG ACA AAA GAC AAG GGG CTG TTA TTA ACC TTT TGC AGC GAT AGC TCA     1296
Gly Thr Lys Asp Lys Gly Leu Leu Leu Thr Phe Cys Ser Asp Ser Ser
            420                 425                 430

GGC ACT CCG ACA AAC CCT GAT GAT GTG ATT CCT CCC GCT ATC AAT GAT     1344
Gly Thr Pro Thr Asn Pro Asp Asp Val Ile Pro Pro Ala Ile Asn Asp
        435                 440                 445

ATT CCA TCG CCG CCA GCC CGC GAA ACA CTG TCA CTG ACG CCG TCA GTT     1392
Ile Pro Ser Pro Pro Ala Arg Glu Thr Leu Ser Leu Thr Pro Val Ser
450                 455                 460

TAT CAA TTG ATG ACC AAT CCG GCA CCG ACA GAA GAT GAT ATT ACC AAC     1440
Tyr Gln Leu Met Thr Asn Pro Ala Pro Thr Glu Asp Asp Ile Thr Asn
465                 470                 475                 480

CAT TAT GGT TTT AAC GGC GCT AGC TTA CGG GCT TCT CCA TTG TCA ACC     1488
His Tyr Gly Phe Asn Gly Ala Ser Leu Arg Ala Ser Pro Leu Ser Thr
                485                 490                 495

AGC GAG TTG ACC AGC AAA CTG AAT TCT ATC GAT ACT TTC TGT GAG AAG     1536
Ser Glu Leu Thr Ser Lys Leu Asn Ser Ile Asp Thr Phe Cys Glu Lys
            500                 505                 510

ACC CGG TTA AGC TTC AAT CAG TTA ATG GAT TTG ACC GCT CAG CAA TCT     1584
Thr Arg Leu Ser Phe Asn Gln Leu Met Asp Leu Thr Ala Gln Gln Ser
        515                 520                 525

TAC AGT CAA AGC AGC ATT GAT GCG AAA GCA GCC AGC CGC TAT GTT CGT     1632
Tyr Ser Gln Ser Ser Ile Asp Ala Lys Ala Ala Ser Arg Tyr Val Arg
530                 535                 540

TTT GGG GAA ACC ACC CCA ACC CGC GTC AAT GTC TAC GGT GCC GCT TAT     1680
Phe Gly Glu Thr Thr Pro Thr Arg Val Asn Val Tyr Gly Ala Ala Tyr
545                 550                 555                 560

CTG AAC AGC ACA CTG GCA GAC GCG GCT GAT GGT CAA TAT CTG TGG ATT     1728
Leu Asn Ser Thr Leu Ala Asp Ala Ala Asp Gly Gln Tyr Leu Trp Ile
                565                 570                 575

CAG ACT GAT GGC AAG AGC CTA AAT TTC ACT GAC GAT ACG GTA GTC GCC     1776
Gln Thr Asp Gly Lys Ser Leu Asn Phe Thr Asp Asp Thr Val Val Ala
            580                 585                 590

TTA GCC GGT CGC GCT GAA AAG CTG GTA CGT TTA TCA TCC CAG ACC GGG     1824
Leu Ala Gly Arg Ala Glu Lys Leu Val Arg Leu Ser Ser Gln Thr Gly
        595                 600                 605

CTA TCA TTT GAA GAA TTG GAC TGG CTG ATT GCC AAT GCC AGT CGT AGT     1872
Leu Ser Phe Glu Glu Leu Asp Trp Leu Ile Ala Asn Ala Ser Arg Ser
```

```
                610                     615                     620
GTG CCG GAC CAC CAC GAC AAA ATT GTG CTG GAT AAG CCG GTC CTT GAA          1920
Val Pro Asp His His Asp Lys Ile Val Leu Asp Lys Pro Val Leu Glu
625                 630                 635                 640

GCA CTG GCA GAG TAT GTC AGC CTA AAA CAG CGC TAT GGG CTT GAT GCC          1968
Ala Leu Ala Glu Tyr Val Ser Leu Lys Gln Arg Tyr Gly Leu Asp Ala
                645                 650                 655

AAT ACC TTT GCG ACC TTC ATT AGT GCA GTA AAT CCT TAT ACG CCA GAT          2016
Asn Thr Phe Ala Thr Phe Ile Ser Ala Val Asn Pro Tyr Thr Pro Asp
            660                 665                 670

CAG ACA CCC AGT TTC TAT GAA ACC GCT TTC CGC TCT GCC GAC GGT AAT          2064
Gln Thr Pro Ser Phe Tyr Glu Thr Ala Phe Arg Ser Ala Asp Gly Asn
        675                 680                 685

CAT GTC ATT GCG CTA GGT ACA GAG GTG AAA TAT GCA GAA AAT GAG CAG          2112
His Val Ile Ala Leu Gly Thr Glu Val Lys Tyr Ala Glu Asn Glu Gln
    690                 695                 700

GAT GAG TTA GCC GCC ATA TGC TGC AAA GCA TTG GGT GTC ACC AGT GAT          2160
Asp Glu Leu Ala Ala Ile Cys Cys Lys Ala Leu Gly Val Thr Ser Asp
705                 710                 715                 720

GAA CTG CTC CGT ATT GGT CGC TAT TGC TTC GGT AAT GCA GGC AGT TTT          2208
Glu Leu Leu Arg Ile Gly Arg Tyr Cys Phe Gly Asn Ala Gly Ser Phe
                725                 730                 735

ACC TTG GAT GAA TAT ACC GCC AGT CAG TTG TAT CGC TTC GGC GCC ATT          2256
Thr Leu Asp Glu Tyr Thr Ala Ser Gln Leu Tyr Arg Phe Gly Ala Ile
            740                 745                 750

CCC CGT TTG TTT GGG CTG ACA TTT GCC CAA GCC GAA ATT TTA TGG CGT          2304
Pro Arg Leu Phe Gly Leu Thr Phe Ala Gln Ala Glu Ile Leu Trp Arg
        755                 760                 765

CTG ATG GAA GGC GGA AAA GAT ATC TTA TTG CAA CAG TTA GGT CAG GCA          2352
Leu Met Glu Gly Gly Lys Asp Ile Leu Leu Gln Gln Leu Gly Gln Ala
770                 775                 780

AAA TCC CTG CAA CCA CTG GCT ATT TTA CGC CGT ACC GAG CAG GTG CTG          2400
Lys Ser Leu Gln Pro Leu Ala Ile Leu Arg Arg Thr Glu Gln Val Leu
785                 790                 795                 800

GAT TGG ATG TCG TCC GTA AAT CTA AGT CTG ACT TAT CTG CAA GGG ATG          2448
Asp Trp Met Ser Ser Val Asn Leu Ser Leu Thr Tyr Leu Gln Gly Met
                805                 810                 815

GTA AGT ACG CAA TGG AGC GGT ACC GCC ACC GCT GAG ATG TTC AAT TTC          2496
Val Ser Thr Gln Trp Ser Gly Thr Ala Thr Ala Glu Met Phe Asn Phe
            820                 825                 830

TTG GAA AAC GTT TGT GAC AGC GTG AAT AGT CAA GCT GCC ACT AAA GAA          2544
Leu Glu Asn Val Cys Asp Ser Val Asn Ser Gln Ala Ala Thr Lys Glu
        835                 840                 845

ACA ATG GAT TCG GCG TTA CAG CAG AAA GTG CTG CGG GCG CTA AGC GCC          2592
Thr Met Asp Ser Ala Leu Gln Gln Lys Val Leu Arg Ala Leu Ser Ala
    850                 855                 860

GGT TTC GGC ATT AAG AGC AAT GTG ATG GGT ATC GTC ACC TTC TGG CTG          2640
Gly Phe Gly Ile Lys Ser Asn Val Met Gly Ile Val Thr Phe Trp Leu
865                 870                 875                 880

GAG AAA ATC ACA ATC GGT AGT GAT AAT CCT TTT ACA TTG GCA AAC TAC          2688
Glu Lys Ile Thr Ile Gly Ser Asp Asn Pro Phe Thr Leu Ala Asn Tyr
                885                 890                 895

TGG CAT GAT ATT CAA ACC CTG TTT AGC CAT GAC AAT GCC ACG TTA GAG          2736
Trp His Asp Ile Gln Thr Leu Phe Ser His Asp Asn Ala Thr Leu Glu
            900                 905                 910

TCC TTA CAA ACC GAC ACT TCT CTG GTA ATT GCT ACT CAG CAA CTT AGC          2784
Ser Leu Gln Thr Asp Thr Ser Leu Val Ile Ala Thr Gln Gln Leu Ser
        915                 920                 925

CAG CTA GTG TTA ATT GTG AAA TGG CTG AGC CTG ACC GAG CAG GAT CTG          2832
```

```
Gln Leu Val Leu Ile Val Lys Trp Leu Ser Leu Thr Glu Gln Asp Leu
            930                 935                 940

CAA TTA CTG ACA ACC TAT CCC GAA CGT TTA ATC AAC GGC ATC ACG AAT         2880
Gln Leu Leu Thr Thr Tyr Pro Glu Arg Leu Ile Asn Gly Ile Thr Asn
945                 950                 955                 960

GTT CCT GTA CCC AAT CCG GAG CTA TTA CTC ACG CTA TCA CGT TTT AAG         2928
Val Pro Val Pro Asn Pro Glu Leu Leu Leu Thr Leu Ser Arg Phe Lys
                965                 970                 975

CAG TGG GAA ACT CAA GTC ACC GTT TCC CGT GAT GAA GCG ATG CGC TGT         2976
Gln Trp Glu Thr Gln Val Thr Val Ser Arg Asp Glu Ala Met Arg Cys
            980                 985                 990

TTC GAT CAA TTA AAT GCC AAT GAT ATG ACG ACT GAA AAT GCA GGT TCA         3024
Phe Asp Gln Leu Asn Ala Asn Asp Met Thr Thr Glu Asn Ala Gly Ser
            995                1000                1005

CTG ATC GCC ACA TTG TAT GAG ATG GAT AAA GGT ACG GGA GCG CAA GTT         3072
Leu Ile Ala Thr Leu Tyr Glu Met Asp Lys Gly Thr Gly Ala Gln Val
        1010                1015                1020

AAT ACC TTG CTA TTA GGT GAA AAT AAC TGG CCG AAA AGT TTT ACC TCT         3120
Asn Thr Leu Leu Leu Gly Glu Asn Asn Trp Pro Lys Ser Phe Thr Ser
1025                1030                1035                1040

CTC TGG CAA CTT CTG ACC TGG TTA CGC GTC GGG CAA AGA CTG AAT GTC         3168
Leu Trp Gln Leu Leu Thr Trp Leu Arg Val Gly Gln Arg Leu Asn Val
                1045                1050                1055

GGT AGT ACC ACT CTG GGC AAT CTG TTG TCC ATG ATG CAA GCA GAC CCT         3216
Gly Ser Thr Thr Leu Gly Asn Leu Leu Ser Met Met Gln Ala Asp Pro
            1060                1065                1070

GCT GCC GAG AGT AGC GCT TTA TTG GCA TCA GTA GCC CAA AAC TTA AGT         3264
Ala Ala Glu Ser Ser Ala Leu Leu Ala Ser Val Ala Gln Asn Leu Ser
        1075                1080                1085

GCC GCA ATC AGC AAT CGT CAG TAA                                         3288
Ala Ala Ile Ser Asn Arg Gln
        1090                1095

(2) INFORMATION FOR SEQ ID NO:34:

(i) SEQUENCE CHARACTERISTICS:
        (A) LENGTH: 1095 amino acids
        (B) TYPE: amino acids
        (D) TOPOLOGY: linear (ii) MOLECULE TYPE: protein (xi) SEQUENCE DESCRIPTION: SEQ ID NO:34:

Met Val Thr Val Met Gln Asn Lys Ile Ser Phe Leu Ser Gly Thr Ser
1               5                   10                  15

Glu Gln Pro Leu Leu Asp Ala Gly Tyr Gln Asn Val Phe Asp Ile Ala
            20                  25                  30

Ser Ile Ser Arg Ala Thr Phe Val Gln Ser Val Pro Thr Leu Pro Val
        35                  40                  45

Lys Glu Ala His Thr Val Tyr Arg Gln Ala Arg Gln Arg Ala Glu Asn
    50                  55                  60

Leu Lys Ser Leu Tyr Arg Ala Trp Gln Leu Arg Gln Glu Pro Val Ile
65                  70                  75                  80

Lys Gly Leu Ala Lys Leu Asn Leu Gln Ser Asn Val Ser Val Leu Gln
                85                  90                  95

Asp Ala Leu Val Glu Asn Ile Gly Gly Asp Gly Asp Phe Ser Asp Leu
            100                 105                 110

Met Asn Arg Ala Ser Gln Tyr Ala Asp Ala Ala Ser Ile Gln Ser Leu
        115                 120                 125
```

-continued

```
Phe Ser Pro Gly Arg Tyr Ala Ser Ala Leu Tyr Arg Val Ala Lys Asp
    130                 135                 140
Leu His Lys Ser Asp Ser Ser Leu His Ile Asp Asn Arg Arg Ala Asp
145                 150                 155                 160
Leu Lys Asp Leu Ile Leu Ser Glu Thr Thr Met Asn Lys Glu Val Thr
                165                 170                 175
Ser Leu Asp Ile Leu Leu Asp Val Leu Gln Lys Gly Gly Lys Asp Ile
            180                 185                 190
Thr Glu Leu Ser Gly Ala Phe Phe Pro Met Thr Leu Pro Tyr Asp Asp
        195                 200                 205
His Leu Ser Gln Ile Asp Ser Ala Leu Ser Ala Gln Ala Arg Thr Leu
    210                 215                 220
Asn Gly Val Trp Asn Thr Leu Thr Asp Thr Thr Ala Gln Ala Val Ser
225                 230                 235                 240
Glu Gln Thr Ser Asn Thr Asn Thr Arg Lys Leu Phe Ala Ala Gln Asp
                245                 250                 255
Gly Asn Gln Asp Thr Phe Phe Ser Gly Asn Thr Phe Tyr Phe Lys Ala
            260                 265                 270
Val Gly Phe Ser Gly Gln Pro Met Val Tyr Leu Ser Gln Tyr Thr Ser
        275                 280                 285
Gly Asn Gly Ile Val Gly Ala Gln Leu Ile Ala Gly Asn Pro Asp Gln
    290                 295                 300
Ala Ala Ala Ile Val Ala Pro Leu Lys Leu Thr Trp Ser Met Ala
305                 310                 315                 320
Lys Gln Cys Tyr Tyr Leu Val Ala Pro Asp Gly Thr Thr Met Gly Asp
                325                 330                 335
Gly Asn Val Leu Thr Gly Cys Phe Leu Arg Gly Asn Ser Pro Thr Asn
            340                 345                 350
Pro Asp Lys Asp Gly Ile Phe Ala Gln Val Ala Asn Lys Ser Gly Ser
        355                 360                 365
Thr Gln Pro Leu Pro Ser Phe His Leu Pro Val Thr Leu Glu His Ser
    370                 375                 380
Glu Asn Lys Asp Gln Tyr Tyr Leu Lys Thr Glu Gln Gly Tyr Ile Thr
385                 390                 395                 400
Val Asp Ser Ser Gly Gln Ser Asn Trp Lys Asn Ala Leu Val Ile Asn
                405                 410                 415
Gly Thr Lys Asp Lys Gly Leu Leu Leu Thr Phe Cys Ser Asp Ser Ser
            420                 425                 430
Gly Thr Pro Thr Asn Pro Asp Asp Val Ile Pro Pro Ala Ile Asn Asp
        435                 440                 445
Ile Pro Ser Pro Pro Ala Arg Glu Thr Leu Ser Leu Thr Pro Val Ser
    450                 455                 460
Tyr Gln Leu Met Thr Asn Pro Ala Pro Thr Glu Asp Asp Ile Thr Asn
465                 470                 475                 480
His Tyr Gly Phe Asn Gly Ala Ser Leu Arg Ala Ser Pro Leu Ser Thr
                485                 490                 495
Ser Glu Leu Thr Ser Lys Leu Asn Ser Ile Asp Thr Phe Cys Glu Lys
            500                 505                 510
Thr Arg Leu Ser Phe Asn Gln Leu Met Asp Leu Thr Ala Gln Gln Ser
        515                 520                 525
Tyr Ser Gln Ser Ser Ile Asp Ala Lys Ala Ala Ser Arg Tyr Val Arg
    530                 535                 540
Phe Gly Glu Thr Thr Pro Thr Arg Val Asn Val Tyr Gly Ala Ala Tyr
```

```
545                 550                 555                 560

Leu Asn Ser Thr Leu Ala Asp Ala Ala Asp Gly Gln Tyr Leu Trp Ile
                565                 570                 575

Gln Thr Asp Gly Lys Ser Leu Asn Phe Thr Asp Thr Val Val Ala
                580                 585                 590

Leu Ala Gly Arg Ala Glu Lys Leu Val Arg Leu Ser Ser Gln Thr Gly
                595                 600                 605

Leu Ser Phe Glu Glu Leu Asp Trp Leu Ile Ala Asn Ala Ser Arg Ser
                610                 615                 620

Val Pro Asp His His Asp Lys Ile Val Leu Asp Lys Pro Val Leu Glu
625                 630                 635                 640

Ala Leu Ala Glu Tyr Val Ser Leu Lys Gln Arg Tyr Gly Leu Asp Ala
                645                 650                 655

Asn Thr Phe Ala Thr Phe Ile Ser Ala Val Asn Pro Tyr Thr Pro Asp
                660                 665                 670

Gln Thr Pro Ser Phe Tyr Glu Thr Ala Phe Arg Ser Ala Asp Gly Asn
                675                 680                 685

His Val Ile Ala Leu Gly Thr Glu Val Lys Tyr Ala Glu Asn Glu Gln
                690                 695                 700

Asp Glu Leu Ala Ala Ile Cys Cys Lys Ala Leu Gly Val Thr Ser Asp
705                 710                 715                 720

Glu Leu Leu Arg Ile Gly Arg Tyr Cys Phe Gly Asn Ala Gly Ser Phe
                725                 730                 735

Thr Leu Asp Glu Tyr Thr Ala Ser Gln Leu Tyr Arg Phe Gly Ala Ile
                740                 745                 750

Pro Arg Leu Phe Gly Leu Thr Phe Ala Gln Ala Glu Ile Leu Trp Arg
                755                 760                 765

Leu Met Glu Gly Gly Lys Asp Ile Leu Leu Gln Gln Leu Gly Gln Ala
                770                 775                 780

Lys Ser Leu Gln Pro Leu Ala Ile Leu Arg Arg Thr Glu Gln Val Leu
785                 790                 795                 800

Asp Trp Met Ser Ser Val Asn Leu Ser Leu Thr Tyr Leu Gln Gly Met
                805                 810                 815

Val Ser Thr Gln Trp Ser Gly Thr Ala Thr Ala Glu Met Phe Asn Phe
                820                 825                 830

Leu Glu Asn Val Cys Asp Ser Val Asn Ser Gln Ala Ala Thr Lys Glu
                835                 840                 845

Thr Met Asp Ser Ala Leu Gln Gln Lys Val Leu Arg Ala Leu Ser Ala
850                 855                 860

Gly Phe Gly Ile Lys Ser Asn Val Met Gly Ile Val Thr Phe Trp Leu
865                 870                 875                 880

Glu Lys Ile Thr Ile Gly Ser Asp Asn Pro Phe Thr Leu Ala Asn Tyr
                885                 890                 895

Trp His Asp Ile Gln Thr Leu Phe Ser His Asp Asn Ala Thr Leu Glu
                900                 905                 910

Ser Leu Gln Thr Asp Thr Ser Leu Val Ile Ala Thr Gln Gln Leu Ser
                915                 920                 925

Gln Leu Val Leu Ile Val Lys Trp Leu Ser Leu Thr Glu Gln Asp Leu
                930                 935                 940

Gln Leu Leu Thr Thr Tyr Pro Glu Arg Leu Ile Asn Gly Ile Thr Asn
945                 950                 955                 960

Val Pro Val Pro Asn Pro Glu Leu Leu Leu Thr Leu Ser Arg Phe Lys
                965                 970                 975
```

```
Gln Trp Glu Thr Gln Val Thr Val Ser Arg Asp Glu Ala Met Arg Cys
            980                 985                 990

Phe Asp Gln Leu Asn Ala Asn Asp Met Thr Thr Glu Asn Ala Gly Ser
            995                1000                1005

Leu Ile Ala Thr Leu Tyr Glu Met Asp Lys Gly Thr Gly Ala Gln Val
           1010                1015                1020

Asn Thr Leu Leu Leu Gly Glu Asn Asn Trp Pro Lys Ser Phe Thr Ser
1025                1030                1035                1040

Leu Trp Gln Leu Leu Thr Trp Leu Arg Val Gly Gln Arg Leu Asn Val
                1045                1050                1055

Gly Ser Thr Thr Leu Gly Asn Leu Leu Ser Met Met Gln Ala Asp Pro
                1060                1065                1070

Ala Ala Glu Ser Ser Ala Leu Leu Ala Ser Val Ala Gln Asn Leu Ser
                1075                1080                1085

Ala Ala Ile Ser Asn Arg Gln
           1090                1095
```

(2) INFORMATION FOR SEQ ID NO:35:

(i) SEQUENCE CHARACTERISTICS:
        (A) LENGTH: 603 amino acids
        (B) TYPE: amino acid
        (D) TOPOLOGY: linear (ii) MOLECULE TYPE: protein (xi) SEQUENCE DESCRIPTION: SEQ ID NO:35:

```
Pro Leu Ser Thr Ser Glu Leu Thr Ser Lys Leu Asn Ser Ile Asp Thr
1               5                  10                  15

Phe Cys Glu Lys Thr Arg Leu Ser Phe Asn Gln Leu Met Asp Leu Thr
            20                  25                  30

Ala Gln Gln Ser Tyr Ser Gln Ser Ile Asp Ala Lys Ala Ala Ser
            35                  40                  45

Arg Tyr Val Arg Phe Gly Glu Thr Thr Pro Thr Arg Val Asn Val Tyr
50                  55                  60

Gly Ala Ala Tyr Leu Asn Ser Thr Leu Ala Asp Ala Asp Gly Gln
65                  70                  75                  80

Tyr Leu Trp Ile Gln Thr Asp Gly Lys Ser Leu Asn Phe Thr Asp Asp
                85                  90                  95

Thr Val Val Ala Leu Ala Gly Arg Ala Glu Lys Leu Val Arg Leu Ser
            100                 105                 110

Ser Gln Thr Gly Leu Ser Phe Glu Glu Leu Asp Trp Leu Ile Ala Asn
            115                 120                 125

Ala Ser Arg Ser Val Pro Asp His His Asp Lys Ile Val Leu Asp Lys
130                 135                 140

Pro Val Leu Glu Ala Leu Ala Glu Tyr Val Ser Leu Lys Gln Arg Tyr
145                 150                 155                 160

Gly Leu Asp Ala Asn Thr Phe Ala Thr Phe Ile Ser Ala Val Asn Pro
                165                 170                 175

Tyr Thr Pro Asp Gln Thr Pro Ser Phe Tyr Glu Thr Ala Phe Arg Ser
            180                 185                 190

Ala Asp Gly Asn His Val Ile Ala Leu Gly Thr Glu Val Lys Tyr Ala
            195                 200                 205

Glu Asn Glu Gln Asp Glu Leu Ala Ala Ile Cys Cys Lys Ala Leu Gly
            210                 215                 220
```

```
Val Thr Ser Asp Glu Leu Leu Arg Ile Gly Arg Tyr Cys Phe Gly Asn
225                 230                 235                 240

Ala Gly Arg Phe Thr Leu Asp Glu Tyr Thr Ala Ser Gln Leu Tyr Arg
                245                 250                 255

Phe Gly Ala Ile Pro Arg Leu Phe Gly Leu Thr Phe Ala Gln Ala Glu
                260                 265                 270

Ile Leu Trp Arg Leu Met Glu Gly Gly Lys Asp Ile Leu Leu Gln Gln
            275                 280                 285

Xaa Gly Gln Ala Lys Ser Leu Gln Pro Leu Ala Ile Leu Arg Arg Thr
290                 295                 300

Glu Gln Val Leu Asp Trp Met Ser Pro Val Asn Leu Ser Leu Thr Tyr
305                 310                 315                 320

Leu Gln Gly Met Val Ser Thr Gln Trp Ser Gly Thr Ala Thr Ala Glu
                325                 330                 335

Met Phe Asn Phe Leu Glu Asn Val Cys Asp Ser Val Asn Ser Gln Ala
                340                 345                 350

Xaa Thr Lys Glu Thr Met Asp Ser Ala Leu Gln Gln Lys Val Leu Arg
                355                 360                 365

Ala Leu Ser Ala Gly Phe Gly Ile Lys Ser Asn Val Met Gly Ile Val
370                 375                 380

Thr Phe Trp Leu Glu Lys Ile Thr Ile Gly Arg Asp Asn Pro Phe Thr
385                 390                 395                 400

Leu Ala Asn Tyr Trp His Asp Ile Gln Thr Leu Phe Ser His Asp Asn
                405                 410                 415

Ala Thr Leu Glu Ser Leu Gln Thr Asp Thr Ser Leu Val Ile Ala Thr
                420                 425                 430

Gln Gln Leu Ser Gln Leu Val Leu Ile Val Lys Trp Val Ser Leu Thr
            435                 440                 445

Glu Gln Asp Leu Gln Leu Leu Thr Thr Tyr Pro Glu Arg Leu Ile Asn
            450                 455                 460

Gly Ile Thr Asn Val Pro Val Pro Asn Pro Glu Leu Leu Thr Leu
465                 470                 475                 480

Ser Arg Phe Lys Gln Trp Glu Thr Gln Val Thr Val Ser Arg Asp Glu
                485                 490                 495

Ala Met Arg Cys Phe Asp Gln Leu Asn Ala Asn Asp Met Thr Thr Glu
                500                 505                 510

Asn Ala Gly Ser Leu Ile Ala Thr Leu Tyr Glu Met Asp Lys Gly Thr
                515                 520                 525

Gly Ala Gln Val Asn Thr Leu Leu Gly Glu Asn Asn Trp Pro Lys
530                 535                 540

Ser Phe Thr Ser Leu Trp Gln Leu Leu Thr Trp Leu Arg Val Gly Gln
545                 550                 555                 560

Arg Leu Asn Val Gly Ser Thr Thr Leu Gly Asn Leu Leu Ser Met Met
                565                 570                 575

Gln Ala Asp Pro Ala Ala Glu Ser Ser Ala Leu Leu Ala Ser Val Ala
                580                 585                 590

Gln Asn Leu Ser Ala Ala Ile Ser Asn Arg Gln
            595                 600

(2) INFORMATION FOR SEQ ID NO:36:

(i) SEQUENCE CHARACTERISTICS:
        (A) LENGTH:  2557 base pairs
        (B) TYPE: nucleic acid
        (C) STRANDEDNESS:  double
```

(D) TOPOLOGY: linear (ii) MOLECULE TYPE: DNA (genomic)

(xi) SEQUENCE DESCRIPTION: SEQ ID NO:36:

| | | | | | |
|---|---|---|---|---|---|
| GAATTCGGCT | TGCGTTTAAT | ATTGATGATG | TCTCGCTCTT | CCGCCTGCTT | AAAATTACCG | 60 |
| ACCATGATAA | TAAAGATGGA | AAAATTAAAA | ATAACCTAAA | GAATCTTTCC | AATTTATATA | 120 |
| TTGGAAAATT | ACTGGCAGAT | ATTCATCAAT | TAACCATTGA | TGAACTGGAT | TTATTACTGA | 180 |
| TTGCCGTAGG | TGAAGGAAAA | ACTAATTTAT | CCGCTATCAG | TGATAAGCAA | TTGGCTACCC | 240 |
| TGATCAGAAA | ACTCAATACT | ATTACCAGCT | GGCTACATAC | ACAGAAGTGG | AGTGTATTCC | 300 |
| AGCTATTTAT | CATGACCTCC | ACCAGCTATA | ACAAAACGCT | AACGCCTGAA | ATTAAGAATT | 360 |
| TGCTGGATAC | CGTCTACCAC | GGTTTACAAG | GTTTTGATAA | AGACAAAGCA | GATTTGCTAC | 420 |
| ATGTCATGGC | GCCCTATATT | GCGGCCACCT | TGCAATTATC | ATCGGAAAAT | GTCGCCCACT | 480 |
| CGGTACTCCT | TTGGGCAGAT | AAGTTACAGC | CCGGCGACGG | CGCAATGACA | GCAGAGGGAN | 540 |
| TCTGGGACTG | GTTGAATACT | AAGTATACGC | CGGGTTCATC | GGAAGCCGTA | GAAACGCAGG | 600 |
| AACATATCGT | TCAGTATTGT | CAGGCTCTGG | CACAATTGGA | AATGGTTTAC | CATTCCACCG | 660 |
| GCATCAACGA | AAACGCCTTC | CGTCTATTTG | TGACAAAACC | AGAGATGTTT | GGCGCTGCAA | 720 |
| CTGGAGCAGC | GCCCGCGCAT | GATGCCCTTT | CACTGATTAT | GCTGACACGT | TTTGCGGATT | 780 |
| GGGTGAACGC | ACTAGGCGAA | AAAGCGTCCT | CGGTGCTAGC | GGCATTTGAA | GCTAACTCGT | 840 |
| TAACGGCAGA | ACAACTGGCT | GATGCCATGA | ATCTTGATGC | TAATTTGCTG | TTGCAAGCCA | 900 |
| GTATTCAAGC | ACAAAATCAT | CAACATCTTC | CCCCAGTAAC | TCCAGAAAAT | GCGTTCTCCT | 960 |
| GTTGGACATC | TATCAATACT | ATCCTGCAAT | GGGTTAATGT | CGCACAACAA | TTGAAATGTC | 1020 |
| GCCCCACAGG | GCGTTTCCGC | TTTGGTCGGG | CTGGATTATA | TTCAATCAAT | GAAAGAGACA | 1080 |
| CCGACCTATG | CCCAGTGGGA | AAACGCGGCA | GGCGTATTAA | CCGCCGGGTT | GAATTCAACA | 1140 |
| ACAGGCTAAT | ACATTACAAC | GCTTTTCTGG | ATGAATCTCG | CAGTGCCGCA | TTAAGCACCT | 1200 |
| ACTATATCCG | TCAAGTCGCC | AAGGCAGCGG | CGGCTATTAA | AAGCCGTGAT | GACTTGTATC | 1260 |
| AATACTTACT | GATTGATAAT | CAGGTTTCTG | CGGCAATAAA | AACCACCCGG | ATCGCCGAAG | 1320 |
| CCATTGCCAG | TATTCAACTG | TACGTCAACC | GGGCATTGGA | AAATGTGGAA | GAAAATGCCA | 1380 |
| ATTCGGGGGT | TATCAGCCGC | CAATTCTTTA | TCGACTGGGA | CAAATACAAT | AAACGCTACA | 1440 |
| GCACTTGGGC | GGGTGTTTCT | CAATTAGTTT | ACTACCCGGA | AAACTATATT | GATCCGACCA | 1500 |
| TGCGTATCGG | ACAAACCAAA | ATGATGGACG | CATTACTGCA | ATCCGTCAGC | CAAAGCCAAT | 1560 |
| TAAACGCCGA | TACCGTCGAA | GATGCCTTTA | TGTCTTATCT | GACATCGTTT | GAACAAGTGG | 1620 |
| CTAATCTTAA | AGTTATTAGC | GCATATCACG | ATAATATTAA | TAACGATCAA | GGGCTGACCT | 1680 |
| ATTTTATCGG | ACTCAGTGAA | ACTGATGCCG | GTGAATATTA | TTGGCGCAGT | GTCGATCACA | 1740 |
| GTAAATTCAA | CGACGGTAAA | TTCGCGGCTA | ATGCCTGGAG | TGAATGGCAT | AAAATTGATT | 1800 |
| GTCCAATTAA | CCCTTATAAA | AGCACTATCC | GTCCAGTGAT | ATATAAATCC | CGCCTGTATC | 1860 |
| TGCTCTGGTT | GGAACAAAAG | GAGATCACCA | AACAGACAGG | AAATAGTAAA | GATGGCTATC | 1920 |
| AAACTGAAAC | GGATTATCGT | TATGAACTAA | AATTGGCGCA | TATCCGCTAT | GATGGCACTT | 1980 |
| GGAATACGCC | AATCACCTTT | GATGTCAATA | AAAAAATATC | CGAGCTAAAA | CTGGAAAAAA | 2040 |
| ATAGAGCGCC | CGGACTCTAT | TGTGCCGGTT | ATCAAGGTGA | AGATACGTTG | CTGGTGATGT | 2100 |
| TTTATAACCA | ACAAGACACA | CTAGATAGTT | ATAAAAACGC | TTCAATGCAA | GGACTATATA | 2160 |
| TCTTTGCTGA | TATGGCATCC | AAAGATATGA | CCCCAGAACA | GAGCAATGTT | TATCGGGATA | 2220 |

-continued

```
ATAGCTATCA ACAATTTGAT ACCAATAATG TCAGAAGAGT GAATAACCGC TATGCAGAGG      2280

ATTATGAGAT TCCTTCTTCG GTAAGTAGCC GTAAAGACTA TGGTTGGGGA GATTATTACC      2340

TCAGCATGGT ATATAACGGA GATATTCCAA CTATCAATTA CAAAGCCGCA TCAAGTGATT      2400

TAAAAATTTA TATTTCACCA AAATTAAGAA TTATTCATAA TGGATATGAA GGACAGAAGC      2460

GCAATCAATG CAATTTGATG AATAAATATG GCAAACTAGG TGATAAATTT ATTGTGTATA      2520

CCAGCCTGGG CGTTAATCCG AATAATAAGC CGAATTC                              2557
```

(2) INFORMATION FOR SEQ ID NO:37:

(i) SEQUENCE CHARACTERISTICS:
        (A) LENGTH: 845 amino acids
        (B) TYPE: amino acids
        (D) TOPOLOGY: linear (ii) MOLECULE TYPE: protein (partial)

(xi) SEQUENCE DESCRIPTION: SEQ ID NO:37:

```
Ala Phe Asn Ile Asp Asp Val Ser Leu Phe Arg Leu Leu Lys Ile Thr
1               5                   10                  15

Asp His Asp Asn Lys Asp Gly Lys Ile Lys Asn Asn Leu Lys Asn Leu
                20                  25                  30

Ser Asn Leu Tyr Ile Gly Lys Leu Leu Ala Asp Ile His Gln Leu Thr
            35                  40                  45

Ile Asp Glu Leu Asp Leu Leu Ile Ala Val Gly Glu Gly Lys Thr
50                  55                  60

Asn Leu Ser Ala Ile Ser Asp Lys Gln Leu Ala Thr Leu Ile Arg Lys
65                  70                  75                  80

Leu Asn Thr Ile Thr Ser Trp Leu His Thr Gln Lys Trp Ser Val Phe
                85                  90                  95

Gln Leu Phe Ile Met Thr Ser Thr Ser Tyr Asn Lys Thr Leu Thr Pro
                100                 105                 110

Glu Ile Lys Asn Leu Leu Asp Thr Val Tyr His Gly Leu Gln Gly Phe
            115                 120                 125

Asp Lys Asp Lys Ala Asp Leu Leu His Val Met Ala Pro Tyr Ile Ala
130                 135                 140

Ala Thr Leu Gln Leu Ser Ser Glu Asn Val Ala His Ser Val Leu Leu
145                 150                 155                 160

Trp Ala Asp Lys Leu Gln Pro Gly Asp Gly Ala Met Thr Ala Glu Gly
                165                 170                 175

Phe Trp Asp Trp Leu Asn Thr Lys Tyr Thr Pro Gly Ser Ser Glu Ala
            180                 185                 190

Val Glu Thr Gln Glu His Ile Val Gln Tyr Cys Gln Ala Leu Ala Gln
                195                 200                 205

Leu Glu Met Val Tyr His Ser Thr Gly Ile Asn Glu Asn Ala Phe Arg
            210                 215                 220

Leu Phe Val Thr Lys Pro Glu Met Phe Gly Ala Ala Thr Gly Ala Ala
225                 230                 235                 240

Pro Ala His Asp Ala Leu Ser Leu Ile Met Leu Thr Arg Phe Ala Asp
                245                 250                 255

Trp Val Asn Ala Leu Gly Glu Lys Ala Ser Ser Val Leu Ala Ala Phe
            260                 265                 270

Glu Ala Asn Ser Leu Thr Ala Glu Gln Leu Ala Asp Ala Met Asn Leu
            275                 280                 285
```

```
Asp Ala Asn Leu Leu Leu Gln Ala Ser Ile Gln Ala Gln Asn His Gln
    290                 295                 300

His Leu Pro Pro Val Thr Pro Glu Asn Ala Phe Ser Cys Trp Thr Ser
305                 310                 315                 320

Ile Asn Thr Ile Leu Gln Trp Val Asn Val Ala Gln Gln Leu Lys Cys
                325                 330                 335

Arg Pro Thr Gly Arg Phe Arg Phe Gly Arg Ala Gly Leu Tyr Ser Ile
            340                 345                 350

Asn Glu Arg Asp Thr Asp Leu Cys Pro Val Gly Lys Arg Gly Arg Arg
        355                 360                 365

Ile Asn Arg Arg Val Glu Phe Asn Asn Arg Leu Ile His Tyr Asn Ala
    370                 375                 380

Phe Leu Asp Glu Ser Arg Ser Ala Ala Leu Ser Thr Tyr Tyr Ile Arg
385                 390                 395                 400

Gln Val Ala Lys Ala Ala Ala Ile Lys Ser Arg Asp Asp Leu Tyr
                405                 410                 415

Gln Tyr Leu Leu Ile Asp Asn Gln Val Ser Ala Ala Ile Lys Thr Thr
            420                 425                 430

Arg Ile Ala Glu Ala Ile Ala Ser Ile Gln Leu Tyr Val Asn Arg Ala
        435                 440                 445

Leu Glu Asn Val Glu Glu Asn Ala Asn Ser Gly Val Ile Ser Arg Gln
    450                 455                 460

Phe Phe Ile Asp Trp Asp Lys Tyr Asn Lys Arg Tyr Ser Thr Trp Ala
465                 470                 475                 480

Gly Val Ser Gln Leu Val Tyr Tyr Pro Glu Asn Tyr Ile Asp Pro Thr
                485                 490                 495

Met Arg Ile Gly Gln Thr Lys Met Met Asp Ala Leu Leu Gln Ser Val
            500                 505                 510

Ser Gln Ser Gln Leu Asn Ala Asp Thr Val Glu Asp Ala Phe Met Ser
        515                 520                 525

Tyr Leu Thr Ser Phe Glu Gln Val Ala Asn Leu Lys Val Ile Ser Ala
    530                 535                 540

Tyr His Asp Asn Ile Asn Asn Asp Gln Gly Leu Thr Tyr Phe Ile Gly
545                 550                 555                 560

Leu Ser Glu Thr Asp Ala Gly Glu Tyr Tyr Trp Arg Ser Val Asp His
                565                 570                 575

Ser Lys Phe Asn Asp Gly Lys Phe Ala Ala Asn Ala Trp Ser Glu Trp
            580                 585                 590

His Lys Ile Asp Cys Pro Ile Asn Pro Tyr Lys Ser Thr Ile Arg Pro
        595                 600                 605

Val Ile Tyr Lys Ser Arg Leu Tyr Leu Leu Trp Leu Glu Gln Lys Glu
    610                 615                 620

Ile Thr Lys Gln Thr Gly Asn Ser Lys Asp Gly Tyr Gln Thr Glu Thr
625                 630                 635                 640

Asp Tyr Arg Tyr Glu Leu Lys Leu Ala His Ile Arg Tyr Asp Gly Thr
                645                 650                 655

Trp Asn Thr Pro Ile Thr Phe Asp Val Asn Lys Lys Ile Ser Glu Leu
            660                 665                 670

Lys Leu Glu Lys Asn Arg Ala Pro Gly Leu Tyr Cys Ala Gly Tyr Gln
        675                 680                 685

Gly Glu Asp Thr Leu Leu Val Met Phe Tyr Asn Gln Gln Asp Thr Leu
    690                 695                 700

Asp Ser Tyr Lys Asn Ala Ser Met Gln Gly Leu Tyr Ile Phe Ala Asp
```

```
                705                 710                 715                 720
Met Ala Ser Lys Asp Met Thr Pro Glu Gln Ser Asn Val Tyr Arg Asp
                    725                 730                 735

Asn Ser Tyr Gln Gln Phe Asp Thr Asn Asn Val Arg Arg Val Asn Asn
            740                 745                 750

Arg Tyr Ala Glu Asp Tyr Glu Ile Pro Ser Ser Val Ser Ser Arg Lys
        755                 760                 765

Asp Tyr Gly Trp Gly Asp Tyr Tyr Leu Ser Met Val Tyr Asn Gly Asp
    770                 775                 780

Ile Pro Thr Ile Asn Tyr Lys Ala Ala Ser Ser Asp Leu Lys Ile Tyr
785                 790                 795                 800

Ile Ser Pro Lys Leu Arg Ile Ile His Asn Gly Tyr Glu Gly Gln Lys
                805                 810                 815

Arg Asn Gln Cys Asn Leu Met Asn Lys Tyr Gly Lys Leu Gly Asp Lys
                    820                 825                 830

Phe Ile Val Tyr Thr Ser Leu Gly Val Asn Pro Asn Asn
    835                 840                 845
```

(2) INFORMATION FOR SEQ ID NO:38:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:38:

```
Arg Tyr Tyr Asn Leu Ser Asp Glu Glu Leu Ser Gln Phe Ile Gly
1               5                   10                  15
Lys
```

(2) INFORMATION FOR SEQ ID NO:39:

(i) SEQUENCE CHARACTERISTICS:
        (A) LENGTH: 20 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:39:

```
Gly Thr Ala Thr Asp Val Ser Gly Pro Val Glu Ile Asn Thr Ala
1               5                   10                  15
Ile Ser Pro Ala Lys
20
```

(2) INFORMATION FOR SEQ ID NO:40:

(i) SEQUENCE CHARACTERISTICS:
        (A) LENGTH: 11 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:40:

```
Ala Asn Ser Leu Tyr Ala Leu Phe Leu Pro Gln
1               5                   10

(2) INFORMATION FOR SEQ ID NO:41:

(i) SEQUENCE CHARACTERISTICS:
        (A) LENGTH:  14 amino acids
        (B) TYPE:  amino acid
        (D) TOPOLOGY:  linear (ii) MOLECULE TYPE: protein (v) FRAGMENT TYPE:   N-terminal (xi) SEQUENCE DESCRIPTION:  SEQ ID NO:41:

Leu Arg Ser Ala Asn Thr Leu Thr Asp Leu Phe Leu Pro Gln
1               5                   10

(2) INFORMATION FOR SEQ ID NO:42:

(i) SEQUENCE CHARACTERISTICS:
        (A) LENGTH:  19 amino acids
        (B) TYPE:  amino acid
        (D) TOPOLOGY:  linear (ii) MOLECULE TYPE: protein (v) FRAGMENT TYPE:   N-terminal (xi) SEQUENCE DESCRIPTION:  SEQ ID NO:42:

Arg Ala Leu Glu Val Glu Arg Thr Val Ser Leu Ala Glu Val Tyr
1               5                   10                  15

Ala Gly Leu Glu (2) INFORMATION FOR SEQ ID NO:43:

(i) SEQUENCE CHARACTERISTICS:
        (A) LENGTH:  11 amino acids
        (B) TYPE:  amino acid
        (D) TOPOLOGY:  linear (ii) MOLECULE TYPE: protein (v) FRAGMENT TYPE:   N-terminal (xi) SEQUENCE DESCRIPTION:  SEQ ID NO:43:

Ile Arg Glu Asp Tyr Pro Ala Ser Leu Gly Lys
1               5                   10

(2) INFORMATION FOR SEQ ID NO:44:

(i) SEQUENCE CHARACTERISTICS:
        (A) LENGTH:  16 amino acids
        (B) TYPE:  amino acid
        (D) TOPOLOGY:  linear (ii) MOLECULE TYPE: protein (v) FRAGMENT TYPE:   N-terminal (xi) SEQUENCE DESCRIPTION:  SEQ ID NO:44:

Asp Asp Ser Gly Asp Asp Asp Lys Val Thr Asn Thr Asp Ile His
1               5                   10                  15

Arg (2) INFORMATION FOR SEQ ID NO:45:

(i) SEQUENCE CHARACTERISTICS:
```

(A) LENGTH: 13 amino acids
(B) TYPE: amino acid
(D) TOPOLOGY: linear (ii) MOLECULE TYPE: protein (v) FRAGMENT TYPE: N-terminal (xi) SEQUENCE DESCRIPTION: SEQ ID NO:45:

Asp Val Xaa Gly Ser Glu Lys Ala Asn Glu Lys Leu Lys
1               5                   10

(2) INFORMATION FOR SEQ ID NO:46:

(i) SEQUENCE CHARACTERISTICS:
(A) LENGTH: 7551 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:46:

| | |
|---|---|
| ATG AAC GAG TCT GTA AAA GAG ATA CCT GAT GTA TTA AAA AGC CAG TGT<br>Met Asn Glu Ser Val Lys Glu Ile Pro Asp Val Leu Lys Ser Gln Cys<br>1               5                   10                  15 | 48 |
| GGT TTT AAT TGT CTG ACA GAT ATT AGC CAC AGC TCT TTT AAT GAA TTT<br>Gly Phe Asn Cys Leu Thr Asp Ile Ser His Ser Ser Phe Asn Glu Phe<br>            20                  25                  30 | 96 |
| CGC CAG CAA GTA TCT GAG CAC CTC TCC TGG TCC GAA ACA CAC GAC TTA<br>Arg Gln Gln Val Ser Glu His Leu Ser Trp Ser Glu Thr His Asp Leu<br>        35                  40                  45 | 144 |
| TAT CAT GAT GCA CAA CAG GCA CAA AAG GAT AAT CGC CTG TAT GAA GCG<br>Tyr His Asp Ala Gln Gln Ala Gln Lys Asp Asn Arg Leu Tyr Glu Ala<br>    50                  55                  60 | 192 |
| CGT ATT CTC AAA CGC GCC AAT CCC CAA TTA CAA AAT GCG GTG CAT CTT<br>Arg Ile Leu Lys Arg Ala Asn Pro Gln Leu Gln Asn Ala Val His Leu<br>65                  70                  75                  80 | 240 |
| GCC ATT CTC GCT CCC AAT GCT GAA CTG ATA GGC TAT AAC AAT CAA TTT<br>Ala Ile Leu Ala Pro Asn Ala Glu Leu Ile Gly Tyr Asn Asn Gln Phe<br>                85                  90                  95 | 288 |
| AGC GGT AGA GCC AGT CAA TAT GTT GCG CCG GGT ACC GTT TCT TCC ATG<br>Ser Gly Arg Ala Ser Gln Tyr Val Ala Pro Gly Thr Val Ser Ser Met<br>            100                 105                 110 | 336 |
| TTC TCC CCC GCC GCT TAT TTG ACT GAA CTT TAT CGT GAA GCA CGC AAT<br>Phe Ser Pro Ala Ala Tyr Leu Thr Glu Leu Tyr Arg Glu Ala Arg Asn<br>        115                 120                 125 | 384 |
| TTA CAC GCA AGT GAC TCC GTT TAT TAT CTG GAT ACC CGC CGC CCA GAT<br>Leu His Ala Ser Asp Ser Val Tyr Tyr Leu Asp Thr Arg Arg Pro Asp<br>    130                 135                 140 | 432 |
| CTC AAA TCA ATG GCG CTC AGT CAG CAA AAT ATG GAT ATA GAA TTA TCC<br>Leu Lys Ser Met Ala Leu Ser Gln Gln Asn Met Asp Ile Glu Leu Ser<br>145                 150                 155                 160 | 480 |
| ACA CTC TCT TTG TCC AAT GAG CTG TTA TTG GAA AGC ATT AAA ACT GAA<br>Thr Leu Ser Leu Ser Asn Glu Leu Leu Leu Glu Ser Ile Lys Thr Glu<br>                165                 170                 175 | 528 |
| TCT AAA CTG GAA AAC TAT ACT AAA GTG ATG GAA ATG CTC TCC ACT TTC<br>Ser Lys Leu Glu Asn Tyr Thr Lys Val Met Glu Met Leu Ser Thr Phe<br>            180                 185                 190 | 576 |
| CGT CCT TCC GGC GCA ACG CCT TAT CAT GAT GCT TAT GAA AAT GTG CGT<br>Arg Pro Ser Gly Ala Thr Pro Tyr His Asp Ala Tyr Glu Asn Val Arg<br>        195                 200                 205 | 624 |
| GAA GTT ATC CAG CTA CAA GAT CCT GGA CTT GAG CAA CTC AAT GCA TCA | 672 |

```
Glu Val Ile Gln Leu Gln Asp Pro Gly Leu Glu Gln Leu Asn Ala Ser
    210                 215                 220

CCG GCA ATT GCC GGG TTG ATG CAT CAA GCC TCC CTA TTG GGT ATT AAC         720
Pro Ala Ile Ala Gly Leu Met His Gln Ala Ser Leu Leu Gly Ile Asn
225                 230                 235                 240

GCT TCA ATC TCG CCT GAG CTA TTT AAT ATT CTG ACG GAG GAG ATT ACC         768
Ala Ser Ile Ser Pro Glu Leu Phe Asn Ile Leu Thr Glu Glu Ile Thr
                    245                 250                 255

GAA GGT AAT GCT GAG GAA CTT TAT AAG AAA AAT TTT GGT AAT ATC GAA         816
Glu Gly Asn Ala Glu Glu Leu Tyr Lys Lys Asn Phe Gly Asn Ile Glu
                260                 265                 270

CCG GCC TCA TTG GCT ATG CCG GAA TAC CTT AAA CGT TAT TAT AAT TTA         864
Pro Ala Ser Leu Ala Met Pro Glu Tyr Leu Lys Arg Tyr Tyr Asn Leu
            275                 280                 285

AGC GAT GAA GAA CTT AGT CAG TTT ATT GGT AAA GCC AGC AAT TTT GGT         912
Ser Asp Glu Glu Leu Ser Gln Phe Ile Gly Lys Ala Ser Asn Phe Gly
        290                 295                 300

CAA CAG GAA TAT AGT AAT AAC CAA CTT ATT ACT CCG GTA GTC AAC AGC         960
Gln Gln Glu Tyr Ser Asn Asn Gln Leu Ile Thr Pro Val Val Asn Ser
305                 310                 315                 320

AGT GAT GGC ACG GTT AAG GTA TAT CGG ATC ACC CGC GAA TAT ACA ACC        1008
Ser Asp Gly Thr Val Lys Val Tyr Arg Ile Thr Arg Glu Tyr Thr Thr
                    325                 330                 335

AAT GCT TAT CAA ATG GAT GTG GAG CTA TTT CCC TTC GGT GGT GAG AAT        1056
Asn Ala Tyr Gln Met Asp Val Glu Leu Phe Pro Phe Gly Gly Glu Asn
                340                 345                 350

TAT CGG TTA GAT TAT AAA TTC AAA AAT TTT TAT AAT GCC TCT TAT TTA        1104
Tyr Arg Leu Asp Tyr Lys Phe Lys Asn Phe Tyr Asn Ala Ser Tyr Leu
            355                 360                 365

TCC ATC AAG TTA AAT GAT AAA AGA GAA CTT GTT CGA ACT GAA GGC GCT        1152
Ser Ile Lys Leu Asn Asp Lys Arg Glu Leu Val Arg Thr Glu Gly Ala
        370                 375                 380

CCT CAA GTC AAT ATA GAA TAC TCC GCA AAT ATC ACA TTA AAT ACC GCT        1200
Pro Gln Val Asn Ile Glu Tyr Ser Ala Asn Ile Thr Leu Asn Thr Ala
385                 390                 395                 400

GAT ATC AGT CAA CCT TTT GAA ATT GGC CTG ACA CGA GTA CTT CCT TCC        1248
Asp Ile Ser Gln Pro Phe Glu Ile Gly Leu Thr Arg Val Leu Pro Ser
                    405                 410                 415

GGT TCT TGG GCA TAT GCC GCC GCA AAA TTT ACC GTT GAA GAG TAT AAC        1296
Gly Ser Trp Ala Tyr Ala Ala Ala Lys Phe Thr Val Glu Glu Tyr Asn
                420                 425                 430

CAA TAC TCT TTT CTG CTA AAA CTT AAC AAG GCT ATT CGT CTA TCA CGT        1344
Gln Tyr Ser Phe Leu Leu Lys Leu Asn Lys Ala Ile Arg Leu Ser Arg
            435                 440                 445

GCG ACA GAA TTG TCA CCC ACG ATT CTG GAA GGC ATT GTG CGC AGT GTT        1392
Ala Thr Glu Leu Ser Pro Thr Ile Leu Glu Gly Ile Val Arg Ser Val
        450                 455                 460

AAT CTA CAA CTG GAT ATC AAC ACA GAC GTA TTA GGT AAA GTT TTT CTG        1440
Asn Leu Gln Leu Asp Ile Asn Thr Asp Val Leu Gly Lys Val Phe Leu
465                 470                 475                 480

ACT AAA TAT TAT ATG CAG CGT TAT GCT ATT CAT GCT GAA ACT GCC CTG        1488
Thr Lys Tyr Tyr Met Gln Arg Tyr Ala Ile His Ala Glu Thr Ala Leu
                    485                 490                 495

ATA CTA TGC AAC GCG CCT ATT TCA CAA CGT TCA TAT GAT AAT CAA CCT        1536
Ile Leu Cys Asn Ala Pro Ile Ser Gln Arg Ser Tyr Asp Asn Gln Pro
                500                 505                 510

AGC CAA TTT GAT CGC CTG TTT AAT ACG CCA TTA CTG AAC GGA CAA TAT        1584
Ser Gln Phe Asp Arg Leu Phe Asn Thr Pro Leu Leu Asn Gly Gln Tyr
            515                 520                 525
```

```
TTT TCT ACC GGC GAT GAG GAG ATT GAT TTA AAT TCA GGT AGC ACC GGC      1632
Phe Ser Thr Gly Asp Glu Glu Ile Asp Leu Asn Ser Gly Ser Thr Gly
    530                 535                 540

GAT TGG CGA AAA ACC ATA CTT AAG CGT GCA TTT AAT ATT GAT GAT GTC      1680
Asp Trp Arg Lys Thr Ile Leu Lys Arg Ala Phe Asn Ile Asp Asp Val
545                 550                 555                 560

TCG CTC TTC CGC CTG CTT AAA ATT ACC GAC CAT GAT AAT AAA GAT GGA      1728
Ser Leu Phe Arg Leu Leu Lys Ile Thr Asp His Asp Asn Lys Asp Gly
                565                 570                 575

AAA ATT AAA AAT AAC CTA AAG AAT CTT TCC AAT TTA TAT ATT GGA AAA      1776
Lys Ile Lys Asn Asn Leu Lys Asn Leu Ser Asn Leu Tyr Ile Gly Lys
            580                 585                 590

TTA CTG GCA GAT ATT CAT CAA TTA ACC ATT GAT GAA CTG GAT TTA TTA      1824
Leu Leu Ala Asp Ile His Gln Leu Thr Ile Asp Glu Leu Asp Leu Leu
        595                 600                 605

CTG ATT GCC GTA GGT GAA GGA AAA ACT AAT TTA TCC GCT ATC AGT GAT      1872
Leu Ile Ala Val Gly Glu Gly Lys Thr Asn Leu Ser Ala Ile Ser Asp
    610                 615                 620

AAG CAA TTG GCT ACC CTG ATC AGA AAA CTC AAT ACT ATT ACC AGC TGG      1920
Lys Gln Leu Ala Thr Leu Ile Arg Lys Leu Asn Thr Ile Thr Ser Trp
625                 630                 635                 640

CTA CAT ACA CAG AAG TGG AGT GTA TTC CAG CTA TTT ATC ATG ACC TCC      1968
Leu His Thr Gln Lys Trp Ser Val Phe Gln Leu Phe Ile Met Thr Ser
                645                 650                 655

ACC AGC TAT AAC AAA ACG CTA ACG CCT GAA ATT AAG AAT TTG CTG GAT      2016
Thr Ser Tyr Asn Lys Thr Leu Thr Pro Glu Ile Lys Asn Leu Leu Asp
            660                 665                 670

ACC GTC TAC CAC GGT TTA CAA GGT TTT GAT AAA GAC AAA GCA GAT TTG      2064
Thr Val Tyr His Gly Leu Gln Gly Phe Asp Lys Asp Lys Ala Asp Leu
        675                 680                 685

CTA CAT GTC ATG GCG CCC TAT ATT GCG GCC ACC TTG CAA TTA TCA TCG      2112
Leu His Val Met Ala Pro Tyr Ile Ala Ala Thr Leu Gln Leu Ser Ser
    690                 695                 700

GAA AAT GTC GCC CAC TCG GTA CTC CTT TGG GCA GAT AAG TTA CAG CCC      2160
Glu Asn Val Ala His Ser Val Leu Leu Trp Ala Asp Lys Leu Gln Pro
705                 710                 715                 720

GGC GAC GGC GCA ATG ACA GCA GAA AAA TTC TGG GAC TGG TTG AAT ACT      2208
Gly Asp Gly Ala Met Thr Ala Glu Lys Phe Trp Asp Trp Leu Asn Thr
                725                 730                 735

AAG TAT ACG CCG GGT TCA TCG GAA GCC GTA GAA ACG CAG GAA CAT ATC      2256
Lys Tyr Thr Pro Gly Ser Ser Glu Ala Val Glu Thr Gln Glu His Ile
            740                 745                 750

GTT CAG TAT TGT CAG GCT CTG GCA CAA TTG GAA ATG GTT TAC CAT TCC      2304
Val Gln Tyr Cys Gln Ala Leu Ala Gln Leu Glu Met Val Tyr His Ser
        755                 760                 765

ACC GGC ATC AAC GAA AAC GCC TTC CGT CTA TTT GTG ACA AAA CCA GAG      2352
Thr Gly Ile Asn Glu Asn Ala Phe Arg Leu Phe Val Thr Lys Pro Glu
    770                 775                 780

ATG TTT GGC GCT GCA ACT GGA GCA GCG CCC GCG CAT GAT GCC CTT TCA      2400
Met Phe Gly Ala Ala Thr Gly Ala Ala Pro Ala His Asp Ala Leu Ser
785                 790                 795                 800

CTG ATT ATG CTG ACA CGT TTT GCG GAT TGG GTG AAC GCA CTA GGC GAA      2448
Leu Ile Met Leu Thr Arg Phe Ala Asp Trp Val Asn Ala Leu Gly Glu
                805                 810                 815

AAA GCG TCC TCG GTG CTA GCG GCA TTT GAA GCT AAC TCG TTA ACG GCA      2496
Lys Ala Ser Ser Val Leu Ala Ala Phe Glu Ala Asn Ser Leu Thr Ala
            820                 825                 830

GAA CAA CTG GCT GAT GCC ATG AAT CTT GAT GCT AAT TTG CTG TTG CAA      2544
Glu Gln Leu Ala Asp Ala Met Asn Leu Asp Ala Asn Leu Leu Leu Gln
        835                 840                 845
```

```
GCC AGT ATT CAA GCA CAA AAT CAT CAA CAT CTT CCC CCA GTA ACT CCA     2592
Ala Ser Ile Gln Ala Gln Asn His Gln His Leu Pro Pro Val Thr Pro
    850                 855                 860

GAA AAT GCG TTC TCC TGT TGG ACA TCT ATC AAT ACT ATC CTG CAA TGG     2640
Glu Asn Ala Phe Ser Cys Trp Thr Ser Ile Asn Thr Ile Leu Gln Trp
865                 870                 875                 880

GTT AAT GTC GCA CAA CAA TTG AAT GTC GCC CCA CAG GGC GTT TCC GCT     2688
Val Asn Val Ala Gln Gln Leu Asn Val Ala Pro Gln Gly Val Ser Ala
                885                 890                 895

TTG GTC GGG CTG GAT TAT ATT CAA TCA ATG AAA GAG ACA CCG ACC TAT     2736
Leu Val Gly Leu Asp Tyr Ile Gln Ser Met Lys Glu Thr Pro Thr Tyr
            900                 905                 910

GCC CAG TGG GAA AAC GCG GCA GGC GTA TTA ACC GCC GGG TTG AAT TCA     2784
Ala Gln Trp Glu Asn Ala Ala Gly Val Leu Thr Ala Gly Leu Asn Ser
        915                 920                 925

CAA CAG GCT AAT ACA TTA CAC GCT TTT CTG GAT GAA TCT CGC AGT GCC     2832
Gln Gln Ala Asn Thr Leu His Ala Phe Leu Asp Glu Ser Arg Ser Ala
    930                 935                 940

GCA TTA AGC ACC TAC TAT ATC CGT CAA GTC GCC AAG GCA GCG GCG GCT     2880
Ala Leu Ser Thr Tyr Tyr Ile Arg Gln Val Ala Lys Ala Ala Ala Ala
945                 950                 955                 960

ATT AAA AGC CGT GAT GAC TTG TAT CAA TAC TTA CTG ATT GAT AAT CAG     2928
Ile Lys Ser Arg Asp Asp Leu Tyr Gln Tyr Leu Leu Ile Asp Asn Gln
                965                 970                 975

GTT TCT GCG GCA ATA AAA ACC ACC CGG ATC GCC GAA GCC ATT GCC AGT     2976
Val Ser Ala Ala Ile Lys Thr Thr Arg Ile Ala Glu Ala Ile Ala Ser
            980                 985                 990

ATT CAA CTG TAC GTC AAC CGG GCA TTG GAA AAT GTG GAA GAA AAT GCC     3024
Ile Gln Leu Tyr Val Asn Arg Ala Leu Glu Asn Val Glu Glu Asn Ala
        995                 1000                1005

AAT TCG GGG GTT ATC AGC CGC CAA TTC TTT ATC GAC TGG GAC AAA TAC     3072
Asn Ser Gly Val Ile Ser Arg Gln Phe Phe Ile Asp Trp Asp Lys Tyr
    1010                1015                1020

AAT AAA CGC TAC AGC ACT TGG GCG GGT GTT TCT CAA TTA GTT TAC TAC     3120
Asn Lys Arg Tyr Ser Thr Trp Ala Gly Val Ser Gln Leu Val Tyr Tyr
1025                1030                1035                1040

CCG GAA AAC TAT ATT GAT CCG ACC ATG CGT ATC GGA CAA ACC AAA ATG     3168
Pro Glu Asn Tyr Ile Asp Pro Thr Met Arg Ile Gly Gln Thr Lys Met
                1045                1050                1055

ATG GAC GCA TTA CTG CAA TCC GTC AGC CAA AGC CAA TTA AAC GCC GAT     3216
Met Asp Ala Leu Leu Gln Ser Val Ser Gln Ser Gln Leu Asn Ala Asp
            1060                1065                1070

ACC GTC GAA GAT GCC TTT ATG TCT TAT CTG ACA TCG TTT GAA CAA GTG     3264
Thr Val Glu Asp Ala Phe Met Ser Tyr Leu Thr Ser Phe Glu Gln Val
        1075                1080                1085

GCT AAT CTT AAA GTT ATT AGC GCA TAT CAC GAT AAT ATT AAT AAC GAT     3312
Ala Asn Leu Lys Val Ile Ser Ala Tyr His Asp Asn Ile Asn Asn Asp
    1090                1095                1100

CAA GGG CTG ACC TAT TTT ATC GGA CTC AGT GAA ACT GAT GCC GGT GAA     3360
Gln Gly Leu Thr Tyr Phe Ile Gly Leu Ser Glu Thr Asp Ala Gly Glu
1105                1110                1115                1120

TAT TAT TGG CGC AGT GTC GAT CAC AGT AAA TTC AAC GAC GGT AAA TTC     3408
Tyr Tyr Trp Arg Ser Val Asp His Ser Lys Phe Asn Asp Gly Lys Phe
                1125                1130                1135

GCG GCT AAT GCC TGG AGT GAA TGG CAT AAA ATT GAT TGT CCA ATT AAC     3456
Ala Ala Asn Ala Trp Ser Glu Trp His Lys Ile Asp Cys Pro Ile Asn
            1140                1145                1150

CCT TAT AAA AGC ACT ATC CGT CCA GTG ATA TAT AAA TCC CGC CTG TAT     3504
Pro Tyr Lys Ser Thr Ile Arg Pro Val Ile Tyr Lys Ser Arg Leu Tyr
```

-continued

```
           1155                1160                1165
CTG CTC TGG TTG GAA CAA AAG GAG ATC ACC AAA CAG ACA GGA AAT AGT          3552
Leu Leu Trp Leu Glu Gln Lys Glu Ile Thr Lys Gln Thr Gly Asn Ser
        1170                1175                1180

AAA GAT GGC TAT CAA ACT GAA ACG GAT TAT CGT TAT GAA CTA AAA TTG          3600
Lys Asp Gly Tyr Gln Thr Glu Thr Asp Tyr Arg Tyr Glu Leu Lys Leu
1185                1190                1195                1200

GCG CAT ATC CGC TAT GAT GGC ACT TGG AAT ACG CCA ATC ACC TTT GAT          3648
Ala His Ile Arg Tyr Asp Gly Thr Trp Asn Thr Pro Ile Thr Phe Asp
            1205                1210                1215

GTC AAT AAA AAA ATA TCC GAG CTA AAA CTG GAA AAA AAT AGA GCG CCC          3696
Val Asn Lys Lys Ile Ser Glu Leu Lys Leu Glu Lys Asn Arg Ala Pro
        1220                1225                1230

GGA CTC TAT TGT GCC GGT TAT CAA GGT GAA GAT ACG TTG CTG GTG ATG          3744
Gly Leu Tyr Cys Ala Gly Tyr Gln Gly Glu Asp Thr Leu Leu Val Met
            1235                1240                1245

TTT TAT AAC CAA CAA GAC ACA CTA GAT AGT TAT AAA AAC GCT TCA ATG          3792
Phe Tyr Asn Gln Gln Asp Thr Leu Asp Ser Tyr Lys Asn Ala Ser Met
        1250                1255                1260

CAA GGA CTA TAT ATC TTT GCT GAT ATG GCA TCC AAA GAT ATG ACC CCA          3840
Gln Gly Leu Tyr Ile Phe Ala Asp Met Ala Ser Lys Asp Met Thr Pro
1265                1270                1275                1280

GAA CAG AGC AAT GTT TAT CGG GAT AAT AGC TAT CAA CAA TTT GAT ACC          3888
Glu Gln Ser Asn Val Tyr Arg Asp Asn Ser Tyr Gln Gln Phe Asp Thr
            1285                1290                1295

AAT AAT GTC AGA AGA GTG AAT AAC CGC TAT GCA GAG GAT TAT GAG ATT          3936
Asn Asn Val Arg Arg Val Asn Asn Arg Tyr Ala Glu Asp Tyr Glu Ile
        1300                1305                1310

CCT TCC TCG GTA AGT AGC CGT AAA GAC TAT GGT TGG GGA GAT TAT TAC          3984
Pro Ser Ser Val Ser Ser Arg Lys Asp Tyr Gly Trp Gly Asp Tyr Tyr
            1315                1320                1325

CTC AGC ATG GTA TAT AAC GGA GAT ATT CCA ACT ATC AAT TAC AAA GCC          4032
Leu Ser Met Val Tyr Asn Gly Asp Ile Pro Thr Ile Asn Tyr Lys Ala
        1330                1335                1340

GCA TCA AGT GAT TTA AAA ATC TAT ATC TCA CCA AAA TTA AGA ATT ATT          4080
Ala Ser Ser Asp Leu Lys Ile Tyr Ile Ser Pro Lys Leu Arg Ile Ile
1345                1350                1355                1360

CAT AAT GGA TAT GAA GGA CAG AAG CGC AAT CAA TGC AAT CTG ATG AAT          4128
His Asn Gly Tyr Glu Gly Gln Lys Arg Asn Gln Cys Asn Leu Met Asn
            1365                1370                1375

AAA TAT GGC AAA CTA GGT GAT AAA TTT ATT GTT TAT ACT AGC TTG GGG          4176
Lys Tyr Gly Lys Leu Gly Asp Lys Phe Ile Val Tyr Thr Ser Leu Gly
        1380                1385                1390

GTC AAT CCA AAT AAC TCG TCA AAT AAG CTC ATG TTT TAC CCC GTC TAT          4224
Val Asn Pro Asn Asn Ser Ser Asn Lys Leu Met Phe Tyr Pro Val Tyr
            1395                1400                1405

CAA TAT AGC GGA AAC ACC AGT GGA CTC AAT CAA GGG AGA CTA CTA TTC          4272
Gln Tyr Ser Gly Asn Thr Ser Gly Leu Asn Gln Gly Arg Leu Leu Phe
        1410                1415                1420

CAC CGT GAC ACC ACT TAT CCA TCT AAA GTA GAA GCT TGG ATT CCT GGA          4320
His Arg Asp Thr Thr Tyr Pro Ser Lys Val Glu Ala Trp Ile Pro Gly
1425                1430                1435                1440

GCA AAA CGT TCT CTA ACC AAC CAA AAT GCC GCC ATT GGT GAT GAT TAT          4368
Ala Lys Arg Ser Leu Thr Asn Gln Asn Ala Ala Ile Gly Asp Asp Tyr
            1445                1450                1455

GCT ACA GAC TCT CTG AAT AAA CCG GAT GAT CTT AAG CAA TAT ATC TTT          4416
Ala Thr Asp Ser Leu Asn Lys Pro Asp Asp Leu Lys Gln Tyr Ile Phe
        1460                1465                1470

ATG ACT GAC AGT AAA GGG ACT GCT ACT GAT GTC TCA GGC CCA GTA GAG          4464
```

```
                                                                            -continued Met Thr Asp Ser Lys Gly Thr Ala Thr Asp Val Ser Gly Pro Val Glu
        1475                1480                1485

ATT AAT ACT GCA ATT TCT CCA GCA AAA GTT CAG ATA ATA GTC AAA GCG           4512
Ile Asn Thr Ala Ile Ser Pro Ala Lys Val Gln Ile Ile Val Lys Ala
    1490                1495                1500

GGT GGC AAG GAG CAA ACT TTT ACC GCA GAT AAA GAT GTC TCC ATT CAG           4560
Gly Gly Lys Glu Gln Thr Phe Thr Ala Asp Lys Asp Val Ser Ile Gln
1505                1510                1515                1520

CCA TCA CCT AGC TTT GAT GAA ATG AAT TAT CAA TTT AAT GCC CTT GAA           4608
Pro Ser Pro Ser Phe Asp Glu Met Asn Tyr Gln Phe Asn Ala Leu Glu
                1525                1530                1535

ATA GAC GGT TCT GGT CTG AAT TTT ATT AAC AAC TCA GCC AGT ATT GAT           4656
Ile Asp Gly Ser Gly Leu Asn Phe Ile Asn Asn Ser Ala Ser Ile Asp
            1540                1545                1550

GTT ACT TTT ACC GCA TTT GCG GAG GAT GGC CGC AAA CTG GGT TAT GAA           4704
Val Thr Phe Thr Ala Phe Ala Glu Asp Gly Arg Lys Leu Gly Tyr Glu
        1555                1560                1565

AGT TTC AGT ATT CCT GTT ACC CTC AAG GTA AGT ACC GAT AAT GCC CTG           4752
Ser Phe Ser Ile Pro Val Thr Leu Lys Val Ser Thr Asp Asn Ala Leu
    1570                1575                1580

ACC CTG CAC CAT AAT GAA AAT GGT GCG CAA TAT ATG CAA TGG CAA TCC           4800
Thr Leu His His Asn Glu Asn Gly Ala Gln Tyr Met Gln Trp Gln Ser
1585                1590                1595                1600

TAT CGT ACC CGC CTG AAT ACT CTA TTT GCC CGC CAG TTG GTT GCA CGC           4848
Tyr Arg Thr Arg Leu Asn Thr Leu Phe Ala Arg Gln Leu Val Ala Arg
                1605                1610                1615

GCC ACC ACC GGA ATC GAT ACA ATT CTG AGT ATG GAA ACT CAG AAT ATT           4896
Ala Thr Thr Gly Ile Asp Thr Ile Leu Ser Met Glu Thr Gln Asn Ile
            1620                1625                1630

CAG GAA CCG CAG TTA GGC AAA GGT TTC TAT GCT ACG TTC GTG ATA CCT           4944
Gln Glu Pro Gln Leu Gly Lys Gly Phe Tyr Ala Thr Phe Val Ile Pro
        1635                1640                1645

CCC TAT AAC CTA TCA ACT CAT GGT GAT GAA CGT TGG TTT AAG CTT TAT           4992
Pro Tyr Asn Leu Ser Thr His Gly Asp Glu Arg Trp Phe Lys Leu Tyr
    1650                1655                1660

ATC AAA CAT GTT GTT GAT AAT AAT TCA CAT ATT ATC TAT TCA GGC CAG           5040
Ile Lys His Val Val Asp Asn Asn Ser His Ile Ile Tyr Ser Gly Gln
1665                1670                1675                1680

CTA ACA GAT ACA AAT ATA AAC ATC ACA TTA TTT ATT CCT CTT GAT GAT           5088
Leu Thr Asp Thr Asn Ile Asn Ile Thr Leu Phe Ile Pro Leu Asp Asp
                1685                1690                1695

GTC CCA TTG AAT CAA GAT TAT CAC GCC AAG GTT TAT ATG ACC TTC AAG           5136
Val Pro Leu Asn Gln Asp Tyr His Ala Lys Val Tyr Met Thr Phe Lys
            1700                1705                1710

AAA TCA CCA TCA GAT GGT ACC TGG TGG GGC CCT CAC TTT GTT AGA GAT           5184
Lys Ser Pro Ser Asp Gly Thr Trp Trp Gly Pro His Phe Val Arg Asp
        1715                1720                1725

GAT AAA GGA ATA GTA ACA ATA AAC CCT AAA TCC ATT TTG ACC CAT TTT           5232
Asp Lys Gly Ile Val Thr Ile Asn Pro Lys Ser Ile Leu Thr His Phe
    1730                1735                1740

GAG AGC GTC AAT GTC CTG AAT AAT ATT AGT AGC GAA CCA ATG GAT TTC           5280
Glu Ser Val Asn Val Leu Asn Asn Ile Ser Ser Glu Pro Met Asp Phe
1745                1750                1755                1760

AGC GGC GCT AAC AGC CTC TAT TTC TGG GAA CTG TTC TAC TAT ACC CCG           5328
Ser Gly Ala Asn Ser Leu Tyr Phe Trp Glu Leu Phe Tyr Tyr Thr Pro
                1765                1770                1775

ATG CTG GTT GCT CAA CGT TTG CTG CAT GAA CAG AAC TTC GAT GAA GCC           5376
Met Leu Val Ala Gln Arg Leu Leu His Glu Gln Asn Phe Asp Glu Ala
            1780                1785                1790
```

```
                                                    -continued

AAC CGT TGG CTG AAA TAT GTC TGG AGT CCA TCC GGT TAT ATT GTC CAC       5424
Asn Arg Trp Leu Lys Tyr Val Trp Ser Pro Ser Gly Tyr Ile Val His
        1795                1800                1805

GGC CAG ATT CAG AAC TAC CAG TGG AAC GTC CGC CCG TTA CTG GAA GAC       5472
Gly Gln Ile Gln Asn Tyr Gln Trp Asn Val Arg Pro Leu Leu Glu Asp
    1810                1815                1820

ACC AGT TGG AAC AGT GAT CCT TTG GAT TCC GTC GAT CCT GAC GCG GTA       5520
Thr Ser Trp Asn Ser Asp Pro Leu Asp Ser Val Asp Pro Asp Ala Val
1825                1830                1835                1840

GCA CAG CAC GAT CCA ATG CAC TAC AAA GTT TCA ACT TTT ATG CGT ACC       5568
Ala Gln His Asp Pro Met His Tyr Lys Val Ser Thr Phe Met Arg Thr
            1845                1850                1855

TTG GAT CTA TTG ATA GCA CGC GGC GAC CAT GCT TAT CGC CAA CTG GAA       5616
Leu Asp Leu Leu Ile Ala Arg Gly Asp His Ala Tyr Arg Gln Leu Glu
        1860                1865                1870

CGA GAT ACA CTC AAC GAA GCG AAG ATG TGG TAT ATG CAA GCG CTG CAT       5664
Arg Asp Thr Leu Asn Glu Ala Lys Met Trp Tyr Met Gln Ala Leu His
    1875                1880                1885

CTA TTA GGT GAC AAA CCT TAT CTA CCG CTG AGT ACG ACA TGG AGT GAT       5712
Leu Leu Gly Asp Lys Pro Tyr Leu Pro Leu Ser Thr Thr Trp Ser Asp
1890                1895                1900

CCA CGA CTA GAC AGA GCC GCG GAT ATC ACT ACC CAA AAT GCT CAC GAC       5760
Pro Arg Leu Asp Arg Ala Ala Asp Ile Thr Thr Gln Asn Ala His Asp
1905                1910                1915                1920

AGC GCA ATA GTC GCT CTG CGG CAG AAT ATA CCT ACA CCG GCA CCT TTA       5808
Ser Ala Ile Val Ala Leu Arg Gln Asn Ile Pro Thr Pro Ala Pro Leu
            1925                1930                1935

TCA TTG CGC AGC GCT AAT ACC CTG ACT GAT CTC TTC CTG CCG CAA ATC       5856
Ser Leu Arg Ser Ala Asn Thr Leu Thr Asp Leu Phe Leu Pro Gln Ile
        1940                1945                1950

AAT GAA GTG ATG ATG AAT TAC TGG CAG ACA TTA GCT CAG AGA GTA TAC       5904
Asn Glu Val Met Met Asn Tyr Trp Gln Thr Leu Ala Gln Arg Val Tyr
    1955                1960                1965

AAT CTG CGT CAT AAC CTC TCT ATC GAC GGC CAG CCG TTA TAT CTG CCA       5952
Asn Leu Arg His Asn Leu Ser Ile Asp Gly Gln Pro Leu Tyr Leu Pro
1970                1975                1980

ATC TAT GCC ACA CCG GCC GAT CCG AAA GCG TTA CTC AGC GCC GCC GTT       6000
Ile Tyr Ala Thr Pro Ala Asp Pro Lys Ala Leu Leu Ser Ala Ala Val
1985                1990                1995                2000

GCC ACT TCT CAA GGT GGA GGC AAG CTA CCG GAA TCA TTT ATG TCC CTG       6048
Ala Thr Ser Gln Gly Gly Gly Lys Leu Pro Glu Ser Phe Met Ser Leu
            2005                2010                2015

TGG CGT TTC CCG CAC ATG CTG GAA AAT GCG CGC GGC ATG GTT AGC CAG       6096
Trp Arg Phe Pro His Met Leu Glu Asn Ala Arg Gly Met Val Ser Gln
        2020                2025                2030

CTC ACC CAG TTC GGC TCC ACG TTA CAA AAT ATT ATC GAA CGT CAG GAC       6144
Leu Thr Gln Phe Gly Ser Thr Leu Gln Asn Ile Ile Glu Arg Gln Asp
    2035                2040                2045

GCG GAA GCG CTC AAT GCG TTA TTA CAA AAT CAG GCC GCC GAG CTG ATA       6192
Ala Glu Ala Leu Asn Ala Leu Leu Gln Asn Gln Ala Ala Glu Leu Ile
2050                2055                2060

TTG ACT AAC CTG AGC ATT CAG GAC AAA ACC ATT GAA GAA TTG GAT GCC       6240
Leu Thr Asn Leu Ser Ile Gln Asp Lys Thr Ile Glu Glu Leu Asp Ala
2065                2070                2075                2080

GAG AAA ACG GTG TTG GAA AAA TCC AAA GCG GGA GCA CAA TCG CGC TTT       6288
Glu Lys Thr Val Leu Glu Lys Ser Lys Ala Gly Ala Gln Ser Arg Phe
            2085                2090                2095

GAT AGC TAC GGC AAA CTG TAC GAT GAG AAT ATC AAC GCC GGT GAA AAC       6336
Asp Ser Tyr Gly Lys Leu Tyr Asp Glu Asn Ile Asn Ala Gly Glu Asn
        2100                2105                2110
```

```
CAA GCC ATG ACG CTA CGA GCG TCC GCC GCC GGG CTT ACC ACG GCA GTT      6384
Gln Ala Met Thr Leu Arg Ala Ser Ala Ala Gly Leu Thr Thr Ala Val
        2115                2120                2125

CAG GCA TCC CGT CTG GCC GGT GCG GCG GCT GAT CTG GTG CCT AAC ATC      6432
Gln Ala Ser Arg Leu Ala Gly Ala Ala Ala Asp Leu Val Pro Asn Ile
        2130                2135                2140

TTC GGC TTT GCC GGT GGC GGC AGC CGT TGG GGG GCT ATC GCT GAG GCG      6480
Phe Gly Phe Ala Gly Gly Gly Ser Arg Trp Gly Ala Ile Ala Glu Ala
        2145                2150                2155                2160

ACA GGT TAT GTG ATG GAA TTC TCC GCG AAT GTT ATG AAC ACC GAA GCG      6528
Thr Gly Tyr Val Met Glu Phe Ser Ala Asn Val Met Asn Thr Glu Ala
                    2165                2170                2175

GAT AAA ATT AGC CAA TCT GAA ACC TAC CGT CGT CGC CGT CAG GAG TGG      6576
Asp Lys Ile Ser Gln Ser Glu Thr Tyr Arg Arg Arg Arg Gln Glu Trp
            2180                2185                2190

GAG ATC CAG CGG AAT AAT GCC GAA GCG GAA TTG AAG CAA ATC GAT GCT      6624
Glu Ile Gln Arg Asn Asn Ala Glu Ala Glu Leu Lys Gln Ile Asp Ala
        2195                2200                2205

CAG CTC AAA TCA CTC GCT GTA CGC CGC GAA GCC GCC GTA TTG CAG AAA      6672
Gln Leu Lys Ser Leu Ala Val Arg Arg Glu Ala Ala Val Leu Gln Lys
        2210                2215                2220

ACC AGT CTG AAA ACC CAA CAA GAA CAG ACC CAA TCT CAA TTG GCC TTC      6720
Thr Ser Leu Lys Thr Gln Gln Glu Gln Thr Gln Ser Gln Leu Ala Phe
2225                2230                2235                2240

CTG CAA CGT AAG TTC AGC AAT CAG GCG TTA TAC AAC TGG CTG CGT GGT      6768
Leu Gln Arg Lys Phe Ser Asn Gln Ala Leu Tyr Asn Trp Leu Arg Gly
            2245                2250                2255

CGA CTG GCG GCG ATT TAC TTC CAG TTC TAC GAT TTG GCC GTC GCG CGT      6816
Arg Leu Ala Ala Ile Tyr Phe Gln Phe Tyr Asp Leu Ala Val Ala Arg
                2260                2265                2270

TGC CTG ATG GCA GAA CAA GCT TAC CGT TGG GAA CTC AAT GAT GAC TCT      6864
Cys Leu Met Ala Glu Gln Ala Tyr Arg Trp Glu Leu Asn Asp Asp Ser
        2275                2280                2285

GCC CGC TTC ATT AAA CCG GGC GCC TGG CAG GGA ACC TAT GCC GGT CTG      6912
Ala Arg Phe Ile Lys Pro Gly Ala Trp Gln Gly Thr Tyr Ala Gly Leu
        2290                2295                2300

CTT GCA GGT GAA ACC TTG ATG CTG AGT CTG GCA CAA ATG GAA GAC GCT      6960
Leu Ala Gly Glu Thr Leu Met Leu Ser Leu Ala Gln Met Glu Asp Ala
2305                2310                2315                2320

CAT CTG AAA CGC GAT AAA CGC GCA TTA GAG GTT GAA CGC ACA GTA TCG      7008
His Leu Lys Arg Asp Lys Arg Ala Leu Glu Val Glu Arg Thr Val Ser
            2325                2330                2335

CTG GCC GAA GTT TAT GCA GGA TTA CCA AAA GAT AAC GGT CCA TTT TCC      7056
Leu Ala Glu Val Tyr Ala Gly Leu Pro Lys Asp Asn Gly Pro Phe Ser
                2340                2345                2350

CTG GCT CAG GAA ATT GAC AAG CTG GTG AGT CAA GGT TCA GGC AGT GCC      7104
Leu Ala Gln Glu Ile Asp Lys Leu Val Ser Gln Gly Ser Gly Ser Ala
        2355                2360                2365

GGC AGT GGT AAT AAT AAT TTG GCG TTC GGC GCC GGC ACG GAC ACT AAA      7152
Gly Ser Gly Asn Asn Asn Leu Ala Phe Gly Ala Gly Thr Asp Thr Lys
        2370                2375                2380

ACC TCT TTG CAG GCA TCA GTT TCA TTC GCT GAT TTG AAA ATT CGT GAA      7200
Thr Ser Leu Gln Ala Ser Val Ser Phe Ala Asp Leu Lys Ile Arg Glu
2385                2390                2395                2400

GAT TAC CCG GCA TCG CTT GGC AAA ATT CGA CGT ATC AAA CAG ATC AGC      7248
Asp Tyr Pro Ala Ser Leu Gly Lys Ile Arg Arg Ile Lys Gln Ile Ser
            2405                2410                2415

GTC ACT TTG CCC GCG CTA CTG GGA CCG TAT CAG GAT GTA CAG GCA ATA      7296
Val Thr Leu Pro Ala Leu Leu Gly Pro Tyr Gln Asp Val Gln Ala Ile
```

```
                        2420                2425                2430
TTG TCT TAC GGC GAT AAA GCC GGA TTA GCT AAC GGC TGT GAA GCG CTG       7344
Leu Ser Tyr Gly Asp Lys Ala Gly Leu Ala Asn Gly Cys Glu Ala Leu
            2435                2440                2445

GCA GTT TCT CAC GGT ATG AAT GAC AGC GGC CAA TTC CAG CTC GAT TTC       7392
Ala Val Ser His Gly Met Asn Asp Ser Gly Gln Phe Gln Leu Asp Phe
        2450                2455                2460

AAC GAT GGC AAA TTC CTG CCA TTC GAA GGC ATC GCC ATT GAT CAA GGC       7440
Asn Asp Gly Lys Phe Leu Pro Phe Glu Gly Ile Ala Ile Asp Gln Gly
2465                2470                2475                2480

ACG CTG ACA CTG AGC TTC CCA AAT GCA TCT ATG CCG GAG AAA GGT AAA       7488
Thr Leu Thr Leu Ser Phe Pro Asn Ala Ser Met Pro Glu Lys Gly Lys
                2485                2490                2495

CAA GCC ACT ATG TTA AAA ACC CTG AAC GAT ATC ATT TTG CAT ATT CGC       7536
Gln Ala Thr Met Leu Lys Thr Leu Asn Asp Ile Ile Leu His Ile Arg
            2500                2505                2510

TAC ACC ATT AAA TAA                                                   7551
Tyr Thr Ile Lys
        2515

(2) INFORMATION FOR SEQ ID NO:47:

(i) SEQUENCE CHARACTERISTICS:
        (A) LENGTH: 2516 amino acids
        (B) TYPE: amino acids
        (D) TOPOLOGY: linear (ii) MOLECULE TYPE: protein (xi) SEQUENCE DESCRIPTION: SEQ ID NO:47:

Met Asn Glu Ser Val Lys Glu Ile Pro Asp Val Leu Lys Ser Gln Cys
1               5                   10                  15

Gly Phe Asn Cys Leu Thr Asp Ile Ser His Ser Ser Phe Asn Glu Phe
                20                  25                  30

Arg Gln Gln Val Ser Glu His Leu Ser Trp Ser Glu Thr His Asp Leu
            35                  40                  45

Tyr His Asp Ala Gln Gln Ala Gln Lys Asp Asn Arg Leu Tyr Glu Ala
        50                  55                  60

Arg Ile Leu Lys Arg Ala Asn Pro Gln Leu Gln Asn Ala Val His Leu
65                  70                  75                  80

Ala Ile Leu Ala Pro Asn Ala Glu Leu Ile Gly Tyr Asn Asn Gln Phe
                85                  90                  95

Ser Gly Arg Ala Ser Gln Tyr Val Ala Pro Gly Thr Val Ser Ser Met
            100                 105                 110

Phe Ser Pro Ala Ala Tyr Leu Thr Glu Leu Tyr Arg Glu Ala Arg Asn
        115                 120                 125

Leu His Ala Ser Asp Ser Val Tyr Tyr Leu Asp Thr Arg Arg Pro Asp
    130                 135                 140

Leu Lys Ser Met Ala Leu Ser Gln Gln Asn Met Asp Ile Glu Leu Ser
145                 150                 155                 160

Thr Leu Ser Leu Ser Asn Glu Leu Leu Leu Glu Ser Ile Lys Thr Glu
                165                 170                 175

Ser Lys Leu Glu Asn Tyr Thr Lys Val Met Glu Met Leu Ser Thr Phe
            180                 185                 190

Arg Pro Ser Gly Ala Thr Pro Tyr His Asp Ala Tyr Glu Asn Val Arg
        195                 200                 205

Glu Val Ile Gln Leu Gln Asp Pro Gly Leu Glu Gln Leu Asn Ala Ser
    210                 215                 220
```

-continued

```
Pro Ala Ile Ala Gly Leu Met His Gln Ala Ser Leu Leu Gly Ile Asn
225                 230                 235                 240

Ala Ser Ile Ser Pro Glu Leu Phe Asn Ile Leu Thr Glu Glu Ile Thr
            245                 250                 255

Glu Gly Asn Ala Glu Glu Leu Tyr Lys Lys Asn Phe Gly Asn Ile Glu
        260                 265                 270

Pro Ala Ser Leu Ala Met Pro Glu Tyr Leu Lys Arg Tyr Tyr Asn Leu
    275                 280                 285

Ser Asp Glu Glu Leu Ser Gln Phe Ile Gly Lys Ala Ser Asn Phe Gly
290                 295                 300

Gln Gln Glu Tyr Ser Asn Asn Gln Leu Ile Thr Pro Val Val Asn Ser
305                 310                 315                 320

Ser Asp Gly Thr Val Lys Val Tyr Arg Ile Thr Arg Glu Tyr Thr Thr
            325                 330                 335

Asn Ala Tyr Gln Met Asp Val Glu Leu Phe Pro Phe Gly Gly Glu Asn
        340                 345                 350

Tyr Arg Leu Asp Tyr Lys Phe Lys Asn Phe Tyr Asn Ala Ser Tyr Leu
    355                 360                 365

Ser Ile Lys Leu Asn Asp Lys Arg Glu Leu Val Arg Thr Glu Gly Ala
370                 375                 380

Pro Gln Val Asn Ile Glu Tyr Ser Ala Asn Ile Thr Leu Asn Thr Ala
385                 390                 395                 400

Asp Ile Ser Gln Pro Phe Glu Ile Gly Leu Thr Arg Val Leu Pro Ser
            405                 410                 415

Gly Ser Trp Ala Tyr Ala Ala Ala Lys Phe Thr Val Glu Glu Tyr Asn
        420                 425                 430

Gln Tyr Ser Phe Leu Leu Lys Leu Asn Lys Ala Ile Arg Leu Ser Arg
    435                 440                 445

Ala Thr Glu Leu Ser Pro Thr Ile Leu Glu Gly Ile Val Arg Ser Val
450                 455                 460

Asn Leu Gln Leu Asp Ile Asn Thr Asp Val Leu Gly Lys Val Phe Leu
465                 470                 475                 480

Thr Lys Tyr Tyr Met Gln Arg Tyr Ala Ile His Ala Glu Thr Ala Leu
            485                 490                 495

Ile Leu Cys Asn Ala Pro Ile Ser Gln Arg Ser Tyr Asp Asn Gln Pro
        500                 505                 510

Ser Gln Phe Asp Arg Leu Phe Asn Thr Pro Leu Leu Asn Gly Gln Tyr
    515                 520                 525

Phe Ser Thr Gly Asp Glu Glu Ile Asp Leu Asn Ser Gly Ser Thr Gly
530                 535                 540

Asp Trp Arg Lys Thr Ile Leu Lys Arg Ala Phe Asn Ile Asp Asp Val
545                 550                 555                 560

Ser Leu Phe Arg Leu Leu Lys Ile Thr Asp His Asp Asn Lys Asp Gly
            565                 570                 575

Lys Ile Lys Asn Asn Leu Lys Asn Leu Ser Asn Leu Tyr Ile Gly Lys
        580                 585                 590

Leu Leu Ala Asp Ile His Gln Leu Thr Ile Asp Glu Leu Asp Leu Leu
    595                 600                 605

Leu Ile Ala Val Gly Glu Gly Lys Thr Asn Leu Ser Ala Ile Ser Asp
610                 615                 620

Lys Gln Leu Ala Thr Leu Ile Arg Lys Leu Asn Thr Ile Thr Ser Trp
625                 630                 635                 640
```

-continued

```
Leu His Thr Gln Lys Trp Ser Val Phe Gln Leu Phe Ile Met Thr Ser
            645                 650                 655

Thr Ser Tyr Asn Lys Thr Leu Thr Pro Glu Ile Lys Asn Leu Leu Asp
            660                 665                 670

Thr Val Tyr His Gly Leu Gln Gly Phe Asp Lys Asp Lys Ala Asp Leu
            675                 680                 685

Leu His Val Met Ala Pro Tyr Ile Ala Thr Leu Gln Leu Ser Ser
            690                 695                 700

Glu Asn Val Ala His Ser Val Leu Leu Trp Ala Asp Lys Leu Gln Pro
705                 710                 715                 720

Gly Asp Gly Ala Met Thr Ala Glu Lys Phe Trp Asp Trp Leu Asn Thr
                    725                 730                 735

Lys Tyr Thr Pro Gly Ser Ser Glu Ala Val Glu Thr Gln Glu His Ile
                    740                 745                 750

Val Gln Tyr Cys Gln Ala Leu Ala Gln Leu Glu Met Val Tyr His Ser
                    755                 760                 765

Thr Gly Ile Asn Glu Asn Ala Phe Arg Leu Phe Val Thr Lys Pro Glu
            770                 775                 780

Met Phe Gly Ala Ala Thr Gly Ala Ala Pro Ala His Asp Ala Leu Ser
785                 790                 795                 800

Leu Ile Met Leu Thr Arg Phe Ala Asp Trp Val Asn Ala Leu Gly Glu
                    805                 810                 815

Lys Ala Ser Ser Val Leu Ala Ala Phe Glu Ala Asn Ser Leu Thr Ala
                    820                 825                 830

Glu Gln Leu Ala Asp Ala Met Asn Leu Asp Ala Asn Leu Leu Leu Gln
            835                 840                 845

Ala Ser Ile Gln Ala Gln Asn His Gln His Leu Pro Pro Val Thr Pro
850                 855                 860

Glu Asn Ala Phe Ser Cys Trp Thr Ser Ile Asn Thr Ile Leu Gln Trp
865                 870                 875                 880

Val Asn Val Ala Gln Gln Leu Asn Val Ala Pro Gln Gly Val Ser Ala
                    885                 890                 895

Leu Val Gly Leu Asp Tyr Ile Gln Ser Met Lys Glu Thr Pro Thr Tyr
            900                 905                 910

Ala Gln Trp Glu Asn Ala Ala Gly Val Leu Thr Ala Gly Leu Asn Ser
            915                 920                 925

Gln Gln Ala Asn Thr Leu His Ala Phe Leu Asp Glu Ser Arg Ser Ala
930                 935                 940

Ala Leu Ser Thr Tyr Tyr Ile Arg Gln Val Ala Lys Ala Ala Ala Ala
945                 950                 955                 960

Ile Lys Ser Arg Asp Asp Leu Tyr Gln Tyr Leu Leu Ile Asp Asn Gln
            965                 970                 975

Val Ser Ala Ala Ile Lys Thr Thr Arg Ile Ala Glu Ala Ile Ala Ser
            980                 985                 990

Ile Gln Leu Tyr Val Asn Arg Ala Leu Glu Asn Val Glu Glu Asn Ala
            995                 1000                1005

Asn Ser Gly Val Ile Ser Arg Gln Phe Phe Ile Asp Trp Asp Lys Tyr
        1010                1015                1020

Asn Lys Arg Tyr Ser Thr Trp Ala Gly Val Ser Gln Leu Val Tyr Tyr
        1025                1030                1035                1040

Pro Glu Asn Tyr Ile Asp Pro Thr Met Arg Ile Gly Gln Thr Lys Met
                    1045                1050                1055

Met Asp Ala Leu Leu Gln Ser Val Ser Gln Ser Gln Leu Asn Ala Asp
```

-continued

```
            1060                1065                1070
Thr Val Glu Asp Ala Phe Met Ser Tyr Leu Thr Ser Phe Glu Gln Val
            1075                1080                1085

Ala Asn Leu Lys Val Ile Ser Ala Tyr His Asp Asn Ile Asn Asn Asp
1090                1095                1100

Gln Gly Leu Thr Tyr Phe Ile Gly Leu Ser Glu Thr Asp Ala Gly Glu
1105                1110                1115                1120

Tyr Tyr Trp Arg Ser Val Asp His Ser Lys Phe Asn Asp Gly Lys Phe
                1125                1130                1135

Ala Ala Asn Ala Trp Ser Glu Trp His Lys Ile Asp Cys Pro Ile Asn
            1140                1145                1150

Pro Tyr Lys Ser Thr Ile Arg Pro Val Ile Tyr Lys Ser Arg Leu Tyr
            1155                1160                1165

Leu Leu Trp Leu Glu Gln Lys Glu Ile Thr Lys Gln Thr Gly Asn Ser
            1170                1175                1180

Lys Asp Gly Tyr Gln Thr Glu Thr Asp Tyr Arg Tyr Glu Leu Lys Leu
1185                1190                1195                1200

Ala His Ile Arg Tyr Asp Gly Thr Trp Asn Thr Pro Ile Thr Phe Asp
                1205                1210                1215

Val Asn Lys Lys Ile Ser Glu Leu Lys Leu Glu Lys Asn Arg Ala Pro
            1220                1225                1230

Gly Leu Tyr Cys Ala Gly Tyr Gln Gly Glu Asp Thr Leu Leu Val Met
            1235                1240                1245

Phe Tyr Asn Gln Gln Asp Thr Leu Asp Ser Tyr Lys Asn Ala Ser Met
            1250                1255                1260

Gln Gly Leu Tyr Ile Phe Ala Asp Met Ala Ser Lys Asp Met Thr Pro
1265                1270                1275                1280

Glu Gln Ser Asn Val Tyr Arg Asp Asn Ser Tyr Gln Gln Phe Asp Thr
                1285                1290                1295

Asn Asn Val Arg Arg Val Asn Asn Arg Tyr Ala Glu Asp Tyr Glu Ile
            1300                1305                1310

Pro Ser Ser Val Ser Ser Arg Lys Asp Tyr Gly Trp Gly Asp Tyr Tyr
            1315                1320                1325

Leu Ser Met Val Tyr Asn Gly Asp Ile Pro Thr Ile Asn Tyr Lys Ala
            1330                1335                1340

Ala Ser Ser Asp Leu Lys Ile Tyr Ile Ser Pro Lys Leu Arg Ile Ile
1345                1350                1355                1360

His Asn Gly Tyr Glu Gly Gln Lys Arg Asn Gln Cys Asn Leu Met Asn
                1365                1370                1375

Lys Tyr Gly Lys Leu Gly Asp Lys Phe Ile Val Tyr Thr Ser Leu Gly
            1380                1385                1390

Val Asn Pro Asn Asn Ser Ser Asn Lys Leu Met Phe Tyr Pro Val Tyr
            1395                1400                1405

Gln Tyr Ser Gly Asn Thr Ser Gly Leu Asn Gln Gly Arg Leu Leu Phe
            1410                1415                1420

His Arg Asp Thr Thr Tyr Pro Ser Lys Val Glu Ala Trp Ile Pro Gly
1425                1430                1435                1440

Ala Lys Arg Ser Leu Thr Asn Gln Asn Ala Ala Ile Gly Asp Asp Tyr
                1445                1450                1455

Ala Thr Asp Ser Leu Asn Lys Pro Asp Asp Leu Lys Gln Tyr Ile Phe
            1460                1465                1470

Met Thr Asp Ser Lys Gly Thr Ala Thr Asp Val Ser Gly Pro Val Glu
            1475                1480                1485
```

```
Ile Asn Thr Ala Ile Ser Pro Ala Lys Val Gln Ile Ile Val Lys Ala
        1490                1495                1500
Gly Gly Lys Glu Gln Thr Phe Thr Ala Asp Lys Asp Val Ser Ile Gln
1505                1510                1515                1520
Pro Ser Pro Ser Phe Asp Glu Met Asn Tyr Gln Phe Asn Ala Leu Glu
            1525                1530                1535
Ile Asp Gly Ser Gly Leu Asn Phe Ile Asn Asn Ser Ala Ser Ile Asp
        1540                1545                1550
Val Thr Phe Thr Ala Phe Ala Glu Asp Gly Arg Lys Leu Gly Tyr Glu
        1555                1560                1565
Ser Phe Ser Ile Pro Val Thr Leu Lys Val Ser Thr Asp Asn Ala Leu
        1570                1575                1580
Thr Leu His His Asn Glu Asn Gly Ala Gln Tyr Met Gln Trp Gln Ser
1585                1590                1595                1600
Tyr Arg Thr Arg Leu Asn Thr Leu Phe Ala Arg Gln Leu Val Ala Arg
            1605                1610                1615
Ala Thr Thr Gly Ile Asp Thr Ile Leu Ser Met Glu Thr Gln Asn Ile
            1620                1625                1630
Gln Glu Pro Gln Leu Gly Lys Gly Phe Tyr Ala Thr Phe Val Ile Pro
            1635                1640                1645
Pro Tyr Asn Leu Ser Thr His Gly Asp Glu Arg Trp Phe Lys Leu Tyr
        1650                1655                1660
Ile Lys His Val Val Asp Asn Asn Ser His Ile Ile Tyr Ser Gly Gln
1665                1670                1675                1680
Leu Thr Asp Thr Asn Ile Asn Ile Thr Leu Phe Ile Pro Leu Asp Asp
            1685                1690                1695
Val Pro Leu Asn Gln Asp Tyr His Ala Lys Val Tyr Met Thr Phe Lys
            1700                1705                1710
Lys Ser Pro Ser Asp Gly Thr Trp Trp Gly Pro His Phe Val Arg Asp
            1715                1720                1725
Asp Lys Gly Ile Val Thr Ile Asn Pro Lys Ser Ile Leu Thr His Phe
        1730                1735                1740
Glu Ser Val Asn Val Leu Asn Asn Ile Ser Ser Glu Pro Met Asp Phe
1745                1750                1755                1760
Ser Gly Ala Asn Ser Leu Tyr Phe Trp Glu Leu Phe Tyr Tyr Thr Pro
            1765                1770                1775
Met Leu Val Ala Gln Arg Leu Leu His Glu Gln Asn Phe Asp Glu Ala
            1780                1785                1790
Asn Arg Trp Leu Lys Tyr Val Trp Ser Pro Ser Gly Tyr Ile Val His
            1795                1800                1805
Gly Gln Ile Gln Asn Tyr Gln Trp Asn Val Arg Pro Leu Leu Glu Asp
        1810                1815                1820
Thr Ser Trp Asn Ser Asp Pro Leu Asp Ser Val Asp Pro Asp Ala Val
1825                1830                1835                1840
Ala Gln His Asp Pro Met His Tyr Lys Val Ser Thr Phe Met Arg Thr
            1845                1850                1855
Leu Asp Leu Leu Ile Ala Arg Gly Asp His Ala Tyr Arg Gln Leu Glu
            1860                1865                1870
Arg Asp Thr Leu Asn Glu Ala Lys Met Trp Tyr Met Gln Ala Leu His
            1875                1880                1885
Leu Leu Gly Asp Lys Pro Tyr Leu Pro Leu Ser Thr Thr Trp Ser Asp
            1890                1895                1900
```

```
Pro Arg Leu Asp Arg Ala Ala Asp Ile Thr Thr Gln Asn Ala His Asp
1905                1910                1915                1920

Ser Ala Ile Val Ala Leu Arg Gln Asn Ile Pro Thr Pro Ala Pro Leu
            1925                1930                1935

Ser Leu Arg Ser Ala Asn Thr Leu Thr Asp Leu Phe Leu Pro Gln Ile
            1940                1945                1950

Asn Glu Val Met Met Asn Tyr Trp Gln Thr Leu Ala Gln Arg Val Tyr
            1955                1960                1965

Asn Leu Arg His Asn Leu Ser Ile Asp Gly Gln Pro Leu Tyr Leu Pro
            1970                1975                1980

Ile Tyr Ala Thr Pro Ala Asp Pro Lys Ala Leu Leu Ser Ala Ala Val
1985                1990                1995                2000

Ala Thr Ser Gln Gly Gly Gly Lys Leu Pro Glu Ser Phe Met Ser Leu
            2005                2010                2015

Trp Arg Phe Pro His Met Leu Glu Asn Ala Arg Gly Met Val Ser Gln
            2020                2025                2030

Leu Thr Gln Phe Gly Ser Thr Leu Gln Asn Ile Ile Glu Arg Gln Asp
            2035                2040                2045

Ala Glu Ala Leu Asn Ala Leu Leu Gln Asn Gln Ala Ala Glu Leu Ile
            2050                2055                2060

Leu Thr Asn Leu Ser Ile Gln Asp Lys Thr Ile Glu Glu Leu Asp Ala
2065                2070                2075                2080

Glu Lys Thr Val Leu Glu Lys Ser Lys Ala Gly Ala Gln Ser Arg Phe
            2085                2090                2095

Asp Ser Tyr Gly Lys Leu Tyr Asp Glu Asn Ile Asn Ala Gly Glu Asn
            2100                2105                2110

Gln Ala Met Thr Leu Arg Ala Ser Ala Ala Gly Leu Thr Thr Ala Val
            2115                2120                2125

Gln Ala Ser Arg Leu Ala Gly Ala Ala Ala Asp Leu Val Pro Asn Ile
            2130                2135                2140

Phe Gly Phe Ala Gly Gly Gly Ser Arg Trp Gly Ala Ile Ala Glu Ala
2145                2150                2155                2160

Thr Gly Tyr Val Met Glu Phe Ser Ala Asn Val Met Asn Thr Glu Ala
            2165                2170                2175

Asp Lys Ile Ser Gln Ser Glu Thr Tyr Arg Arg Arg Gln Glu Trp
            2180                2185                2190

Glu Ile Gln Arg Asn Asn Ala Glu Ala Glu Leu Lys Gln Ile Asp Ala
            2195                2200                2205

Gln Leu Lys Ser Leu Ala Val Arg Arg Glu Ala Ala Val Leu Gln Lys
            2210                2215                2220

Thr Ser Leu Lys Thr Gln Gln Glu Gln Thr Gln Ser Gln Leu Ala Phe
2225                2230                2235                2240

Leu Gln Arg Lys Phe Ser Asn Gln Ala Leu Tyr Asn Trp Leu Arg Gly
            2245                2250                2255

Arg Leu Ala Ala Ile Tyr Phe Gln Phe Tyr Asp Leu Ala Val Ala Arg
            2260                2265                2270

Cys Leu Met Ala Glu Gln Ala Tyr Arg Trp Glu Leu Asn Asp Asp Ser
            2275                2280                2285

Ala Arg Phe Ile Lys Pro Gly Ala Trp Gln Gly Thr Tyr Ala Gly Leu
            2290                2295                2300

Leu Ala Gly Glu Thr Leu Met Leu Ser Leu Ala Gln Met Glu Asp Ala
2305                2310                2315                2320

His Leu Lys Arg Asp Lys Arg Ala Leu Glu Val Glu Arg Thr Val Ser
```

```
                    2325                2330                2335
Leu Ala Glu Val Tyr Ala Gly Leu Pro Lys Asp Asn Gly Pro Phe Ser
                2340                2345                2350
Leu Ala Gln Glu Ile Asp Lys Leu Val Ser Gln Gly Ser Gly Ser Ala
            2355                2360                2365
Gly Ser Gly Asn Asn Leu Ala Phe Gly Ala Gly Thr Asp Thr Lys
        2370                2375                2380
Thr Ser Leu Gln Ala Ser Val Ser Phe Ala Asp Leu Lys Ile Arg Glu
2385                2390                2395                2400
Asp Tyr Pro Ala Ser Leu Gly Lys Ile Arg Arg Ile Lys Gln Ile Ser
                2405                2410                2415
Val Thr Leu Pro Ala Leu Leu Gly Pro Tyr Gln Asp Val Gln Ala Ile
                2420                2425                2430
Leu Ser Tyr Gly Asp Lys Ala Gly Leu Ala Asn Gly Cys Glu Ala Leu
            2435                2440                2445
Ala Val Ser His Gly Met Asn Asp Ser Gly Gln Phe Gln Leu Asp Phe
        2450                2455                2460
Asn Asp Gly Lys Phe Leu Pro Phe Glu Gly Ile Ala Ile Asp Gln Gly
2465                2470                2475                2480
Thr Leu Thr Leu Ser Phe Pro Asn Ala Ser Met Pro Glu Lys Gly Lys
                2485                2490                2495
Gln Ala Thr Met Leu Lys Thr Leu Asn Asp Ile Ile Leu His Ile Arg
                2500                2505                2510
Tyr Thr Ile Lys
        2515

(2) INFORMATION FOR SEQ ID NO:48:

(i) SEQUENCE CHARACTERISTICS:
        (A) LENGTH: 5547 base pairs
        (B) TYPE: nucleic acid
        (C) STRANDEDNESS: double
        (D) TOPOLOGY: linear (ii) MOLECULE TYPE:  DNA (genomic)

(xi) SEQUENCE DESCRIPTION: SEQ ID NO:48:

CTG ATA GGC TAT AAC AAT CAA TTT AGC GGT AGA GCC AGT CAA TAT GTT         48
Leu Ile Gly Tyr Asn Asn Gln Phe Ser Gly Arg Ala Ser Gln Tyr Val
1               5                   10                  15

GCG CCG GGT ACC GTT TCT TCC ATG TTC TCC CCC GCC GCT TAT TTG ACT         96
Ala Pro Gly Thr Val Ser Ser Met Phe Ser Pro Ala Ala Tyr Leu Thr
                20                  25                  30

GAA CTT TAT CGT GAA GCA CGC AAT TTA CAC GCA AGT GAC TCC GTT TAT        144
Glu Leu Tyr Arg Glu Ala Arg Asn Leu His Ala Ser Asp Ser Val Tyr
            35                  40                  45

TAT CTG GAT ACC CGC CGC CCA GAT CTC AAA TCA ATG GCG CTC AGT CAG        192
Tyr Leu Asp Thr Arg Arg Pro Asp Leu Lys Ser Met Ala Leu Ser Gln
        50                  55                  60

CAA AAT ATG GAT ATA GAA TTA TCC ACA CTC TCT TTG TCC AAT GAG CTG        240
Gln Asn Met Asp Ile Glu Leu Ser Thr Leu Ser Leu Ser Asn Glu Leu
65                  70                  75                  80

TTA TTG GAA AGC ATT AAA ACT GAA TCT AAA CTG GAA AAC TAT ACT AAA        288
Leu Leu Glu Ser Ile Lys Thr Glu Ser Lys Leu Glu Asn Tyr Thr Lys
                85                  90                  95

GTG ATG GAA ATG CTC TCC ACT TTC CGT CCT TCC GGC GCA ACG CCT TAT        336
Val Met Glu Met Leu Ser Thr Phe Arg Pro Ser Gly Ala Thr Pro Tyr
                100                 105                 110
```

```
CAT GAT GCT TAT GAA AAT GTG CGT GAA GTT ATC CAG CTA CAA GAT CCT        384
His Asp Ala Tyr Glu Asn Val Arg Glu Val Ile Gln Leu Gln Asp Pro
            115                 120                 125

GGA CTT GAG CAA CTC AAT GCA TCA CCG GCA ATT GCC GGG TTG ATG CAT        432
Gly Leu Glu Gln Leu Asn Ala Ser Pro Ala Ile Ala Gly Leu Met His
130                 135                 140

CAA GCC TCC CTA TTG GGT ATT AAC GCT TCA ATC TCG CCT GAG CTA TTT        480
Gln Ala Ser Leu Leu Gly Ile Asn Ala Ser Ile Ser Pro Glu Leu Phe
145                 150                 155                 160

AAT ATT CTG ACG GAG GAG ATT ACC GAA GGT AAT GCT GAG GAA CTT TAT        528
Asn Ile Leu Thr Glu Glu Ile Thr Glu Gly Asn Ala Glu Glu Leu Tyr
            165                 170                 175

AAG AAA AAT TTT GGT AAT ATC GAA CCG GCC TCA TTG GCT ATG CCG GAA        576
Lys Lys Asn Phe Gly Asn Ile Glu Pro Ala Ser Leu Ala Met Pro Glu
            180                 185                 190

TAC CTT AAA CGT TAT TAT AAT TTA AGC GAT GAA GAA CTT AGT CAG TTT        624
Tyr Leu Lys Arg Tyr Tyr Asn Leu Ser Asp Glu Glu Leu Ser Gln Phe
            195                 200                 205

ATT GGT AAA GCC AGC AAT TTT GGT CAA CAG GAA TAT AGT AAT AAC CAA        672
Ile Gly Lys Ala Ser Asn Phe Gly Gln Gln Glu Tyr Ser Asn Asn Gln
            210                 215                 220

CTT ATT ACT CCG GTA GTC AAC AGC AGT GAT GGC ACG GTT AAG GTA TAT        720
Leu Ile Thr Pro Val Val Asn Ser Ser Asp Gly Thr Val Lys Val Tyr
225                 230                 235                 240

CGG ATC ACC CGC GAA TAT ACA ACC AAT GCT TAT CAA ATG GAT GTG GAG        768
Arg Ile Thr Arg Glu Tyr Thr Thr Asn Ala Tyr Gln Met Asp Val Glu
            245                 250                 255

CTA TTT CCC TTC GGT GGT GAG AAT TAT CGG TTA GAT TAT AAA TTC AAA        816
Leu Phe Pro Phe Gly Gly Glu Asn Tyr Arg Leu Asp Tyr Lys Phe Lys
            260                 265                 270

AAT TTT TAT AAT GCC TCT TAT TTA TCC ATC AAG TTA AAT GAT AAA AGA        864
Asn Phe Tyr Asn Ala Ser Tyr Leu Ser Ile Lys Leu Asn Asp Lys Arg
            275                 280                 285

GAA CTT GTT CGA ACT GAA GGC GCT CCT CAA GTC AAT ATA GAA TAC TCC        912
Glu Leu Val Arg Thr Glu Gly Ala Pro Gln Val Asn Ile Glu Tyr Ser
290                 295                 300

GCA AAT ATC ACA TTA AAT ACC GCT GAT ATC AGT CAA CCT TTT GAA ATT        960
Ala Asn Ile Thr Leu Asn Thr Ala Asp Ile Ser Gln Pro Phe Glu Ile
305                 310                 315                 320

GGC CTG ACA CGA GTA CTT CCT TCC GGT TCT TGG GCA TAT GCC GCC GCA       1008
Gly Leu Thr Arg Val Leu Pro Ser Gly Ser Trp Ala Tyr Ala Ala Ala
            325                 330                 335

AAA TTT ACC GTT GAA GAG TAT AAC CAA TAC TCT TTT CTG CTA AAA CTT       1056
Lys Phe Thr Val Glu Glu Tyr Asn Gln Tyr Ser Phe Leu Leu Lys Leu
            340                 345                 350

AAC AAG GCT ATT CGT CTA TCA CGT GCG ACA GAA TTG TCA CCC ACG ATT       1104
Asn Lys Ala Ile Arg Leu Ser Arg Ala Thr Glu Leu Ser Pro Thr Ile
            355                 360                 365

CTG GAA GGC ATT GTG CGC AGT GTT AAT CTA CAA CTG GAT ATC AAC ACA       1152
Leu Glu Gly Ile Val Arg Ser Val Asn Leu Gln Leu Asp Ile Asn Thr
370                 375                 380

GAC GTA TTA GGT AAA GTT TTT CTG ACT AAA TAT TAT ATG CAG CGT TAT       1200
Asp Val Leu Gly Lys Val Phe Leu Thr Lys Tyr Tyr Met Gln Arg Tyr
385                 390                 395                 400

GCT ATT CAT GCT GAA ACT GCC CTG ATA CTA TGC AAC GCG CCT ATT TCA       1248
Ala Ile His Ala Glu Thr Ala Leu Ile Leu Cys Asn Ala Pro Ile Ser
            405                 410                 415

CAA CGT TCA TAT GAT AAT CAA CCT AGC CAA TTT GAT CGC CTG TTT AAT       1296
Gln Arg Ser Tyr Asp Asn Gln Pro Ser Gln Phe Asp Arg Leu Phe Asn
            420                 425                 430
```

```
ACG CCA TTA CTG AAC GGA CAA TAT TTT TCT ACC GGC GAT GAG GAG ATT      1344
Thr Pro Leu Leu Asn Gly Gln Tyr Phe Ser Thr Gly Asp Glu Glu Ile
        435                 440                 445

GAT TTA AAT TCA GGT AGC ACC GGC GAT TGG CGA AAA ACC ATA CTT AAG      1392
Asp Leu Asn Ser Gly Ser Thr Gly Asp Trp Arg Lys Thr Ile Leu Lys
        450                 455                 460

CGT GCA TTT AAT ATT GAT GAT GTC TCG CTC TTC CGC CTG CTT AAA ATT      1440
Arg Ala Phe Asn Ile Asp Asp Val Ser Leu Phe Arg Leu Leu Lys Ile
465                 470                 475                 480

ACC GAC CAT GAT AAT AAA GAT GGA AAA ATT AAA AAT AAC CTA AAG AAT      1488
Thr Asp His Asp Asn Lys Asp Gly Lys Ile Lys Asn Asn Leu Lys Asn
                485                 490                 495

CTT TCC AAT TTA TAT ATT GGA AAA TTA CTG GCA GAT ATT CAT CAA TTA      1536
Leu Ser Asn Leu Tyr Ile Gly Lys Leu Leu Ala Asp Ile His Gln Leu
        500                 505                 510

ACC ATT GAT GAA CTG GAT TTA TTA CTG ATT GCC GTA GGT GAA GGA AAA      1584
Thr Ile Asp Glu Leu Asp Leu Leu Leu Ile Ala Val Gly Glu Gly Lys
        515                 520                 525

ACT AAT TTA TCC GCT ATC AGT GAT AAG CAA TTG GCT ACC CTG ATC AGA      1632
Thr Asn Leu Ser Ala Ile Ser Asp Lys Gln Leu Ala Thr Leu Ile Arg
530                 535                 540

AAA CTC AAT ACT ATT ACC AGC TGG CTA CAT ACA CAG AAG TGG AGT GTA      1680
Lys Leu Asn Thr Ile Thr Ser Trp Leu His Thr Gln Lys Trp Ser Val
545                 550                 555                 560

TTC CAG CTA TTT ATC ATG ACC TCC ACC AGC TAT AAC AAA ACG CTA ACG      1728
Phe Gln Leu Phe Ile Met Thr Ser Thr Ser Tyr Asn Lys Thr Leu Thr
                565                 570                 575

CCT GAA ATT AAG AAT TTG CTG GAT ACC GTC TAC CAC GGT TTA CAA GGT      1776
Pro Glu Ile Lys Asn Leu Leu Asp Thr Val Tyr His Gly Leu Gln Gly
        580                 585                 590

TTT GAT AAA GAC AAA GCA GAT TTG CTA CAT GTC ATG GCG CCC TAT ATT      1824
Phe Asp Lys Asp Lys Ala Asp Leu Leu His Val Met Ala Pro Tyr Ile
        595                 600                 605

GCG GCC ACC TTG CAA TTA TCA TCG GAA AAT GTC GCC CAC TCG GTA CTC      1872
Ala Ala Thr Leu Gln Leu Ser Ser Glu Asn Val Ala His Ser Val Leu
        610                 615                 620

CTT TGG GCA GAT AAG TTA CAG CCC GGC GAC GGC GCA ATG ACA GCA GAA      1920
Leu Trp Ala Asp Lys Leu Gln Pro Gly Asp Gly Ala Met Thr Ala Glu
625                 630                 635                 640

AAA TTC TGG GAC TGG TTG AAT ACT AAG TAT ACG CCG GGT TCA TCG GAA      1968
Lys Phe Trp Asp Trp Leu Asn Thr Lys Tyr Thr Pro Gly Ser Ser Glu
                645                 650                 655

GCC GTA GAA ACG CAG GAA CAT ATC GTT CAG TAT TGT CAG GCT CTG GCA      2016
Ala Val Glu Thr Gln Glu His Ile Val Gln Tyr Cys Gln Ala Leu Ala
        660                 665                 670

CAA TTG GAA ATG GTT TAC CAT TCC ACC GGC ATC AAC GAA AAC GCC TTC      2064
Gln Leu Glu Met Val Tyr His Ser Thr Gly Ile Asn Glu Asn Ala Phe
        675                 680                 685

CGT CTA TTT GTG ACA AAA CCA GAG ATG TTT GGC GCT GCA ACT GGA GCA      2112
Arg Leu Phe Val Thr Lys Pro Glu Met Phe Gly Ala Ala Thr Gly Ala
        690                 695                 700

GCG CCC GCG CAT GAT GCC CTT TCA CTG ATT ATG CTG ACA CGT TTT GCG      2160
Ala Pro Ala His Asp Ala Leu Ser Leu Ile Met Leu Thr Arg Phe Ala
705                 710                 715                 720

GAT TGG GTG AAC GCA CTA GGC GAA AAA GCG TCC TCG GTG CTA GCG GCA      2208
Asp Trp Val Asn Ala Leu Gly Glu Lys Ala Ser Ser Val Leu Ala Ala
                725                 730                 735

TTT GAA GCT AAC TCG TTA ACG GCA GAA CAA CTG GCT GAT GCC ATG AAT      2256
Phe Glu Ala Asn Ser Leu Thr Ala Glu Gln Leu Ala Asp Ala Met Asn
```

-continued

```
                        740                          745                          750
CTT GAT GCT AAT TTG CTG TTG CAA GCC AGT ATT CAA GCA CAA AAT CAT                 2304
Leu Asp Ala Asn Leu Leu Leu Gln Ala Ser Ile Gln Ala Gln Asn His
        755                          760                          765

CAA CAT CTT CCC CCA GTA ACT CCA GAA AAT GCG TTC TCC TGT TGG ACA                 2352
Gln His Leu Pro Pro Val Thr Pro Glu Asn Ala Phe Ser Cys Trp Thr
        770                          775                          780

TCT ATC AAT ACT ATC CTG CAA TGG GTT AAT GTC GCA CAA CAA TTG AAT                 2400
Ser Ile Asn Thr Ile Leu Gln Trp Val Asn Val Ala Gln Gln Leu Asn
785                          790                          795                          800

GTC GCC CCA CAG GGC GTT TCC GCT TTG GTC GGG CTG GAT TAT ATT CAA                 2448
Val Ala Pro Gln Gly Val Ser Ala Leu Val Gly Leu Asp Tyr Ile Gln
                    805                          810                          815

TCA ATG AAA GAG ACA CCG ACC TAT GCC CAG TGG GAA AAC GCG GCA GGC                 2496
Ser Met Lys Glu Thr Pro Thr Tyr Ala Gln Trp Glu Asn Ala Ala Gly
            820                          825                          830

GTA TTA ACC GCC GGG TTG AAT TCA CAA CAG GCT AAT ACA TTA CAC GCT                 2544
Val Leu Thr Ala Gly Leu Asn Ser Gln Gln Ala Asn Thr Leu His Ala
                835                          840                          845

TTT CTG GAT GAA TCT CGC AGT GCC GCA TTA AGC ACC TAC TAT ATC CGT                 2592
Phe Leu Asp Glu Ser Arg Ser Ala Ala Leu Ser Thr Tyr Tyr Ile Arg
        850                          855                          860

CAA GTC GCC AAG GCA GCG GCG GCT ATT AAA AGC CGT GAT GAC TTG TAT                 2640
Gln Val Ala Lys Ala Ala Ala Ala Ile Lys Ser Arg Asp Asp Leu Tyr
865                          870                          875                          880

CAA TAC TTA CTG ATT GAT AAT CAG GTT TCT GCG GCA ATA AAA ACC ACC                 2688
Gln Tyr Leu Leu Ile Asp Asn Gln Val Ser Ala Ala Ile Lys Thr Thr
                    885                          890                          895

CGG ATC GCC GAA GCC ATT GCC AGT ATT CAA CTG TAC GTC AAC CGG GCA                 2736
Arg Ile Ala Glu Ala Ile Ala Ser Ile Gln Leu Tyr Val Asn Arg Ala
            900                          905                          910

TTG GAA AAT GTG GAA GAA AAT GCC AAT TCG GGG GTT ATC AGC CGC CAA                 2784
Leu Glu Asn Val Glu Glu Asn Ala Asn Ser Gly Val Ile Ser Arg Gln
                915                          920                          925

TTC TTT ATC GAC TGG GAC AAA TAC AAT AAA CGC TAC AGC ACT TGG GCG                 2832
Phe Phe Ile Asp Trp Asp Lys Tyr Asn Lys Arg Tyr Ser Thr Trp Ala
        930                          935                          940

GGT GTT TCT CAA TTA GTT TAC TAC CCG GAA AAC TAT ATT GAT CCG ACC                 2880
Gly Val Ser Gln Leu Val Tyr Tyr Pro Glu Asn Tyr Ile Asp Pro Thr
945                          950                          955                          960

ATG CGT ATC GGA CAA ACC AAA ATG ATG GAC GCA TTA CTG CAA TCC GTC                 2928
Met Arg Ile Gly Gln Thr Lys Met Met Asp Ala Leu Leu Gln Ser Val
                    965                          970                          975

AGC CAA AGC CAA TTA AAC GCC GAT ACC GTC GAA GAT GCC TTT ATG TCT                 2976
Ser Gln Ser Gln Leu Asn Ala Asp Thr Val Glu Asp Ala Phe Met Ser
            980                          985                          990

TAT CTG ACA TCG TTT GAA CAA GTG GCT AAT CTT AAA GTT ATT AGC GCA                 3024
Tyr Leu Thr Ser Phe Glu Gln Val Ala Asn Leu Lys Val Ile Ser Ala
                995                          1000                         1005

TAT CAC GAT AAT ATT AAT AAC GAT CAA GGG CTG ACC TAT TTT ATC GGA                 3072
Tyr His Asp Asn Ile Asn Asn Asp Gln Gly Leu Thr Tyr Phe Ile Gly
        1010                         1015                         1020

CTC AGT GAA ACT GAT GCC GGT GAA TAT TAT TGG CGC AGT GTC GAT CAC                 3120
Leu Ser Glu Thr Asp Ala Gly Glu Tyr Tyr Trp Arg Ser Val Asp His
1025                         1030                         1035                         1040

AGT AAA TTC AAC GAC GGT AAA TTC GCG GCT AAT GCC TGG AGT GAA TGG                 3168
Ser Lys Phe Asn Asp Gly Lys Phe Ala Ala Asn Ala Trp Ser Glu Trp
                    1045                         1050                         1055

CAT AAA ATT GAT TGT CCA ATT AAC CCT TAT AAA AGC ACT ATC CGT CCA                 3216
```

```
                                                            -continued

His Lys Ile Asp Cys Pro Ile Asn Pro Tyr Lys Ser Thr Ile Arg Pro
        1060                1065                1070

GTG ATA TAT AAA TCC CGC CTG TAT CTG CTC TGG TTG GAA CAA AAG GAG      3264
Val Ile Tyr Lys Ser Arg Leu Tyr Leu Leu Trp Leu Glu Gln Lys Glu
        1075                1080                1085

ATC ACC AAA CAG ACA GGA AAT AGT AAA GAT GGC TAT CAA ACT GAA ACG      3312
Ile Thr Lys Gln Thr Gly Asn Ser Lys Asp Gly Tyr Gln Thr Glu Thr
        1090                1095                1100

GAT TAT CGT TAT GAA CTA AAA TTG GCG CAT ATC CGC TAT GAT GGC ACT      3360
Asp Tyr Arg Tyr Glu Leu Lys Leu Ala His Ile Arg Tyr Asp Gly Thr
1105                1110                1115                1120

TGG AAT ACG CCA ATC ACC TTT GAT GTC AAT AAA AAA ATA TCC GAG CTA      3408
Trp Asn Thr Pro Ile Thr Phe Asp Val Asn Lys Lys Ile Ser Glu Leu
                1125                1130                1135

AAA CTG GAA AAA AAT AGA GCG CCC GGA CTC TAT TGT GCC GGT TAT CAA      3456
Lys Leu Glu Lys Asn Arg Ala Pro Gly Leu Tyr Cys Ala Gly Tyr Gln
        1140                1145                1150

GGT GAA GAT ACG TTG CTG GTG ATG TTT TAT AAC CAA CAA GAC ACA CTA      3504
Gly Glu Asp Thr Leu Leu Val Met Phe Tyr Asn Gln Gln Asp Thr Leu
        1155                1160                1165

GAT AGT TAT AAA AAC GCT TCA ATG CAA GGA CTA TAT ATC TTT GCT GAT      3552
Asp Ser Tyr Lys Asn Ala Ser Met Gln Gly Leu Tyr Ile Phe Ala Asp
        1170                1175                1180

ATG GCA TCC AAA GAT ATG ACC CCA GAA CAG AGC AAT GTT TAT CGG GAT      3600
Met Ala Ser Lys Asp Met Thr Pro Glu Gln Ser Asn Val Tyr Arg Asp
1185                1190                1195                1200

AAT AGC TAT CAA CAA TTT GAT ACC AAT AAT GTC AGA AGA GTG AAT AAC      3648
Asn Ser Tyr Gln Gln Phe Asp Thr Asn Asn Val Arg Arg Val Asn Asn
                1205                1210                1215

CGC TAT GCA GAG GAT TAT GAG ATT CCT TCC TCG GTA AGT AGC CGT AAA      3696
Arg Tyr Ala Glu Asp Tyr Glu Ile Pro Ser Ser Val Ser Ser Arg Lys
        1220                1225                1230

GAC TAT GGT TGG GGA GAT TAT TAC CTC AGC ATG GTA TAT AAC GGA GAT      3744
Asp Tyr Gly Trp Gly Asp Tyr Tyr Leu Ser Met Val Tyr Asn Gly Asp
        1235                1240                1245

ATT CCA ACT ATC AAT TAC AAA GCC GCA TCA AGT GAT TTA AAA ATC TAT      3792
Ile Pro Thr Ile Asn Tyr Lys Ala Ala Ser Ser Asp Leu Lys Ile Tyr
        1250                1255                1260

ATC TCA CCA AAA TTA AGA ATT ATT CAT AAT GGA TAT GAA GGA CAG AAG      3840
Ile Ser Pro Lys Leu Arg Ile Ile His Asn Gly Tyr Glu Gly Gln Lys
1265                1270                1275                1280

CGC AAT CAA TGC AAT CTG ATG AAT AAA TAT GGC AAA CTA GGT GAT AAA      3888
Arg Asn Gln Cys Asn Leu Met Asn Lys Tyr Gly Lys Leu Gly Asp Lys
                1285                1290                1295

TTT ATT GTT TAT ACT AGC TTG GGG GTC AAT CCA AAT AAC TCG TCA AAT      3936
Phe Ile Val Tyr Thr Ser Leu Gly Val Asn Pro Asn Asn Ser Ser Asn
        1300                1305                1310

AAG CTC ATG TTT TAC CCC GTC TAT CAA TAT AGC GGA AAC ACC AGT GGA      3984
Lys Leu Met Phe Tyr Pro Val Tyr Gln Tyr Ser Gly Asn Thr Ser Gly
        1315                1320                1325

CTC AAT CAA GGG AGA CTA CTA TTC CAC CGT GAC ACC ACT TAT CCA TCT      4032
Leu Asn Gln Gly Arg Leu Leu Phe His Arg Asp Thr Thr Tyr Pro Ser
        1330                1335                1340

AAA GTA GAA GCT TGG ATT CCT GGA GCA AAA CGT TCT CTA ACC AAC CAA      4080
Lys Val Glu Ala Trp Ile Pro Gly Ala Lys Arg Ser Leu Thr Asn Gln
1345                1350                1355                1360

AAT GCC GCC ATT GGT GAT GAT TAT GCT ACA GAC TCT CTG AAT AAA CCG      4128
Asn Ala Ala Ile Gly Asp Asp Tyr Ala Thr Asp Ser Leu Asn Lys Pro
                1365                1370                1375
```

```
GAT GAT CTT AAG CAA TAT ATC TTT ATG ACT GAC AGT AAA GGG ACT GCT        4176
Asp Asp Leu Lys Gln Tyr Ile Phe Met Thr Asp Ser Lys Gly Thr Ala
                1380                1385                1390

ACT GAT GTC TCA GGC CCA GTA GAG ATT AAT ACT GCA ATT TCT CCA GCA        4224
Thr Asp Val Ser Gly Pro Val Glu Ile Asn Thr Ala Ile Ser Pro Ala
                1395                1400                1405

AAA GTT CAG ATA ATA GTC AAA GCG GGT GGC AAG GAG CAA ACT TTT ACC        4272
Lys Val Gln Ile Ile Val Lys Ala Gly Gly Lys Glu Gln Thr Phe Thr
                1410                1415                1420

GCA GAT AAA GAT GTC TCC ATT CAG CCA TCA CCT AGC TTT GAT GAA ATG        4320
Ala Asp Lys Asp Val Ser Ile Gln Pro Ser Pro Ser Phe Asp Glu Met
1425                1430                1435                1440

AAT TAT CAA TTT AAT GCC CTT GAA ATA GAC GGT TCT GGT CTG AAT TTT        4368
Asn Tyr Gln Phe Asn Ala Leu Glu Ile Asp Gly Ser Gly Leu Asn Phe
                1445                1450                1455

ATT AAC AAC TCA GCC AGT ATT GAT GTT ACT TTT ACC GCA TTT GCG GAG        4416
Ile Asn Asn Ser Ala Ser Ile Asp Val Thr Phe Thr Ala Phe Ala Glu
                1460                1465                1470

GAT GGC CGC AAA CTG GGT TAT GAA AGT TTC AGT ATT CCT GTT ACC CTC        4464
Asp Gly Arg Lys Leu Gly Tyr Glu Ser Phe Ser Ile Pro Val Thr Leu
                1475                1480                1485

AAG GTA AGT ACC GAT AAT GCC CTG ACC CTG CAC CAT AAT GAA AAT GGT        4512
Lys Val Ser Thr Asp Asn Ala Leu Thr Leu His His Asn Glu Asn Gly
                1490                1495                1500

GCG CAA TAT ATG CAA TGG CAA TCC TAT CGT ACC CGC CTG AAT ACT CTA        4560
Ala Gln Tyr Met Gln Trp Gln Ser Tyr Arg Thr Arg Leu Asn Thr Leu
1505                1510                1515                1520

TTT GCC CGC CAG TTG GTT GCA CGC GCC ACC ACC GGA ATC GAT ACA ATT        4608
Phe Ala Arg Gln Leu Val Ala Arg Ala Thr Thr Gly Ile Asp Thr Ile
                1525                1530                1535

CTG AGT ATG GAA ACT CAG AAT ATT CAG GAA CCG CAG TTA GGC AAA GGT        4656
Leu Ser Met Glu Thr Gln Asn Ile Gln Glu Pro Gln Leu Gly Lys Gly
                1540                1545                1550

TTC TAT GCT ACG TTC GTG ATA CCT CCC TAT AAC CTA TCA ACT CAT GGT        4704
Phe Tyr Ala Thr Phe Val Ile Pro Pro Tyr Asn Leu Ser Thr His Gly
                1555                1560                1565

GAT GAA CGT TGG TTT AAG CTT TAT ATC AAA CAT GTT GTT GAT AAT AAT        4752
Asp Glu Arg Trp Phe Lys Leu Tyr Ile Lys His Val Val Asp Asn Asn
                1570                1575                1580

TCA CAT ATT ATC TAT TCA GGC CAG CTA ACA GAT ACA AAT ATA AAC ATC        4800
Ser His Ile Ile Tyr Ser Gly Gln Leu Thr Asp Thr Asn Ile Asn Ile
1585                1590                1595                1600

ACA TTA TTT ATT CCT CTT GAT GAT GTC CCA TTG AAT CAA GAT TAT CAC        4848
Thr Leu Phe Ile Pro Leu Asp Asp Val Pro Leu Asn Gln Asp Tyr His
                1605                1610                1615

GCC AAG GTT TAT ATG ACC TTC AAG AAA TCA CCA TCA GAT GGT ACC TGG        4896
Ala Lys Val Tyr Met Thr Phe Lys Lys Ser Pro Ser Asp Gly Thr Trp
                1620                1625                1630

TGG GGC CCT CAC TTT GTT AGA GAT GAT AAA GGA ATA GTA ACA ATA AAC        4944
Trp Gly Pro His Phe Val Arg Asp Asp Lys Gly Ile Val Thr Ile Asn
                1635                1640                1645

CCT AAA TCC ATT TTG ACC CAT TTT GAG AGC GTC AAT GTC CTG AAT AAT        4992
Pro Lys Ser Ile Leu Thr His Phe Glu Ser Val Asn Val Leu Asn Asn
                1650                1655                1660

ATT AGT AGC GAA CCA ATG GAT TTC AGC GGC GCT AAC AGC CTC TAT TTC        5040
Ile Ser Ser Glu Pro Met Asp Phe Ser Gly Ala Asn Ser Leu Tyr Phe
1665                1670                1675                1680

TGG GAA CTG TTC TAC TAT ACC CCG ATG CTG GTT GCT CAA CGT TTG CTG        5088
Trp Glu Leu Phe Tyr Tyr Thr Pro Met Leu Val Ala Gln Arg Leu Leu
                1685                1690                1695
```

```
CAT GAA CAG AAC TTC GAT GAA GCC AAC CGT TGG CTG AAA TAT GTC TGG      5136
His Glu Gln Asn Phe Asp Glu Ala Asn Arg Trp Leu Lys Tyr Val Trp
            1700                1705                1710

AGT CCA TCC GGT TAT ATT GTC CAC GGC CAG ATT CAG AAC TAC CAG TGG      5184
Ser Pro Ser Gly Tyr Ile Val His Gly Gln Ile Gln Asn Tyr Gln Trp
        1715                1720                1725

AAC GTC CGC CCG TTA CTG GAA GAC ACC AGT TGG AAC AGT GAT CCT TTG      5232
Asn Val Arg Pro Leu Leu Glu Asp Thr Ser Trp Asn Ser Asp Pro Leu
        1730                1735                1740

GAT TCC GTC GAT CCT GAC GCG GTA GCA CAG CAC GAT CCA ATG CAC TAC      5280
Asp Ser Val Asp Pro Asp Ala Val Ala Gln His Asp Pro Met His Tyr
1745                1750                1755                1760

AAA GTT TCA ACT TTT ATG CGT ACC TTG GAT CTA TTG ATA GCA CGC GGC      5328
Lys Val Ser Thr Phe Met Arg Thr Leu Asp Leu Leu Ile Ala Arg Gly
                1765                1770                1775

GAC CAT GCT TAT CGC CAA CTG GAA CGA GAT ACA CTC AAC GAA GCG AAG      5376
Asp His Ala Tyr Arg Gln Leu Glu Arg Asp Thr Leu Asn Glu Ala Lys
        1780                1785                1790

ATG TGG TAT ATG CAA GCG CTG CAT CTA TTA GGT GAC AAA CCT TAT CTA      5424
Met Trp Tyr Met Gln Ala Leu His Leu Leu Gly Asp Lys Pro Tyr Leu
        1795                1800                1805

CCG CTG AGT ACG ACA TGG AGT GAT CCA CGA CTA GAC AGA GCC GCG GAT      5472
Pro Leu Ser Thr Thr Trp Ser Asp Pro Arg Leu Asp Arg Ala Ala Asp
        1810                1815                1820

ATC ACT ACC CAA AAT GCT CAC GAC AGC GCA ATA GTC GCT CTG CGG CAG      5520
Ile Thr Thr Gln Asn Ala His Asp Ser Ala Ile Val Ala Leu Arg Gln
1825                1830                1835                1840

AAT ATA CCT ACA CCG GCA CCT TTA TCA                                  5547
Asn Ile Pro Thr Pro Ala Pro Leu Ser
                1845
```

(2) INFORMATION FOR SEQ ID NO:49:

(i) SEQUENCE CHARACTERISTICS:
        (A) LENGTH: 1849 amino acids
        (B) TYPE: amino acids
        (D) TOPOLOGY: linear (ii) MOLECULE TYPE: protein (xi) SEQUENCE DESCRIPTION: SEQ ID NO:49:

```
Leu Ile Gly Tyr Asn Asn Gln Phe Ser Gly Arg Ala Ser Gln Tyr Val
1               5                   10                  15

Ala Pro Gly Thr Val Ser Ser Met Phe Ser Pro Ala Ala Tyr Leu Thr
            20                  25                  30

Glu Leu Tyr Arg Glu Ala Arg Asn Leu His Ala Ser Asp Ser Val Tyr
        35                  40                  45

Tyr Leu Asp Thr Arg Arg Pro Asp Leu Lys Ser Met Ala Leu Ser Gln
    50                  55                  60

Gln Asn Met Asp Ile Glu Leu Ser Thr Leu Ser Leu Ser Asn Glu Leu
65                  70                  75                  80

Leu Leu Glu Ser Ile Lys Thr Glu Ser Lys Leu Glu Asn Tyr Thr Lys
                85                  90                  95

Val Met Glu Met Leu Ser Thr Phe Arg Pro Ser Gly Ala Thr Pro Tyr
                100                 105                 110

His Asp Ala Tyr Glu Asn Val Arg Glu Val Ile Gln Leu Gln Asp Pro
            115                 120                 125

Gly Leu Glu Gln Leu Asn Ala Ser Pro Ala Ile Ala Gly Leu Met His
130                 135                 140
```

-continued

```
Gln Ala Ser Leu Leu Gly Ile Asn Ala Ser Ile Ser Pro Glu Leu Phe
145                 150                 155                 160

Asn Ile Leu Thr Glu Glu Ile Thr Glu Gly Asn Ala Glu Glu Leu Tyr
                165                 170                 175

Lys Lys Asn Phe Gly Asn Ile Glu Pro Ala Ser Leu Ala Met Pro Glu
            180                 185                 190

Tyr Leu Lys Arg Tyr Tyr Asn Leu Ser Asp Glu Glu Leu Ser Gln Phe
        195                 200                 205

Ile Gly Lys Ala Ser Asn Phe Gly Gln Gln Glu Tyr Ser Asn Asn Gln
210                 215                 220

Leu Ile Thr Pro Val Val Asn Ser Ser Asp Gly Thr Val Lys Val Tyr
225                 230                 235                 240

Arg Ile Thr Arg Glu Tyr Thr Thr Asn Ala Tyr Gln Met Asp Val Glu
                245                 250                 255

Leu Phe Pro Phe Gly Gly Glu Asn Tyr Arg Leu Asp Tyr Lys Phe Lys
            260                 265                 270

Asn Phe Tyr Asn Ala Ser Tyr Leu Ser Ile Lys Leu Asn Asp Lys Arg
        275                 280                 285

Glu Leu Val Arg Thr Glu Gly Ala Pro Gln Val Asn Ile Glu Tyr Ser
290                 295                 300

Ala Asn Ile Thr Leu Asn Thr Ala Asp Ile Ser Gln Pro Phe Glu Ile
305                 310                 315                 320

Gly Leu Thr Arg Val Leu Pro Ser Gly Ser Trp Ala Tyr Ala Ala Ala
                325                 330                 335

Lys Phe Thr Val Glu Glu Tyr Asn Gln Tyr Ser Phe Leu Leu Lys Leu
            340                 345                 350

Asn Lys Ala Ile Arg Leu Ser Arg Ala Thr Glu Leu Ser Pro Thr Ile
        355                 360                 365

Leu Glu Gly Ile Val Arg Ser Val Asn Leu Gln Leu Asp Ile Asn Thr
370                 375                 380

Asp Val Leu Gly Lys Val Phe Leu Thr Lys Tyr Tyr Met Gln Arg Tyr
385                 390                 395                 400

Ala Ile His Ala Glu Thr Ala Leu Ile Leu Cys Asn Ala Pro Ile Ser
                405                 410                 415

Gln Arg Ser Tyr Asp Asn Gln Pro Ser Gln Phe Asp Arg Leu Phe Asn
            420                 425                 430

Thr Pro Leu Leu Asn Gly Gln Tyr Phe Ser Thr Gly Asp Glu Glu Ile
        435                 440                 445

Asp Leu Asn Ser Gly Ser Thr Gly Asp Trp Arg Lys Thr Ile Leu Lys
450                 455                 460

Arg Ala Phe Asn Ile Asp Asp Val Ser Leu Phe Arg Leu Leu Lys Ile
465                 470                 475                 480

Thr Asp His Asp Asn Lys Asp Gly Lys Ile Lys Asn Asn Leu Lys Asn
                485                 490                 495

Leu Ser Asn Leu Tyr Ile Gly Lys Leu Leu Ala Asp Ile His Gln Leu
            500                 505                 510

Thr Ile Asp Glu Leu Asp Leu Leu Ile Ala Val Gly Glu Gly Lys
        515                 520                 525

Thr Asn Leu Ser Ala Ile Ser Asp Lys Gln Leu Ala Thr Leu Ile Arg
530                 535                 540

Lys Leu Asn Thr Ile Thr Ser Trp Leu His Thr Gln Lys Trp Ser Val
545                 550                 555                 560
```

-continued

Phe Gln Leu Phe Ile Met Thr Ser Thr Ser Tyr Asn Lys Thr Leu Thr
                565                 570                 575

Pro Glu Ile Lys Asn Leu Leu Asp Thr Val Tyr His Gly Leu Gln Gly
            580                 585                 590

Phe Asp Lys Asp Lys Ala Asp Leu Leu His Val Met Ala Pro Tyr Ile
        595                 600                 605

Ala Ala Thr Leu Gln Leu Ser Ser Glu Asn Val Ala His Ser Val Leu
    610                 615                 620

Leu Trp Ala Asp Lys Leu Gln Pro Gly Asp Gly Ala Met Thr Ala Glu
625                 630                 635                 640

Lys Phe Trp Asp Trp Leu Asn Thr Lys Tyr Thr Pro Gly Ser Ser Glu
                645                 650                 655

Ala Val Glu Thr Gln Glu His Ile Val Gln Tyr Cys Gln Ala Leu Ala
            660                 665                 670

Gln Leu Glu Met Val Tyr His Ser Thr Gly Ile Asn Glu Asn Ala Phe
        675                 680                 685

Arg Leu Phe Val Thr Lys Pro Glu Met Phe Gly Ala Ala Thr Gly Ala
    690                 695                 700

Ala Pro Ala His Asp Ala Leu Ser Leu Ile Met Leu Thr Arg Phe Ala
705                 710                 715                 720

Asp Trp Val Asn Ala Leu Gly Glu Lys Ala Ser Ser Val Leu Ala Ala
                725                 730                 735

Phe Glu Ala Asn Ser Leu Thr Ala Glu Gln Leu Ala Asp Ala Met Asn
            740                 745                 750

Leu Asp Ala Asn Leu Leu Leu Gln Ala Ser Ile Gln Ala Gln Asn His
        755                 760                 765

Gln His Leu Pro Pro Val Thr Pro Glu Asn Ala Phe Ser Cys Trp Thr
    770                 775                 780

Ser Ile Asn Thr Ile Leu Gln Trp Val Asn Val Ala Gln Gln Leu Asn
785                 790                 795                 800

Val Ala Pro Gln Gly Val Ser Ala Leu Val Gly Leu Asp Tyr Ile Gln
                805                 810                 815

Ser Met Lys Glu Thr Pro Thr Tyr Ala Gln Trp Glu Asn Ala Ala Gly
            820                 825                 830

Val Leu Thr Ala Gly Leu Asn Ser Gln Gln Ala Asn Thr Leu His Ala
        835                 840                 845

Phe Leu Asp Glu Ser Arg Ser Ala Ala Leu Ser Thr Tyr Tyr Ile Arg
    850                 855                 860

Gln Val Ala Lys Ala Ala Ala Ile Lys Ser Arg Asp Asp Leu Tyr
865                 870                 875                 880

Gln Tyr Leu Leu Ile Asp Asn Gln Val Ser Ala Ala Ile Lys Thr Thr
                885                 890                 895

Arg Ile Ala Glu Ala Ile Ala Ser Ile Gln Leu Tyr Val Asn Arg Ala
            900                 905                 910

Leu Glu Asn Val Glu Glu Asn Ala Asn Ser Gly Val Ile Ser Arg Gln
        915                 920                 925

Phe Phe Ile Asp Trp Asp Lys Tyr Asn Lys Arg Tyr Ser Thr Trp Ala
    930                 935                 940

Gly Val Ser Gln Leu Val Tyr Tyr Pro Glu Asn Tyr Ile Asp Pro Thr
945                 950                 955                 960

Met Arg Ile Gly Gln Thr Lys Met Met Asp Ala Leu Leu Gln Ser Val
                965                 970                 975

Ser Gln Ser Gln Leu Asn Ala Asp Thr Val Glu Asp Ala Phe Met Ser

```
                    980             985             990
Tyr Leu Thr Ser Phe Glu Gln Val Ala Asn Leu Lys Val Ile Ser Ala
            995             1000            1005

Tyr His Asp Asn Ile Asn Asn Asp Gln Gly Leu Thr Tyr Phe Ile Gly
1010            1015            1020

Leu Ser Glu Thr Asp Ala Gly Glu Tyr Tyr Trp Arg Ser Val Asp His
1025            1030            1035            1040

Ser Lys Phe Asn Asp Gly Lys Phe Ala Ala Asn Ala Trp Ser Glu Trp
            1045            1050            1055

His Lys Ile Asp Cys Pro Ile Asn Pro Tyr Lys Ser Thr Ile Arg Pro
            1060            1065            1070

Val Ile Tyr Lys Ser Arg Leu Tyr Leu Leu Trp Leu Glu Gln Lys Glu
            1075            1080            1085

Ile Thr Lys Gln Thr Gly Asn Ser Lys Asp Gly Tyr Gln Thr Glu Thr
            1090            1095            1100

Asp Tyr Arg Tyr Glu Leu Lys Leu Ala His Ile Arg Tyr Asp Gly Thr
1105            1110            1115            1120

Trp Asn Thr Pro Ile Thr Phe Asp Val Asn Lys Ile Ser Glu Leu
            1125            1130            1135

Lys Leu Glu Lys Asn Arg Ala Pro Gly Leu Tyr Cys Ala Gly Tyr Gln
            1140            1145            1150

Gly Glu Asp Thr Leu Leu Val Met Phe Tyr Asn Gln Gln Asp Thr Leu
            1155            1160            1165

Asp Ser Tyr Lys Asn Ala Ser Met Gln Gly Leu Tyr Ile Phe Ala Asp
            1170            1175            1180

Met Ala Ser Lys Asp Met Thr Pro Glu Gln Ser Asn Val Tyr Arg Asp
1185            1190            1195            1200

Asn Ser Tyr Gln Gln Phe Asp Thr Asn Val Arg Arg Val Asn Asn
            1205            1210            1215

Arg Tyr Ala Glu Asp Tyr Glu Ile Pro Ser Ser Val Ser Ser Arg Lys
            1220            1225            1230

Asp Tyr Gly Trp Gly Asp Tyr Tyr Leu Ser Met Val Tyr Asn Gly Asp
            1235            1240            1245

Ile Pro Thr Ile Asn Tyr Lys Ala Ala Ser Ser Asp Leu Lys Ile Tyr
            1250            1255            1260

Ile Ser Pro Lys Leu Arg Ile Ile His Asn Gly Tyr Glu Gly Gln Lys
1265            1270            1275            1280

Arg Asn Gln Cys Asn Leu Met Asn Lys Tyr Gly Lys Leu Gly Asp Lys
            1285            1290            1295

Phe Ile Val Tyr Thr Ser Leu Gly Val Asn Pro Asn Asn Ser Ser Asn
            1300            1305            1310

Lys Leu Met Phe Tyr Pro Val Tyr Gln Tyr Ser Gly Asn Thr Ser Gly
            1315            1320            1325

Leu Asn Gln Gly Arg Leu Leu Phe His Arg Asp Thr Thr Tyr Pro Ser
            1330            1335            1340

Lys Val Glu Ala Trp Ile Pro Gly Ala Lys Arg Ser Leu Thr Asn Gln
1345            1350            1355            1360

Asn Ala Ala Ile Gly Asp Asp Tyr Ala Thr Asp Ser Leu Asn Lys Pro
            1365            1370            1375

Asp Asp Leu Lys Gln Tyr Ile Phe Met Thr Asp Ser Lys Gly Thr Ala
            1380            1385            1390

Thr Asp Val Ser Gly Pro Val Glu Ile Asn Thr Ala Ile Ser Pro Ala
            1395            1400            1405
```

-continued

Lys Val Gln Ile Ile Val Lys Ala Gly Gly Lys Glu Gln Thr Phe Thr
     1410                1415                1420

Ala Asp Lys Asp Val Ser Ile Gln Pro Ser Pro Ser Phe Asp Glu Met
1425                1430                1435                1440

Asn Tyr Gln Phe Asn Ala Leu Glu Ile Asp Gly Ser Gly Leu Asn Phe
                1445                1450                1455

Ile Asn Asn Ser Ala Ser Ile Asp Val Thr Phe Thr Ala Phe Ala Glu
            1460                1465                1470

Asp Gly Arg Lys Leu Gly Tyr Glu Ser Phe Ser Ile Pro Val Thr Leu
        1475                1480                1485

Lys Val Ser Thr Asp Asn Ala Leu Thr Leu His His Asn Glu Asn Gly
    1490                1495                1500

Ala Gln Tyr Met Gln Trp Gln Ser Tyr Arg Thr Arg Leu Asn Thr Leu
1505                1510                1515                1520

Phe Ala Arg Gln Leu Val Ala Arg Ala Thr Thr Gly Ile Asp Thr Ile
                1525                1530                1535

Leu Ser Met Glu Thr Gln Asn Ile Gln Glu Pro Gln Leu Gly Lys Gly
            1540                1545                1550

Phe Tyr Ala Thr Phe Val Ile Pro Pro Tyr Asn Leu Ser Thr His Gly
        1555                1560                1565

Asp Glu Arg Trp Phe Lys Leu Tyr Ile Lys His Val Val Asp Asn Asn
    1570                1575                1580

Ser His Ile Ile Tyr Ser Gly Gln Leu Thr Asp Thr Asn Ile Asn Ile
1585                1590                1595                1600

Thr Leu Phe Ile Pro Leu Asp Asp Val Pro Leu Asn Gln Asp Tyr His
                1605                1610                1615

Ala Lys Val Tyr Met Thr Phe Lys Lys Ser Pro Ser Asp Gly Thr Trp
            1620                1625                1630

Trp Gly Pro His Phe Val Arg Asp Asp Lys Gly Ile Val Thr Ile Asn
        1635                1640                1645

Pro Lys Ser Ile Leu Thr His Phe Glu Ser Val Asn Val Leu Asn Asn
    1650                1655                1660

Ile Ser Ser Glu Pro Met Asp Phe Ser Gly Ala Asn Ser Leu Tyr Phe
1665                1670                1675                1680

Trp Glu Leu Phe Tyr Tyr Thr Pro Met Leu Val Ala Gln Arg Leu Leu
                1685                1690                1695

His Glu Gln Asn Phe Asp Glu Ala Asn Arg Trp Leu Lys Tyr Val Trp
            1700                1705                1710

Ser Pro Ser Gly Tyr Ile Val His Gly Gln Ile Gln Asn Tyr Gln Trp
        1715                1720                1725

Asn Val Arg Pro Leu Leu Glu Asp Thr Ser Trp Asn Ser Asp Pro Leu
    1730                1735                1740

Asp Ser Val Asp Pro Asp Ala Val Ala Gln His Asp Pro Met His Tyr
1745                1750                1755                1760

Lys Val Ser Thr Phe Met Arg Thr Leu Asp Leu Leu Ile Ala Arg Gly
                1765                1770                1775

Asp His Ala Tyr Arg Gln Leu Glu Arg Asp Thr Leu Asn Glu Ala Lys
            1780                1785                1790

Met Trp Tyr Met Gln Ala Leu His Leu Leu Gly Asp Lys Pro Tyr Leu
        1795                1800                1805

Pro Leu Ser Thr Thr Trp Ser Asp Pro Arg Leu Asp Arg Ala Ala Asp
    1810                1815                1820

```
Ile Thr Thr Gln Asn Ala His Asp Ser Ala Ile Val Ala Leu Arg Gln
1825                1830                1835                1840

Asn Ile Pro Thr Pro Ala Pro Leu Ser
                1845

(2) INFORMATION FOR SEQ ID NO:50:

(i) SEQUENCE CHARACTERISTICS:
        (A) LENGTH: 1740 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:50:

TTG CGC AGC GCT AAT ACC CTG ACT GAT CTC TTC CTG CCG CAA ATC AAT        48
Leu Arg Ser Ala Asn Thr Leu Thr Asp Leu Phe Leu Pro Gln Ile Asn
  1               5                  10                  15

GAA GTG ATG ATG AAT TAC TGG CAG ACA TTA GCT CAG AGA GTA TAC AAT        96
Glu Val Met Met Asn Tyr Trp Gln Thr Leu Ala Gln Arg Val Tyr Asn
                 20                  25                  30

CTG CGT CAT AAC CTC TCT ATC GAC GGC CAG CCG TTA TAT CTG CCA ATC       144
Leu Arg His Asn Leu Ser Ile Asp Gly Gln Pro Leu Tyr Leu Pro Ile
             35                  40                  45

TAT GCC ACA CCG GCC GAT CCG AAA GCG TTA CTC AGC GCC GCC GTT GCC       192
Tyr Ala Thr Pro Ala Asp Pro Lys Ala Leu Leu Ser Ala Ala Val Ala
 50                  55                  60

ACT TCT CAA GGT GGA GGC AAG CTA CCG GAA TCA TTT ATG TCC CTG TGG       240
Thr Ser Gln Gly Gly Gly Lys Leu Pro Glu Ser Phe Met Ser Leu Trp
 65                  70                  75                  80

CGT TTC CCG CAC ATG CTG GAA AAT GCG CGC GGC ATG GTT AGC CAG CTC       288
Arg Phe Pro His Met Leu Glu Asn Ala Arg Gly Met Val Ser Gln Leu
                 85                  90                  95

ACC CAG TTC GGC TCC ACG TTA CAA AAT ATT ATC GAA CGT CAG GAC GCG       336
Thr Gln Phe Gly Ser Thr Leu Gln Asn Ile Ile Glu Arg Gln Asp Ala
                100                 105                 110

GAA GCG CTC AAT GCG TTA TTA CAA AAT CAG GCC GCC GAG CTG ATA TTG       384
Glu Ala Leu Asn Ala Leu Leu Gln Asn Gln Ala Ala Glu Leu Ile Leu
            115                 120                 125

ACT AAC CTG AGC ATT CAG GAC AAA ACC ATT GAA GAA TTG GAT GCC GAG       432
Thr Asn Leu Ser Ile Gln Asp Lys Thr Ile Glu Glu Leu Asp Ala Glu
        130                 135                 140

AAA ACG GTG TTG GAA AAA TCC AAA GCG GGA GCA CAA TCG CGC TTT GAT       480
Lys Thr Val Leu Glu Lys Ser Lys Ala Gly Ala Gln Ser Arg Phe Asp
145                 150                 155                 160

AGC TAC GGC AAA CTG TAC GAT GAG AAT ATC AAC GCC GGT GAA AAC CAA       528
Ser Tyr Gly Lys Leu Tyr Asp Glu Asn Ile Asn Ala Gly Glu Asn Gln
                165                 170                 175

GCC ATG ACG CTA CGA GCG TCC GCC GCC GGG CTT ACC ACG GCA GTT CAG       576
Ala Met Thr Leu Arg Ala Ser Ala Ala Gly Leu Thr Thr Ala Val Gln
            180                 185                 190

GCA TCC CGT CTG GCC GGT GCG GCG GCT GAT CTG GTG CCT AAC ATC TTC       624
Ala Ser Arg Leu Ala Gly Ala Ala Ala Asp Leu Val Pro Asn Ile Phe
        195                 200                 205

GGC TTT GCC GGT GGC GGC AGC CGT TGG GGG GCT ATC GCT GAG GCG ACA       672
Gly Phe Ala Gly Gly Gly Ser Arg Trp Gly Ala Ile Ala Glu Ala Thr
    210                 215                 220

GGT TAT GTG ATG GAA TTC TCC GCG AAT GTT ATG AAC ACC GAA GCG GAT       720
Gly Tyr Val Met Glu Phe Ser Ala Asn Val Met Asn Thr Glu Ala Asp
225                 230                 235                 240
```

```
AAA ATT AGC CAA TCT GAA ACC TAC CGT CGT CGC CGT CAG GAG TGG GAG         768
Lys Ile Ser Gln Ser Glu Thr Tyr Arg Arg Arg Arg Gln Glu Trp Glu
            245                 250                 255

ATC CAG CGG AAT AAT GCC GAA GCG GAA TTG AAG CAA ATC GAT GCT CAG         816
Ile Gln Arg Asn Asn Ala Glu Ala Glu Leu Lys Gln Ile Asp Ala Gln
                260                 265                 270

CTC AAA TCA CTC GCT GTA CGC CGC GAA GCC GCC GTA TTG CAG AAA ACC         864
Leu Lys Ser Leu Ala Val Arg Arg Glu Ala Ala Val Leu Gln Lys Thr
            275                 280                 285

AGT CTG AAA ACC CAA CAA GAA CAG ACC CAA TCT CAA TTG GCC TTC CTG         912
Ser Leu Lys Thr Gln Gln Glu Gln Thr Gln Ser Gln Leu Ala Phe Leu
        290                 295                 300

CAA CGT AAG TTC AGC AAT CAG GCG TTA TAC AAC TGG CTG CGT GGT CGA         960
Gln Arg Lys Phe Ser Asn Gln Ala Leu Tyr Asn Trp Leu Arg Gly Arg
305                 310                 315                 320

CTG GCG GCG ATT TAC TTC CAG TTC TAC GAT TTG GCC GTC GCG CGT TGC        1008
Leu Ala Ala Ile Tyr Phe Gln Phe Tyr Asp Leu Ala Val Ala Arg Cys
                325                 330                 335

CTG ATG GCA GAA CAA GCT TAC CGT TGG GAA CTC AAT GAT GAC TCT GCC        1056
Leu Met Ala Glu Gln Ala Tyr Arg Trp Glu Leu Asn Asp Asp Ser Ala
            340                 345                 350

CGC TTC ATT AAA CCG GGC GCC TGG CAG GGA ACC TAT GCC GGT CTG CTT        1104
Arg Phe Ile Lys Pro Gly Ala Trp Gln Gly Thr Tyr Ala Gly Leu Leu
        355                 360                 365

GCA GGT GAA ACC TTG ATG CTG AGT CTG GCA CAA ATG GAA GAC GCT CAT        1152
Ala Gly Glu Thr Leu Met Leu Ser Leu Ala Gln Met Glu Asp Ala His
    370                 375                 380

CTG AAA CGC GAT AAA CGC GCA TTA GAG GTT GAA CGC ACA GTA TCG CTG        1200
Leu Lys Arg Asp Lys Arg Ala Leu Glu Val Glu Arg Thr Val Ser Leu
385                 390                 395                 400

GCC GAA GTT TAT GCA GGA TTA CCA AAA GAT AAC GGT CCA TTT TCC CTG        1248
Ala Glu Val Tyr Ala Gly Leu Pro Lys Asp Asn Gly Pro Phe Ser Leu
                405                 410                 415

GCT CAG GAA ATT GAC AAG CTG GTG AGT CAA GGT TCA GGC AGT GCC GGC        1296
Ala Gln Glu Ile Asp Lys Leu Val Ser Gln Gly Ser Gly Ser Ala Gly
            420                 425                 430

AGT GGT AAT AAT AAT TTG GCG TTC GGC GCC GGC ACG GAC ACT AAA ACC        1344
Ser Gly Asn Asn Asn Leu Ala Phe Gly Ala Gly Thr Asp Thr Lys Thr
        435                 440                 445

TCT TTG CAG GCA TCA GTT TCA TTC GCT GAT TTG AAA ATT CGT GAA GAT        1392
Ser Leu Gln Ala Ser Val Ser Phe Ala Asp Leu Lys Ile Arg Glu Asp
    450                 455                 460

TAC CCG GCA TCG CTT GGC AAA ATT CGA CGT ATC AAA CAG ATC AGC GTC        1440
Tyr Pro Ala Ser Leu Gly Lys Ile Arg Arg Ile Lys Gln Ile Ser Val
465                 470                 475                 480

ACT TTG CCC GCG CTA CTG GGA CCG TAT CAG GAT GTA CAG GCA ATA TTG        1488
Thr Leu Pro Ala Leu Leu Gly Pro Tyr Gln Asp Val Gln Ala Ile Leu
                485                 490                 495

TCT TAC GGC GAT AAA GCC GGA TTA GCT AAC GGC TGT GAA GCG CTG GCA        1536
Ser Tyr Gly Asp Lys Ala Gly Leu Ala Asn Gly Cys Glu Ala Leu Ala
            500                 505                 510

GTT TCT CAC GGT ATG AAT GAC AGC GGC CAA TTC CAG CTC GAT TTC AAC        1584
Val Ser His Gly Met Asn Asp Ser Gly Gln Phe Gln Leu Asp Phe Asn
        515                 520                 525

GAT GGC AAA TTC CTG CCA TTC GAA GGC ATC GCC ATT GAT CAA GGC ACG        1632
Asp Gly Lys Phe Leu Pro Phe Glu Gly Ile Ala Ile Asp Gln Gly Thr
    530                 535                 540

CTG ACA CTG AGC TTC CCA AAT GCA TCT ATG CCG GAG AAA GGT AAA CAA        1680
Leu Thr Leu Ser Phe Pro Asn Ala Ser Met Pro Glu Lys Gly Lys Gln
545                 550                 555                 560
```

```
GCC ACT ATG TTA AAA ACC CTG AAC GAT ATC ATT TTG CAT ATT CGC TAC     1728
Ala Thr Met Leu Lys Thr Leu Asn Asp Ile Ile Leu His Ile Arg Tyr
            565                 570                 575

ACC ATT AAA TAA                                                    1740
Thr Ile Lys
```

(2) INFORMATION FOR SEQ ID NO:51:

(i) SEQUENCE CHARACTERISTICS:
        (A) LENGTH: 579 amino acids
        (B) TYPE: amino acids
        (D) TOPOLOGY: linear (ii) MOLECULE TYPE: protein (xi) SEQUENCE DESCRIPTION: SEQ ID NO:51:

```
Leu Arg Ser Ala Asn Thr Leu Thr Asp Leu Phe Leu Pro Gln Ile Asn
1               5                   10                  15

Glu Val Met Met Asn Tyr Trp Gln Thr Leu Ala Gln Arg Val Tyr Asn
            20                  25                  30

Leu Arg His Asn Leu Ser Ile Asp Gly Gln Pro Leu Tyr Leu Pro Ile
        35                  40                  45

Tyr Ala Thr Pro Ala Asp Pro Lys Ala Leu Leu Ser Ala Ala Val Ala
    50                  55                  60

Thr Ser Gln Gly Gly Lys Leu Pro Glu Ser Phe Met Ser Leu Trp
65                  70                  75                  80

Arg Phe Pro His Met Leu Glu Asn Ala Arg Gly Met Val Ser Gln Leu
                85                  90                  95

Thr Gln Phe Gly Ser Thr Leu Gln Asn Ile Ile Glu Arg Gln Asp Ala
            100                 105                 110

Glu Ala Leu Asn Ala Leu Leu Gln Asn Gln Ala Ala Glu Leu Ile Leu
        115                 120                 125

Thr Asn Leu Ser Ile Gln Asp Lys Thr Ile Glu Glu Leu Asp Ala Glu
    130                 135                 140

Lys Thr Val Leu Glu Lys Ser Lys Ala Gly Ala Gln Ser Arg Phe Asp
145                 150                 155                 160

Ser Tyr Gly Lys Leu Tyr Asp Glu Asn Ile Asn Ala Gly Glu Asn Gln
                165                 170                 175

Ala Met Thr Leu Arg Ala Ser Ala Ala Gly Leu Thr Thr Ala Val Gln
            180                 185                 190

Ala Ser Arg Leu Ala Gly Ala Ala Asp Leu Val Pro Asn Ile Phe
        195                 200                 205

Gly Phe Ala Gly Gly Ser Arg Trp Gly Ala Ile Ala Glu Ala Thr
    210                 215                 220

Gly Tyr Val Met Glu Phe Ser Ala Asn Val Met Asn Thr Glu Ala Asp
225                 230                 235                 240

Lys Ile Ser Gln Ser Glu Thr Tyr Arg Arg Arg Gln Glu Trp Glu
                245                 250                 255

Ile Gln Arg Asn Asn Ala Glu Ala Leu Lys Gln Ile Asp Ala Gln
            260                 265                 270

Leu Lys Ser Leu Ala Val Arg Arg Glu Ala Ala Val Leu Gln Lys Thr
        275                 280                 285

Ser Leu Lys Thr Gln Gln Glu Gln Thr Gln Ser Gln Leu Ala Phe Leu
    290                 295                 300

Gln Arg Lys Phe Ser Asn Gln Ala Leu Tyr Asn Trp Leu Arg Gly Arg
305                 310                 315                 320
```

```
Leu Ala Ala Ile Tyr Phe Gln Phe Tyr Asp Leu Ala Val Ala Arg Cys
            325                 330                 335

Leu Met Ala Glu Gln Ala Tyr Arg Trp Glu Leu Asn Asp Asp Ser Ala
            340                 345                 350

Arg Phe Ile Lys Pro Gly Ala Trp Gln Gly Thr Tyr Ala Gly Leu Leu
            355                 360                 365

Ala Gly Glu Thr Leu Met Leu Ser Leu Ala Gln Met Glu Asp Ala His
            370                 375                 380

Leu Lys Arg Asp Lys Arg Ala Leu Glu Val Glu Arg Thr Val Ser Leu
385                 390                 395                 400

Ala Glu Val Tyr Ala Gly Leu Pro Lys Asp Asn Gly Pro Phe Ser Leu
            405                 410                 415

Ala Gln Glu Ile Asp Lys Leu Val Ser Gln Gly Ser Gly Ser Ala Gly
            420                 425                 430

Ser Gly Asn Asn Asn Leu Ala Phe Gly Ala Gly Thr Asp Thr Lys Thr
            435                 440                 445

Ser Leu Gln Ala Ser Val Ser Phe Ala Asp Leu Lys Ile Arg Glu Asp
            450                 455                 460

Tyr Pro Ala Ser Leu Gly Lys Ile Arg Arg Ile Lys Gln Ile Ser Val
465                 470                 475                 480

Thr Leu Pro Ala Leu Leu Gly Pro Tyr Gln Asp Val Gln Ala Ile Leu
            485                 490                 495

Ser Tyr Gly Asp Lys Ala Gly Leu Ala Asn Gly Cys Glu Ala Leu Ala
            500                 505                 510

Val Ser His Gly Met Asn Asp Ser Gly Gln Phe Gln Leu Asp Phe Asn
            515                 520                 525

Asp Gly Lys Phe Leu Pro Phe Glu Gly Ile Ala Ile Asp Gln Gly Thr
            530                 535                 540

Leu Thr Leu Ser Phe Pro Asn Ala Ser Met Pro Glu Lys Gly Lys Gln
545                 550                 555                 560

Ala Thr Met Leu Lys Thr Leu Asn Asp Ile Ile Leu His Ile Arg Tyr
            565                 570                 575

Thr Ile Lys (2) INFORMATION FOR SEQ ID NO:52:

(i) SEQUENCE CHARACTERISTICS:
        (A) LENGTH: 5532 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:52:

TTT ATA CAA GGT TAT AGT GAT CTG TTT GGT AAT CGT GCT GAT AAC TAT        48
Phe Ile Gln Gly Tyr Ser Asp Leu Phe Gly Asn Arg Ala Asp Asn Tyr
1               5                   10                  15

GCC GCG CCG GGC TCG GTT GCA TCG ATG TTC TCA CCG GCG GCT TAT TTG        96
Ala Ala Pro Gly Ser Val Ala Ser Met Phe Ser Pro Ala Ala Tyr Leu
                20                  25                  30

ACG GAA TTG TAC CGT GAA GCC AAA AAC TTG CAT GAC AGC AGC TCA ATT       144
Thr Glu Leu Tyr Arg Glu Ala Lys Asn Leu His Asp Ser Ser Ser Ile
            35                  40                  45

TAT TAC CTA GAT AAA CGT CGC CCG GAT TTA GCA AGC TTA ATG CTC AGC       192
Tyr Tyr Leu Asp Lys Arg Arg Pro Asp Leu Ala Ser Leu Met Leu Ser
        50                  55                  60
```

```
CAG AAA AAT ATG GAT GAG GAA ATT TCA ACG CTG GCT CTC TCT AAT GAA        240
Gln Lys Asn Met Asp Glu Glu Ile Ser Thr Leu Ala Leu Ser Asn Glu
 65              70                  75                  80

TTG TGC CTT GCC GGG ATC GAA ACA AAA ACA GGA AAA TCA CAA GAT GAA        288
Leu Cys Leu Ala Gly Ile Glu Thr Lys Thr Gly Lys Ser Gln Asp Glu
                 85                  90                  95

GTG ATG GAT ATG TTG TCA ACT TAT CGT TTA AGT GGA GAG ACA CCT TAT        336
Val Met Asp Met Leu Ser Thr Tyr Arg Leu Ser Gly Glu Thr Pro Tyr
            100                 105                 110

CAT CAC GCT TAT GAA ACT GTT CGT GAA ATC GTT CAT GAA CGT GAT CCA        384
His His Ala Tyr Glu Thr Val Arg Glu Ile Val His Glu Arg Asp Pro
             115                 120                 125

GGA TTT CGT CAT TTG TCA CAG GCA CCC ATT GTT GCT GCT AAG CTC GAT        432
Gly Phe Arg His Leu Ser Gln Ala Pro Ile Val Ala Ala Lys Leu Asp
        130                 135                 140

CCT GTG ACT TTG TTG GGT ATT AGC TCC CAT ATT TCG CCA GAA CTG TAT        480
Pro Val Thr Leu Leu Gly Ile Ser Ser His Ile Ser Pro Glu Leu Tyr
145                 150                 155                 160

AAC TTG CTG ATT GAG GAG ATC CCG GAA AAA GAT GAA GCC GCG CTT GAT        528
Asn Leu Leu Ile Glu Glu Ile Pro Glu Lys Asp Glu Ala Ala Leu Asp
                165                 170                 175

ACG CTT TAT AAA ACA AAC TTT GGC GAT ATT ACT ACT GCT CAG TTA ATG        576
Thr Leu Tyr Lys Thr Asn Phe Gly Asp Ile Thr Thr Ala Gln Leu Met
            180                 185                 190

TCC CCA AGT TAT CTG GCC CGG TAT TAT GGC GTC TCA CCG GAA GAT ATT        624
Ser Pro Ser Tyr Leu Ala Arg Tyr Tyr Gly Val Ser Pro Glu Asp Ile
            195                 200                 205

GCC TAC GTG ACG ACT TCA TTA TCA CAT GTT GGA TAT AGC AGT GAT ATT        672
Ala Tyr Val Thr Thr Ser Leu Ser His Val Gly Tyr Ser Ser Asp Ile
210                 215                 220

CTG GTT ATT CCG TTG GTC GAT GGT GTG GGT AAG ATG GAA GTA GTT CGT        720
Leu Val Ile Pro Leu Val Asp Gly Val Gly Lys Met Glu Val Val Arg
225                 230                 235                 240

GTT ACC CGA ACA CCA TCG GAT AAT TAT ACC AGT CAG ACG AAT TAT ATT        768
Val Thr Arg Thr Pro Ser Asp Asn Tyr Thr Ser Gln Thr Asn Tyr Ile
                245                 250                 255

GAG CTG TAT CCA CAG GGT GGC GAC AAT TAT TTG ATC AAA TAC AAT CTA        816
Glu Leu Tyr Pro Gln Gly Gly Asp Asn Tyr Leu Ile Lys Tyr Asn Leu
            260                 265                 270

AGC AAT AGT TTT GGT TTG GAT GAT TTT TAT CTG CAA TAT AAA GAT GGT        864
Ser Asn Ser Phe Gly Leu Asp Asp Phe Tyr Leu Gln Tyr Lys Asp Gly
        275                 280                 285

TCC GCT GAT TGG ACT GAG ATT GCC CAT AAT CCC TAT CCT GAT ATG GTC        912
Ser Ala Asp Trp Thr Glu Ile Ala His Asn Pro Tyr Pro Asp Met Val
290                 295                 300

ATA AAT CAA AAG TAT GAA TCA CAG GCG ACA ATC AAA CGT AGT GAC TCT        960
Ile Asn Gln Lys Tyr Glu Ser Gln Ala Thr Ile Lys Arg Ser Asp Ser
305                 310                 315                 320

GAC AAT ATA CTC AGT ATA GGG TTA CAA AGA TGG CAT AGC GGT AGT TAT       1008
Asp Asn Ile Leu Ser Ile Gly Leu Gln Arg Trp His Ser Gly Ser Tyr
                325                 330                 335

AAT TTT GCC GCC GCC AAT TTT AAA ATT GAC CAA TAC TCC CCG AAA GCT       1056
Asn Phe Ala Ala Ala Asn Phe Lys Ile Asp Gln Tyr Ser Pro Lys Ala
            340                 345                 350

TTC CTG CTT AAA ATG AAT AAG GCT ATT CGG TTG CTC AAA GCT ACC GGC       1104
Phe Leu Leu Lys Met Asn Lys Ala Ile Arg Leu Leu Lys Ala Thr Gly
        355                 360                 365

CTC TCT TTT GCT ACG TTG GAG CGT ATT GTT GAT AGT GTT AAT AGC ACC       1152
Leu Ser Phe Ala Thr Leu Glu Arg Ile Val Asp Ser Val Asn Ser Thr
```

```
           370                 375                 380
AAA TCC ATC ACG GTT GAG GTA TTA AAC AAG GTT TAT CGG GTA AAA TTC   1200
Lys Ser Ile Thr Val Glu Val Leu Asn Lys Val Tyr Arg Val Lys Phe
385                     390                 395                 400

TAT ATT GAT CGT TAT GGC ATC AGT GAA GAG ACA GCC GCT ATT TTG GCT   1248
Tyr Ile Asp Arg Tyr Gly Ile Ser Glu Glu Thr Ala Ala Ile Leu Ala
                    405                 410                 415

AAT ATT AAT ATC TCT CAG CAA GCT GTT GGC AAT CAG CTT AGC CAG TTT   1296
Asn Ile Asn Ile Ser Gln Gln Ala Val Gly Asn Gln Leu Ser Gln Phe
                420                 425                 430

GAG CAA CTA TTT AAT CAC CCG CCG CTC AAT GGT ATT CGC TAT GAA ATC   1344
Glu Gln Leu Phe Asn His Pro Pro Leu Asn Gly Ile Arg Tyr Glu Ile
            435                 440                 445

AGT GAG GAC AAC TCC AAA CAT CTT CCT AAT CCT GAT CTG AAC CTT AAA   1392
Ser Glu Asp Asn Ser Lys His Leu Pro Asn Pro Asp Leu Asn Leu Lys
450                 455                 460

CCA GAC AGT ACC GGT GAT GAT CAA CGC AAG GCG GTT TTA AAA CGC GCG   1440
Pro Asp Ser Thr Gly Asp Asp Gln Arg Lys Ala Val Leu Lys Arg Ala
465                 470                 475                 480

TTT CAG GTT AAC GCC AGT GAG TTG TAT CAG ATG TTA TTG ATC ACT GAT   1488
Phe Gln Val Asn Ala Ser Glu Leu Tyr Gln Met Leu Leu Ile Thr Asp
                485                 490                 495

CGT AAA GAA GAC GGT GTT ATC AAA AAT AAC TTA GAG AAT TTG TCT GAT   1536
Arg Lys Glu Asp Gly Val Ile Lys Asn Asn Leu Glu Asn Leu Ser Asp
            500                 505                 510

CTG TAT TTG GTT AGT TTG CTG GCC CAG ATT CAT AAC CTG ACT ATT GCT   1584
Leu Tyr Leu Val Ser Leu Leu Ala Gln Ile His Asn Leu Thr Ile Ala
        515                 520                 525

GAA TTG AAC ATT TTG TTG GTG ATT TGT GGC TAT GGC GAC ACC AAC ATT   1632
Glu Leu Asn Ile Leu Leu Val Ile Cys Gly Tyr Gly Asp Thr Asn Ile
    530                 535                 540

TAT CAG ATT ACC GAC GAT AAT TTA GCC AAA ATA GTG GAA ACA TTG TTG   1680
Tyr Gln Ile Thr Asp Asp Asn Leu Ala Lys Ile Val Glu Thr Leu Leu
545                 550                 555                 560

TGG ATC ACT CAA TGG TTG AAG ACC CAA AAA TGG ACA GTT ACC GAC CTG   1728
Trp Ile Thr Gln Trp Leu Lys Thr Gln Lys Trp Thr Val Thr Asp Leu
                565                 570                 575

TTT CTG ATG ACC ACG GCC ACT TAC AGC ACC ACT TTA ACG CCA GAA ATT   1776
Phe Leu Met Thr Thr Ala Thr Tyr Ser Thr Thr Leu Thr Pro Glu Ile
            580                 585                 590

AGC AAT CTG ACG GCT ACG TTG TCT TCA ACT TTG CAT GGC AAA GAG AGT   1824
Ser Asn Leu Thr Ala Thr Leu Ser Ser Thr Leu His Gly Lys Glu Ser
        595                 600                 605

CTG ATT GGG GAA GAT CTG AAA AGA GCA ATG GCG CCT TGC TTC ACT TCG   1872
Leu Ile Gly Glu Asp Leu Lys Arg Ala Met Ala Pro Cys Phe Thr Ser
    610                 615                 620

GCT TTG CAT TTG ACT TCT CAA GAA GTT GCG TAT GAC CTG CTG TTG TGG   1920
Ala Leu His Leu Thr Ser Gln Glu Val Ala Tyr Asp Leu Leu Leu Trp
625                 630                 635                 640

ATA GAC CAG ATT CAA CCG GCA CAA ATA ACT GTT GAT GGG TTT TGG GAA   1968
Ile Asp Gln Ile Gln Pro Ala Gln Ile Thr Val Asp Gly Phe Trp Glu
                645                 650                 655

GAA GTG CAA ACA ACA CCA ACC AGC TTG AAG GTG ATT ACC TTT GCT CAG   2016
Glu Val Gln Thr Thr Pro Thr Ser Leu Lys Val Ile Thr Phe Ala Gln
            660                 665                 670

GTG CTG GCA CAA TTG AGC CTG ATC TAT CGT CGT ATT GGG TTA AGT GAA   2064
Val Leu Ala Gln Leu Ser Leu Ile Tyr Arg Arg Ile Gly Leu Ser Glu
        675                 680                 685

ACG GAA CTG TCA CTG ATC GTG ACT CAA TCT TCT CTG CTA GTG GCA GGC   2112
```

```
Thr Glu Leu Ser Leu Ile Val Thr Gln Ser Ser Leu Leu Val Ala Gly
    690                 695                 700

AAA AGC ATA CTG GAT CAC GGT CTG TTA ACC CTG ATG GCC TTG GAA GGT        2160
Lys Ser Ile Leu Asp His Gly Leu Leu Thr Leu Met Ala Leu Glu Gly
705                 710                 715                 720

TTT CAT ACC TGG GTT AAT GGC TTG GGG CAA CAT GCC TCC TTG ATA TTG        2208
Phe His Thr Trp Val Asn Gly Leu Gly Gln His Ala Ser Leu Ile Leu
                725                 730                 735

GCG GCG TTG AAA GAC GGA GCC TTG ACA GTT ACC GAT GTA GCA CAA GCT        2256
Ala Ala Leu Lys Asp Gly Ala Leu Thr Val Thr Asp Val Ala Gln Ala
            740                 745                 750

ATG AAT AAG GAG GAA TCT CTC CTA CAA ATG GCA GCT AAT CAG GTG GAG        2304
Met Asn Lys Glu Glu Ser Leu Leu Gln Met Ala Ala Asn Gln Val Glu
        755                 760                 765

AAG GAT CTA ACA AAA CTG ACC AGT TGG ACA CAG ATT GAC GCT ATT CTG        2352
Lys Asp Leu Thr Lys Leu Thr Ser Trp Thr Gln Ile Asp Ala Ile Leu
770                 775                 780

CAA TGG TTA CAG ATG TCT TCG GCC TTG GCG GTT TCT CCA CTG GAT CTG        2400
Gln Trp Leu Gln Met Ser Ser Ala Leu Ala Val Ser Pro Leu Asp Leu
785                 790                 795                 800

GCA GGG ATG ATG GCC CTG AAA TAT GGG ATA GAT CAT AAC TAT GCT GCC        2448
Ala Gly Met Met Ala Leu Lys Tyr Gly Ile Asp His Asn Tyr Ala Ala
                805                 810                 815

TGG CAA GCT GCG GCG GCT GCG CTG ATG GCT GAT CAT GCT AAT CAG GCA        2496
Trp Gln Ala Ala Ala Ala Ala Leu Met Ala Asp His Ala Asn Gln Ala
            820                 825                 830

CAG AAA AAA CTG GAT GAG ACG TTC AGT AAG GCA TTA TGT AAC TAT TAT        2544
Gln Lys Lys Leu Asp Glu Thr Phe Ser Lys Ala Leu Cys Asn Tyr Tyr
        835                 840                 845

ATT AAT GCT GTT GTC GAT AGT GCT GCT GGA GTA CGT GAT CGT AAC GGT        2592
Ile Asn Ala Val Val Asp Ser Ala Ala Gly Val Arg Asp Arg Asn Gly
850                 855                 860

TTA TAT ACC TAT TTG CTG ATT GAT AAT CAG GTT TCT GCC GAT GTG ATC        2640
Leu Tyr Thr Tyr Leu Leu Ile Asp Asn Gln Val Ser Ala Asp Val Ile
865                 870                 875                 880

ACT TCA CGT ATT GCA GAA GCT ATC GCC GGT ATT CAA CTG TAC GTT AAC        2688
Thr Ser Arg Ile Ala Glu Ala Ile Ala Gly Ile Gln Leu Tyr Val Asn
                885                 890                 895

CGG GCT TTA AAC CGA GAT GAA GGT CAG CTT GCA TCG GAC GTT AGT ACC        2736
Arg Ala Leu Asn Arg Asp Glu Gly Gln Leu Ala Ser Asp Val Ser Thr
            900                 905                 910

CGT CAG TTC TTC ACT GAC TGG GAA CGT TAC AAT AAA CGT TAC AGT ACT        2784
Arg Gln Phe Phe Thr Asp Trp Glu Arg Tyr Asn Lys Arg Tyr Ser Thr
        915                 920                 925

TGG GCT GGT GTC TCT GAA CTG GTC TAT TAT CCA GAA AAC TAT GTT GAT        2832
Trp Ala Gly Val Ser Glu Leu Val Tyr Tyr Pro Glu Asn Tyr Val Asp
930                 935                 940

CCC ACT CAG CGC ATT GGG CAA ACC AAA ATG ATG GAT GCG CTG TTG CAA        2880
Pro Thr Gln Arg Ile Gly Gln Thr Lys Met Met Asp Ala Leu Leu Gln
945                 950                 955                 960

TCC ATC AAC CAG AGC CAG CTA AAT GCG GAT ACG GTG GAA GAT GCT TTC        2928
Ser Ile Asn Gln Ser Gln Leu Asn Ala Asp Thr Val Glu Asp Ala Phe
                965                 970                 975

AAA ACT TAT TTG ACC AGC TTT GAG CAG GTA GCA AAT CTG AAA GTA ATT        2976
Lys Thr Tyr Leu Thr Ser Phe Glu Gln Val Ala Asn Leu Lys Val Ile
            980                 985                 990

AGT GCT TAC CAC GAT AAT GTG AAT GTG GAT CAA GGA TTA ACT TAT TTT        3024
Ser Ala Tyr His Asp Asn Val Asn Val Asp Gln Gly Leu Thr Tyr Phe
        995                 1000                1005
```

```
ATC GGT ATC GAC CAA GCA GCT CCG GGT ACG TAT TAC TGG CGT AGT GTT    3072
Ile Gly Ile Asp Gln Ala Ala Pro Gly Thr Tyr Tyr Trp Arg Ser Val
        1010                1015                1020

GAT CAC AGC AAA TGT GAA AAT GGC AAG TTT GCC GCT AAT GCT TGG GGT    3120
Asp His Ser Lys Cys Glu Asn Gly Lys Phe Ala Ala Asn Ala Trp Gly
1025                1030                1035                1040

GAG TGG AAT AAA ATT ACC TGT GCT GTC AAT CCT TGG AAA AAT ATC ATC    3168
Glu Trp Asn Lys Ile Thr Cys Ala Val Asn Pro Trp Lys Asn Ile Ile
                1045                1050                1055

CGT CCG GTT GTT TAT ATG TCC CGC TTA TAT CTG CTA TGG CTG GAG CAG    3216
Arg Pro Val Val Tyr Met Ser Arg Leu Tyr Leu Leu Trp Leu Glu Gln
            1060                1065                1070

CAA TCA AAG AAA AGT GAT GAT GGT AAA ACC ACG ATT TAT CAA TAT AAC    3264
Gln Ser Lys Lys Ser Asp Asp Gly Lys Thr Thr Ile Tyr Gln Tyr Asn
        1075                1080                1085

TTA AAA CTG GCT CAT ATT CGT TAC GAC GGT AGT TGG AAT ACA CCA TTT    3312
Leu Lys Leu Ala His Ile Arg Tyr Asp Gly Ser Trp Asn Thr Pro Phe
1090                1095                1100

ACT TTT GAT GTG ACA GAA AAG GTA AAA AAT TAC ACG TCG AGT ACT GAT    3360
Thr Phe Asp Val Thr Glu Lys Val Lys Asn Tyr Thr Ser Ser Thr Asp
1105                1110                1115                1120

GCT GCT GAA TCT TTA GGG TTG TAT TGT ACT GGT TAT CAA GGG GAA GAC    3408
Ala Ala Glu Ser Leu Gly Leu Tyr Cys Thr Gly Tyr Gln Gly Glu Asp
                1125                1130                1135

ACT CTA TTA GTT ATG TTC TAT TCG ATG CAG AGT AGT TAT AGC TCC TAT    3456
Thr Leu Leu Val Met Phe Tyr Ser Met Gln Ser Ser Tyr Ser Ser Tyr
            1140                1145                1150

ACC GAT AAT AAT GCG CCG GTC ACT GGG CTA TAT ATT TTC GCT GAT ATG    3504
Thr Asp Asn Asn Ala Pro Val Thr Gly Leu Tyr Ile Phe Ala Asp Met
        1155                1160                1165

TCA TCA GAC AAT ATG ACG AAT GCA CAA GCA ACT AAC TAT TGG AAT AAC    3552
Ser Ser Asp Asn Met Thr Asn Ala Gln Ala Thr Asn Tyr Trp Asn Asn
1170                1175                1180

AGT TAT CCG CAA TTT GAT ACT GTG ATG GCA GAT CCG GAT AGC GAC AAT    3600
Ser Tyr Pro Gln Phe Asp Thr Val Met Ala Asp Pro Asp Ser Asp Asn
1185                1190                1195                1200

AAA AAA GTC ATA ACC AGA AGA GTT AAT AAC CGT TAT GCG GAG GAT TAT    3648
Lys Lys Val Ile Thr Arg Arg Val Asn Asn Arg Tyr Ala Glu Asp Tyr
                1205                1210                1215

GAA ATT CCT TCC TCT GTG ACA AGT AAC AGT AAT TAT TCT TGG GGT GAT    3696
Glu Ile Pro Ser Ser Val Thr Ser Asn Ser Asn Tyr Ser Trp Gly Asp
            1220                1225                1230

CAC AGT TTA ACC ATG CTT TAT GGT GGT AGT GTT CCT AAT ATT ACT TTT    3744
His Ser Leu Thr Met Leu Tyr Gly Gly Ser Val Pro Asn Ile Thr Phe
        1235                1240                1245

GAA TCG GCG GCA GAA GAT TTA AGG CTA TCT ACC AAT ATG GCA TTG AGT    3792
Glu Ser Ala Ala Glu Asp Leu Arg Leu Ser Thr Asn Met Ala Leu Ser
1250                1255                1260

ATT ATT CAT AAT GGA TAT GCG GGA ACC CGC CGT ATA CAA TGT AAT CTT    3840
Ile Ile His Asn Gly Tyr Ala Gly Thr Arg Arg Ile Gln Cys Asn Leu
1265                1270                1275                1280

ATG AAA CAA TAC GCT TCA TTA GGT GAT AAA TTT ATA ATT TAT GAT TCA    3888
Met Lys Gln Tyr Ala Ser Leu Gly Asp Lys Phe Ile Ile Tyr Asp Ser
                1285                1290                1295

TCA TTT GAT GAT GCA AAC CGT TTT AAT CTG GTG CCA TTG TTT AAA TTC    3936
Ser Phe Asp Asp Ala Asn Arg Phe Asn Leu Val Pro Leu Phe Lys Phe
            1300                1305                1310

GGA AAA GAC GAG AAC TCA GAT GAT AGT ATT TGT ATA TAT AAT GAA AAC    3984
Gly Lys Asp Glu Asn Ser Asp Asp Ser Ile Cys Ile Tyr Asn Glu Asn
        1315                1320                1325
```

-continued

```
CCT TCC TCT GAA GAT AAG AAG TGG TAT TTT TCT TCG AAA GAT GAC AAT    4032
Pro Ser Ser Glu Asp Lys Lys Trp Tyr Phe Ser Ser Lys Asp Asp Asn
        1330                1335                1340

AAA ACA GCG GAT TAT AAT GGT GGA ACT CAA TGT ATA GAT GCT GGA ACC    4080
Lys Thr Ala Asp Tyr Asn Gly Gly Thr Gln Cys Ile Asp Ala Gly Thr
1345                1350                1355                1360

AGT AAC AAA GAT TTT TAT TAT AAT CTC CAG GAG ATT GAA GTA ATT AGT    4128
Ser Asn Lys Asp Phe Tyr Tyr Asn Leu Gln Glu Ile Glu Val Ile Ser
            1365                1370                1375

GTT ACT GGT GGG TAT TGG TCG AGT TAT AAA ATA TCC AAC CCG ATT AAT    4176
Val Thr Gly Gly Tyr Trp Ser Ser Tyr Lys Ile Ser Asn Pro Ile Asn
        1380                1385                1390

ATC AAT ACG GGC ATT GAT AGT GCT AAA GTA AAA GTC ACC GTA AAA GCG    4224
Ile Asn Thr Gly Ile Asp Ser Ala Lys Val Lys Val Thr Val Lys Ala
        1395                1400                1405

GGT GGT GAC GAT CAA ATC TTT ACT GCT GAT AAT AGT ACC TAT GTT CCT    4272
Gly Gly Asp Asp Gln Ile Phe Thr Ala Asp Asn Ser Thr Tyr Val Pro
    1410                1415                1420

CAG CAA CCG GCA CCC AGT TTT GAG GAG ATG ATT TAT CAG TTC AAT AAC    4320
Gln Gln Pro Ala Pro Ser Phe Glu Glu Met Ile Tyr Gln Phe Asn Asn
1425                1430                1435                1440

CTG ACA ATA GAT TGT AAG AAT TTA AAT TTC ATC GAC AAT CAG GCA CAT    4368
Leu Thr Ile Asp Cys Lys Asn Leu Asn Phe Ile Asp Asn Gln Ala His
            1445                1450                1455

ATT GAG ATT GAT TTC ACC GCT ACG GCA CAA GAT GGC CGA TTC TTG GGT    4416
Ile Glu Ile Asp Phe Thr Ala Thr Ala Gln Asp Gly Arg Phe Leu Gly
        1460                1465                1470

GCA GAA ACT TTT ATT ATC CCG GTA ACT AAA AAA GTT CTC GGT ACT GAG    4464
Ala Glu Thr Phe Ile Ile Pro Val Thr Lys Lys Val Leu Gly Thr Glu
    1475                1480                1485

AAC GTG ATT GCG TTA TAT AGC GAA AAT AAC GGT GTT CAA TAT ATG CAA    4512
Asn Val Ile Ala Leu Tyr Ser Glu Asn Asn Gly Val Gln Tyr Met Gln
        1490                1495                1500

ATT GGC GCA TAT CGT ACC CGT TTG AAT ACG TTA TTC GCT CAA CAG TTG    4560
Ile Gly Ala Tyr Arg Thr Arg Leu Asn Thr Leu Phe Ala Gln Gln Leu
1505                1510                1515                1520

GTT AGC CGT GCT AAT CGT GGC ATT GAT GCA GTG CTC AGT ATG GAA ACT    4608
Val Ser Arg Ala Asn Arg Gly Ile Asp Ala Val Leu Ser Met Glu Thr
            1525                1530                1535

CAG AAT ATT CAG GAA CCG CAA TTA GGA GCG GGC ACA TAT GTG CAG CTT    4656
Gln Asn Ile Gln Glu Pro Gln Leu Gly Ala Gly Thr Tyr Val Gln Leu
        1540                1545                1550

GTG TTG GAT AAA TAT GAT GAG TCT ATT CAT GGC ACT AAT AAA AGC TTT    4704
Val Leu Asp Lys Tyr Asp Glu Ser Ile His Gly Thr Asn Lys Ser Phe
    1555                1560                1565

GCT ATT GAA TAT GTT GAT ATA TTT AAA GAG AAC GAT AGT TTT GTG ATT    4752
Ala Ile Glu Tyr Val Asp Ile Phe Lys Glu Asn Asp Ser Phe Val Ile
        1570                1575                1580

TAT CAA GGA GAA CTT AGC GAA ACA AGT CAA ACT GTT GTG AAA GTT TTC    4800
Tyr Gln Gly Glu Leu Ser Glu Thr Ser Gln Thr Val Val Lys Val Phe
1585                1590                1595                1600

TTA TCC TAT TTT ATA GAG GCG ACT GGA AAT AAG AAC CAC TTA TGG GTA    4848
Leu Ser Tyr Phe Ile Glu Ala Thr Gly Asn Lys Asn His Leu Trp Val
            1605                1610                1615

CGT GCT AAA TAC CAA AAG GAA ACG ACT GAT AAG ATC TTG TTC GAC CGT    4896
Arg Ala Lys Tyr Gln Lys Glu Thr Thr Asp Lys Ile Leu Phe Asp Arg
        1620                1625                1630

ACT GAT GAG AAA GAT CCG CAC GGT TGG TTT CTC AGC GAC GAT CAC AAG    4944
Thr Asp Glu Lys Asp Pro His Gly Trp Phe Leu Ser Asp Asp His Lys
```

-continued

```
               1635                1640                1645
ACC TTT AGT GGT CTC TCT TCC GCA CAG GCA TTA AAG AAC GAC AGT GAA       4992
Thr Phe Ser Gly Leu Ser Ser Ala Gln Ala Leu Lys Asn Asp Ser Glu
        1650                1655                1660

CCG ATG GAT TTC TCT GGC GCC AAT GCT CTC TAT TTC TGG GAA CTG TTC       5040
Pro Met Asp Phe Ser Gly Ala Asn Ala Leu Tyr Phe Trp Glu Leu Phe
1665                1670                1675                1680

TAT TAC ACG CCG ATG ATG ATG GCT CAT CGT TTG TTG CAG GAA CAG AAT       5088
Tyr Tyr Thr Pro Met Met Met Ala His Arg Leu Leu Gln Glu Gln Asn
                1685                1690                1695

TTT GAT GCG GCG AAC CAT TGG TTC CGT TAT GTC TGG AGT CCA TCC GGT       5136
Phe Asp Ala Ala Asn His Trp Phe Arg Tyr Val Trp Ser Pro Ser Gly
        1700                1705                1710

TAT ATC GTT GAT GGT AAA ATT GCT ATC TAC CAC TGG AAC GTG CGA CCG       5184
Tyr Ile Val Asp Gly Lys Ile Ala Ile Tyr His Trp Asn Val Arg Pro
            1715                1720                1725

CTG GAA GAA GAC ACC AGT TGG AAT GCA CAA CAA CTG GAC TCC ACC GAT       5232
Leu Glu Glu Asp Thr Ser Trp Asn Ala Gln Gln Leu Asp Ser Thr Asp
        1730                1735                1740

CCA GAT GCT GTA GCC CAA GAT GAT CCG ATG CAC TAC AAG GTG GCT ACC       5280
Pro Asp Ala Val Ala Gln Asp Asp Pro Met His Tyr Lys Val Ala Thr
1745                1750                1755                1760

TTT ATG GCG ACG TTG GAT CTG CTA ATG GCC CGT GGT GAT GCT GCT TAC       5328
Phe Met Ala Thr Leu Asp Leu Leu Met Ala Arg Gly Asp Ala Ala Tyr
                1765                1770                1775

CGC CAG TTA GAG CGT GAT ACG TTG GCT GAA GCT AAA ATG TGG TAT ACA       5376
Arg Gln Leu Glu Arg Asp Thr Leu Ala Glu Ala Lys Met Trp Tyr Thr
        1780                1785                1790

CAG GCG CTT AAT CTG TTG GGT GAT GAG CCA CAA GTG ATG CTG AGT ACG       5424
Gln Ala Leu Asn Leu Leu Gly Asp Glu Pro Gln Val Met Leu Ser Thr
            1795                1800                1805

ACT TGG GCT AAT CCA ACA TTG GGT AAT GCT GCT TCA AAA ACC ACA CAG       5472
Thr Trp Ala Asn Pro Thr Leu Gly Asn Ala Ala Ser Lys Thr Thr Gln
        1810                1815                1820

CAG GTT CGT CAG CAA GTG CTT ACC CAG TTG CGT CTC AAT AGC AGG GTA       5520
Gln Val Arg Gln Gln Val Leu Thr Gln Leu Arg Leu Asn Ser Arg Val
1825                1830                1835                1840

AAA ACC CCG TTG                                                       5532
Lys Thr Pro Leu
        1844
```

(2) INFORMATION FOR SEQ ID NO:53:

(i) SEQUENCE CHARACTERISTICS:
        (A) LENGTH: 1844 amino acids
        (B) TYPE: amino acids
        (D) TOPOLOGY: linear (ii) MOLECULE TYPE: protein (xi) SEQUENCE DESCRIPTION: SEQ ID NO:53:

```
Phe Ile Gln Gly Tyr Ser Asp Leu Phe Gly Asn Arg Ala Asp Asn Tyr
1               5                   10                  15

Ala Ala Pro Gly Ser Val Ala Ser Met Phe Ser Pro Ala Ala Tyr Leu
                20                  25                  30

Thr Glu Leu Tyr Arg Glu Ala Lys Asn Leu His Asp Ser Ser Ser Ile
            35                  40                  45

Tyr Tyr Leu Asp Lys Arg Arg Pro Asp Leu Ala Ser Leu Met Leu Ser
        50                  55                  60

Gln Lys Asn Met Asp Glu Glu Ile Ser Thr Leu Ala Leu Ser Asn Glu
```

-continued

```
 65                  70                  75                  80
Leu Cys Leu Ala Gly Ile Glu Thr Lys Thr Gly Lys Ser Gln Asp Glu
                85                  90                  95
Val Met Asp Met Leu Ser Thr Tyr Arg Leu Ser Gly Glu Thr Pro Tyr
               100                 105                 110
His His Ala Tyr Glu Thr Val Arg Glu Ile Val His Glu Arg Asp Pro
               115                 120                 125
Gly Phe Arg His Leu Ser Gln Ala Pro Ile Val Ala Ala Lys Leu Asp
           130                 135                 140
Pro Val Thr Leu Leu Gly Ile Ser Ser His Ile Ser Pro Glu Leu Tyr
145                 150                 155                 160
Asn Leu Leu Ile Glu Glu Ile Pro Glu Lys Asp Glu Ala Ala Leu Asp
               165                 170                 175
Thr Leu Tyr Lys Thr Asn Phe Gly Asp Ile Thr Thr Ala Gln Leu Met
           180                 185                 190
Ser Pro Ser Tyr Leu Ala Arg Tyr Tyr Gly Val Ser Pro Glu Asp Ile
           195                 200                 205
Ala Tyr Val Thr Thr Ser Leu Ser His Val Gly Tyr Ser Ser Asp Ile
       210                 215                 220
Leu Val Ile Pro Leu Val Asp Gly Val Gly Lys Met Glu Val Val Arg
225                 230                 235                 240
Val Thr Arg Thr Pro Ser Asp Asn Tyr Thr Ser Gln Thr Asn Tyr Ile
               245                 250                 255
Glu Leu Tyr Pro Gln Gly Gly Asp Asn Tyr Leu Ile Lys Tyr Asn Leu
           260                 265                 270
Ser Asn Ser Phe Gly Leu Asp Asp Phe Tyr Leu Gln Tyr Lys Asp Gly
       275                 280                 285
Ser Ala Asp Trp Thr Glu Ile Ala His Asn Pro Tyr Pro Asp Met Val
       290                 295                 300
Ile Asn Gln Lys Tyr Glu Ser Gln Ala Thr Ile Lys Arg Ser Asp Ser
305                 310                 315                 320
Asp Asn Ile Leu Ser Ile Gly Leu Gln Arg Trp His Ser Gly Ser Tyr
               325                 330                 335
Asn Phe Ala Ala Ala Asn Phe Lys Ile Asp Gln Tyr Ser Pro Lys Ala
           340                 345                 350
Phe Leu Leu Lys Met Asn Lys Ala Ile Arg Leu Leu Lys Ala Thr Gly
           355                 360                 365
Leu Ser Phe Ala Thr Leu Glu Arg Ile Val Asp Ser Val Asn Ser Thr
       370                 375                 380
Lys Ser Ile Thr Val Glu Val Leu Asn Lys Val Tyr Arg Val Lys Phe
385                 390                 395                 400
Tyr Ile Asp Arg Tyr Gly Ile Ser Glu Glu Thr Ala Ala Ile Leu Ala
               405                 410                 415
Asn Ile Asn Ile Ser Gln Gln Ala Val Gly Asn Gln Leu Ser Gln Phe
           420                 425                 430
Glu Gln Leu Phe Asn His Pro Pro Leu Asn Gly Ile Arg Tyr Glu Ile
           435                 440                 445
Ser Glu Asp Asn Ser Lys His Leu Pro Asn Pro Asp Leu Asn Leu Lys
       450                 455                 460
Pro Asp Ser Thr Gly Asp Asp Gln Arg Lys Ala Val Leu Lys Arg Ala
465                 470                 475                 480
Phe Gln Val Asn Ala Ser Glu Leu Tyr Gln Met Leu Leu Ile Thr Asp
               485                 490                 495
```

-continued

```
Arg Lys Glu Asp Gly Val Ile Lys Asn Asn Leu Glu Asn Leu Ser Asp
            500                 505                 510
Leu Tyr Leu Val Ser Leu Leu Ala Gln Ile His Asn Leu Thr Ile Ala
        515                 520                 525
Glu Leu Asn Ile Leu Leu Val Ile Cys Gly Tyr Gly Asp Thr Asn Ile
        530                 535                 540
Tyr Gln Ile Thr Asp Asp Asn Leu Ala Lys Ile Val Glu Thr Leu Leu
545                 550                 555                 560
Trp Ile Thr Gln Trp Leu Lys Thr Gln Lys Trp Thr Val Thr Asp Leu
                565                 570                 575
Phe Leu Met Thr Thr Ala Thr Tyr Ser Thr Thr Leu Thr Pro Glu Ile
            580                 585                 590
Ser Asn Leu Thr Ala Thr Leu Ser Ser Thr Leu His Gly Lys Glu Ser
        595                 600                 605
Leu Ile Gly Glu Asp Leu Lys Arg Ala Met Ala Pro Cys Phe Thr Ser
        610                 615                 620
Ala Leu His Leu Thr Ser Gln Glu Val Ala Tyr Asp Leu Leu Leu Trp
625                 630                 635                 640
Ile Asp Gln Ile Gln Pro Ala Gln Ile Thr Val Asp Gly Phe Trp Glu
                645                 650                 655
Glu Val Gln Thr Thr Pro Thr Ser Leu Lys Val Ile Thr Phe Ala Gln
                660                 665                 670
Val Leu Ala Gln Leu Ser Leu Ile Tyr Arg Arg Ile Gly Leu Ser Glu
            675                 680                 685
Thr Glu Leu Ser Leu Ile Val Thr Gln Ser Ser Leu Leu Val Ala Gly
        690                 695                 700
Lys Ser Ile Leu Asp His Gly Leu Leu Thr Leu Met Ala Leu Glu Gly
705                 710                 715                 720
Phe His Thr Trp Val Asn Gly Leu Gly Gln His Ala Ser Leu Ile Leu
                725                 730                 735
Ala Ala Leu Lys Asp Gly Ala Leu Thr Val Thr Asp Val Ala Gln Ala
            740                 745                 750
Met Asn Lys Glu Glu Ser Leu Leu Gln Met Ala Ala Asn Gln Val Glu
        755                 760                 765
Lys Asp Leu Thr Lys Leu Thr Ser Trp Thr Gln Ile Asp Ala Ile Leu
        770                 775                 780
Gln Trp Leu Gln Met Ser Ser Ala Leu Ala Val Ser Pro Leu Asp Leu
785                 790                 795                 800
Ala Gly Met Met Ala Leu Lys Tyr Gly Ile Asp His Asn Tyr Ala Ala
                805                 810                 815
Trp Gln Ala Ala Ala Ala Leu Met Ala Asp His Ala Asn Gln Ala
            820                 825                 830
Gln Lys Lys Leu Asp Glu Thr Phe Ser Lys Ala Leu Cys Asn Tyr Tyr
        835                 840                 845
Ile Asn Ala Val Val Asp Ser Ala Ala Gly Val Arg Asp Arg Asn Gly
        850                 855                 860
Leu Tyr Thr Tyr Leu Leu Ile Asp Asn Gln Val Ser Ala Asp Val Ile
865                 870                 875                 880
Thr Ser Arg Ile Ala Glu Ala Ile Ala Gly Ile Gln Leu Tyr Val Asn
                885                 890                 895
Arg Ala Leu Asn Arg Asp Glu Gly Gln Leu Ala Ser Asp Val Ser Thr
            900                 905                 910
```

-continued

```
Arg Gln Phe Phe Thr Asp Trp Glu Arg Tyr Asn Lys Arg Tyr Ser Thr
        915                 920                 925

Trp Ala Gly Val Ser Glu Leu Val Tyr Tyr Pro Glu Asn Tyr Val Asp
        930                 935                 940

Pro Thr Gln Arg Ile Gly Gln Thr Lys Met Met Asp Ala Leu Leu Gln
945                 950                 955                 960

Ser Ile Asn Gln Ser Gln Leu Asn Ala Asp Thr Val Glu Asp Ala Phe
                965                 970                 975

Lys Thr Tyr Leu Thr Ser Phe Glu Gln Val Ala Asn Leu Lys Val Ile
            980                 985                 990

Ser Ala Tyr His Asp Asn Val Asn Val Asp Gln Gly Leu Thr Tyr Phe
        995                 1000                1005

Ile Gly Ile Asp Gln Ala Ala Pro Gly Thr Tyr Tyr Trp Arg Ser Val
    1010                1015                1020

Asp His Ser Lys Cys Glu Asn Gly Lys Phe Ala Ala Asn Ala Trp Gly
1025                1030                1035                1040

Glu Trp Asn Lys Ile Thr Cys Ala Val Asn Pro Trp Lys Asn Ile Ile
                1045                1050                1055

Arg Pro Val Val Tyr Met Ser Arg Leu Tyr Leu Trp Leu Glu Gln
            1060                1065                1070

Gln Ser Lys Lys Ser Asp Asp Gly Lys Thr Thr Ile Tyr Gln Tyr Asn
        1075                1080                1085

Leu Lys Leu Ala His Ile Arg Tyr Asp Gly Ser Trp Asn Thr Pro Phe
    1090                1095                1100

Thr Phe Asp Val Thr Glu Lys Val Lys Asn Tyr Thr Ser Ser Thr Asp
1105                1110                1115                1120

Ala Ala Glu Ser Leu Gly Leu Tyr Cys Thr Gly Tyr Gln Gly Glu Asp
                1125                1130                1135

Thr Leu Leu Val Met Phe Tyr Ser Met Gln Ser Ser Tyr Ser Ser Tyr
            1140                1145                1150

Thr Asp Asn Asn Ala Pro Val Thr Gly Leu Tyr Ile Phe Ala Asp Met
        1155                1160                1165

Ser Ser Asp Asn Met Thr Asn Ala Gln Ala Thr Asn Tyr Trp Asn Asn
    1170                1175                1180

Ser Tyr Pro Gln Phe Asp Thr Val Met Ala Asp Pro Asp Ser Asp Asn
1185                1190                1195                1200

Lys Lys Val Ile Thr Arg Arg Val Asn Asn Arg Tyr Ala Glu Asp Tyr
                1205                1210                1215

Glu Ile Pro Ser Ser Val Thr Ser Asn Ser Asn Tyr Ser Trp Gly Asp
            1220                1225                1230

His Ser Leu Thr Met Leu Tyr Gly Gly Ser Val Pro Asn Ile Thr Phe
        1235                1240                1245

Glu Ser Ala Ala Glu Asp Leu Arg Leu Ser Thr Asn Met Ala Leu Ser
    1250                1255                1260

Ile Ile His Asn Gly Tyr Ala Gly Thr Arg Arg Ile Gln Cys Asn Leu
1265                1270                1275                1280

Met Lys Gln Tyr Ala Ser Leu Gly Asp Lys Phe Ile Ile Tyr Asp Ser
                1285                1290                1295

Ser Phe Asp Asp Ala Asn Arg Phe Asn Leu Val Pro Leu Phe Lys Phe
            1300                1305                1310

Gly Lys Asp Glu Asn Ser Asp Asp Ser Ile Cys Ile Tyr Asn Glu Asn
        1315                1320                1325

Pro Ser Ser Glu Asp Lys Lys Trp Tyr Phe Ser Ser Lys Asp Asp Asn
```

-continued

```
            1330                1335                1340
Lys Thr Ala Asp Tyr Asn Gly Gly Thr Gln Cys Ile Asp Ala Gly Thr
1345                1350                1355                1360
Ser Asn Lys Asp Phe Tyr Tyr Asn Leu Gln Glu Ile Glu Val Ile Ser
                1365                1370                1375
Val Thr Gly Gly Tyr Trp Ser Ser Tyr Lys Ile Ser Asn Pro Ile Asn
            1380                1385                1390
Ile Asn Thr Gly Ile Asp Ser Ala Lys Val Lys Val Thr Val Lys Ala
                1395                1400                1405
Gly Gly Asp Asp Gln Ile Phe Thr Ala Asp Asn Ser Thr Tyr Val Pro
            1410                1415                1420
Gln Gln Pro Ala Pro Ser Phe Glu Glu Met Ile Tyr Gln Phe Asn Asn
1425                1430                1435                1440
Leu Thr Ile Asp Cys Lys Asn Leu Asn Phe Ile Asp Asn Gln Ala His
                1445                1450                1455
Ile Glu Ile Asp Phe Thr Ala Thr Ala Gln Asp Gly Arg Phe Leu Gly
                1460                1465                1470
Ala Glu Thr Phe Ile Ile Pro Val Thr Lys Lys Val Leu Gly Thr Glu
            1475                1480                1485
Asn Val Ile Ala Leu Tyr Ser Glu Asn Asn Gly Val Gln Tyr Met Gln
            1490                1495                1500
Ile Gly Ala Tyr Arg Thr Arg Leu Asn Thr Leu Phe Ala Gln Gln Leu
1505                1510                1515                1520
Val Ser Arg Ala Asn Arg Gly Ile Asp Ala Val Leu Ser Met Glu Thr
                1525                1530                1535
Gln Asn Ile Gln Glu Pro Gln Leu Gly Ala Gly Thr Tyr Val Gln Leu
            1540                1545                1550
Val Leu Asp Lys Tyr Asp Glu Ser Ile His Gly Thr Asn Lys Ser Phe
            1555                1560                1565
Ala Ile Glu Tyr Val Asp Ile Phe Lys Glu Asn Asp Ser Phe Val Ile
            1570                1575                1580
Tyr Gln Gly Glu Leu Ser Glu Thr Ser Gln Thr Val Val Lys Val Phe
1585                1590                1595                1600
Leu Ser Tyr Phe Ile Glu Ala Thr Gly Asn Lys Asn His Leu Trp Val
                1605                1610                1615
Arg Ala Lys Tyr Gln Lys Glu Thr Thr Asp Lys Ile Leu Phe Asp Arg
                1620                1625                1630
Thr Asp Glu Lys Asp Pro His Gly Trp Phe Leu Ser Asp Asp His Lys
                1635                1640                1645
Thr Phe Ser Gly Leu Ser Ser Ala Gln Ala Leu Lys Asn Asp Ser Glu
                1650                1655                1660
Pro Met Asp Phe Ser Gly Ala Asn Ala Leu Tyr Phe Trp Glu Leu Phe
1665                1670                1675                1680
Tyr Tyr Thr Pro Met Met Met Ala His Arg Leu Leu Gln Glu Gln Asn
                1685                1690                1695
Phe Asp Ala Ala Asn His Trp Phe Arg Tyr Val Trp Ser Pro Ser Gly
                1700                1705                1710
Tyr Ile Val Asp Gly Lys Ile Ala Ile Tyr His Trp Asn Val Arg Pro
                1715                1720                1725
Leu Glu Glu Asp Thr Ser Trp Asn Ala Gln Gln Leu Asp Ser Thr Asp
            1730                1735                1740
Pro Asp Ala Val Ala Gln Asp Pro Met His Tyr Lys Val Ala Thr
1745                1750                1755                1760
```

```
Phe Met Ala Thr Leu Asp Leu Leu Met Ala Arg Gly Asp Ala Ala Tyr
            1765                1770                1775

Arg Gln Leu Glu Arg Asp Thr Leu Ala Glu Ala Lys Met Trp Tyr Thr
            1780                1785                1790

Gln Ala Leu Asn Leu Leu Gly Asp Glu Pro Gln Val Met Leu Ser Thr
            1795                1800                1805

Thr Trp Ala Asn Pro Thr Leu Gly Asn Ala Ala Ser Lys Thr Thr Gln
            1810                1815                1820

Gln Val Arg Gln Val Leu Thr Gln Leu Arg Leu Asn Ser Arg Val
1825                1830                1835                1840

Lys Thr Pro Leu (2) INFORMATION FOR SEQ ID NO:54:

(i) SEQUENCE CHARACTERISTICS:
        (A) LENGTH: 1722 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:54:

CTA GGA ACA GCC AAT TCC CTG ACC GCT TTA TTC CTG CCG CAG GAA AAT        48
Leu Gly Thr Ala Asn Ser Leu Thr Ala Leu Phe Leu Pro Gln Glu Asn
1               5                   10                  15

AGC AAG CTC AAA GGC TAC TGG CGG ACA CTG GCG CAG CGT ATG TTT AAT        96
Ser Lys Leu Lys Gly Tyr Trp Arg Thr Leu Ala Gln Arg Met Phe Asn
                20                  25                  30

TTA CGT CAT AAT CTG TCG ATT GAC GGC CAG CCG CTC TCC TTG CCG CTG       144
Leu Arg His Asn Leu Ser Ile Asp Gly Gln Pro Leu Ser Leu Pro Leu
            35                  40                  45

TAT GCT AAA CCG GCT GAT CCA AAA GCT TTA CTG AGT GCG GCG GTT TCA       192
Tyr Ala Lys Pro Ala Asp Pro Lys Ala Leu Leu Ser Ala Ala Val Ser
    50                  55                  60

GCT TCT CAA GGG GGA GCC GAC TTG CCG AAG GCG CCG CTG ACT ATT CAC       240
Ala Ser Gln Gly Gly Ala Asp Leu Pro Lys Ala Pro Leu Thr Ile His
65                  70                  75                  80

CGC TTC CCT CAA ATG CTA GAA GGG GCA CGG GGC TTG GTT AAC CAG CTT       288
Arg Phe Pro Gln Met Leu Glu Gly Ala Arg Gly Leu Val Asn Gln Leu
                85                  90                  95

ATA CAG TTC GGT AGT TCA CTA TTG GGG TAC AGT GAG CGT CAG GAT GCG       336
Ile Gln Phe Gly Ser Ser Leu Leu Gly Tyr Ser Glu Arg Gln Asp Ala
            100                 105                 110

GAA GCT ATG AGT CAA CTA CTG CAA ACC CAA GCC AGC GAG TTA ATA CTG       384
Glu Ala Met Ser Gln Leu Leu Gln Thr Gln Ala Ser Glu Leu Ile Leu
    115                 120                 125

ACC AGT ATT CGT ATG CAG GAT AAC CAA TTG GCA GAG CTG GAT TCG GAA       432
Thr Ser Ile Arg Met Gln Asp Asn Gln Leu Ala Glu Leu Asp Ser Glu
130                 135                 140

AAA ACC GCC TTG CAA GTC TCT TTA GCT GGA GTG CAA CAA CGG TTT GAC       480
Lys Thr Ala Leu Gln Val Ser Leu Ala Gly Val Gln Gln Arg Phe Asp
145                 150                 155                 160

AGC TAT AGC CAA CTG TAT GAG GAG AAC ATC AAC GCA GGT GAG CAG CGA       528
Ser Tyr Ser Gln Leu Tyr Glu Glu Asn Ile Asn Ala Gly Glu Gln Arg
                165                 170                 175

GCG CTG GCG TTA CGC TCA GAA TCT GCT ATT GAG TCT CAG GGA GCG CAG       576
Ala Leu Ala Leu Arg Ser Glu Ser Ala Ile Glu Ser Gln Gly Ala Gln
            180                 185                 190
```

```
ATT TCC CGT ATG GCA GGC GCG GGT GTT GAT ATG GCA CCA AAT ATC TTC      624
Ile Ser Arg Met Ala Gly Ala Gly Val Asp Met Ala Pro Asn Ile Phe
        195                 200                 205

GGC CTG GCT GAT GGC GGC ATG CAT TAT GGT GCT ATT GCC TAT GCC ATC      672
Gly Leu Ala Asp Gly Gly Met His Tyr Gly Ala Ile Ala Tyr Ala Ile
    210                 215                 220

GCT GAC GGT ATT GAG TTG AGT GCT TCT GCC AAG ATG GTT GAT GCG GAG      720
Ala Asp Gly Ile Glu Leu Ser Ala Ser Ala Lys Met Val Asp Ala Glu
225                 230                 235                 240

AAA GTT GCT CAG TCG GAA ATA TAT CGC CGT CGC CGT CAA GAA TGG AAA      768
Lys Val Ala Gln Ser Glu Ile Tyr Arg Arg Arg Arg Gln Glu Trp Lys
            245                 250                 255

ATT CAG CGT GAC AAC GCA CAA GCG GAG ATT AAC CAG TTA AAC GCG CAA      816
Ile Gln Arg Asp Asn Ala Gln Ala Glu Ile Asn Gln Leu Asn Ala Gln
        260                 265                 270

CTG GAA TCA CTG TCT ATT CGC CGT GAA GCC GCT GAA ATG CAA AAA GAG      864
Leu Glu Ser Leu Ser Ile Arg Arg Glu Ala Ala Glu Met Gln Lys Glu
    275                 280                 285

TAC CTG AAA ACC CAG CAA GCT CAG GCG CAG GCA CAA CTT ACT TTC TTA      912
Tyr Leu Lys Thr Gln Gln Ala Gln Ala Gln Ala Gln Leu Thr Phe Leu
290                 295                 300

AGA AGC AAA TTC AGT AAT CAA GCG TTA TAT AGT TGG TTA CGA GGG CGT      960
Arg Ser Lys Phe Ser Asn Gln Ala Leu Tyr Ser Trp Leu Arg Gly Arg
305                 310                 315                 320

TTG TCA GGT ATT TAT TTC CAG TTC TAT GAC TTG GCC GTA TCA CGT TGC     1008
Leu Ser Gly Ile Tyr Phe Gln Phe Tyr Asp Leu Ala Val Ser Arg Cys
            325                 330                 335

CTG ATG GCA GAG CAA TCC TAT CAA TGG GAA GCT AAT GAT AAT TCC ATT     1056
Leu Met Ala Glu Gln Ser Tyr Gln Trp Glu Ala Asn Asp Asn Ser Ile
        340                 345                 350

AGC TTT GTC AAA CCG GGT GCA TGG CAA GGA ACT TAC GCC GGC TTA TTG     1104
Ser Phe Val Lys Pro Gly Ala Trp Gln Gly Thr Tyr Ala Gly Leu Leu
    355                 360                 365

TGT GGA GAA GCT TTG ATA CAA AAT CTG GCA CAA ATG GAA GAG GCA TAT     1152
Cys Gly Glu Ala Leu Ile Gln Asn Leu Ala Gln Met Glu Glu Ala Tyr
370                 375                 380

CTG AAA TGG GAA TCT CGC GCT TTG GAA GTA GAA CGC ACG GTT TCA TTG     1200
Leu Lys Trp Glu Ser Arg Ala Leu Glu Val Glu Arg Thr Val Ser Leu
385                 390                 395                 400

GCA GTG GTT TAT GAT TCA CTG GAA GGT AAT GAT CGT TTT AAT TTA GCG     1248
Ala Val Val Tyr Asp Ser Leu Glu Gly Asn Asp Arg Phe Asn Leu Ala
            405                 410                 415

GAA CAA ATA CCT GCA TTA TTG GAT AAG GGG GAG GGA ACA GCA GGA ACT     1296
Glu Gln Ile Pro Ala Leu Leu Asp Lys Gly Glu Gly Thr Ala Gly Thr
        420                 425                 430

AAA GAA AAT GGG TTA TCA TTG GCT AAT GCT ATC CTG TCA GCT TCG GTC     1344
Lys Glu Asn Gly Leu Ser Leu Ala Asn Ala Ile Leu Ser Ala Ser Val
    435                 440                 445

AAA TTG TCC GAC TTG AAA CTG GGA ACG GAT TAT CCA GAC AGT ATC GTT     1392
Lys Leu Ser Asp Leu Lys Leu Gly Thr Asp Tyr Pro Asp Ser Ile Val
450                 455                 460

GGT AGC AAC AAG GTT CGT CGT ATT AAG CAA ATC AGT GTT TCG CTA CCT     1440
Gly Ser Asn Lys Val Arg Arg Ile Lys Gln Ile Ser Val Ser Leu Pro
465                 470                 475                 480

GCA TTG GTT GGG CCT TAT CAG GAT GTT CAG GCT ATG CTC AGC TAT GGT     1488
Ala Leu Val Gly Pro Tyr Gln Asp Val Gln Ala Met Leu Ser Tyr Gly
            485                 490                 495

GGC AGT ACT CAA TTG CCG AAA GGT TGT TCA GCG TTG GCT GTG TCT CAT     1536
Gly Ser Thr Gln Leu Pro Lys Gly Cys Ser Ala Leu Ala Val Ser His
        500                 505                 510
```

```
GGT ACC AAT GAT AGT GGT CAG TTC CAG TTG GAT TTC AAT GAC GGC AAA      1584
Gly Thr Asn Asp Ser Gly Gln Phe Gln Leu Asp Phe Asn Asp Gly Lys
        515                 520                 525

TAC CTG CCA TTT GAA GGT ATT GCT CTT GAT GAT CAG GGT ACA CTG AAT      1632
Tyr Leu Pro Phe Glu Gly Ile Ala Leu Asp Asp Gln Gly Thr Leu Asn
        530                 535                 540

CTT CAA TTT CCG AAT GCT ACC GAC AAG CAG AAA GCA ATA TTG CAA ACT      1680
Leu Gln Phe Pro Asn Ala Thr Asp Lys Gln Lys Ala Ile Leu Gln Thr
545                 550                 555                 560

ATG AGC GAT ATT ATT TTG CAT ATT CGT TAT ACC ATC CGT TAA              1722
Met Ser Asp Ile Ile Leu His Ile Arg Tyr Thr Ile Arg
                565                 570         573

(2) INFORMATION FOR SEQ ID NO:55:

(i) SEQUENCE CHARACTERISTICS:
        (A) LENGTH:  573 amino acids
        (B) TYPE: amino acids
        (C) STRANDEDNESS: single
        (D) TOPOLOGY: linear (ii) MOLECULE TYPE:  protein (xi) SEQUENCE DESCRIPTION: SEQ ID NO:55:

Leu Gly Thr Ala Asn Ser Leu Thr Ala Leu Phe Leu Pro Gln Glu Asn
1               5                   10                  15

Ser Lys Leu Lys Gly Tyr Trp Arg Thr Leu Ala Gln Arg Met Phe Asn
                20                  25                  30

Leu Arg His Asn Leu Ser Ile Asp Gly Gln Pro Leu Ser Leu Pro Leu
                35                  40                  45

Tyr Ala Lys Pro Ala Asp Pro Lys Ala Leu Leu Ser Ala Ala Val Ser
        50                  55                  60

Ala Ser Gln Gly Gly Ala Asp Leu Pro Lys Ala Pro Leu Thr Ile His
65                  70                  75                  80

Arg Phe Pro Gln Met Leu Glu Gly Ala Arg Gly Leu Val Asn Gln Leu
                85                  90                  95

Ile Gln Phe Gly Ser Ser Leu Leu Gly Tyr Ser Glu Arg Gln Asp Ala
                100                 105                 110

Glu Ala Met Ser Gln Leu Leu Gln Thr Gln Ala Ser Glu Leu Ile Leu
                115                 120                 125

Thr Ser Ile Arg Met Gln Asp Asn Gln Leu Ala Glu Leu Asp Ser Glu
                130                 135                 140

Lys Thr Ala Leu Gln Val Ser Leu Ala Gly Val Gln Gln Arg Phe Asp
145                 150                 155                 160

Ser Tyr Ser Gln Leu Tyr Glu Glu Asn Ile Asn Ala Gly Glu Gln Arg
                165                 170                 175

Ala Leu Ala Leu Arg Ser Glu Ser Ala Ile Glu Ser Gln Gly Ala Gln
                180                 185                 190

Ile Ser Arg Met Ala Gly Ala Val Asp Met Ala Pro Asn Ile Phe
                195                 200                 205

Gly Leu Ala Asp Gly Gly Met His Tyr Gly Ala Ile Ala Tyr Ala Ile
        210                 215                 220

Ala Asp Gly Ile Glu Leu Ser Ala Ser Ala Lys Met Val Asp Ala Glu
225                 230                 235                 240

Lys Val Ala Gln Ser Glu Ile Tyr Arg Arg Arg Gln Glu Trp Lys
                245                 250                 255

Ile Gln Arg Asp Asn Ala Gln Ala Glu Ile Asn Gln Leu Asn Ala Gln
```

```
                  260                 265                 270
Leu Glu Ser Leu Ser Ile Arg Arg Glu Ala Ala Glu Met Gln Lys Glu
            275                 280                 285

Tyr Leu Lys Thr Gln Gln Ala Gln Ala Gln Ala Gln Leu Thr Phe Leu
    290                 295                 300

Arg Ser Lys Phe Ser Asn Gln Ala Leu Tyr Ser Trp Leu Arg Gly Arg
305                 310                 315                 320

Leu Ser Gly Ile Tyr Phe Gln Phe Tyr Asp Leu Ala Val Ser Arg Cys
                325                 330                 335

Leu Met Ala Glu Gln Ser Tyr Gln Trp Glu Ala Asn Asp Asn Ser Ile
            340                 345                 350

Ser Phe Val Lys Pro Gly Ala Trp Gln Gly Thr Tyr Ala Gly Leu Leu
    355                 360                 365

Cys Gly Glu Ala Leu Ile Gln Asn Leu Ala Gln Met Glu Glu Ala Tyr
370                 375                 380

Leu Lys Trp Glu Ser Arg Ala Leu Glu Val Glu Arg Thr Val Ser Leu
385                 390                 395                 400

Ala Val Val Tyr Asp Ser Leu Glu Gly Asn Asp Arg Phe Asn Leu Ala
                405                 410                 415

Glu Gln Ile Pro Ala Leu Leu Asp Lys Gly Glu Gly Thr Ala Gly Thr
            420                 425                 430

Lys Glu Asn Gly Leu Ser Leu Ala Asn Ala Ile Leu Ser Ala Ser Val
    435                 440                 445

Lys Leu Ser Asp Leu Lys Leu Gly Thr Asp Tyr Pro Asp Ser Ile Val
    450                 455                 460

Gly Ser Asn Lys Val Arg Arg Ile Lys Gln Ile Ser Val Ser Leu Pro
465                 470                 475                 480

Ala Leu Val Gly Pro Tyr Gln Asp Val Gln Ala Met Leu Ser Tyr Gly
                485                 490                 495

Gly Ser Thr Gln Leu Pro Lys Gly Cys Ser Ala Leu Ala Val Ser His
            500                 505                 510

Gly Thr Asn Asp Ser Gly Gln Phe Gln Leu Asp Phe Asn Asp Gly Lys
    515                 520                 525

Tyr Leu Pro Phe Glu Gly Ile Ala Leu Asp Asp Gln Gly Thr Leu Asn
    530                 535                 540

Leu Gln Phe Pro Asn Ala Thr Asp Lys Gln Lys Ala Ile Leu Gln Thr
545                 550                 555                 560

Met Ser Asp Ile Ile Leu His Ile Arg Tyr Thr Ile Arg
                565                 570

(2) INFORMATION FOR SEQ ID NO:56:

(i) SEQUENCE CHARACTERISTICS:
        (A) LENGTH: 2994 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:56:

ATG AAT CAA CTC GCC AGT CCC CTG ATT TCC CGC ACC GAA GAG ATC CAC    48
Met Asn Gln Leu Ala Ser Pro Leu Ile Ser Arg Thr Glu Glu Ile His
1               5                   10                  15

AAC TTA CCC GGT AAA TTG ACC GAT CTT GGT TAT ACC TCA GTG TTT GAT    96
Asn Leu Pro Gly Lys Leu Thr Asp Leu Gly Tyr Thr Ser Val Phe Asp
            20                  25                  30
```

```
GTG GTA CGT ATG CCG CGT GAG CGT TTT ATT CGT GAG CAT CGT GCT GAT        144
Val Val Arg Met Pro Arg Glu Arg Phe Ile Arg Glu His Arg Ala Asp
        35                  40                  45

CTC GGG CGC AGT GCT GAA AAA ATG TAT GAC CTG GCA GTG GGC TAT GCT        192
Leu Gly Arg Ser Ala Glu Lys Met Tyr Asp Leu Ala Val Gly Tyr Ala
    50                  55                  60

CAT CAG GTG TTA CAC CAT TTT CGC CGT AAT TCT CTT AGT GAA GCT GTT        240
His Gln Val Leu His His Phe Arg Arg Asn Ser Leu Ser Glu Ala Val
65                  70                  75                  80

CAG TTT GGC TTG AGA AGT CCG TTC TCC GTA TCA GGC CCG GAT TAC GCC        288
Gln Phe Gly Leu Arg Ser Pro Phe Ser Val Ser Gly Pro Asp Tyr Ala
                85                  90                  95

AAT CAG TTT CTT GAT GCA AAC ACG GGT TGG AAA GAT AAA GCA CCA AGT        336
Asn Gln Phe Leu Asp Ala Asn Thr Gly Trp Lys Asp Lys Ala Pro Ser
            100                 105                 110

GGA TCA CCG GAA GCC AAT GAT GCG CCG GTA GCC TAT CTG ACT CAT ATT        384
Gly Ser Pro Glu Ala Asn Asp Ala Pro Val Ala Tyr Leu Thr His Ile
        115                 120                 125

TAT CAA TTG GCC CTT GAA CAG GAA AAG AAT GGC GCC ACT ACC ATT ATG        432
Tyr Gln Leu Ala Leu Glu Gln Glu Lys Asn Gly Ala Thr Thr Ile Met
    130                 135                 140

AAT ACG CTG GCG GAG CGT CGC CCC GAT CTG GGT GCT TTG TTA ATT AAT        480
Asn Thr Leu Ala Glu Arg Arg Pro Asp Leu Gly Ala Leu Leu Ile Asn
145                 150                 155                 160

GAT AAA GCA ATC AAT GAG GTG ATA CCG CAA TTG CAG TTG GTC AAT GAA        528
Asp Lys Ala Ile Asn Glu Val Ile Pro Gln Leu Gln Leu Val Asn Glu
                165                 170                 175

ATT CTG TCC AAA GCT ATT CAG AAG AAA CTG AGT TTG ACT GAT CTG GAA        576
Ile Leu Ser Lys Ala Ile Gln Lys Lys Leu Ser Leu Thr Asp Leu Glu
            180                 185                 190

GCG GTA AAC GCC AGA CTT TCC ACT ACC CGT TAC CCG AAT AAT CTG CCG        624
Ala Val Asn Ala Arg Leu Ser Thr Thr Arg Tyr Pro Asn Asn Leu Pro
        195                 200                 205

TAT CAT TAT GGT CAT CAG CAG ATT CAG ACA GCT CAA TCG GTA TTG GGT        672
Tyr His Tyr Gly His Gln Gln Ile Gln Thr Ala Gln Ser Val Leu Gly
    210                 215                 220

ACT ACG TTG CAA GAT ATC ACT TTG CCA CAG ACG CTG GAT CTG CCG CAA        720
Thr Thr Leu Gln Asp Ile Thr Leu Pro Gln Thr Leu Asp Leu Pro Gln
225                 230                 235                 240

AAC TTC TGG GCA ACA GCA AAA GGA AAA CTG AGC GAT ACG ACT GCC AGT        768
Asn Phe Trp Ala Thr Ala Lys Gly Lys Leu Ser Asp Thr Thr Ala Ser
                245                 250                 255

GCT TTG ACC CGA CTG CAA ATC ATG GCG AGT CAG TTT TCG CCA GAG CAG        816
Ala Leu Thr Arg Leu Gln Ile Met Ala Ser Gln Phe Ser Pro Glu Gln
            260                 265                 270

CAG AAA ATC ATT ACG GAG ACT GTC GGT CAG GAT TTC TAT CAG CTT AAC        864
Gln Lys Ile Ile Thr Glu Thr Val Gly Gln Asp Phe Tyr Gln Leu Asn
        275                 280                 286

TAT GGT GAC AGT TCG CTT ACT GTG AAT AGT TTC AGC GAC ATG ACC ATA        912
Tyr Gly Asp Ser Ser Leu Thr Val Asn Ser Phe Ser Asp Met Thr Ile
    290                 295                 300

ATG ACT GAT CGA ACA AGT TTG ACT GTA CCC CAG GTA GAA CTG ATG TTG        960
Met Thr Asp Arg Thr Ser Leu Thr Val Pro Gln Val Glu Leu Met Leu
305                 310                 315                 320

TGT TCA ACT GTC GGA GGT TCT ACG GTT GTT AAG TCT GAT AAT GTG AGT       1008
Cys Ser Thr Val Gly Gly Ser Thr Val Val Lys Ser Asp Asn Val Ser
                325                 330                 335

TCT GGT GAC ACG ACA GCG ACG CCA TTT GCG TAT GGC GCC CGC TTT ATT       1056
Ser Gly Asp Thr Thr Ala Thr Pro Phe Ala Tyr Gly Ala Arg Phe Ile
```

-continued

```
              340                 345                 350
CAT GCC GGT AAG CCG GAG GCG ATT ACC CTG AGT CGC AGT GGT GCG GAG         1104
His Ala Gly Lys Pro Glu Ala Ile Thr Leu Ser Arg Ser Gly Ala Glu
            355                 360                 365

GCG CAT TTT GCT CTG ACG GTT AAC AAT CTG ACA GAT GAC AAG TTG GAC         1152
Ala His Phe Ala Leu Thr Val Asn Asn Leu Thr Asp Asp Lys Leu Asp
        370                 375                 380

CGT ATT AAC CGC ACA GTG CGC CTG CAA AAA TGG CTG AAT CTG CCT TAT         1200
Arg Ile Asn Arg Thr Val Arg Leu Gln Lys Trp Leu Asn Leu Pro Tyr
385                 390                 395                 400

GAG GAT ATT GAC CTG TTA GTG ACT TCT GCT ATG GAT GCG GAA ACA GGA         1248
Glu Asp Ile Asp Leu Leu Val Thr Ser Ala Met Asp Ala Glu Thr Gly
                405                 410                 415

AAT ACC GCG CTG TCG ATG AAC GAC AAT ACG CTG CGT ATG TTG GGA GTG         1296
Asn Thr Ala Leu Ser Met Asn Asp Asn Thr Leu Arg Met Leu Gly Val
            420                 425                 430

TTC AAA CAT TAT CAG GCG AAG TAT GGT GTT AGC GCT AAA CAA TTT GCT         1344
Phe Lys His Tyr Gln Ala Lys Tyr Gly Val Ser Ala Lys Gln Phe Ala
        435                 440                 445

GGC TGG CTG CGC GTA GTG GCC CCG TTT GCC ATT ACA CCG GCA ACG CCG         1392
Gly Trp Leu Arg Val Val Ala Pro Phe Ala Ile Thr Pro Ala Thr Pro
450                 455                 460

TTT TTA GAC CAA GTG TTT AAC TCC GTC GGC ACC TTT GAT ACA CCG TTT         1440
Phe Leu Asp Gln Val Phe Asn Ser Val Gly Thr Phe Asp Thr Pro Phe
465                 470                 475                 480

GTG ATA GAT AAT CAG GAT TTT GTC TAT ACA TTG ACC ACC GGG GGC GAT         1488
Val Ile Asp Asn Gln Asp Phe Val Tyr Thr Leu Thr Thr Gly Gly Asp
                485                 490                 495

GGG GCG CGT GTT AAG CAT ATC AGC ACG GCA CTG GGC CTC AAT CAT CGT         1536
Gly Ala Arg Val Lys His Ile Ser Thr Ala Leu Gly Leu Asn His Arg
            500                 505                 510

CAG TTC CTG TTA TTG GCG GAT AAT ATT GCC CGT CAA CAG GGG AAT GTC         1584
Gln Phe Leu Leu Leu Ala Asp Asn Ile Ala Arg Gln Gln Gly Asn Val
        515                 520                 525

ACG CAA AGC ACA CTC AAC TGT AAT CTG TTT GTG GTG TCA GCT TTC TAC         1632
Thr Gln Ser Thr Leu Asn Cys Asn Leu Phe Val Val Ser Ala Phe Tyr
530                 535                 540

CGT CTG GCT AAT TTG GCG CGC ACA TTG GGG ATA AAT CCA GAG TCT TTC         1680
Arg Leu Ala Asn Leu Ala Arg Thr Leu Gly Ile Asn Pro Glu Ser Phe
545                 550                 555                 560

TGT GCC TTG GTT GAT CGA TTA GAT GCA GGT ACA GGC ATC GTC TGG CAG         1728
Cys Ala Leu Val Asp Arg Leu Asp Ala Gly Thr Gly Ile Val Trp Gln
                565                 570                 575

CAA TTG GCA GGG AAA CCC ACA ATC ACG GTA CCA CAA AAA GAT TCC CCG         1776
Gln Leu Ala Gly Lys Pro Thr Ile Thr Val Pro Gln Lys Asp Ser Pro
            580                 585                 590

CTG GCG GCG GAT ATT CTG AGT TTG CTG CAA GCG CTA AGT GCG ATT GCT         1824
Leu Ala Ala Asp Ile Leu Ser Leu Leu Gln Ala Leu Ser Ala Ile Ala
        595                 600                 605

CAA TGG CAA CAA CAG CAC GAT TTA GAA TTT TCA GCA CTG CTT TTG CTG         1872
Gln Trp Gln Gln Gln His Asp Leu Glu Phe Ser Ala Leu Leu Leu Leu
610                 615                 620

TTG AGT GAC AAC CCT ATT TCT ACC TCG CAG GGC ACT GAC GAT CAA TTG         1920
Leu Ser Asp Asn Pro Ile Ser Thr Ser Gln Gly Thr Asp Asp Gln Leu
625                 630                 635                 640

AAC TTT ATC CGT CAA GTG TGG CAG AAC CTA GGC AGT ACG TTT GTG GGT         1968
Asn Phe Ile Arg Gln Val Trp Gln Asn Leu Gly Ser Thr Phe Val Gly
                645                 650                 655

GCA ACA TTG TTG TCC CGC AGT GGG GCA CCA TTA GTC GAT ACC AAC GGC         2016
```

```
Ala Thr Leu Leu Ser Arg Ser Gly Ala Pro Leu Val Asp Thr Asn Gly
        660                 665                 670

CAC GCT ATT GAC TGG TTT GCT CTG CTC TCA GCA GGT AAT AGT CCG CTT    2064
His Ala Ile Asp Trp Phe Ala Leu Leu Ser Ala Gly Asn Ser Pro Leu
            675                 680                 685

ATC GAT AAG GTT GGT CTG GTG ACT GAT GCT GGC ATA CAA AGT GTT ATA    2112
Ile Asp Lys Val Gly Leu Val Thr Asp Ala Gly Ile Gln Ser Val Ile
    690                 695                 700

GCA ACG GTG GTC AAT ACA CAA AGC TTA TCT GAT GAA GAT AAG AAG CTG    2160
Ala Thr Val Val Asn Thr Gln Ser Leu Ser Asp Glu Asp Lys Lys Leu
705                 710                 715                 720

GCA ATC ACT ACT CTG ACT AAT ACG TTG AAT CAG GTA CAG AAA ACT CAA    2208
Ala Ile Thr Thr Leu Thr Asn Thr Leu Asn Gln Val Gln Lys Thr Gln
                725                 730                 735

CAG GGC GTG GCC GTC AGT CTG TTG GCG CAG ACT CTG AAC GTG AGT CAG    2256
Gln Gly Val Ala Val Ser Leu Leu Ala Gln Thr Leu Asn Val Ser Gln
            740                 745                 750

TCA CTG CCT GCG TTA TTG TTG CGC TGG AGT GGA CAA ACA ACC TAC CAG    2304
Ser Leu Pro Ala Leu Leu Leu Arg Trp Ser Gly Gln Thr Thr Tyr Gln
        755                 760                 765

TGG TTG AGT GCG ACT TGG GCA TTG AAG GAT GCC GTT AAG ACT GCC GCC    2352
Trp Leu Ser Ala Thr Trp Ala Leu Lys Asp Ala Val Lys Thr Ala Ala
    770                 775                 780

GAT ATT CCC GCT GAC TAT CTG CGT CAA TTA CGT GAA GTG GTA CGC CGC    2400
Asp Ile Pro Ala Asp Tyr Leu Arg Gln Leu Arg Glu Val Val Arg Arg
785                 790                 795                 800

TCC TTG TTG ACC CAA CAA TTC ACG CTG AGT CCT GCA ATG GTG CAA ACC    2448
Ser Leu Leu Thr Gln Gln Phe Thr Leu Ser Pro Ala Met Val Gln Thr
                805                 810                 815

TTG CTG GAC TAT CCA GCC TAT TTT GGC GCT TCC GCA GAA ACA GTG ACC    2496
Leu Leu Asp Tyr Pro Ala Tyr Phe Gly Ala Ser Ala Glu Thr Val Thr
            820                 825                 830

GAT ATC AGT TTG TGG ATG CTT TAT ACC CTG AGC TGT TAT AGC GAT TTA    2544
Asp Ile Ser Leu Trp Met Leu Tyr Thr Leu Ser Cys Tyr Ser Asp Leu
        835                 840                 845

TTG CTC CAA ATG GGT GAA GCT GGT GGT ACC GAA GAT GAT GTA CTG GCC    2592
Leu Leu Gln Met Gly Glu Ala Gly Gly Thr Glu Asp Asp Val Leu Ala
    850                 855                 860

TAC TTA CGC ACA GCT AAT GCT ACC ACA CCG TTG AGC CAA TCT GAT GCT    2640
Tyr Leu Arg Thr Ala Asn Ala Thr Thr Pro Leu Ser Gln Ser Asp Ala
865                 870                 875                 880

GCA CAG ACG TTG GCA ACG CTA TTG GGT TGG GAG GTT AAC GAG TTG CAA    2688
Ala Gln Thr Leu Ala Thr Leu Leu Gly Trp Glu Val Asn Glu Leu Gln
                885                 890                 895

GCC GCT TGG TCG GTA TTG GGC GGG ATT GCC AAA ACC ACA CCG CAA CTG    2736
Ala Ala Trp Ser Val Leu Gly Gly Ile Ala Lys Thr Thr Pro Gln Leu
            900                 905                 910

GAT GCG CTT CTG CGT TTG CAA CAG GCA CAG AAC CAA ACT GGT CTT GGC    2784
Asp Ala Leu Leu Arg Leu Gln Gln Ala Gln Asn Gln Thr Gly Leu Gly
        915                 920                 925

GTT ACA CAG CAA CAG CAA GGC TAT CTC CTG AGT CGT GAC AGT GAT TAT    2832
Val Thr Gln Gln Gln Gln Gly Tyr Leu Leu Ser Arg Asp Ser Asp Tyr
    930                 935                 940

ACC CTT TGG CAA AGC ACC GGT CAG GCG CTG GTG GCT GGC GTA TCC CAT    2880
Thr Leu Trp Gln Ser Thr Gly Gln Ala Leu Val Ala Gly Val Ser His
945                 950                 955                 960

GTC AAG GGC AGT AAC TGA GCATGGCAGA GCTCACTACC TGAGTGGATT TGATTT     2934
Val Lys Gly Ser Asn
                965
```

TTCCGTATGG CCTAATGAGG CTATTTCTAA ACCGCCATTT AAGTAAGGCA GATAATTATG    2994

(2) INFORMATION FOR SEQ ID NO:57:

(i) SEQUENCE CHARACTERISTICS:
        (A) LENGTH: 965 amino acids
        (B) TYPE: amino acid
        (D) TOPOLOGY: linear (ii) MOLECULE TYPE: protein (xi) SEQUENCE DESCRIPTION: SEQ ID NO:57:

```
Met Asn Gln Leu Ala Ser Pro Leu Ile Ser Arg Thr Glu Glu Ile His
 1               5                  10                  15

Asn Leu Pro Gly Lys Leu Thr Asp Leu Gly Tyr Thr Ser Val Phe Asp
            20                  25                  30

Val Val Arg Met Pro Arg Glu Arg Phe Ile Arg Glu His Arg Ala Asp
        35                  40                  45

Leu Gly Arg Ser Ala Glu Lys Met Tyr Asp Leu Ala Val Gly Tyr Ala
    50                  55                  60

His Gln Val Leu His His Phe Arg Arg Asn Ser Leu Ser Glu Ala Val
65                  70                  75                  80

Gln Phe Gly Leu Arg Ser Pro Phe Ser Val Ser Gly Pro Asp Tyr Ala
                85                  90                  95

Asn Gln Phe Leu Asp Ala Asn Thr Gly Trp Lys Asp Lys Ala Pro Ser
            100                 105                 110

Gly Ser Pro Glu Ala Asn Asp Ala Pro Val Ala Tyr Leu Thr His Ile
        115                 120                 125

Tyr Gln Leu Ala Leu Glu Gln Glu Lys Asn Gly Ala Thr Thr Ile Met
    130                 135                 140

Asn Thr Leu Ala Glu Arg Arg Pro Asp Leu Gly Ala Leu Leu Ile Asn
145                 150                 155                 160

Asp Lys Ala Ile Asn Glu Val Ile Pro Gln Leu Gln Leu Val Asn Glu
                165                 170                 175

Ile Leu Ser Lys Ala Ile Gln Lys Lys Leu Ser Leu Thr Asp Leu Glu
            180                 185                 190

Ala Val Asn Ala Arg Leu Ser Thr Thr Arg Tyr Pro Asn Asn Leu Pro
        195                 200                 205

Tyr His Tyr Gly His Gln Gln Ile Gln Thr Ala Gln Ser Val Leu Gly
    210                 215                 220

Thr Thr Leu Gln Asp Ile Thr Leu Pro Gln Thr Leu Asp Leu Pro Gln
225                 230                 235                 240

Asn Phe Trp Ala Thr Ala Lys Gly Lys Leu Ser Asp Thr Thr Ala Ser
                245                 250                 255

Ala Leu Thr Arg Leu Gln Ile Met Ala Ser Gln Phe Ser Pro Glu Gln
            260                 265                 270

Gln Lys Ile Ile Thr Glu Thr Val Gly Gln Asp Phe Tyr Gln Leu Asn
        275                 280                 286

Tyr Gly Asp Ser Ser Leu Thr Val Asn Ser Phe Ser Asp Met Thr Ile
    290                 295                 300

Met Thr Asp Arg Thr Ser Leu Thr Val Pro Gln Val Glu Leu Met Leu
305                 310                 315                 320

Cys Ser Thr Val Gly Gly Ser Thr Val Val Lys Ser Asp Asn Val Ser
                325                 330                 335

Ser Gly Asp Thr Thr Ala Thr Pro Phe Ala Tyr Gly Ala Arg Phe Ile
            340                 345                 350
```

-continued

```
His Ala Gly Lys Pro Glu Ala Ile Thr Leu Ser Arg Ser Gly Ala Glu
        355                 360                 365

Ala His Phe Ala Leu Thr Val Asn Asn Leu Thr Asp Asp Lys Leu Asp
    370                 375                 380

Arg Ile Asn Arg Thr Val Arg Leu Gln Lys Trp Leu Asn Leu Pro Tyr
385                 390                 395                 400

Glu Asp Ile Asp Leu Leu Val Thr Ser Ala Met Asp Ala Glu Thr Gly
                405                 410                 415

Asn Thr Ala Leu Ser Met Asn Asp Asn Thr Leu Arg Met Leu Gly Val
            420                 425                 430

Phe Lys His Tyr Gln Ala Lys Tyr Gly Val Ser Ala Lys Gln Phe Ala
        435                 440                 445

Gly Trp Leu Arg Val Val Ala Pro Phe Ala Ile Thr Pro Ala Thr Pro
    450                 455                 460

Phe Leu Asp Gln Val Phe Asn Ser Val Gly Thr Phe Asp Thr Pro Phe
465                 470                 475                 480

Val Ile Asp Asn Gln Asp Phe Val Tyr Thr Leu Thr Thr Gly Gly Asp
                485                 490                 495

Gly Ala Arg Val Lys His Ile Ser Thr Ala Leu Gly Leu Asn His Arg
            500                 505                 510

Gln Phe Leu Leu Leu Ala Asp Asn Ile Ala Arg Gln Gln Gly Asn Val
        515                 520                 525

Thr Gln Ser Thr Leu Asn Cys Asn Leu Phe Val Val Ser Ala Phe Tyr
    530                 535                 540

Arg Leu Ala Asn Leu Ala Arg Thr Leu Gly Ile Asn Pro Glu Ser Phe
545                 550                 555                 560

Cys Ala Leu Val Asp Arg Leu Asp Ala Gly Thr Gly Ile Val Trp Gln
                565                 570                 575

Gln Leu Ala Gly Lys Pro Thr Ile Thr Val Pro Gln Lys Asp Ser Pro
            580                 585                 590

Leu Ala Ala Asp Ile Leu Ser Leu Leu Gln Ala Leu Ser Ala Ile Ala
        595                 600                 605

Gln Trp Gln Gln Gln His Asp Leu Glu Phe Ser Ala Leu Leu Leu Leu
    610                 615                 620

Leu Ser Asp Asn Pro Ile Ser Thr Ser Gln Gly Thr Asp Asp Gln Leu
625                 630                 635                 640

Asn Phe Ile Arg Gln Val Trp Gln Asn Leu Gly Ser Thr Phe Val Gly
                645                 650                 655

Ala Thr Leu Leu Ser Arg Ser Gly Ala Pro Leu Val Asp Thr Asn Gly
            660                 665                 670

His Ala Ile Asp Trp Phe Ala Leu Leu Ser Ala Gly Asn Ser Pro Leu
        675                 680                 685

Ile Asp Lys Val Gly Leu Val Thr Asp Ala Gly Ile Gln Ser Val Ile
    690                 695                 700

Ala Thr Val Val Asn Thr Gln Ser Leu Ser Asp Glu Asp Lys Lys Leu
705                 710                 715                 720

Ala Ile Thr Thr Leu Thr Asn Thr Leu Asn Gln Val Gln Lys Thr Gln
                725                 730                 735

Gln Gly Val Ala Val Ser Leu Leu Ala Gln Thr Leu Asn Val Ser Gln
            740                 745                 750

Ser Leu Pro Ala Leu Leu Leu Arg Trp Ser Gly Gln Thr Thr Tyr Gln
        755                 760                 765
```

```
Trp Leu Ser Ala Thr Trp Ala Leu Lys Asp Ala Val Lys Thr Ala Ala
    770                 775                 780

Asp Ile Pro Ala Asp Tyr Leu Arg Gln Leu Arg Glu Val Val Arg Arg
785                 790                 795                 800

Ser Leu Leu Thr Gln Gln Phe Thr Leu Ser Pro Ala Met Val Gln Thr
                805                 810                 815

Leu Leu Asp Tyr Pro Ala Tyr Phe Gly Ala Ser Ala Glu Thr Val Thr
            820                 825                 830

Asp Ile Ser Leu Trp Met Leu Tyr Thr Leu Ser Cys Tyr Ser Asp Leu
            835                 840                 845

Leu Leu Gln Met Gly Glu Ala Gly Thr Glu Asp Asp Val Leu Ala
    850                 855                 860

Tyr Leu Arg Thr Ala Asn Ala Thr Thr Pro Leu Ser Gln Ser Asp Ala
865                 870                 875                 880

Ala Gln Thr Leu Ala Thr Leu Leu Gly Trp Glu Val Asn Glu Leu Gln
                885                 890                 895

Ala Ala Trp Ser Val Leu Gly Gly Ile Ala Lys Thr Thr Pro Gln Leu
                900                 905                 910

Asp Ala Leu Leu Arg Leu Gln Gln Ala Gln Asn Gln Thr Gly Leu Gly
            915                 920                 925

Val Thr Gln Gln Gln Gly Tyr Leu Leu Ser Arg Asp Ser Asp Tyr
    930                 935                 940

Thr Leu Trp Gln Ser Thr Gly Gln Ala Leu Val Ala Gly Val Ser His
945                 950                 955                 960

Val Lys Gly Ser Asn
                965

(2) INFORMATION FOR SEQ ID NO:58:

(i) SEQUENCE CHARACTERISTICS:
        (A) LENGTH:  4832 base pairs
        (B) TYPE: nucleic acid
        (C) STRANDEDNESS: double
        (D) TOPOLOGY: linear (ii) MOLECULE TYPE:  DNA (genomic)

(xi) SEQUENCE DESCRIPTION: SEQ ID NO:58:

ATG TTA TCG ACA ATG GAA AAA CAA CTG AAT GAA TCC CAG CGT GAT GCG         48
Met Leu Ser Thr Met Glu Lys Gln Leu Asn Glu Ser Gln Arg Asp Ala
1               5                   10                  15

TTG GTG ACT GGC TAT ATG AAT TTT GTG GCG CCG ACG TTG AAA GGC GTC         96
Leu Val Thr Gly Tyr Met Asn Phe Val Ala Pro Thr Leu Lys Gly Val
                20                  25                  30

AGT GGT CAG CCG GTG ACG GTG GAA GAT TTA TAC GAA TAT TTG CTG ATT        144
Ser Gly Gln Pro Val Thr Val Glu Asp Leu Tyr Glu Tyr Leu Leu Ile
            35                  40                  45

GAC CCG GAA GTG GCT GAT GAG GTT GAG ACG AGT CGG GTA GCA CAA GCG        192
Asp Pro Glu Val Ala Asp Glu Val Glu Thr Ser Arg Val Ala Gln Ala
50                  55                  60

ATT GCC AGC ATA CAG CAA TAT ATG ACT CGT CTG GTC AAC GGC TCT GAA        240
Ile Ala Ser Ile Gln Gln Tyr Met Thr Arg Leu Val Asn Gly Ser Glu
65                  70                  75                  80

CCG GGG CGT CAG GCG ATG GAG CCT TCT ACA GCT AAC GAA TGG CGT GAT        288
Pro Gly Arg Gln Ala Met Glu Pro Ser Thr Ala Asn Glu Trp Arg Asp
                85                  90                  95

AAT GAT AAC CAA TAT GCT ATC TGG GCT GCG GGG GCT GAG GTT CGA AAT        336
Asn Asp Asn Gln Tyr Ala Ile Trp Ala Ala Gly Ala Glu Val Arg Asn
                100                 105                 110
```

```
TAC GCT GAA AAC TAT ATT TCA CCC ATC ACC CGG CAG GAA AAA AGC CAT      384
Tyr Ala Glu Asn Tyr Ile Ser Pro Ile Thr Arg Gln Glu Lys Ser His
            115                 120                 125

TAT TTC TCG GAG CTG GAG ACG ACT TTA AAT CAG AAT CGA CTC GAT CCG      432
Tyr Phe Ser Glu Leu Glu Thr Thr Leu Asn Gln Asn Arg Leu Asp Pro
            130                 135                 140

GAT CGT GTG CAG GAT GCT GTT TTG GCG TAT CTC AAT GAG TTT GAG GCA      480
Asp Arg Val Gln Asp Ala Val Leu Ala Tyr Leu Asn Glu Phe Glu Ala
145                 150                 155                 160

GTG AGT AAT CTA TAT GTG CTC AGT GGT TAT ATT AAT CAG GAT AAA TTT      528
Val Ser Asn Leu Tyr Val Leu Ser Gly Tyr Ile Asn Gln Asp Lys Phe
                165                 170                 175

GAC CAA GCT ATC TAC TAC TTT ATT GGT CGC ACT ACC ACT AAA CCG TAT      576
Asp Gln Ala Ile Tyr Tyr Phe Ile Gly Arg Thr Thr Thr Lys Pro Tyr
            180                 185                 190

CGC TAC TAC TGG CGT CAG ATG GAT TTG AGT AAG AAC CGT CAA GAT CCG      624
Arg Tyr Tyr Trp Arg Gln Met Asp Leu Ser Lys Asn Arg Gln Asp Pro
            195                 200                 205

GCA GGG AAT CCG GTG ACG CCA AAT TGC TGG AAT GAT TGG CAG GAA ATC      672
Ala Gly Asn Pro Val Thr Pro Asn Cys Trp Asn Asp Trp Gln Glu Ile
            210                 215                 220

ACT TTG CCG CTG TCT GGT GAT ACG GTG CTG GAG CAT ACA GTT CGC CCG      720
Thr Leu Pro Leu Ser Gly Asp Thr Val Leu Glu His Thr Val Arg Pro
225                 230                 235                 240

GTA TTT TAT AAT GAT CGA CTA TAT GTG GCT TGG GTT GAG CGT GAC CCG      768
Val Phe Tyr Asn Asp Arg Leu Tyr Val Ala Trp Val Glu Arg Asp Pro
                245                 250                 255

GCA GTA CAG AAG GAT GCT GAC GGT AAA AAC ATC GGT AAA ACC CAT GCC      816
Ala Val Gln Lys Asp Ala Asp Gly Lys Asn Ile Gly Lys Thr His Ala
            260                 265                 270

TAC AAC ATA AAG TTT GGT TAT AAA CGT TAT GAT GAT ACT TGG ACA GCG      864
Tyr Asn Ile Lys Phe Gly Tyr Lys Arg Tyr Asp Asp Thr Trp Thr Ala
            275                 280                 285

CCG AAT ACG ACC ACG TTA ATG ACA CAA CAA GCA GGG GAA AGT TCA GAA      912
Pro Asn Thr Thr Thr Leu Met Thr Gln Gln Ala Gly Glu Ser Ser Glu
290                 295                 300

ACA CAG CGA TCC AGC CTG CTG ATT GAT GAA TCT AGC ACC ACA TTG CGC      960
Thr Gln Arg Ser Ser Leu Leu Ile Asp Glu Ser Ser Thr Thr Leu Arg
305                 310                 315                 320

CAA GTT AAT CTG TTG GCT ACC ACC GAT TTT AGT ATC GAT CCG ACG GAG     1008
Gln Val Asn Leu Leu Ala Thr Thr Asp Phe Ser Ile Asp Pro Thr Glu
                325                 330                 335

GAA ACG GAC AGT AAC CCG TAT GGC CGC CTA ATG TTG GGG GTG TTT GTC     1056
Glu Thr Asp Ser Asn Pro Tyr Gly Arg Leu Met Leu Gly Val Phe Val
            340                 345                 350

CGT CAA TTT GAA GGT GAT GGG GCC AAT AGA AAA AAT AAA CCC GTT GTT     1104
Arg Gln Phe Glu Gly Asp Gly Ala Asn Arg Lys Asn Lys Pro Val Val
            355                 360                 365

TAT GGT TAT CTC TAT TGT GAC TCA GCT TTC AAT CGT CAT GTT CTC AGG     1152
Tyr Gly Tyr Leu Tyr Cys Asp Ser Ala Phe Asn Arg His Val Leu Arg
370                 375                 380

CCG TTA AGT AAG AAC TTT TTG TTC AGT ACT TAC CGT GAT GAA ACG GAT     1200
Pro Leu Ser Lys Asn Phe Leu Phe Ser Thr Tyr Arg Asp Glu Thr Asp
385                 390                 395                 400

GGT CAA AAC AGC TTG CAA TTT GCG GTA TAC GAT AAA AAG TAT GTA ATT     1248
Gly Gln Asn Ser Leu Gln Phe Ala Val Tyr Asp Lys Lys Tyr Val Ile
                405                 410                 415

ACT AAG GTT GTT ACA GGT GCA ACG GAA GAT CCC GAA AAT ACA GGA TGG     1296
Thr Lys Val Val Thr Gly Ala Thr Glu Asp Pro Glu Asn Thr Gly Trp
```

```
                420             425             430
GTA AGT AAA GTT GAT GAC TTG AAA CAA GGC ACT ACT GGG GCC TAT GTG    1344
Val Ser Lys Val Asp Asp Leu Lys Gln Gly Thr Thr Gly Ala Tyr Val
        435             440             445

TAT ATC GAT CAA GAT GGC CTG ACG CTT CAT ATA CAA ACC ACA ACT AAT    1392
Tyr Ile Asp Gln Asp Gly Leu Thr Leu His Ile Gln Thr Thr Thr Asn
    450             455             460

GGG GAT TTT ATT AAC CGT CAT ACG TTT GGA TAT AAC GAT CTT GTA TAT    1440
Gly Asp Phe Ile Asn Arg His Thr Phe Gly Tyr Asn Asp Leu Val Tyr
465             470             475             480

GAT TCT AAG TCT GGT TAT GGT TTC ACG TGG TCA GGA AAT GAA GGT TTT    1488
Asp Ser Lys Ser Gly Tyr Gly Phe Thr Trp Ser Gly Asn Glu Gly Phe
        485             490             495

TAT CTG GAT TAC CAT GAT GGA AAT TAT TAC ACC TTT CAT AAT GCA ATA    1536
Tyr Leu Asp Tyr His Asp Gly Asn Tyr Tyr Thr Phe His Asn Ala Ile
        500             505             510

ATC AAC TAC TAT CCG TCT GGA TAT GGT GGT GGA TCT GTT CCT AAT GGA    1584
Ile Asn Tyr Tyr Pro Ser Gly Tyr Gly Gly Gly Ser Val Pro Asn Gly
        515             520             525

ACG TGG GCG TTA GAG CAA AGG ATT AAT GAG GGA TGG GCT ATT GCT CCC    1632
Thr Trp Ala Leu Glu Gln Arg Ile Asn Glu Gly Trp Ala Ile Ala Pro
        530             535             540

CTG CTT GAT ACT CTC CAT ACT GTT ACT GTG AAG GGC AGT TAT ATC GCT    1680
Leu Leu Asp Thr Leu His Thr Val Thr Val Lys Gly Ser Tyr Ile Ala
545             550             555             560

TGG GAA GGG GAA ACA CCT ACC GGT TAT AAT CTG TAT ATT CCA GAT GGT    1728
Trp Glu Gly Glu Thr Pro Thr Gly Tyr Asn Leu Tyr Ile Pro Asp Gly
        565             570             575

ACC GTG TTG CTA GAT TGG TTT GAT AAA ATA AAT TTT GCT ATT GGT CTT    1776
Thr Val Leu Leu Asp Trp Phe Asp Lys Ile Asn Phe Ala Ile Gly Leu
        580             585             590

AAT AAG CTT GAG TCT GTA TTT ACG TCG CCA GAT TGG CCA ACA CTA ACC    1824
Asn Lys Leu Glu Ser Val Phe Thr Ser Pro Asp Trp Pro Thr Leu Thr
        595             600             605

ACT ATC AAA AAT TTC AGT AAA ATC GCC GAT AAC CGC AAA TTC TAT CAG    1872
Thr Ile Lys Asn Phe Ser Lys Ile Ala Asp Asn Arg Lys Phe Tyr Gln
610             615             620

GAA ATC AAT GCT GAG ACG GCG GAT GGA CGC AAC CTG TTT AAA CGT TAC    1920
Glu Ile Asn Ala Glu Thr Ala Asp Gly Arg Asn Leu Phe Lys Arg Tyr
625             630             635             640

AGT ACT CAA ACT TTC GGA CTT ACC AGC GGT GCG ACT TAT TCT ACA ACT    1968
Ser Thr Gln Thr Phe Gly Leu Thr Ser Gly Ala Thr Tyr Ser Thr Thr
        645             650             655

TAT ACT TTG TCT GAG GCG GAT TTC TCC ACT GAT CCG GAC AAA AAC TAC    2016
Tyr Thr Leu Ser Glu Ala Asp Phe Ser Thr Asp Pro Asp Lys Asn Tyr
        660             665             670

CTA CAG GTT TGT TTG AAT GTC GTG TGG GAT CAT TAT GAC CGC CCG TCA    2064
Leu Gln Val Cys Leu Asn Val Val Trp Asp His Tyr Asp Arg Pro Ser
        675             680             685

GGG AAA AAA GGG GCT TAT TCT TGG GTC AGT AAG TGG TTT AAC GTC TAT    2112
Gly Lys Lys Gly Ala Tyr Ser Trp Val Ser Lys Trp Phe Asn Val Tyr
        690             695             700

GTT GCG TTG CAA GAT AGC AAA GCT CCG GAT GCC ATT CCT CGA TTA GTT    2160
Val Ala Leu Gln Asp Ser Lys Ala Pro Asp Ala Ile Pro Arg Leu Val
705             710             715             720

TCC CGT TAC GAT AGT AAA CGT GGT CTG GTG CAA TAT CTG GAC TTC TGG    2208
Ser Arg Tyr Asp Ser Lys Arg Gly Leu Val Gln Tyr Leu Asp Phe Trp
        725             730             735

ACC TCA TCA TTA CCC GCG AAA ACC CGT CTT AAC ACC ACC TTT GTG CGT    2256
```

```
                                                              -continued

Thr Ser Ser Leu Pro Ala Lys Thr Arg Leu Asn Thr Thr Phe Val Arg
        740                 745                 750

ACT TTG ATT GAG AAG GCT AAT CTG GGG CTG GAT AGT TTG CTG GAT TAC       2304
Thr Leu Ile Glu Lys Ala Asn Leu Gly Leu Asp Ser Leu Leu Asp Tyr
            755                 760                 765

ACC TTG CAG GCA GAT CCT TCT CTG GAA GCA GAT TTA GTG ACT GAC GGC       2352
Thr Leu Gln Ala Asp Pro Ser Leu Glu Ala Asp Leu Val Thr Asp Gly
770                 775                 780

AAA AGC GAA CCA ATG GAC TTT AAT GGT TCA AAC GGT CTC TAT TTC TGG       2400
Lys Ser Glu Pro Met Asp Phe Asn Gly Ser Asn Gly Leu Tyr Phe Trp
785                 790                 795                 800

GAA TTG TTC TTT CAC CTG CCG TTT TTG GTT GCT ACA CGC TTT GCC AAC       2448
Glu Leu Phe Phe His Leu Pro Phe Leu Val Ala Thr Arg Phe Ala Asn
                805                 810                 815

GAA CAG CAA TTT TCG CCG GCA CAA AAG AGT TTG CAT TAC ATC TTT GAC       2496
Glu Gln Gln Phe Ser Pro Ala Gln Lys Ser Leu His Tyr Ile Phe Asp
                    820                 825                 830

CCG GCG ATG AAA AAC AAG CCA CAC AAT GCC CCG GCT TAT TGG AAT GTA       2544
Pro Ala Met Lys Asn Lys Pro His Asn Ala Pro Ala Tyr Trp Asn Val
                835                 840                 845

CGT CCG TTG GTT GAA GGA AAC AGC GAT TTG TCA CGT CAT TTG GAC GAT       2592
Arg Pro Leu Val Glu Gly Asn Ser Asp Leu Ser Arg His Leu Asp Asp
        850                 855                 860

TCT ATA GAC CCA GAT ACT CAA GCT TAT GCT CAT CCG GTG ATA TAC CAG       2640
Ser Ile Asp Pro Asp Thr Gln Ala Tyr Ala His Pro Val Ile Tyr Gln
865                 870                 875                 880

AAA GCG GTG TTT ATT GCC TAT GTC AGT AAC CTG ATT GCT CAG GGA GAT       2688
Lys Ala Val Phe Ile Ala Tyr Val Ser Asn Leu Ile Ala Gln Gly Asp
                885                 890                 895

ATG TGG TAT CGC CAA TTG ACT CGT GAC GGT CTG ACT CAG GCC CGT GTC       2736
Met Trp Tyr Arg Gln Leu Thr Arg Asp Gly Leu Thr Gln Ala Arg Val
                900                 905                 910

TAT TAC AAT CTG GCC GCT GAA TTG CTA GGG CCT CGT CCG GAT GTA TCG       2784
Tyr Tyr Asn Leu Ala Ala Glu Leu Leu Gly Pro Arg Pro Asp Val Ser
            915                 920                 925

CTG AGT AGC ATT TGG ACG CCG CAA ACC CTG GAT ACC TTA GCA GCC GGG       2832
Leu Ser Ser Ile Trp Thr Pro Gln Thr Leu Asp Thr Leu Ala Ala Gly
        930                 935                 940

CAA AAA GCG GTT TTA CGT GAT TTT GAG CAC CAG TTG GCT AAT AGT GAT       2880
Gln Lys Ala Val Leu Arg Asp Phe Glu His Gln Leu Ala Asn Ser Asp
945                 950                 955                 960

ACC GCT TTA CCC GCA TTG CCG GGC CGC AAT GTC AGC TAC TTG AAA CTG       2928
Thr Ala Leu Pro Ala Leu Pro Gly Arg Asn Val Ser Tyr Leu Lys Leu
                965                 970                 975

GCA GAT AAT GGC TAC TTT AAT GAA CCG CTC AAT GTT CTG ATG TTG TCT       2976
Ala Asp Asn Gly Tyr Phe Asn Glu Pro Leu Asn Val Leu Met Leu Ser
                980                 985                 990

CAC TGG GAT ACG TTG GAT GCA CGG TTA TAC AAT CTG CGT CAT AAC CTG       3024
His Trp Asp Thr Leu Asp Ala Arg Leu Tyr Asn Leu Arg His Asn Leu
            995                 1000                1005

ACC GTT GAT GGC AAG CCG CTT TCG CTG CCG CTG TAT GCT GCG CCT GTT       3072
Thr Val Asp Gly Lys Pro Leu Ser Leu Pro Leu Tyr Ala Ala Pro Val
        1010                1015                1020

GAT CCG GTA GCG TTG TTG GCT CAG CGT GCT CAG TCC GGC ACG TTG ACG       3120
Asp Pro Val Ala Leu Leu Ala Gln Arg Ala Gln Ser Gly Thr Leu Thr
1025                1030                1035                1040

AAT GGC GTC AGT GGC GCC ATG TTG ACG GTG CCG CCA TAC CGT TTC AGC       3168
Asn Gly Val Ser Gly Ala Met Leu Thr Val Pro Pro Tyr Arg Phe Ser
                1045                1050                1055
```

```
GCT ATG TTG CCG CGA GCT TAC AGC GCC GTG GGT ACG TTG ACC AGT TTT      3216
Ala Met Leu Pro Arg Ala Tyr Ser Ala Val Gly Thr Leu Thr Ser Phe
        1060                1065                1070

GGT CAG AAC CTG CTT AGT TTG TTG GAA CGT AGC GAA CGA GCC TGT CAA      3264
Gly Gln Asn Leu Leu Ser Leu Leu Glu Arg Ser Glu Arg Ala Cys Gln
        1075                1080                1085

GAA GAG TTG GCG CAA CAG CAA CTG TTG GAT ATG TCC AGC TAT GCC ATC      3312
Glu Glu Leu Ala Gln Gln Gln Leu Leu Asp Met Ser Ser Tyr Ala Ile
        1090                1095                1100

ACG TTG CAA CAA CAG GCG CTG GAT GGA TTG GCG GCA GAT CGT CTG GCG      3360
Thr Leu Gln Gln Gln Ala Leu Asp Gly Leu Ala Ala Asp Arg Leu Ala
1105                1110                1115                1120

CTG CTA GCT AGT CAG GCT ACG GCA CAA CAG CGT CAT GAC CAT TAT TAC      3408
Leu Leu Ala Ser Gln Ala Thr Ala Gln Gln Arg His Asp His Tyr Tyr
            1125                1130                1135

ACT CTG TAT CAG AAC AAC ATC TCC AGT GCG GAA CAA CTG GTG ATG GAC      3456
Thr Leu Tyr Gln Asn Asn Ile Ser Ser Ala Glu Gln Leu Val Met Asp
        1140                1145                1150

ACC CAA ACG TCA GCA CAA TCC CTG ATT TCT TCT TCC ACT GGT GTA CAA      3504
Thr Gln Thr Ser Ala Gln Ser Leu Ile Ser Ser Ser Thr Gly Val Gln
        1155                1160                1165

ACT GCC AGT GGG GCA CTG AAA GTG ATC CCG AAT ATC TTT GGT TTG GCT      3552
Thr Ala Ser Gly Ala Leu Lys Val Ile Pro Asn Ile Phe Gly Leu Ala
        1170                1175                1180

GAT GGC GGC TCG CGC TAT GAA GGA GTA ACG GAA GCG ATT GCC ATC GGG      3600
Asp Gly Gly Ser Arg Tyr Glu Gly Val Thr Glu Ala Ile Ala Ile Gly
1185                1190                1195                1200

TTA ATG GCT GCC GGA CAA GCC ACC AGC GTG GTG GCC GAG CGT CTG GCA      3648
Leu Met Ala Ala Gly Gln Ala Thr Ser Val Val Ala Glu Arg Leu Ala
                1205                1210                1215

ACC ACG GAG AAT TAC CGC CGC CGC CGT GAA GAG TGG CAA ATC CAA TAC      3696
Thr Thr Glu Asn Tyr Arg Arg Arg Arg Glu Glu Trp Gln Ile Gln Tyr
        1220                1225                1230

CAG CAG GCA CAG TCT GAG GTC GAC GCA TTA CAG AAA CAG TTG GAT GCG      3744
Gln Gln Ala Gln Ser Glu Val Asp Ala Leu Gln Lys Gln Leu Asp Ala
        1235                1240                1245

CTG GCA GTG CGC GAG AAA GCA GCT CAA ACT TCC CTG CAA CAG GCG AAG      3792
Leu Ala Val Arg Glu Lys Ala Ala Gln Thr Ser Leu Gln Gln Ala Lys
        1250                1255                1260

GCA CAG CAG GTA CAA ATT CGG ACC ATG CTG ACT TAC TTA ACT ACT CGT      3840
Ala Gln Gln Val Gln Ile Arg Thr Met Leu Thr Tyr Leu Thr Thr Arg
1265                1270                1275                1280

TTC ACC CAG GCG ACT CTG TAC CAG TGG CTG AGT GGT CAA TTA TCC GCG      3888
Phe Thr Gln Ala Thr Leu Tyr Gln Trp Leu Ser Gly Gln Leu Ser Ala
                1285                1290                1295

TTG TAT TAT CAA GCG TAT GAT GCC GTG GTT GCT CTC TGC CTC TCC GCC      3936
Leu Tyr Tyr Gln Ala Tyr Asp Ala Val Val Ala Leu Cys Leu Ser Ala
            1300                1305                1310

CAA GCT TGC TGG CAG TAT GAA TTG GGT GAT TAC GCT ACC ACT TTT ATC      3984
Gln Ala Cys Trp Gln Tyr Glu Leu Gly Asp Tyr Ala Thr Thr Phe Ile
        1315                1320                1325

CAG ACC GGT ACC TGG AAC GAC CAT TAC CGT GGT TTG CAA GTG GGG GAG      4032
Gln Thr Gly Thr Trp Asn Asp His Tyr Arg Gly Leu Gln Val Gly Glu
        1330                1335                1340

ACA CTG CAA CTC AAT TTG CAT CAG ATG GAA GCG GCC TAT TTA GTT CGT      4080
Thr Leu Gln Leu Asn Leu His Gln Met Glu Ala Ala Tyr Leu Val Arg
1345                1350                1355                1360

CAC GAA CGC CGT CTT AAT GTG ATC CGT ACT GTG TCG CTC AAA AGC CTA      4128
His Glu Arg Arg Leu Asn Val Ile Arg Thr Val Ser Leu Lys Ser Leu
                1365                1370                1375
```

```
TTG GGT GAT GAT GGT TTT GGT AAG TTA AAA ACC GAA GGC AAA GTC GAC    4176
Leu Gly Asp Asp Gly Phe Gly Lys Leu Lys Thr Glu Gly Lys Val Asp
            1380                1385                1390

TTT CCA TTA AGC GAA AAG CTG TTT GAC AAC GAC TAT CCG GGG CAC TAT    4224
Phe Pro Leu Ser Glu Lys Leu Phe Asp Asn Asp Tyr Pro Gly His Tyr
        1395                1400                1405

TTG CGC CAG ATT AAA ACT GTG TCA GTG ACG TTG CCG ACG TTA GTC GGG    4272
Leu Arg Gln Ile Lys Thr Val Ser Val Thr Leu Pro Thr Leu Val Gly
    1410                1415                1420

CCG TAT CAA AAC GTG AAG GCA ACG CTC ACT CAG ACC AGC AGC AGT ATA    4320
Pro Tyr Gln Asn Val Lys Ala Thr Leu Thr Gln Thr Ser Ser Ser Ile
1425                1430                1435                1440

TTG TTA GCA GCA GAT ATC AAT GGT GTT AAA CGT CTC AAT GAT CCG ACA    4368
Leu Leu Ala Ala Asp Ile Asn Gly Val Lys Arg Leu Asn Asp Pro Thr
                1445                1450                1455

GGT AAA GAG GGT GAT GCG ACG CAT ATT GTC ACC AAT CTG CGT GCC AGC    4416
Gly Lys Glu Gly Asp Ala Thr His Ile Val Thr Asn Leu Arg Ala Ser
        1460                1465                1470

CAG CAG GTG GCG CTC TCT TCT GGC ATT AAT GAT GCC GGT AGC TTT GAG    4464
Gln Gln Val Ala Leu Ser Ser Gly Ile Asn Asp Ala Gly Ser Phe Glu
    1475                1480                1485

TTG CGT TTG GAA GAT GAG CGC TAT CTA TCA TTT GAG GGG ACT GGA GCT    4512
Leu Arg Leu Glu Asp Glu Arg Tyr Leu Ser Phe Glu Gly Thr Gly Ala
        1490                1495                1500

GTT TCC AAA TGG ACT CTT AAC TTC CCG CGT TCT GTG GAT GAG CAT ATT    4560
Val Ser Lys Trp Thr Leu Asn Phe Pro Arg Ser Val Asp Glu His Ile
1505                1510                1515                1520

GAC GAT AAG ACA TTG AAA GCG GAT GAG ATG CAG GCC GCA CTG TTG GCG    4608
Asp Asp Lys Thr Leu Lys Ala Asp Glu Met Gln Ala Ala Leu Leu Ala
            1525                1530                1535

AAT ATG GAT GAT GTG CTG GTG CAG GTG CAT TAT ACC GCC TGC GAC GGC    4656
Asn Met Asp Asp Val Leu Val Gln Val His Tyr Thr Ala Cys Asp Gly
        1540                1545                1550

GGC GCC AGT TTC GCA AAC CAG GTC AAG AAA ACA CTC TCT TAA             4698
Gly Ala Ser Phe Ala Asn Gln Val Lys Lys Thr Leu Ser
    1555                1560                1565

CATTAACTTT TAACTAATCC CTCCCACTCT GTTCGCCAGA GTGGGAGAAG GTTTGTCATA   4758

TCTAAAATCA ATCTTGCGAT CTTTCTCCAT TTCATTGGAA GGGAAGCTGT AAAACAAATA   4818

AGGAATATGA TATG                                                     4832

(2) INFORMATION FOR SEQ ID NO:59:

(i) SEQUENCE CHARACTERISTICS:
        (A) LENGTH:  1565 amino acids
        (B) TYPE:  amino acid
        (D) TOPOLOGY:  linear (ii) MOLECULE TYPE:  protein (xi) SEQUENCE DESCRIPTION: SEQ ID NO:59:

Met Leu Ser Thr Met Glu Lys Gln Leu Asn Glu Ser Gln Arg Asp Ala
1               5                   10                  15

Leu Val Thr Gly Tyr Met Asn Phe Val Ala Pro Thr Leu Lys Gly Val
            20                  25                  30

Ser Gly Gln Pro Val Thr Val Glu Asp Leu Tyr Glu Tyr Leu Leu Ile
        35                  40                  45

Asp Pro Glu Val Ala Asp Glu Val Glu Thr Ser Arg Val Ala Gln Ala
    50                  55                  60
```

-continued

```
Ile Ala Ser Ile Gln Gln Tyr Met Thr Arg Leu Val Asn Gly Ser Glu
 65                  70                  75                  80

Pro Gly Arg Gln Ala Met Glu Pro Ser Thr Ala Asn Glu Trp Arg Asp
                 85                  90                  95

Asn Asp Asn Gln Tyr Ala Ile Trp Ala Ala Gly Ala Glu Val Arg Asn
                100                 105                 110

Tyr Ala Glu Asn Tyr Ile Ser Pro Ile Thr Arg Gln Glu Lys Ser His
                115                 120                 125

Tyr Phe Ser Glu Leu Glu Thr Thr Leu Asn Gln Asn Arg Leu Asp Pro
        130                 135                 140

Asp Arg Val Gln Asp Ala Val Leu Ala Tyr Leu Asn Glu Phe Glu Ala
145                 150                 155                 160

Val Ser Asn Leu Tyr Val Leu Ser Gly Tyr Ile Asn Gln Asp Lys Phe
                165                 170                 175

Asp Gln Ala Ile Tyr Tyr Phe Ile Gly Arg Thr Thr Thr Lys Pro Tyr
                180                 185                 190

Arg Tyr Tyr Trp Arg Gln Met Asp Leu Ser Lys Asn Arg Gln Asp Pro
                195                 200                 205

Ala Gly Asn Pro Val Thr Pro Asn Cys Trp Asn Asp Trp Gln Glu Ile
                210                 215                 220

Thr Leu Pro Leu Ser Gly Asp Thr Val Leu Glu His Thr Val Arg Pro
225                 230                 235                 240

Val Phe Tyr Asn Asp Arg Leu Tyr Val Ala Trp Val Glu Arg Asp Pro
                245                 250                 255

Ala Val Gln Lys Asp Ala Asp Gly Lys Asn Ile Gly Lys Thr His Ala
                260                 265                 270

Tyr Asn Ile Lys Phe Gly Tyr Lys Arg Tyr Asp Asp Thr Trp Thr Ala
                275                 280                 285

Pro Asn Thr Thr Thr Leu Met Thr Gln Gln Ala Gly Glu Ser Ser Glu
                290                 295                 300

Thr Gln Arg Ser Ser Leu Leu Ile Asp Glu Ser Ser Thr Thr Leu Arg
305                 310                 315                 320

Gln Val Asn Leu Leu Ala Thr Thr Asp Phe Ser Ile Asp Pro Thr Glu
                325                 330                 335

Glu Thr Asp Ser Asn Pro Tyr Gly Arg Leu Met Leu Gly Val Phe Val
                340                 345                 350

Arg Gln Phe Glu Gly Asp Gly Ala Asn Arg Lys Asn Lys Pro Val Val
                355                 360                 365

Tyr Gly Tyr Leu Tyr Cys Asp Ser Ala Phe Asn Arg His Val Leu Arg
                370                 375                 380

Pro Leu Ser Lys Asn Phe Leu Phe Ser Thr Tyr Arg Asp Glu Thr Asp
385                 390                 395                 400

Gly Gln Asn Ser Leu Gln Phe Ala Val Tyr Asp Lys Lys Tyr Val Ile
                405                 410                 415

Thr Lys Val Val Thr Gly Ala Thr Glu Asp Pro Glu Asn Thr Gly Trp
                420                 425                 430

Val Ser Lys Val Asp Asp Leu Lys Gln Gly Thr Thr Gly Ala Tyr Val
                435                 440                 445

Tyr Ile Asp Gln Asp Gly Leu Thr Leu His Ile Gln Thr Thr Thr Asn
                450                 455                 460

Gly Asp Phe Ile Asn Arg His Thr Phe Gly Tyr Asn Asp Leu Val Tyr
465                 470                 475                 480

Asp Ser Lys Ser Gly Tyr Gly Phe Thr Trp Ser Gly Asn Glu Gly Phe
```

-continued

```
                    485                 490                     495
Tyr Leu Asp Tyr His Asp Gly Asn Tyr Tyr Thr Phe His Asn Ala Ile
                500                 505                 510
Ile Asn Tyr Tyr Pro Ser Gly Tyr Gly Gly Ser Val Pro Asn Gly
            515                 520                 525
Thr Trp Ala Leu Glu Gln Arg Ile Asn Glu Gly Trp Ala Ile Ala Pro
        530                 535                 540
Leu Leu Asp Thr Leu His Thr Val Thr Val Lys Gly Ser Tyr Ile Ala
545                 550                 555                 560
Trp Glu Gly Glu Thr Pro Thr Gly Tyr Asn Leu Tyr Ile Pro Asp Gly
                565                 570                 575
Thr Val Leu Leu Asp Trp Phe Asp Lys Ile Asn Phe Ala Ile Gly Leu
            580                 585                 590
Asn Lys Leu Glu Ser Val Phe Thr Ser Pro Asp Trp Pro Thr Leu Thr
                595                 600                 605
Thr Ile Lys Asn Phe Ser Lys Ile Ala Asp Asn Arg Lys Phe Tyr Gln
            610                 615                 620
Glu Ile Asn Ala Glu Thr Ala Asp Gly Arg Asn Leu Phe Lys Arg Tyr
625                 630                 635                 640
Ser Thr Gln Thr Phe Gly Leu Thr Ser Gly Ala Thr Tyr Ser Thr Thr
                645                 650                 655
Tyr Thr Leu Ser Glu Ala Asp Phe Ser Thr Asp Pro Asp Lys Asn Tyr
                660                 665                 670
Leu Gln Val Cys Leu Asn Val Val Trp Asp His Tyr Asp Arg Pro Ser
            675                 680                 685
Gly Lys Lys Gly Ala Tyr Ser Trp Val Ser Lys Trp Phe Asn Val Tyr
        690                 695                 700
Val Ala Leu Gln Asp Ser Lys Ala Pro Asp Ala Ile Pro Arg Leu Val
705                 710                 715                 720
Ser Arg Tyr Asp Ser Lys Arg Gly Leu Val Gln Tyr Leu Asp Phe Trp
                725                 730                 735
Thr Ser Ser Leu Pro Ala Lys Thr Arg Leu Asn Thr Thr Phe Val Arg
            740                 745                 750
Thr Leu Ile Glu Lys Ala Asn Leu Gly Leu Asp Ser Leu Leu Asp Tyr
            755                 760                 765
Thr Leu Gln Ala Asp Pro Ser Leu Glu Ala Asp Leu Val Thr Asp Gly
        770                 775                 780
Lys Ser Glu Pro Met Asp Phe Asn Gly Ser Asn Gly Leu Tyr Phe Trp
785                 790                 795                 800
Glu Leu Phe Phe His Leu Pro Phe Leu Val Ala Thr Arg Phe Ala Asn
                805                 810                 815
Glu Gln Gln Phe Ser Pro Ala Gln Lys Ser Leu His Tyr Ile Phe Asp
                820                 825                 830
Pro Ala Met Lys Asn Lys Pro His Asn Ala Pro Ala Tyr Trp Asn Val
            835                 840                 845
Arg Pro Leu Val Glu Gly Asn Ser Asp Leu Ser Arg His Leu Asp Asp
        850                 855                 860
Ser Ile Asp Pro Asp Thr Gln Ala Tyr Ala His Pro Val Ile Tyr Gln
865                 870                 875                 880
Lys Ala Val Phe Ile Ala Tyr Val Ser Asn Leu Ile Ala Gln Gly Asp
                885                 890                 895
Met Trp Tyr Arg Gln Leu Thr Arg Asp Gly Leu Thr Gln Ala Arg Val
            900                 905                 910
```

-continued

Tyr Tyr Asn Leu Ala Ala Glu Leu Gly Pro Arg Pro Asp Val Ser
        915                 920                 925

Leu Ser Ser Ile Trp Thr Pro Gln Thr Leu Asp Thr Leu Ala Ala Gly
        930                 935                 940

Gln Lys Ala Val Leu Arg Asp Phe Glu His Gln Leu Ala Asn Ser Asp
945                 950                 955                 960

Thr Ala Leu Pro Ala Leu Pro Gly Arg Asn Val Ser Tyr Leu Lys Leu
                965                 970                 975

Ala Asp Asn Gly Tyr Phe Asn Glu Pro Leu Asn Val Leu Met Leu Ser
            980                 985                 990

His Trp Asp Thr Leu Asp Ala Arg Leu Tyr Asn Leu Arg His Asn Leu
        995                 1000                1005

Thr Val Asp Gly Lys Pro Leu Ser Leu Pro Leu Tyr Ala Ala Pro Val
    1010                1015                1020

Asp Pro Val Ala Leu Leu Ala Gln Arg Ala Gln Ser Gly Thr Leu Thr
1025                1030                1035                1040

Asn Gly Val Ser Gly Ala Met Leu Thr Val Pro Pro Tyr Arg Phe Ser
                1045                1050                1055

Ala Met Leu Pro Arg Ala Tyr Ser Ala Val Gly Thr Leu Thr Ser Phe
            1060                1065                1070

Gly Gln Asn Leu Leu Ser Leu Leu Glu Arg Ser Glu Arg Ala Cys Gln
        1075                1080                1085

Glu Glu Leu Ala Gln Gln Leu Leu Asp Met Ser Ser Tyr Ala Ile
    1090                1095                1100

Thr Leu Gln Gln Gln Ala Leu Asp Gly Leu Ala Ala Asp Arg Leu Ala
1105                1110                1115                1120

Leu Leu Ala Ser Gln Ala Thr Ala Gln Gln Arg His Asp His Tyr Tyr
                1125                1130                1135

Thr Leu Tyr Gln Asn Asn Ile Ser Ser Ala Glu Gln Leu Val Met Asp
            1140                1145                1150

Thr Gln Thr Ser Ala Gln Ser Leu Ile Ser Ser Thr Gly Val Gln
        1155                1160                1165

Thr Ala Ser Gly Ala Leu Lys Val Ile Pro Asn Ile Phe Gly Leu Ala
    1170                1175                1180

Asp Gly Gly Ser Arg Tyr Glu Gly Val Thr Glu Ala Ile Ala Ile Gly
1185                1190                1195                1200

Leu Met Ala Ala Gly Gln Ala Thr Ser Val Val Ala Glu Arg Leu Ala
                1205                1210                1215

Thr Thr Glu Asn Tyr Arg Arg Arg Glu Glu Trp Gln Ile Gln Tyr
            1220                1225                1230

Gln Gln Ala Gln Ser Glu Val Asp Ala Leu Gln Lys Gln Leu Asp Ala
        1235                1240                1245

Leu Ala Val Arg Glu Lys Ala Ala Gln Thr Ser Leu Gln Gln Ala Lys
    1250                1255                1260

Ala Gln Gln Val Gln Ile Arg Thr Met Leu Thr Tyr Leu Thr Thr Arg
1265                1270                1275                1280

Phe Thr Gln Ala Thr Leu Tyr Gln Trp Leu Ser Gly Gln Leu Ser Ala
                1285                1290                1295

Leu Tyr Tyr Gln Ala Tyr Asp Ala Val Val Ala Leu Cys Leu Ser Ala
            1300                1305                1310

Gln Ala Cys Trp Gln Tyr Glu Leu Gly Asp Tyr Ala Thr Thr Phe Ile
        1315                1320                1325

```
Gln Thr Gly Thr Trp Asn Asp His Tyr Arg Gly Leu Gln Val Gly Glu
    1330                1335                1340

Thr Leu Gln Leu Asn Leu His Gln Met Glu Ala Ala Tyr Leu Val Arg
1345                1350                1355                1360

His Glu Arg Arg Leu Asn Val Ile Arg Thr Val Ser Leu Lys Ser Leu
                1365                1370                1375

Leu Gly Asp Asp Gly Phe Gly Lys Leu Lys Thr Glu Gly Lys Val Asp
            1380                1385                1390

Phe Pro Leu Ser Glu Lys Leu Phe Asp Asn Asp Tyr Pro Gly His Tyr
        1395                1400                1405

Leu Arg Gln Ile Lys Thr Val Ser Val Thr Leu Pro Thr Leu Val Gly
    1410                1415                1420

Pro Tyr Gln Asn Val Lys Ala Thr Leu Thr Gln Thr Ser Ser Ser Ile
1425                1430                1435                1440

Leu Leu Ala Ala Asp Ile Asn Gly Val Lys Arg Leu Asn Asp Pro Thr
                1445                1450                1455

Gly Lys Glu Gly Asp Ala Thr His Ile Val Thr Asn Leu Arg Ala Ser
            1460                1465                1470

Gln Gln Val Ala Leu Ser Ser Gly Ile Asn Asp Ala Gly Ser Phe Glu
        1475                1480                1485

Leu Arg Leu Glu Asp Glu Arg Tyr Leu Ser Phe Glu Gly Thr Gly Ala
    1490                1495                1500

Val Ser Lys Trp Thr Leu Asn Phe Pro Arg Ser Val Asp Glu His Ile
1505                1510                1515                1520

Asp Asp Lys Thr Leu Lys Ala Asp Glu Met Gln Ala Ala Leu Leu Ala
                1525                1530                1535

Asn Met Asp Asp Val Leu Val Gln Val His Tyr Thr Ala Cys Asp Gly
            1540                1545                1550

Gly Ala Ser Phe Ala Asn Gln Val Lys Lys Thr Leu Ser
        1555                1560                1565

(2) INFORMATION FOR SEQ ID NO:60:

(i) SEQUENCE CHARACTERISTICS:
        (A) LENGTH: 3132 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:60:

ATG AGT CCG TCT GAG ACT ACT CTT TAT ACT CAA ACC CCA ACA GTC AGC        48
Met Ser Pro Ser Glu Thr Thr Leu Tyr Thr Gln Thr Pro Thr Val Ser
1                5                   10                  15

GTG TTA GAT AAT CGC GGT CTG TCC ATT CGT GAT ATT GGT TTT CAC CGT        96
Val Leu Asp Asn Arg Gly Leu Ser Ile Arg Asp Ile Gly Phe His Arg
                20                  25                  30

ATT GTA ATC GGG GGG GAT ACT GAC ACC CGC GTC ACC CGT CAC CAG TAT       144
Ile Val Ile Gly Gly Asp Thr Asp Thr Arg Val Thr Arg His Gln Tyr
            35                  40                  45

GAT GCC CGT GGA CAC CTG AAC TAC AGT ATT GAC CCA CGC TTG TAT GAT       192
Asp Ala Arg Gly His Leu Asn Tyr Ser Ile Asp Pro Arg Leu Tyr Asp
        50                  55                  60

GCA AAG CAG GCT GAT AAC TCA GTA AAG CCT AAT TTT GTC TGG CAG CAT       240
Ala Lys Gln Ala Asp Asn Ser Val Lys Pro Asn Phe Val Trp Gln His
65                  70                  75                  80

GAT CTG GCC GGT CAT GCC CTG CGG ACA GAG AGT GTC GAT GCT GGT CGT       288
```

```
                                                            -continued

Asp Leu Ala Gly His Ala Leu Arg Thr Glu Ser Val Asp Ala Gly Arg
             85                  90                  95

ACT GTT GCA TTG AAT GAT ATT GAA GGT CGT TCG GTA ATG ACA ATG AAT    336
Thr Val Ala Leu Asn Asp Ile Glu Gly Arg Ser Val Met Thr Met Asn
            100                 105                 110

GCG ACC GGT GTT CGT CAG ACC CGT CGC TAT GAA GGC AAC ACC TTG CCC    384
Ala Thr Gly Val Arg Gln Thr Arg Arg Tyr Glu Gly Asn Thr Leu Pro
        115                 120                 125

GGT CGC TTG TTA TCT GTG AGC GAG CAA GTT TTC AAC CAA GAG AGT GCT    432
Gly Arg Leu Leu Ser Val Ser Glu Gln Val Phe Asn Gln Glu Ser Ala
    130                 135                 140

AAA GTG ACA GAG CGC TTT ATC TGG GCT GGG AAT ACA ACC TCG GAG AAA    480
Lys Val Thr Glu Arg Phe Ile Trp Ala Gly Asn Thr Thr Ser Glu Lys
145                 150                 155                 160

GAG TAT AAC CTC TCC GGT CTG TGT ATA CGC CAC TAC GAC ACA GCG GGA    528
Glu Tyr Asn Leu Ser Gly Leu Cys Ile Arg His Tyr Asp Thr Ala Gly
                165                 170                 175

GTG ACC CGG TTG ATG AGT CAG TCA CTG GCG GGC GCC ATG CTA TCC CAA    576
Val Thr Arg Leu Met Ser Gln Ser Leu Ala Gly Ala Met Leu Ser Gln
            180                 185                 190

TCT CAC CAA TTG CTG GCG GAA GGG CAG GAG GCT AAC TGG AGC GGT GAC    624
Ser His Gln Leu Leu Ala Glu Gly Gln Glu Ala Asn Trp Ser Gly Asp
        195                 200                 205

GAC GAA ACT GTC TGG CAG GGA ATG CTG GCA AGT GAG GTC TAT ACG ACA    672
Asp Glu Thr Val Trp Gln Gly Met Leu Ala Ser Glu Val Tyr Thr Thr
    210                 215                 220

CAA AGT ACC ACT AAT GCC ATC GGG GCT TTA CTG ACC CAA ACC GAT GCG    720
Gln Ser Thr Thr Asn Ala Ile Gly Ala Leu Leu Thr Gln Thr Asp Ala
225                 230                 235                 240

AAA GGC AAT ATT CAG CGT CTG GCT TAT GAC ATT GCC GGT CAG TTA AAA    768
Lys Gly Asn Ile Gln Arg Leu Ala Tyr Asp Ile Ala Gly Gln Leu Lys
                245                 250                 255

GGG AGT TGG TTG ACG GTG AAA GGC CAG AGT GAA CAG GTG ATT GTT AAG    816
Gly Ser Trp Leu Thr Val Lys Gly Gln Ser Glu Gln Val Ile Val Lys
            260                 265                 270

TCC CTG AGC TGG TCA GCC GCA GGT CAT AAA TTG CGT GAA GAG CAC GGT    864
Ser Leu Ser Trp Ser Ala Ala Gly His Lys Leu Arg Glu Glu His Gly
        275                 280                 285

AAC GGC GTG GTT ACG GAG TAC AGT TAT GAG CCG GAA ACT CAA CGT CTG    912
Asn Gly Val Val Thr Glu Tyr Ser Tyr Glu Pro Glu Thr Gln Arg Leu
    290                 295                 300

ATA GGT ATC ACC ACC CGG CGT GCC GAA GGG AGT CAA TCA GGA GCC AGA    960
Ile Gly Ile Thr Thr Arg Arg Ala Glu Gly Ser Gln Ser Gly Ala Arg
305                 310                 315                 320

GTA TTG CAG GAT CTA CGC TAT AAG TAT GAT CCG GTG GGG AAT GTT ATC   1008
Val Leu Gln Asp Leu Arg Tyr Lys Tyr Asp Pro Val Gly Asn Val Ile
                325                 330                 335

AGT ATC CAT AAT GAT GCC GAA GCT ACC CGC TTT TGG CGT AAT CAG AAA   1056
Ser Ile His Asn Asp Ala Glu Ala Thr Arg Phe Trp Arg Asn Gln Lys
            340                 345                 350

GTG GAG CCG GAG AAT CGC TAT GTT TAT GAT TCT CTG TAT CAG CTT ATG   1104
Val Glu Pro Glu Asn Arg Tyr Val Tyr Asp Ser Leu Tyr Gln Leu Met
        355                 360                 365

AGT GCG ACA GGG CGT GAA ATG GCT AAT ATC GGT CAG CAA AGC AAC CAA   1152
Ser Ala Thr Gly Arg Glu Met Ala Asn Ile Gly Gln Gln Ser Asn Gln
    370                 375                 380

CTT CCC TCA CCC GTT ATA CCT GTT CCT ACT GAC GAC AGC ACT TAT ACC   1200
Leu Pro Ser Pro Val Ile Pro Val Pro Thr Asp Asp Ser Thr Tyr Thr
385                 390                 395                 400
```

-continued

```
AAT TAC CTT CGT ACC TAT ACT TAT GAC CGT GGC GGT AAT TTG GTT CAA        1248
Asn Tyr Leu Arg Thr Tyr Thr Tyr Asp Arg Gly Gly Asn Leu Val Gln
                405                 410                 415

ATC CGA CAC AGT TCA CCC GCG ACT CAA AAT AGT TAC ACC ACA GAT ATC        1296
Ile Arg His Ser Ser Pro Ala Thr Gln Asn Ser Tyr Thr Thr Asp Ile
                420                 425                 430

ACC GTT TCA AGC CGC AGT AAC CGG GCG GTA TTG AGT ACA TTA ACG ACA        1344
Thr Val Ser Ser Arg Ser Asn Arg Ala Val Leu Ser Thr Leu Thr Thr
                435                 440                 445

GAT CCA ACC CGA GTG GAT GCG CTA TTT GAT TCC GGC GGT CAT CAG AAG        1392
Asp Pro Thr Arg Val Asp Ala Leu Phe Asp Ser Gly Gly His Gln Lys
    450                 455                 460

ATG TTA ATA CCG GGG CAA AAT CTG GAT TGG AAT ATT CGG GGT GAA TTG        1440
Met Leu Ile Pro Gly Gln Asn Leu Asp Trp Asn Ile Arg Gly Glu Leu
465                 470                 475                 480

CAA CGA GTC ACA CCG GTG AGC CGT GAA AAT AGC AGT GAC AGT GAA TGG        1488
Gln Arg Val Thr Pro Val Ser Arg Glu Asn Ser Ser Asp Ser Glu Trp
                485                 490                 495

TAT CGC TAT AGC AGT GAT GGC ATG CGG CTG CTA AAA GTG AGT GAA CAG        1536
Tyr Arg Tyr Ser Ser Asp Gly Met Arg Leu Leu Lys Val Ser Glu Gln
                500                 505                 510

CAG ACG GGC AAC AGT ACT CAA GTA CAA CGG GTG ACT TAT CTG CCG GGA        1584
Gln Thr Gly Asn Ser Thr Gln Val Gln Arg Val Thr Tyr Leu Pro Gly
                515                 520                 525

TTA GAG CTA CGG ACA ACT GGG GTT GCA GAT AAA ACA ACC GAA GAT TTG        1632
Leu Glu Leu Arg Thr Thr Gly Val Ala Asp Lys Thr Thr Glu Asp Leu
    530                 535                 540

CAG GTG ATT ACG GTA GGT GAA GCG GGT CGC GCA CAG GTA AGG GTA TTG        1680
Gln Val Ile Thr Val Gly Glu Ala Gly Arg Ala Gln Val Arg Val Leu
545                 550                 555                 560

CAC TGG GAA AGT GGT AAG CCG ACA GAT ATT GAC AAC AAT CAG GTG CGC        1728
His Trp Glu Ser Gly Lys Pro Thr Asp Ile Asp Asn Asn Gln Val Arg
                565                 570                 575

TAC AGC TAC GAT AAT CTG CTT GGC TCC AGC CAG CTT GAA CTG GAT AGC        1776
Tyr Ser Tyr Asp Asn Leu Leu Gly Ser Ser Gln Leu Glu Leu Asp Ser
                580                 585                 590

GAA GGG CAG ATT CTC AGT CAG GAA GAG TAT TAT CCG TAT GGC GGT ACG        1824
Glu Gly Gln Ile Leu Ser Gln Glu Glu Tyr Tyr Pro Tyr Gly Gly Thr
                595                 600                 605

GCG ATA TGG GCG GCG AGA AAT CAG ACA GAA GCC AGC TAC AAA TTT ATT        1872
Ala Ile Trp Ala Ala Arg Asn Gln Thr Glu Ala Ser Tyr Lys Phe Ile
    610                 615                 620

CGT TAC TCC GGT AAA GAG CGG GAT GCC ACT GGA TTG TAT TAT TAC GGC        1920
Arg Tyr Ser Gly Lys Glu Arg Asp Ala Thr Gly Leu Tyr Tyr Tyr Gly
625                 630                 635                 640

TAC CGT TAT TAT CAA CCT TGG GTG GGT CGA TGG TTG AGT GCT GAT CCG        1968
Tyr Arg Tyr Tyr Gln Pro Trp Val Gly Arg Trp Leu Ser Ala Asp Pro
                645                 650                 655

GCG GGA ACC GTG GAT GGG CTG AAT TTG TAC CGA ATG GTG AGG AAT AAC        2016
Ala Gly Thr Val Asp Gly Leu Asn Leu Tyr Arg Met Val Arg Asn Asn
                660                 665                 670

CCC ATC ACA TTG ACT GAC CAT GAC GGA TTA GCA CCG TCT CCA AAT AGA        2064
Pro Ile Thr Leu Thr Asp His Asp Gly Leu Ala Pro Ser Pro Asn Arg
                675                 680                 685

AAT CGA AAT ACA TTT TGG TTT GCT TCA TTT TTG TTT CGT AAA CCT GAT        2112
Asn Arg Asn Thr Phe Trp Phe Ala Ser Phe Leu Phe Arg Lys Pro Asp
    690                 695                 700

GAG GGA ATG TCC GCG TCA ATG AGA CGG GGA CAA AAA ATT GGC AGA GCC        2160
Glu Gly Met Ser Ala Ser Met Arg Arg Gly Gln Lys Ile Gly Arg Ala
705                 710                 715                 720
```

```
ATT GCC GGC GGG ATT GCG ATT GGC GGT CTT GCG GCT ACC ATT GCC GCT       2208
Ile Ala Gly Gly Ile Ala Ile Gly Gly Leu Ala Ala Thr Ile Ala Ala
             725                 730                 735

ACG GCT GGC GCG GCT ATC CCC GTC ATT CTG GGG GTT GCG GCC GTA GGC       2256
Thr Ala Gly Ala Ala Ile Pro Val Ile Leu Gly Val Ala Ala Val Gly
             740                 745                 750

GCG GGG ATT GGC GCG TTG ATG GGA TAT AAC GTC GGT AGC CTG CTG GAA       2304
Ala Gly Ile Gly Ala Leu Met Gly Tyr Asn Val Gly Ser Leu Leu Glu
             755                 760                 765

AAA GGC GGG GCA TTA CTT GCT CGA CTC GTA CAG GGG AAA TCG ACG TTA       2352
Lys Gly Gly Ala Leu Leu Ala Arg Leu Val Gln Gly Lys Ser Thr Leu
    770                 775                 780

GTA CAG TCG GCG GCT GGC GCG GCT GCC GGA GCG AGT TCA GCC GCG GCT       2400
Val Gln Ser Ala Ala Gly Ala Ala Gly Ala Ser Ser Ala Ala Ala
785                 790                 795                 800

TAT GGC GCA CGG GCA CAA GGT GTC GGT GTT GCA TCA GCC GCC GGG GCG       2448
Tyr Gly Ala Arg Ala Gln Gly Val Gly Val Ala Ser Ala Ala Gly Ala
             805                 810                 815

GTA ACA GGG GCT GTG GGA TCA TGG ATA AAT AAT GCT GAT CGG GGG ATT       2496
Val Thr Gly Ala Val Gly Ser Trp Ile Asn Asn Ala Asp Arg Gly Ile
             820                 825                 830

GGC GGC GCT ATT GGG GCC GGG AGT GCG GTA GGC ACC ATT GAT ACT ATG       2544
Gly Gly Ala Ile Gly Ala Gly Ser Ala Val Gly Thr Ile Asp Thr Met
             835                 840                 845

TTA GGG ACT GCC TCT ACC CTT ACC CAT GAA GTC GGG GCA GCG GCG GGT       2592
Leu Gly Thr Ala Ser Thr Leu Thr His Glu Val Gly Ala Ala Ala Gly
    850                 855                 860

GGG GCG GCG GGT GGG ATG ATC ACC GGT ACG CAA GGG AGT ACT CGG GCA       2640
Gly Ala Ala Gly Gly Met Ile Thr Gly Thr Gln Gly Ser Thr Arg Ala
865                 870                 875                 880

GGT ATC CAT GCC GGT ATT GGC ACC TAT TAT GGC TCC TGG ATT GGT TTT       2688
Gly Ile His Ala Gly Ile Gly Thr Tyr Tyr Gly Ser Trp Ile Gly Phe
             885                 890                 895

GGT TTA GAT GTC GCT AGT AAC CCC GCC GGA CAT TTA GCG AAT TAC GCA       2736
Gly Leu Asp Val Ala Ser Asn Pro Ala Gly His Leu Ala Asn Tyr Ala
             900                 905                 910

GTG GGT TAT GCC GCT GGT TTG GGT GCT GAA ATG GCT GTC AAC AGA ATA       2784
Val Gly Tyr Ala Ala Gly Leu Gly Ala Glu Met Ala Val Asn Arg Ile
             915                 920                 925

ATG GGT GGT GGA TTT TTG AGT AGG CTC TTA GGC CGG GTT GTC AGC CCA       2832
Met Gly Gly Gly Phe Leu Ser Arg Leu Leu Gly Arg Val Val Ser Pro
    930                 935                 940

TAT GCC GCC GGT TTA GCC AGA CAA TTA GTA CAT TTC AGT GTC GCC AGA       2880
Tyr Ala Ala Gly Leu Ala Arg Gln Leu Val His Phe Ser Val Ala Arg
945                 950                 955                 960

CCT GTC TTT GAG CCG ATA TTT AGT GTT CTC GGC GGG CTT GTC GGT GGT       2928
Pro Val Phe Glu Pro Ile Phe Ser Val Leu Gly Gly Leu Val Gly Gly
             965                 970                 975

ATT GGA ACT GGC CTG CAC AGA GTG ATG GGA AGA GAG AGT TGG ATT TCC       2976
Ile Gly Thr Gly Leu His Arg Val Met Gly Arg Glu Ser Trp Ile Ser
             980                 985                 990

AGA GCG TTA AGT GCT GCC GGT AGT GGT ATA GAT CAT GTC GCT GGC ATG       3024
Arg Ala Leu Ser Ala Ala Gly Ser Gly Ile Asp His Val Ala Gly Met
             995                 1000                1005

ATT GGT AAT CAG ATC AGA GGC AGG GTC TTG ACC ACA ACC GGG ATC GCT       3072
Ile Gly Asn Gln Ile Arg Gly Arg Val Leu Thr Thr Thr Gly Ile Ala
    1010                1015                1020

AAT GCG ATA GAC TAT GGC ACC AGT GCT GTG GGA GCC GCA CGA CGA GTT       3120
Asn Ala Ile Asp Tyr Gly Thr Ser Ala Val Gly Ala Ala Arg Arg Val
```

-continued

```
1025            1030            1035            1040

TTT TCT TTG TAA                                                 3132
Phe Ser Leu
```

(2) INFORMATION FOR SEQ ID NO:61:

(i) SEQUENCE CHARACTERISTICS:
        (A) LENGTH: 1043 amino acids
        (B) TYPE: amino acid
        (C) TOPOLOGY: linear (ii) MOLECULE TYPE: protein (xi) SEQUENCE DESCRIPTION: SEQ ID NO:61:

```
Met Ser Pro Ser Glu Thr Thr Leu Tyr Thr Gln Thr Pro Thr Val Ser
1               5                   10                  15

Val Leu Asp Asn Arg Gly Leu Ser Ile Arg Asp Ile Gly Phe His Arg
                20                  25                  30

Ile Val Ile Gly Gly Asp Thr Asp Thr Arg Val Thr Arg His Gln Tyr
            35                  40                  45

Asp Ala Arg Gly His Leu Asn Tyr Ser Ile Asp Pro Arg Leu Tyr Asp
        50                  55                  60

Ala Lys Gln Ala Asp Asn Ser Val Lys Pro Asn Phe Val Trp Gln His
65                  70                  75                  80

Asp Leu Ala Gly His Ala Leu Arg Thr Glu Ser Val Asp Ala Gly Arg
                85                  90                  95

Thr Val Ala Leu Asn Asp Ile Glu Gly Arg Ser Val Met Thr Met Asn
                100                 105                 110

Ala Thr Gly Val Arg Gln Thr Arg Arg Tyr Glu Gly Asn Thr Leu Pro
            115                 120                 125

Gly Arg Leu Leu Ser Val Ser Glu Gln Val Phe Asn Gln Glu Ser Ala
        130                 135                 140

Lys Val Thr Glu Arg Phe Ile Trp Ala Gly Asn Thr Thr Ser Glu Lys
145                 150                 155                 160

Glu Tyr Asn Leu Ser Gly Leu Cys Ile Arg His Tyr Asp Thr Ala Gly
                165                 170                 175

Val Thr Arg Leu Met Ser Gln Ser Leu Ala Gly Ala Met Leu Ser Gln
                180                 185                 190

Ser His Gln Leu Leu Ala Glu Gly Gln Glu Ala Asn Trp Ser Gly Asp
            195                 200                 205

Asp Glu Thr Val Trp Gln Gly Met Leu Ala Ser Glu Val Tyr Thr Thr
        210                 215                 220

Gln Ser Thr Thr Asn Ala Ile Gly Ala Leu Leu Thr Gln Thr Asp Ala
225                 230                 235                 240

Lys Gly Asn Ile Gln Arg Leu Ala Tyr Asp Ile Ala Gly Gln Leu Lys
                245                 250                 255

Gly Ser Trp Leu Thr Val Lys Gly Gln Ser Glu Gln Val Ile Val Lys
                260                 265                 270

Ser Leu Ser Trp Ser Ala Ala Gly His Lys Leu Arg Glu Glu His Gly
            275                 280                 285

Asn Gly Val Val Thr Glu Tyr Ser Tyr Glu Pro Glu Thr Gln Arg Leu
        290                 295                 300

Ile Gly Ile Thr Thr Arg Arg Ala Glu Gly Ser Gln Ser Gly Ala Arg
305                 310                 315                 320

Val Leu Gln Asp Leu Arg Tyr Lys Tyr Asp Pro Val Gly Asn Val Ile
                325                 330                 335
```

-continued

```
Ser Ile His Asn Asp Ala Glu Ala Thr Arg Phe Trp Arg Asn Gln Lys
            340                 345                 350

Val Glu Pro Glu Asn Arg Tyr Val Tyr Asp Ser Leu Tyr Gln Leu Met
        355                 360                 365

Ser Ala Thr Gly Arg Glu Met Ala Asn Ile Gly Gln Gln Ser Asn Gln
    370                 375                 380

Leu Pro Ser Pro Val Ile Pro Val Pro Thr Asp Asp Ser Thr Tyr Thr
385                 390                 395                 400

Asn Tyr Leu Arg Thr Tyr Thr Tyr Asp Arg Gly Gly Asn Leu Val Gln
                405                 410                 415

Ile Arg His Ser Ser Pro Ala Thr Gln Asn Ser Tyr Thr Thr Asp Ile
            420                 425                 430

Thr Val Ser Ser Arg Ser Asn Arg Ala Val Leu Ser Thr Leu Thr Thr
        435                 440                 445

Asp Pro Thr Arg Val Asp Ala Leu Phe Asp Ser Gly His Gln Lys
    450                 455                 460

Met Leu Ile Pro Gly Gln Asn Leu Asp Trp Asn Ile Arg Gly Glu Leu
465                 470                 475                 480

Gln Arg Val Thr Pro Val Ser Arg Glu Asn Ser Ser Asp Ser Glu Trp
                485                 490                 495

Tyr Arg Tyr Ser Ser Asp Gly Met Arg Leu Leu Lys Val Ser Glu Gln
            500                 505                 510

Gln Thr Gly Asn Ser Thr Gln Val Gln Arg Val Thr Tyr Leu Pro Gly
        515                 520                 525

Leu Glu Leu Arg Thr Thr Gly Val Ala Asp Lys Thr Thr Glu Asp Leu
    530                 535                 540

Gln Val Ile Thr Val Gly Glu Ala Gly Arg Ala Gln Val Arg Val Leu
545                 550                 555                 560

His Trp Glu Ser Gly Lys Pro Thr Asp Ile Asp Asn Asn Gln Val Arg
                565                 570                 575

Tyr Ser Tyr Asp Asn Leu Leu Gly Ser Ser Gln Leu Glu Leu Asp Ser
            580                 585                 590

Glu Gly Gln Ile Leu Ser Gln Glu Glu Tyr Tyr Pro Tyr Gly Gly Thr
        595                 600                 605

Ala Ile Trp Ala Ala Arg Asn Gln Thr Glu Ala Ser Tyr Lys Phe Ile
    610                 615                 620

Arg Tyr Ser Gly Lys Glu Arg Asp Ala Thr Gly Leu Tyr Tyr Tyr Gly
625                 630                 635                 640

Tyr Arg Tyr Tyr Gln Pro Trp Val Gly Arg Trp Leu Ser Ala Asp Pro
                645                 650                 655

Ala Gly Thr Val Asp Gly Leu Asn Leu Tyr Arg Met Val Arg Asn Asn
            660                 665                 670

Pro Ile Thr Leu Thr Asp His Asp Gly Leu Ala Pro Ser Pro Asn Arg
        675                 680                 685

Asn Arg Asn Thr Phe Trp Phe Ala Ser Phe Leu Phe Arg Lys Pro Asp
    690                 695                 700

Glu Gly Met Ser Ala Ser Met Arg Arg Gly Gln Lys Ile Gly Arg Ala
705                 710                 715                 720

Ile Ala Gly Gly Ile Ala Ile Gly Gly Leu Ala Ala Thr Ile Ala Ala
                725                 730                 735

Thr Ala Gly Ala Ala Ile Pro Val Ile Leu Gly Val Ala Ala Val Gly
            740                 745                 750
```

```
Ala Gly Ile Gly Ala Leu Met Gly Tyr Asn Val Gly Ser Leu Leu Glu
        755                 760                 765

Lys Gly Gly Ala Leu Leu Ala Arg Leu Val Gln Gly Lys Ser Thr Leu
        770                 775             780

Val Gln Ser Ala Ala Gly Ala Ala Gly Ala Ser Ser Ala Ala Ala
785                 790                 795                 800

Tyr Gly Ala Arg Ala Gln Gly Val Gly Val Ala Ser Ala Ala Gly Ala
                805                 810                 815

Val Thr Gly Ala Val Gly Ser Trp Ile Asn Asn Ala Asp Arg Gly Ile
                820                 825                 830

Gly Gly Ala Ile Gly Ala Gly Ser Ala Val Gly Thr Ile Asp Thr Met
            835                 840                 845

Leu Gly Thr Ala Ser Thr Leu Thr His Glu Val Gly Ala Ala Ala Gly
        850                 855                 860

Gly Ala Ala Gly Gly Met Ile Thr Gly Thr Gln Gly Ser Thr Arg Ala
865                 870                 875                 880

Gly Ile His Ala Gly Ile Gly Thr Tyr Tyr Gly Ser Trp Ile Gly Phe
                885                 890                 895

Gly Leu Asp Val Ala Ser Asn Pro Ala Gly His Leu Ala Asn Tyr Ala
                900                 905                 910

Val Gly Tyr Ala Ala Gly Leu Gly Ala Glu Met Ala Val Asn Arg Ile
            915                 920                 925

Met Gly Gly Gly Phe Leu Ser Arg Leu Leu Gly Arg Val Val Ser Pro
        930                 935                 940

Tyr Ala Ala Gly Leu Ala Arg Gln Leu Val His Phe Ser Val Ala Arg
945                 950                 955                 960

Pro Val Phe Glu Pro Ile Phe Ser Val Leu Gly Gly Leu Val Gly Gly
                965                 970                 975

Ile Gly Thr Gly Leu His Arg Val Met Gly Arg Glu Ser Trp Ile Ser
            980                 985                 990

Arg Ala Leu Ser Ala Ala Gly Ser Gly Ile Asp His Val Ala Gly Met
        995                 1000                1005

Ile Gly Asn Gln Ile Arg Gly Arg Val Leu Thr Thr Thr Gly Ile Ala
    1010                1015                1020

Asn Ala Ile Asp Tyr Gly Thr Ser Ala Val Gly Ala Ala Arg Arg Val
1025                1030                1035                1040

Phe Ser Leu (2) INFORMATION FOR SEQ ID NO:62:

(i) SEQUENCE CHARACTERISTICS:
        (A) LENGTH: 5 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:62:

Asn Ile Gly Gly Asp
1               5

(2) INFORMATION FOR SEQ ID NO:63:

(i) SEQUENCE CHARACTERISTICS:
        (A) LENGTH: 20 amino acids
        (B) TYPE: amino acid
```

(D) TOPOLOGY: linear (ii) MOLECULE TYPE: protein (v) FRAGMENT TYPE: internal (xi) SEQUENCE DESCRIPTION: SEQ ID NO:63:

Cys Leu Arg Gly Asn Ser Pro Thr Asn Pro Asp Lys Asp Gly Ile
1               5                   10                  15

Phe Ala Gln Val Ala
            20

(2) INFORMATION FOR SEQ ID NO:64:

(i) SEQUENCE CHARACTERISTICS:
        (A) LENGTH: 20 amino acids
        (B) TYPE: amino acid
        (D) TOPOLOGY: linear (ii) MOLECULE TYPE: protein (v) FRAGMENT TYPE: Internal (xi) SEQUENCE DESCRIPTION: SEQ ID NO:64:

Cys Tyr Thr Pro Asp Gln Thr Pro Ser Phe Tyr Glu Thr Ala Phe
1               5                   10                  15

Arg Ser Ala Asp Gly
            20

(2) INFORMATION FOR SEQ ID NO:65:

(i) SEQUENCE CHARACTERISTICS:
        (A) LENGTH: 19 amino acids
        (B) TYPE: amino acid
        (D) TOPOLOGY: linear (ii) MOLECULE TYPE: protein (v) FRAGMENT TYPE: Internal (xi) SEQUENCE DESCRIPTION: SEQ ID NO:65:

His Gly Gln Ser Tyr Asn Asp Asn Asn Tyr Cys Asn Phe Thr Leu
1               5                   10                  15

Ser Ile Asn Thr (2) INFORMATION FOR SEQ ID NO:66:

(i) SEQUENCE CHARACTERISTICS:
        (A) LENGTH: 20 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:66:

Cys Val Asp Pro Lys Thr Leu Gln Arg Gln Gln Ala Gly Gly Asp
1               5                   10                  15

Gly Thr Gly Ser Ser
            20

(2) INFORMATION FOR SEQ ID NO:67:

(i) SEQUENCE CHARACTERISTICS:
        (A) LENGTH: 20 amino acids
        (B) TYPE: amino acid (D) TOPOLOGY: linear (ii) MOLECULE TYPE: protein (iii) FRAGMENT TYPE: internal (xi) SEQUENCE DESCRIPTION: SEQ ID NO:67:

Cys Tyr Lys Ala Pro Gln Arg Gln Glu Asp Gly Asp Ser Asn Ala
1               5                   10                  15

Val Thr Tyr Asp Lys
20

(2) INFORMATION FOR SEQ ID NO:68:

(i) SEQUENCE CHARACTERISTICS:
            (A) LENGTH: 20 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:68:

Cys Tyr Asn Glu Asn Pro Ser Ser Glu Asp Lys Lys Trp Tyr Phe
1               5                   10                  15

Ser Ser Lys Asp Asp
20

(2) INFORMATION FOR SEQ ID NO:69:

(i) SEQUENCE CHARACTERISTICS:
            (A) LENGTH: 20 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:69:

Cys Phe Asp Ser Tyr Ser Gln Leu Tyr Glu Glu Asn Ile Asn Ala
1               5                   10                  15

Gly Glu Gln Arg Ala
20

(2) INFORMATION FOR SEQ ID NO:70:

(i) SEQUENCE CHARACTERISTICS:
            (A) LENGTH: 22 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:70:

Cys Asn Pro Asn Asn Ser Ser Asn Lys Leu Met Phe Tyr Pro Val
1               5                   10                  15

Tyr Gln Tyr Ser Gly Asn Thr
20

(2) INFORMATION FOR SEQ ID NO:71:

(i) SEQUENCE CHARACTERISTICS:
            (A) LENGTH: 20 amino acids

```
        (B) TYPE: amino acid
        (D) TOPOLOGY: linear (ii) MOLECULE TYPE: protein (v) FRAGMENT TYPE: internal (xi) SEQUENCE DESCRIPTION:  SEQ ID NO:71:

Val Ser Gln Gly Ser Gly Ser Ala Gly Ser Gly Asn Asn Asn Leu
1               5                  10                  15

Ala Phe Gly Ala Gly
 20

(2) INFORMATION FOR SEQ ID NO:72:

(i) SEQUENCE CHARACTERISTICS:
        (A) LENGTH: 12 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION:  SEQ ID NO:72:

Met Gln Asp Ser Pro Glu Val Ala Ile Thr Thr Leu
1               5                  10

(2) INFORMATION FOR SEQ ID NO:73:

(i) SEQUENCE CHARACTERISTICS:
        (A) LENGTH: 8 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION:  SEQ ID NO:73:

Met Gln Arg Ser Ser Glu Val Ser
1               5

(2) INFORMATION FOR SEQ ID NO:74:

(i) SEQUENCE CHARACTERISTICS:
        (A) LENGTH: 10 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION:  SEQ ID NO:74:

Met Gln Asp Ile Pro Glu Val Gln Leu Asn
1               5                  10

(2) INFORMATION FOR SEQ ID NO:75:

(i) SEQUENCE CHARACTERISTICS:
        (A) LENGTH: 12 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION:SEQ ID NO:75:
```

```
Met Gln Asp Ser Pro Glu Val Ser Val Thr Gln Asn
1               5                  10
```

(2) INFORMATION FOR SEQ ID NO:76:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:76:

```
Ser Glu Ser Leu Phe Thr Gln Ser Leu Lys Glu Ala Arg Arg Asp
1               5                  10                  15
```

(2) INFORMATION FOR SEQ ID NO:77:

(i) SEQUENCE CHARACTERISTICS:
        (A) LENGTH: 14 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:77:

```
Met Asn Leu Ile Glu Ala Lys Leu Gln Glu Asn Arg Asp Ala
1               5                  10
```

(2) INFORMATION FOR SEQ ID NO:78:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:78:

```
Met Leu Ser Thr Met Glu Lys Gln Leu Asn Glu Ser Gln Arg Asp
1               5                  10                  15
```

(2) INFORMATION FOR SEQ ID NO:79:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:79:

```
Met Leu Asp Ile Met Glu Lys Gln Leu Asn Glu Ser Glu Arg Asp
1               5                  10                  15
```

(2) INFORMATION FOR SEQ ID NO:80:

(i) SEQUENCE CHARACTERISTICS:
        (A) LENGTH: 8 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:80:

Met Gln Asp Ser Arg Glu Val Ser
1               5

(2) INFORMATION FOR SEQ ID NO:81:

(i) SEQUENCE CHARACTERISTICS:
        (A) LENGTH: 12 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:81:

Leu Arg Ser Ala Xaa Ser Ala Leu Thr Thr Leu Leu
1               5                   10

(2) INFORMATION FOR SEQ ID NO:82:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:82:

Leu Lys Leu Ala Asp Asn Gly Tyr Phe Asn Glu Pro Leu Asn Val
1               5                   10                  15

(2) INFORMATION FOR SEQ ID NO:83:

(i) SEQUENCE CHARACTERISTICS:
        (A) LENGTH: 14 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:83:

Leu Lys Leu Ala Asp Asn Ser Tyr Phe Asn Glu Pro Leu Asn
1               5                   10

(2) INFORMATION FOR SEQ ID NO:84:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:84:

Ser Lys Asp Glu Ser Lys Ala Asp Ser Gln Leu Val Tyr His Thr
1               5                   10                  15

(2) INFORMATION FOR SEQ ID NO:85:

(i) SEQUENCE CHARACTERISTICS:
        (A) LENGTH: 14 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:85:

```
Met Lys Lys Arg Gly Leu Thr Thr Asn Ala Gly Ala Pro Val
1               5                   10
```

(2) INFORMATION FOR SEQ ID NO:86:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:86:

```
Met Leu Asn Pro Ile Val Arg Lys Phe Glu Tyr Gly Glu His Thr
1               5                   10                  15
```

(2) INFORMATION FOR SEQ ID NO:87:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:87:

```
Ala Glu Ile Tyr Asn Lys Asp Gly Asn Lys Leu Asp Leu Tyr Gly
1               5                   10                  15
```

(2) INFORMATION FOR SEQ ID NO:88:

(i) SEQUENCE CHARACTERISTICS:
        (A) LENGTH: 14 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:88:

```
Asn Leu Ile Glu Ala Thr Leu Glu Gln Asn Leu Arg Asp Ala
1               5                   10
```

We claim:

1. A purified protein comprising an amino acid sequence of SEQ ID NO:12.

2. A method of protecting a plant from an insect which comprises spraying on the plant a toxin comprising the amino acid sequence of SEQ ID NO:12.

* * * * *